US010136995B2

(12) United States Patent
Donner et al.

(10) Patent No.: US 10,136,995 B2
(45) Date of Patent: Nov. 27, 2018

(54) METHOD OF FUSING A SACROILIAC JOINT WITH AN IMPLANT WITH STRUTS

(71) Applicant: JCBD, LLC, Fort Collins, CO (US)

(72) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 0 days.

(21) Appl. No.: 15/993,170

(22) Filed: May 30, 2018

(65) Prior Publication Data

US 2018/0271663 A1    Sep. 27, 2018

Related U.S. Application Data

(60) Continuation of application No. 15/910,753, filed on Mar. 2, 2018, which is a continuation of application
(Continued)

(51) Int. Cl.
*A61F 2/30*        (2006.01)
*A61F 2/46*        (2006.01)
(Continued)

(52) U.S. Cl.
CPC ...... *A61F 2/30988* (2013.01); *A61B 17/1626* (2013.01); *A61B 17/1739* (2013.01);
(Continued)

(58) Field of Classification Search
CPC .............. A61F 2/30988; A61F 2/4455; A61F 2002/30995
See application file for complete search history.

(56) References Cited

U.S. PATENT DOCUMENTS 6,053,916 A * 4/2000 Moore ................ A61F 2/30988
                                                  606/86 R
9,254,130 B2   2/2016 Hollis
(Continued)

OTHER PUBLICATIONS

Australian Examination Report, AU2016204937, dated May 21, 2018.
(Continued)

*Primary Examiner* — Christian Sevilla
(74) *Attorney, Agent, or Firm* — Polsinelli PC; Joshua J. Pranckun; Samuel Wade Johnson

(57) ABSTRACT

A method for fixating a dysfunctional sacroiliac joint including implanting a joint implant at the sacroiliac joint. The joint implant may include: a length extending between a proximal end and a distal end; an exterior surface extending the length; an interior surface opposite the exterior surface and extending the length, the interior surface defining an internal volume therein; a wall thickness defined between the external surface and the interior surface; a proximal opening extending into the internal volume; a first wall section comprising a first plurality of struts arranged along the length and defining a first plurality of openings extending through the wall thickness; and a second wall section including a second plurality of struts arranged along the length and defining a second plurality of opening extending through the wall thickness. Each opening of the first and second plurality of openings may be generally polygonal in shape.

51 Claims, 217 Drawing Sheets

Related U.S. Application Data

No. 15/828,677, filed on Dec. 1, 2017, now Pat. No. 9,931,212, which is a continuation of application No. 15/061,524, filed on Mar. 4, 2016, now Pat. No. 9,833,320, which is a division of application No. 13/946,790, filed on Jul. 19, 2013, now Pat. No. 9,333,090, which is a continuation-in-part of application No. 13/475,695, filed on May 18, 2012, now Pat. No. 9,381,045, which is a continuation-in-part of application No. 13/236,411, filed on Sep. 19, 2011, now Pat. No. 9,017,407, which is a continuation-in-part of application No. 12/998,712, filed as application No. PCT/US2011/000070 on Jan. 13, 2011, now Pat. No. 8,979,928.

(60) Provisional application No. 61/800,120, filed on Mar. 15, 2013, provisional application No. 61/674,277, filed on Jul. 20, 2012, provisional application No. 61/674,130, filed on Jul. 20, 2012, provisional application No. 61/335,947, filed on Jan. 13, 2010.

(51) Int. Cl.
| | |
|---|---|
| *A61F 2/44* | (2006.01) |
| *A61B 17/16* | (2006.01) |
| *A61B 17/17* | (2006.01) |
| *B33Y 80/00* | (2015.01) |
| *A61B 17/02* | (2006.01) |
| *A61B 17/70* | (2006.01) |
| *A61B 17/86* | (2006.01) |
| *A61B 17/00* | (2006.01) |

(52) U.S. Cl.
CPC ...... *A61B 17/1757* (2013.01); *A61B 17/7055* (2013.01); *A61B 17/7074* (2013.01); *A61F 2/4455* (2013.01); *A61F 2/4611* (2013.01); A61B 17/025 (2013.01); A61B 17/7043 (2013.01); A61B 17/8645 (2013.01); A61B 2017/0046 (2013.01); A61F 2002/304 (2013.01); A61F 2002/3055 (2013.01); A61F 2002/30163 (2013.01); A61F 2002/30382 (2013.01); A61F 2002/30401 (2013.01); A61F 2002/30428 (2013.01); A61F 2002/30484 (2013.01); A61F 2002/30504 (2013.01); A61F 2002/30509 (2013.01); A61F 2002/30579 (2013.01); A61F 2002/30601 (2013.01); A61F 2002/30622 (2013.01); A61F 2002/30774 (2013.01); A61F 2002/30828 (2013.01); *A61F 2002/30995* (2013.01); *A61F 2002/4623* (2013.01); *A61F 2002/4687* (2013.01); *A61F 2310/00017* (2013.01); *A61F 2310/00023* (2013.01); *A61F 2310/00179* (2013.01); *A61F 2310/00359* (2013.01); *B33Y 80/00* (2014.12)

(56) References Cited

U.S. PATENT DOCUMENTS

| | | | |
|---|---|---|---|
| 9,480,511 | B2 | 11/2016 | Butters |
| 9,931,212 | B1* | 4/2018 | Donner ................. A61F 2/4455 |
| 2004/0193271 | A1 | 9/2004 | Fraser |
| 2007/0239278 | A1 | 10/2007 | Heinz |
| 2008/0021461 | A1 | 1/2008 | Barker et al. |
| 2009/0088857 | A1* | 4/2009 | Michelson ......... A61B 17/1671 623/17.16 |
| 2009/0099659 | A1* | 4/2009 | Oh ........................ A61F 2/4455 623/17.16 |
| 2009/0204215 | A1* | 8/2009 | McClintock ............... A61F 2/44 623/17.11 |
| 2010/0168861 | A1* | 7/2010 | Yundt ..................... A61F 2/441 623/17.16 |
| 2011/0160866 | A1 | 6/2011 | Laurence |
| 2011/0230968 | A1* | 9/2011 | Perisic .................. A61F 2/4455 623/17.16 |
| 2012/0253406 | A1 | 10/2012 | Bae |
| 2016/0278818 | A1* | 9/2016 | Donner ............. A61B 17/7055 |
| 2016/0278819 | A1* | 9/2016 | Donner ............. A61B 17/7055 |
| 2018/0193154 | A1* | 7/2018 | Donner ................. A61F 2/4455 |
| 2018/0193155 | A1 | 7/2018 | Donner et al. |

OTHER PUBLICATIONS

Canadian Office Action, CA2849095, dated May 28, 2018.
EP Examination Report, EP12799773.2, dated Jun. 4, 2018.
Non-Final Office Action, U.S. Appl. No. 15/729,273, dated May 2, 2018.
Notice of Allowance, U.S. Appl. No. 14/344,876, dated May 18, 2018.
Notice of Allowance, U.S. Appl. No. 15/912,216, dated Jun. 20, 2018.
Notice of Allowance, U.S. Appl. 15/912,260, dated May 10, 2018.
Response to Non-Final Office Action, U.S. Appl. No. 14/660,784, dated Jun. 4, 2018.
Response to Restriction, U.S. Appl. No. 15/216,472, dated Jun. 4, 2018.

* cited by examiner

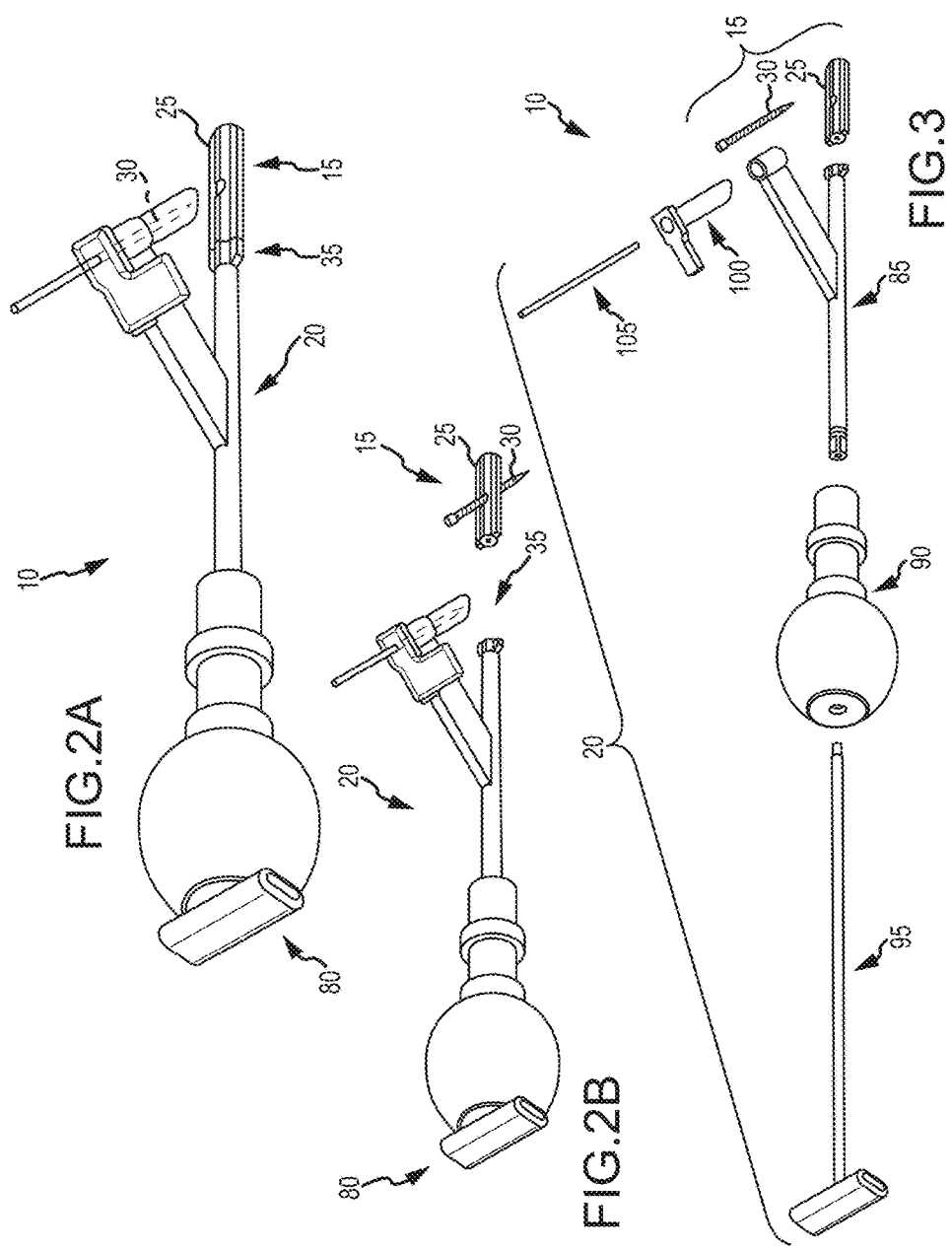

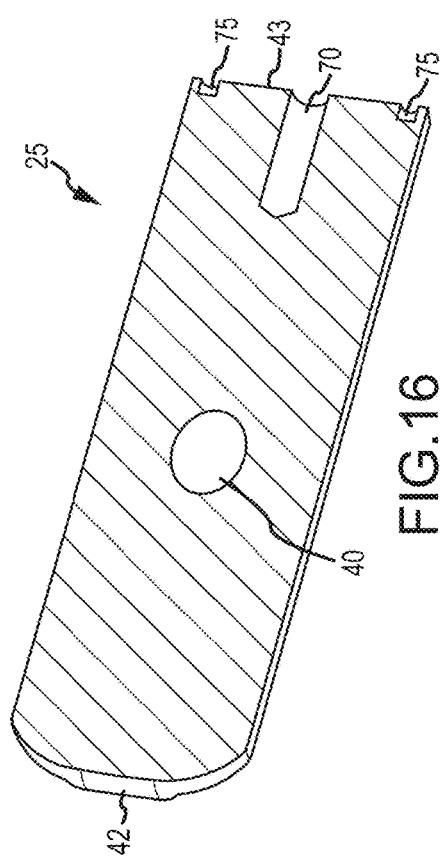
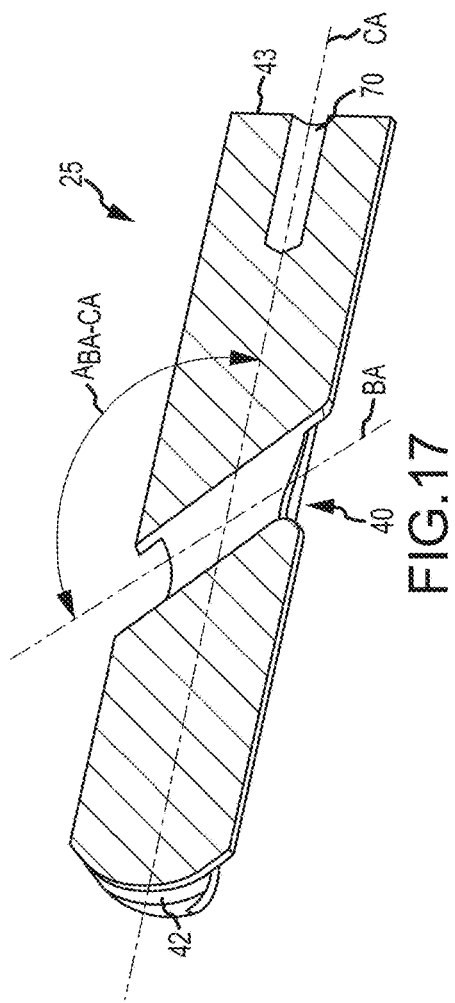

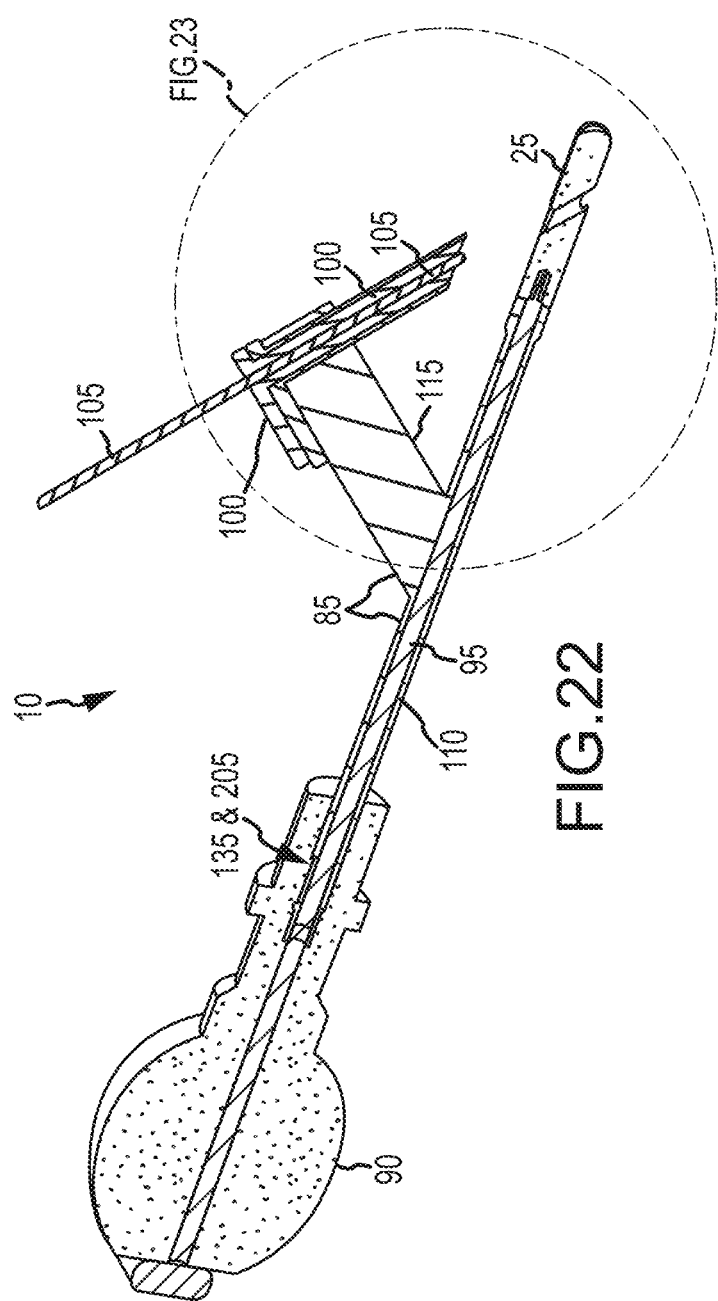

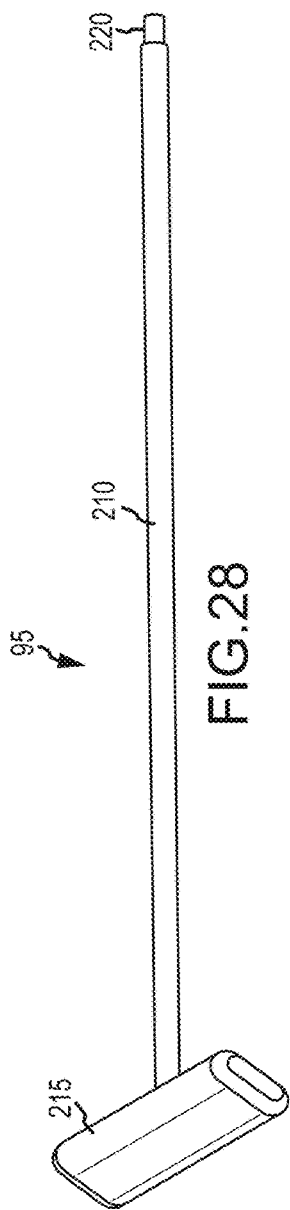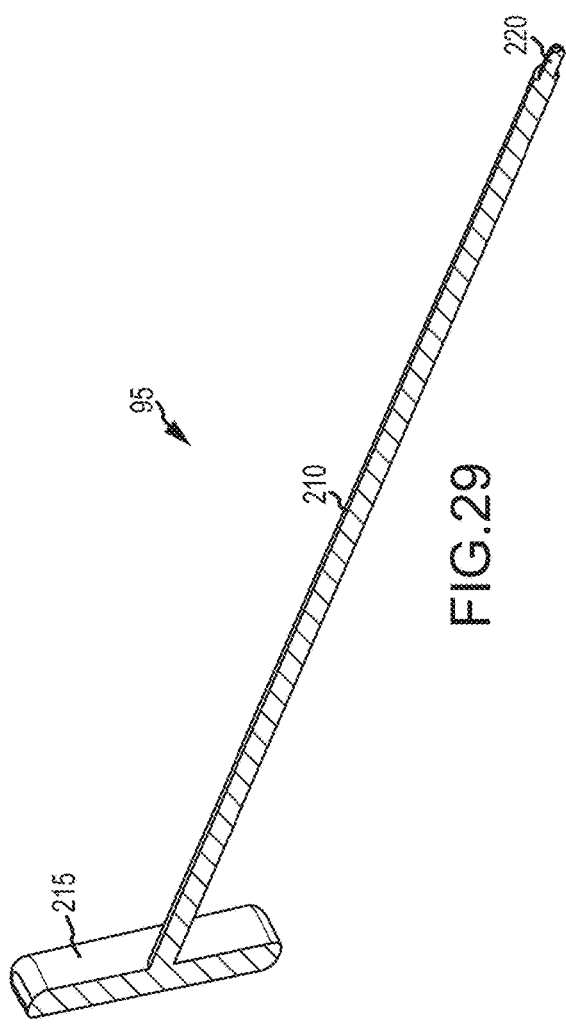
FIG. 28
FIG. 29

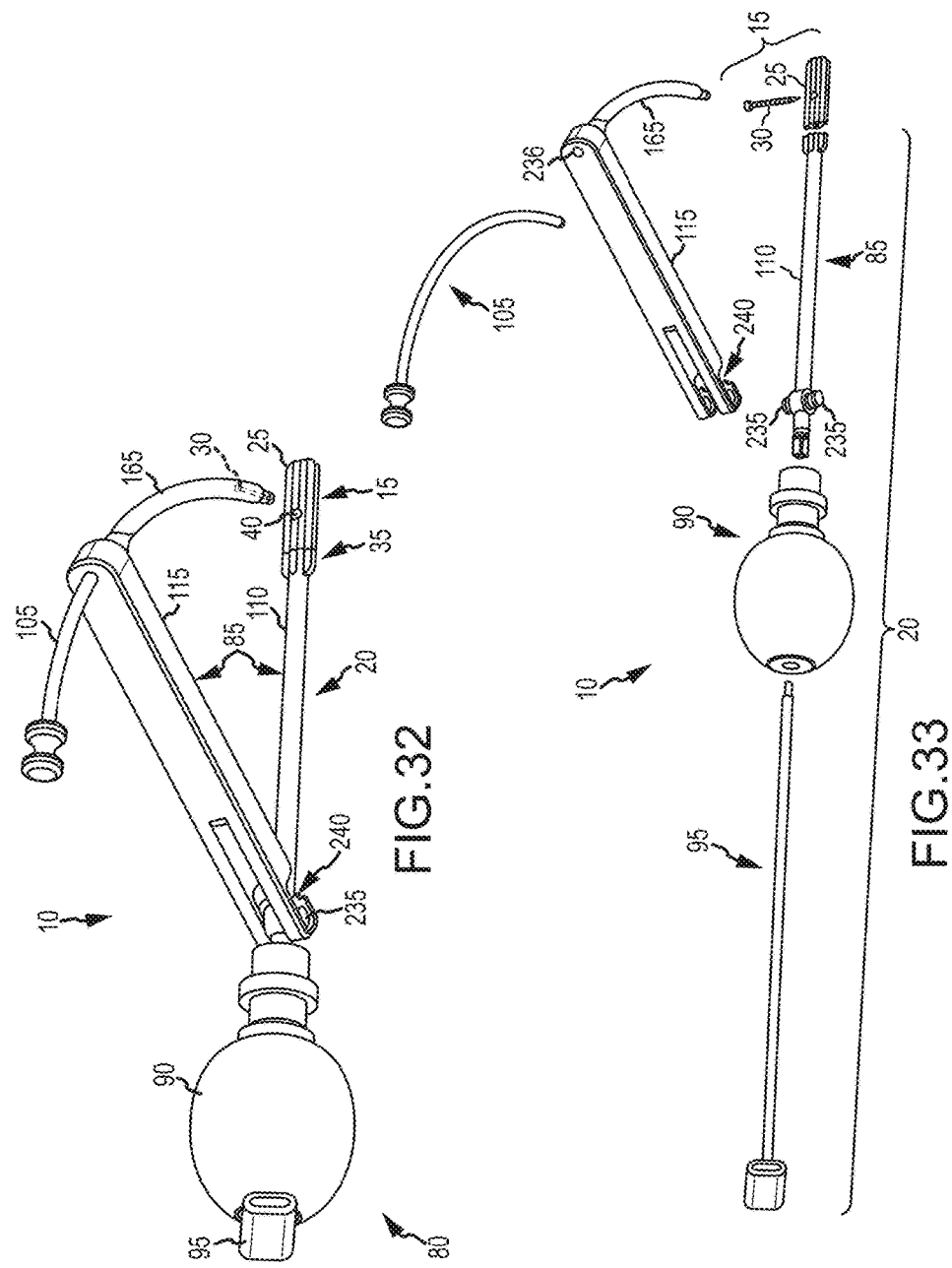

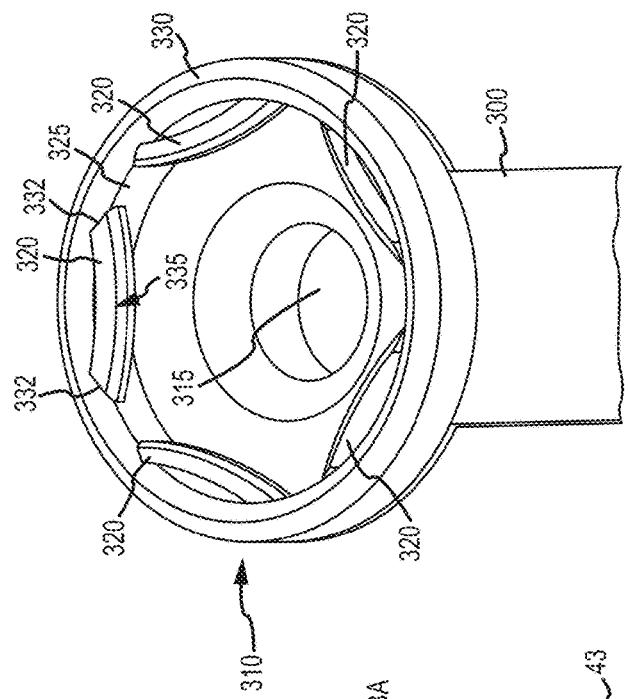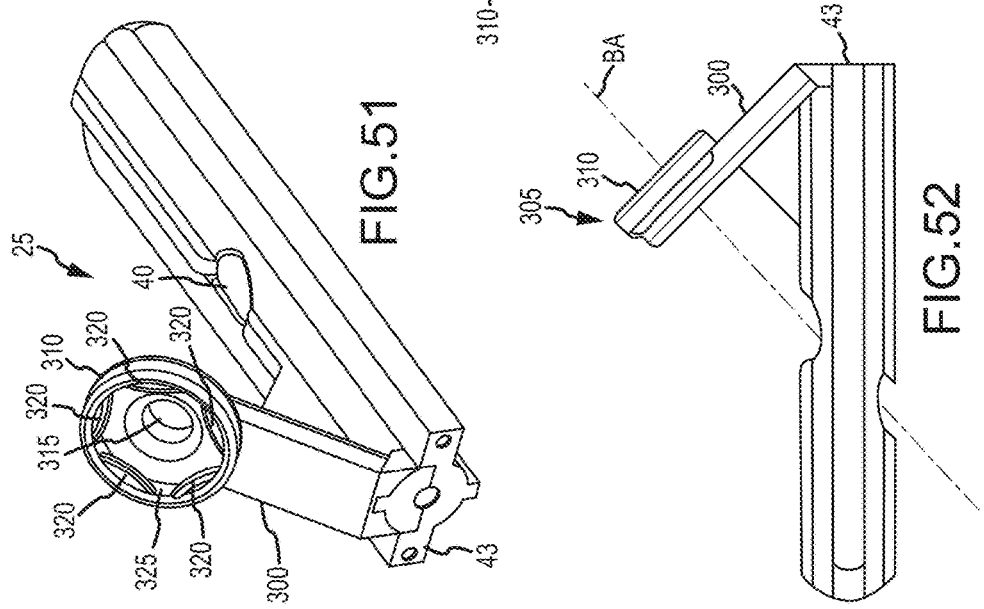

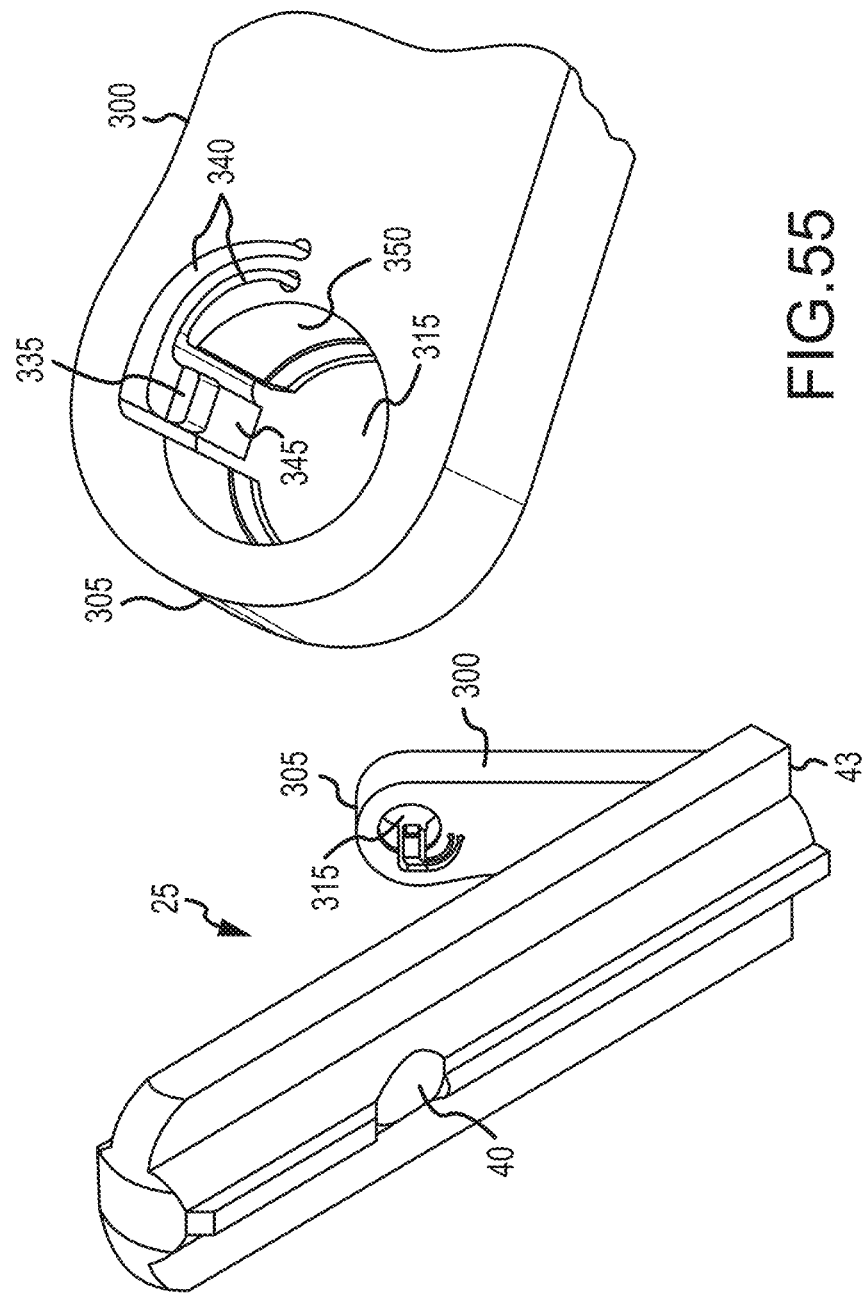

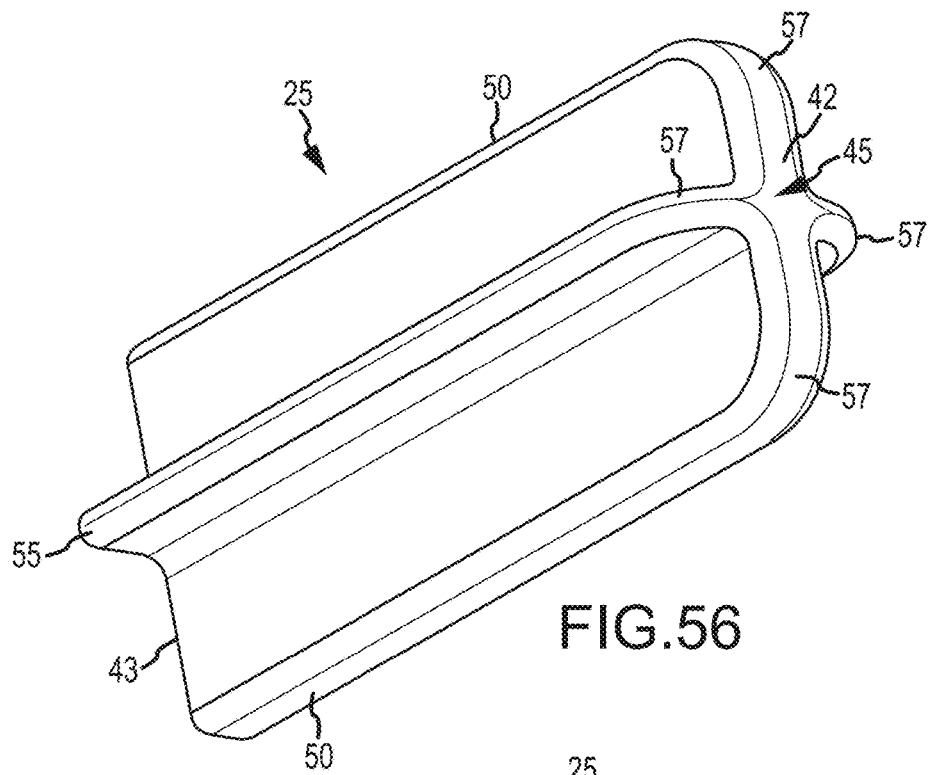
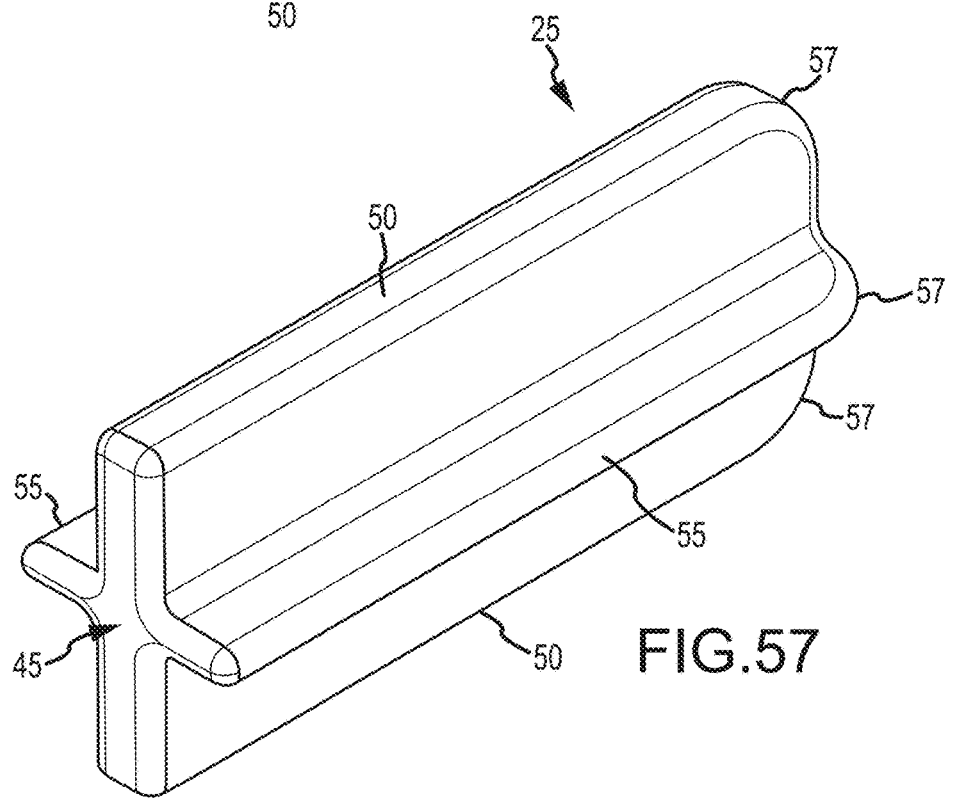

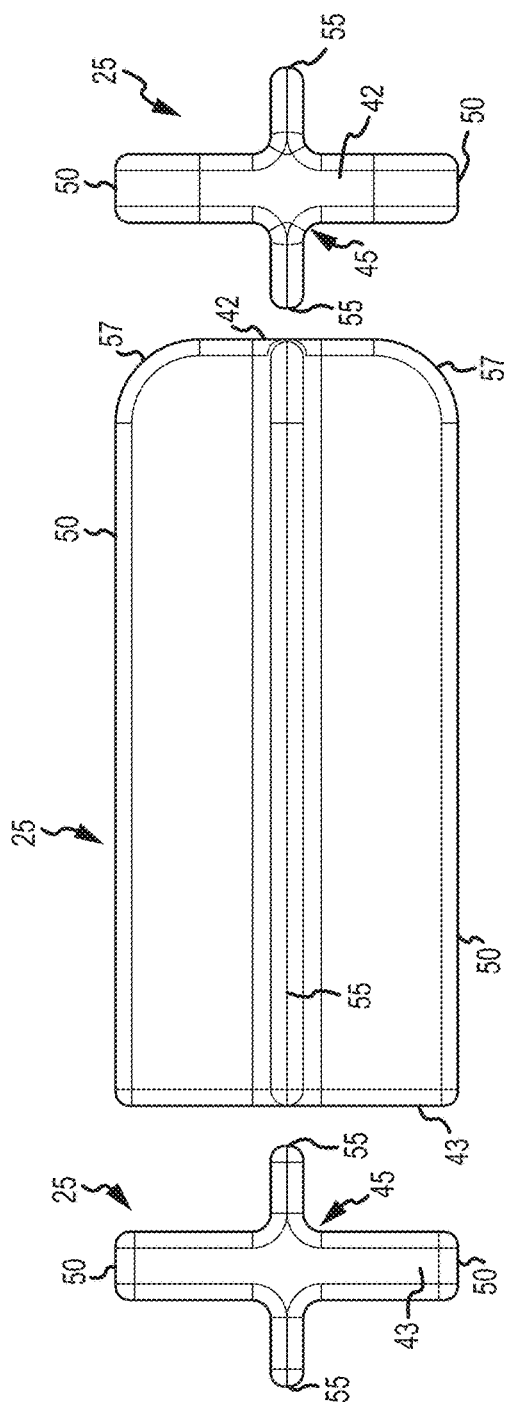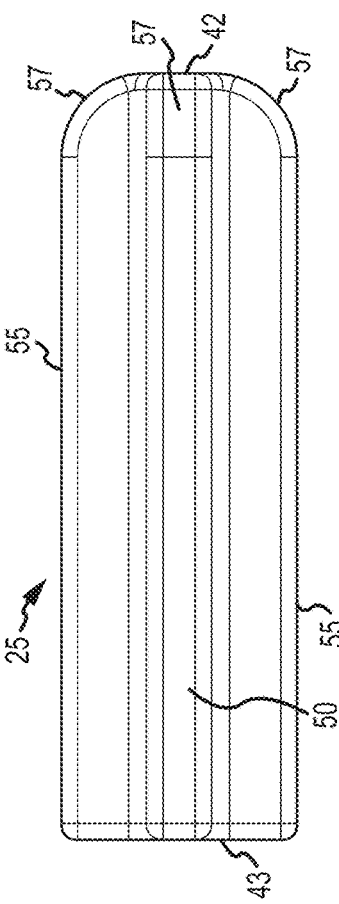

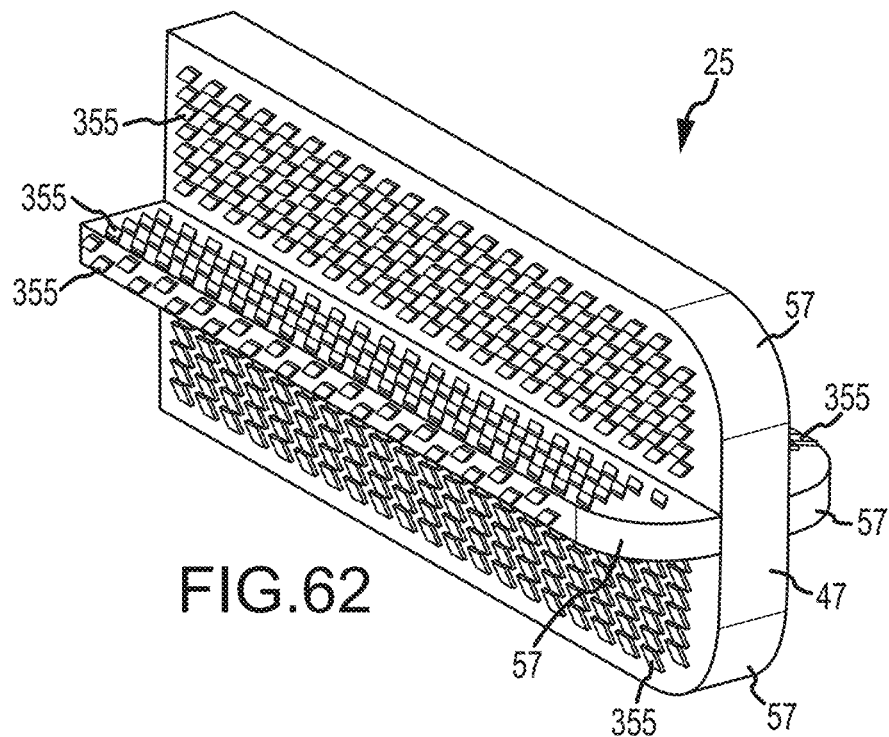
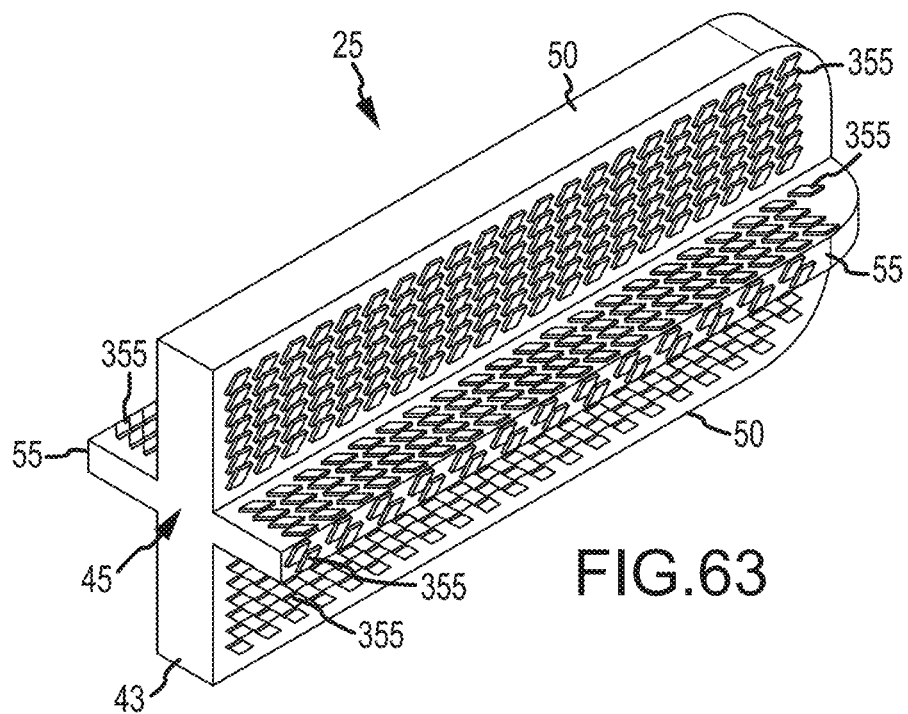

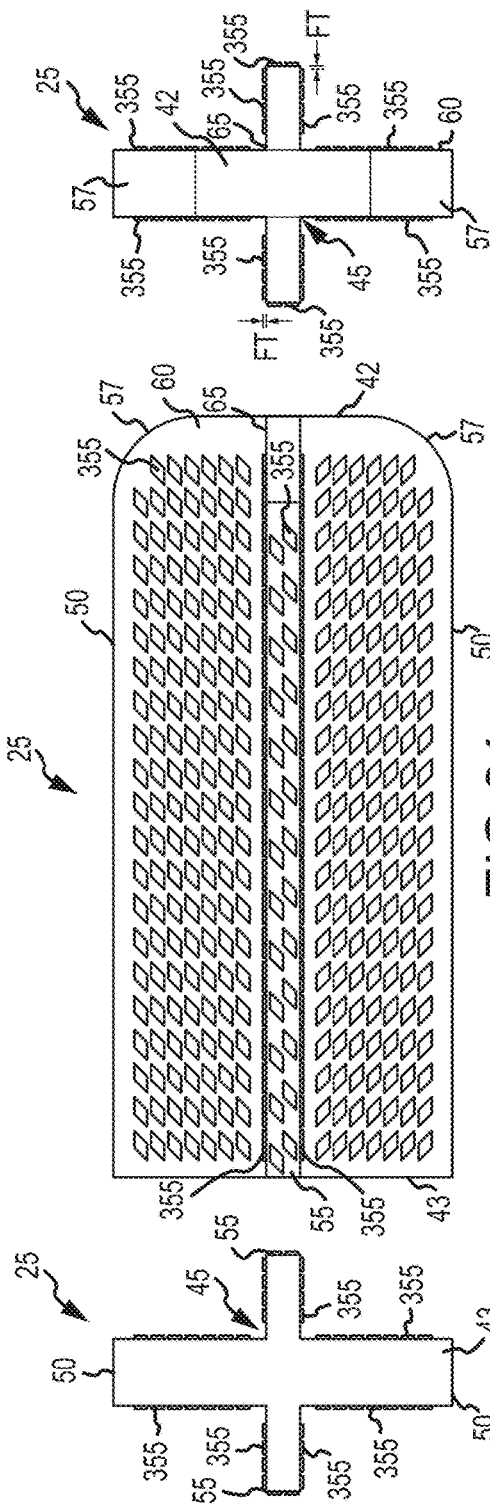
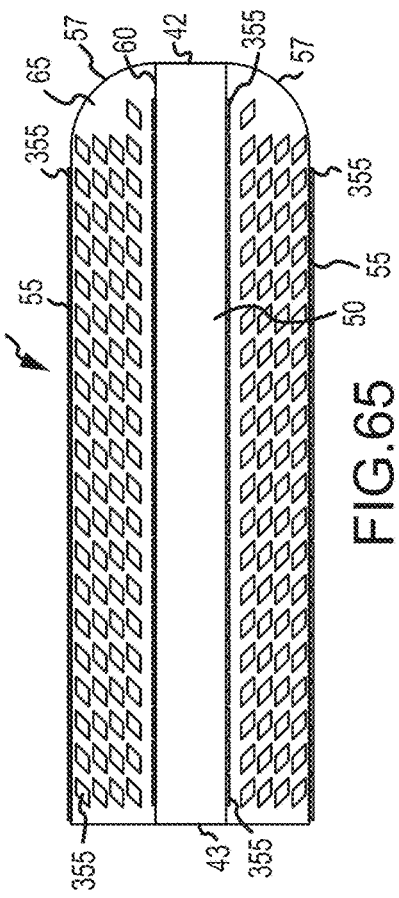
FIG.64
FIG.65
FIG.66
FIG.67

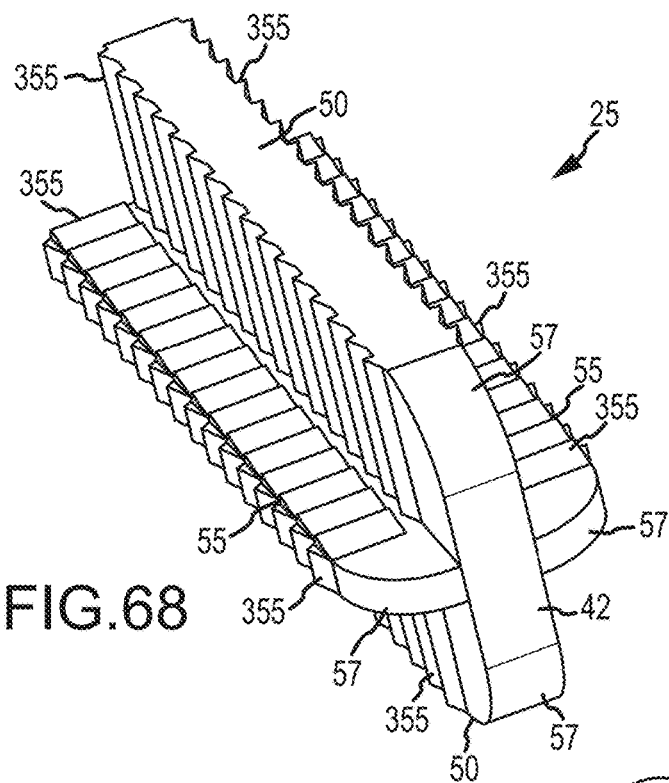
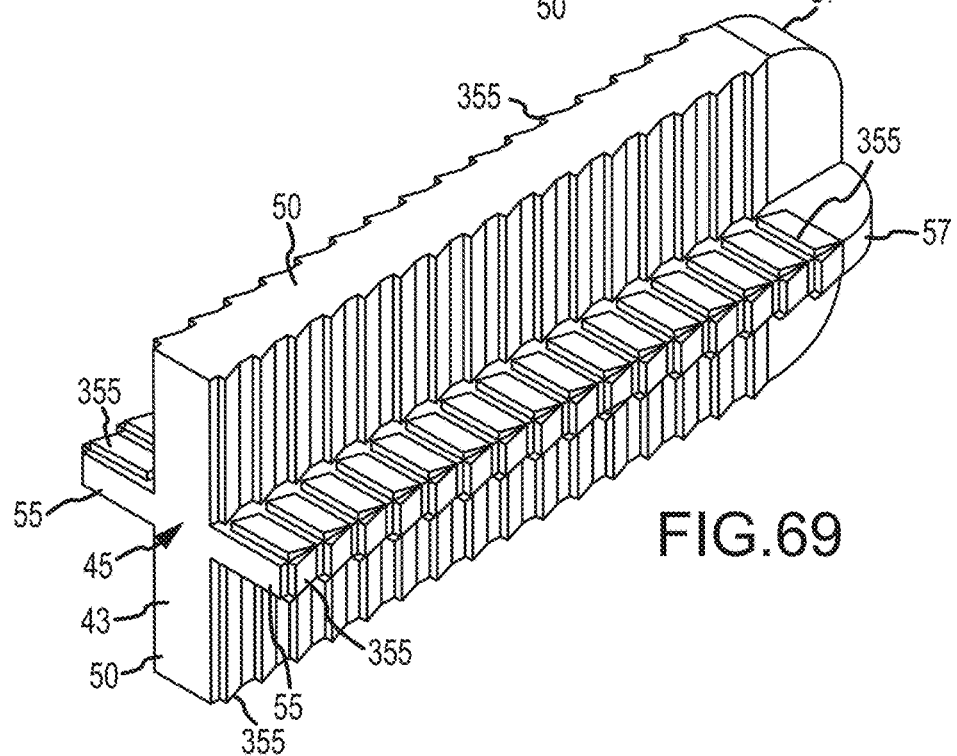

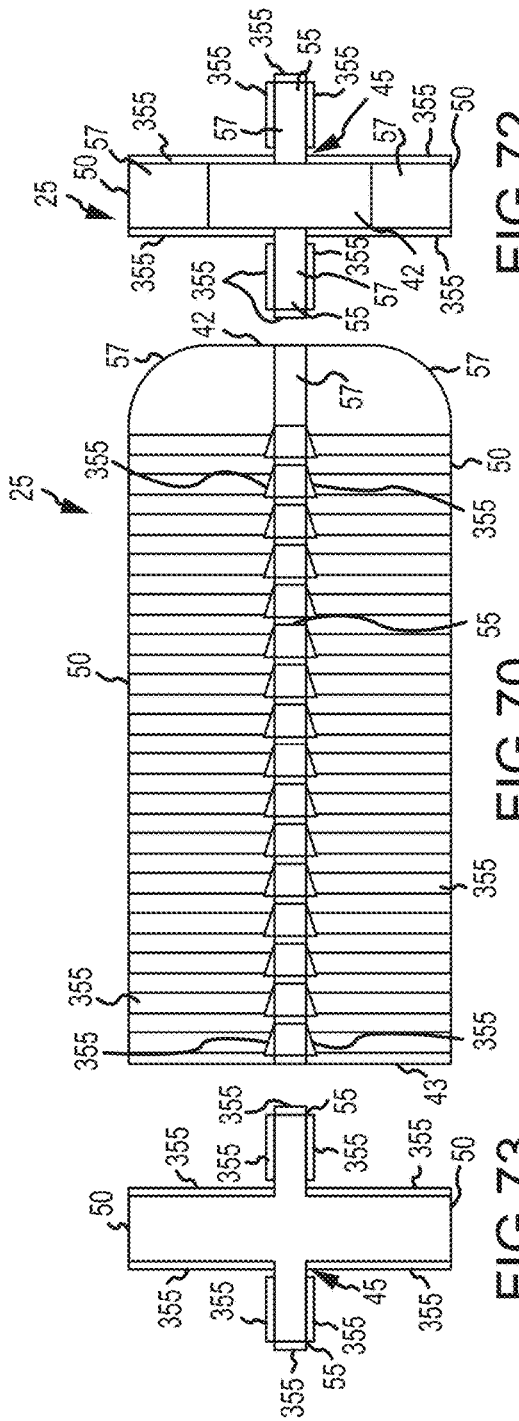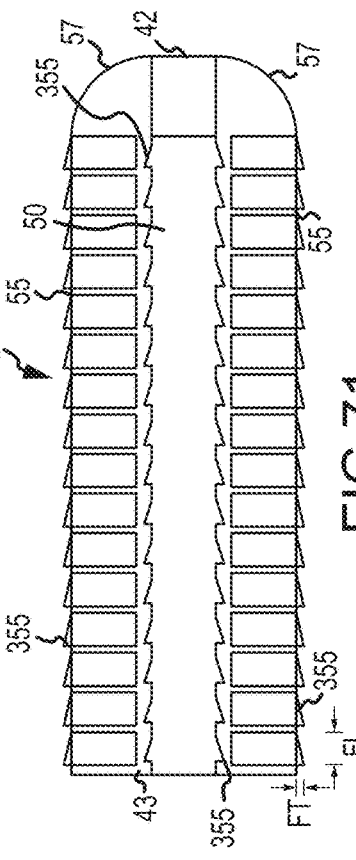

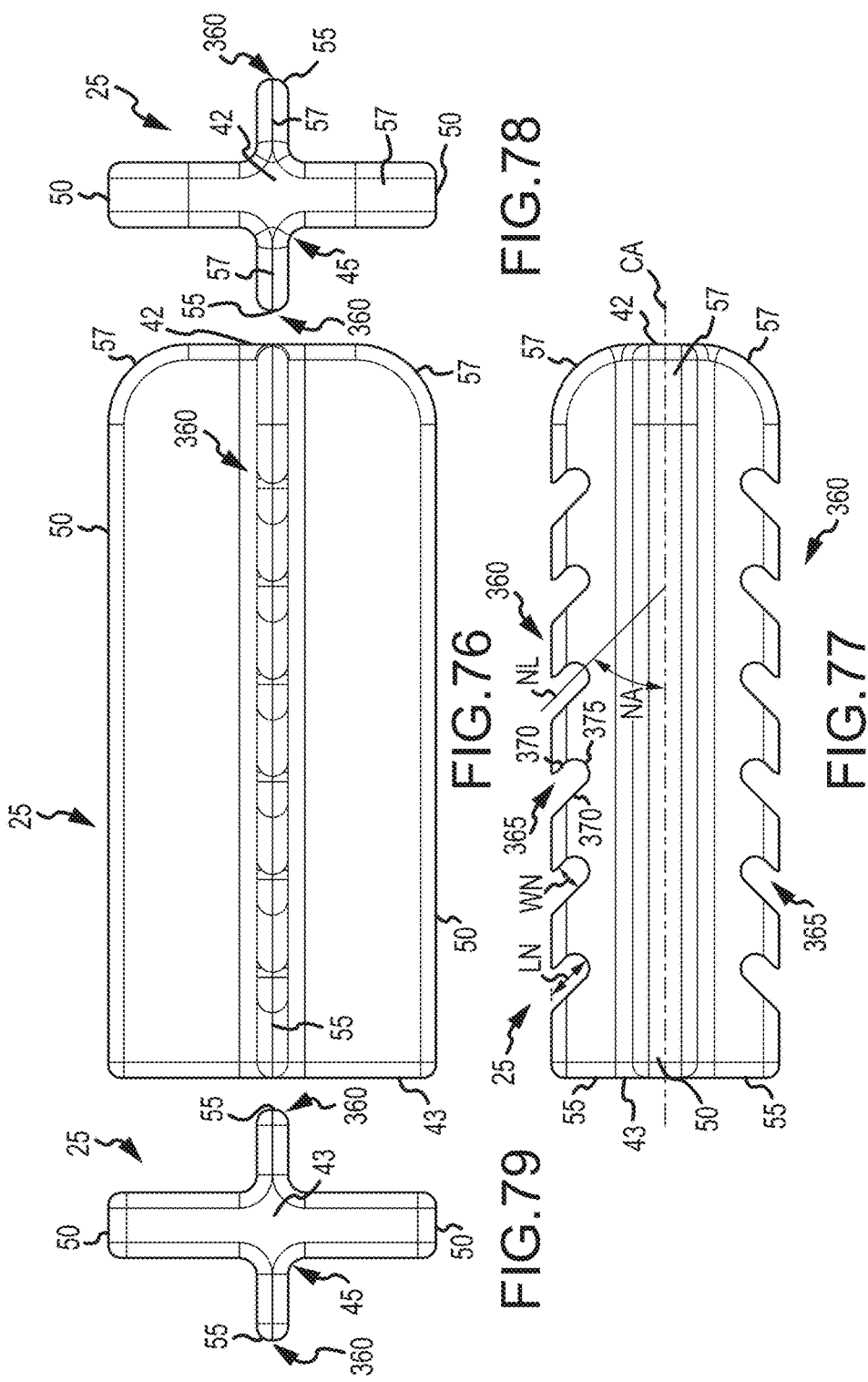

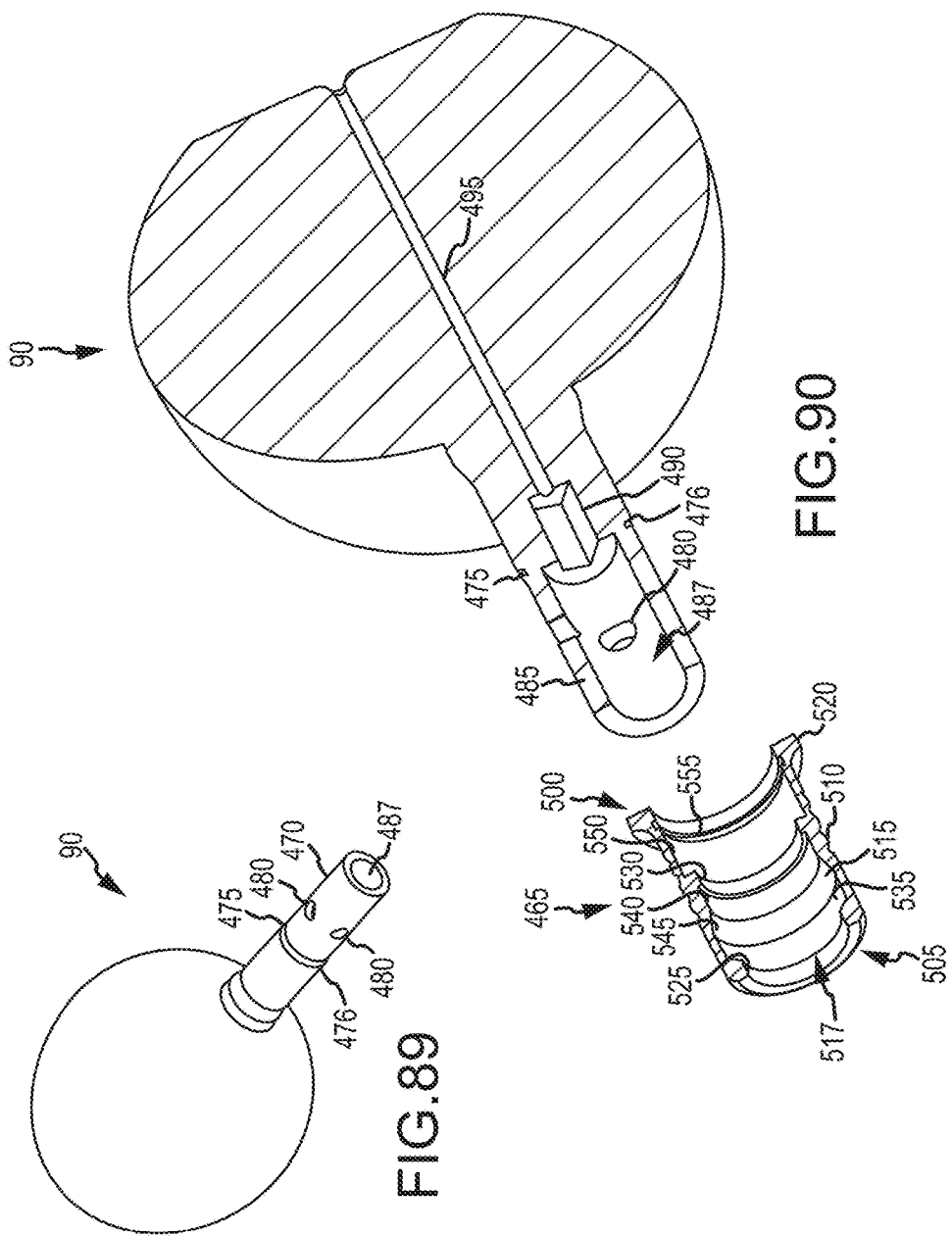

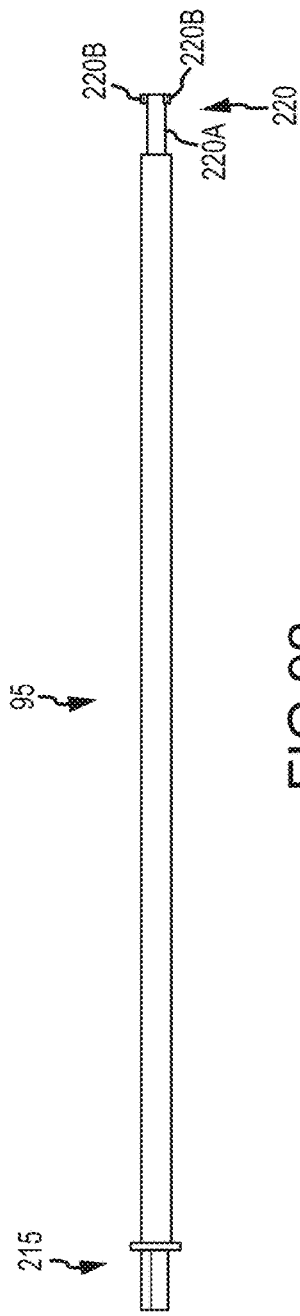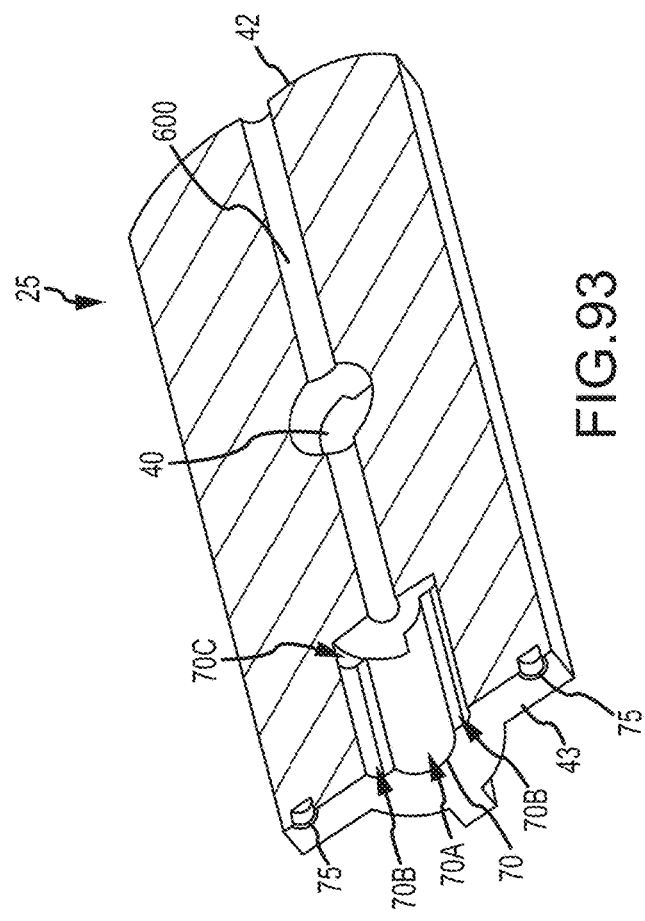

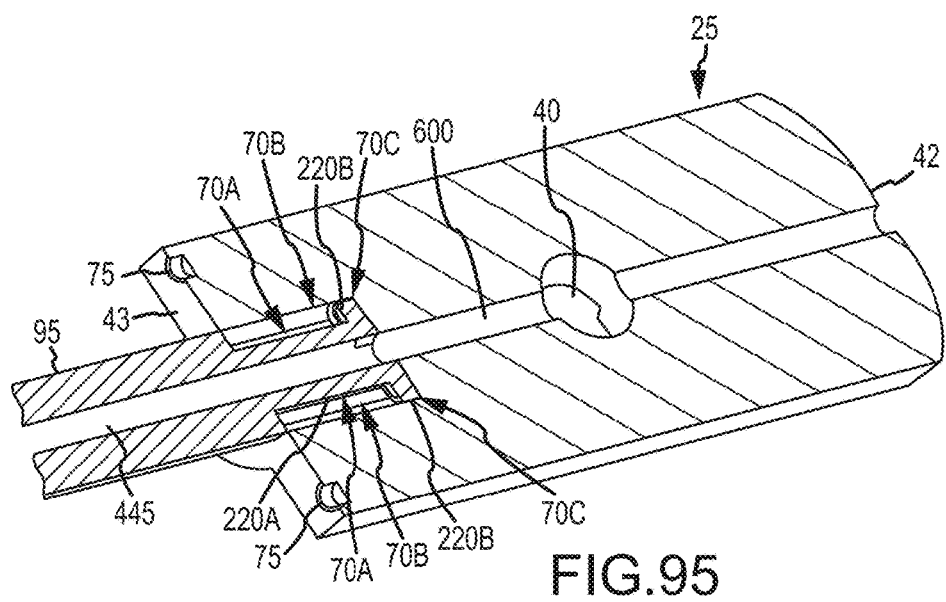

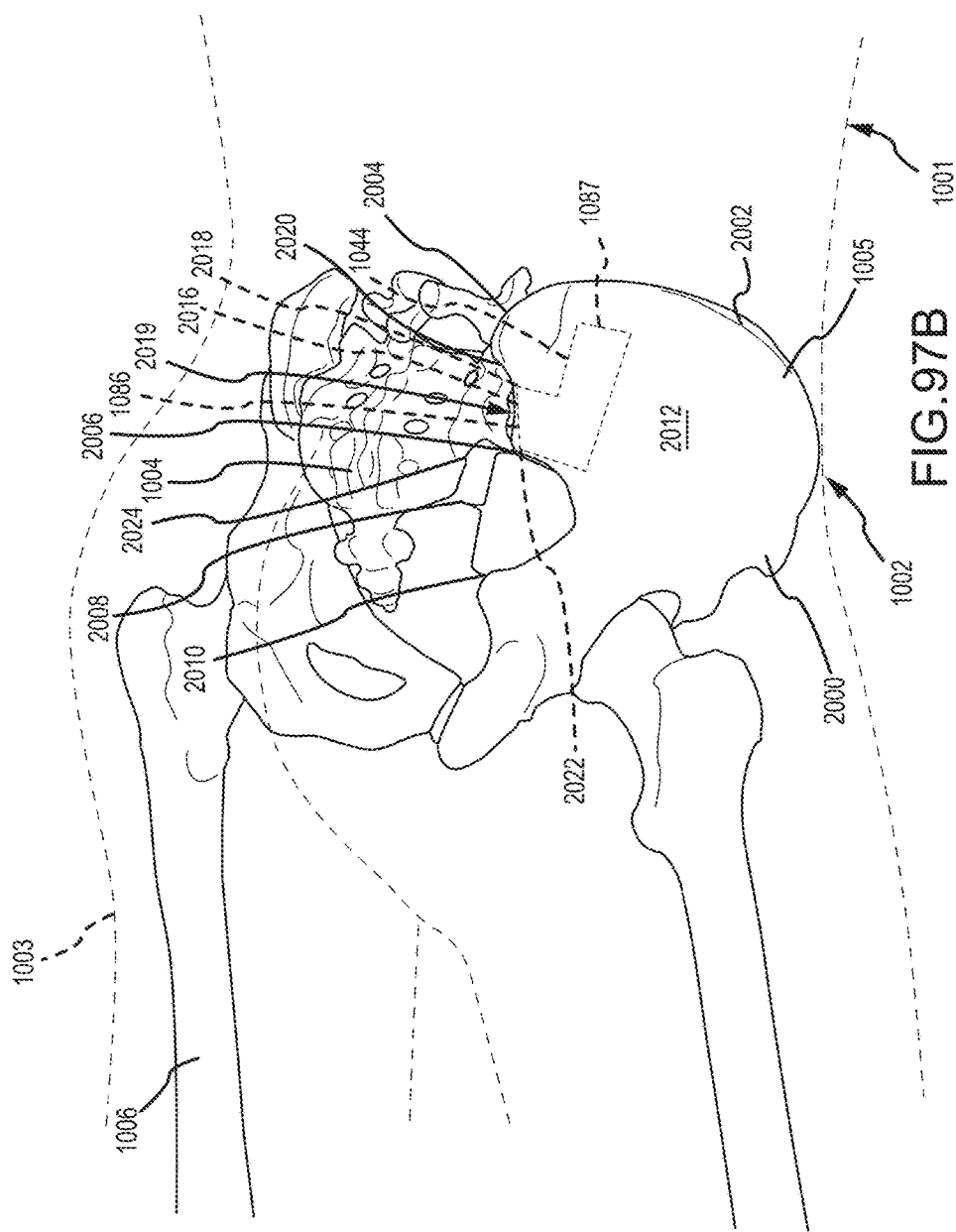

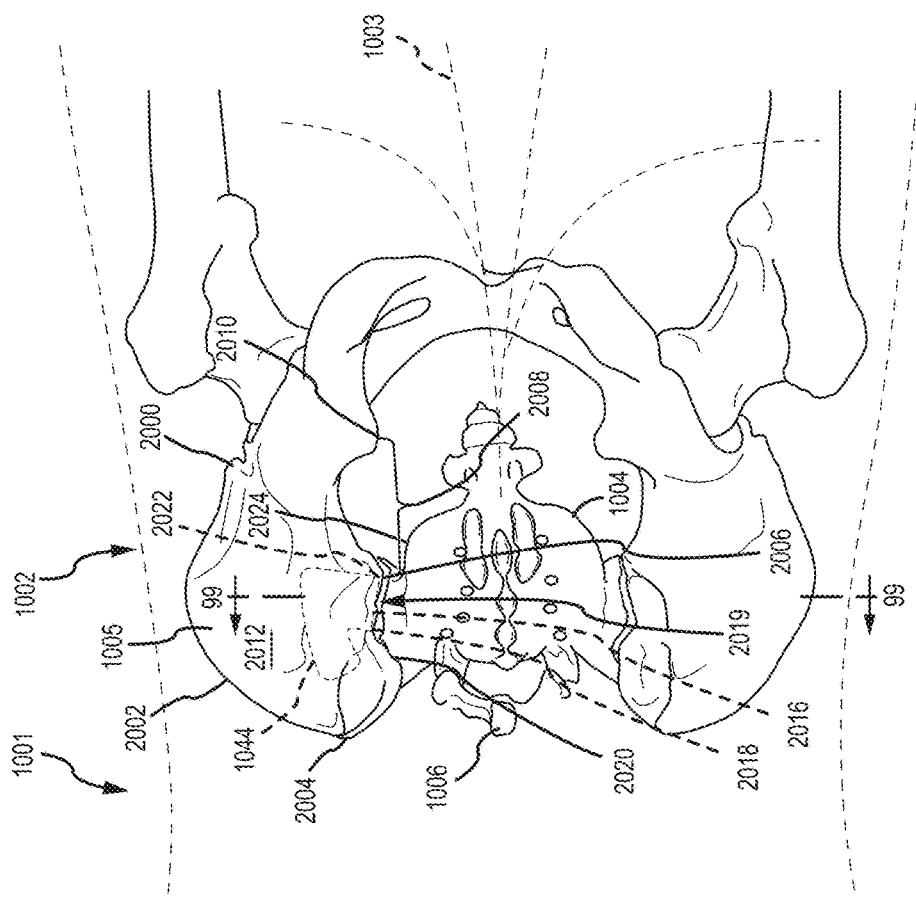

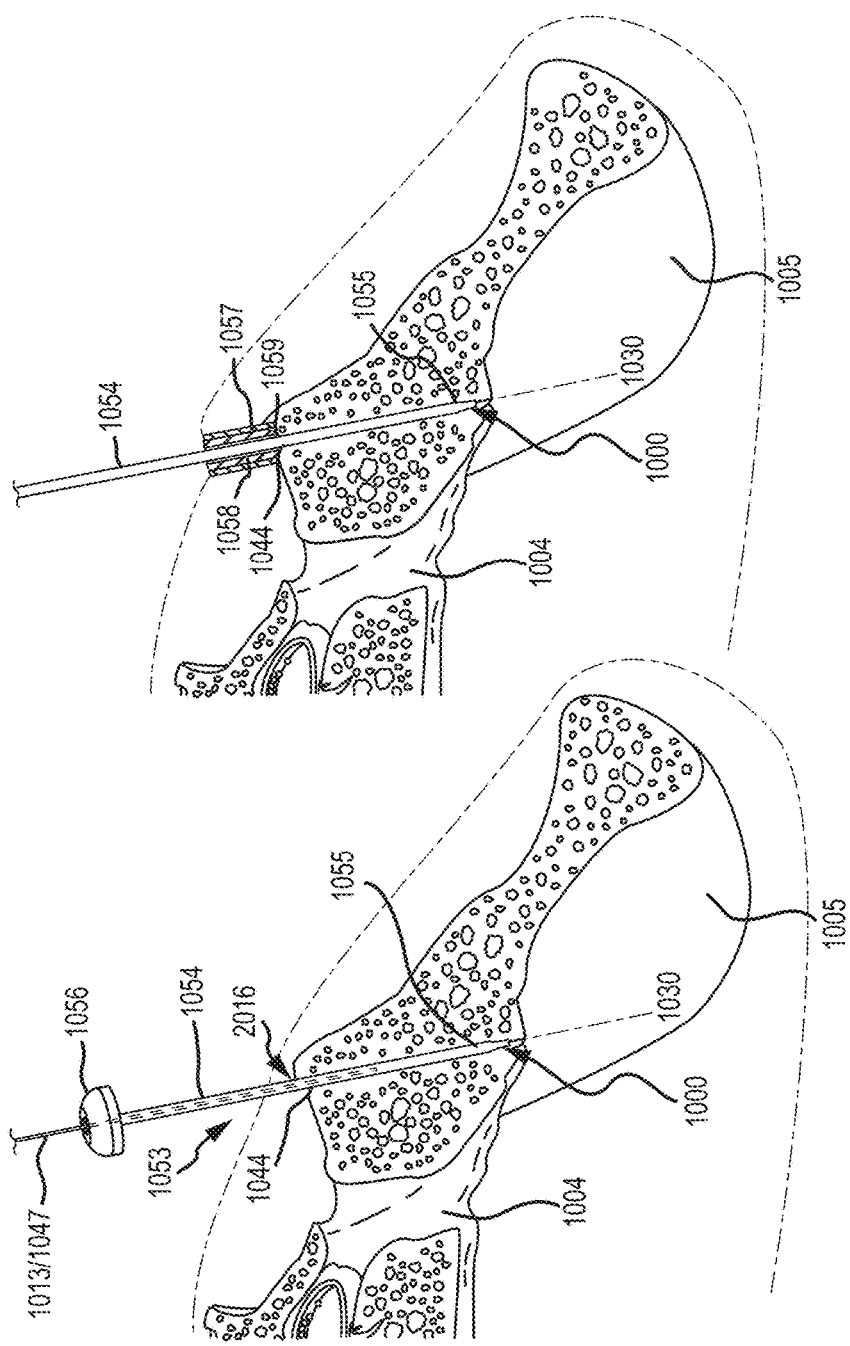

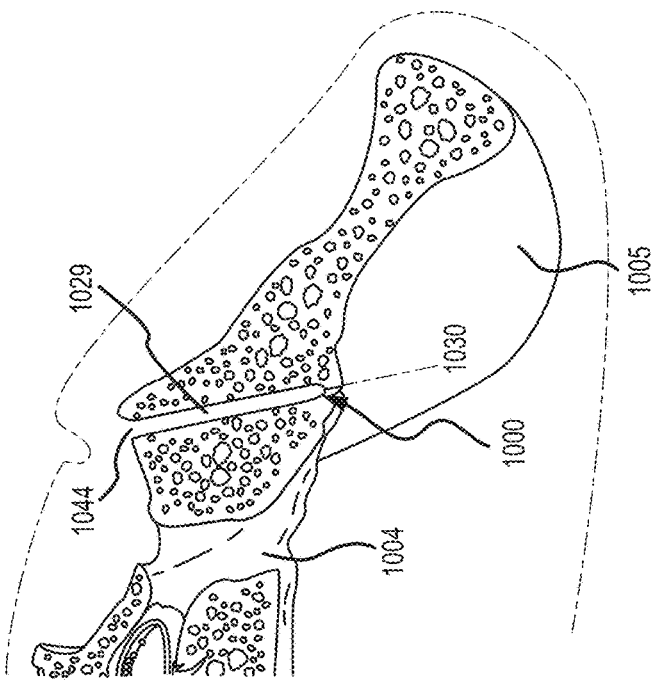
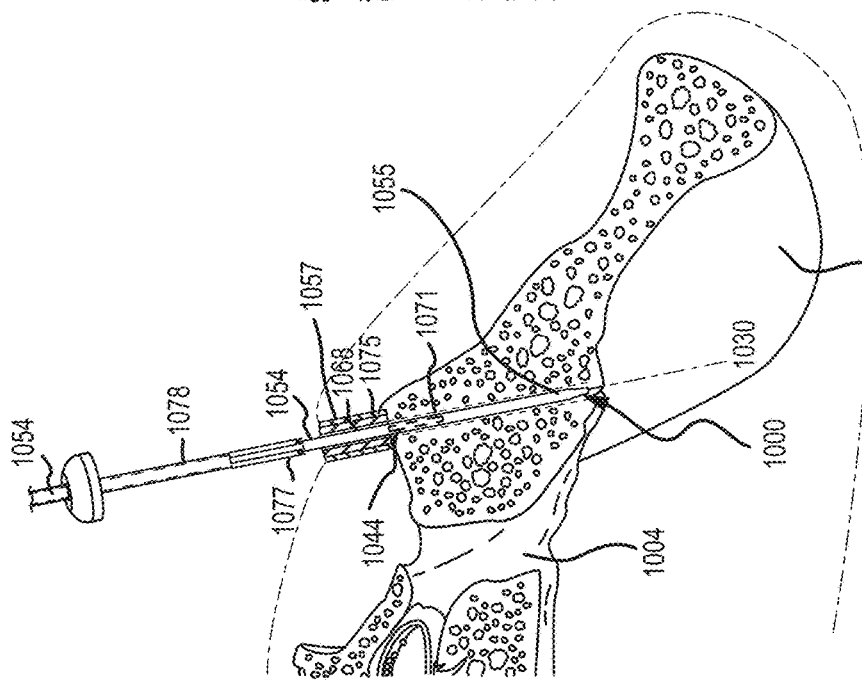

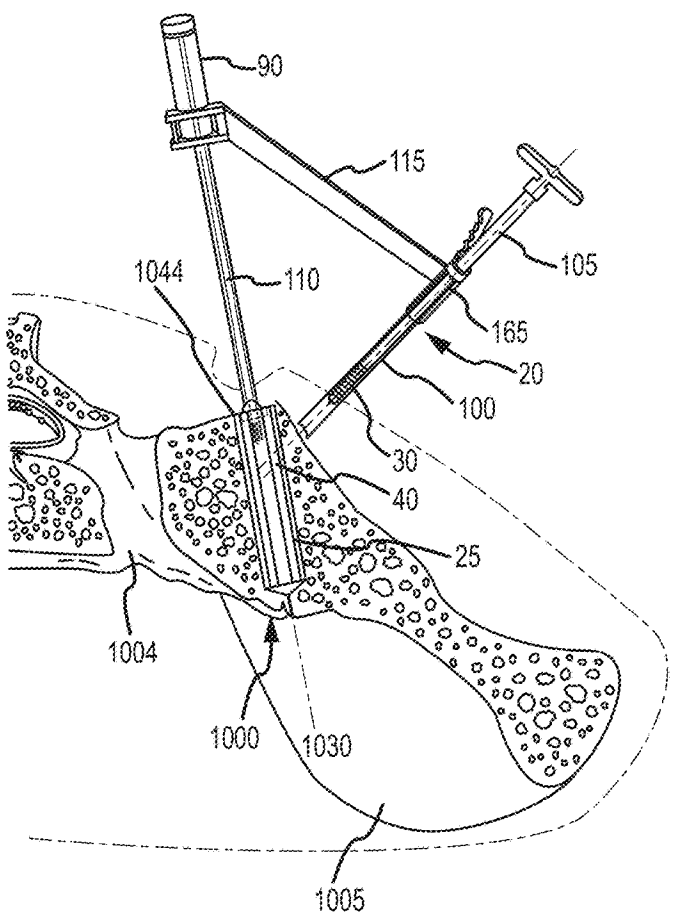
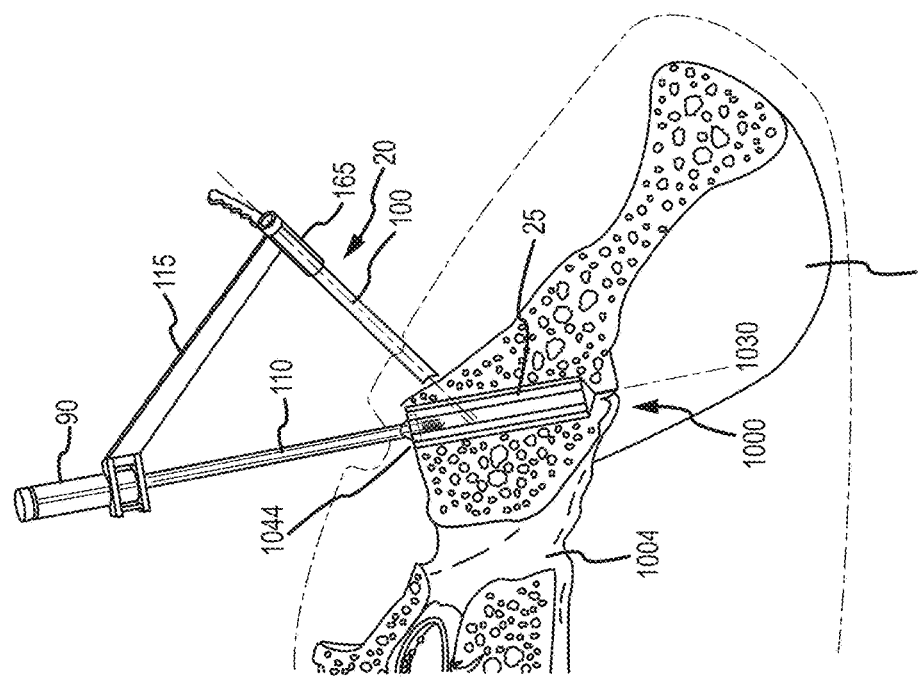

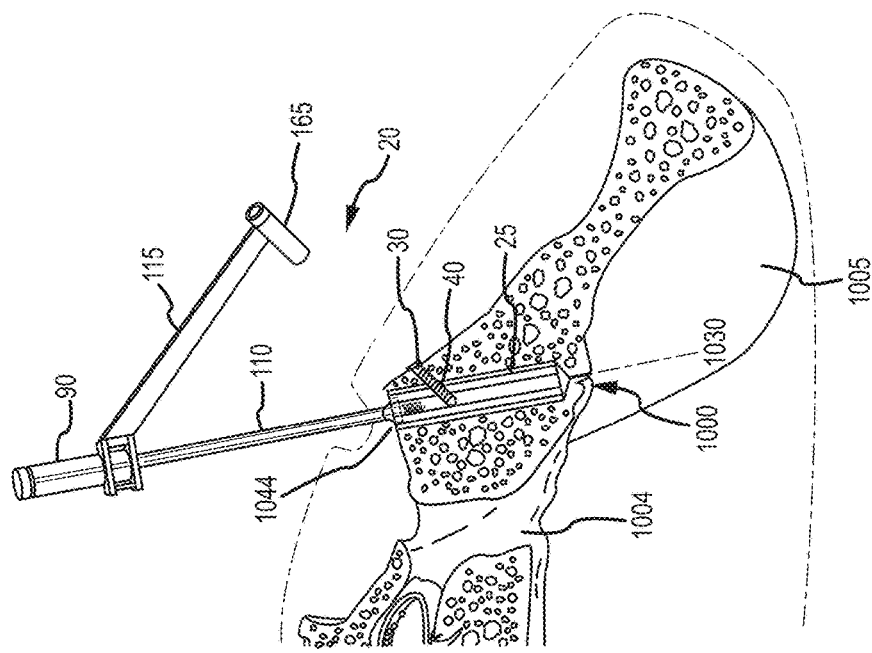
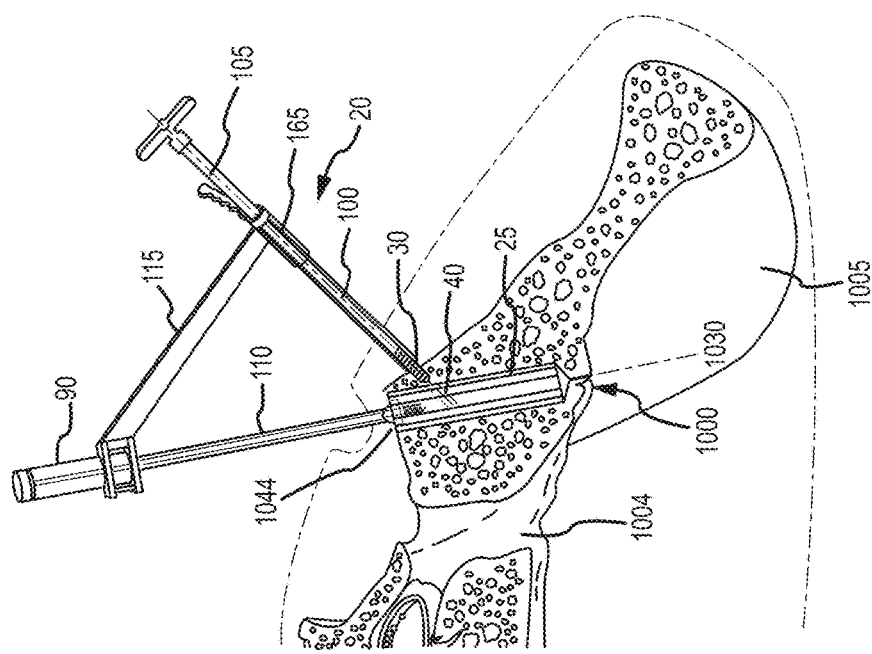

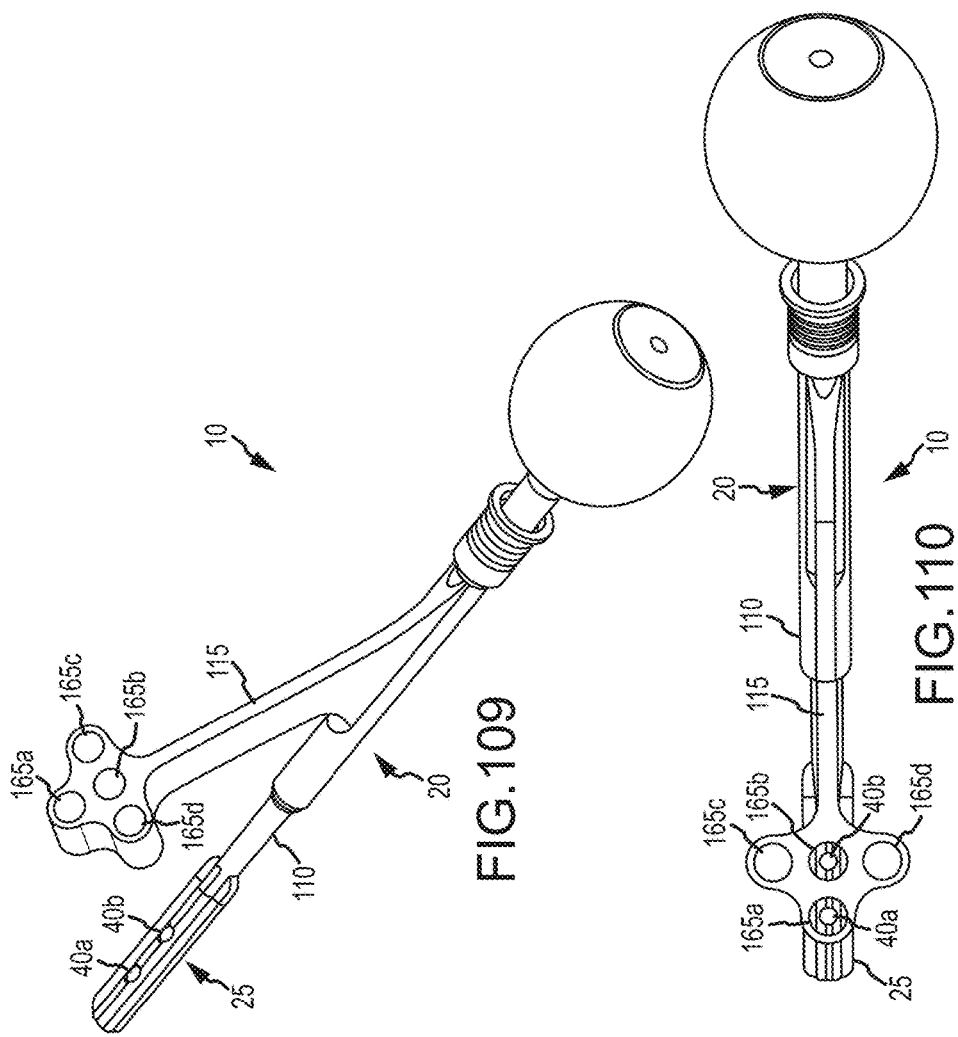

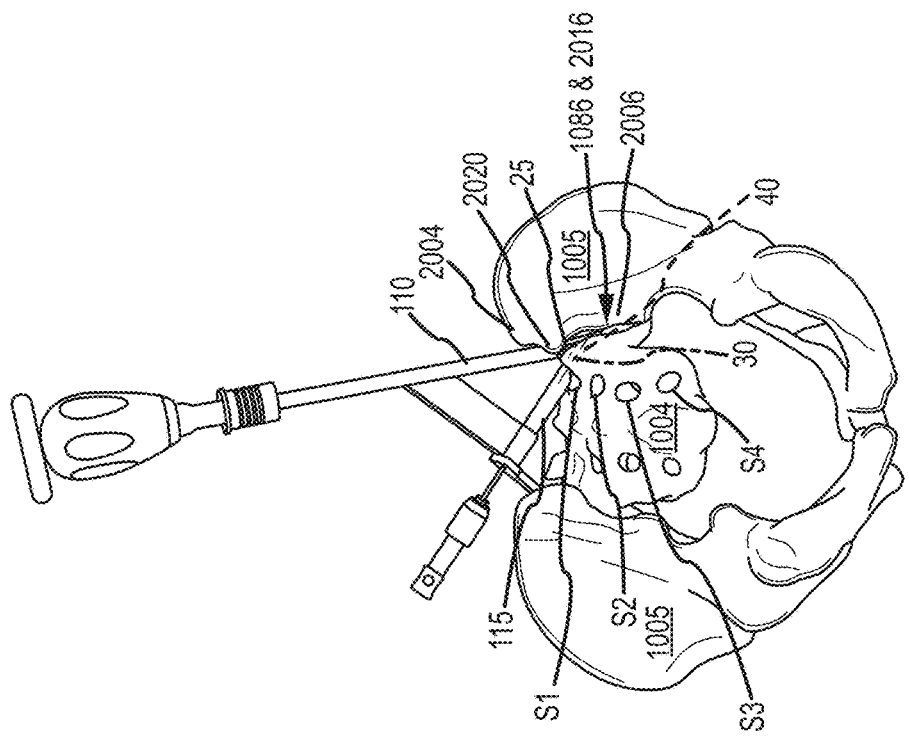
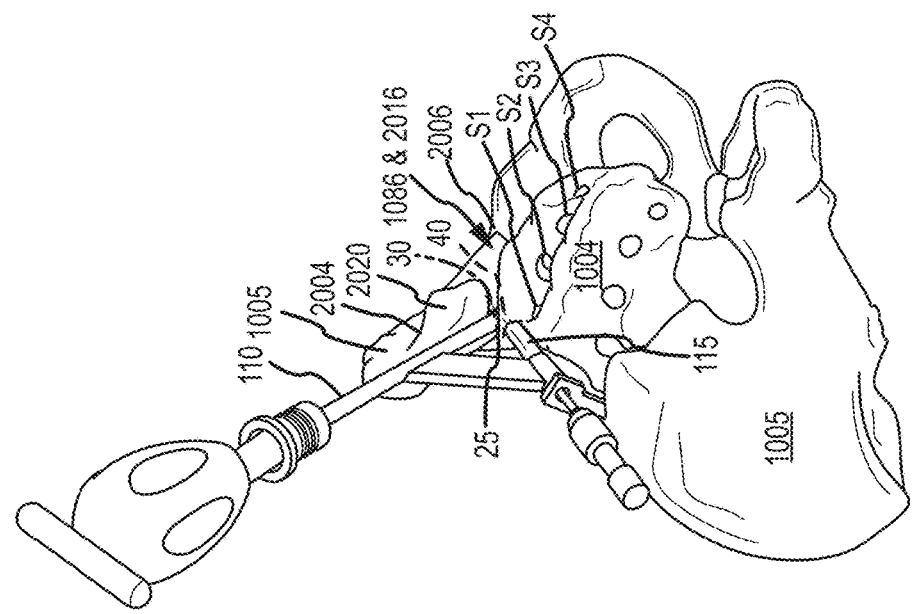
FIG. 117A
FIG. 117B

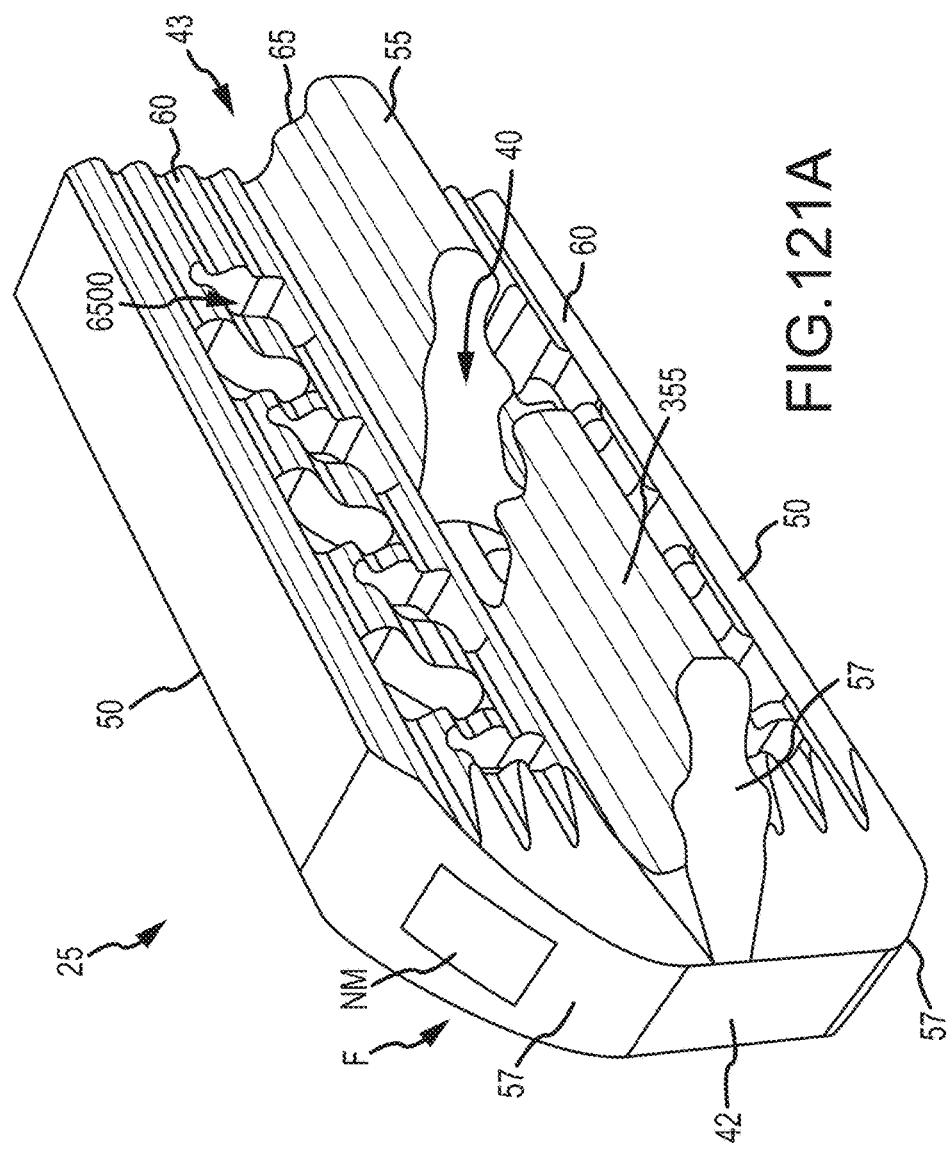

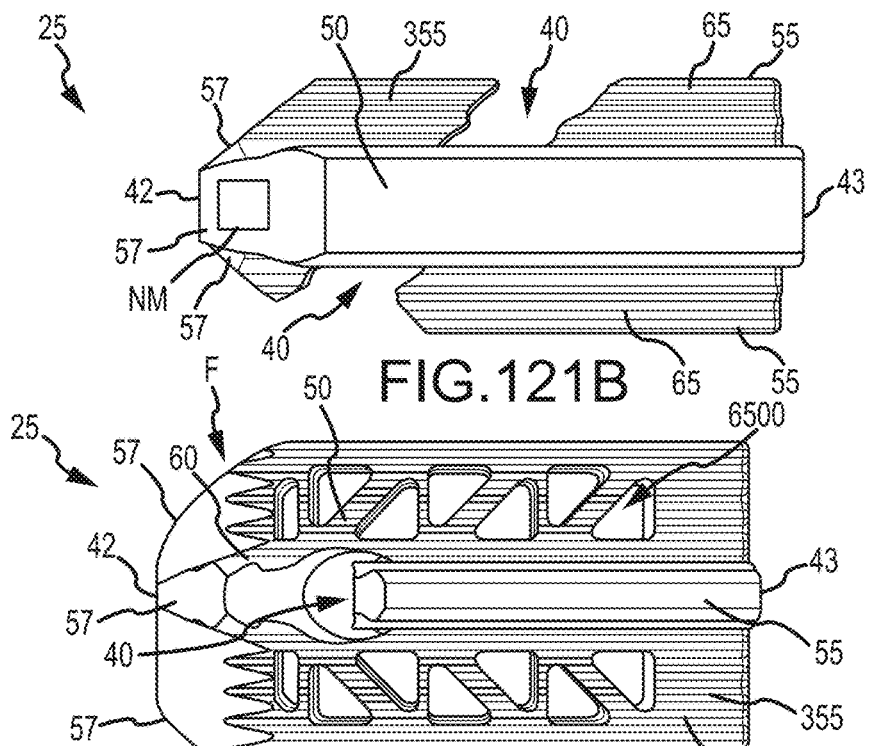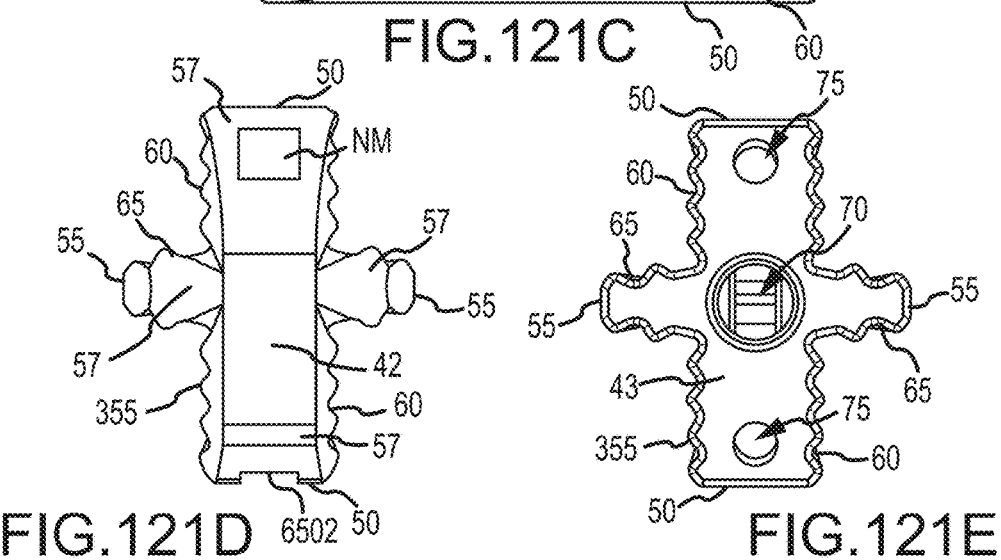

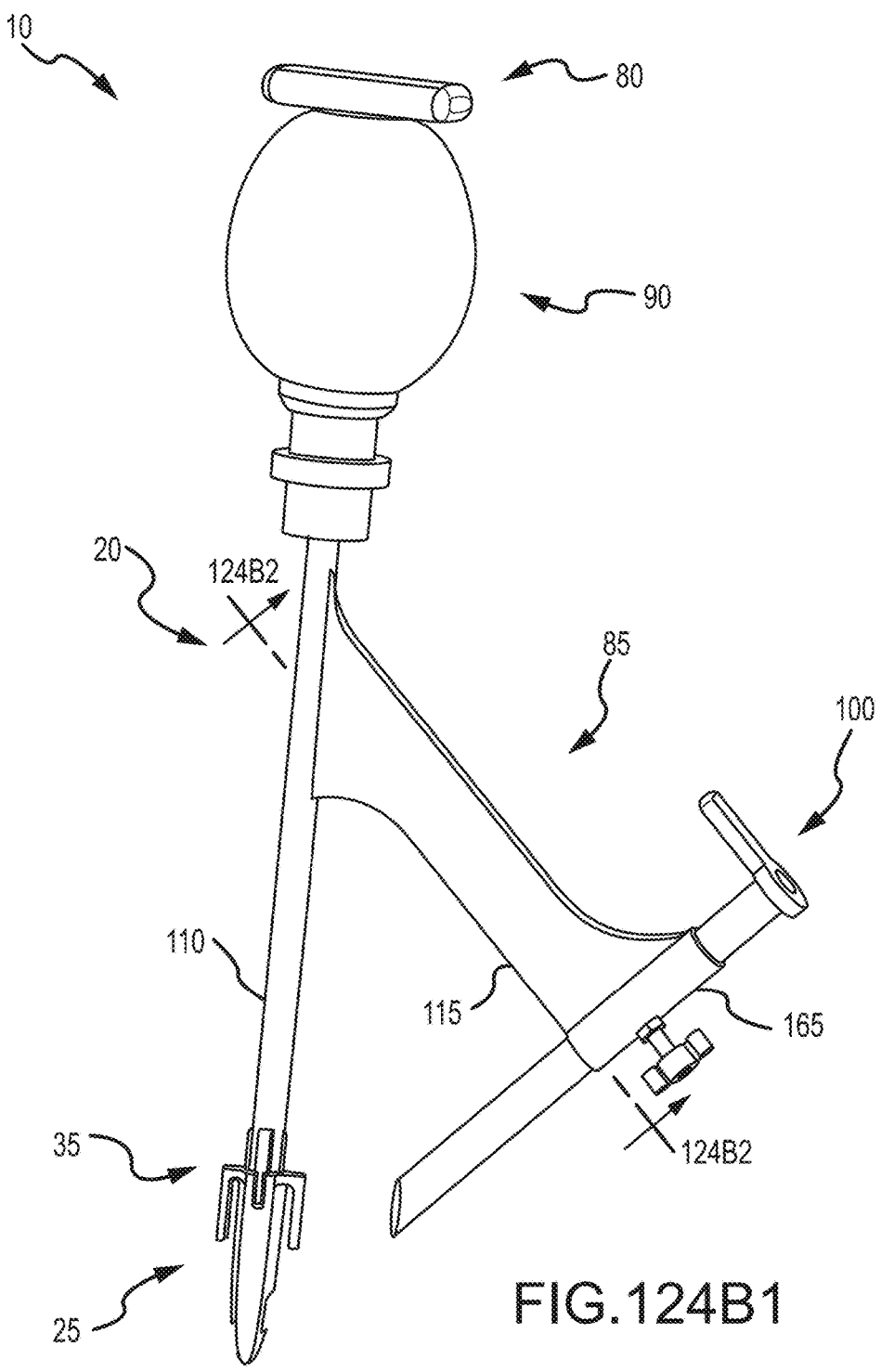
FIG.124B1

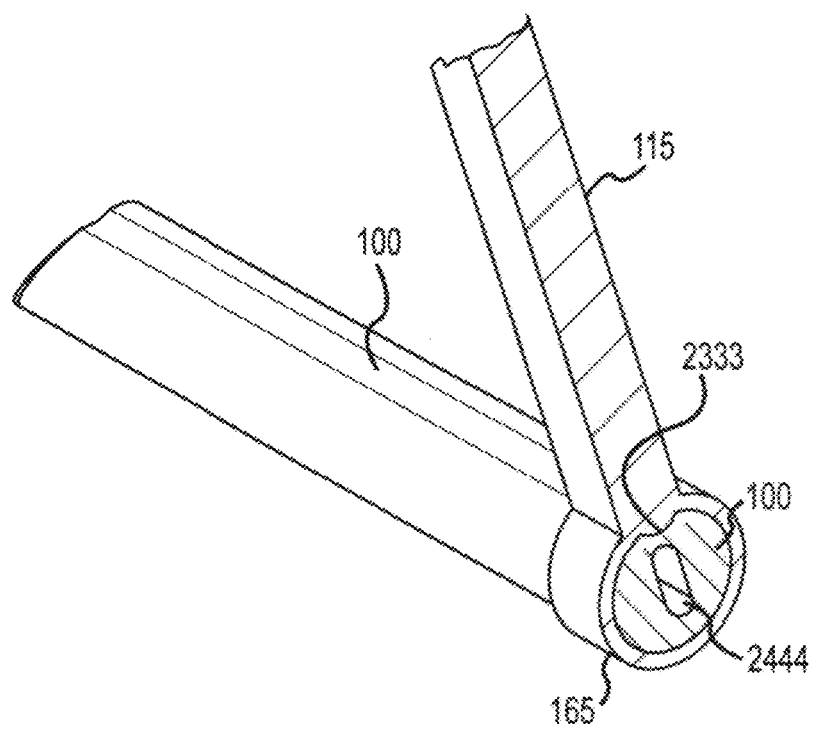
FIG.124B2


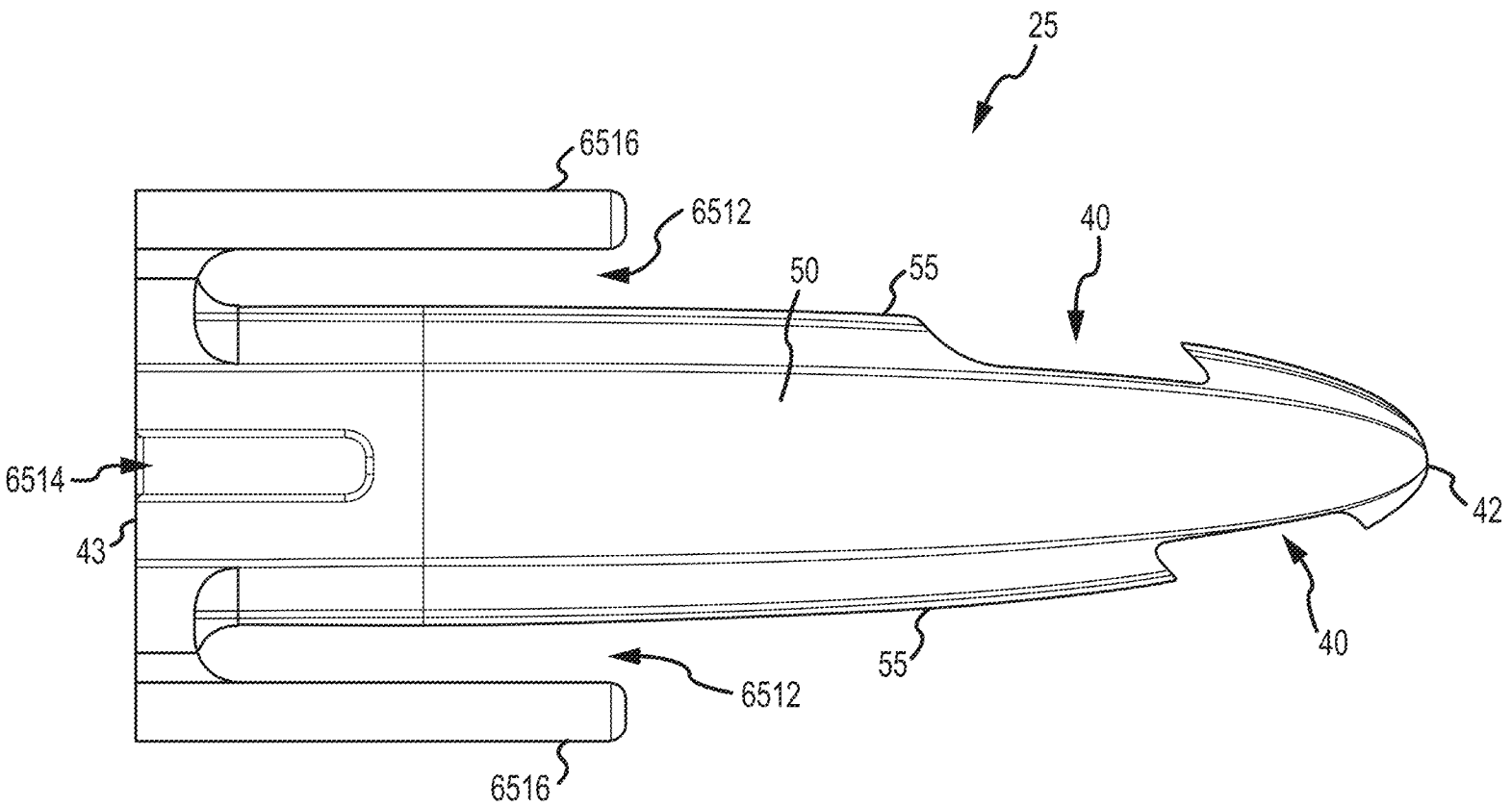

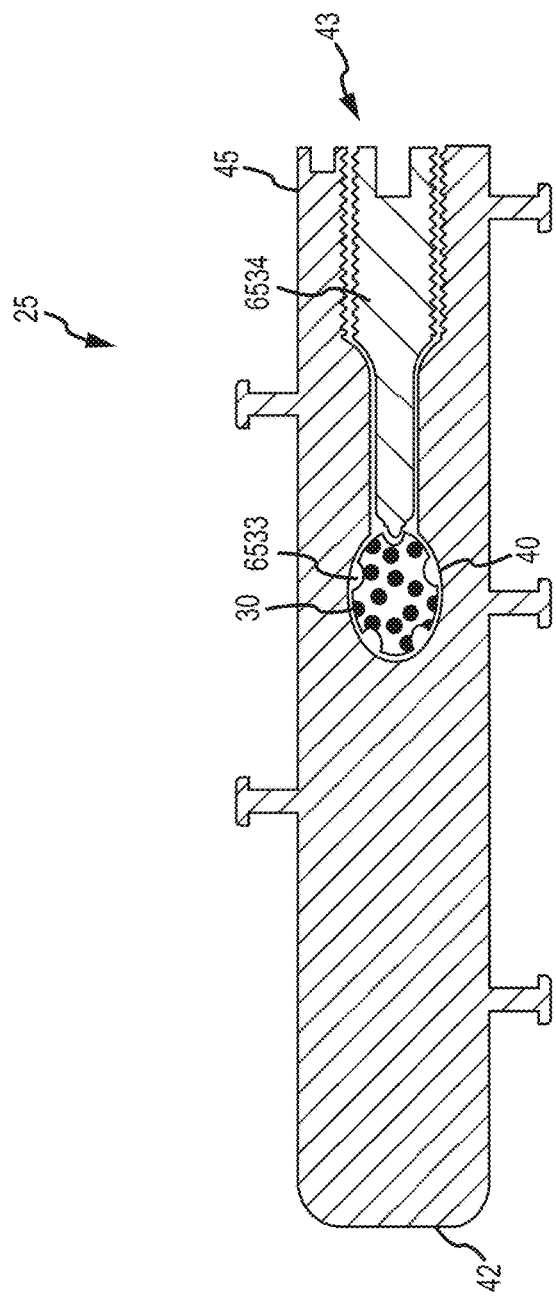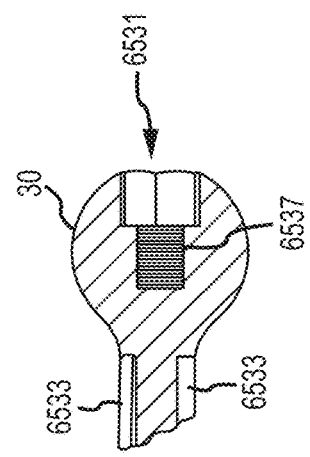
FIG.126B
FIG.126C

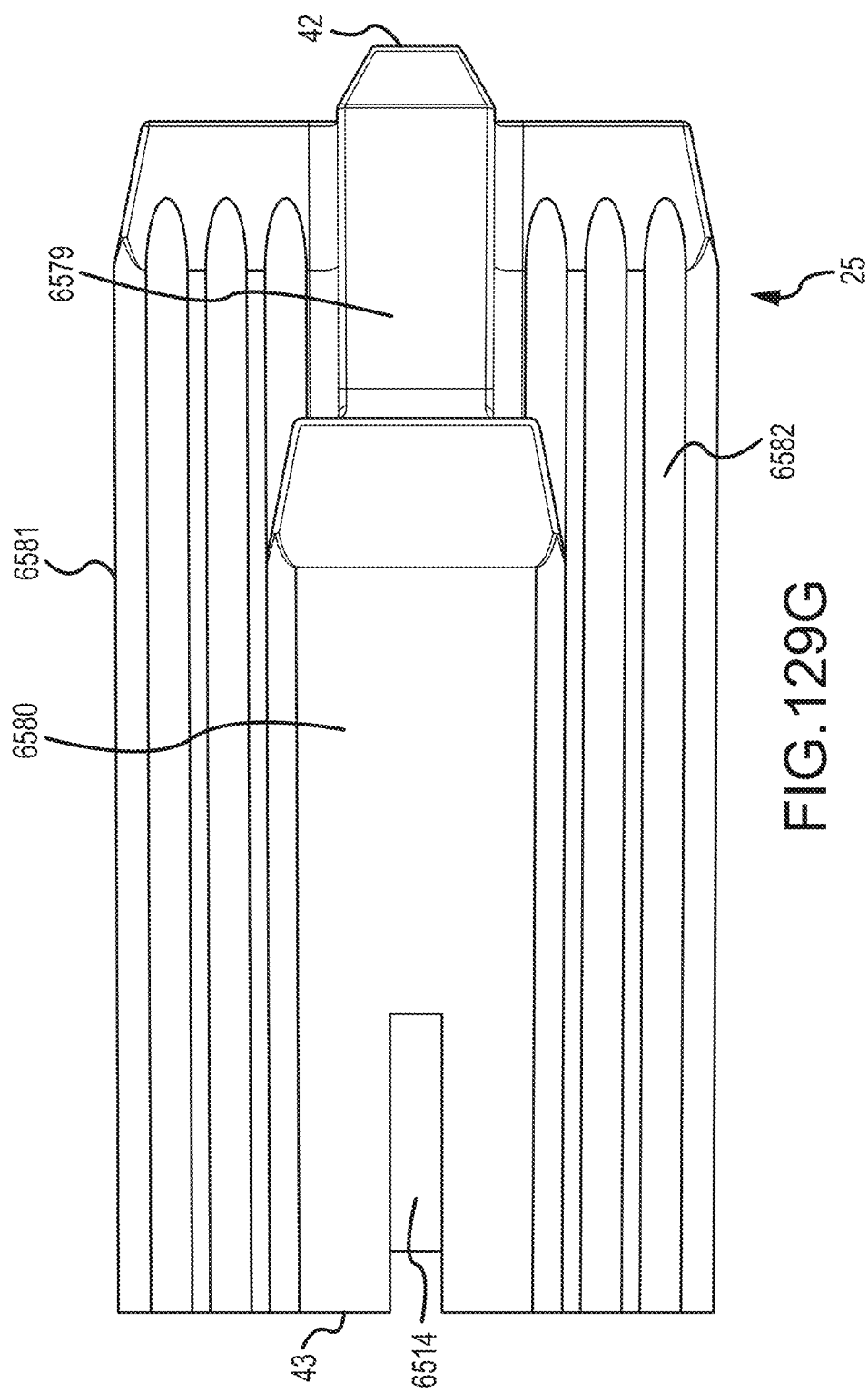

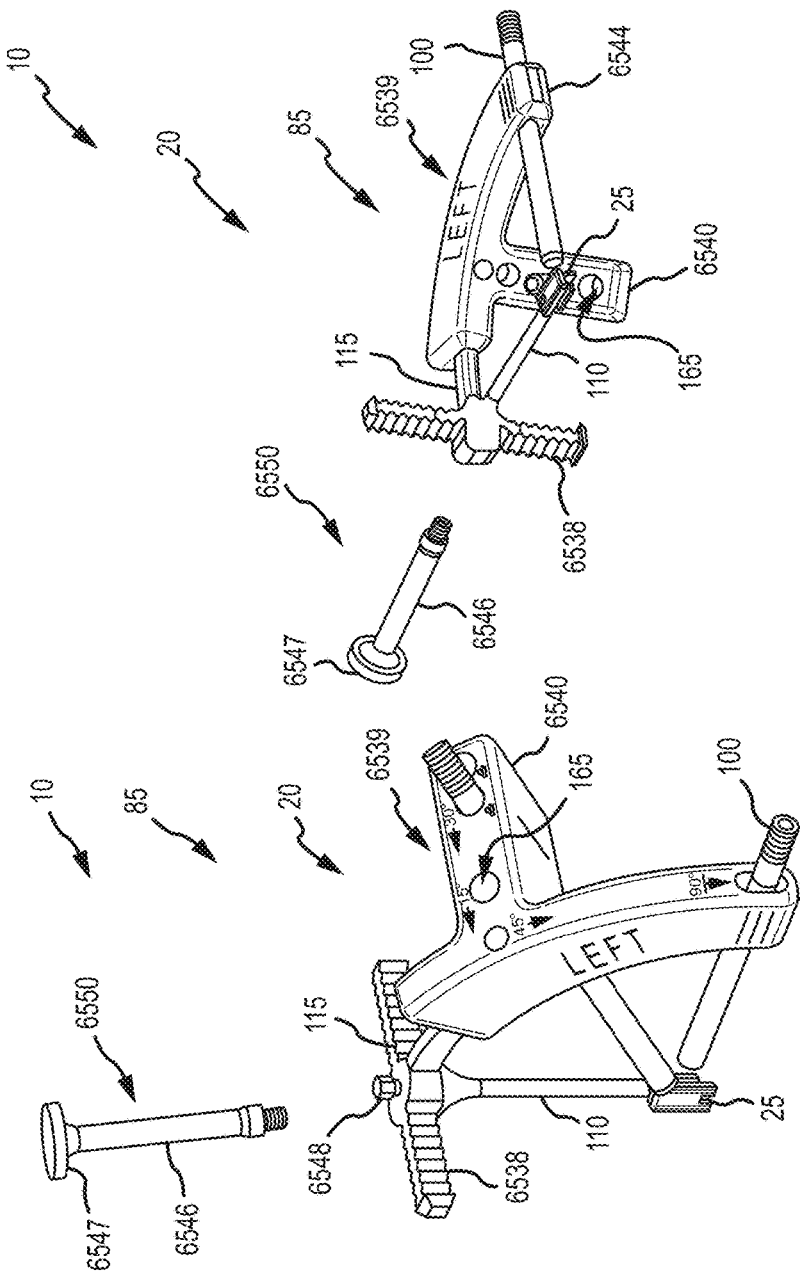

METHOD OF FUSING A SACROILIAC JOINT WITH AN IMPLANT WITH STRUTS

CROSS REFERENCE TO RELATED APPLICATIONS

The present application is a continuation of U.S. application Ser. No. 15/910,753 filed Mar. 2, 2018, which application is a continuation of U.S. application Ser. No. 15/828,677 filed Dec. 1, 2017, now U.S. Pat. No. 9,931,212, which application is a continuation of U.S. application Ser. No. 15/061,524 filed Mar. 4, 2016, now U.S. Pat. No. 9,833,320, which application is a divisional of U.S. application Ser. No. 13/946,790 filed Jul. 19, 2013, now U.S. Pat. No. 9,333,090, which application claims priority to and incorporates by reference in its entirety U.S. Provisional Patent Application Nos. 61/674,277, filed Jul. 20, 2012; 61/800,120, filed Mar. 15, 2013; and 61/674,130, filed Jul. 20, 2012.

Application Ser. No. 13/946,790 is also a continuation-in-part (CIP) application of U.S. patent application Ser. No. 13/475,695 ("the '695 application"), which was filed May 18, 2012, now U.S. Pat. No. 9,381,045. The '695 application is a continuation-in-part (CIP) application of and claims priority to U.S. patent application Ser. No. 13/236,411 ("the '411 application), which is entitled "Systems for and Methods of Fusing a Sacroiliac Joint" and was filed Sep. 19, 2011, now U.S. Pat. No. 9,017,407.

The '411 application is a continuation-in-part (CIP) application of and claims priority to U.S. patent application Ser. No. 12/998,712 ("the '712 application"), which was filed May 23, 2011, now U.S. Pat. No. 8,979,928. The '712 application is the National Stage of International Patent Cooperation Treaty Patent Application PCT/US2011/000070 (the "PCT application"), which was filed Jan. 13, 2011. The PCT application claims priority to U.S. Provisional Patent Application 61/335,947, which was filed Jan. 13, 2010.

All of the aforementioned applications are hereby incorporated by reference in their entireties into the present application.

The delivery approaches and methodologies disclosed in the above-listed applications and incorporated herein are applicable to the implants and delivery tools disclosed in the present application.

FIELD OF THE INVENTION

Aspects of the present invention relate to medical apparatus and methods. More specifically, the present invention relates to devices and methods for fusing a sacroiliac joint.

BACKGROUND OF THE INVENTION

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods encompassing an anterior approach, a posterior approach, and a lateral approach with or without percutaneous screw or other type implant fixation. However, while each of these methods has been utilized for fixation and fusion of the sacroiliac joint over the past several decades, substantial problems with respect to the fixation and fusion of the sacroiliac joint remain unresolved.

A significant problem with certain conventional methods for fixation and fusion of the sacroiliac joint including the anterior approach, posterior approach, or lateral approach may be that the surgeon has to make a substantial incision in the skin and tissues for direct access to the sacroiliac joint involved. These invasive approaches allow the sacroiliac joint to be seen and touched directly by the surgeon. Often referred to as an "open surgery", these procedures have the attendant disadvantages of requiring general anesthesia and can involve increased operative time, hospitalization, pain, and recovery time due to the extensive soft tissue damage resulting from the open surgery.

A danger to open surgery using the anterior approach can be damage to the L5 nerve root, which lies approximately two centimeters medial to the sacroiliac joint or damage to the major blood vessels. Additionally, these procedures typically involve fixation of the sacroiliac joint (immobilization of the articular surfaces of the sacroiliac joint in relation to one another) by placement of one or more screws or one or more trans-sacroiliac implants (as shown by the non-limiting example of FIG. 1) or by placement of implants into the S1 pedicle and iliac bone.

Use of trans-sacroiliac and S1 pedicle-iliac bone implants can also involve the risk of damage to the lumbosacral neurovascular elements. Damage to the lumbosacral neurovascular elements as well as delayed union or non-union of the sacroiliac joint by use of these procedures may require revision surgery to remove all or a portion of the implants or repeat surgery as to these complications.

Another significant problem with conventional procedures utilizing minimally invasive small opening procedures can be that the procedures are technically difficult, requiring biplanar fluoroscopy of the articular surfaces of the sacroiliac joint and extensive surgical training and experience. Despite the level of surgical training and experience, there is a substantial incidence of damage to the lumbosacral neurovascular elements. Additionally, sacral anomalies can further lead to mal-placement of implants leading to damage of surrounding structures. Additionally, these procedures are often performed without fusion of the sacroiliac joint, which does not remove the degenerative joint surface and thereby does not address the degenerative condition of the sacroiliac joint, which may lead to continued or recurrent sacroiliac joint pain.

Another significant problem with conventional procedures can be the utilization of multiple trans-sacroiliac elongate implants, which do not include a threaded surface. This approach requires the creation of trans-sacroiliac bores in the pelvis and nearby sacral foramen, which can be of relatively large dimension and which are subsequently broached with instruments, which can result in bone being impacted into the pelvis and neuroforamen.

The creation of the trans-sacroiliac bores and subsequent broaching of the bores requires a guide pin, which may be inadvertently advanced into the pelvis or sacral foramen, resulting in damage to other structures. Additionally, producing the trans-sacroiliac bores, broaching, or placement of the elongate implants may result in damage to the lumbosacral neurovascular elements, as above discussed. Additionally, there may be no actual fusion of the articular portion of the sacroiliac joint, which may result in continued or recurrent pain requiring additional surgery.

Another substantial problem with conventional procedures can be that placement of posterior extra-articular distracting fusion implants and bone grafts may be inadequate with respect to removal of the articular surface or preparation of cortical bone, the implant structure and fixation of the sacroiliac joint. The conventional procedures may not remove sufficient amounts of the articular surfaces or cortical surfaces of the sacroiliac joint to relieve pain in the sacroiliac joint. The conventional implant structures may have insufficient or avoid engagement with the articular surfaces or cortical bone of the sacroiliac joint for adequate fixation or fusion. The failure to sufficiently stabilize and fuse the sacroiliac joint with the conventional implant structures and methods may result in a failure to relieve the condition of sacroiliac joint being treated. Additionally, conventional methods of driving apart a sacrum and ilium may lead to mal-alignment of the sacroiliac joint and increased pain.

The inventive sacroiliac fusion system described herein addresses the problems associated with conventional methods and apparatuses used in fixation and fusion of the sacroiliac joint.

BRIEF SUMMARY OF THE INVENTION

One implementation of the present disclosure may take the form of a sacroiliac joint fusion system including a joint implant, an anchor element and a delivery tool. The joint implant includes a distal end, a proximal end, a body extending between the proximal and distal ends, and a first bore extending non-parallel to a longitudinal axis of the body. The anchor element includes a distal end and a proximal end and is configured to be received in the first bore. The delivery tool includes an implant arm and an anchor arm. The implant arm includes a proximal end and a distal end. The distal end of the implant arm is configured to releasably couple to the proximal end of the joint implant such that a longitudinal axis of the implant arm is substantially at least one of coaxial or parallel with the longitudinal axis of the body of the joint implant. The anchor arm includes a proximal end and a distal end. The distal end of the anchor arm is configured to engage the proximal end of the anchor element. The anchor arm is operably coupled to the implant arm in an arrangement such that the longitudinal axis of the anchor element is generally coaxially aligned with a longitudinal axis of the first bore when the distal end of the implant arm is releasably coupled with the proximal end of the joint implant and the distal end of the anchor arm is engaged with the proximal end of the anchor element. The arrangement is fixed and nonadjustable.

Another implementation of the present disclosure may take the form of a sacroiliac joint fusion system including a joint implant, an anchor element and a delivery tool. The joint implant includes a distal end, a proximal end, a body extending between the proximal and distal ends, and a first bore extending non-parallel to a longitudinal axis of the body. The anchor element includes a distal end and a proximal end and is configured to be received in the first bore. The delivery tool includes an implant arm and an anchor arm. The implant arm includes a proximal end and a distal end. The distal end of the implant arm is configured to releasably couple to the proximal end of the joint implant such that a longitudinal axis of the implant arm is substantially at least one of coaxial or parallel with the longitudinal axis of the body of the joint implant. The anchor arm includes a proximal end and a distal end. The distal end of the anchor arm includes a guide. The anchor arm is pivotally coupled to the implant arm and configured such that a center of the guide moves along an arc that extends through generally the center of the first bore of the implant when the distal end of the implant arm is releasably coupled with the proximal end of the joint implant. The anchor arm is configured to deliver the anchor element to the first bore.

Yet another implementation of the present disclosure may take the form of a sacroiliac joint fusion system including a joint implant and a tool. In one embodiment, the joint implant includes a longitudinal axis and a first bore extending non-parallel to the longitudinal axis. The anchor element is configured to be received in the first bore. The delivery tool includes an implant arm and an anchor arm. The implant arm is configured to releasably couple to the joint implant. The anchor arm is coupled to the implant arm and configured to deliver the anchor element to the first bore. The final manufactured configuration of the tool and final manufactured configuration of the joint implant are such that, when the system is assembled such that the implant arm is releasably coupled to the joint implant, a delivery arrangement automatically exists such that the anchor arm is correctly oriented to deliver the anchor element to the first bore.

Another implementation of the present disclosure may take the form of a method of sacroiliac joint fusion. In one embodiment, the method includes: a) approaching a sacroiliac joint space with a joint implant comprising at least first and second planar members radially extending generally coplanar with each other from opposite sides of a body of the joint implant; b) delivering the joint implant into a sacroiliac joint space, the joint implant being oriented in the sacroiliac joint space such that the first and second planar members are generally coplanar with a joint plane of the sacroiliac joint space; and c) causing an anchor element to be driven generally transverse to the joint plane through bone material defining at least a portion of the sacroiliac joint space and into a bore of the joint implant that extends generally transverse to the body of the joint implant.

Yet another implementation of the present disclosure may take the form of a medical kit for the fusion of a sacroiliac joint including a caudal access region and a joint plane. In one embodiment, the kit includes: a) a delivery tool comprising an implant arm and an anchor arm coupled to the implant arm; b) a joint implant comprising a bore defined therein that extends generally transverse to a longitudinal length of the joint implant; and c) an anchor element configured to be received in the bore of the joint implant. The bore of the implant, the implant, the implant arm and the anchor arm have an as-manufactured configuration that allows the anchor arm to properly align the anchor element to be received in the bore of the implant when the implant is coupled to the implant arm.

One implementation of the present disclosure may take the form of various embodiments of a sacroiliac joint fusion system including joint implants and delivery tools.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 2A is an isometric view of a first embodiment of a system for fusing a sacroiliac joint.

FIG. 2B is the same view as FIG. 2A, except the delivery tool and implant assembly are decoupled from each other.

FIG. 3 is the same view as FIG. 2A, except the system is exploded to better illustrate its components.

FIG. 16 is an isometric longitudinal cross section of the implant as taken along section line 16-16 of FIG. 11.

FIG. 17 is an isometric longitudinal cross section of the implant as taken along section line 17-17 of FIG. 13.

FIG. 22 is the same view as FIG. 21A, except shown as a longitudinal cross section.

FIG. 28 is an isometric view of the implant retainer.

FIG. 29 is a longitudinal cross sectional isometric view of the implant retainer.

FIG. 32 is an isometric view of a second embodiment of a system for fusing a sacroiliac joint.

FIG. 33 is the same view as FIG. 32, except the system is exploded to better illustrate its components.

FIGS. 51-52 are, respectively, isometric and side elevation views of an implant having an anchor member receiving arm.

FIG. 53 is an enlarged view of the disk-shaped seat of the implant arm of FIG. 51.

FIG. 54 is an isometric view of an implant with another type of anchor member locking mechanism.

FIG. 55 is an enlarged view of the free end of the anchor member locking mechanism of FIG. 54.

FIGS. 56-61 are, respectively, front isometric, rear isometric, side elevation, plan, front elevation, and rear elevation views of another embodiment of the implant.

FIGS. 62-67 are, respectively, front isometric, rear isometric, side elevation, plan, front elevation, and rear elevation views of yet another embodiment of the implant.

FIGS. 68-73 are, respectively, front isometric, rear isometric, side elevation, plan, front elevation, and rear elevation views of still another embodiment of the implant.

FIGS. 74-79 are, respectively, front isometric, rear isometric, side elevation, plan, front elevation, and rear elevation views of yet another embodiment of the implant.

FIG. 89 is an isometric view of the handle.

FIG. 90 is an exploded isometric view of the retaining collar and handle shown in longitudinal cross section.

FIG. 92 is a side view of an implant retainer similar to that described with respect to FIGS. 86-91, except having a modified distal end.

FIGS. 93-94 are, respectively, longitudinal and transverse cross sectional views of an implant with an engagement hole configured to complementarily engage with the T-shaped distal end of the retainer of FIG. 92.

FIG. 95 is the same view as FIG. 93, except with the retainer received in the hole.

FIG. 97B is an enlarged view of the hip region of FIG. 97A.

FIG. 98B is an enlarged view of the hip region of FIG. 98A.

FIG. 109 is an isometric view of the system wherein the tool is attached to the implant for delivery of the implant to the sacroiliac joint.

FIG. 110 is a view of the system wherein the implant and anchor arm are shown in plan view.

FIG. 117A is a lateral-inferior-posterior view of the patient's hip skeletal structure similar to the view depicted in FIG. 111C.

FIG. 117B is an inferior-posterior view of the patient's hip skeletal structure similar to the view depicted in FIG. 111A.

FIGS. 121A-121G are, respectively, distal end isometric, side elevation, plan, distal end elevation, proximal end elevation, proximal end isometric, and side elevation views of still another embodiment of the implant.

FIGS. 124A and 124B1 are isometric views of another embodiment of the delivery tool coupled and decoupled with the implant, respectively.

FIG. 124B2 is a cross section view as taken along section line 124B2-124B2 in FIG. 124B1.

FIG. 124C is an isometric view of the delivery tool in an exploded state.

FIG. 124D is an enlarged view of the distal end of the implant arm of the delivery tool.

FIGS. 124E-124H are, respectively, distal end isometric, side elevation, plan, and opposite plan views of a version of the embodiment of the implant of FIGS. 123A-123E, wherein the version includes a bore for receiving an anchor.

FIG. 126B is a longitudinal cross section view of the implant of FIG. 126A.

FIG. 126C is a longitudinal cross section of the proximal head of the anchor of FIG. 126A.

FIG. 128A is an isometric view of another embodiment of the sleeve of FIG. 127.

FIG. 128B is an end view of sleeve of FIG. 127.

FIG. 128C is a posterior view of the hip region, wherein the sleeve of FIG. 127 is being employed.

Figure 129A:
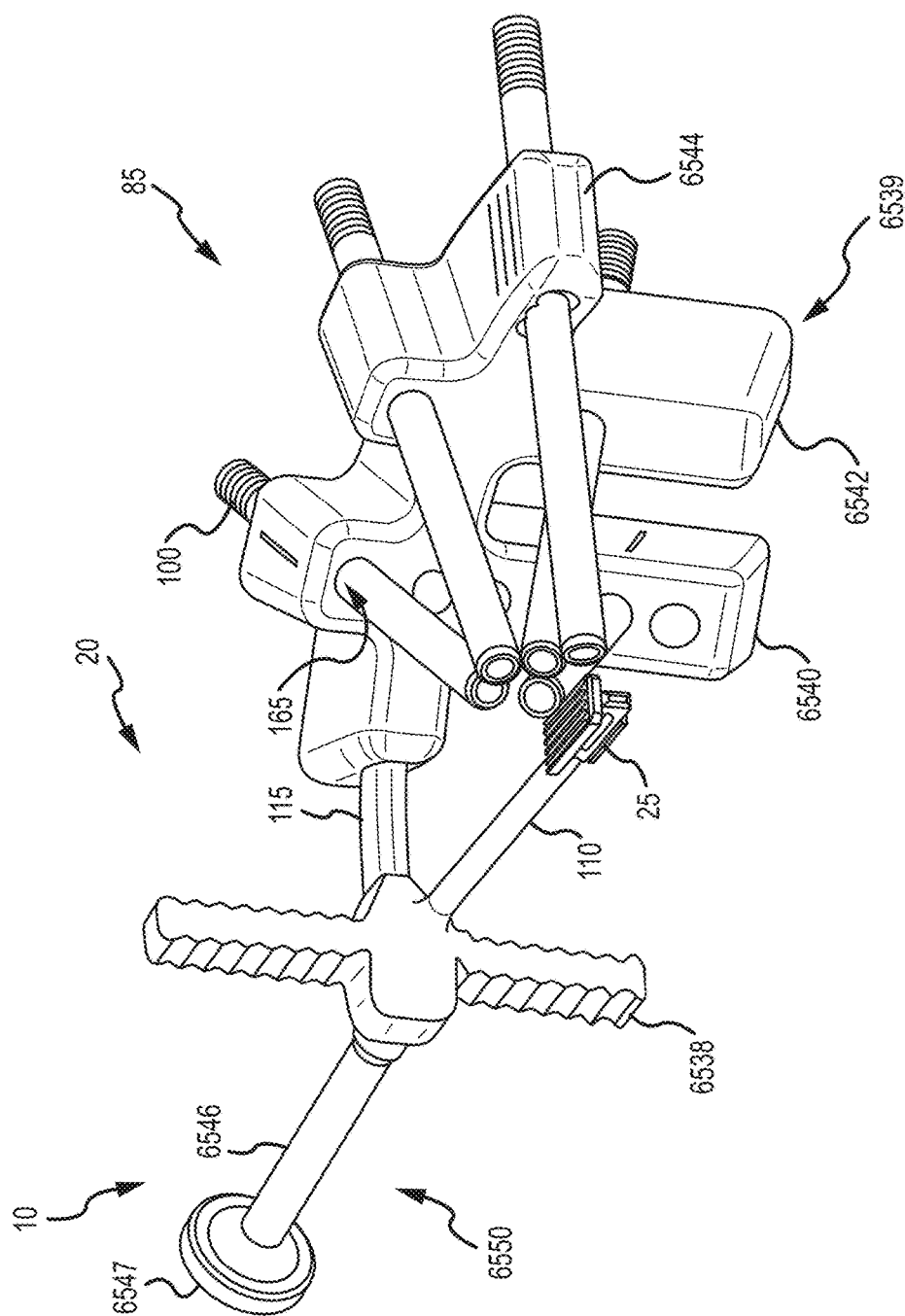
Figure 129B:
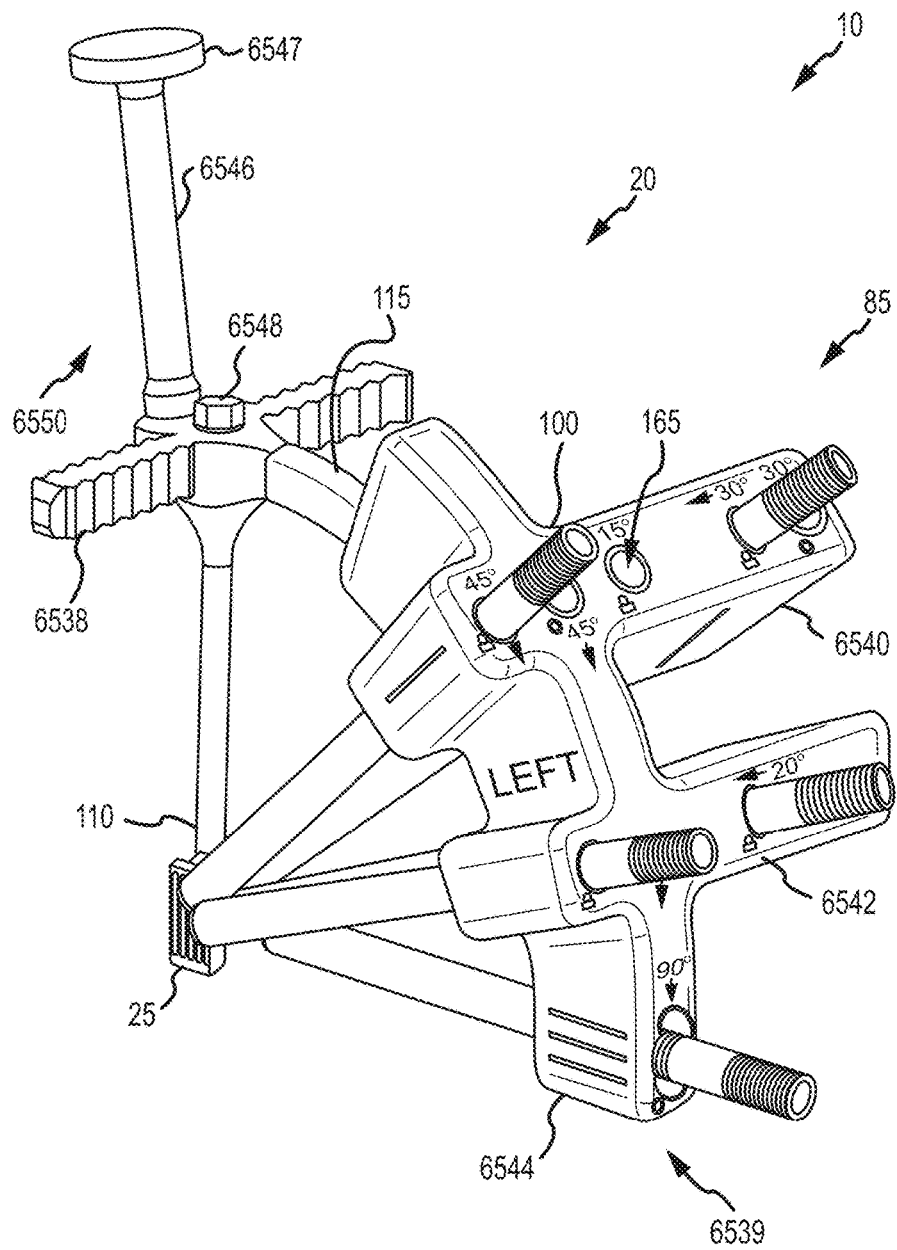

FIGS. 129A-129B show isometric views of another embodiment of the system, wherein the delivery tool has a series of interchangeable anchor arms that may be coupled to the implant arm to adjust the tool for the patient, but maintain the angular relationship between the components of system that allows the anchor member to be delivered into the implant bore and/or another location adjacent to the implant without adjustment to the delivery tool.

Figure 129C:
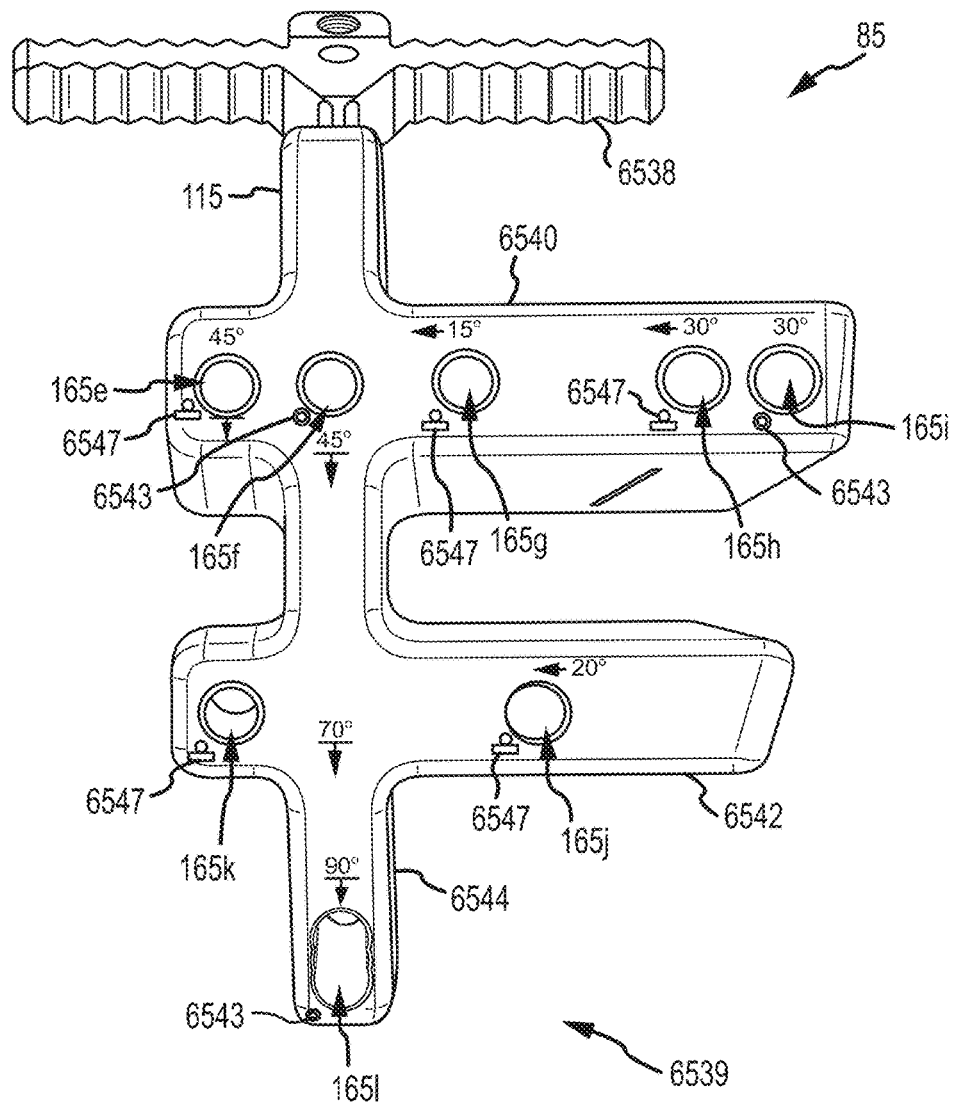

FIG. 129C shows an enlarged view of the arm assembly of the delivery tool of FIGS. 129A-129B.

FIGS. 129D-129K are, respectively, distal end isometric, proximal end isometric, side elevation, opposite side elevation, plan, opposite plan, proximal end elevation, and distal end elevation views of an embodiment of the implant intended for use with the system of FIGS. 129A-129C.

Figure 129D:
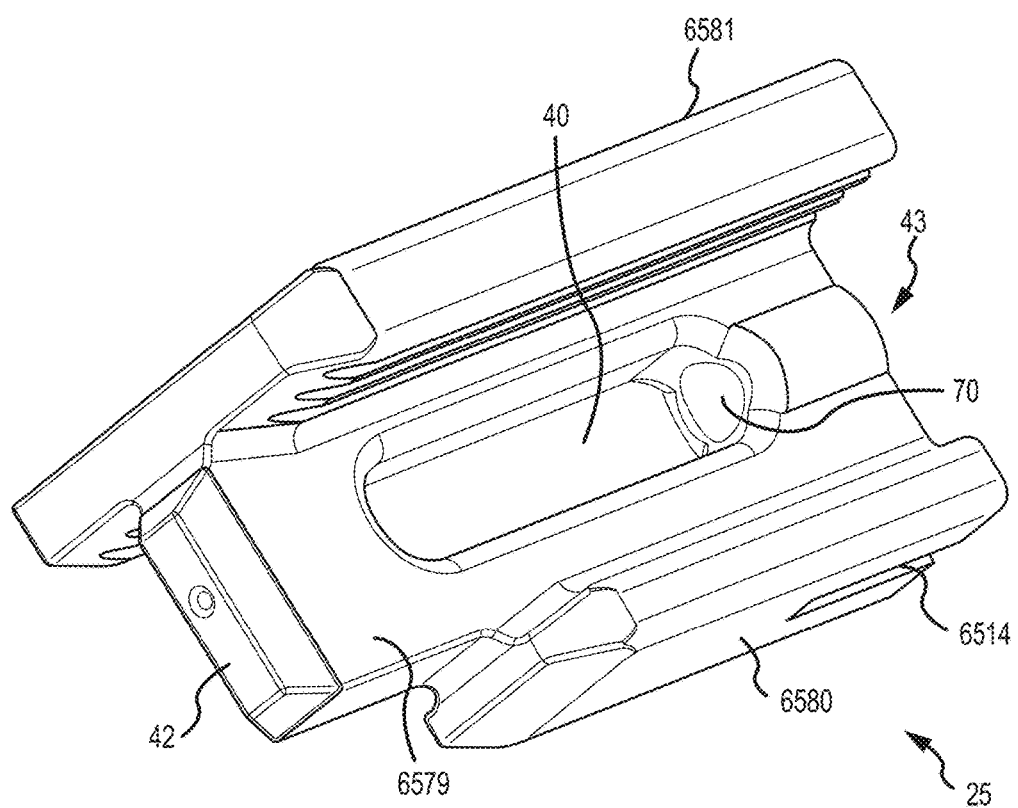
Figure 129E:
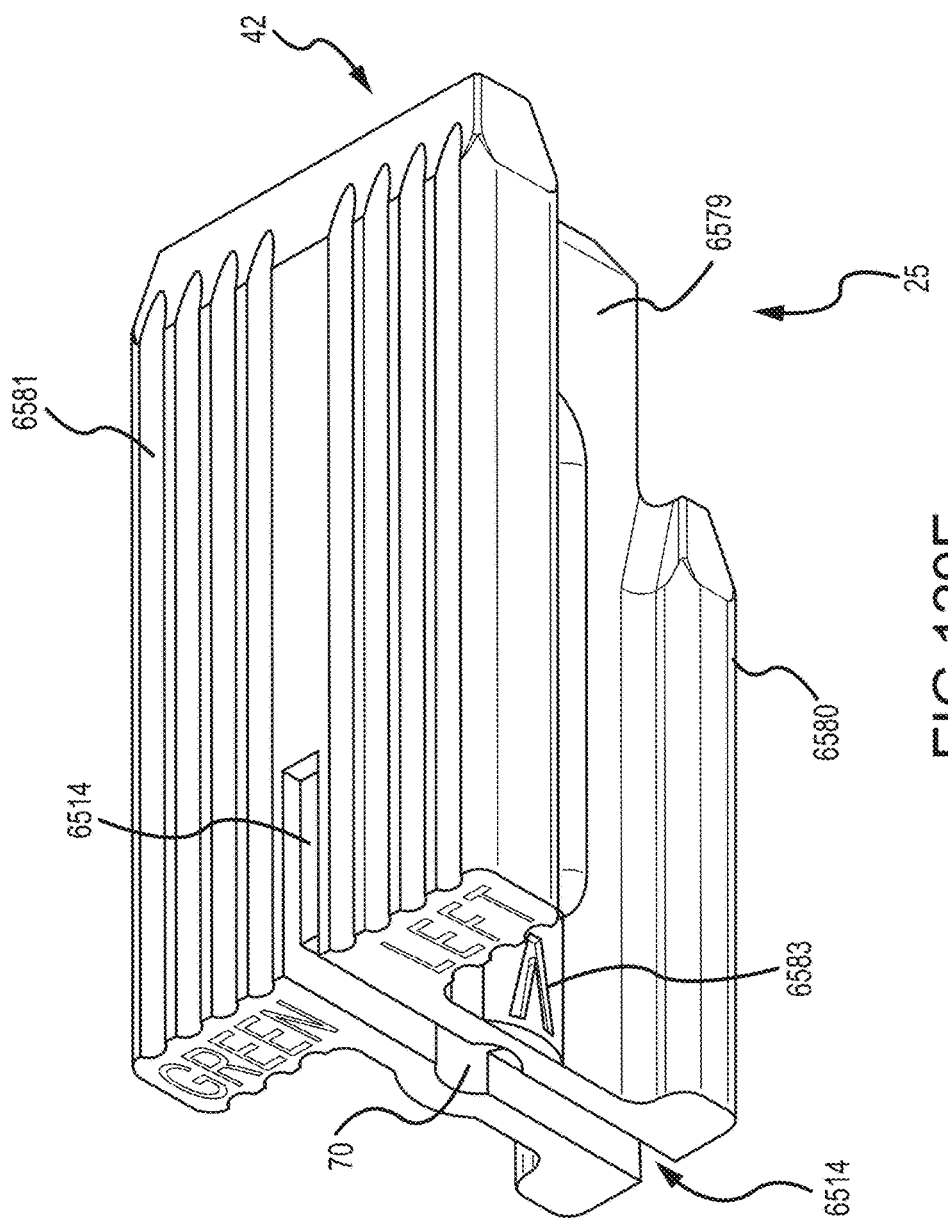
Figure 129F:
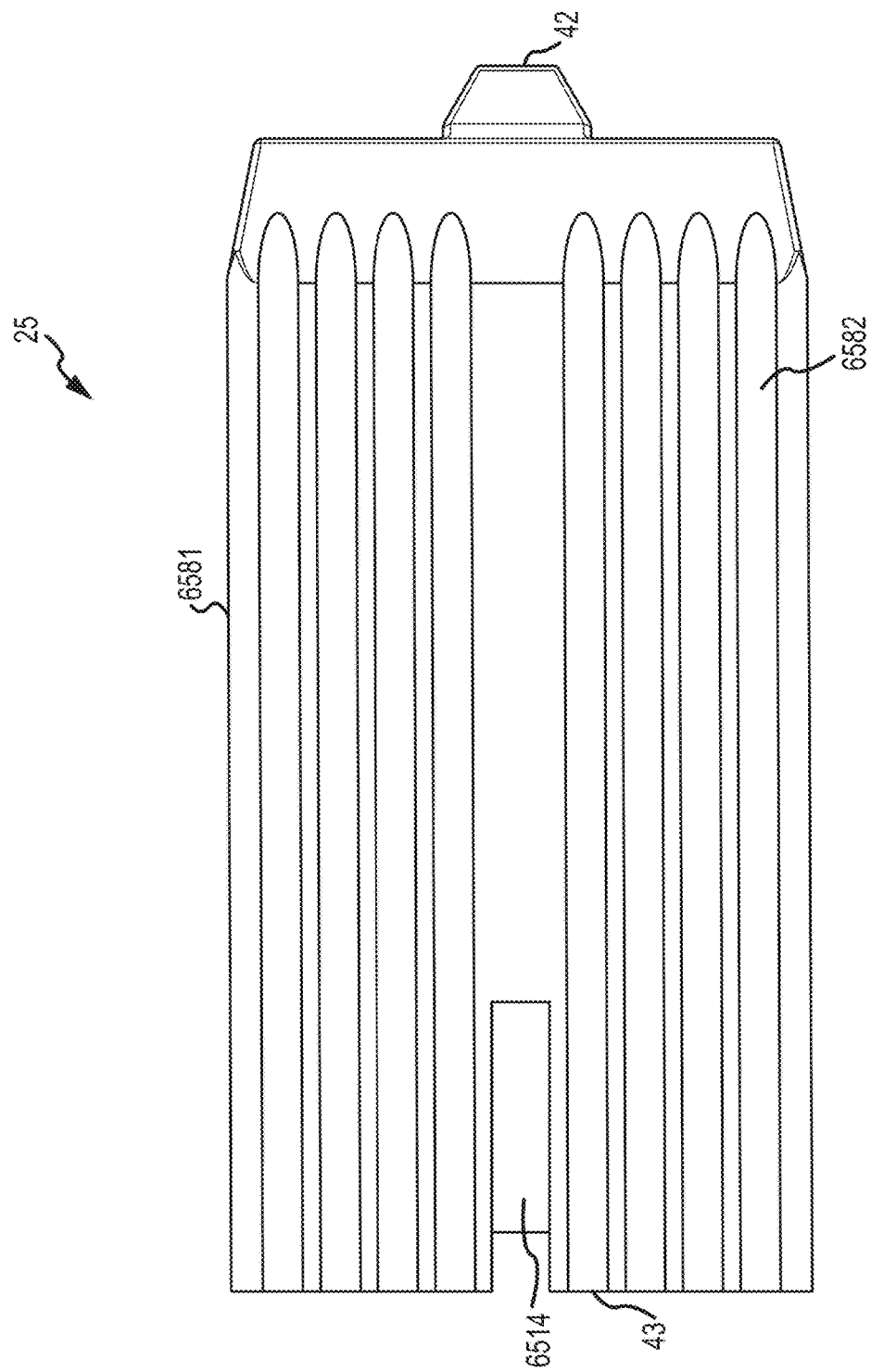
Figure 129H:
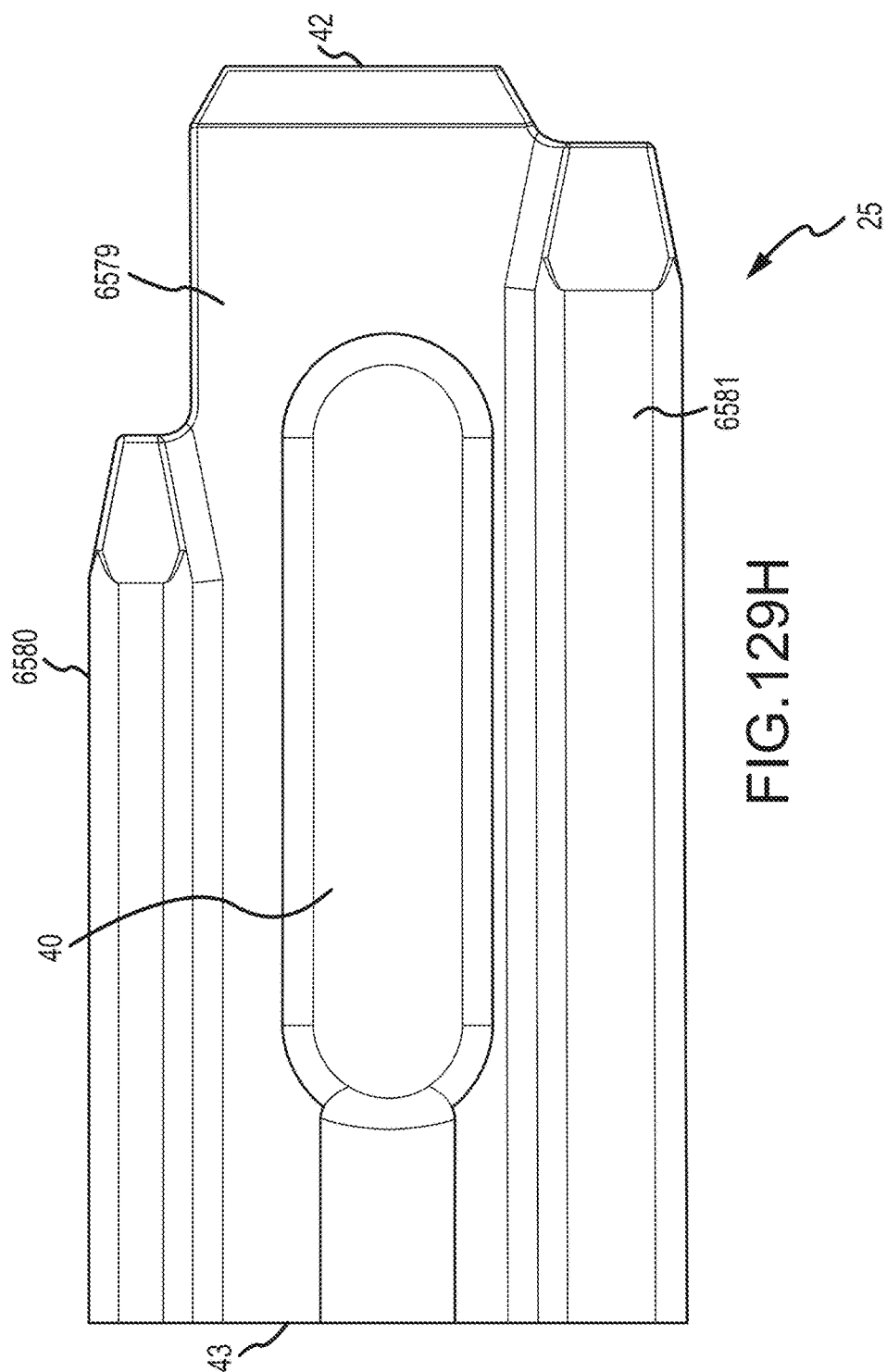
Figure 129I:
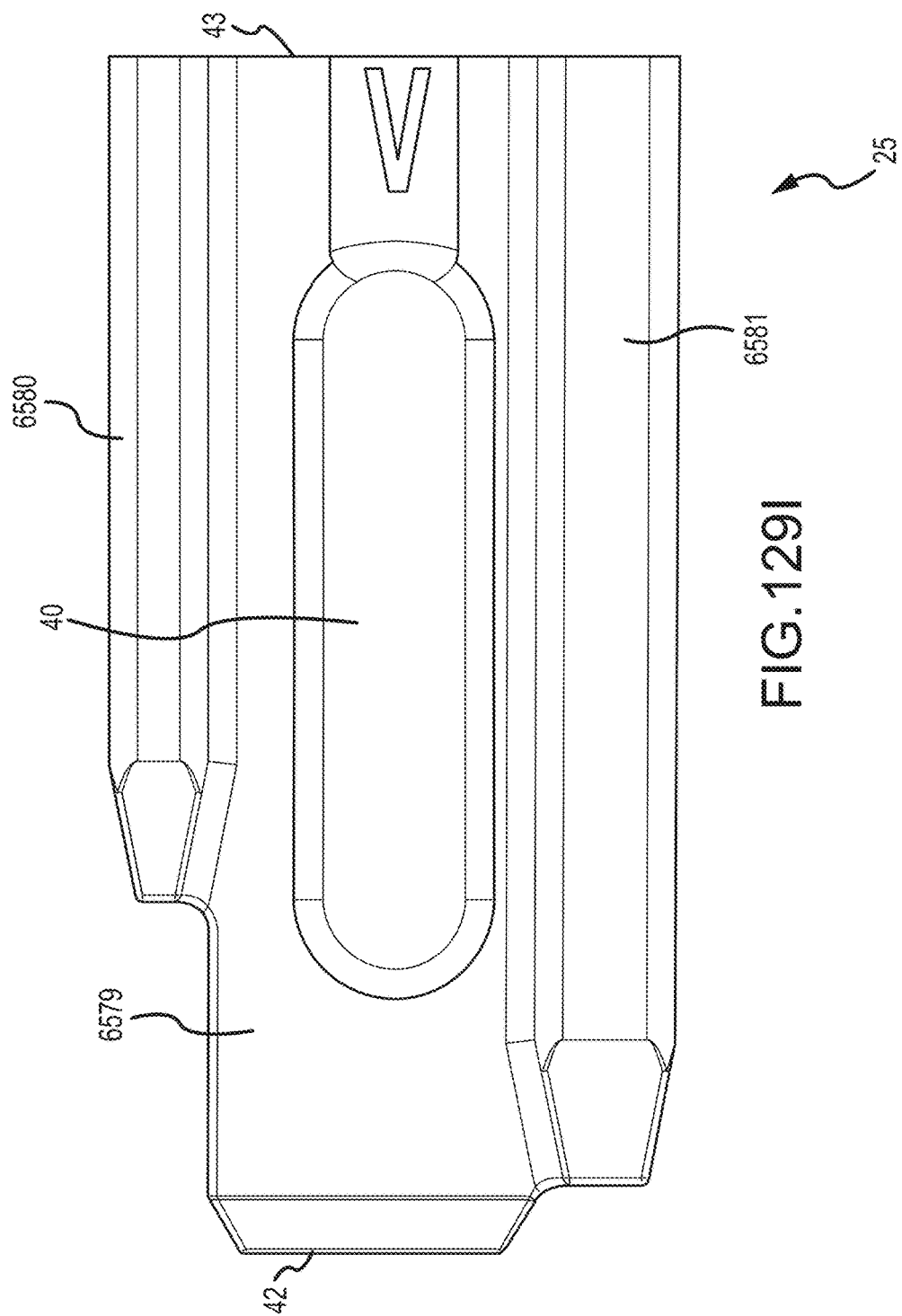
Figure 129J:
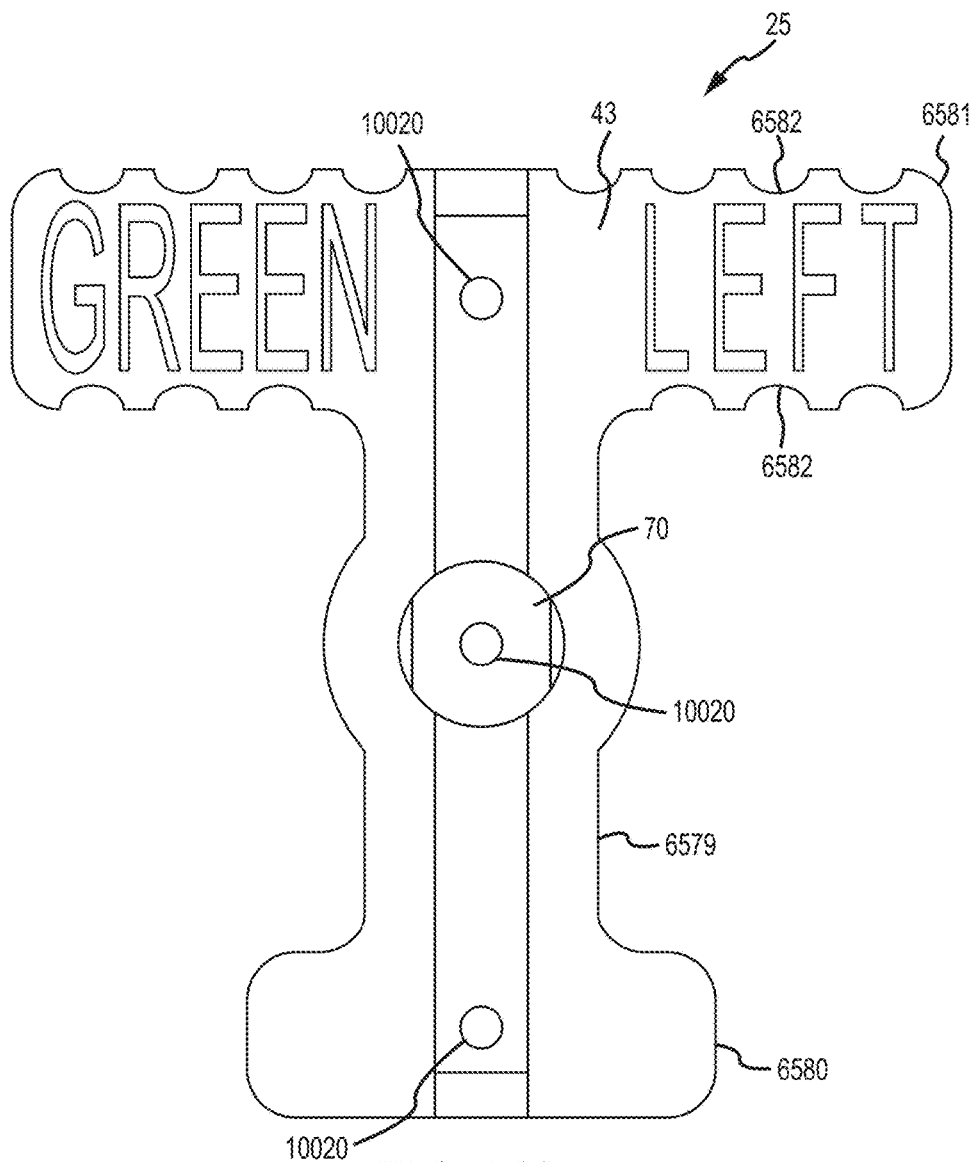
Figure 129K:
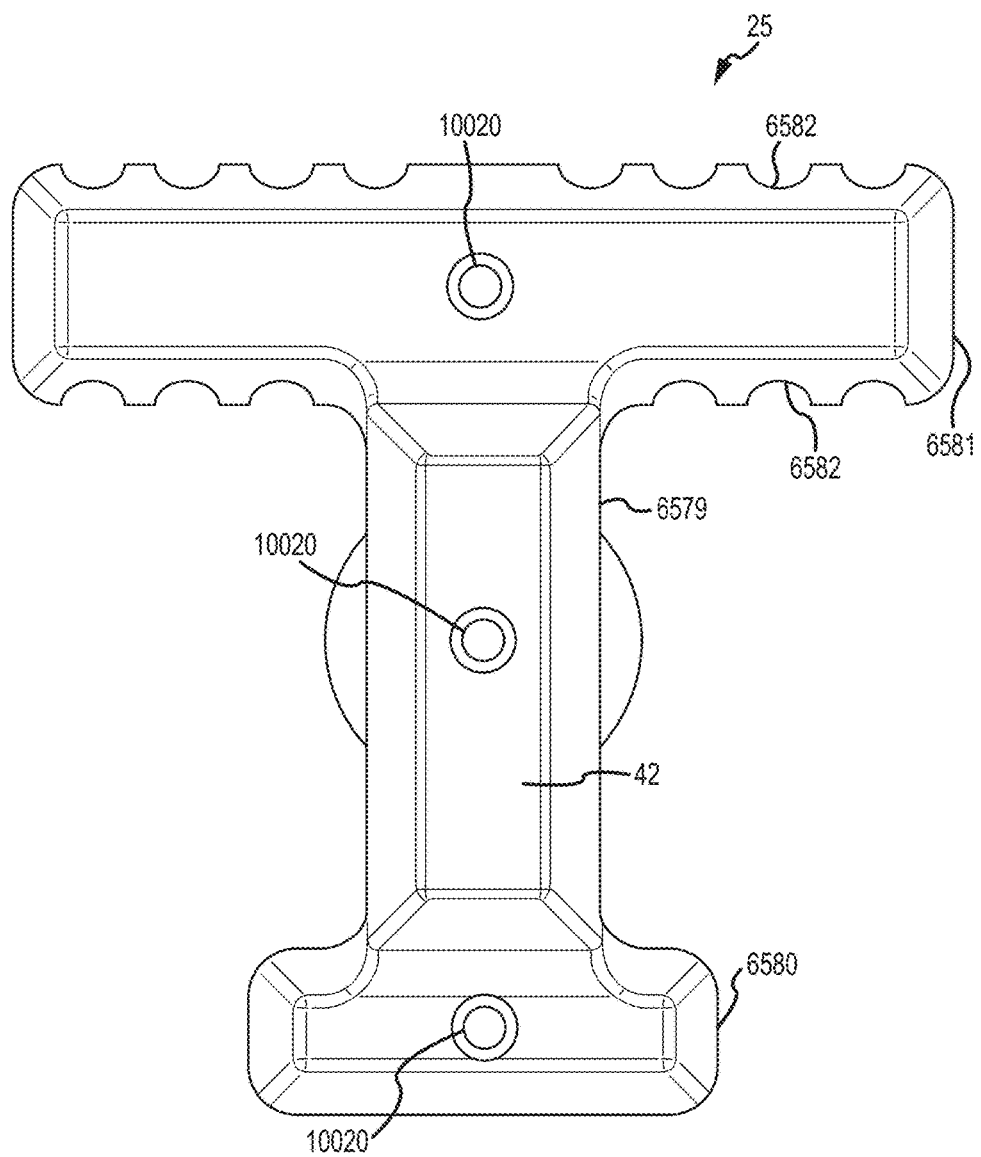
Figure 129L:
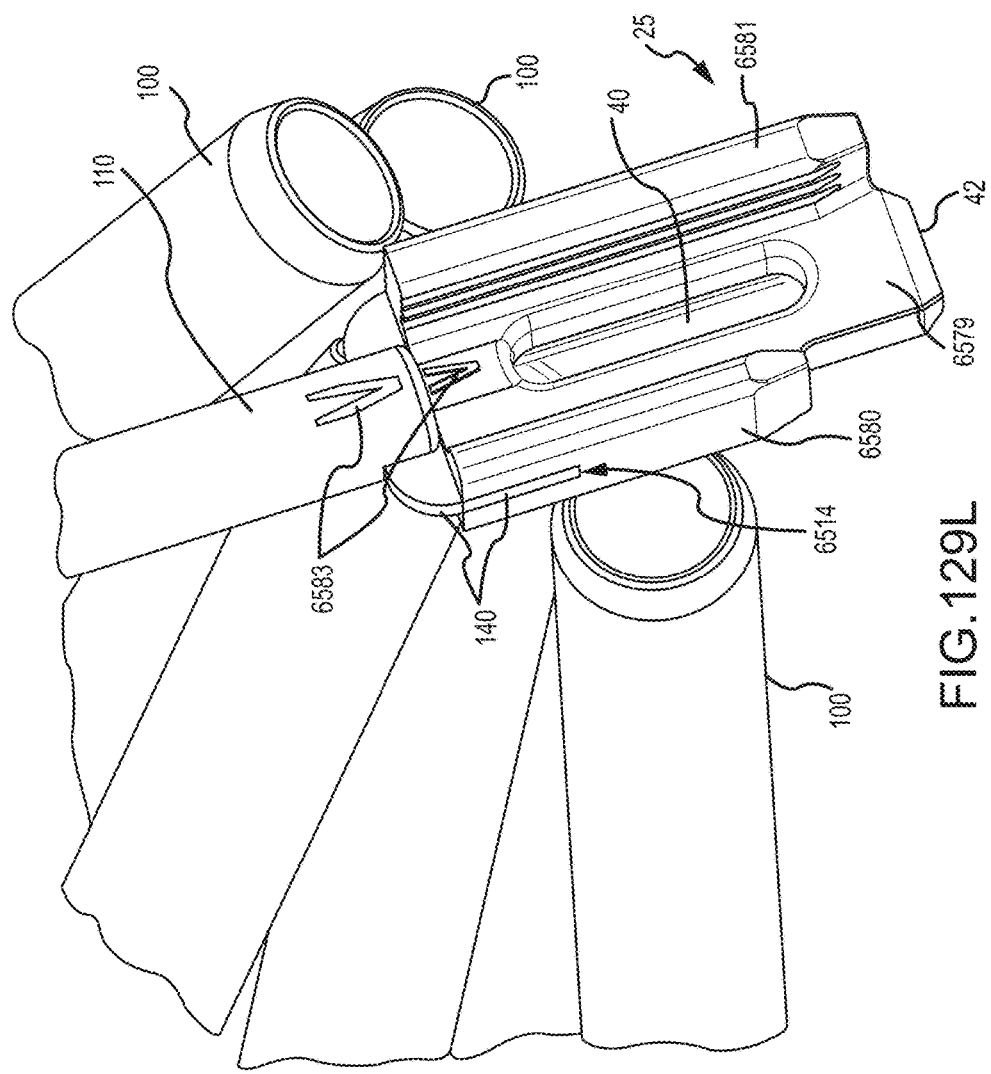

FIG. 129L is an enlarged isometric view of the implant of FIGS. 129D-129K mounted on the extreme distal end of the implant arm of the delivery tool of FIGS. 129A-129C.

Figure 129M:
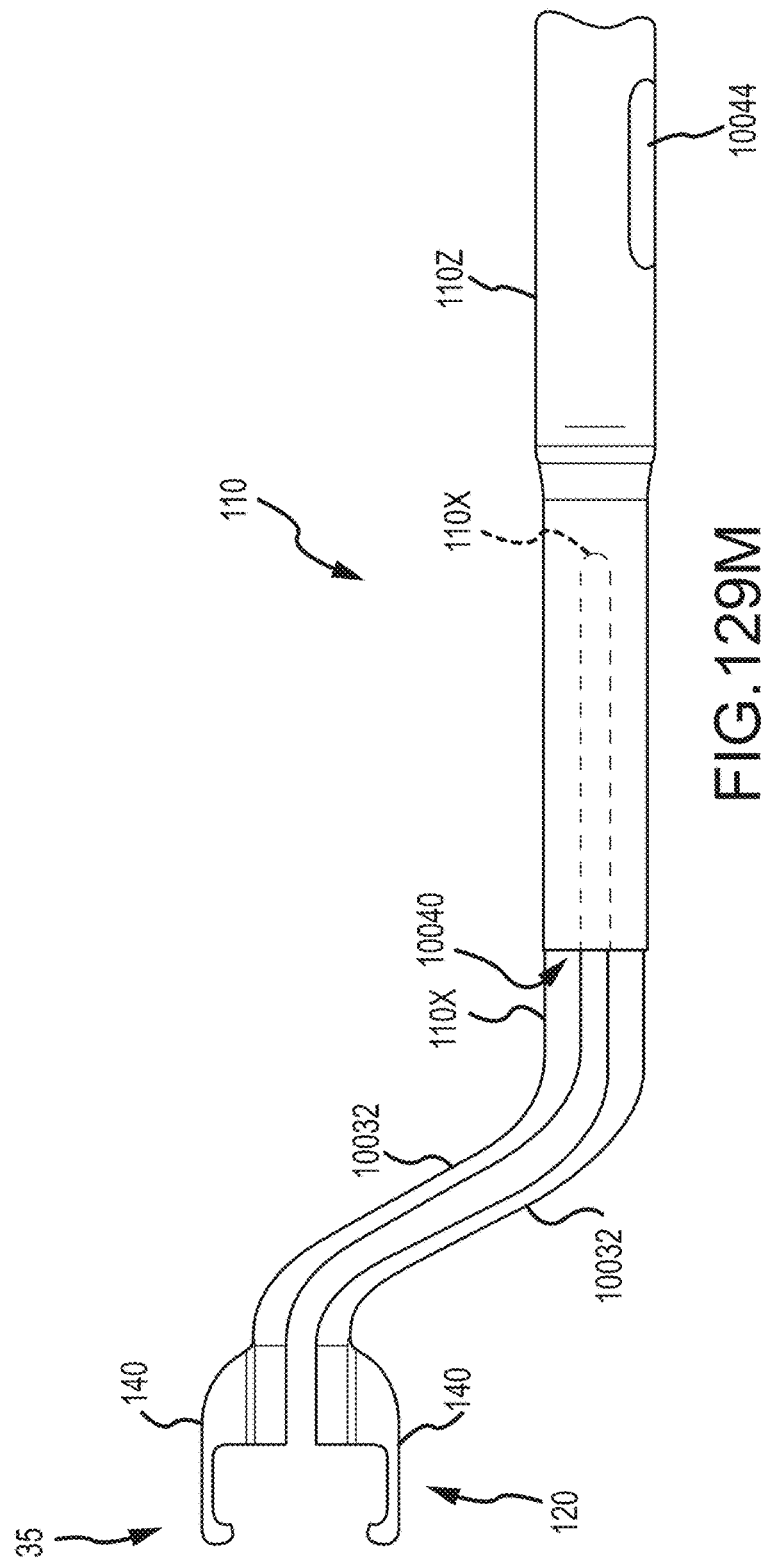
Figure 129N:
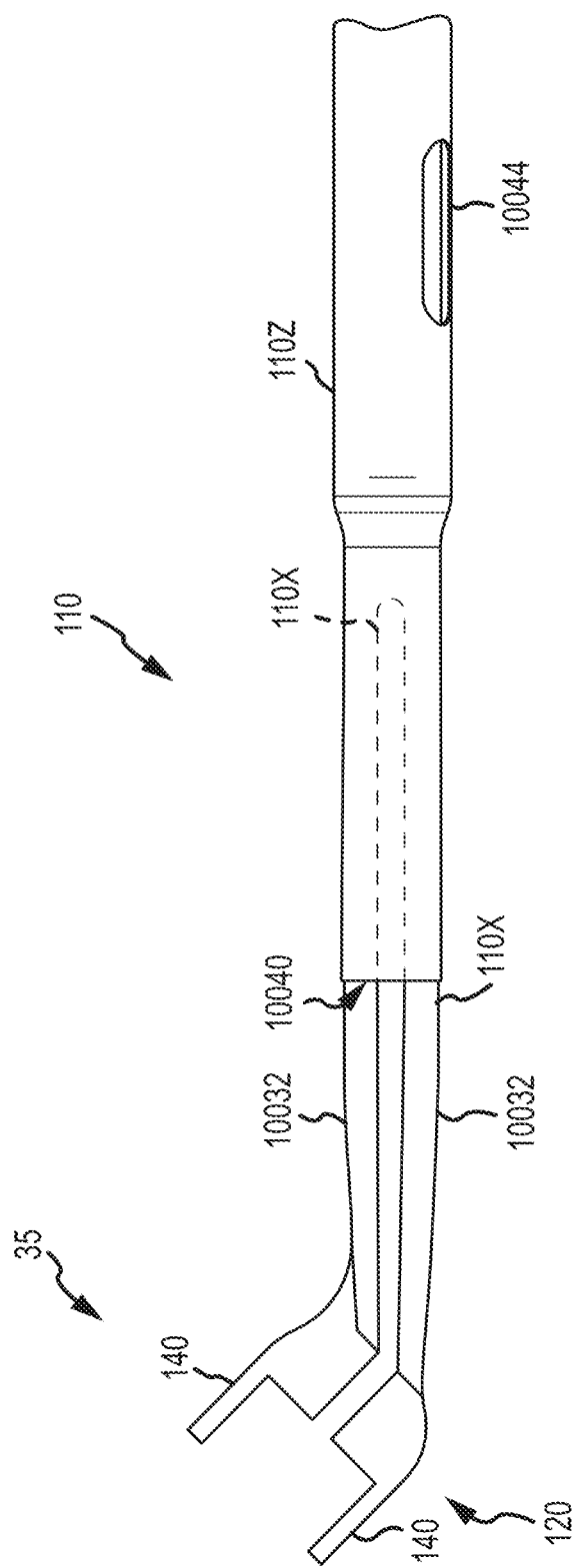

FIGS. 129M and 129N are side views of the distal regions of two alternative implant arms arrangements.

Figure 129O:
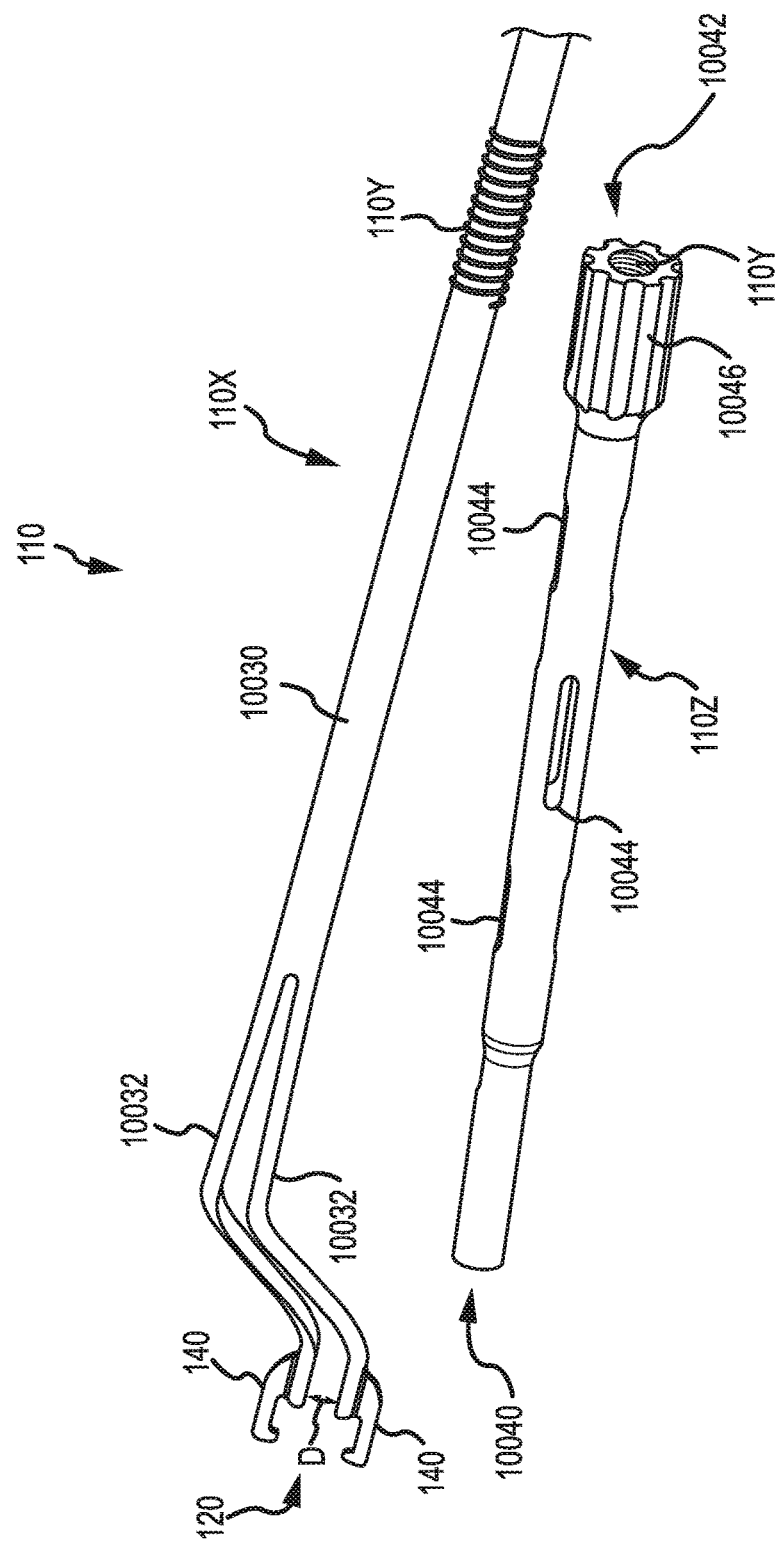

FIG. 129O is an exploded isometric view of the implant arm of FIG. 129M.

Figure 130A:
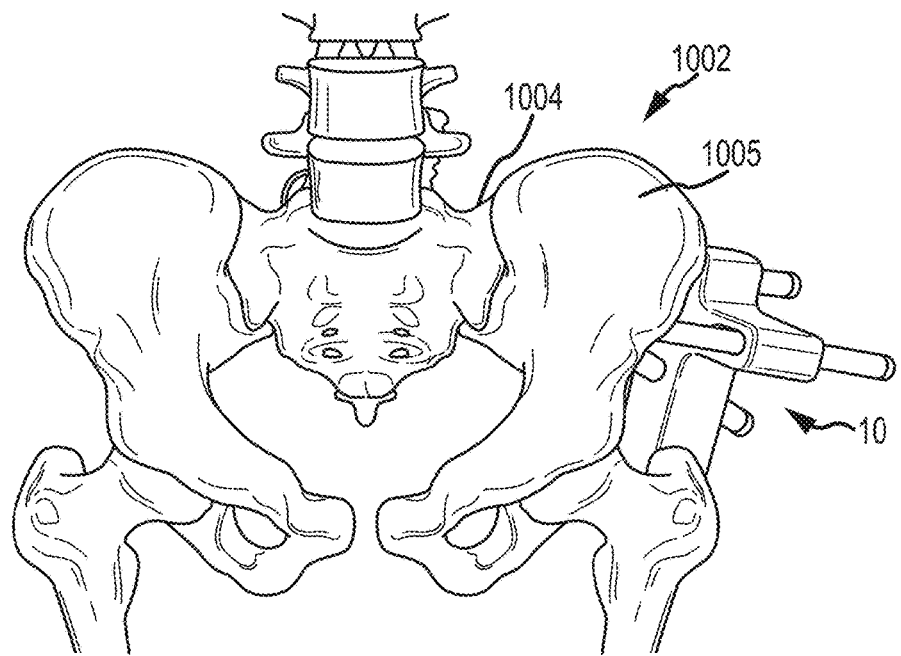
Figure 130B:
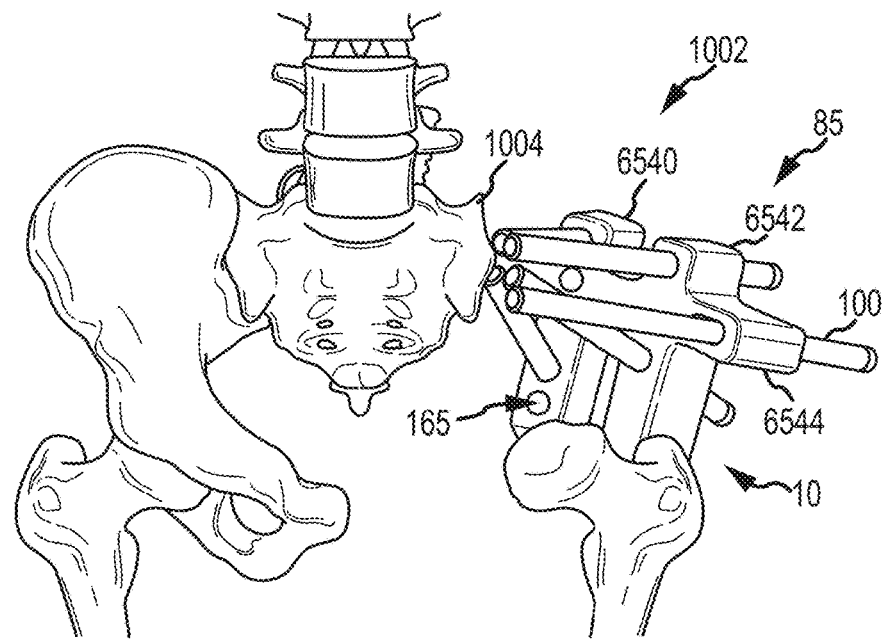
Figure 130C:
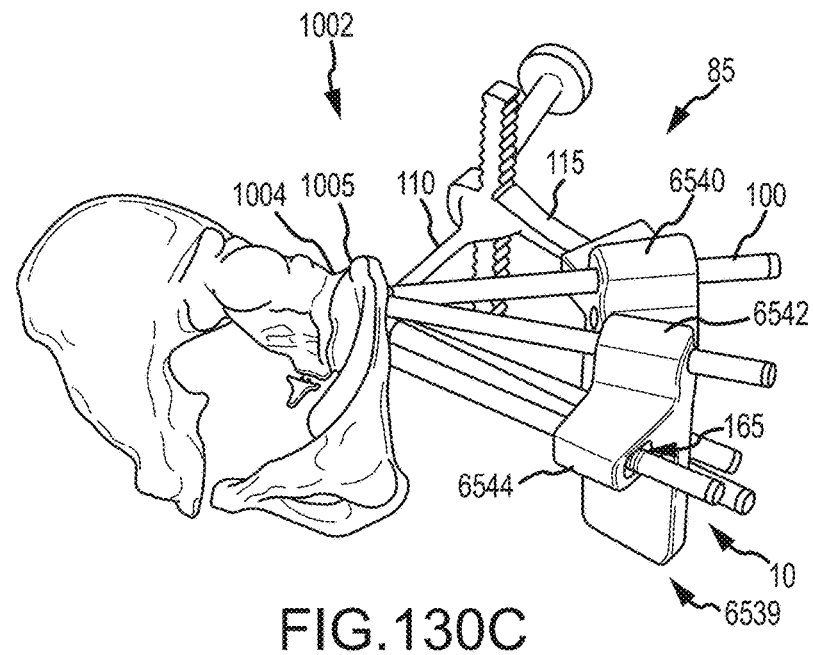
Figure 130D:
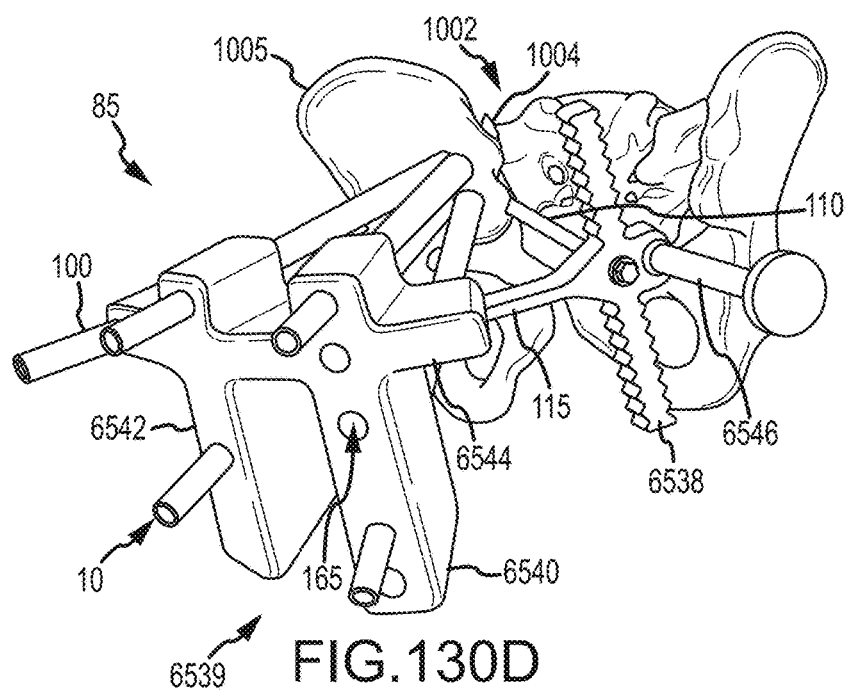
Figure 130E:
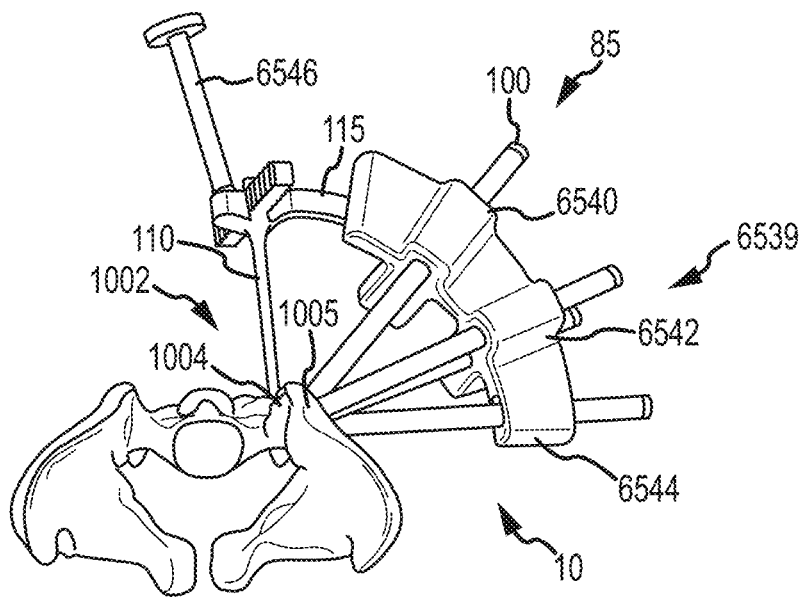
Figure 130F:
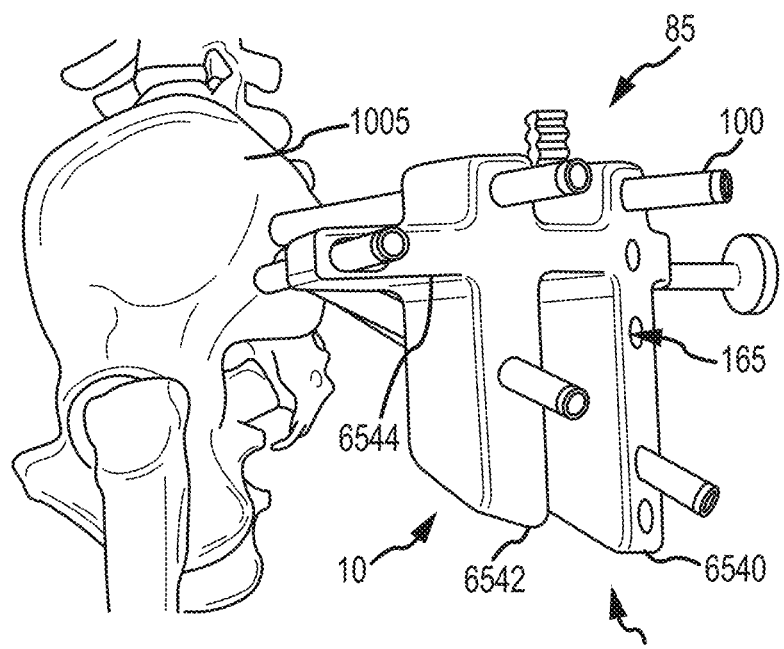
Figure 130G:
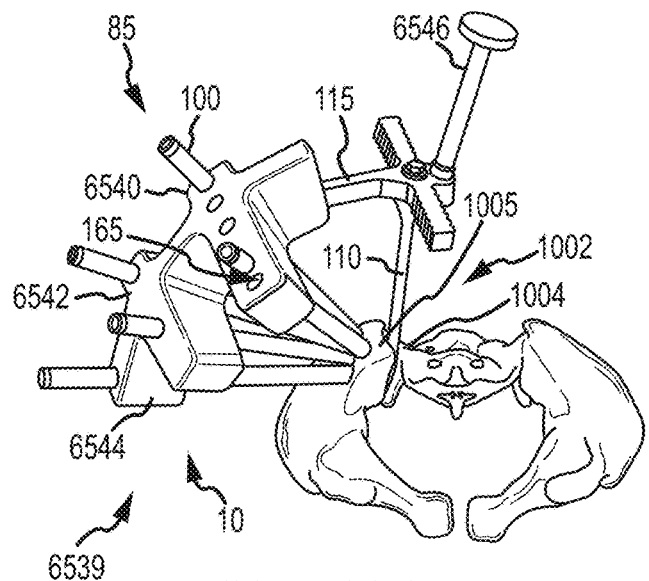

FIGS. 130A-130B show anterior views of the hip region with the system of FIGS. 129A-129C, wherein the ilium is shown and hidden, respectively.

FIGS. 130C-130G show anterior-superior-lateral, posterior, superior, lateral, and inferior views of the hip region with the system of FIGS. 129A-129C.

Figure 130H:
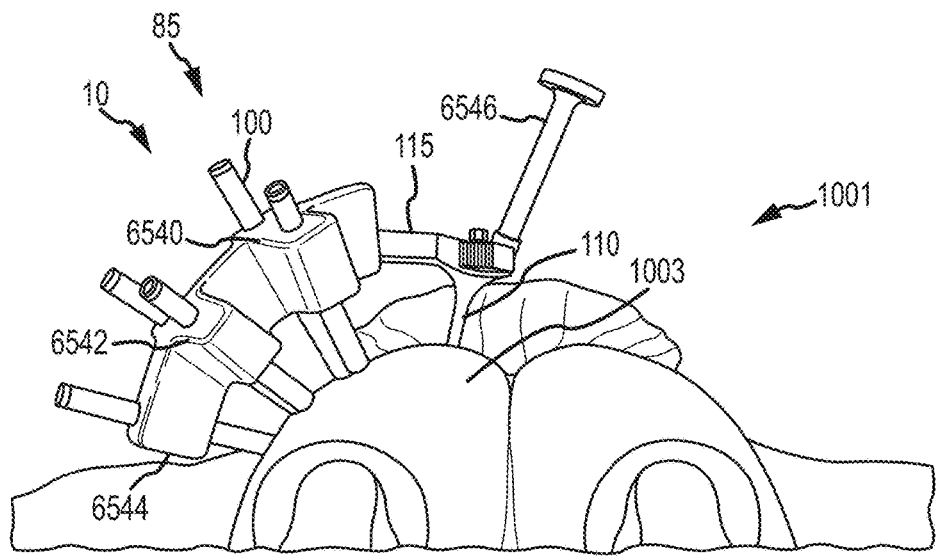
Figure 130I:
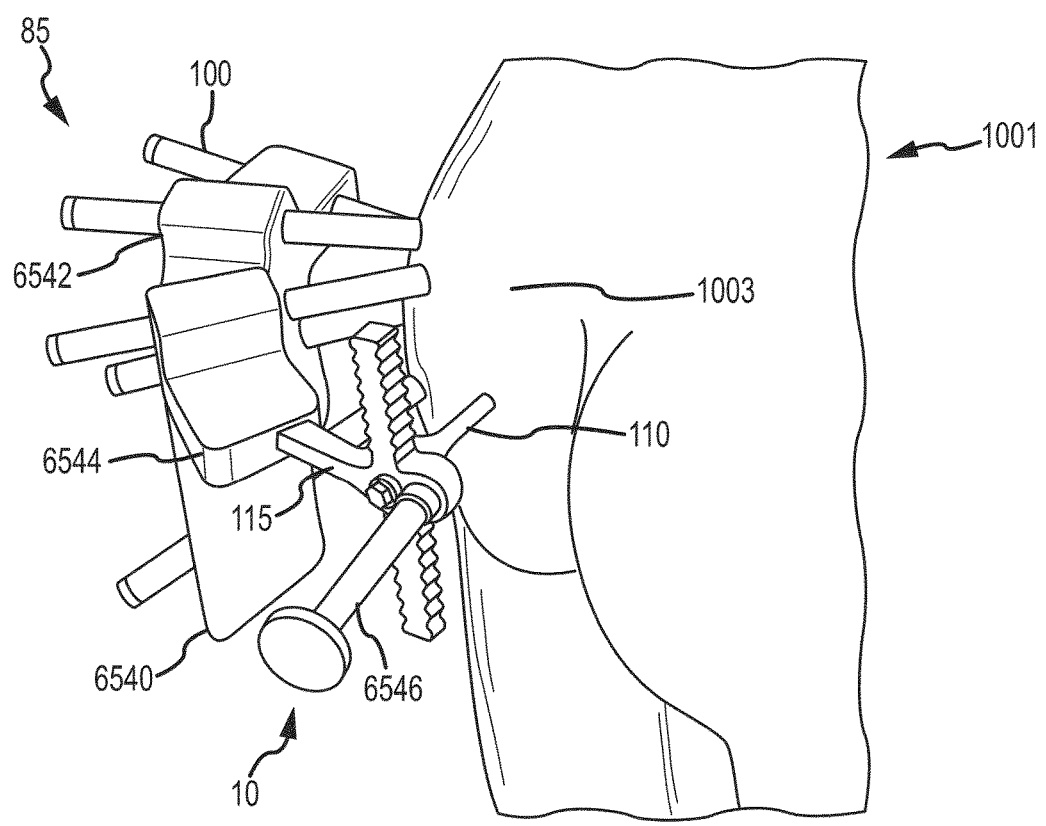

FIGS. 130H and 130I show inferior and posterior-lateral views of a patient, wherein the system of FIGS. 129A-129C is inserted through the soft tissue of the hip region.

FIGS. 131A-131B show isometric views of another embodiment of the system.

Figure 131C:
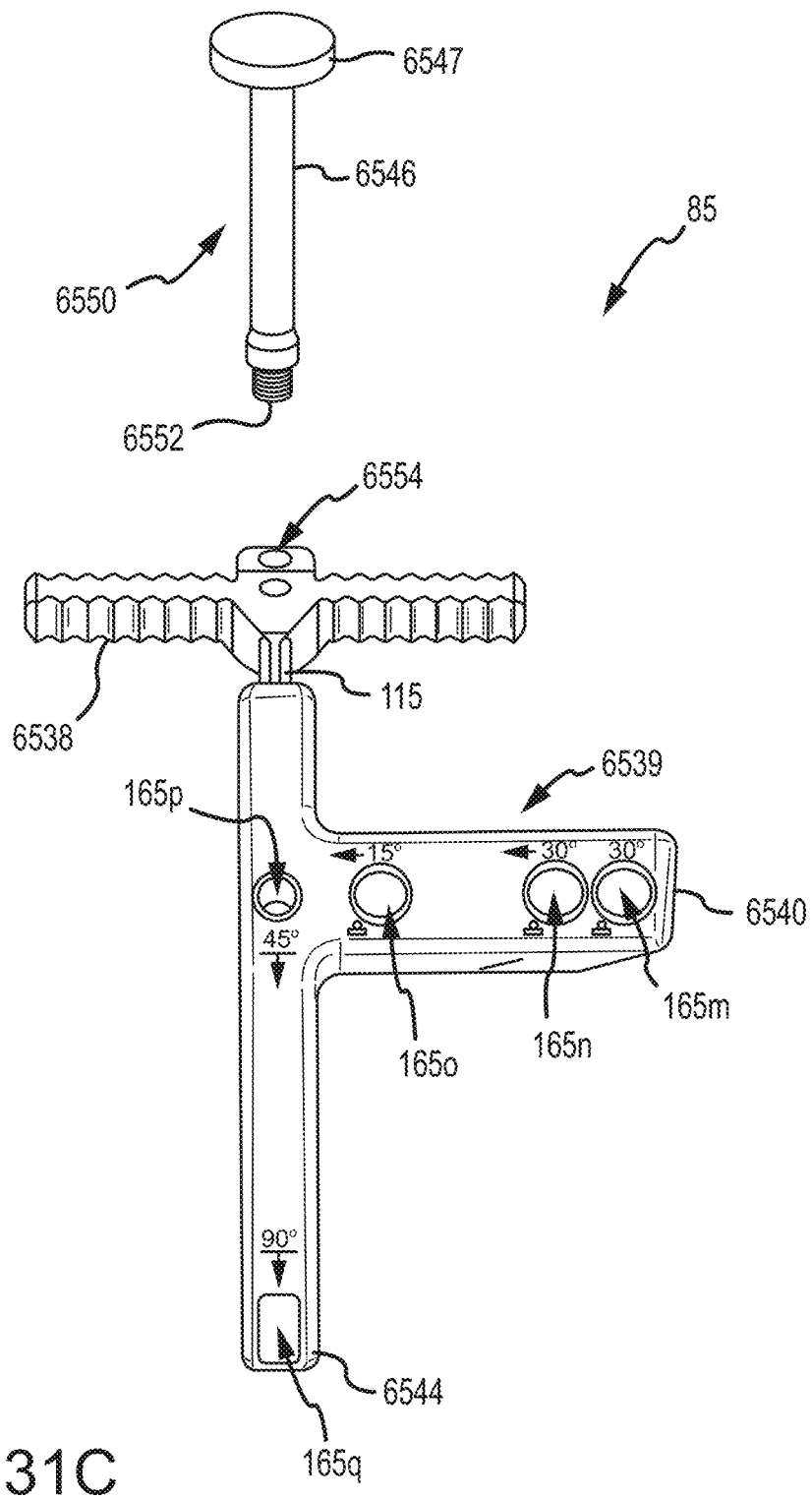

FIG. 131C shows an enlarged plan view of the arm assembly of the delivery tool of FIGS. 131A-131B.

Figure 131D:
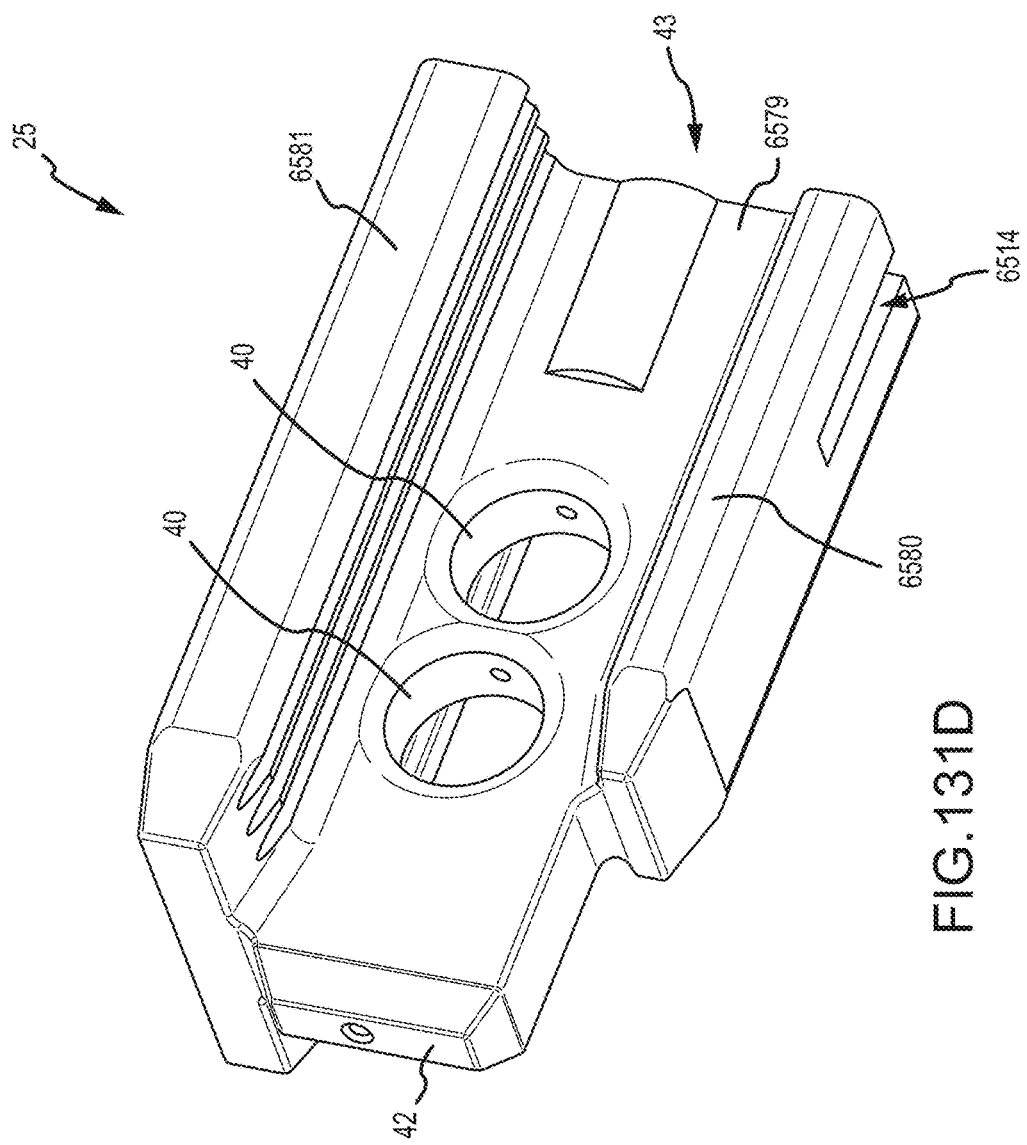
Figure 131E:
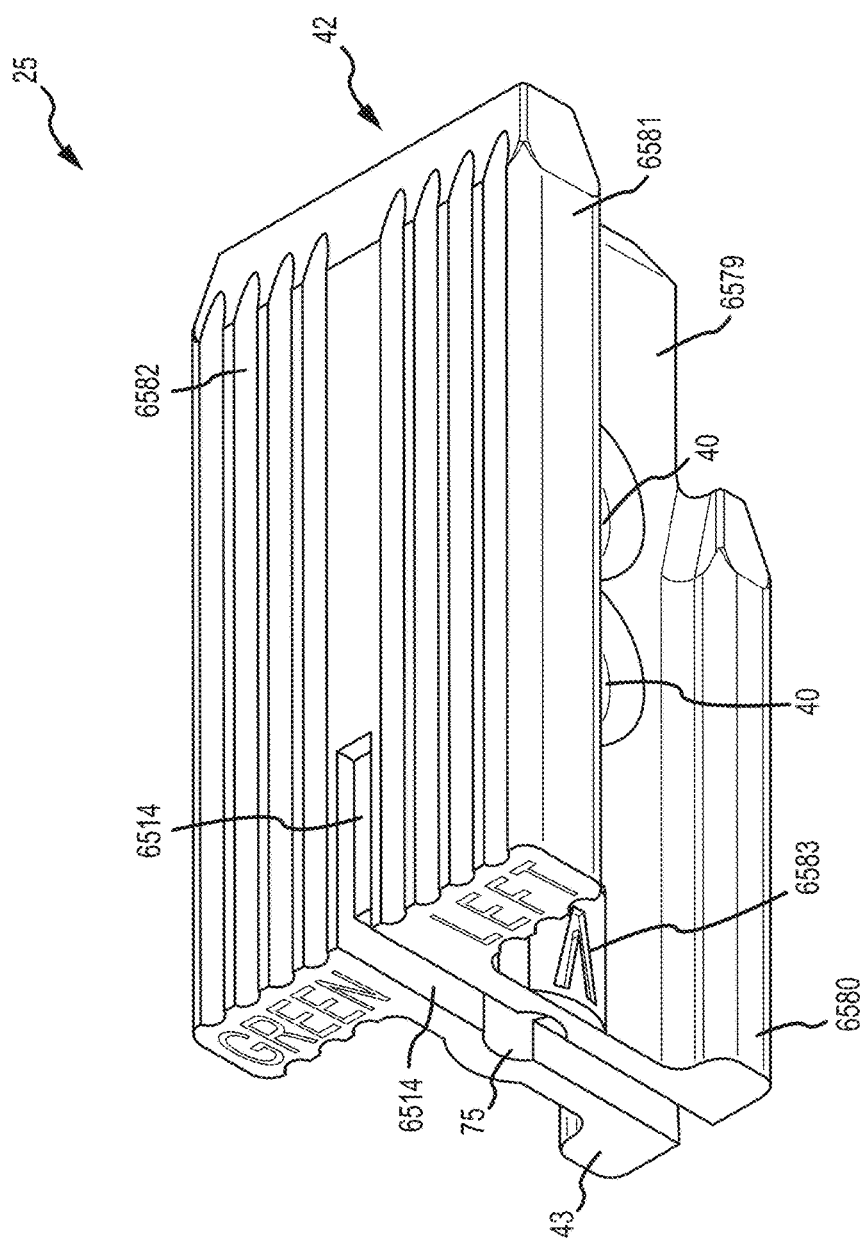

FIGS. 131D-131E are isometric view of a version of the implant of FIGS. 129D-121K adapted for use with the delivery system of FIGS. 131A-131C.

Figure 131F:
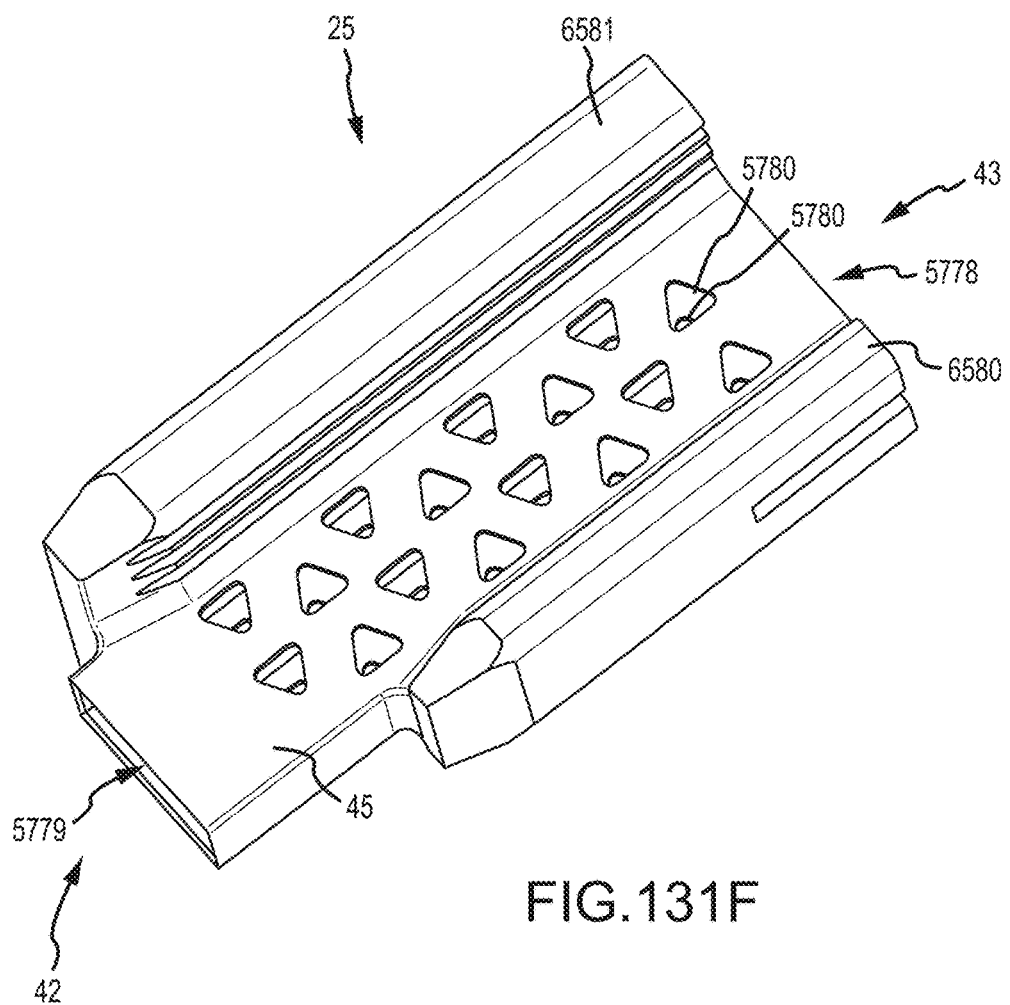

FIG. 131F is an isometric view of a version of the implant of FIGS. 129D-129K, wherein the body of the implant is hollow and configured to work with a distal end of an implant arm configured to remove cartilage.

Figure 131G:
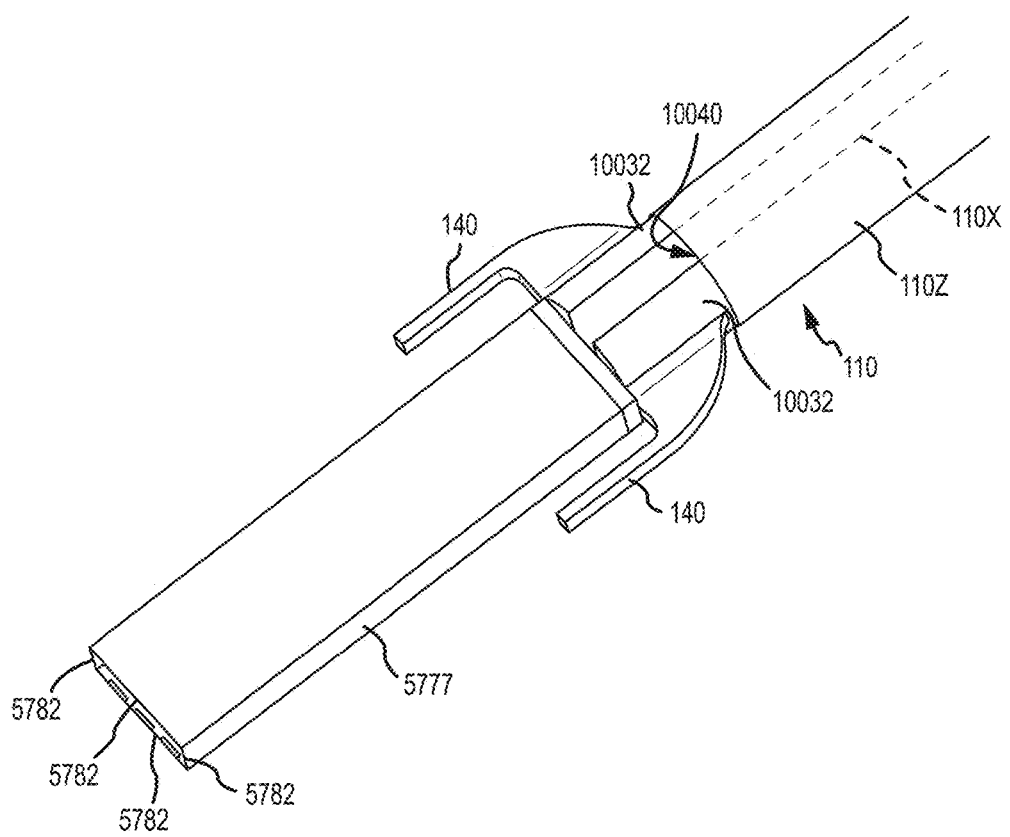

FIG. 131G is an isometric view of the distal end of the implant arm configured to be received in the hollow body of the implant of FIG. 131F, wherein the distal end of the implant arm is configured to remove cartilage.

Figure 131H:
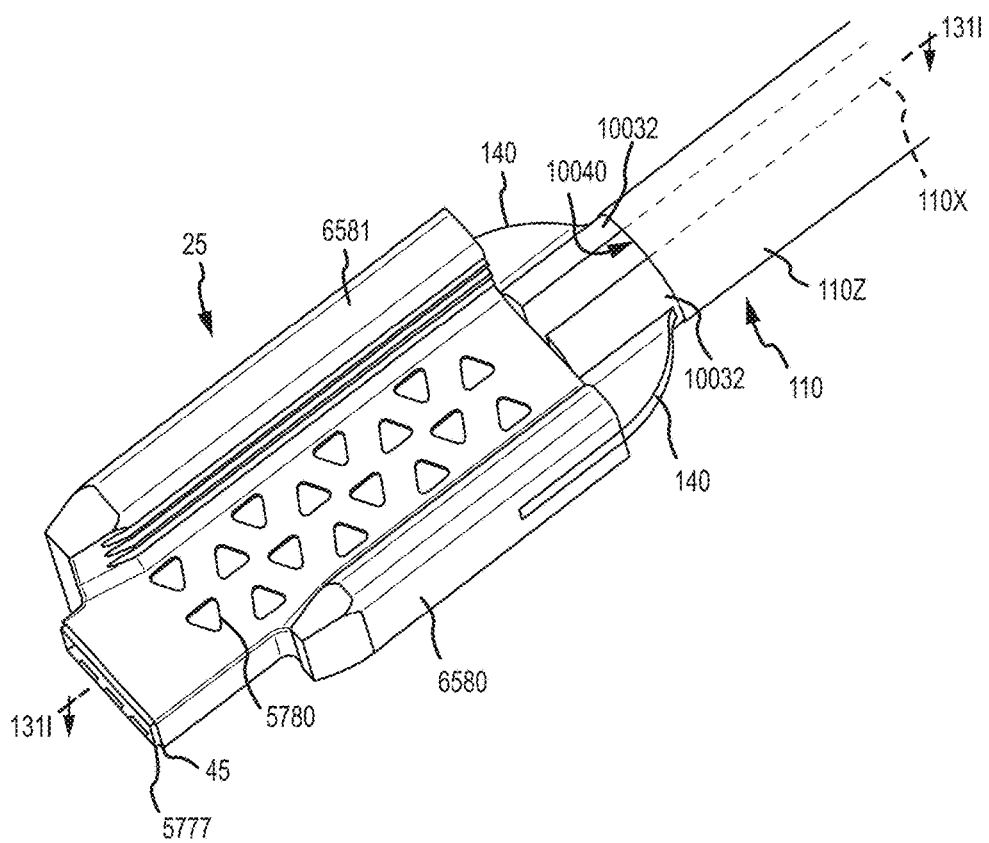

FIG. 131H is an isometric view of the implant arm distal end of FIG. 131G received in the implant of FIG. 131F.

Figure 131I:
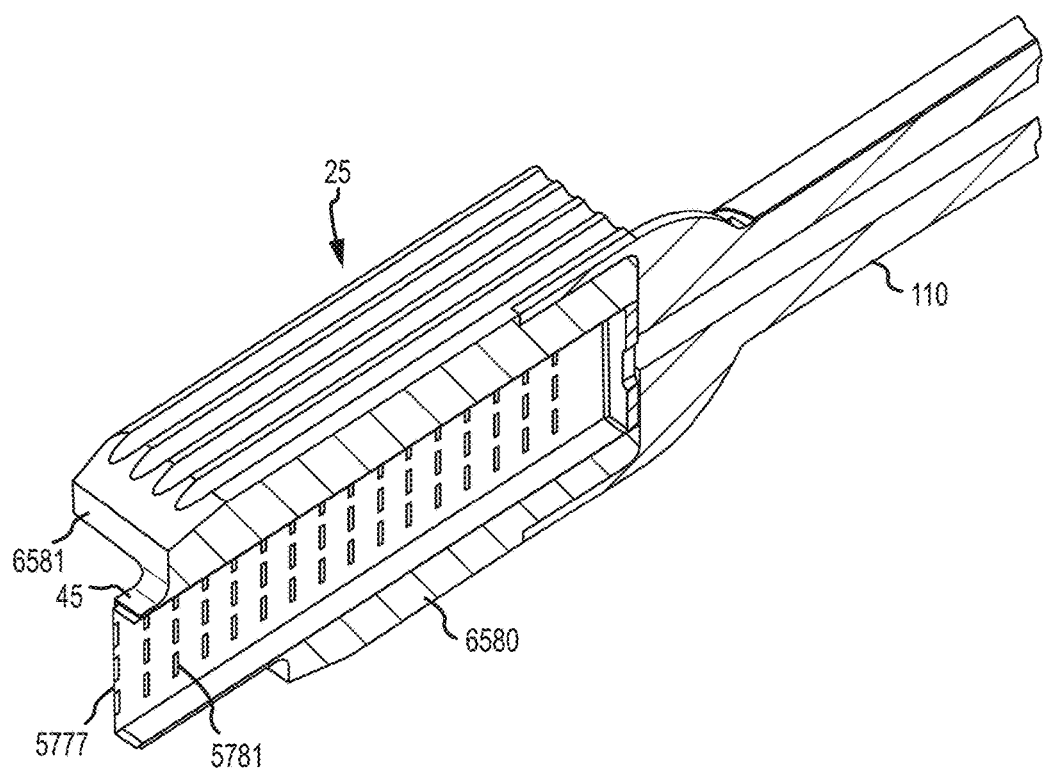

FIG. 131I is an isometric longitudinal cross section of the implant arm distal end and implant supported thereon as taken along section line 131I-131I of FIG. 131H.

Figure 132A:
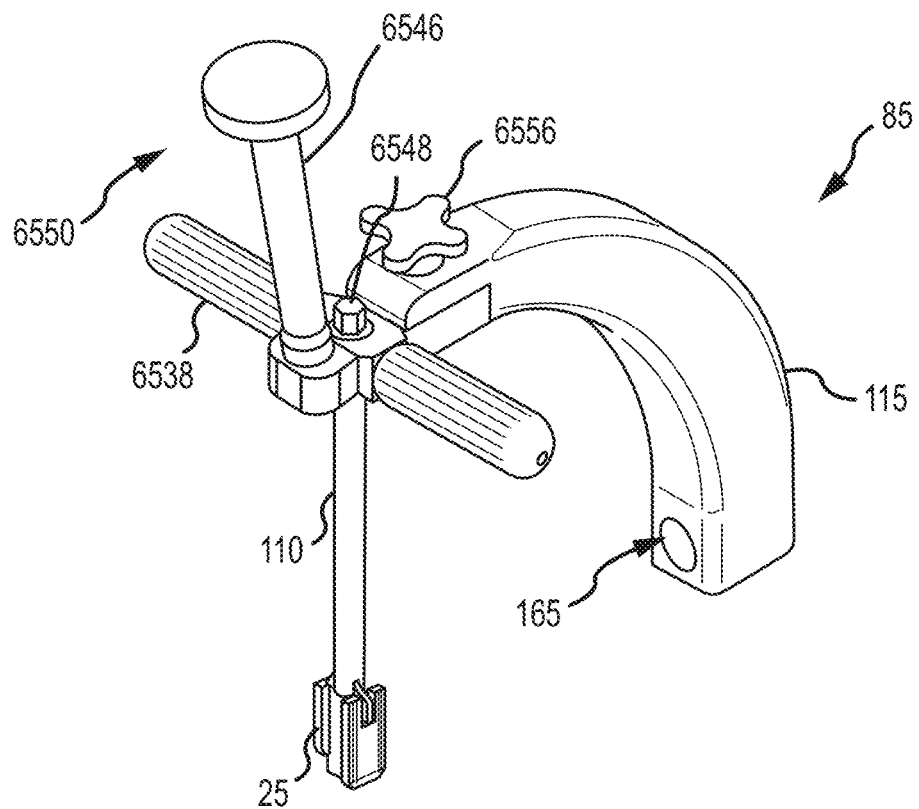

FIG. 132A is an isometric view of yet another embodiment of the system for fusing a sacroiliac joint.

Figure 132B:
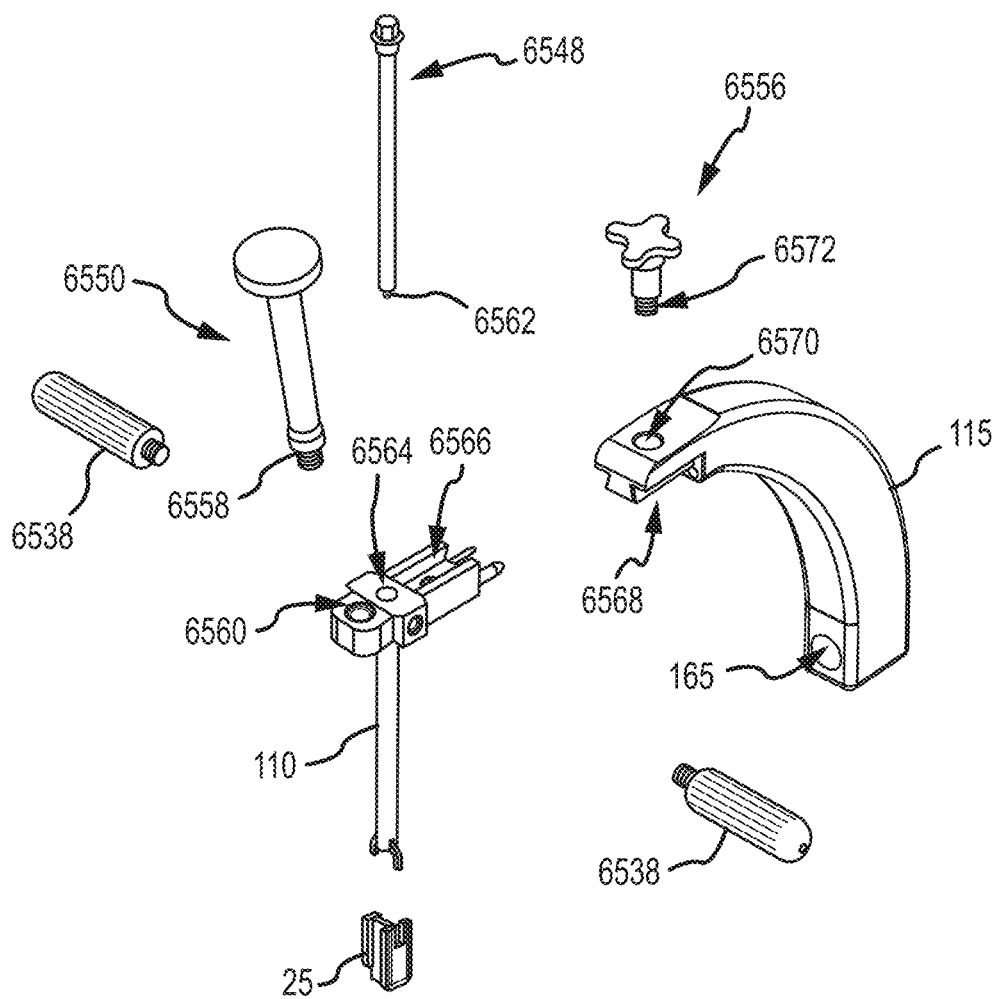

FIG. 132B is the same view as FIG. 132A, except the system is exploded to better illustrate its components.

Figure 133A:
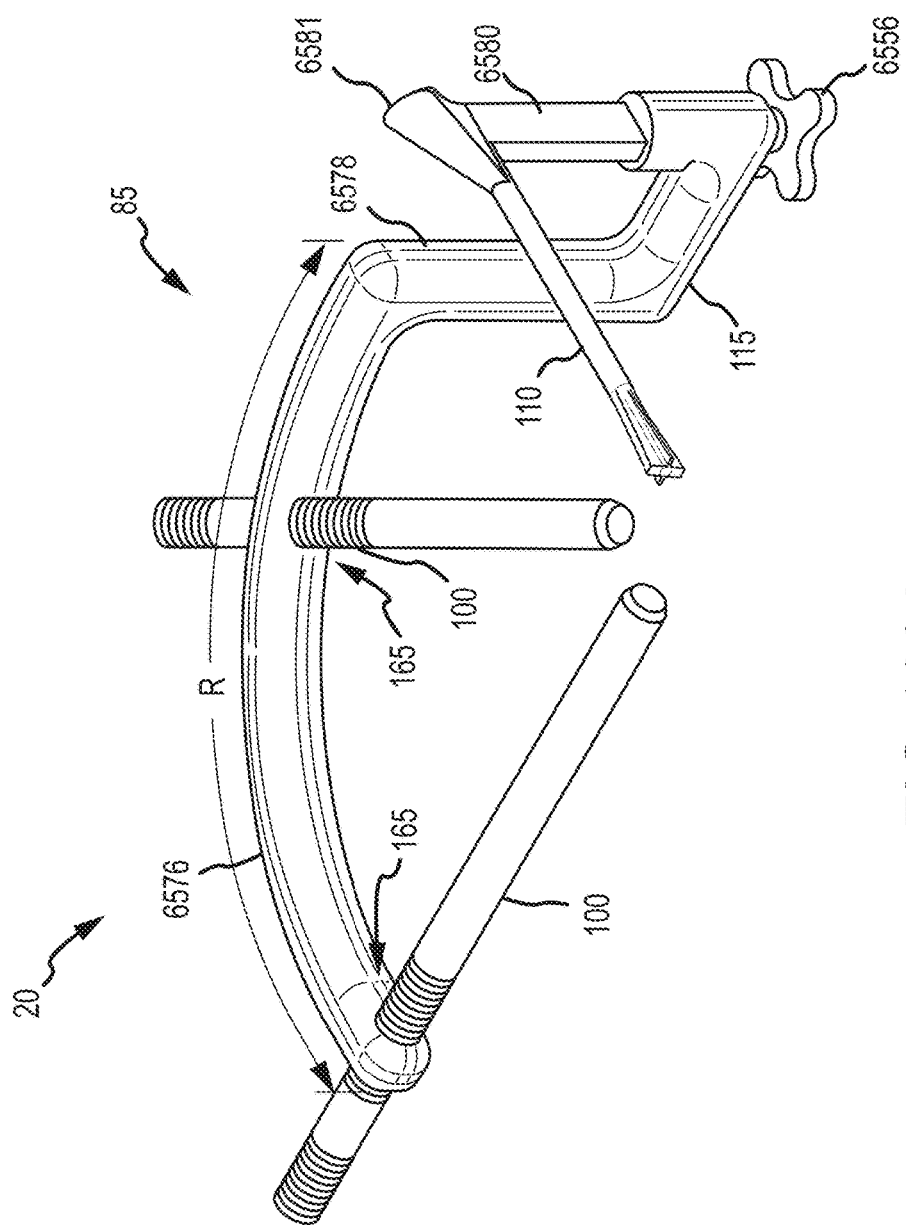

FIG. 133A is an isometric view of yet another embodiment of the system for fusing a sacroiliac joint.

Figure 133B:
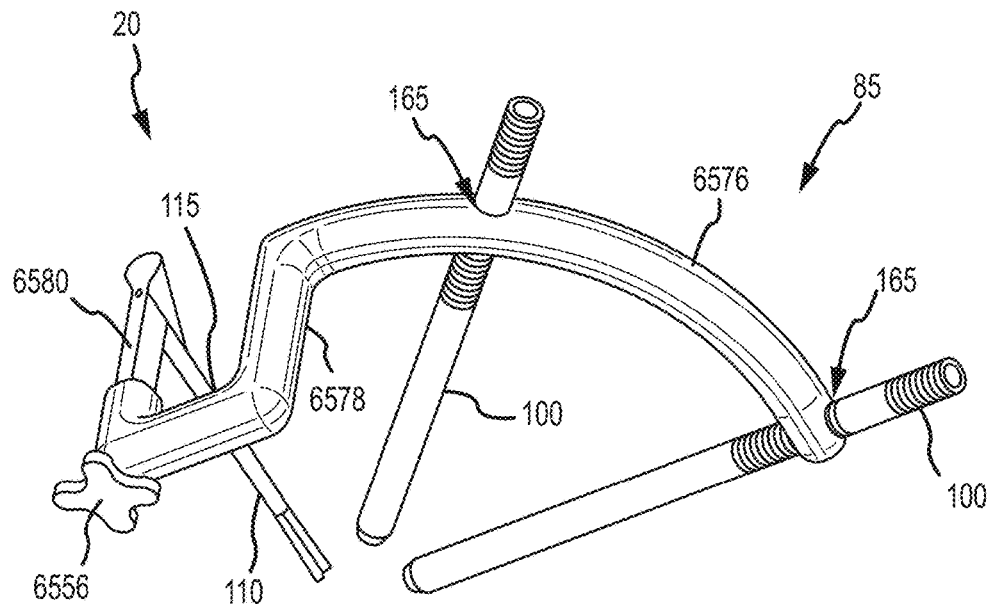

FIG. 133B shows another isometric view of the system of FIG. 133A.

Figure 133C:
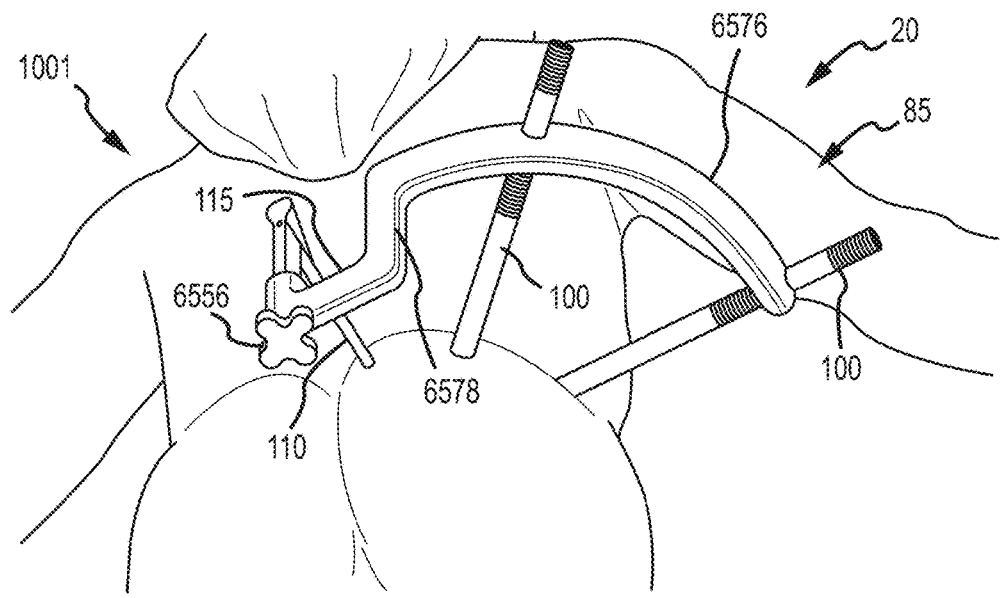

FIG. 133C shows the same view as FIG. 133B, except the system is inserted through the soft tissue of the hip region of the patient.

Figure 133D:
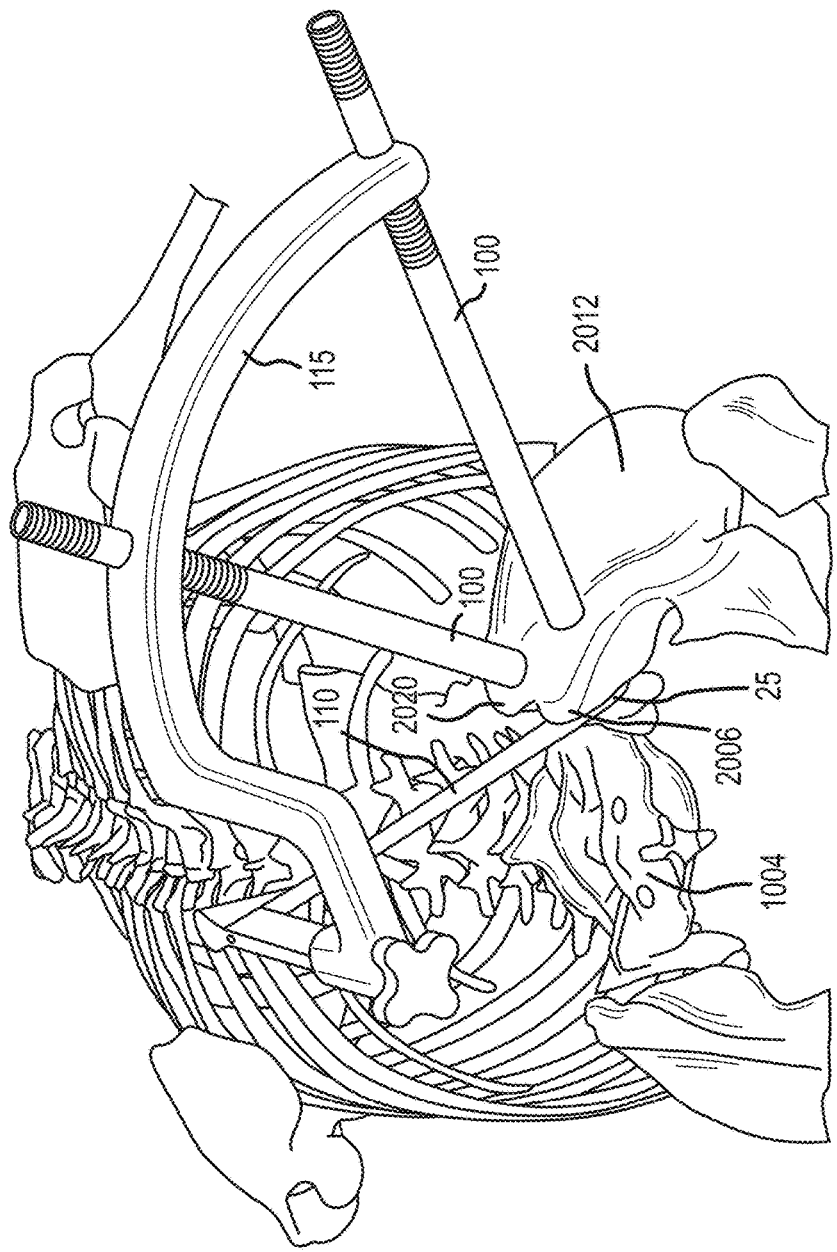

FIG. 133D is the same view as FIG. 133C, except the soft tissue is hidden to show the patient bone structure.

Figure 133E:
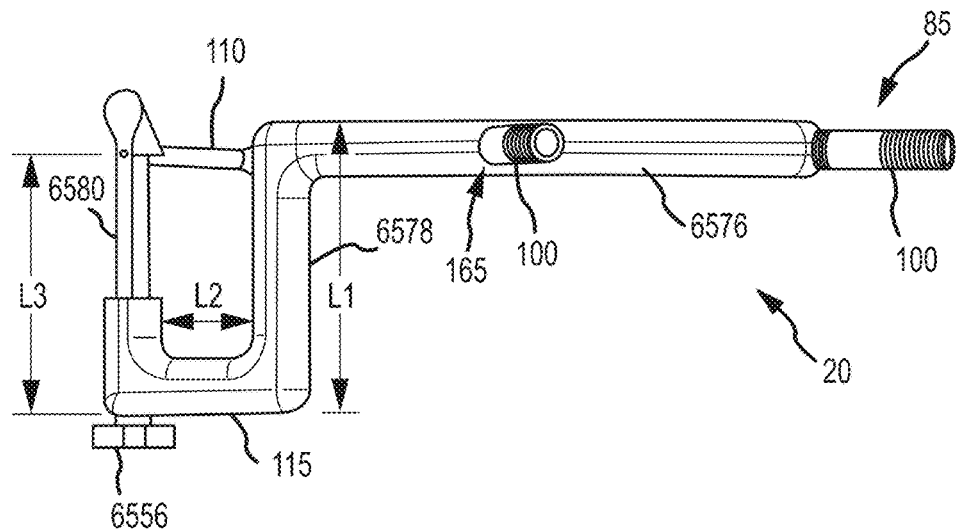

FIG. 133E shows a rear elevation view of the system of FIG. 133A.

Figure 133F:
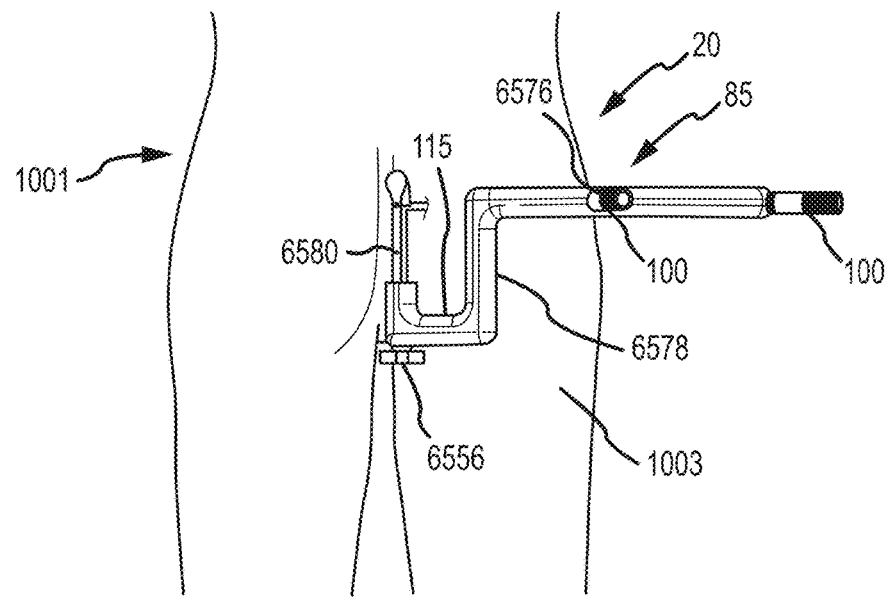

FIG. 133F shows the same view as FIG. 133E, except the system is inserted through the soft tissue of the hip region of the patient.

Figure 133G:
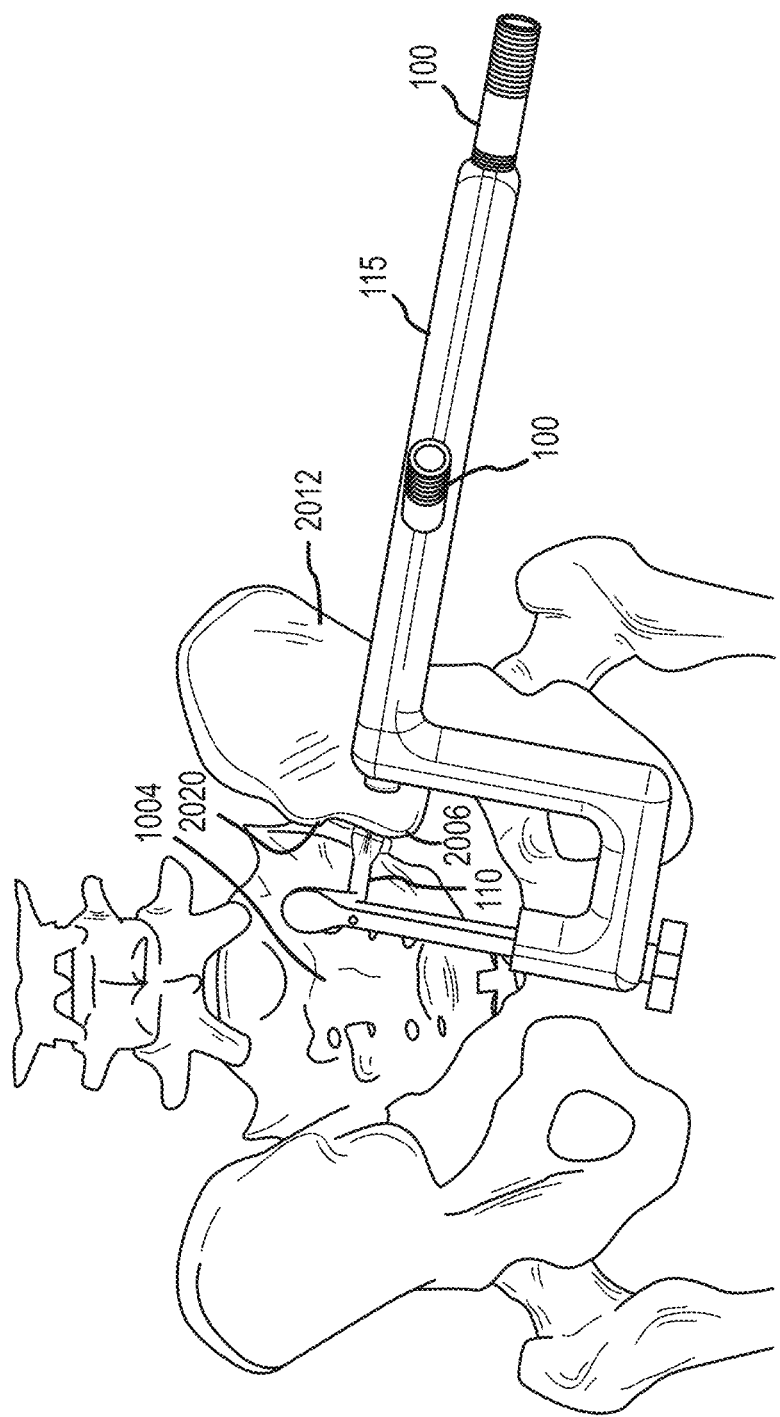

FIG. 133G is the same view as FIG. 133F, except the soft tissue is hidden to show the patient bone structure.

Figure 134A:
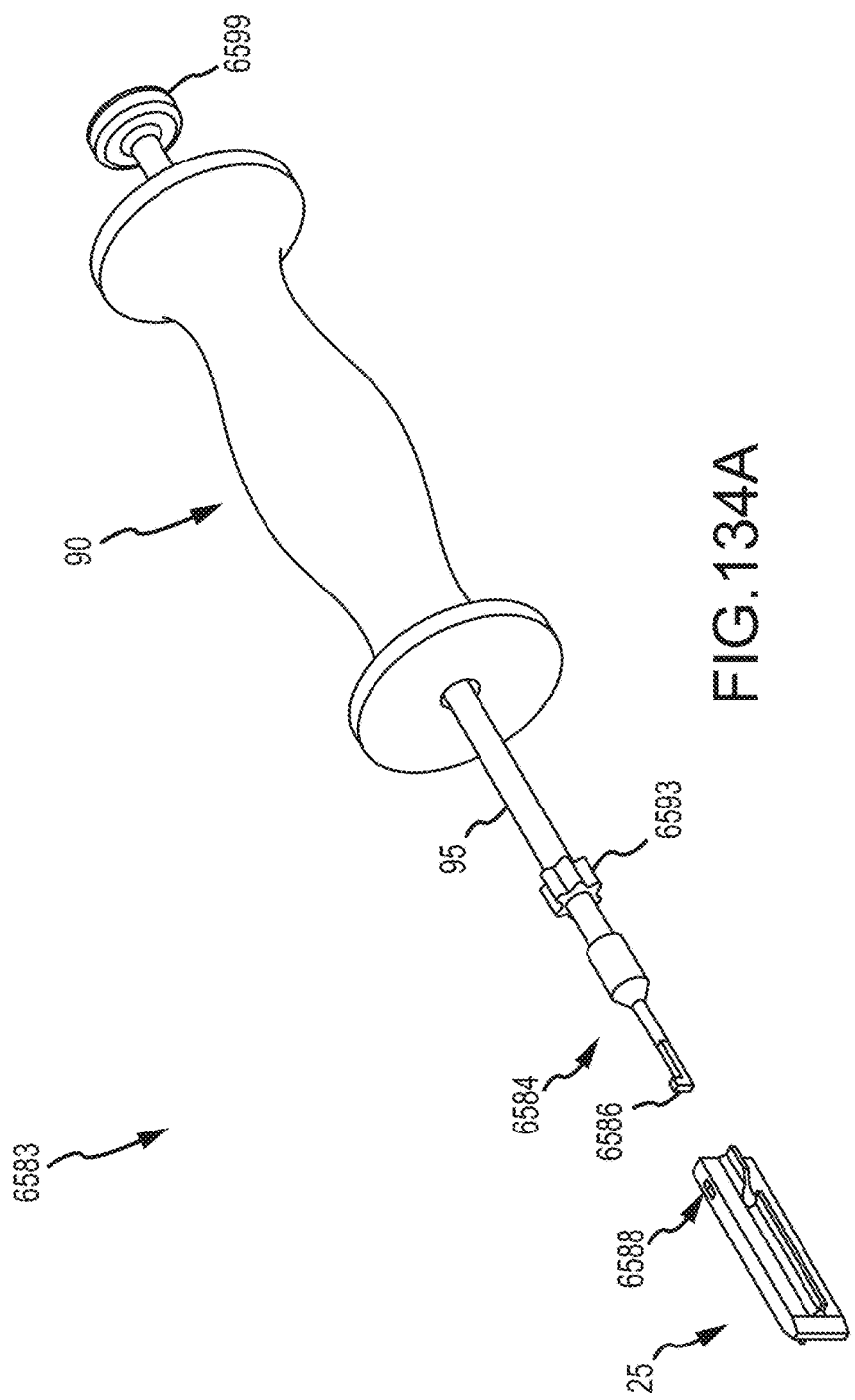

FIG. 134A illustrates an embodiment of a system for extracting an implant.

Figure 134B:
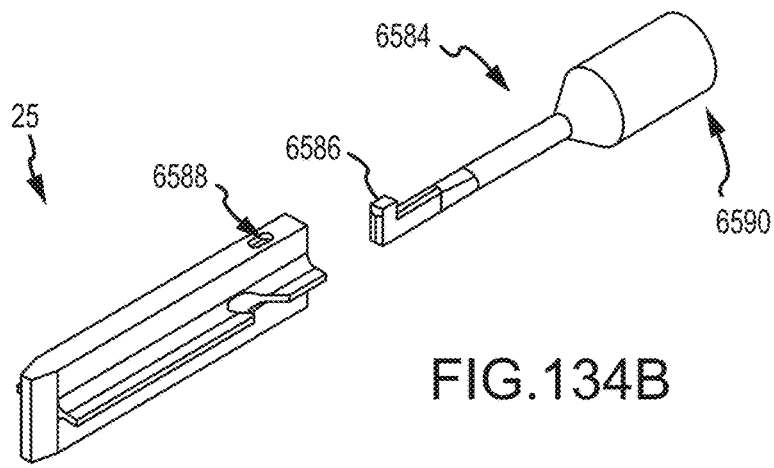
Figure 134C:
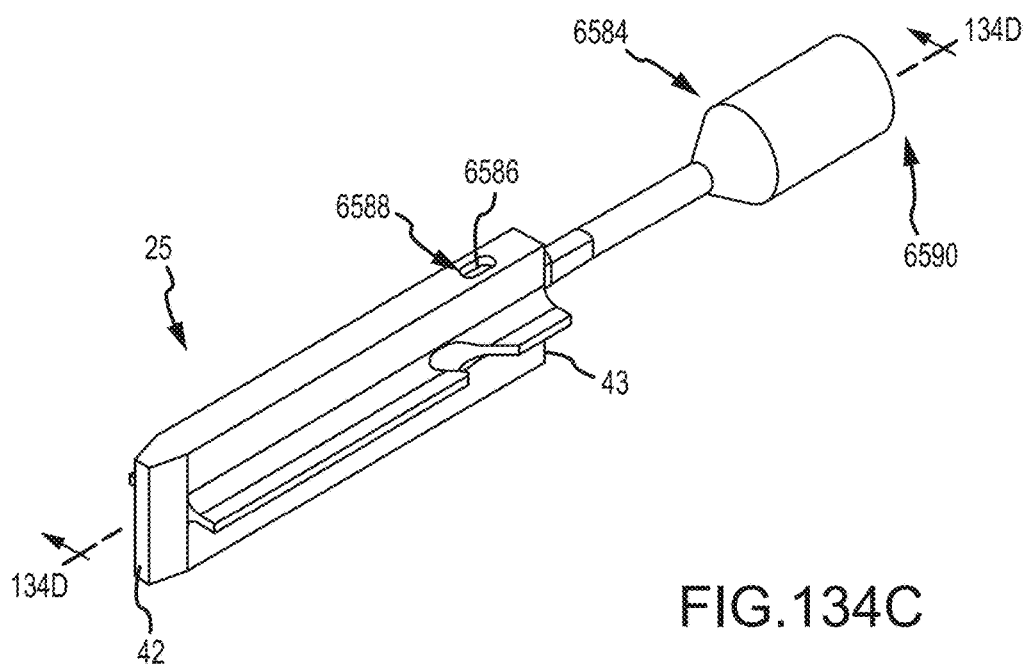

FIGS. 134B-134C show enlarged views of the distal end of the system of FIG. 134A, wherein the distal end is decoupled and coupled to the implant, respectively.

Figure 134D:
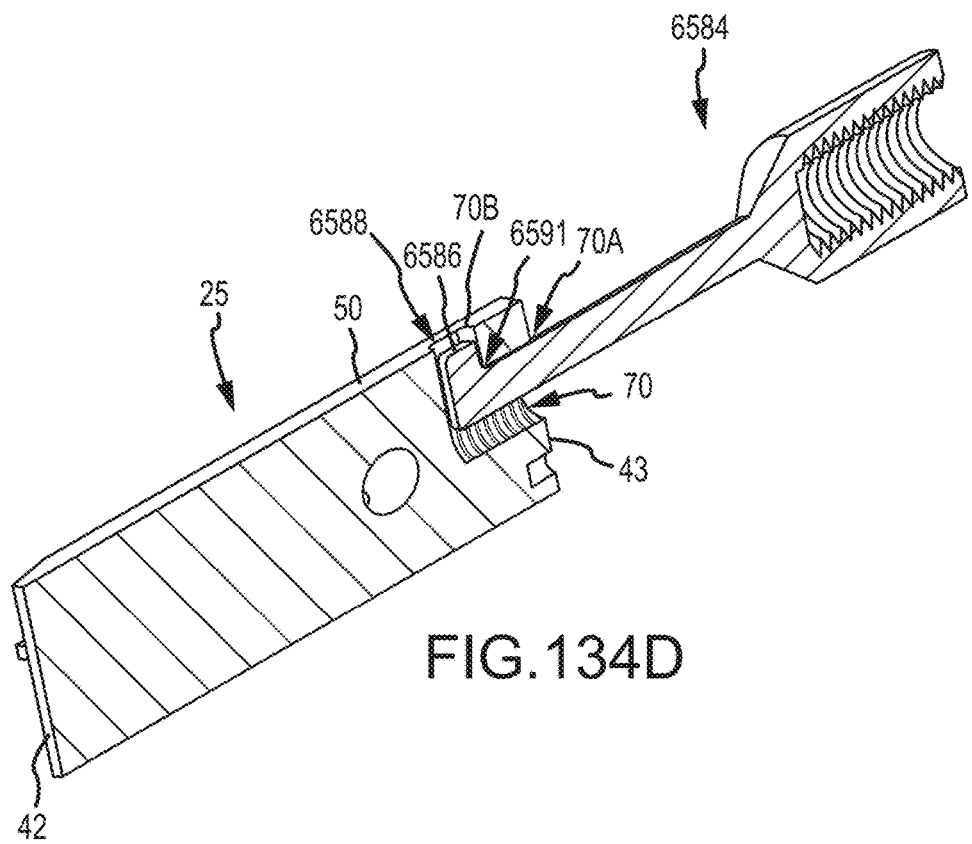

FIG. 134D is a longitudinal cross section as taken along section line 134D-134D of FIG. 134C.

Figure 134E:
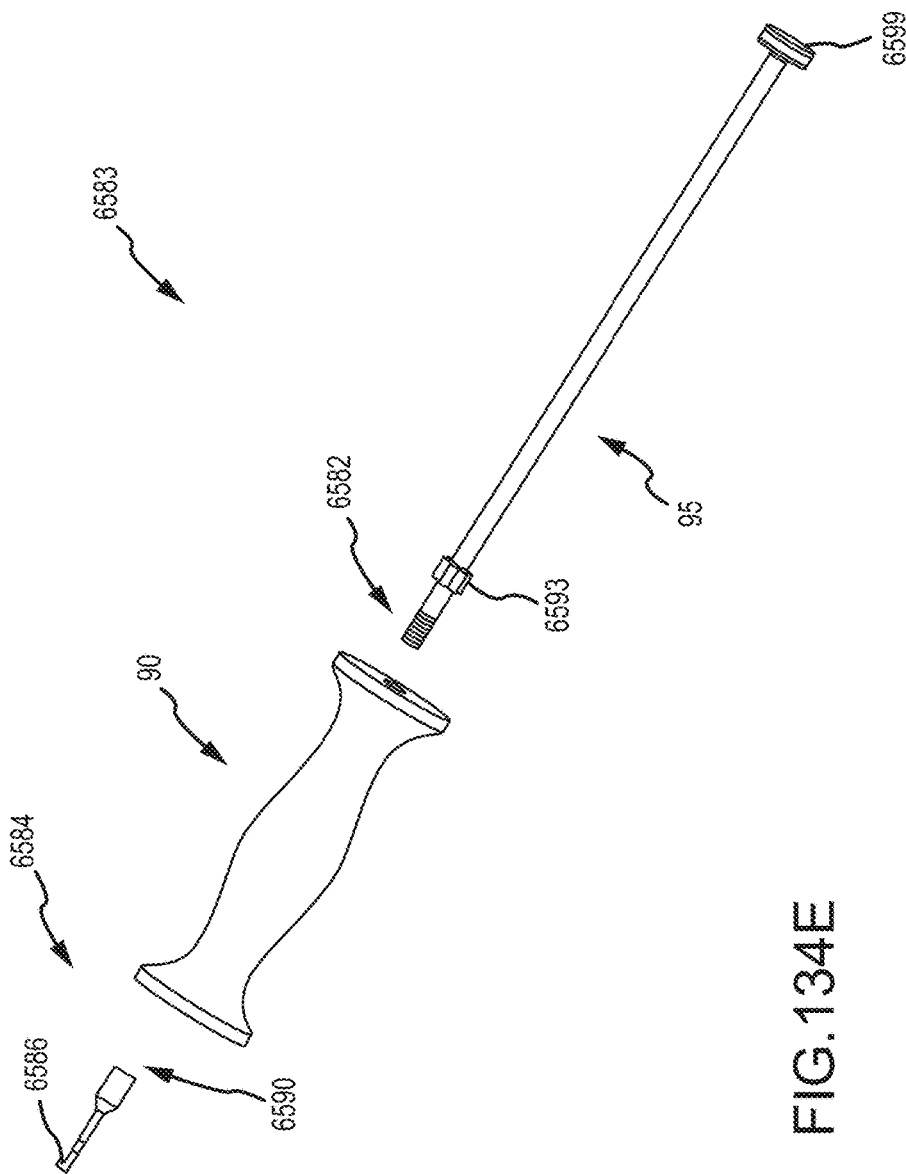

FIG. 134E is the same view as FIG. 134A, except the system is exploded to better illustrate its components.

Figure 134F:
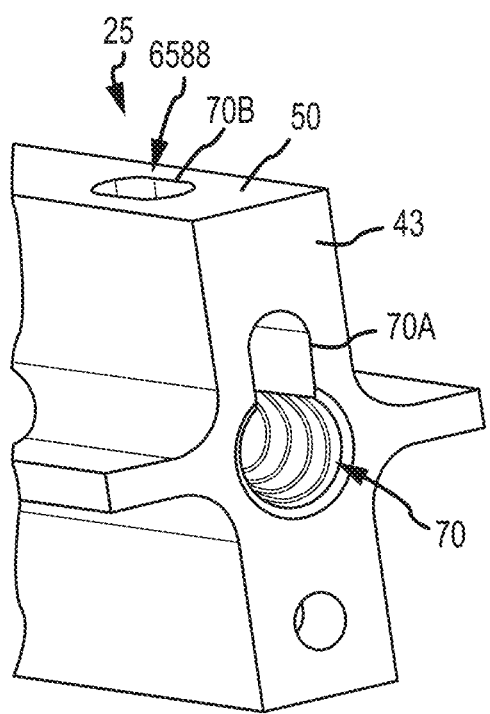

FIG. 134F is an isometric view of the proximal end of the implant of FIGS. 134B-134C.

Figure 135A:
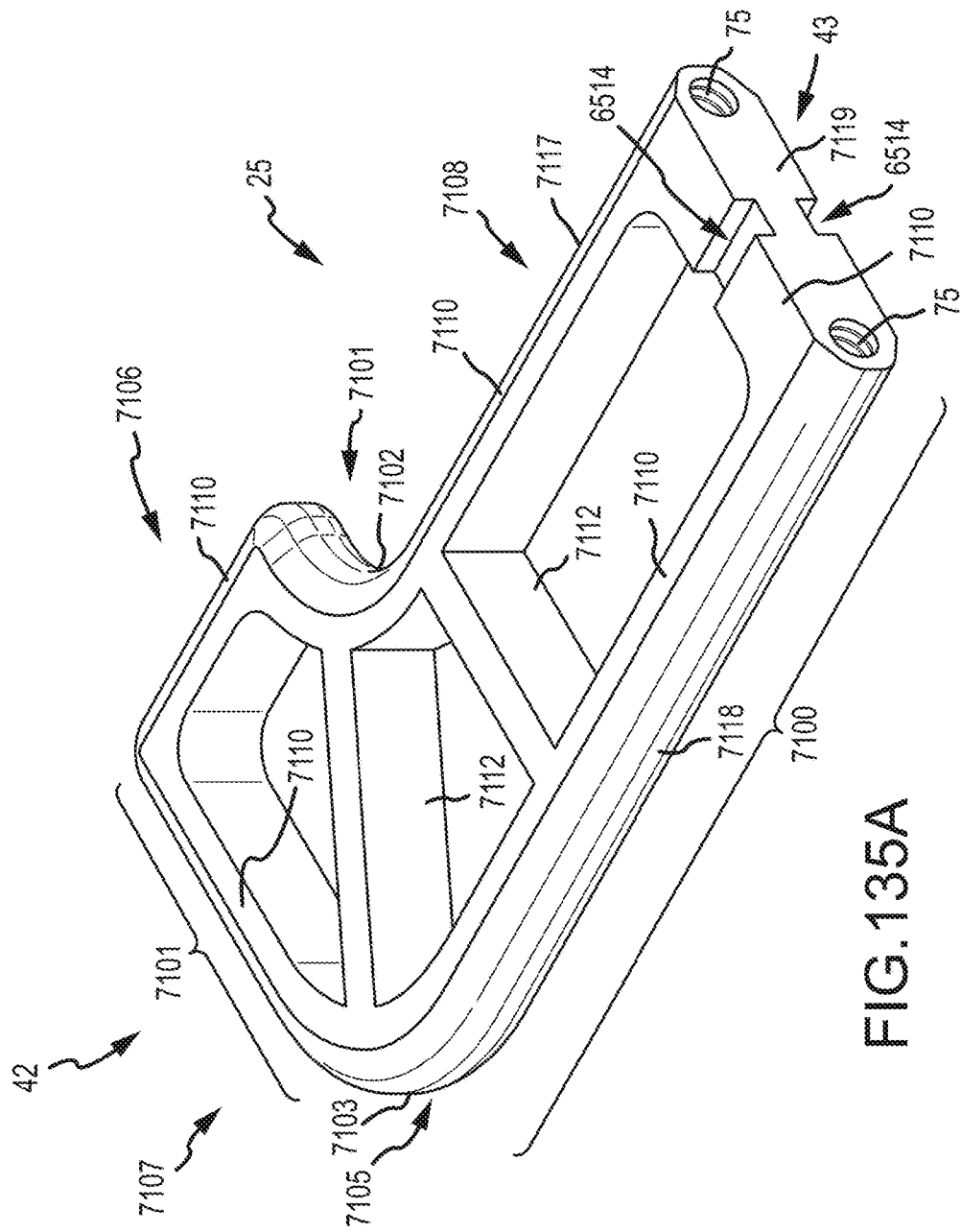
Figure 135B:
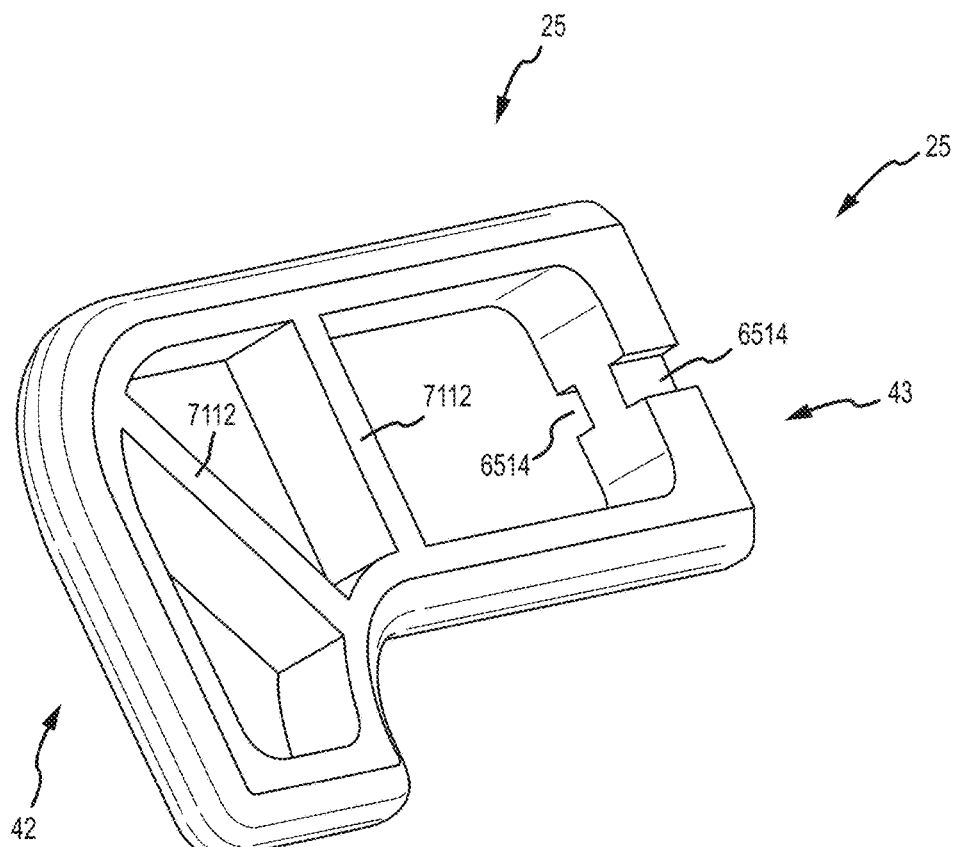
Figure 135C:
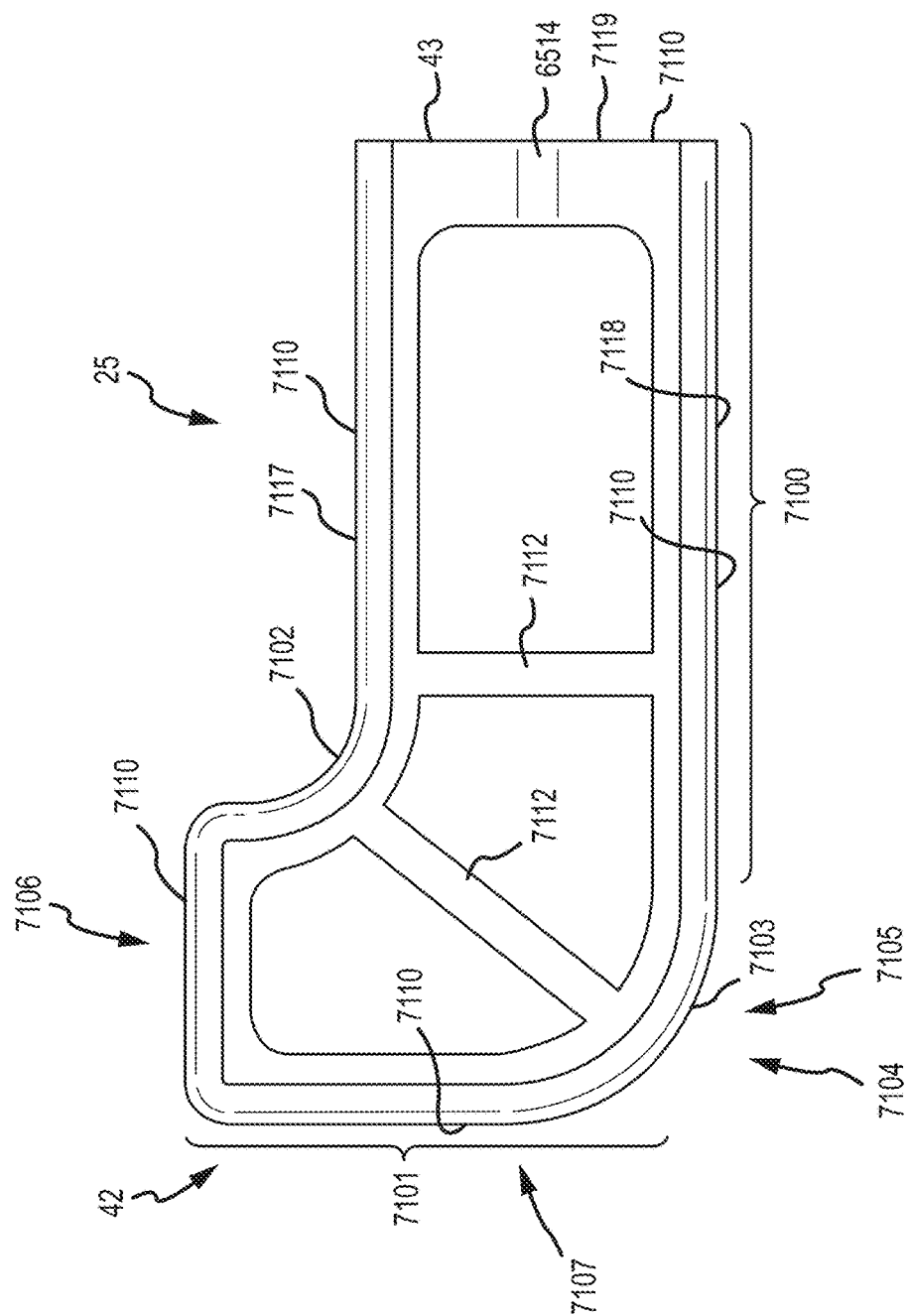

FIGS. 135A-135C are respectively a first isometric, a second isometric and a plan view of an implant embodiment having a shape that generally mimics or resembles that of a sacroiliac joint space as viewed from a substantially lateral view.

FIGS. 136A-136D are generally opposite isometric views of an implant embodiment that is configured to transition from a generally linear, rectangular arrangement (shown in FIGS. 136A-136B) to a boot or L-shaped configuration (shown in FIGS. 136C-136D) that generally fills and/or mimics the shape of the sacroiliac joint space.

Figure 136A:
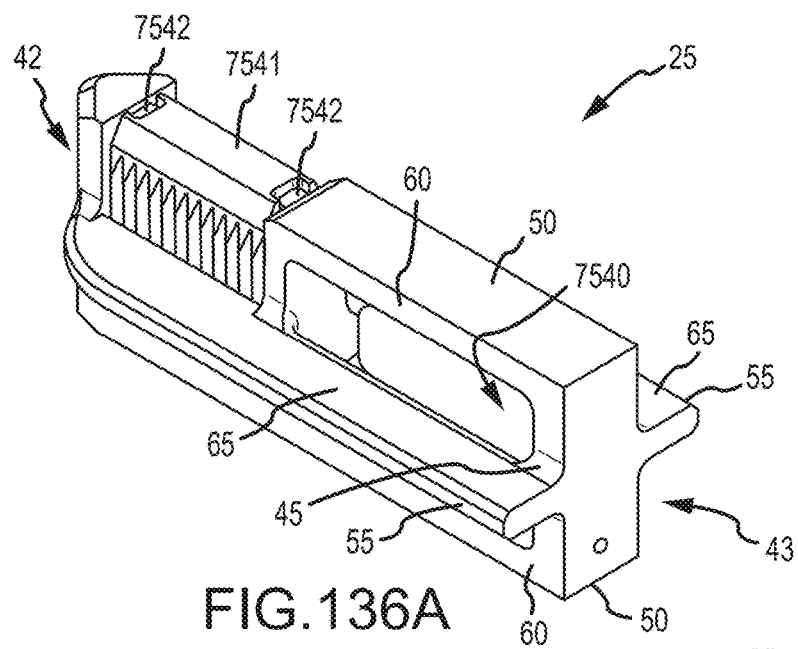
Figure 136B:
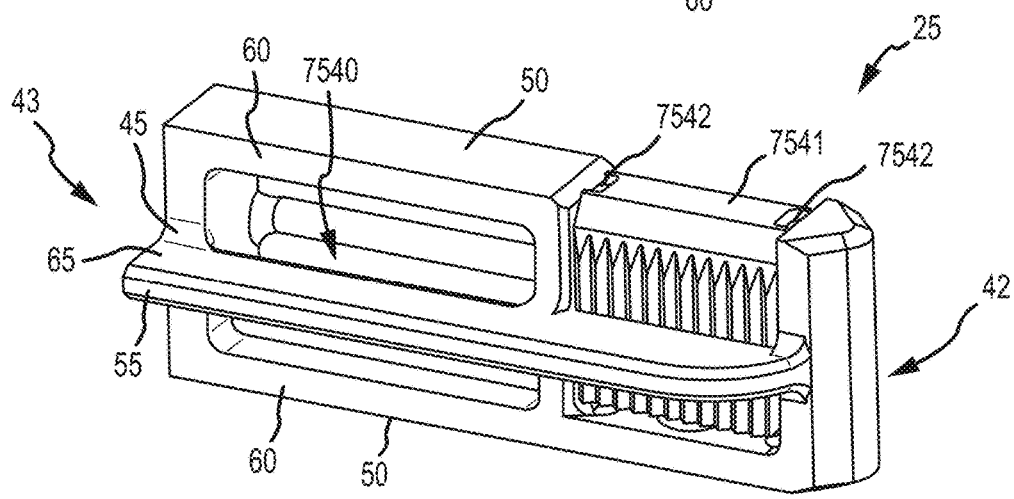
Figure 136C:
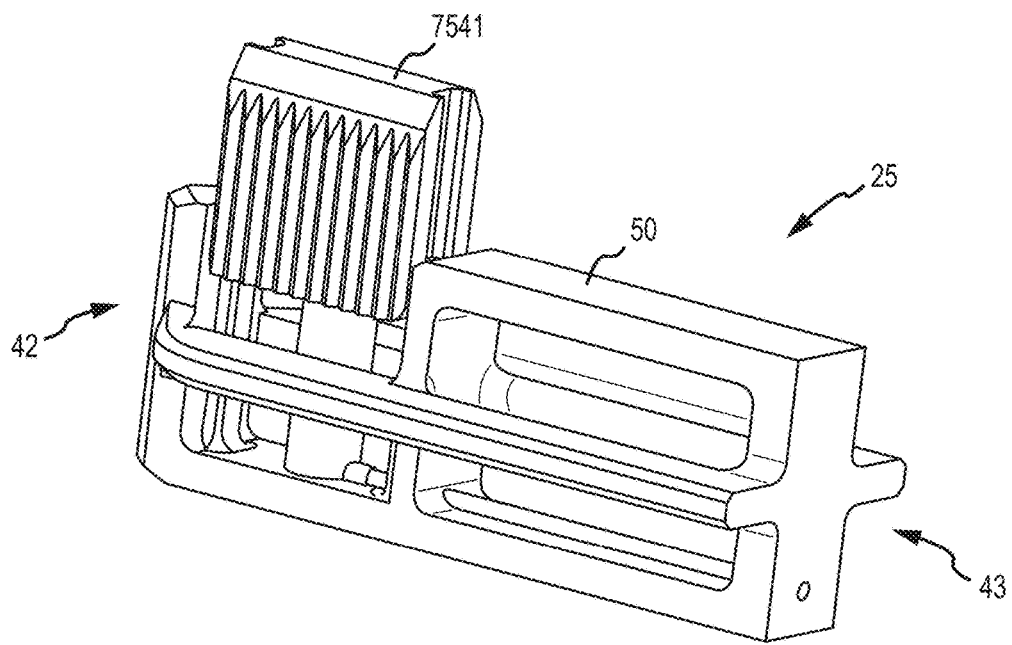
Figure 136D:
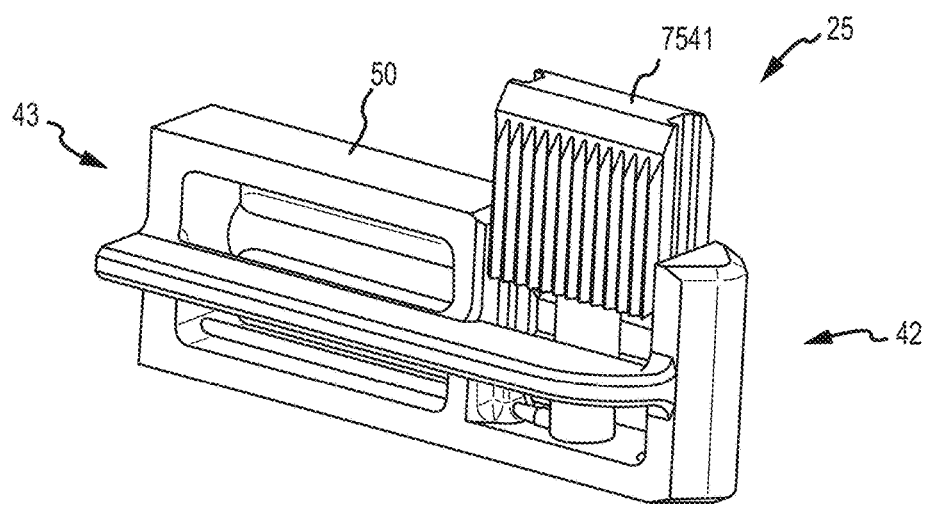
Figure 136E:
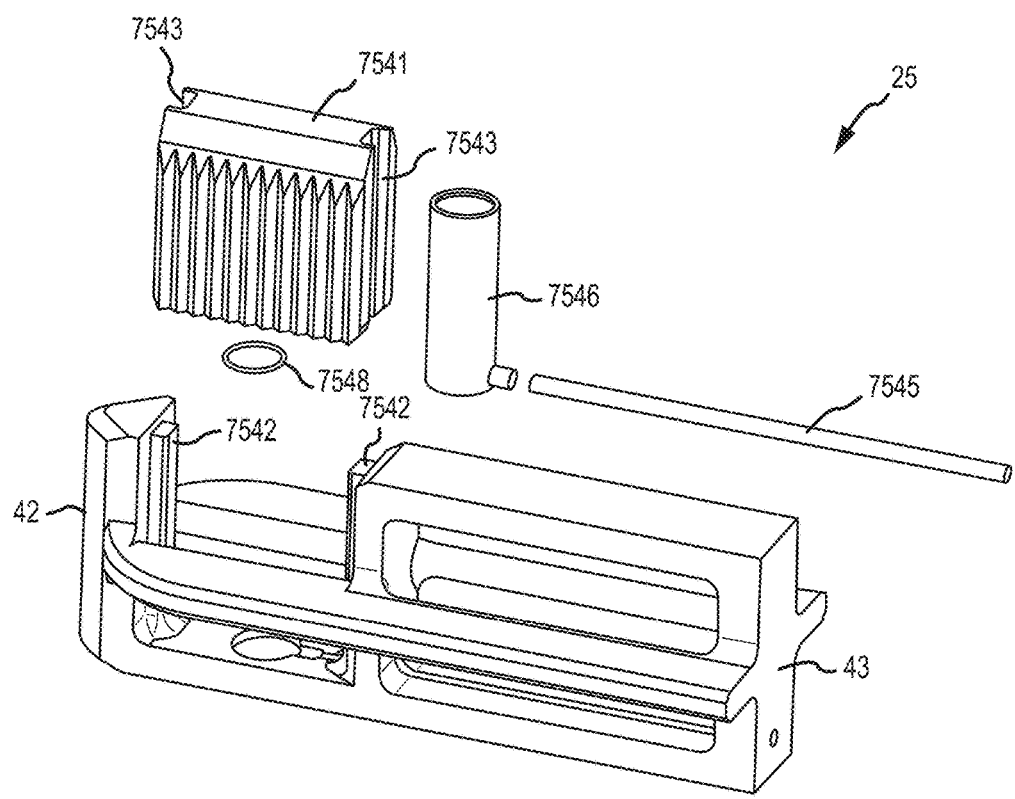

FIG. 136E is an exploded isometric view of the implant of FIGS. 136A-136D.

Figure 136F:
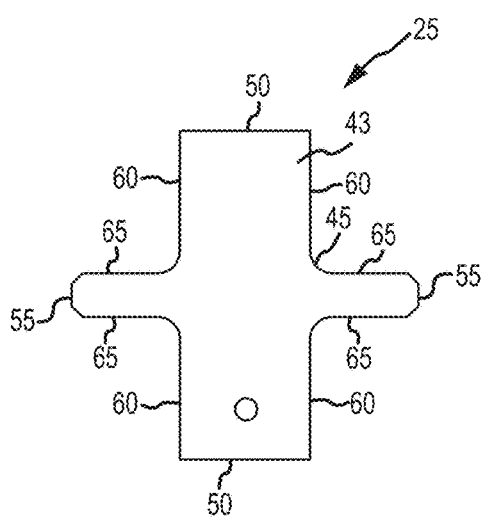
Figure 136G:
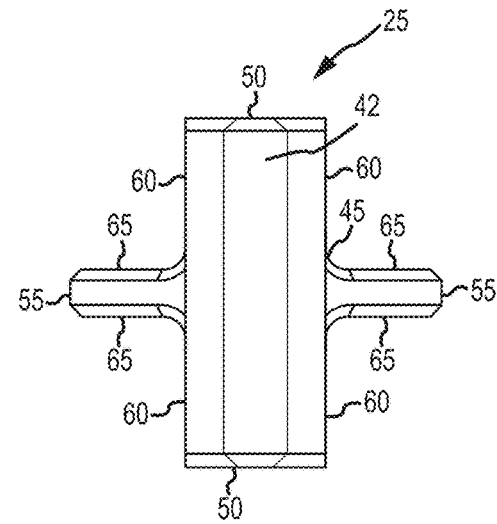

FIGS. 136F and 136G are, respectively, proximal and distal elevations of the implant of FIGS. 136A-136D.

Figure 136H:
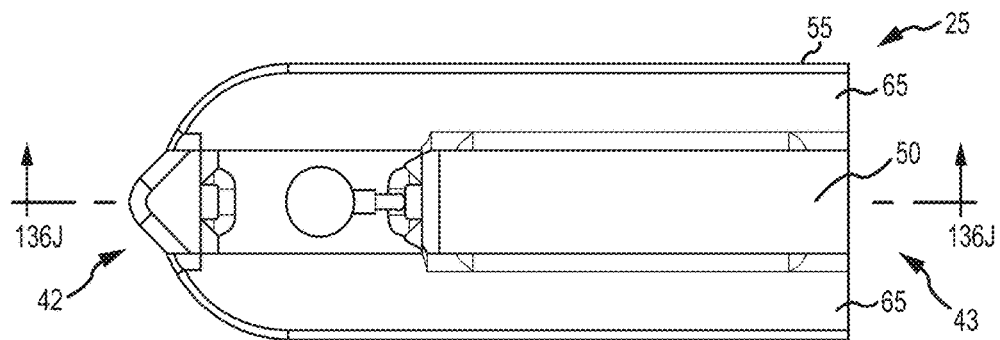
Figure 136I:
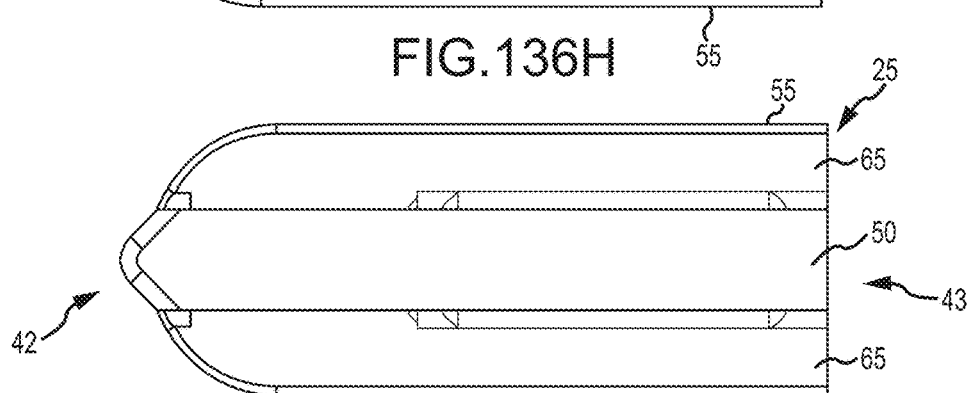

FIGS. 136H and 136I are, respectively, top and bottom plan views of the implant of FIGS. 136A-136D.

FIG. 136I is a longitudinal cross sectional elevation of the implant of FIGS. 136A-136D as taken along section line 136J-136J.

Figure 136J:
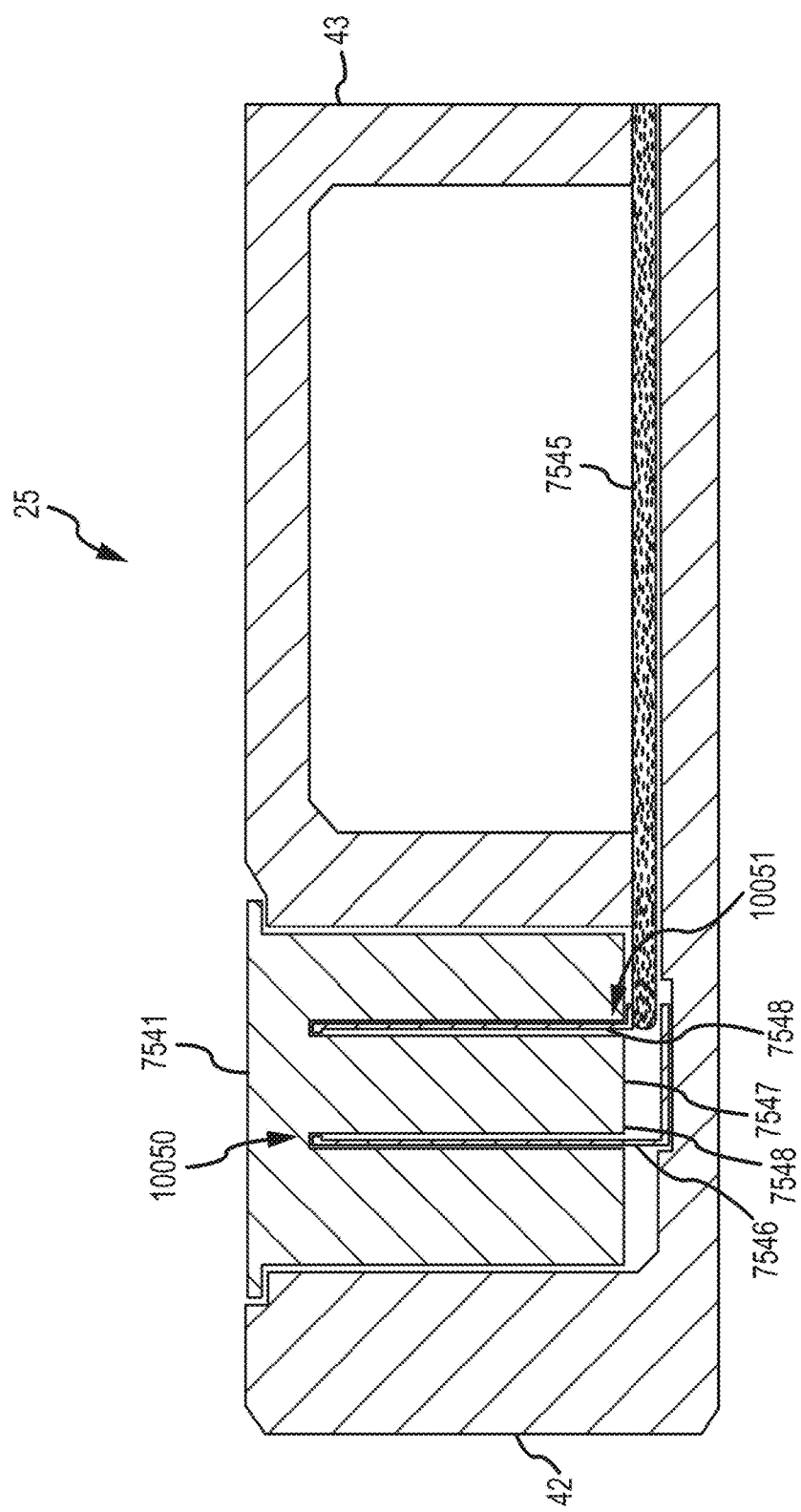
Figure 136L:
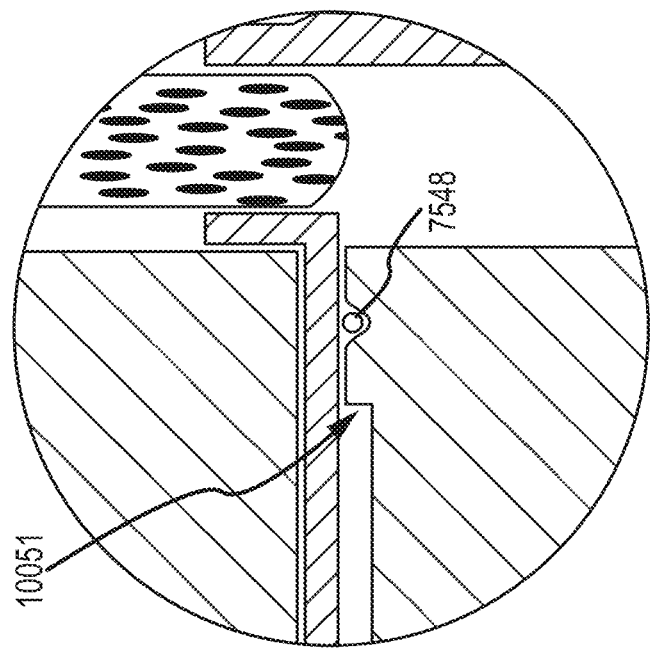
Figure 136K:
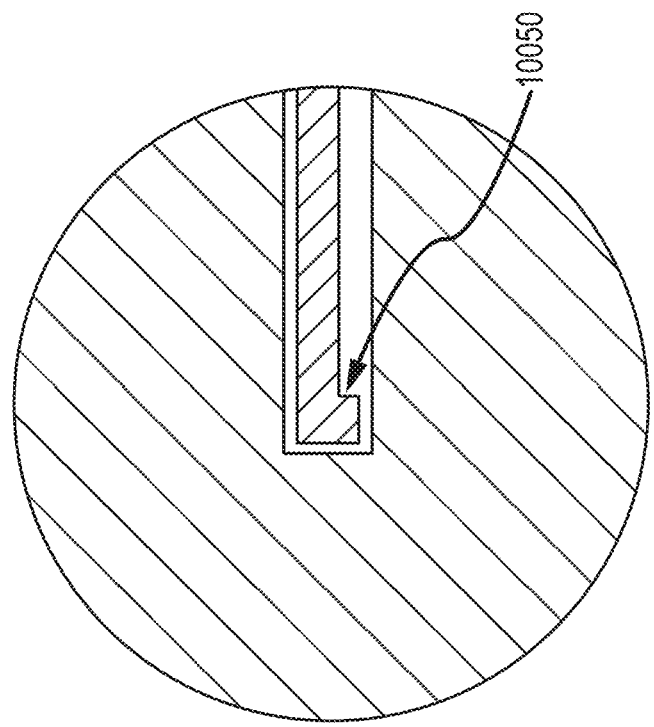

FIGS. 136K and 136L are respective enlarged views of the upper and lower cylinder regions of FIG. 136J.

Figure 137A:
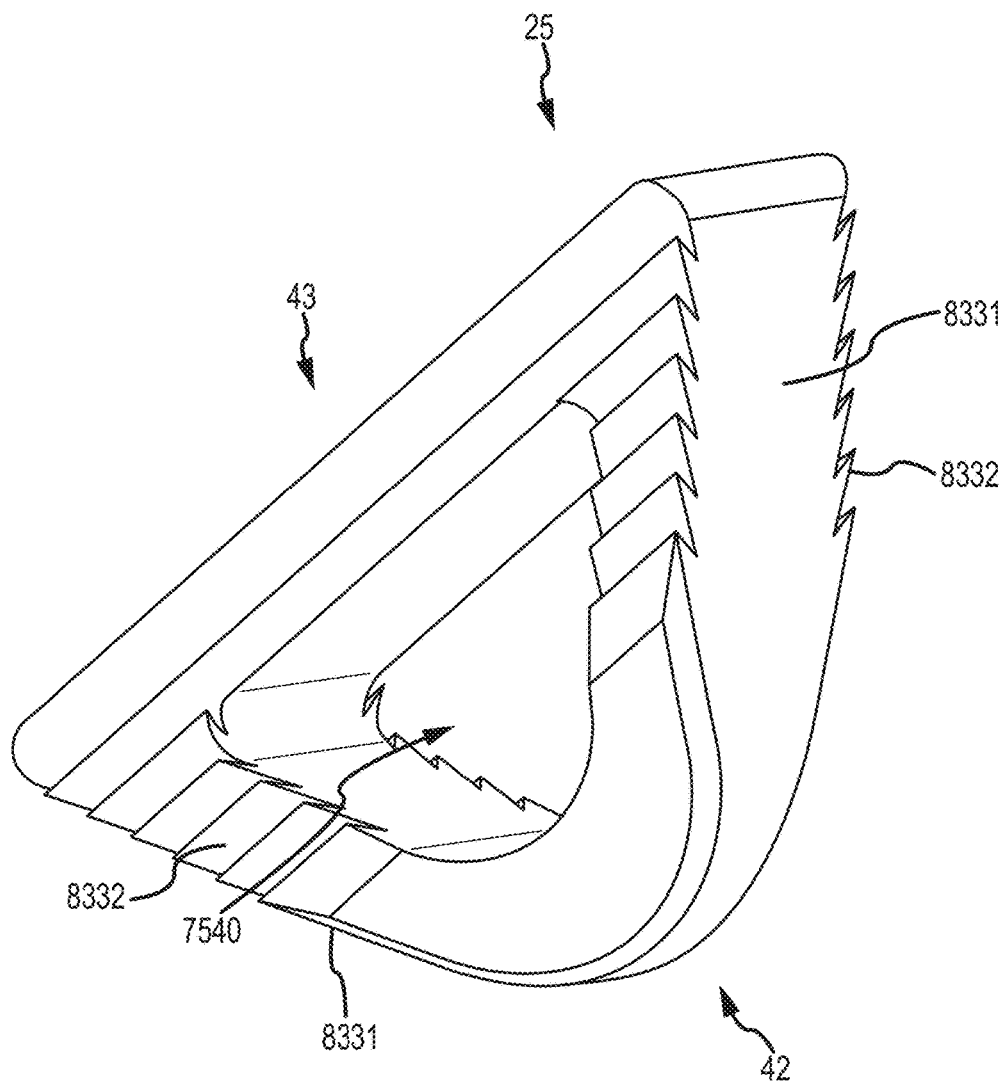
Figure 137B:
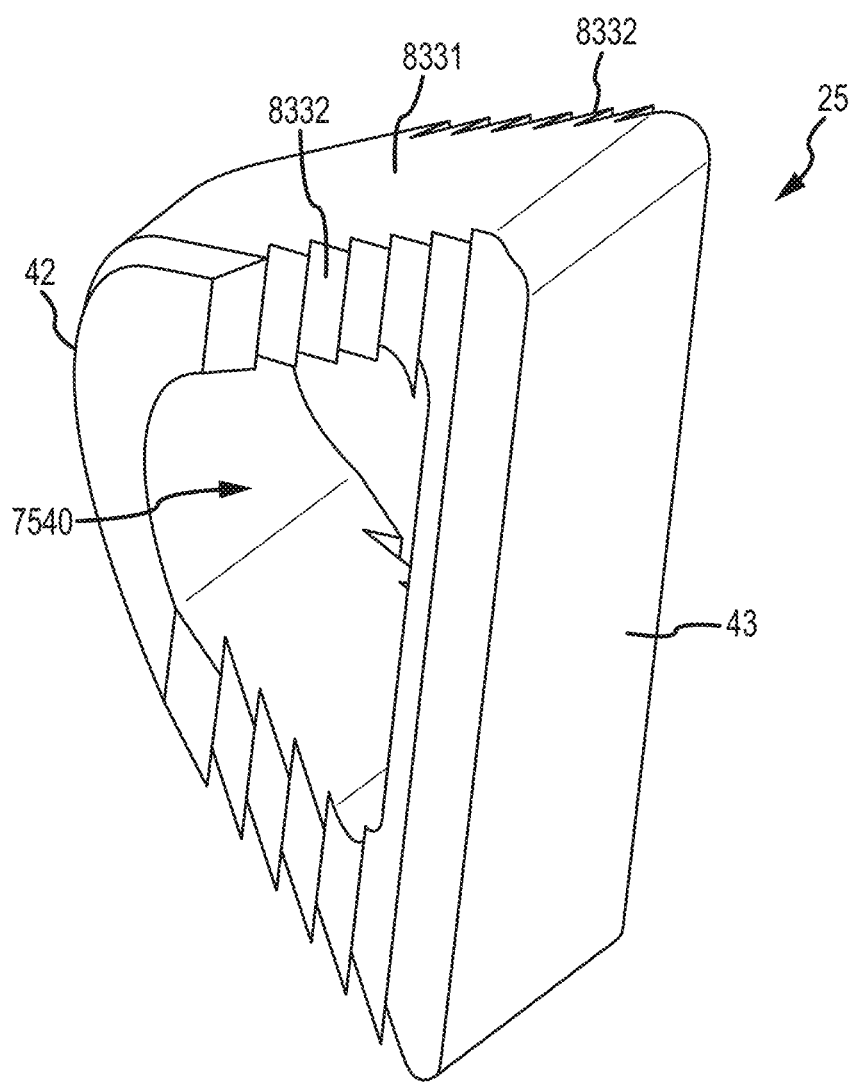

FIGS. 137A and 137B are generally opposite isometric views of an implant embodiment configured to essentially mimic at least a portion of the sacroiliac joint space.

FIGS. 137C-137F are, respectively, a top plan view, a distal end elevation, a side elevation, and a proximal elevation of the implant of FIGS. 137A and 137B.

Figure 138A:
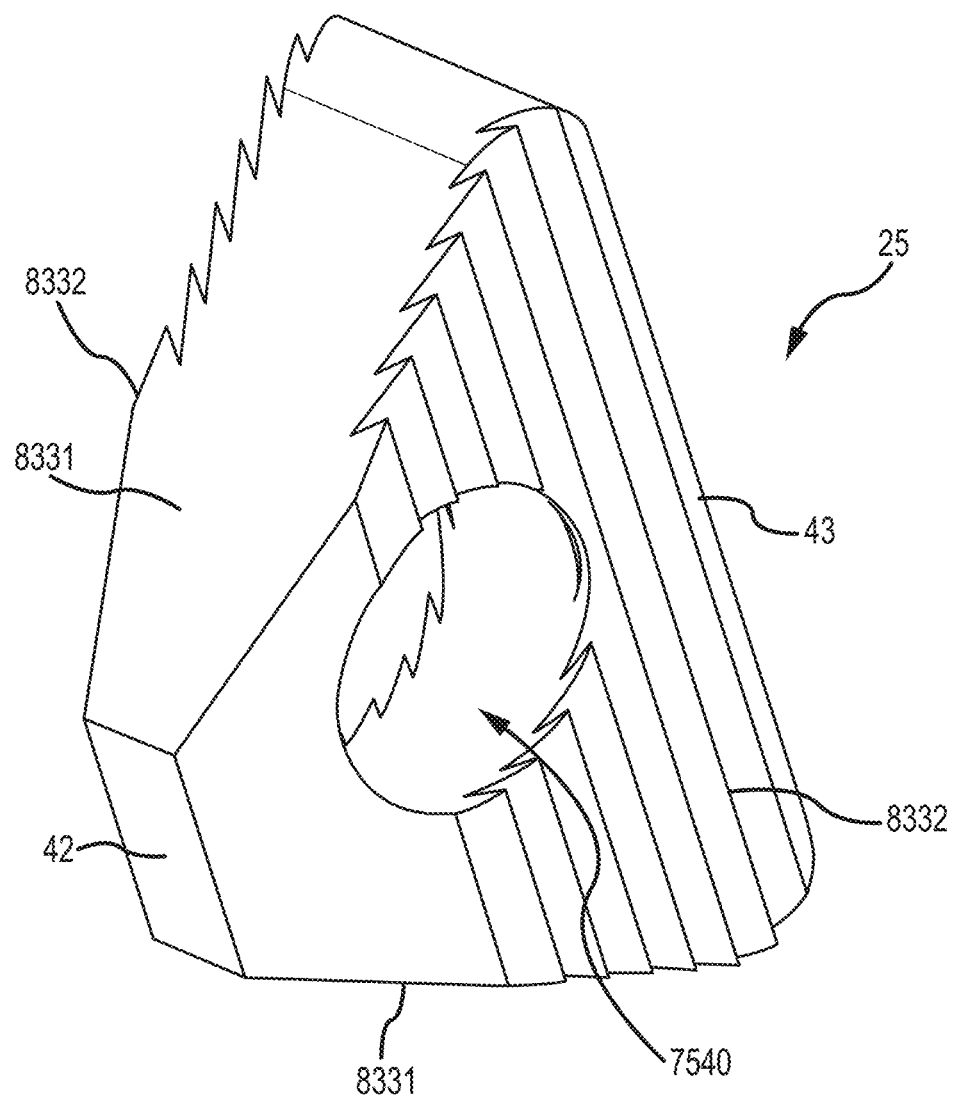
Figure 138B:
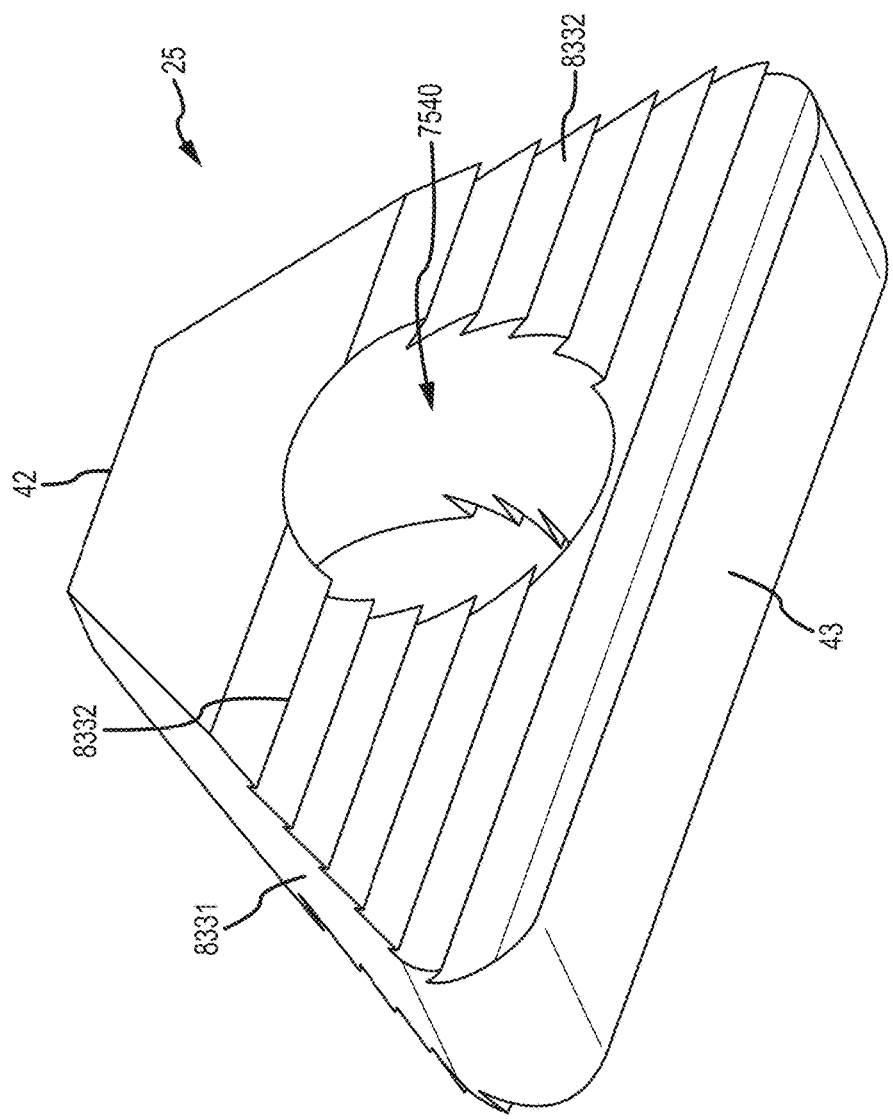
Figure 138C:
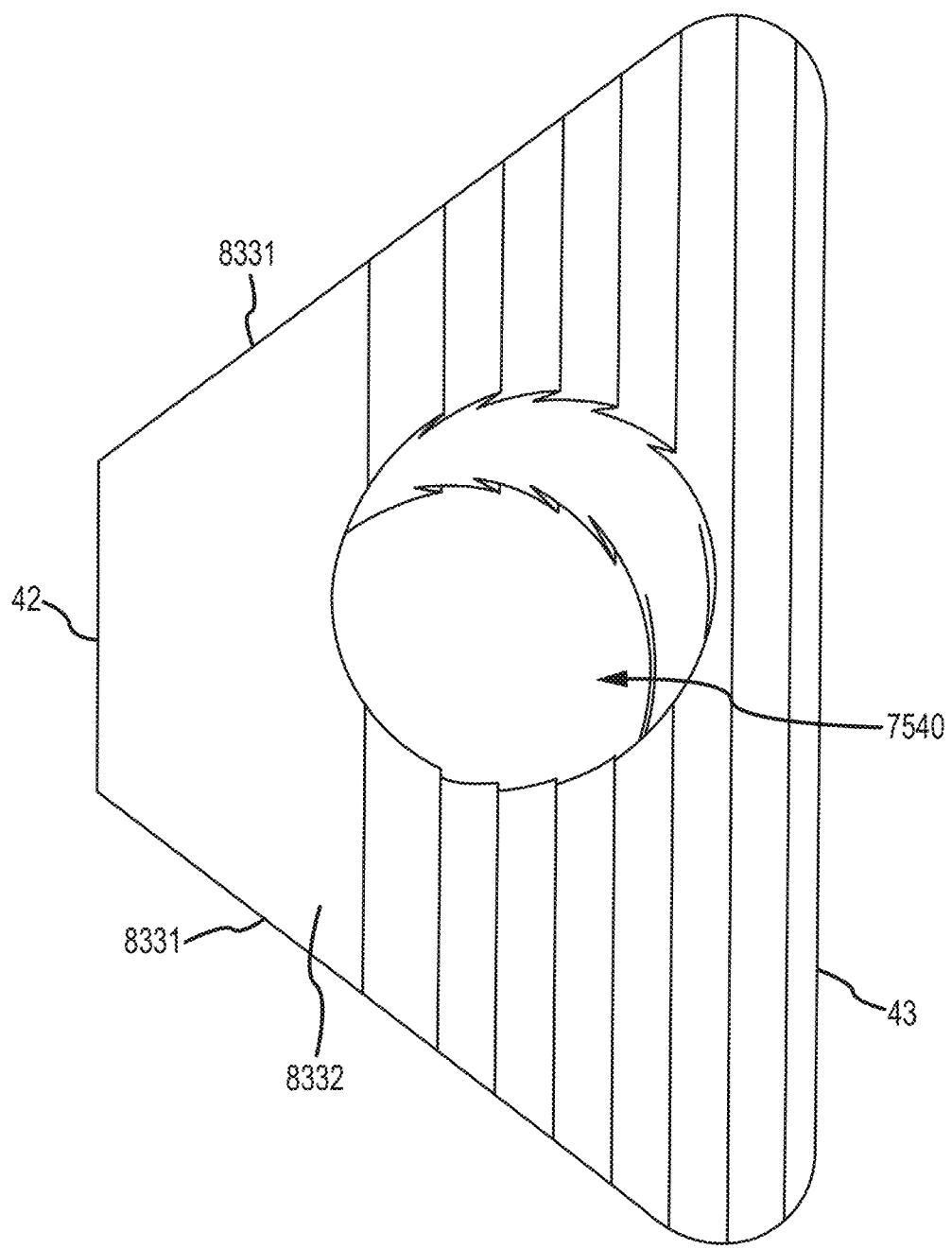
Figure 138D:
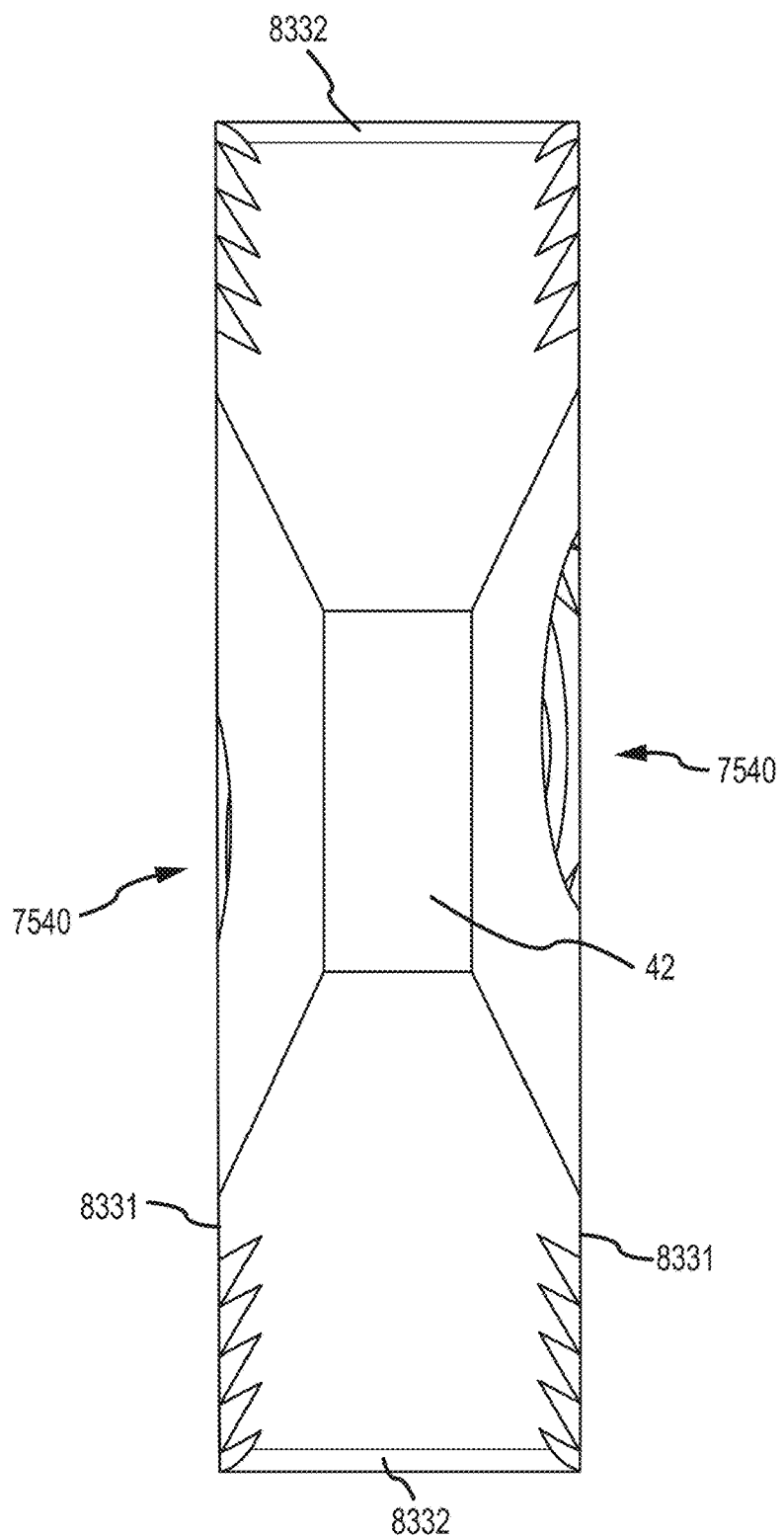
Figure 138E:
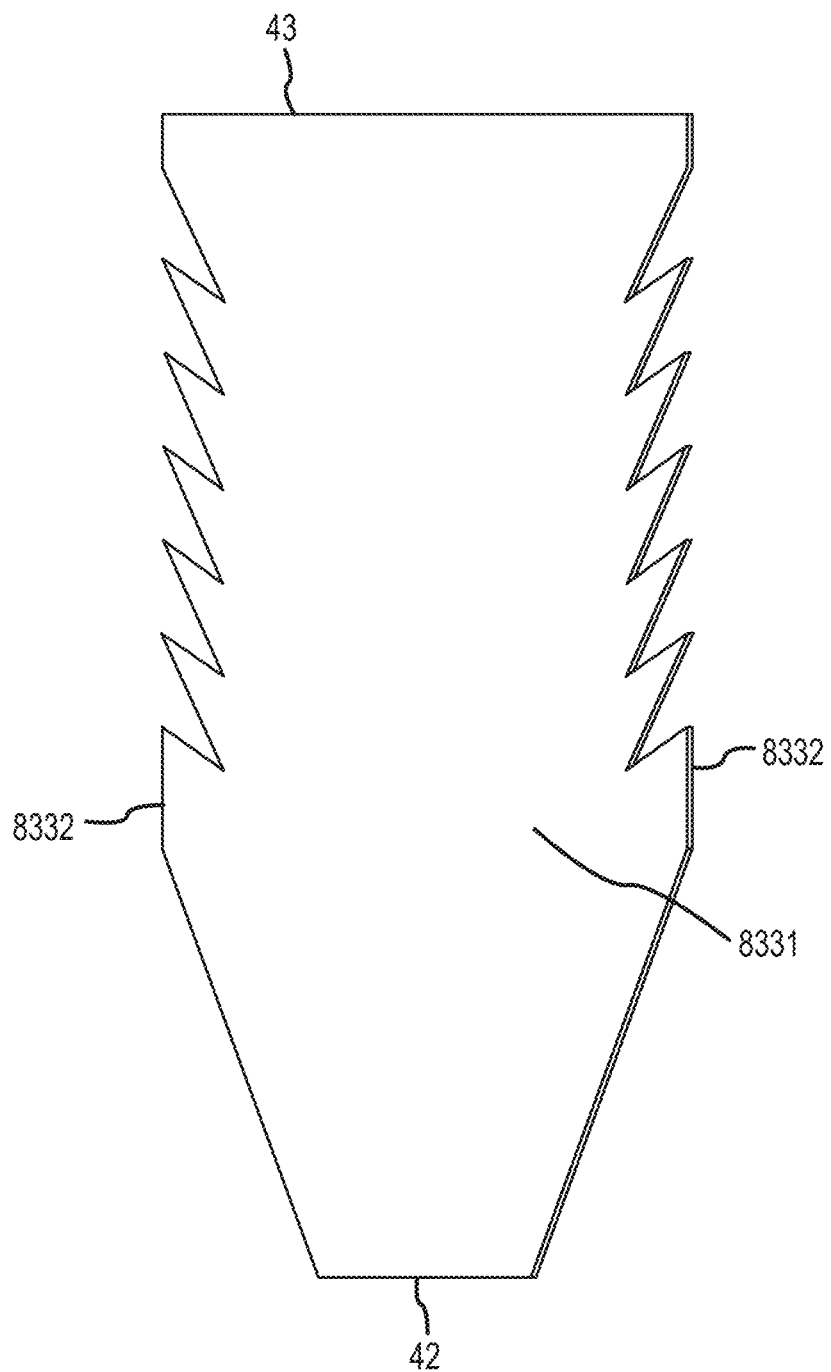
Figure 138F:
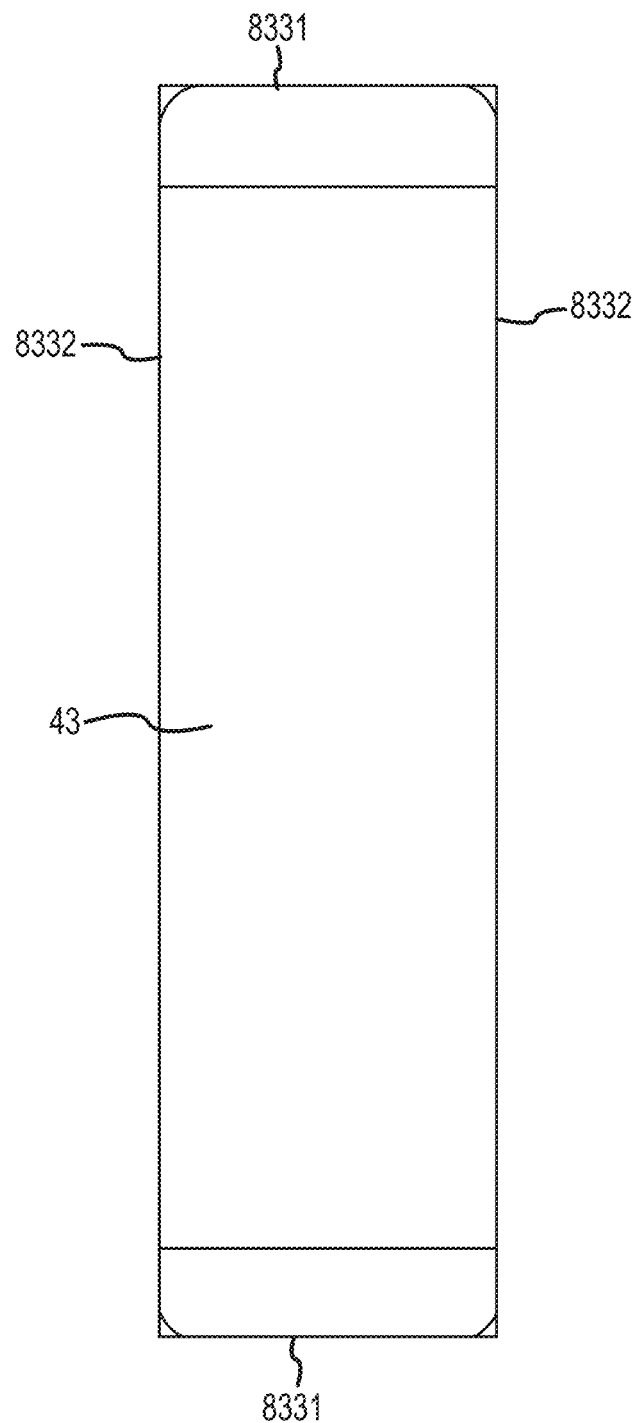

FIGS. 138A and 138B are generally opposite isometric views of an implant embodiment configured to essentially mimic at least a portion of the sacroiliac joint space.

FIGS. 138C-138F are, respectively, a top plan view, a distal end elevation, a side elevation, and a proximal elevation of the implant of FIGS. 138A and 138B.

FIGS. 139-154 are various views of an embodiment of an implant assembly for fusing a sacroiliac joint.

Figure 155:
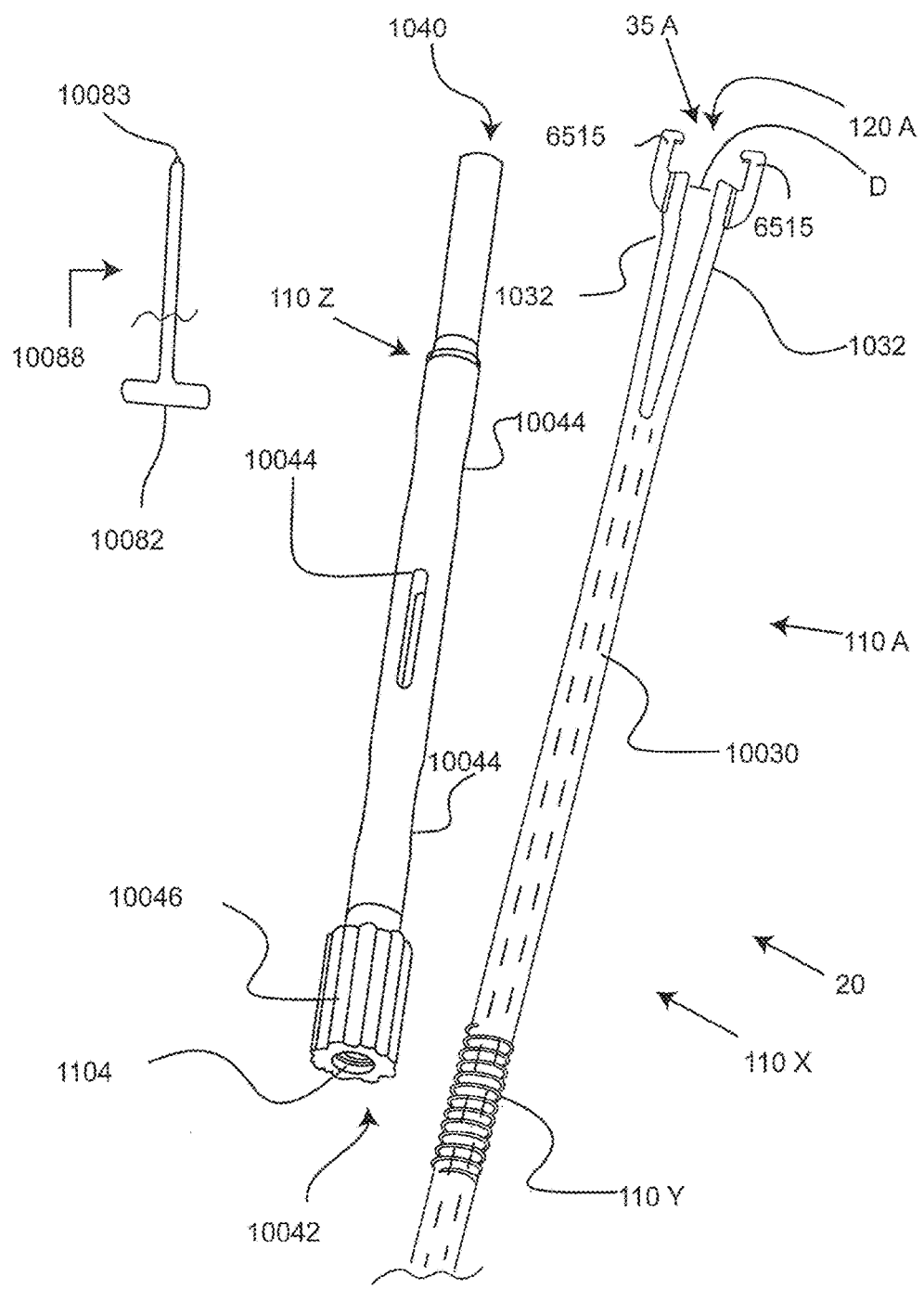

FIG. 155 is an isometric view of an implant delivery tool for use with the implant assembly of FIGS. 139-154.

Figure 156:
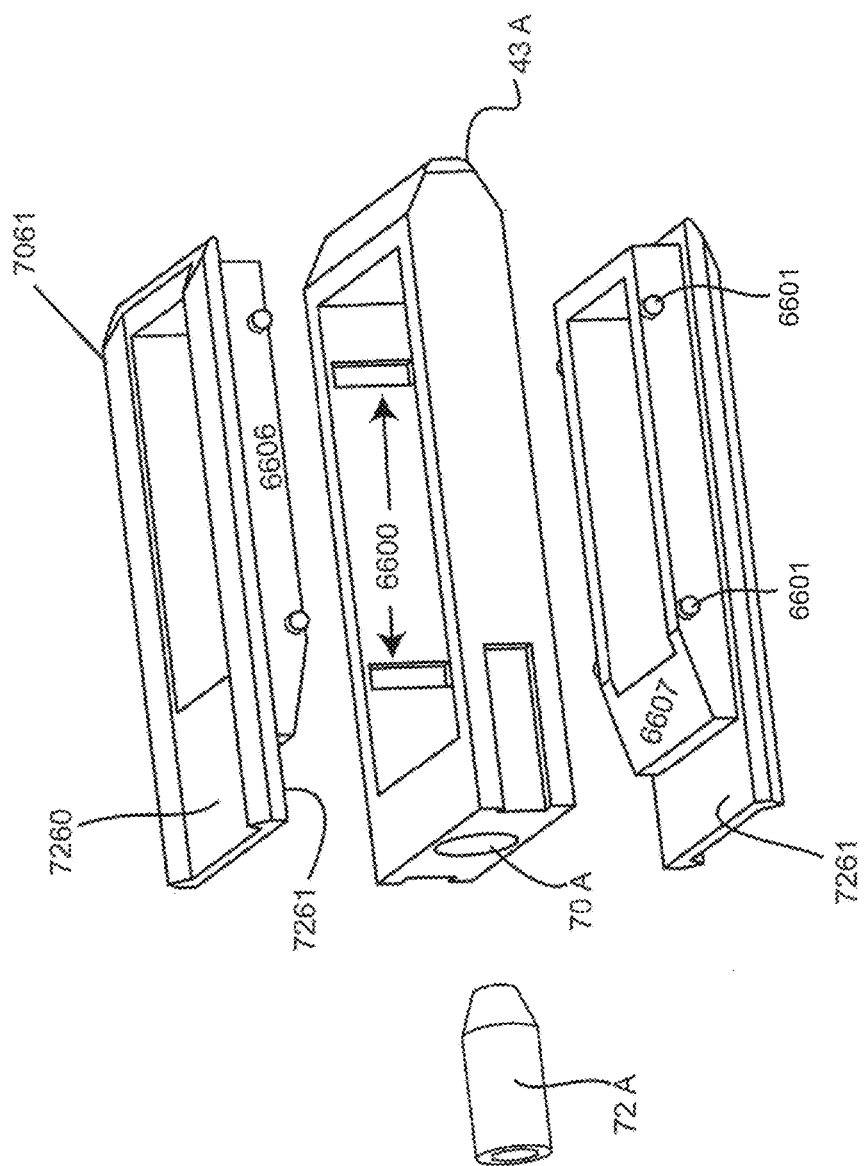
Figure 157:
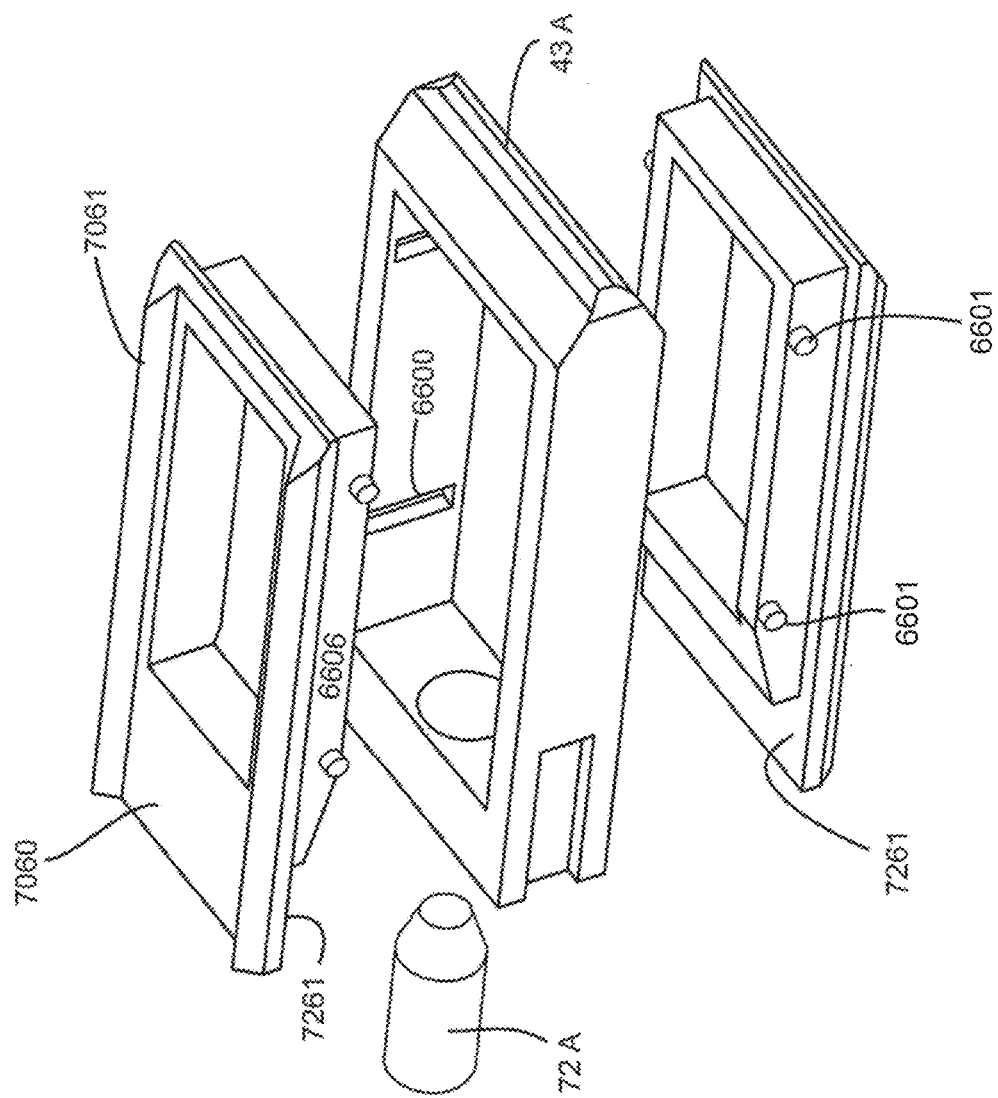
Figure 158:
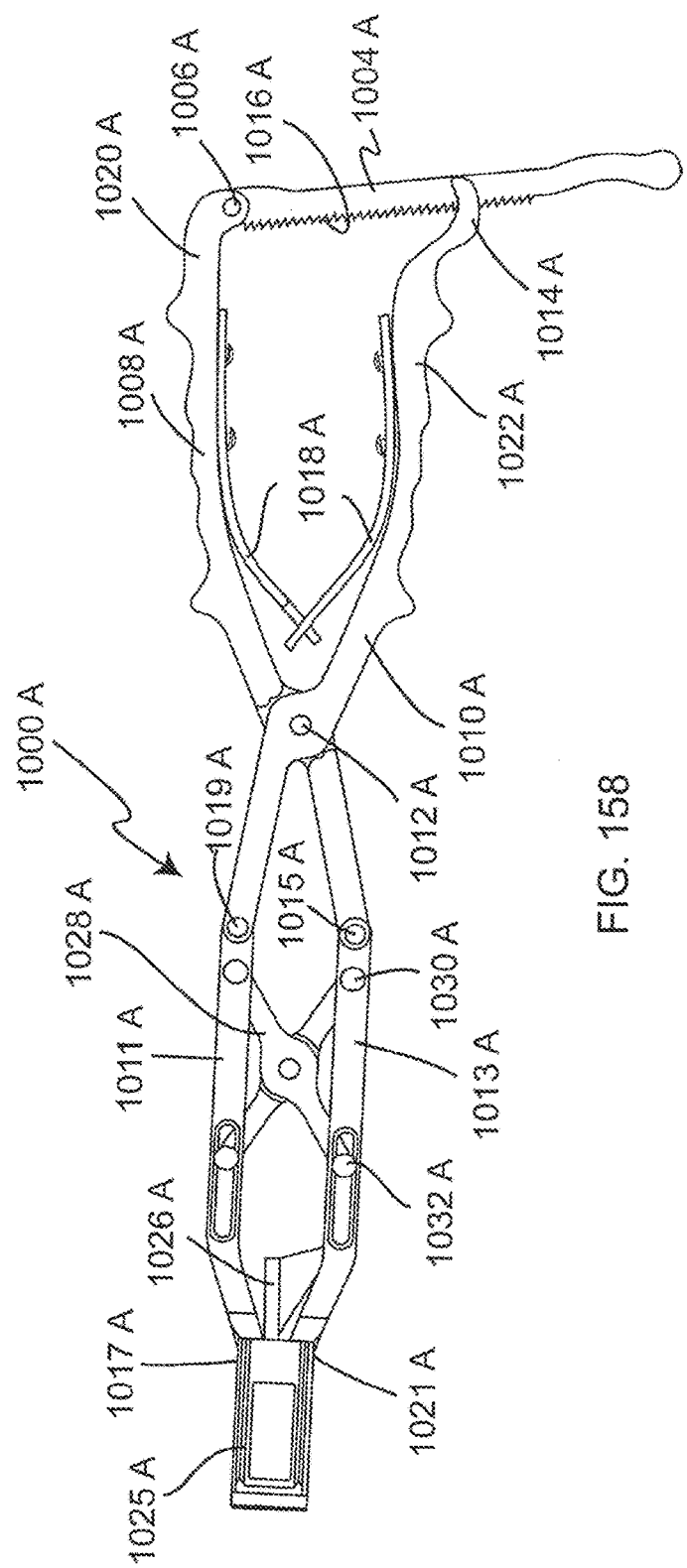
Figure 159:
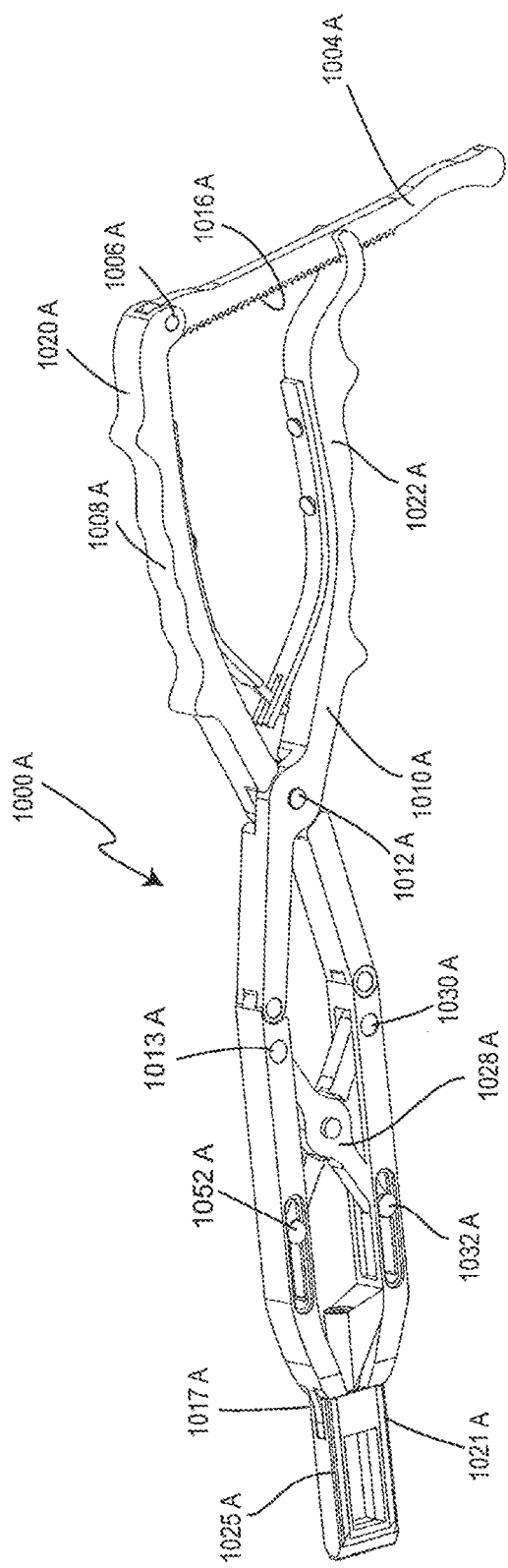
Figure 160:
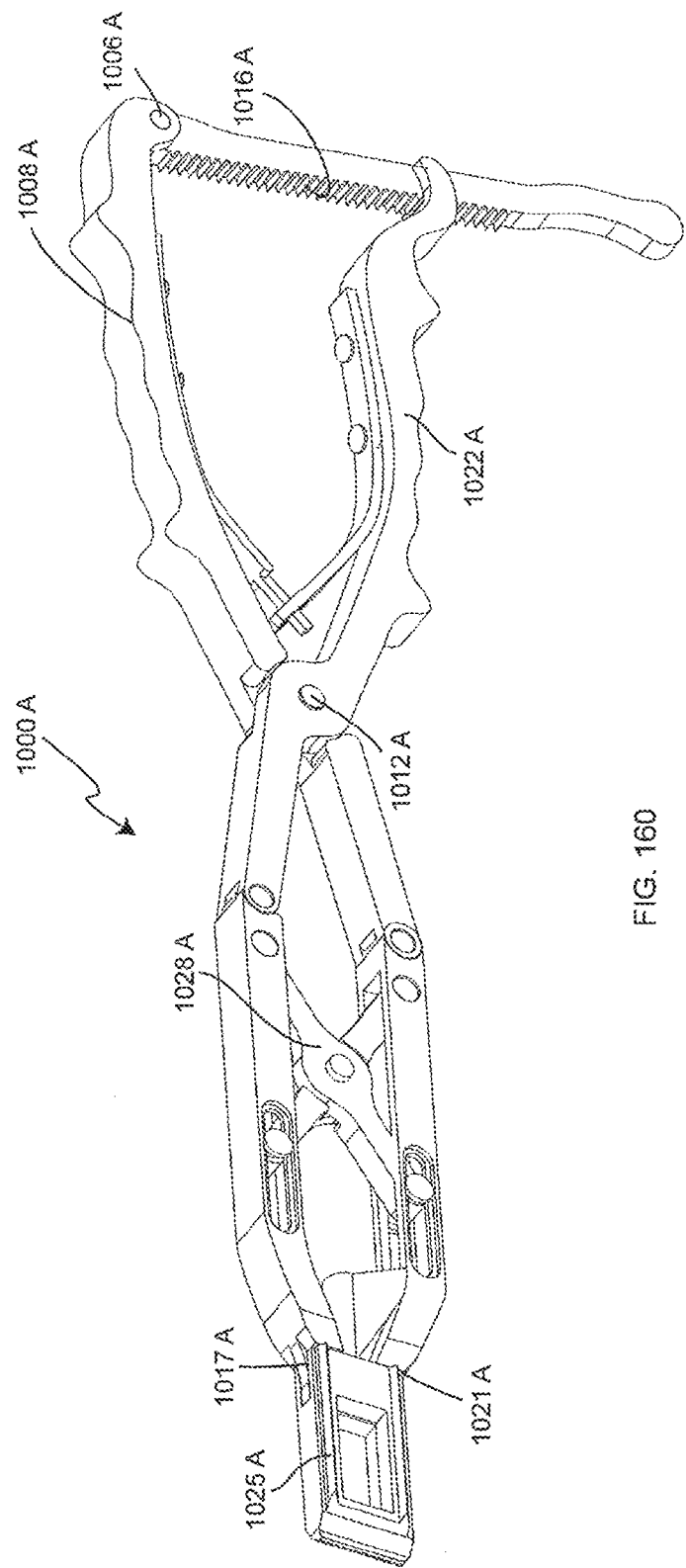
Figure 161:
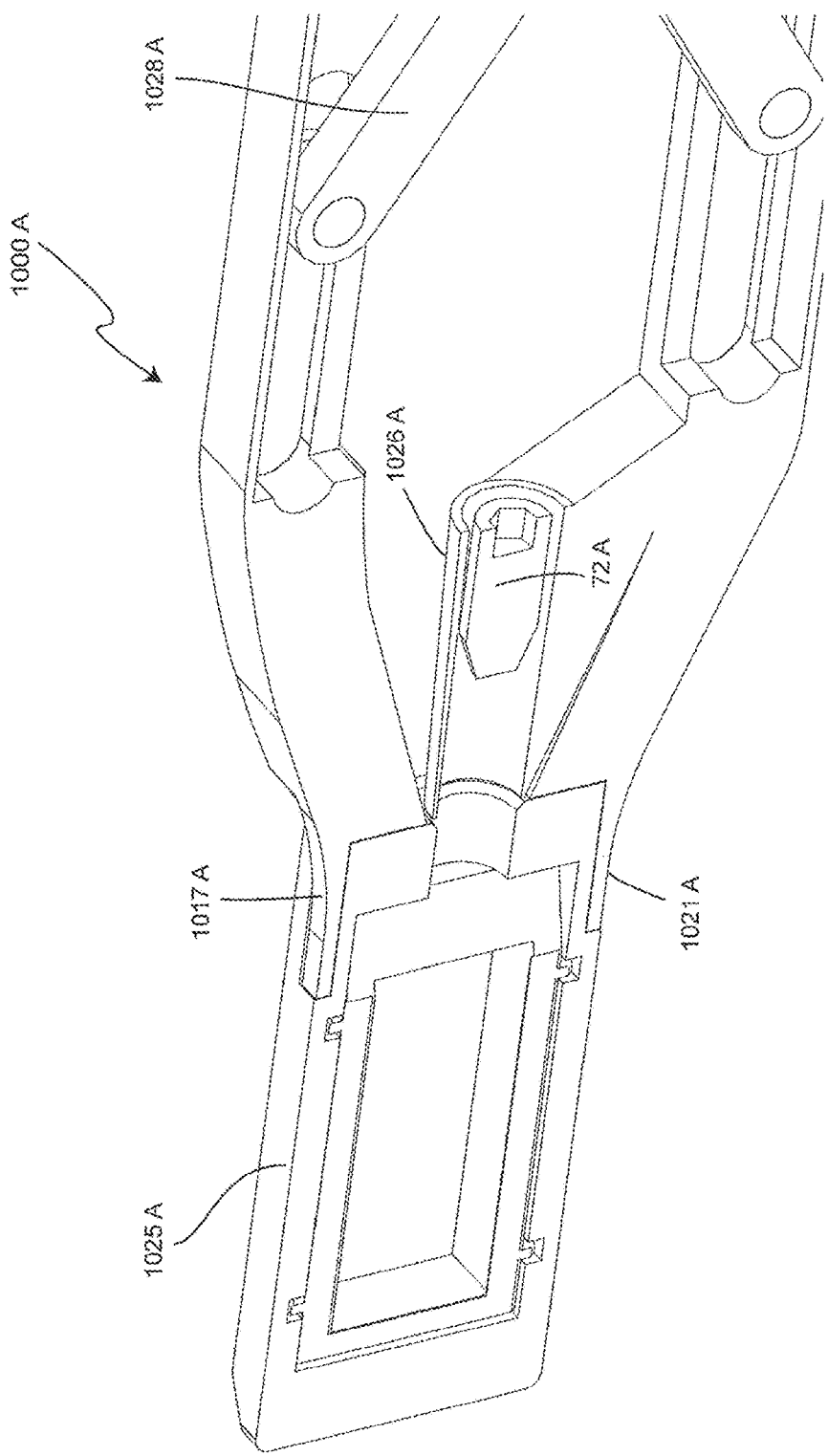
Figure 162:
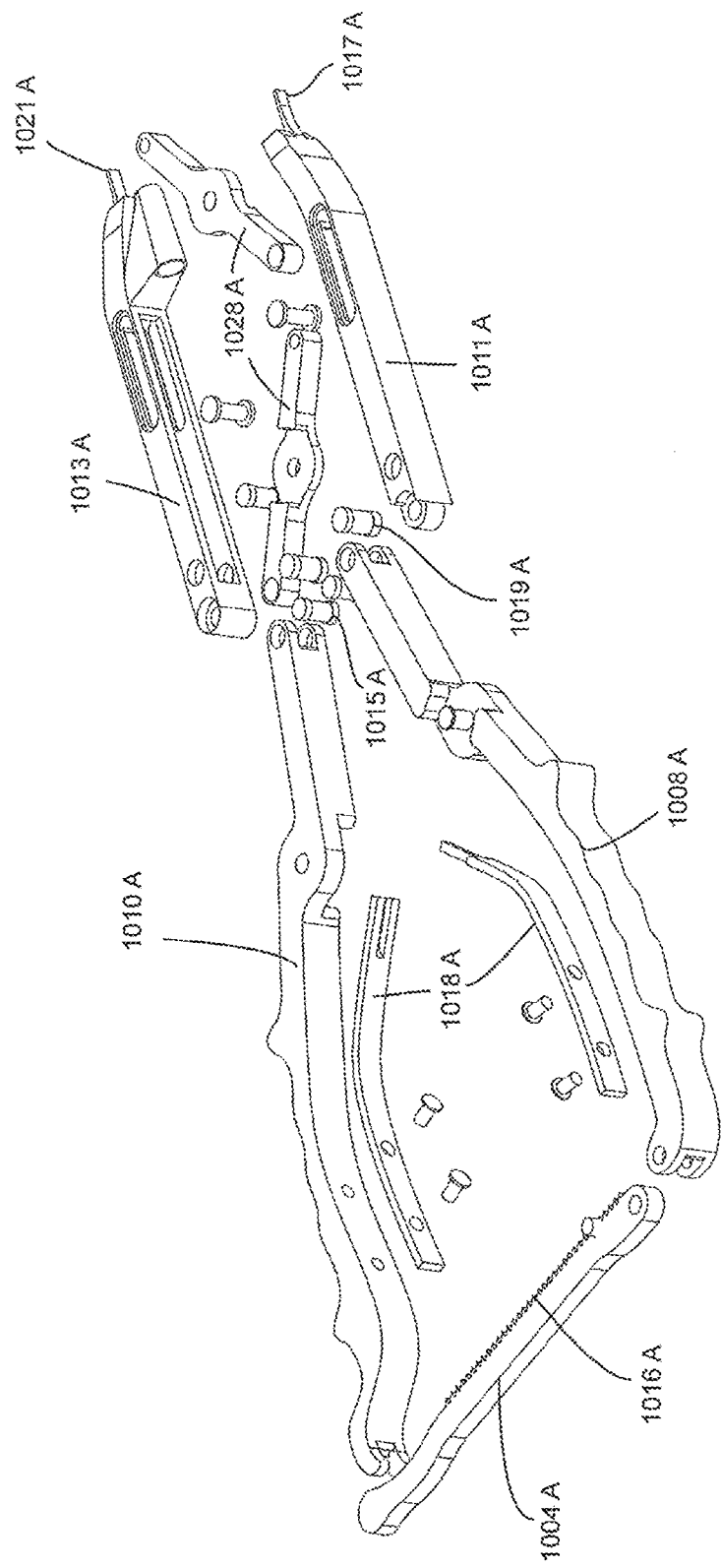
Figure 163:
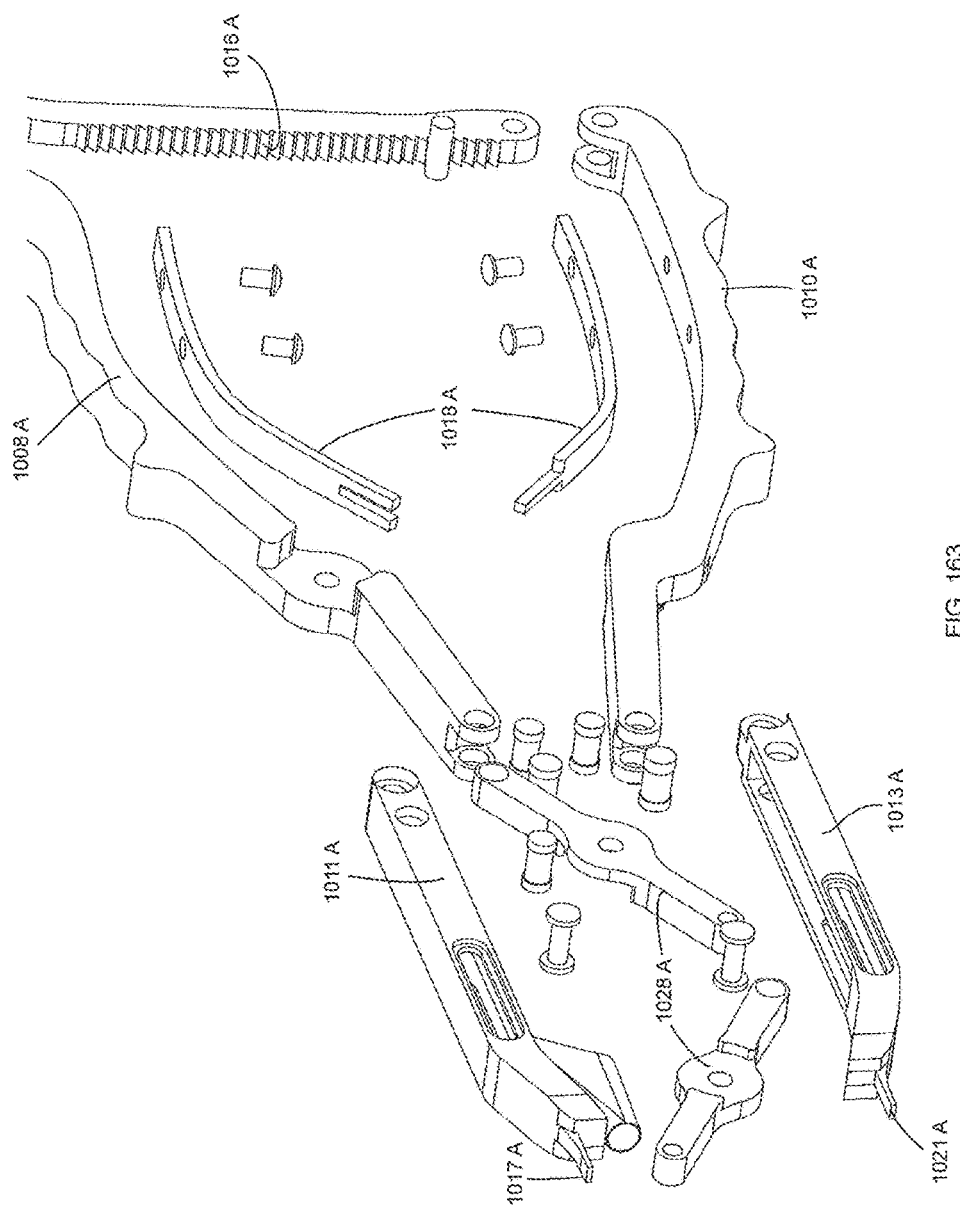
Figure 164:
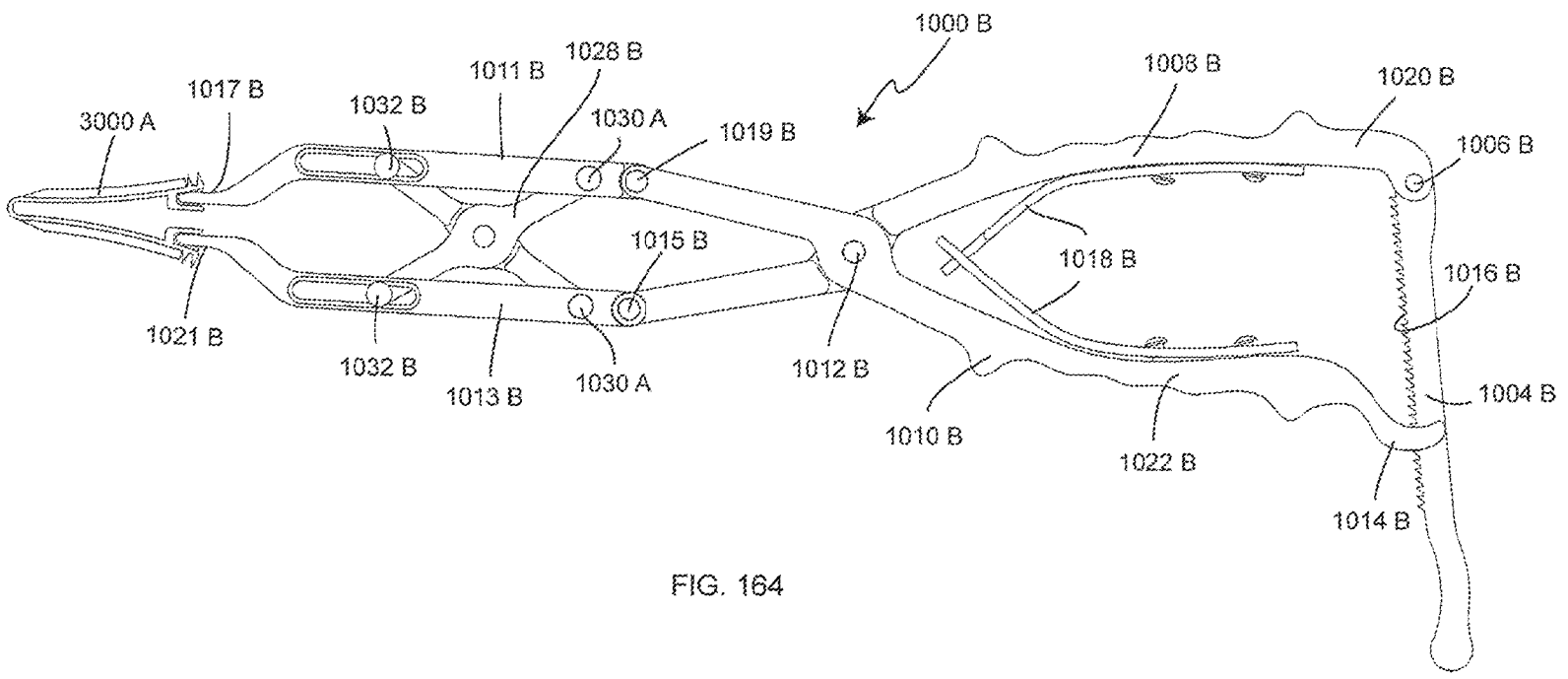
Figure 165:
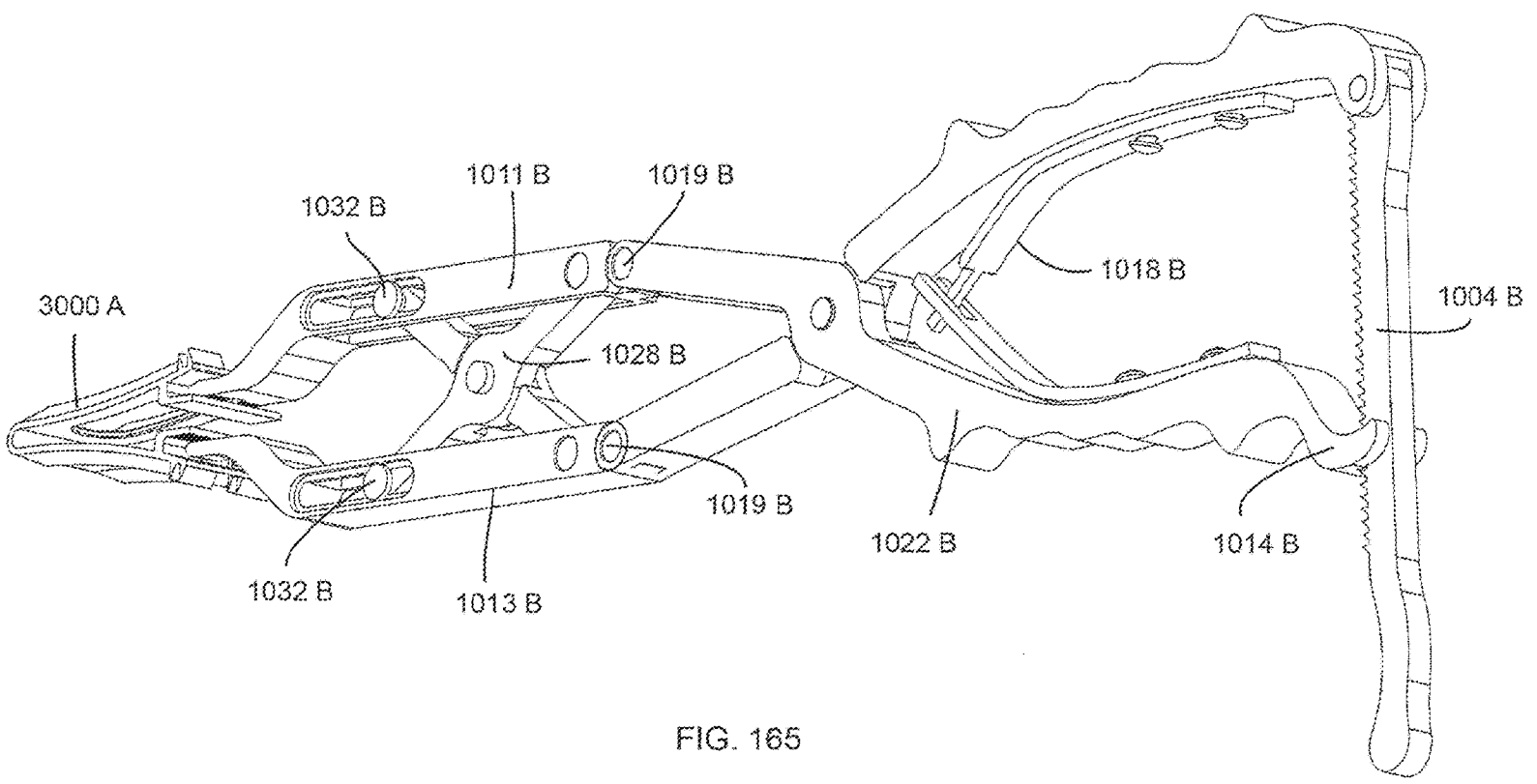
Figure 166:

Figure 167:
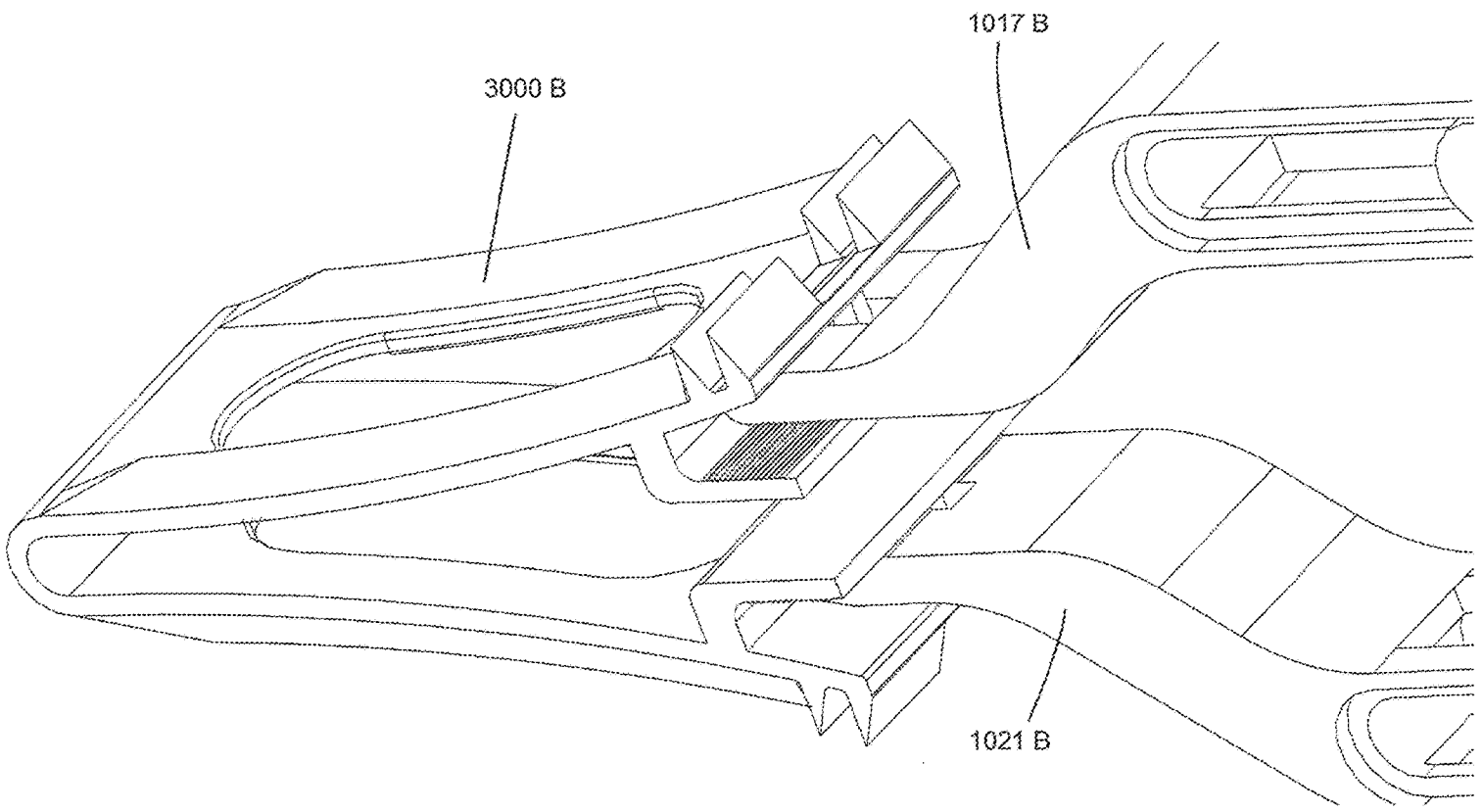
Figure 168:
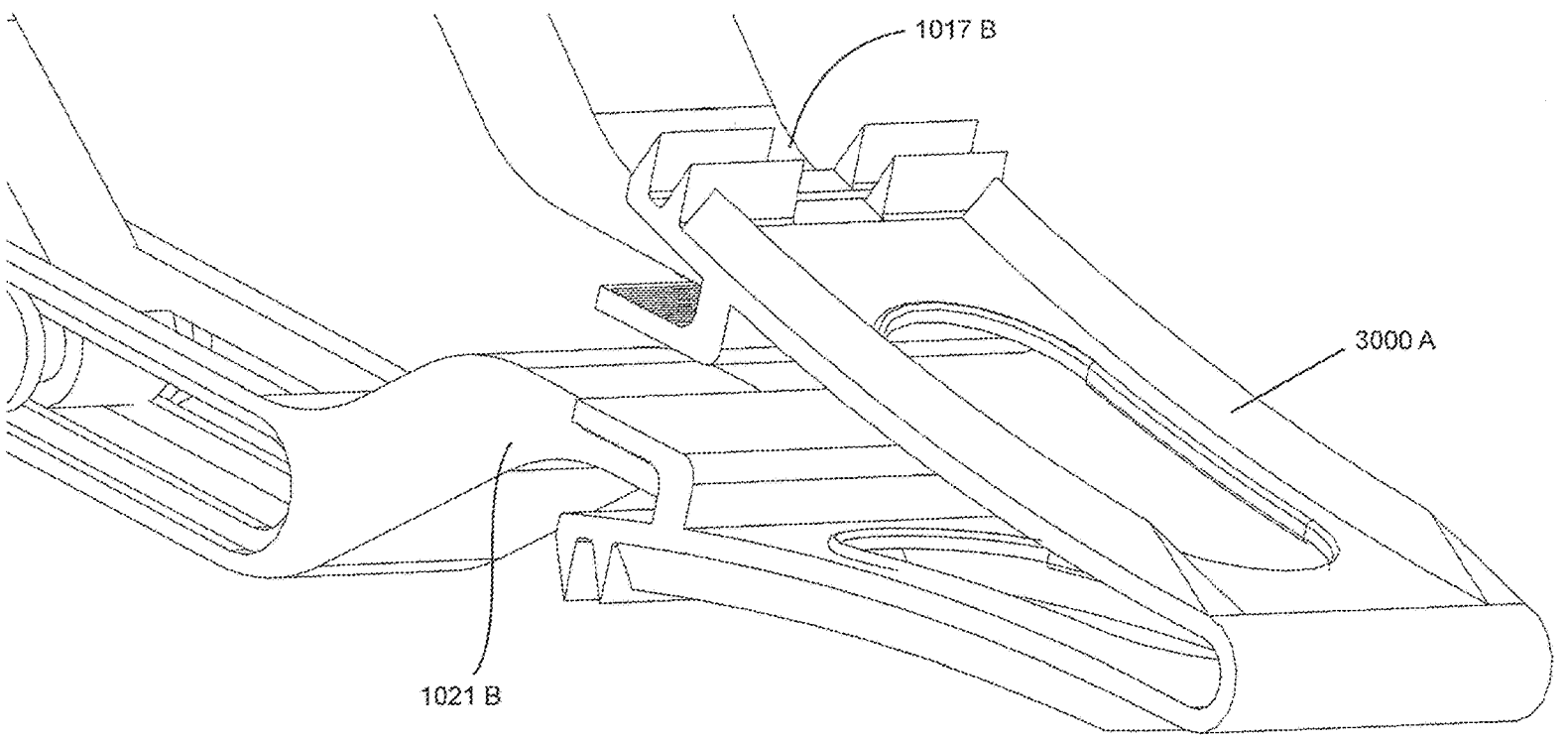

FIGS. 156 and 157 are exploded views of the implant assembly of FIGS. 139-154.

FIGS. 158-163 are various views of an implant delivery tool in accordance with an embodiment of the present invention.

FIGS. 164-168 are various views of an implant delivery tool in accordance with another embodiment of the present invention.

Figure 169:
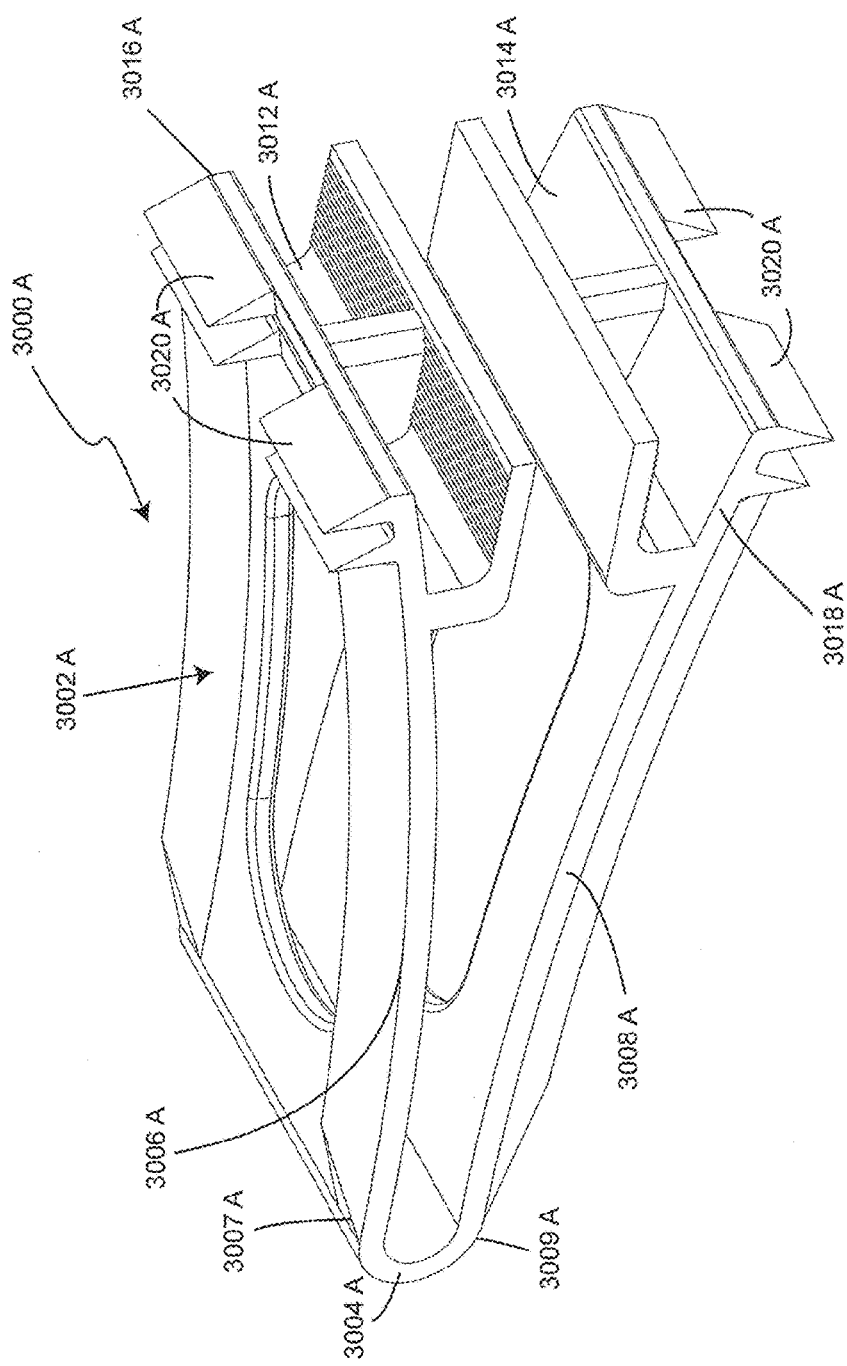
Figure 170:
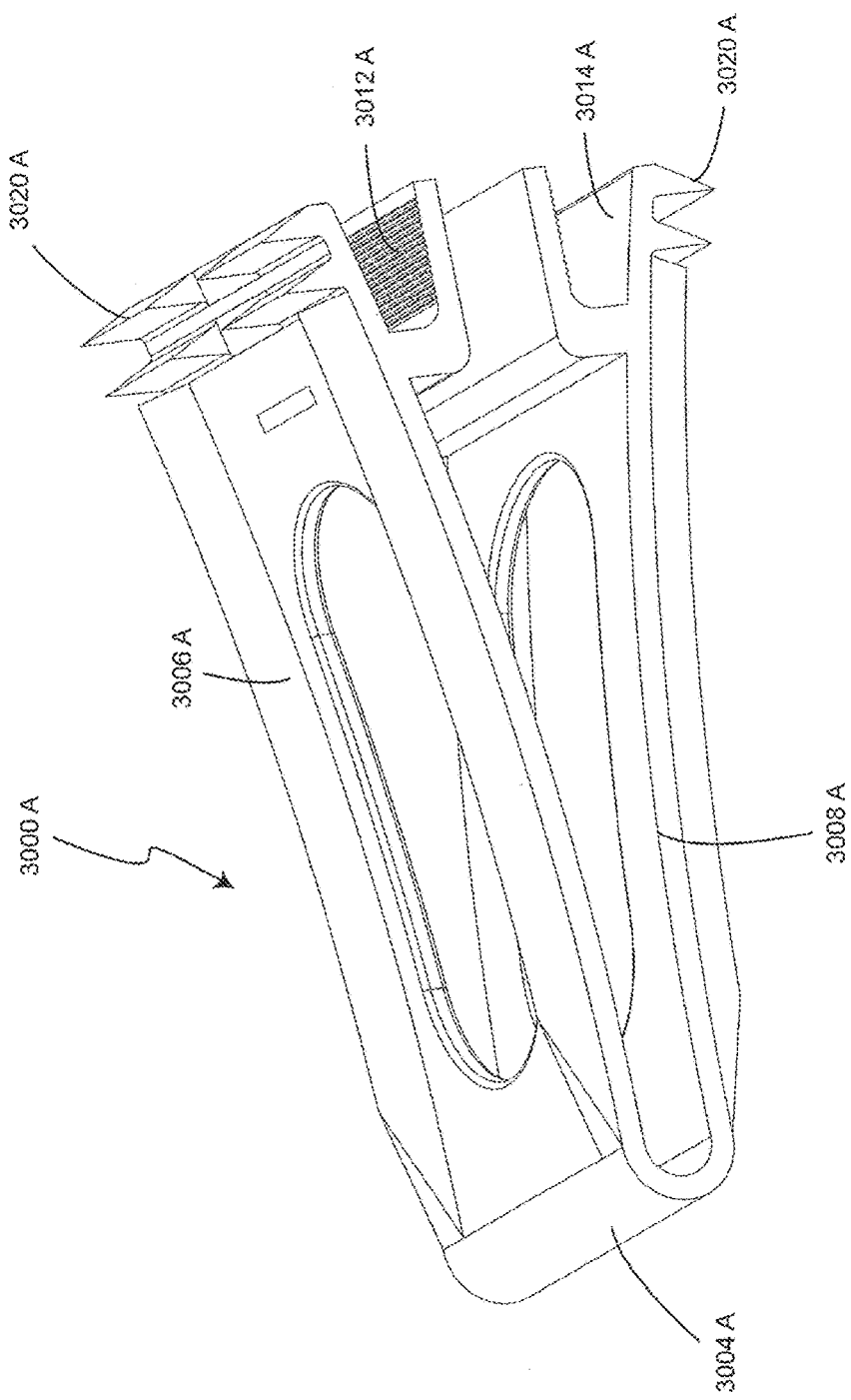

FIGS. 169-170 are front and rear perspective views of an implant for fusing a sacroiliac joint in accordance with another embodiment of the present invention.

Figure 171:
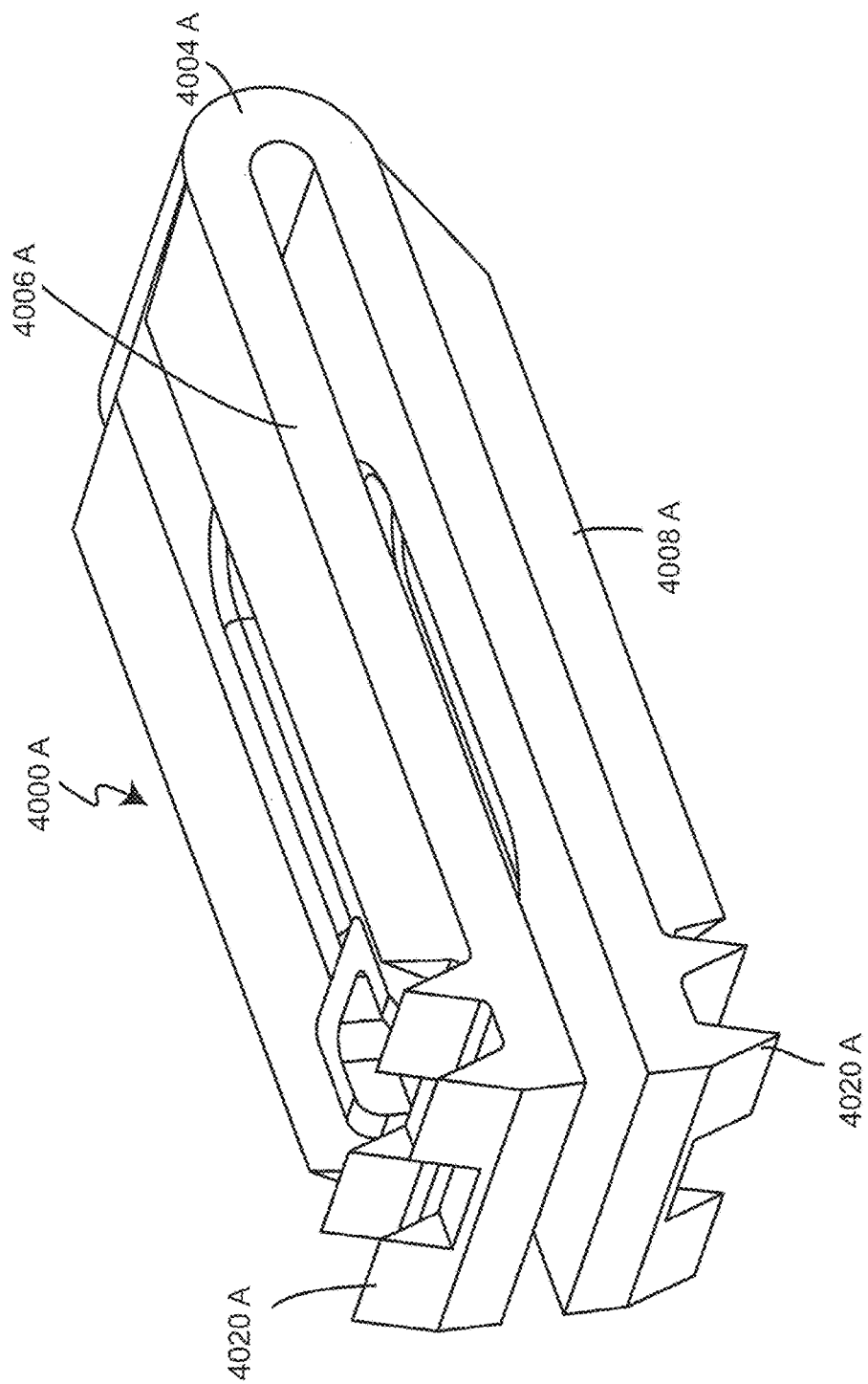
Figure 172:
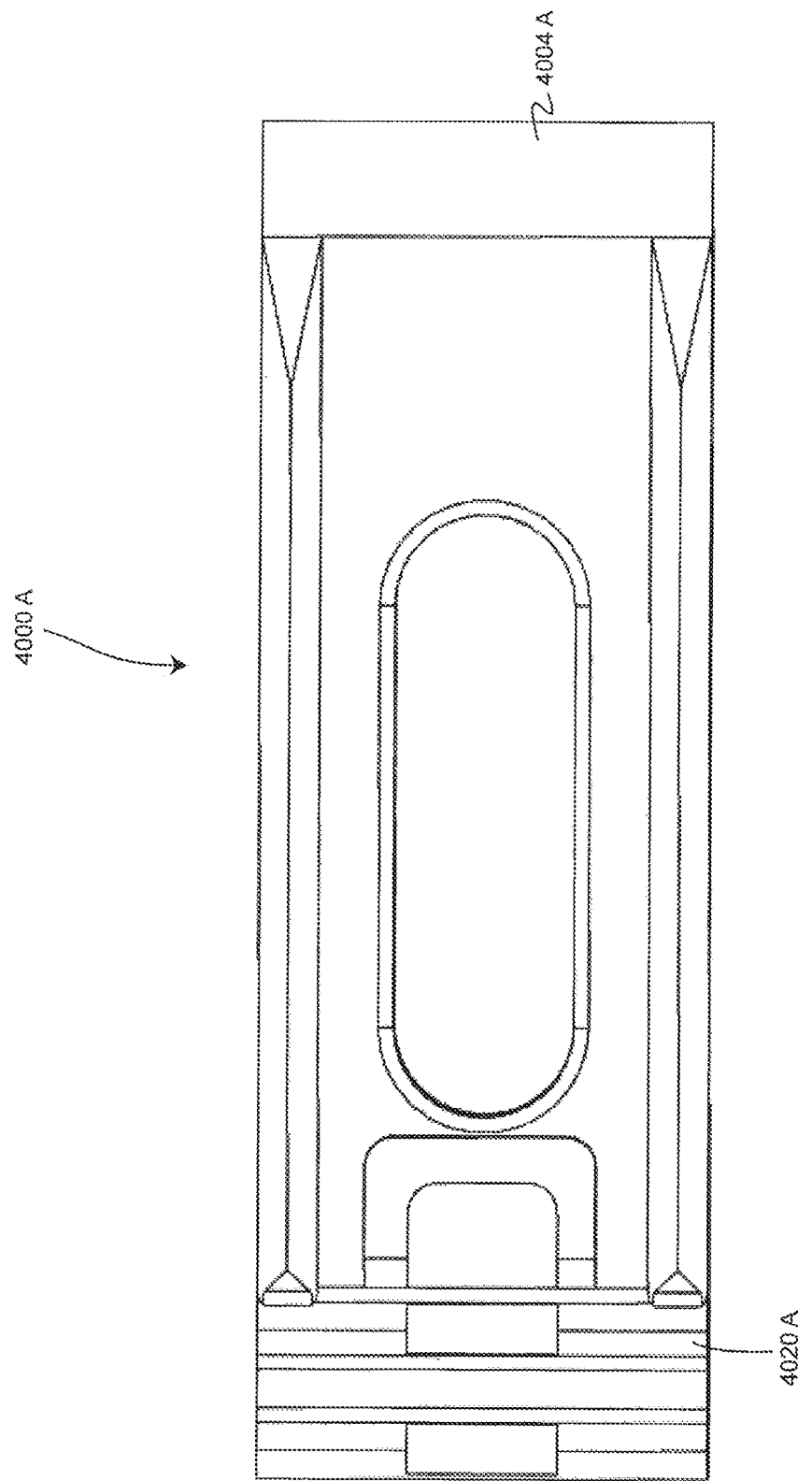
Figure 173:
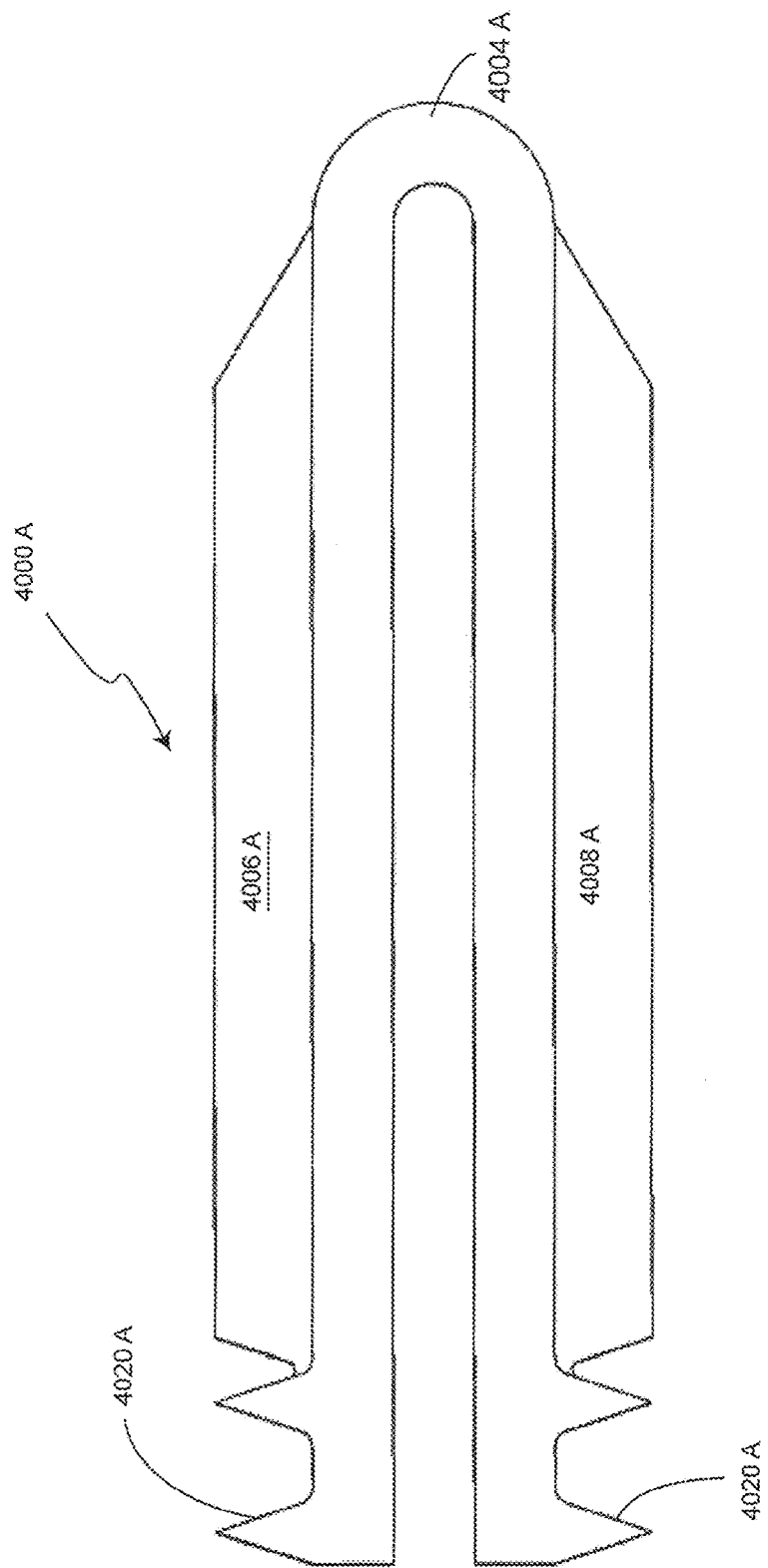

FIGS. 171-173 are various views of an implant for fusing a sacroiliac joint in accordance with another embodiment of the present invention.

Figure 174:
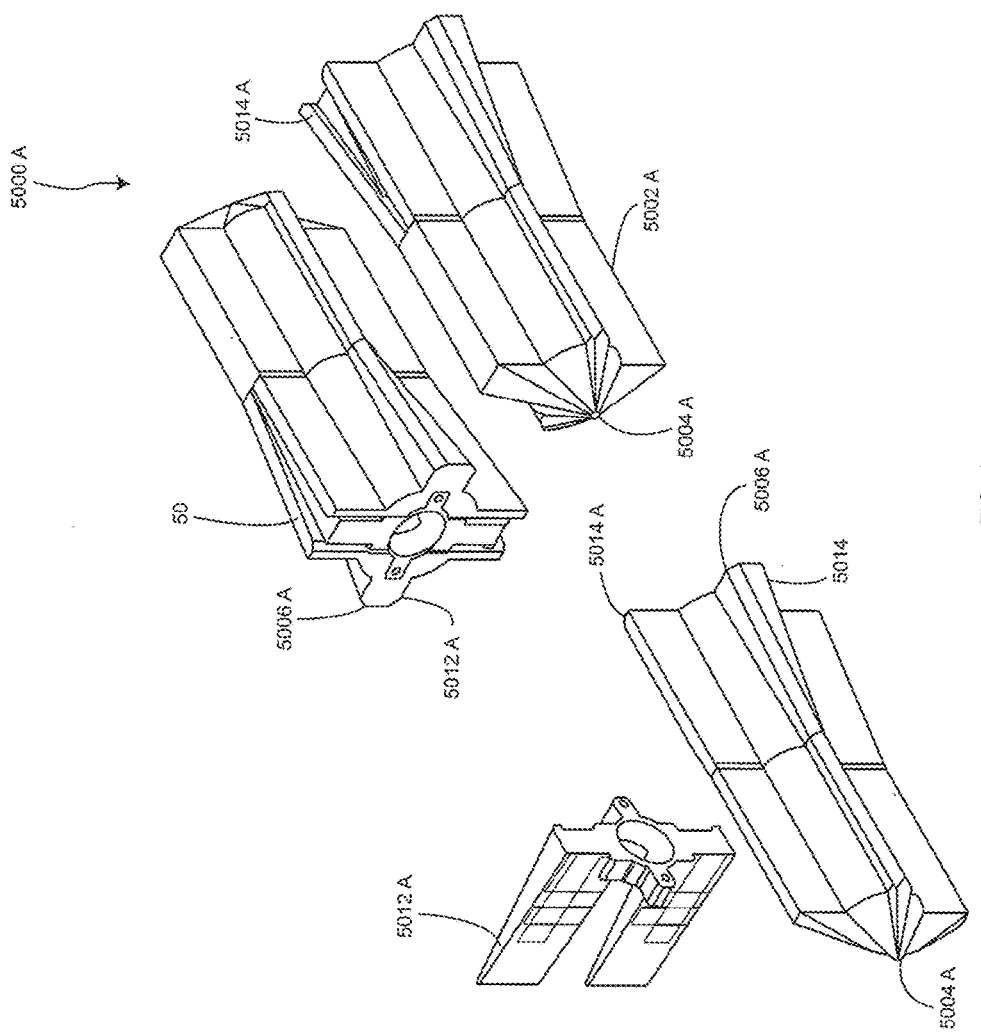

FIG. 174 includes various perspective views of an implant for fusing a sacroiliac joint in accordance with yet another embodiment of the present invention.

Figure 175:
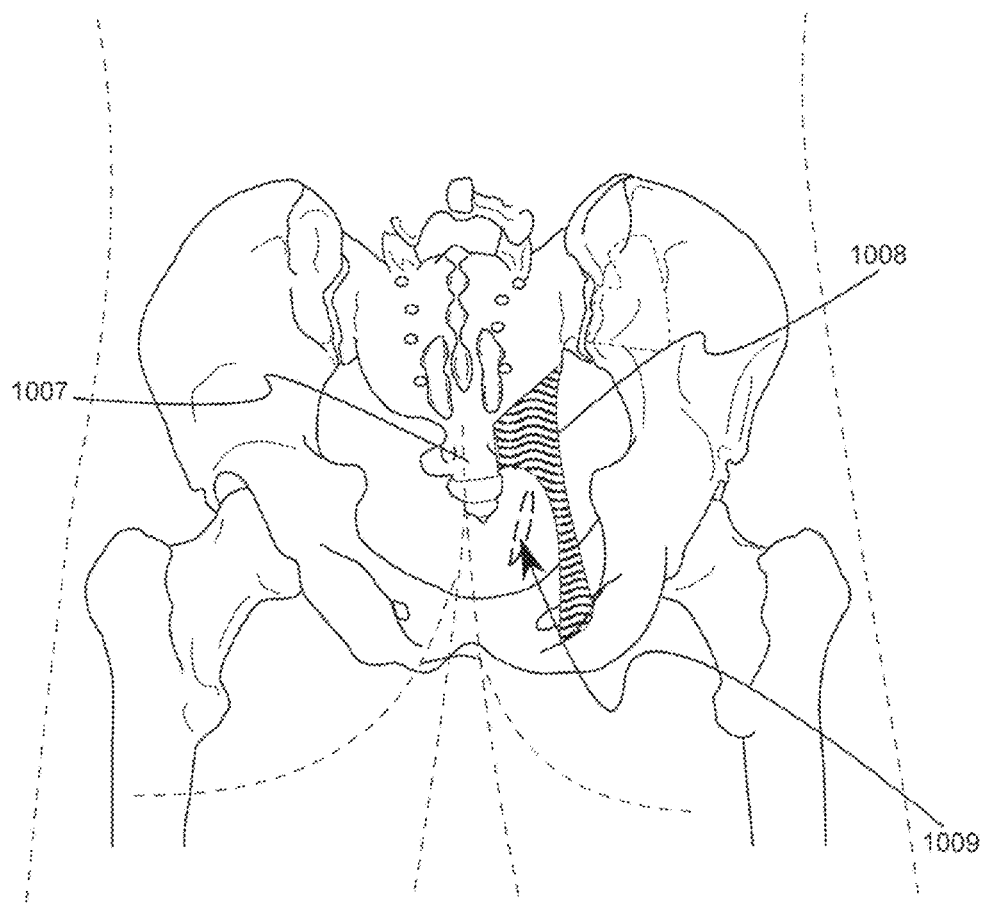
Figure 176:
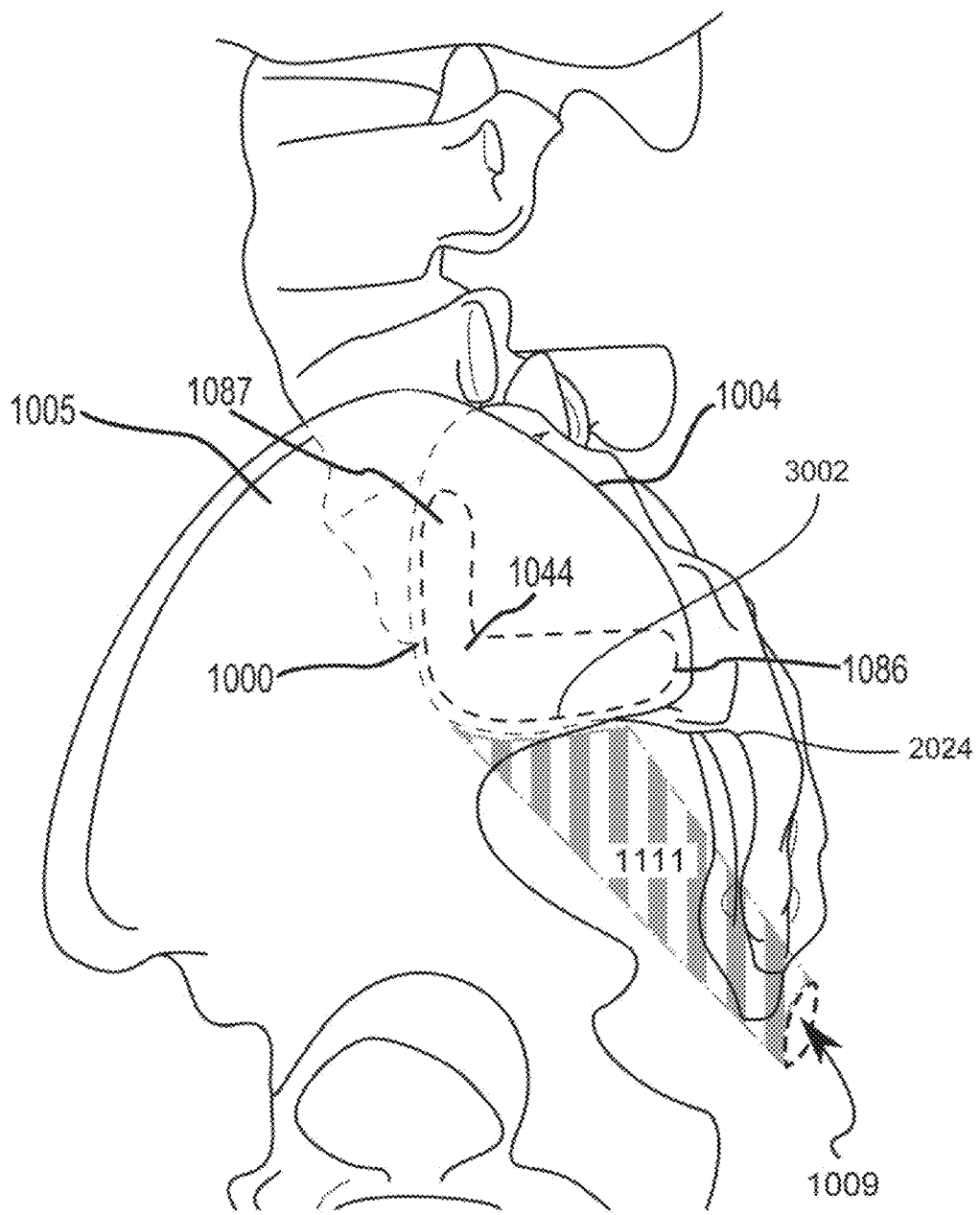

FIGS. 175 and 176 are, respectively, posterior and lateral views of a patient hip region illustrating a surgical approach employing an entry point near the coccyx and the sacrotuberous ligament.

Figure 177:
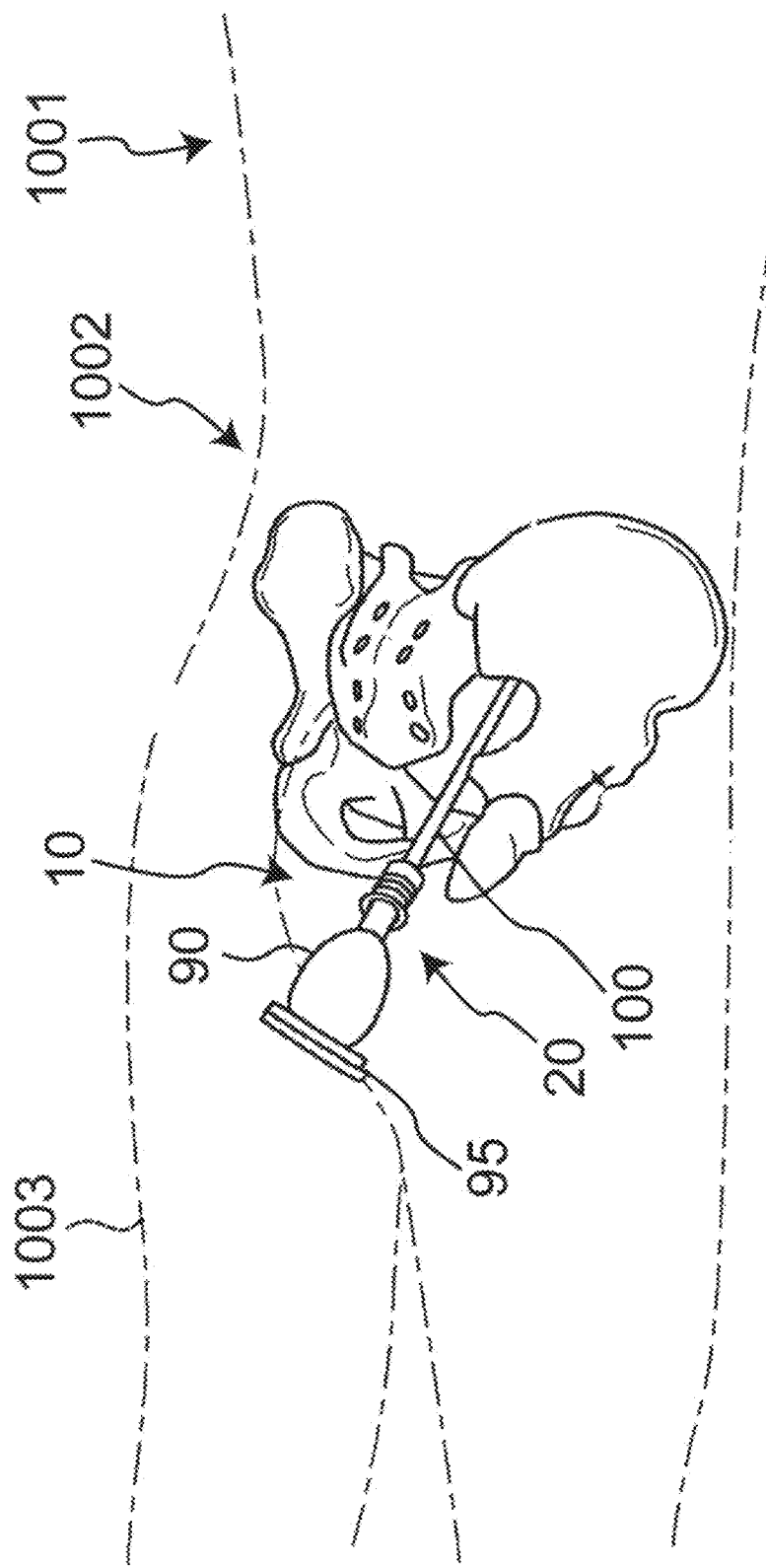

FIG. 177 is a posterior-lateral view of the patient hip region illustrating the delivery tool extending along the surgical approach of FIGS. 175 and 176.

DETAILED DESCRIPTION

Implementations of the present disclosure involve a system 10 for fusing a sacroiliac joint. The system 10 includes a delivery tool 20 and an implant assembly 15 for delivery to a sacroiliac joint via the delivery tool 20. The implant assembly 15, which includes an implant 25 and anchor 30, is configured to fuse a sacroiliac joint once implanted at the joint. The tool 20 is configured such that the anchor 30 can be quickly, accurately and reliably delivered to a bore 40 of an implant 25 supported off of the tool distal end in a sacroiliac joint.

To begin a detailed discussion of a first embodiment of the system 10, reference is made to FIGS. 2A-3. FIG. 2A is an isometric view of the system 10. FIG. 2B is the same view as FIG. 2A, except an implant assembly 15 of the system 10 is separated from a delivery tool 20 of the system 10. FIG. 3 is the same view as FIG. 2A, except the system 10 is shown exploded to better illustrate the components of the system 10.

As can be understood from FIGS. 2A and 2B, the system 10 includes a delivery tool 20 and an implant assembly 15 for implanting at the sacroiliac joint via the delivery tool 20, the implant assembly 15 being for fusing the sacroiliac joint. As indicated in FIG. 3, the implant assembly 15 includes an implant 25 and an anchor element 30 (e.g., a bone screw or other elongated body). As discussed below in greater detail, during the implantation of the implant assembly 15 at the sacroiliac joint, the implant 25 and anchor element 30 are supported by a distal end 35 of the delivery tool 20, as illustrated in FIG. 2A. In one embodiment, the distal end 35 may be fixed or non-removable from the rest of the delivery tool 20. In other embodiments, the distal end 35 of the delivery tool 20 may be removable so as to allow interchanging of different sized or shaped distal ends 35 to allow matching to particular implant embodiments without requiring the use of a different delivery tool 20 and while maintaining the alignment between components (e.g., anchor 30 aligned with bore 40) The delivery tool 20 is used to deliver the implant 25 into the sacroiliac joint space. The delivery tool 20 is then used to cause the anchor element 30 to extend through the ilium, sacrum and implant 25 generally transverse to the sacroiliac joint and implant 25. The delivery tool 20 is then decoupled from the implanted implant assembly 15, as can be understood from FIG. 2B.

Figure 4:

FIG. 4 is a top-side isometric view of the implant assembly.
Figure 5:
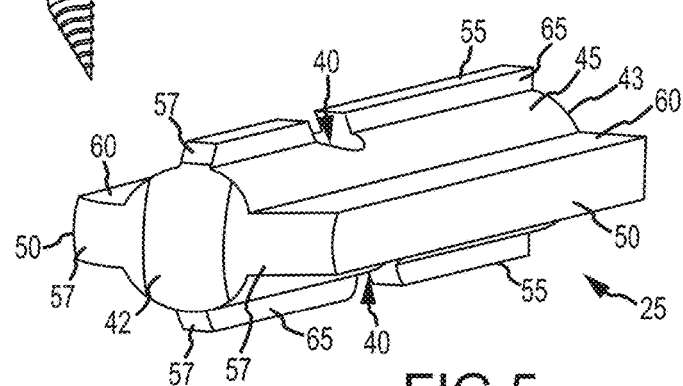
FIG. 5 is a distal end isometric view of the implant of the implant assembly of FIG. 4.

To begin a detailed discussion of components of an embodiment of the implant assembly 15, reference is made to FIG. 4, which is a side isometric view of the implant assembly 15. As shown in FIG. 4, the implant assembly 15 includes an implant 25 and an anchor element 30. The anchor element 30 may be in the form of an elongated body such as, for example, a nail, rod, pin, threaded screw, expanding body, a cable (e.g., configured with a ball end), etc. The anchor element 30 is configured to be received in a bore 40 defined through the implant 25. The bore 40 extends through the implant 25 and is sized such that the anchor element 30 can at least extend into or through the implant 25 as illustrated in FIG. 4.

Figure 12:
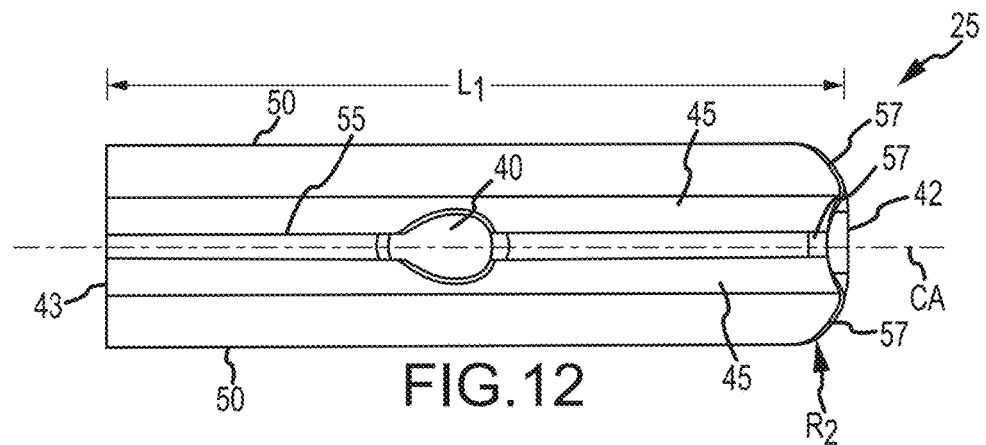
FIGS. 12 and 13 are opposite plan views of the implant.
Figure 13:
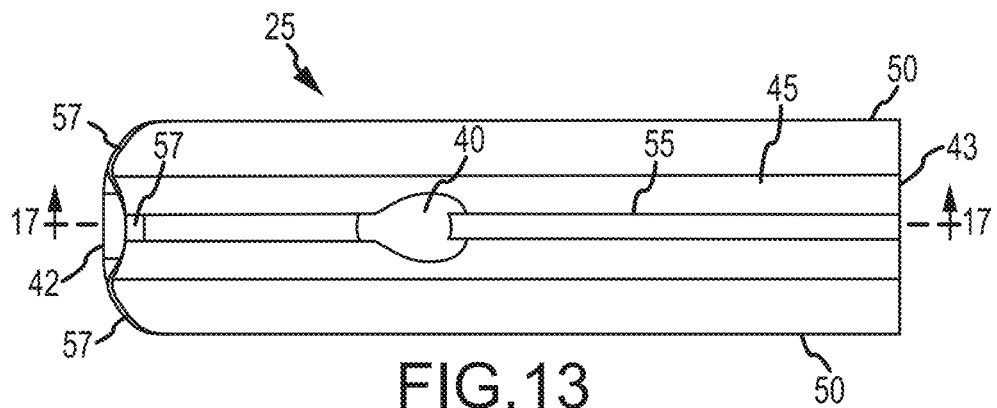

For a detailed discussion of the implant 25, reference is made to FIGS. 5-17. FIGS. 5-9 are various isometric views of the implant 25. FIGS. 12 and 13 are opposite plan views of the implant 25, and FIGS. 10, 11, 14 and 15 are various elevation views of the implant. FIGS. 16 and 17 are isometric longitudinal cross sections of the implant 25 as taken along corresponding section lines in FIGS. 11 and 13, respectively.

As shown in FIGS. 5-15, in one embodiment, the implant 25 includes a distal or leading end 42, a proximal or trailing end 43, a longitudinally extending body 45, a bore 40 extending through the body, and keels, fins or planar members 50, 55 that radially extend outwardly away from the body 45. In one embodiment, the radially extending planar members 50, 55 may be grouped into pairs of planar members 50, 55 that are generally coplanar with each other. For example, planar members 50 that are opposite the body 45 from each other generally exist in the same plane. More specifically, as best understood from FIGS. 14 and 15, the planar faces 60 of a first planar member 50 are generally coplanar with the planar faces 60 of a second planar member 50 opposite the body 45 from the first planar member 50. Likewise, the planar faces 65 of a third planar member 55 are generally coplanar with the planar faces 65 of a fourth planar member 55 opposite the body 45 from the third planar member 55.

Figure 14:
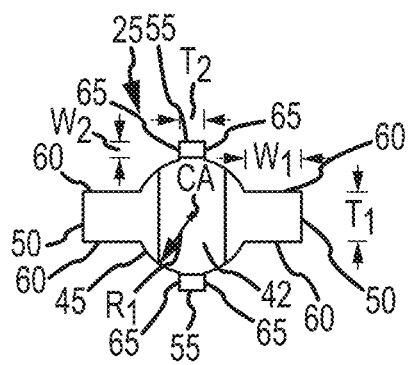
FIG. 14 is a distal end elevation of the implant.
Figure 15:
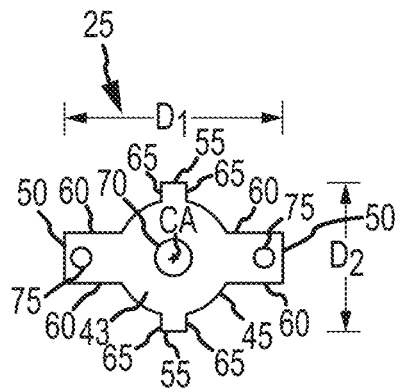
FIG. 15 is a proximal end elevation of the implant.

As best understood from FIGS. 14 and 15, one set of planar members 50 (i.e., the large planar members 50) may extend radially a greater distance $D_1$ than the distance $D_2$ extended radially by the other set of planar members 55 (i.e., the small planar members 55). Also, the width $W_1$ of a large planar member 50 from its outer edge to its intersection with the body 45 may be greater than the width $W_2$ of a small planar member 55 from its outer edge to its intersection with the body 45. Also, the thickness $T_1$ of the large planar members 50 may be greater than the thickness $T_2$ of the small planar members 55. Thus, one set of planar members 50 may be both wider and thicker than the other set of planar members 55. In other words, one set of planar members 50 may be larger than the other set of planar members 55.

In one embodiment, the distance $D_1$ spanned by the large planar members 50 is between approximately 5 mm and approximately 30 mm, with one embodiment having a distance $D_1$ of approximately 20 mm, and the distance $D_2$ spanned by the small planar members 55 is between approximately 5 mm and approximately 20 mm, with one embodiment having a distance $D_2$ of approximately 14 mm. The width $W_1$ of a large planar member 50 is between approximately 2.5 mm and approximately 15 mm, with one embodiment having a width $W_1$ of approximately 5 mm, and the width $W_2$ of a small planar member 55 is between approximately 1 mm and approximately 10 mm, with one embodiment having a width $W_2$ of approximately 3 mm. The thickness $T_1$ of a large planar member 50 is between approximately 2 mm and approximately 20 mm, with one embodiment having a thickness $T_1$ of approximately 4 mm, and the thickness $T_2$ of a small planar member 55 is between approximately 1 mm and approximately 10 mm, with one embodiment having a thickness $T_2$ of approximately 2 mm.

As indicated in FIGS. 5-15, the first set of planar members 50 are generally perpendicular with the second set of planar members 55. Since the sets of planar members 50, 55 are perpendicular to each other, in one embodiment; the intersection of the planar members 50, 55 at a central longitudinal axis of the implant 25 may form the body 45 of the implant 25. In other embodiments, and as illustrated in FIGS. 5-14, the body 45 may be of a distinct shape so as to have, for example, a cylindrical or other configuration. In one embodiment, as indicated in FIG. 14, the cylindrical body 45 has a radius $R_1$ of between approximately 1 mm and approximately 20 mm, with one embodiment having a radius $R_1$ of approximately 10 mm.

As illustrated in FIG. 12, in one embodiment, the implant 25 has a length $L_1$ of between approximately 5 mm and approximately 70 mm, with one embodiment having a length $L_1$ of approximately 45 mm.

As indicated in FIGS. 5 and 9-14, the implant distal end 42 may have a bullet nose or otherwise rounded configuration, wherein the rounded configuration extends outward away from the distal extremity of the body 45 and along the distal or leading edges of the planar members 50, 55. Thus, as can be understood from FIGS. 5 and 9-13, the leading or distal edges 57 of the planar members 50, 55 may be rounded in the radially extending length of the lead or distal edges and/or in a direction transverse to the radially extending length of the lead or distal edges. In one embodiment, the leading edges 57 of the planar members 50, 55 each have a radius $R_2$ of between approximately 1 mm and approximately 15 mm, with one embodiment having a radius $R_2$ of approximately 10 mm. In one embodiment, the leading end 42 of the implant body 45 and the leading edges 57 of the planar members 50, 55 have a generally conical point configuration.

As indicated in FIGS. 6-8, 10-13, and 15, the implant proximal end 43 has a generally planar face that is generally perpendicular to a longitudinal center axis CA of the implant 25. A center attachment bore 70 and two lateral attachment bores 75 on opposite sides of the center bore 70 are defined in the implant proximal end 43. The center bore 70 is centered about the longitudinal center axis CA, and the lateral attachment bores 75 are near outer ends of the long planar members 50, generally centered in the thickness of the larger planar members 50. Alternatively, in particular embodiments, the implant proximal end 43 can be configured to have a face similarly configured to the implant distal end 42 (i.e. rounded, bullet nosed, etc.) to allow for a simplified removal of implant 25 during a revision surgery.

As indicated in FIGS. 16 and 17, the center bore 70 may be a blind hole in that it only has a single opening. Alternatively, the center bore 70 may be configured as a hole that communicates between the implant proximal end 43 and implant bore 40. A center bore so configured may be able to receive a fastener to permit interference with the anchor member 30 extending through the bore 40 after implantation to resist migration of said anchor member.

As illustrated in FIG. 16, the lateral bores 75 are also blind holes and can be configured to not extend nearly as far into the body 45 as the center hole 70 and can be configured to be not nearly as great in diameter as the center hole 70. In one embodiment, the center attachment bore 70 has a diameter of between approximately 2 mm and approximately 10 mm, with one embodiment having a diameter of approximately 5 mm. In one embodiment, the lateral attachment bores 75 can each have a diameter of between approximately 0.5 mm and approximately 3 mm, with one embodiment having a diameter of approximately 1.5 mm.

As can be understood from FIG. 17, the implant bore 40, which is configured to receive the anchor member 30, has a longitudinal center axis BA that is generally transverse to the longitudinal center axis CA of the implant 25. In one embodiment, the implant bore longitudinal center axis BA forms an angle $A_{BA-CA}$ with the implant longitudinal center axis CA. For example, the angle $A_{BA-CA}$ may be between approximately 15 degrees and approximately 135 degrees, with one embodiment being approximately 45 degrees.

As shown in FIGS. 4-17, the bore 40 is generally located within a plane with which the small radial planar members 55 are located. That the bore 40 is located in the same plane as occupied by the small radial planar members 55 is also the case where the bore 40 angularly deviates from being perpendicular with the longitudinal axis of the implant body 45.

In one embodiment, the implant 25 may be machined, molded, formed, or otherwise manufactured from stainless steel, titanium, ceramic, polymer, composite, bone or other biocompatible materials. The anchor member 30 may be machined, molded, formed or otherwise manufactured from similar biocompatible materials.

Figure 118A:
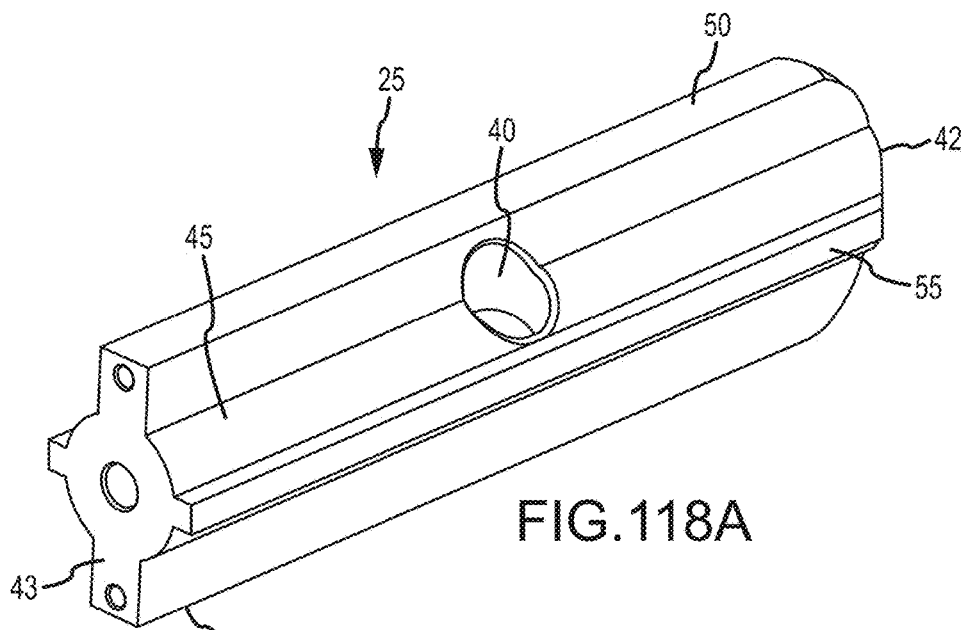
FIGS. 118A-118C are, respectively, isometric and opposite plan views of an implant with a side-to-side deviated bore.
Figure 118B:
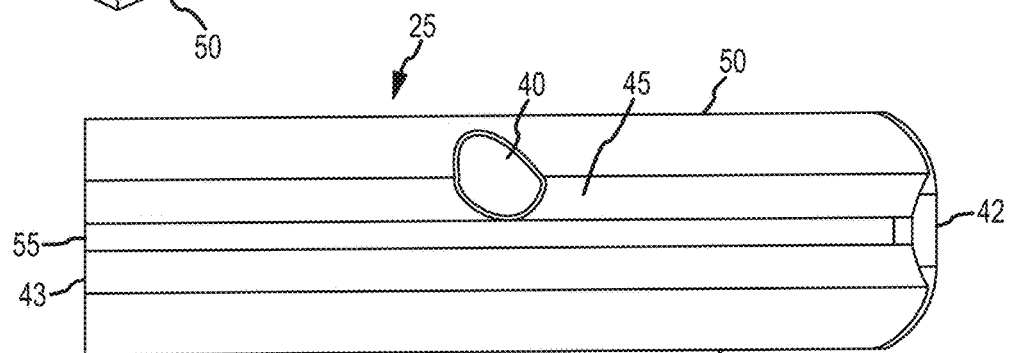
Figure 118C:
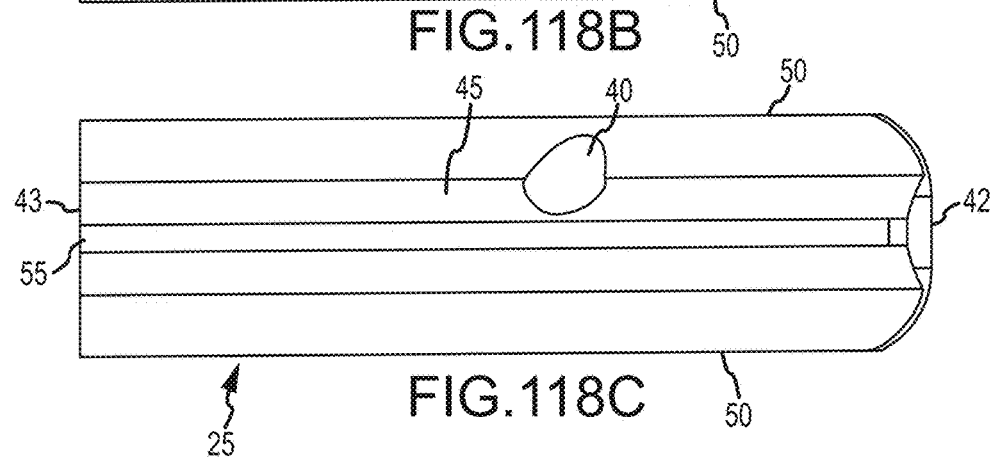
Figure 119A:
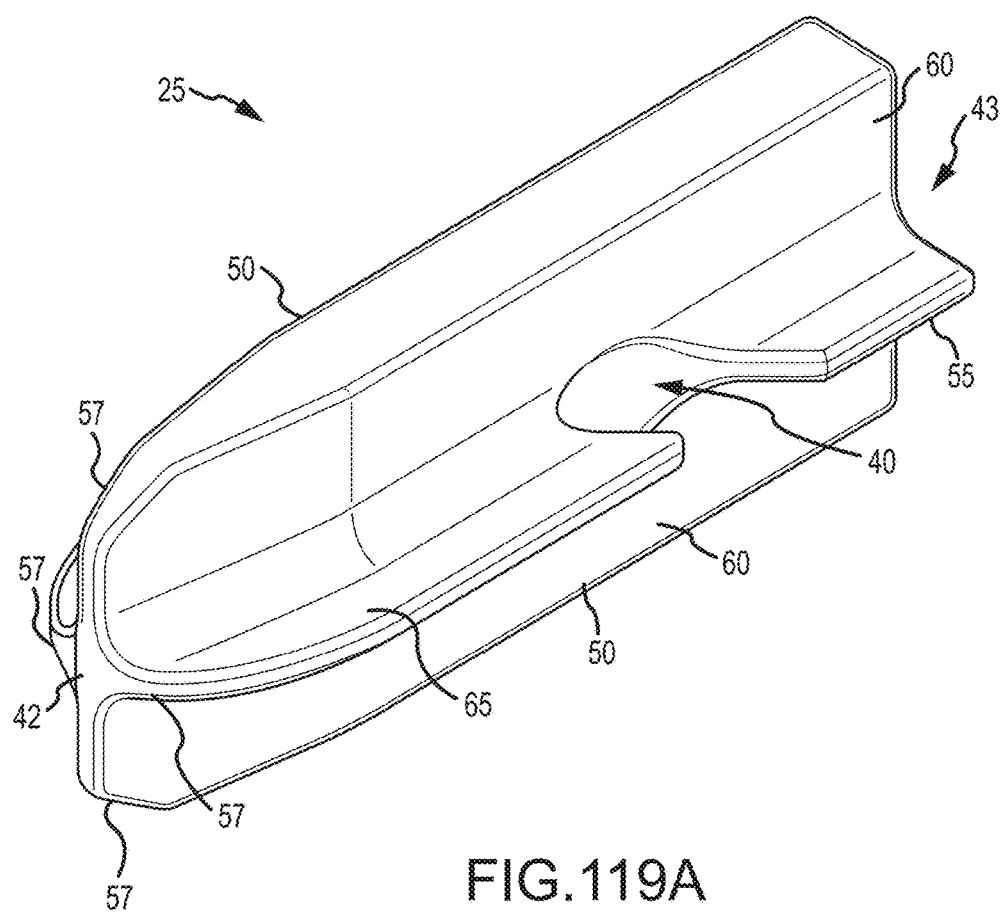
FIGS. 119A-119E are, respectively, distal end isometric, side elevation, plan, distal end elevation, and proximal end elevation views of another embodiment of the implant.
Figure 119B:
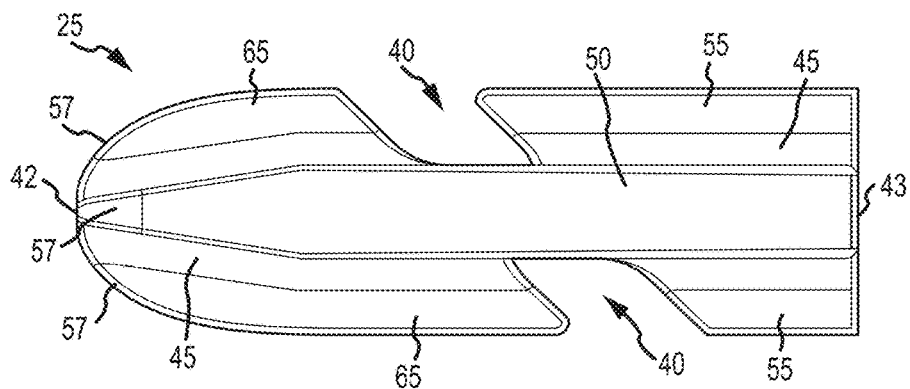
Figure 119C:
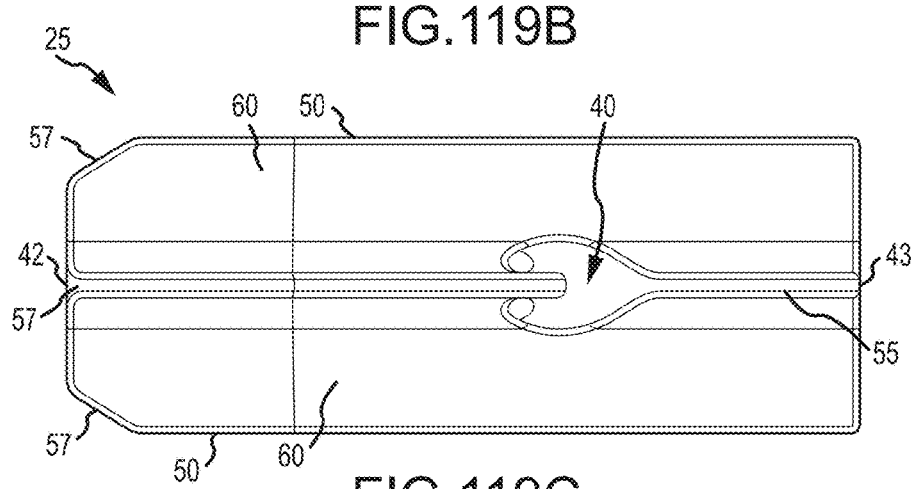
Figure 119D:
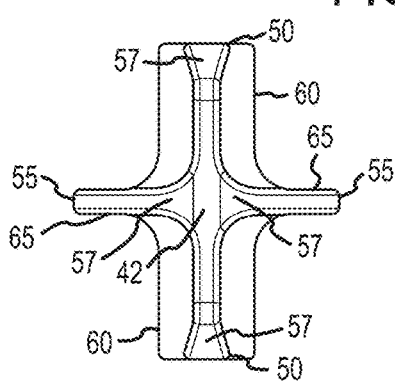
Figure 119E:
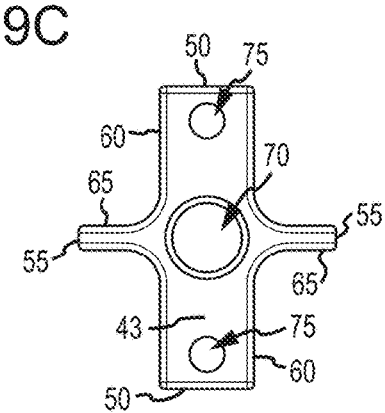

In some embodiments, the implant 25 may be substantially as described above with respect to FIGS. 4-17, except the bore 40 of the implant 25 may be angled side-to-side relative to the longitudinal axis of the implant body 45 such that the bore 40 is not contained in the plane occupied by the small radial planar members 55. For example, as shown in FIGS. 118A-118C, which are, respectively, isometric and opposite plan views of an implant 25 with such a side-to-side deviated bore 40, the bore 40 daylights in the body 45 and large radial planar members 50. In doing so, the bore 40 deviates side-to-side from the plane in which the small planar members 55 are located. Since the bore daylights in the body 45 and large planar members 50, the bore 40 of FIGS. 118A-118C differs from that of FIGS. 4-17, wherein the bore 40 daylights in the small radial members 55.

Just like delivery tool 20 of FIG. 2A has an as-manufactured configuration that allows the anchor arm 115 to deliver the anchor element 30 to the bore 40 of the implant 25 of FIGS. 4-17 without necessitating modification of the delivery tool 20 configuration subsequent to the tool 20 leaving its manufacturing facility, a delivery tool 20 can be configured to similarly interact with the bore 40 of the implant 25 of FIGS. 118A-118C.

In some embodiments, the implant 25 may be substantially as described above with respect to FIGS. 4-17, except the implant 25 may further include an anchor member receiving arm 300. For example, as shown in FIGS. 51-52, which are, respectively, isometric and side elevation views of an implant 25 having an anchor member receiving arm 300, the arm 300 may be generally cantilevered off of the proximal end 43 of the implant 25. The arm 300 includes a free end 305 with a disk-shaped seat 310 having a center hole 315 with a center axis that is coaxially aligned with the center axis BA of the bore 40.

In one embodiment, the arm 300 is rigidly fixed to the implant proximal end 43. In other embodiments, the arm 300 may be in a pivotable or hinged configuration with the implant proximal end 43 to allow movement between the implant 25 and arm 300. Such a hinged arm configuration may be further configured to have a free end 305 which may have a hole 315 (or slot). Due to the hinged configuration of the arm, the arm may be pivoted relative to the rest of the implant such that the center axis of hole 315 may be directed to avoid placing an anchor in a bore 40 or hit the implant 25. In other words, because of the hinged configuration, the arm may be oriented relative to the rest of the implant such that the axis of hole 315 directs an anchor 40 around an implant 25 (i.e., the axis of hole 315 will avoid intersecting the implant 25).

As illustrated in FIG. 53, which is an enlarged view of the disk-shaped seat 310, the disk-shaped seat 310 has a plurality of arcuate members 320 distributed along an inner circumferential boundary 325 of a rim 330 of the disk-shaped seat 310. There may be five or more or less arcuate members 320 distributed generally evenly about the inner circumferential surface 325 of the rim 330.

In one embodiment, each arcuate member 320 has ends 332 that intersect the inner circumferential surface 325 of the rim 330, with a center point 335 of the arcuate member 320 that is offset or spaced apart from inner circumferential surface 325 of the rim 330. Thus, in one embodiment, the arcuate members 320 may be deflectable so as to allow the head of the anchor member 30 to pass between the center points 335 of the members 330 as the head of the anchor member 30 is seated in the seat 310. As a result, the arcuate members 320 can act against the head of the anchor member 30 to prevent the anchor member from working its way out of the bore 40 and opening 315 of the implant 25, thereby serving as an anchor member locking mechanism.

Other arms 300 may have an anchor member locking mechanism with a different configuration. For example, as illustrated in FIG. 54, which is an isometric view of an implant 25 with another type of anchor member locking mechanism, the arm 300 may be generally cantilevered off of the proximal end 43 of the implant 25. The arm 300 includes a free end 305 with a center hole 315 with a center axis that is coaxially aligned with the center axis BA of the bore 40. As illustrated in FIG. 55, which is an enlarged view of the free end 305, the hole 315 has a cantilevered abutment arm 335 defined in the body of the arm 300 via a series of parallel arcuate slots 340.

In one embodiment, a face 345 of the abutment arm 335 is deflectable and biased radially inward of the inner circumferential surface 350 of the hole 315 such that when the anchor member 30 is extended through the hole 315, the face 345 abuts against the anchor member to prevent the anchor member from working its way out of the bore 40 and opening 315 of the implant 25, thereby serving as an anchor member locking mechanism.

While in the implant embodiment discussed with respect to FIGS. 4-17 may have a cylindrical body 45 at which the planar members 50, 55 intersect, in other embodiments the body 45 of the implant 25 may simply be the region 45 of the implant 25 where the planar members 50, 55 intersect. For example, as shown in FIGS. 56-61, which are, respectively, front isometric, rear isometric, side elevation, plan, front elevation, and rear elevation views of an implant 25, the body 45 of the implant 25 is simply the region 45 of the implant 25 where the planar members 50, 55 intersect. Although not shown in FIGS. 56-61, in one embodiment, the implant 25 has the bore 40 and holes 70, 75 substantially as depicted and discussed with respect to the implant of FIGS. 4-17. Also, the rest of the features of the implant 25 of FIGS. 56-61 are substantially as discussed with respect to the implant 25 of FIGS. 4-17, a main difference being the lack of the cylindrical body 45 and the edges of adjacent intersecting surfaces of the implant 25 of FIGS. 56-61 being rounded or arcuate as opposed to sharp or well-defined edges, as is the case between adjacent intersecting surfaces of the implant embodiment of FIGS. 4-17.

Depending on the embodiment, the implant 25 may have surface features or texture designed to prevent migration of the implant once implanted in the joint space. For example, as shown in FIGS. 62-67, which are, respectively, front isometric, rear isometric, side elevation, plan, front elevation, and rear elevation views of an implant 25 with anti-migration surface features 355, the body 45 of the implant 25 is simply the region 45 of the implant 25 where the planar members 50, 55 intersect. Although not shown in FIGS. 62-67, in one embodiment, the implant 25 has the bore 40 and holes 70, 75 substantially as depicted and discussed with respect to the implant of FIGS. 4-17. Also, the rest of the features of the implant 25 of FIGS. 62-67 are substantially as discussed with respect to the implant 25 of FIGS. 56-61, a main difference being the edges of adjacent intersecting surfaces the implant 25 of FIGS. 56-61 being sharp or well defined edges as opposed to round or arcuate edges, as is the case between adjacent intersecting surfaces of the implant embodiment of FIGS. 56-61.

As to particular embodiments as shown in FIGS. 56-61, and in other embodiments as disclosed throughout, the implants described herein can be configured to be used as trials during certain steps of the procedure to determine appropriate implant sizes and to allow a physician, who is presented with a kit containing the delivery system 20 and multiple sizes of the implant 20, to evaluate particular embodiments of an implant as described herein that would be best suited to a particular patient, application or implant receiving space.

As shown in FIGS. 62-67, the anti-migration features 355 are generally evenly distributed along the planar surfaces 60, 65 of the planar members 50, 55 in a rows and columns arrangement. The anti-migration features 355 are generally similarly distributed along the planar surfaces of the edges of the planar members 55. The anti-migration features 355 may be in the form of trapezoids, squares, rectangles, etc. As indicated in FIG. 66, the anti-migration features 355 may have a rectangular cross sectional elevation with a thickness FT of between approximately 0.2 mm and approximately 5 mm, with one embodiment having a thickness FT of approximately 1 mm.

As another example, as shown in FIGS. 68-73, which are, respectively, front isometric, rear isometric, side elevation, plan, front elevation, and rear elevation views of an implant 25 with another type of anti-migration surface features 355, the body 45 of the implant 25 is simply the region 45 of the implant 25 where the planar members 50, 55 intersect. Although not shown in FIGS. 68-73, in one embodiment, the implant 25 has the bore 40 and holes 70, 75 substantially as depicted and discussed with respect to the implant of FIGS. 4-17. Also, the rest of the features of the implant 25 of FIGS. 68-73 are substantially as discussed with respect to the implant 25 of FIGS. 62-67, including the sharp or well defined edges between adjacent intersecting surfaces of the implant 25.

As shown in FIGS. 68-73, the anti-migration features 355 are in the form of unidirectional serrated teeth or ridges 355, wherein the ridges 355 have a triangular cross sectional elevation best understood from FIGS. 70 and 71, wherein the rearward or trailing end of the features 355 are the truncated or vertical end of the triangle cross sectional elevation, and the front or leading end of the features 355 are the point end of the triangle cross sectional elevation. As indicated in FIG. 71, the anti-migration features 355 with the triangular cross sectional elevations have a thickness FT of between approximately 0.2 mm and approximately 5 mm, with one embodiment having a thickness FT of approximately 1 mm, and a length FL of between approximately 0.5 mm and approximately 15 mm, with one embodiment having a thickness FT of approximately 2.5 mm. The triangular ridges 355 are generally evenly distributed along the planar surfaces 60, 65 of the planar members 50, 55 in ridges that run transverse to the length of the implant 25. The anti-migration features 355 are generally similarly distributed along the planar surfaces of the edges of the planar members 55.

In continuing reference to FIGS. 68-73, although the anti-migration features 355 are depicted in the form of unidirectional serrated teeth or ridges 355 on each of the textured surfaces of the implant, the invention is not so limited and, as to particular embodiments, can be configured to have said features 355 arranged in multiple directions, unidirectional, or a combination of multiple direction on some surfaces of the implant and unidirectional on other surfaces of the implant. Accordingly, the features 355 can be so arranged on the various surfaces of the implant so as to prevent undesired migration in particular directions due to the forces present at the sacroiliac joint 1000.

Depending on the embodiment, the implant 25 may have an edge configuration of the planar members 55 designed to prevent migration of the implant once implanted in the joint space. For example, as shown in FIGS. 74-79 which are, respectively, front isometric, rear isometric, side elevation, plan, front elevation, and rear elevation views of an implant 25 with anti-migration edges or ends 360, the body 45 of the implant 25 is simply the region 45 of the implant 25 where the planar members 50, 55 intersect. Although not shown in FIGS. 74-79, in one embodiment, the implant 25 has the bore 40 and holes 70, 75 substantially as depicted and discussed with respect to the implant of FIGS. 4-17. Also, the rest of the features of the implant 25 of FIGS. 74-79 are substantially as discussed with respect to the implant 25 of FIGS. 56-61, with the exception of the anti-migration edges 360 of the implant embodiment of FIGS. 74-79.

As shown in FIGS. 74-79, the anti-migration edges 360 of the planar members 55 are in the form of notches 365 generally evenly distributed along longitudinally extending free edges or ends of the planar members 55. As indicated in FIG. 77, the notches 365 may have parallel sides 370 inwardly terminating as an arcuate end 375. The orientation of each notch 365 may be such that the center line NL of the notch 365 forms an angle NA with the center axis CA of the implant 25 that is between approximately 90 degrees and approximately 15 degrees, with one embodiment having an angle NA of approximately 45 degrees. As indicated in FIG. 77, each notch 365 may have a length LN between the extreme point on the arcuate end 375 and the outer edge boundary of the notch of between approximately 0.2 mm and approximately 10 mm, with one embodiment having a length LN of approximately 3 mm. Each notch 365 may have a width WN of between approximately 0.5 mm and approximately 20 mm, with one embodiment having a width WN of approximately 2 mm.

As another example, as shown in FIGS. 80-85, which are, respectively, front isometric, rear isometric, side elevation, plan, front elevation, and rear elevation views of an implant 25 with another type of anti-migration edges or ends 360, the body 45 of the implant 25 is simply the region 45 of the implant 25 where the planar members 50, 55 intersect. Although not shown in FIGS. 80-85, in one embodiment, the implant 25 has the bore 40 and holes 70, 75 substantially as depicted and discussed with respect to the implant of FIGS. 4-17. Also, with the exception of its anti-migration edges 360 and its more arcuate distal or leading end 42, the rest of the features of the implant 25 of FIGS. 80-85 are substantially as discussed with respect to the implant 25 of FIGS. 62-67, including the sharp or well defined edges between adjacent intersecting surfaces of the implant 25.

As shown in FIGS. 80-85, the anti-migration edges 360 are flared longitudinally extending free edges or ends of the planar members 55. The edges 360 include a series of ridges 370 that are generally evenly distributed along the length of the edges 360 and oriented transverse to the length of the edges 360.

Figure 83:
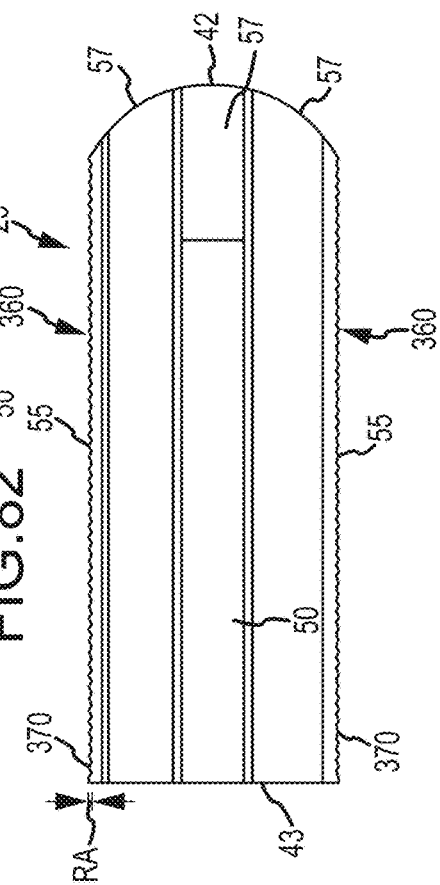
Figure 85:
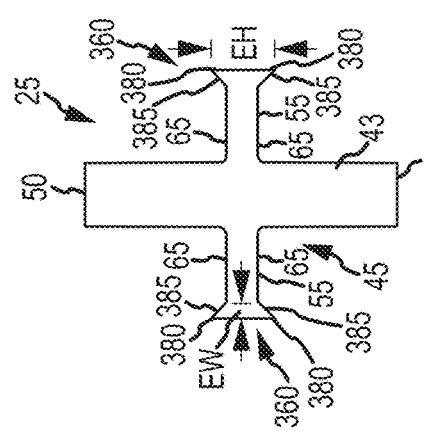

As indicated in FIG. 83, the ridges 370 have triangular cross sectional elevations with an overall height RA of between approximately 0.2 mm and approximately 8 mm, with one embodiment having a width RA of approximately 1 mm. As illustrated in FIG. 85, the flared longitudinally extending free edges or ends of the planar members 55 have rim edges 380 defining the top and bottom edges of the anti-migration edges 360 of the planar members 55, wherein the rim edges 380 have slopes 385 transitioning between the planar surfaces 65 of the planar members 55 and the rim edges 380.

The edges 360 have a height EH between the edges 380 of between approximately 0.5 mm and approximately 15 mm, with one embodiment having a height EH of approximately 4 mm. The width EW of the flared edge 360 from the beginning of the sloped transition 385 to the face of the edge 360 is between approximately 0.2 mm and approximately 9 mm, with one embodiment having a width EW of approximately 1 mm.

In particular embodiments, the implants with features as described above with respect to FIGS. 62-83 can alternatively be configured to function as a broach or other surgical site preparation tool that can assist in the removal of certain tissues, for example, cartilage or bone, during certain steps of a procedure.

To begin a detailed discussion of components of an embodiment of the delivery tool 20, reference is again made to FIGS. 2A-3. As shown in FIG. 2A, the delivery tool 20 includes a distal end 35 and a proximal end 80. The distal end 35 supports the implant assembly 15 components 25, 30, and the proximal end 80 is configured to be grasped and manipulated to facilitate the implantation of the implant assembly 15 in the sacroiliac joint.

Figure 18:
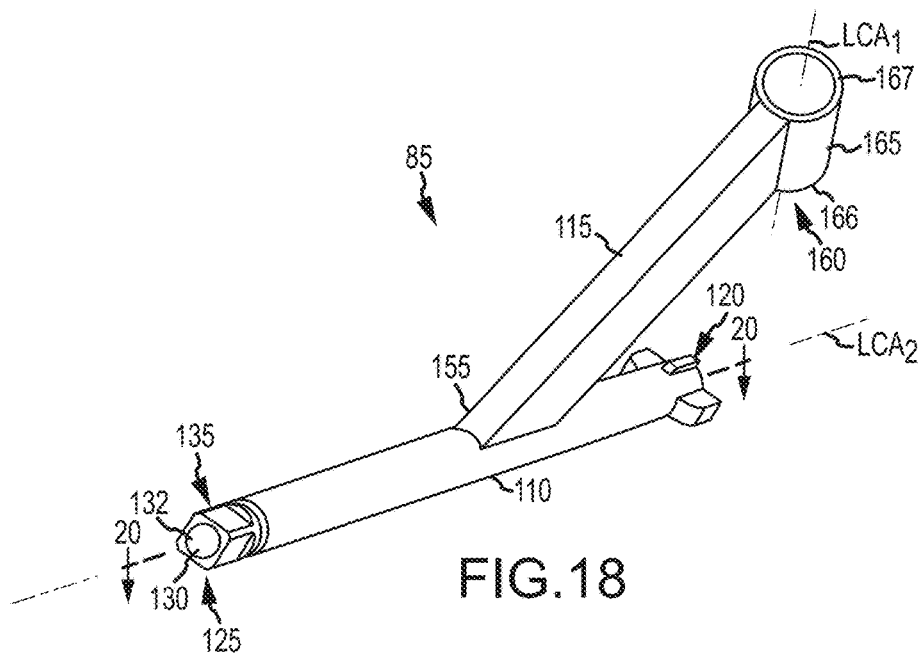
FIG. 18 is a proximal isometric view of the arm assembly.

As illustrated in FIG. 3, the delivery tool 20 further includes an arm assembly 85, a handle 90, an implant retainer 95, a sleeve 100 and a trocar or guidewire 105. As shown in FIG. 18, which is a proximal isometric view of the arm assembly 85, the arm assembly 85 includes an implant arm 110 and an anchor arm 115 supported off of the implant arm 110. The implant arm 110 includes a distal end 120, a proximal end 125 and a proximal cylindrical opening 130 of a cylindrical bore 132. The proximal end 125 includes a squared outer surface configuration 135 that facilitates a mechanical engagement arrangement with the handle 90 such as the mechanical arrangement that exists between a wrench and nut.

Figure 19:
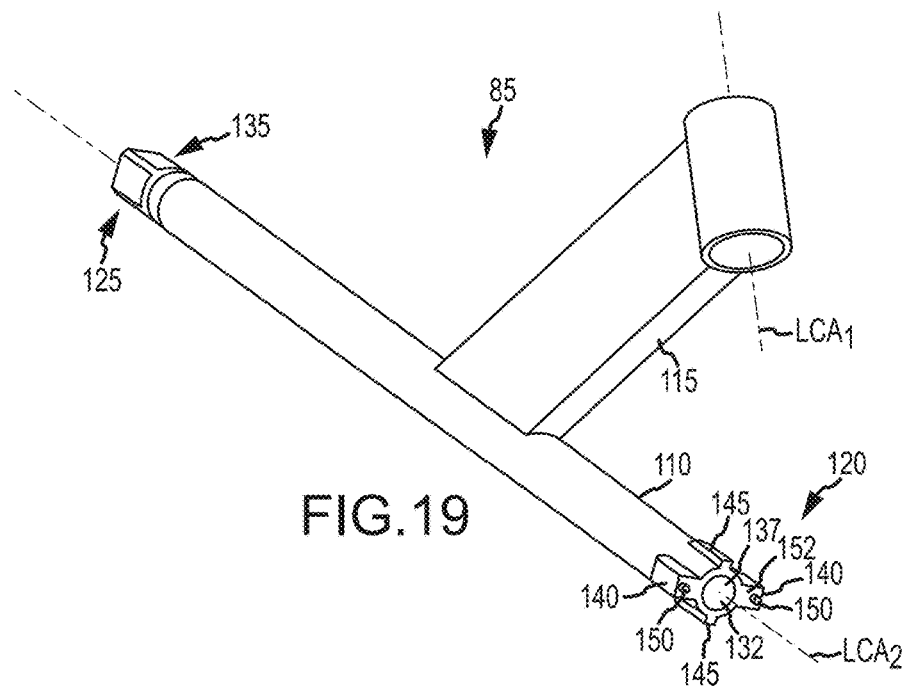
FIG. 19 is a distal isometric view of the arm assembly 85.
Figure 20:
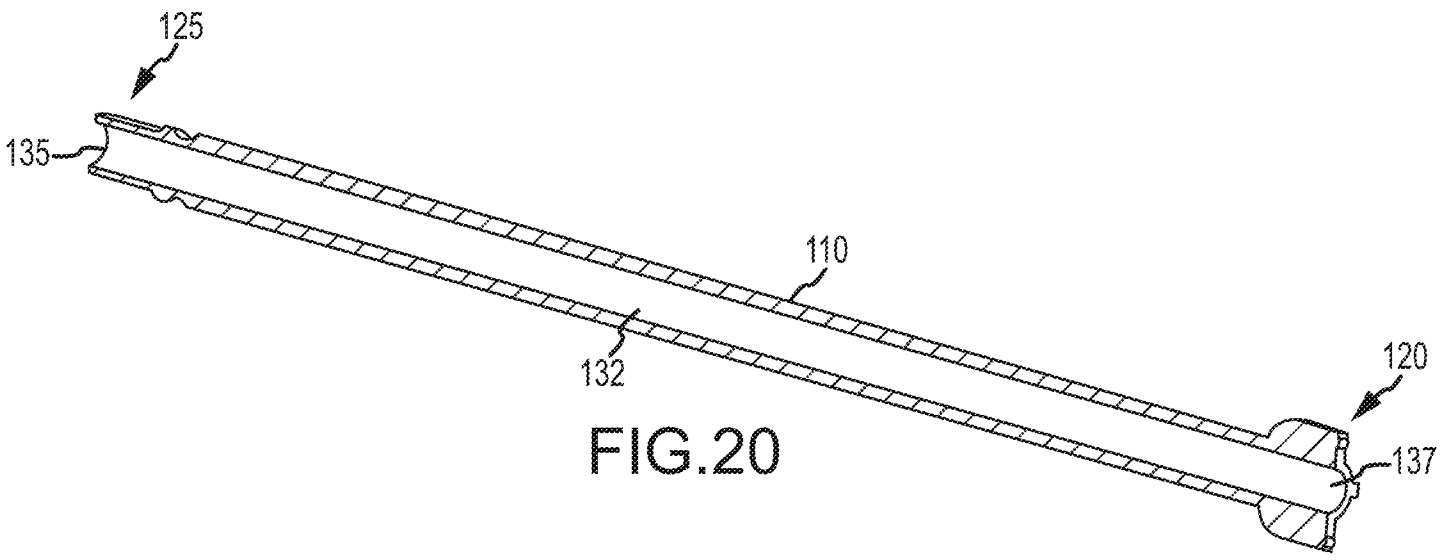
FIG. 20 is a longitudinal cross section of the implant arm as taken along section line 20-20 in FIG. 18.

As shown in FIG. 19, which is a distal isometric view of the arm assembly 85, the distal end 120 includes cylindrical opening 137 of a cylindrical bore 132, large planar members, keels, or fins 140 and small planar members, keels, or fins 145, pins 150, and a planar extreme distal face 152. As depicted in FIG. 20, which is a longitudinal cross section of the implant arm 110 as taken along section line 20-20 in FIG. 18, the cylindrical bore 132 extends the full length of the implant arm 110 between the proximal opening 135 and the distal opening 137.

Figure 21A:
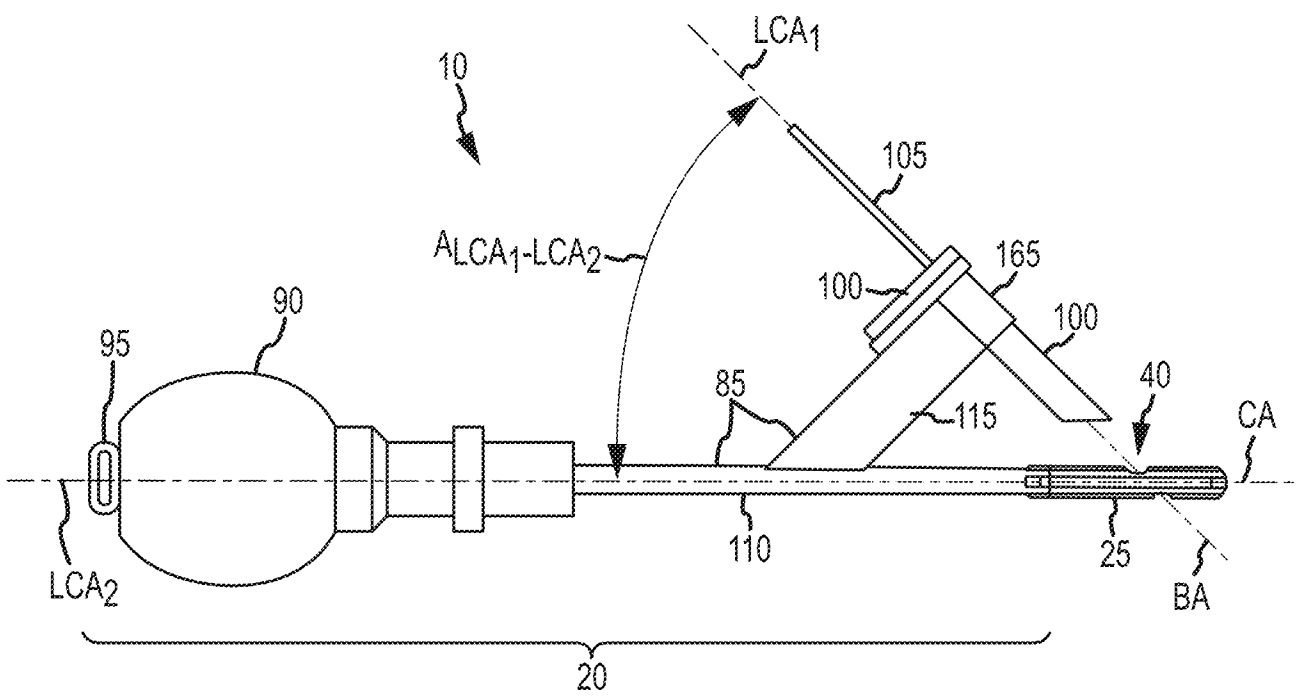
FIG. 21A is a side elevation of the system wherein the tool is attached to the implant assembly for delivery of the implant assembly to the sacroiliac joint.
Figure 23:
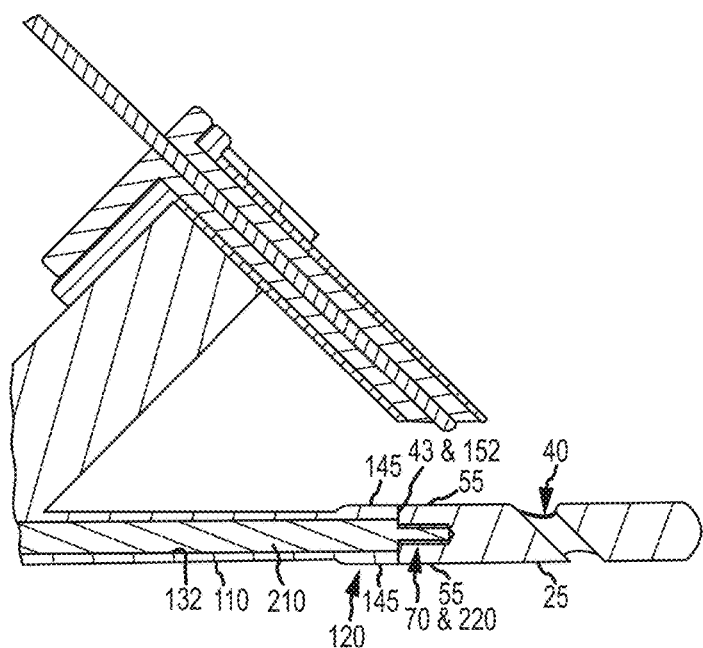
FIG. 23 is an enlarged view of the distal region of the system circled in FIG. 22.
Figure 24:
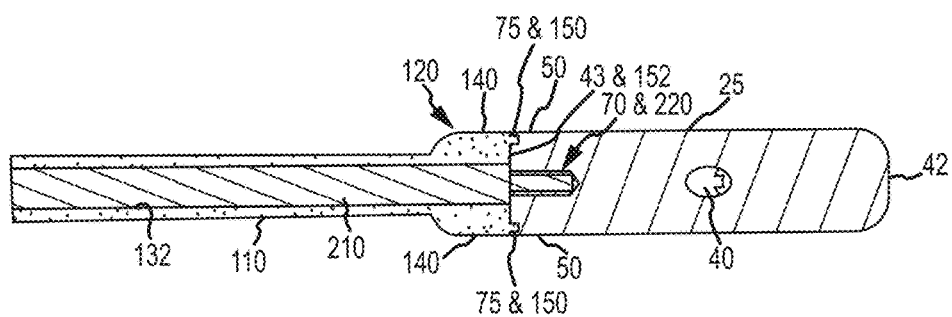
FIG. 24 is an enlarged cross sectional plan view taken in a plane 90 degrees from the section plane of FIG. 23.

For a detailed discussion of the interaction between the features of the implant arm distal end 120 and the proximal end 43 of the implant 25, reference is now made to FIGS. 2A and 21A and 22-24. FIG. 21A is a side elevation of the system 10 wherein the tool 20 is attached to the implant assembly 15 for delivery of the implant assembly 15 to the sacroiliac joint. FIG. 22 is the same view as FIG. 21A, except shown as a longitudinal cross section. FIG. 23 is an enlarged view of the distal region of the system 10 circled in FIG. 22. FIG. 24 is an enlarged cross sectional plan view taken in a plane 90 degrees from the section plane of FIG. 23.

As can be understood from FIGS. 2A and 21A and 22-24, when the system 10 is assembled for the delivery of the implant assembly 15 to the sacroiliac joint, the proximal end 43 of the implant 25 (see FIG. 6) is supported off of the implant arm distal end 120 (see FIG. 19). As can be understood from a comparison of FIGS. 6 and 19 and more clearly depicted in FIGS. 23 and 24, the cylindrical body 45, and planar members 50, 55 of the implant 25 and the cylindrical implant arm 110 and planar members 140, 145 of the implant arm 110 respectively correspond with respect to both shape and size such that when the implant 25 is supported off of the implant arm distal end 120 as depicted in FIGS. 2A and 21A and 22-24, the respective outer surfaces of the implant 25 and implant arm distal end 120 transition smoothly moving from the implant 25 to the implant arm distal end 120, and vice versa. Also, as shown in FIGS. 23 and 24, when the system 10 is assembled for the delivery of the implant assembly 15 to the sacroiliac joint, the planar extreme proximal face 43 of the implant 25 abuts against the planar extreme distal face 152 of the implant arm distal end 120, the pins 150 being received in a recessed fashion in the lateral bores 75. The pins 150 being received in the lateral bores 75 prevents the implant 25 from pivoting relative to the implant arm 110. The pins 150 can be configured to have a rectangular, circular or any other cross section and the corresponding lateral bores 75 can also be configured to have corresponding shapes in cross section.

Alternatively, in order to further restrict undesirable movement between components of a system 10, namely between that of a delivery tool 20 and an implant 25, the distal face 152 of the implant arm distal end 120 can be configured to rap around, and can also be recessed into or grappled to, the exterior surface of the elongate body 45, or planar members 50, or 55 of the implant 25 a distance DE, from about 0.2 mm to about 20 mm (e.g., 10 mm), in the direction of implant distal end 42. According to particular embodiments, a recess can extend a distance DA from said exterior surfaces in the general direction of implant longitudinal axis CA, from about 0.25 mm to 5 mm (e.g., 1.25 mm). In a non-limiting example of a particular embodiment, the distal face 152 of the implant arm distal end 120 can be further configured to wrap completely or only a portion of the periphery of an implant by occupying only a portion, CAR, as defined by a number of degrees around implant longitudinal axis CA, from about 1 degree to about 180 degrees (e.g., 30 degrees). In particular embodiments, said features can be configured to be located in the area between the planar members 50 and 55.

As shown in FIGS. 18 and 19, the anchor arm 115 is supported off of the implant arm 110 at an angle and includes a proximal end 155 and a distal end 160 distally terminating in a sleeve or collar 165 having a longitudinal center axis $LCA_1$ that is generally transverse to the longitudinal axis of the anchor arm 115. Collar 165 has a length of between approximately 10 mm and approximately 60 mm (e.g., 20 mm) disposed between collar ends 166 and 167 configured to permit and maintain accurate alignment of the first sleeve 100 along $LCA_1$ during the course of the procedure. The anchor arm proximal end 155 intersects the implant arm 110 at a location between the proximal and distal ends of the implant arm.

As indicated in FIGS. 18 and 19, the implant arm 110 also includes a longitudinal center axis $LCA_2$. As shown in FIG. 21A, when the system 10 is assembled such that the implant 25 is mounted on the distal end of the implant arm 110, the longitudinal center axis CA of the implant 25 is coaxially aligned with the longitudinal center axis $LCA_2$ of the implant arm 110, and the longitudinal center axis BA of the implant bore 40 is coaxially aligned with the longitudinal center axis $LCA_1$ of the anchor arm collar 165. Thus, the longitudinal center axis CA of the implant 25 and the longitudinal center axis $LCA_2$ of the implant arm 110 exist on a first common longitudinally extending axis, and the longitudinal center axis BA of the implant bore 40 and the longitudinal center axis $LCA_1$ of the anchor arm collar 165 exist on a second common longitudinally extending axis.

In one embodiment, the longitudinal center axis $LCA_1$ of the anchor arm collar 165 forms an angle $A_{LCA1\text{-}LCA2}$ with the longitudinal center axis $LCA_2$ of the implant arm 110. For example, the angle $A_{LCA1\text{-}LCA2}$ may be between approximately 15 degrees and approximately 135 degrees, with one embodiment being approximately 45 degrees.

As can be understood from FIG. 21A, when the system 10 is assembled such that the implant 25 is mounted on the distal end of the implant arm 110, the longitudinal center axis $LCA_2$ of the implant arm 110 is coaxial with the longitudinal center axis CA of the implant 25 and the longitudinal center axis of the handle 90. Thus, the line of action for the insertion of the implant 25 into the sacroiliac joint is coaxial with the longitudinal center axes of the implant 25, implant arm 110 and handle 90.

As can be understood from the preceding discussion, in one embodiment, when the system 10 is assembled such that the implant 25 is mounted on the distal end of the implant arm 110, the angle $A_{BA\text{-}CA}$ may be substantially the same as the angle $A_{LCA1\text{-}LCA2}$. Also, the longitudinal center axis BA of the implant bore 40 is coaxially aligned with the longitudinal center axis $LCA_1$ of the anchor arm collar 165. Thus, as will be described in detail below, the anchor arm collar 165 is oriented so as to guide drills and other tools in creating a channel through tissue and bone leading to the implant bore 40 when the implant 25 is positioned in the sacroiliac joint while the implant 25 is still attached to the distal end of the implant arm 110, as shown in FIG. 21. Additionally, the anchor arm collar 165 is oriented so as to guide the anchor member 30 into the implant bore 40 when the implant 25 is positioned in the sacroiliac joint while the implant 25 is still attached to the distal end of the implant arm 110, as shown in FIG. 21A.

As can be understood from FIG. 21A, in one embodiment, the above-described coaxial and angular relationships are rigidly maintained due to the anchor arm 115 and its collar 165 being in a fixed, non-adjustable configuration, and the interconnection between the proximal end of the anchor arm 115 and the implant arm 110 being a fixed, non-adjustable configuration at least with respect to the angle $A_{LCA1\text{-}LCA2}$ between the longitudinal center axis $LCA_1$ of the anchor arm collar 165 and the longitudinal center axis $LCA_2$ of the implant arm 110. Thus, in one embodiment, the delivery tool 20 comes from the manufacture to the physician in a fixed, non-adjustable configuration having the coaxial and angular relationships articulated above with respect to FIG. 21A.

Figure 21B:
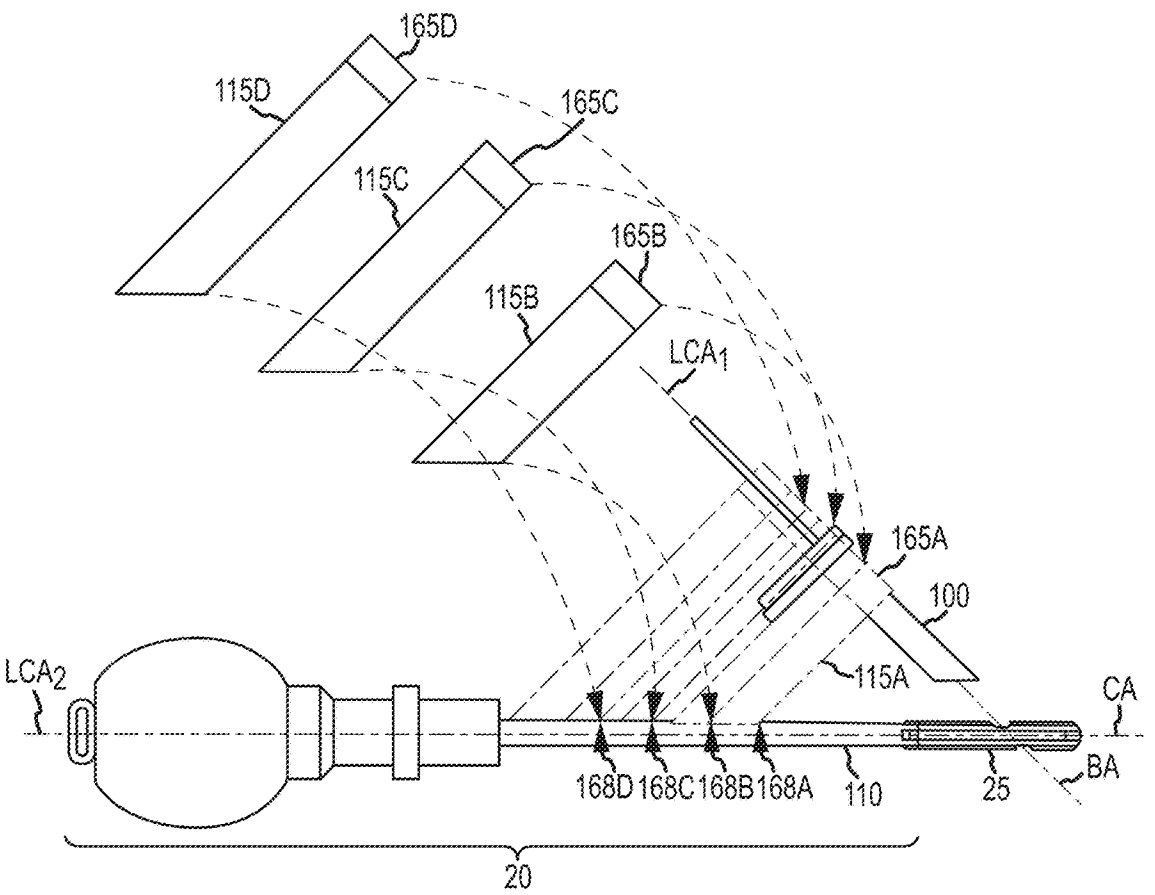
FIG. 21B is the same view as FIG. 21A, except illustrating a series of interchangeable anchor arms that may be coupled to the implant arm to adjust the tool for the patient, but maintain the angular relationship between the components of system that allows the anchor member to be delivered into the implant bore without adjustment to the delivery tool.

FIG. 21B is the same view as FIG. 21A, except of another embodiment of the delivery tool 20 wherein the tool 20 includes multiple anchor arms 115A-115D that can be coupled to specific respective locations 168A-168D on the implant arm 110 to account for different patient sizes, yet still maintain the coaxial and angular relationships set out above. As shown in FIG. 21B, the delivery tool 20 may include two or more, for example, four, anchor arms 115A-115D, each anchor arm having a different overall length. Despite having different overall lengths, because each anchor arm 115A-115D is configured to couple to a specific respective location 168A-168D on the implant arm 110, the longitudinal center axis $LCA_1$ of each anchor arm collar 165A-165D is still coaxially aligned with the longitudinal center axis BA of the implant bore 40 when each anchor arm is mounted at its correct respective location 168A-168D on the implant arm 110. Thus, although the embodiment depicted in FIG. 21B is adjustable with respect to patient size via the interchangeable anchor arms 115A-115D, the above-described coaxial and angular relationships are rigidly maintained due to the anchor arms 115A-115D and their collars 165 being in a fixed, non-adjustable configuration, and the interconnection between the proximal end of the anchor arms 115A-115D and the implant arm 110 being, a fixed, non-adjustable configuration at least with respect to the angle $A_{LCA1\text{-}LCA2}$ between the longitudinal center axis $LCA_1$ of the anchor arm collar 165 and the longitudinal center axis $LCA_2$ of the implant arm 110. Thus, although the embodiment depicted in FIG. 21B is adjustable with respect to the patient size via the interchangeable anchor arms 115A-115D, the delivery tool 20 comes from the manufacture to the physician in a fixed, non-adjustable configuration with respect to the coaxial and angular relationships articulated above with respect to FIG. 21A.

Although not shown in FIG. 21B, in some embodiments, multiple sleeves 100 may be provided with the system 10. For example, the system 10 may include four anchor arms 165A-165D of different lengths and the system may also include four sleeves 100 of different lengths, each sleeve 100 being configured for use with a specific anchor arm. For example, since anchor arm 165D is the longest anchor arm, its corresponding sleeve 100 may be the longest of the sleeves. Similarly, since anchor arm 165A is the shortest anchor arm, its corresponding sleeve 100 may be the shortest of the sleeves.

Because of the multiple interchangeable anchor arms 165A-165D that are each configured for attachment to a specific respective location 168A-168D on the implant arm 110, the delivery tool 20 may be adjusted to accommodate patients of different sizes and still maintain the angular relationships between the components of system 10 that allows the anchor member 30 to be delivered into the implant bore 40 without any further adjustment to the delivery tool. Because the angular relationships are rigidly maintained between the arms 110, 115, the collar 165, and the implant bore 40 despite the anchor arms 115A-115B being interchangeable, the anchoring of the implant 25 in the sacroiliac joint via the anchor member 30 may be achieved quickly and safely. In other words, because the tool does not need to be adjusted with respect to angular relationships, the surgery is simplified, reduced in duration, and reduces the risk of the anchor member 30 being driven through a nerve, artery or vein.

Figure 21C:
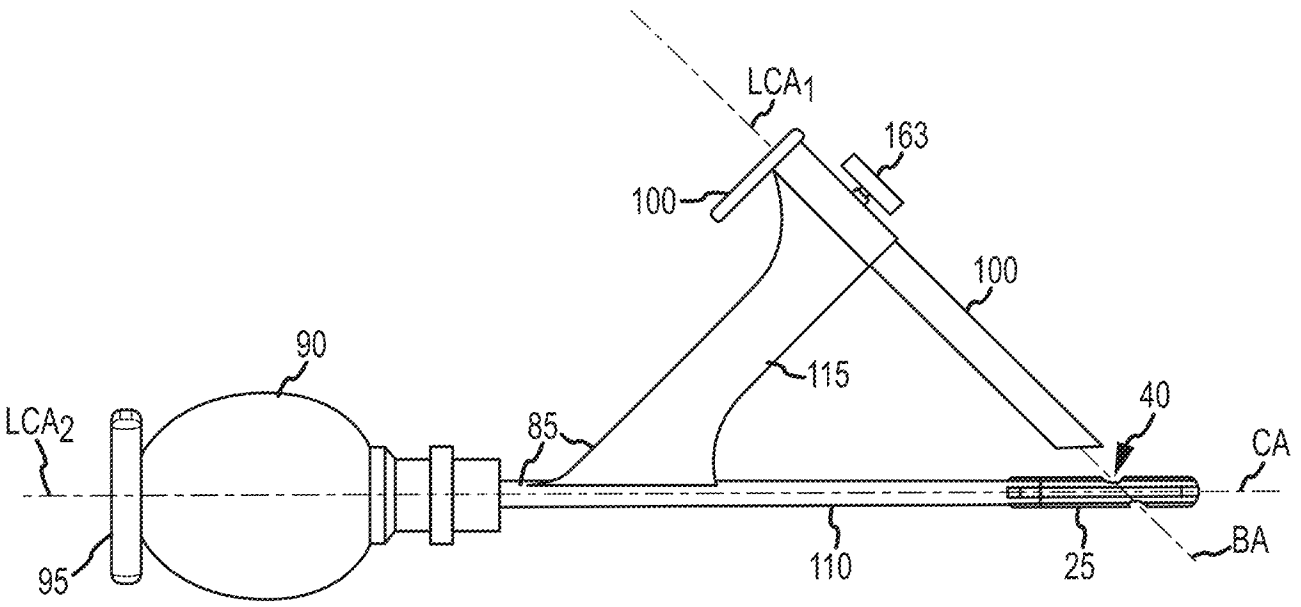
FIG. 21C is the same view of FIG. 21A, except illustrating a version of the same embodiment wherein the anchor arm is more proximally located along the implant arm.

In some embodiments, the system 10 may be provided with two or more tools 20, each tool having a configuration for a specific size of patient. For example, the tool 20 depicted in FIG. 21A may be provided for smaller patients in that there is reduced distance between the anchor arm collar 165 and the implant 25. As depicted in FIG. 21C, which is the same view of FIG. 21A, except illustrating a version of the same tool 20 configured to accommodate larger patients, the distance between anchor arm collar 165 and implant 25 is greater due to the anchor arm 165 being more proximally located on the implant arm 110 as compared to the configuration depicted in FIG. 21A. It should be noted that, although the version depicted in FIG. 21C is configured to accommodate larger patients, the coaxial and angular relationships discussed above with respect to FIG. 21A are the same for the version depicted in FIG. 21C. For the version depicted in FIG. 21C, the sleeve 100 is substantially elongated as compared to the sleeve 100 of FIG. 21A. Depending on the size of the patient, the physician may select or be provided with one of the tool configurations shown in FIG. 21A or 21C.

Additionally, the sleeve 100 of FIG. 21C can be prevented from undesired migration within the anchor arm collar 165 during a procedure by utilizing a locking mechanism 163 in close proximity to the collar 165. As a non-limiting example, a locking mechanism can be configured as a fastener 163, which, in certain embodiments, can be threaded and rotatably advanced into the collar 165 to cause a greater amount of friction upon the sleeve 100.

Figure 25:
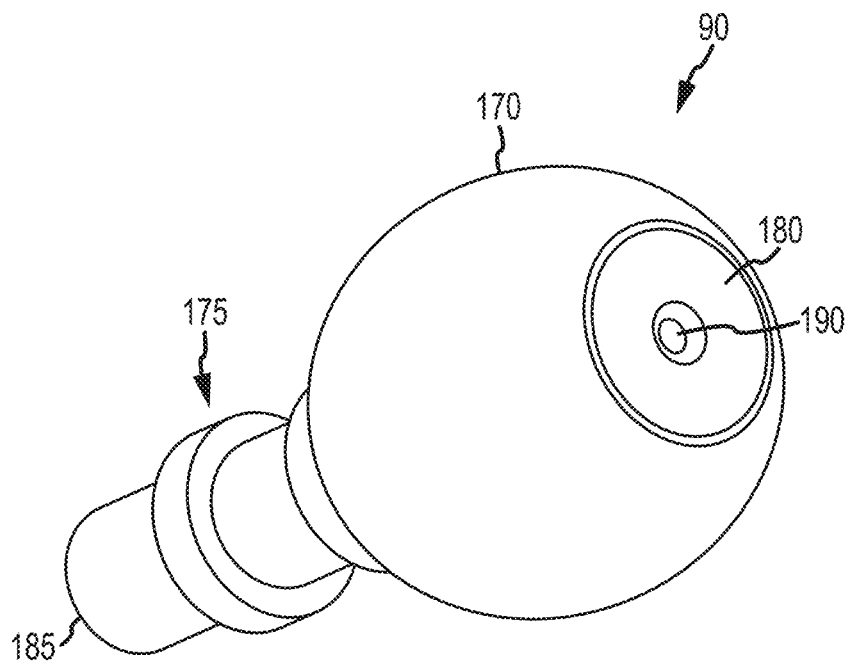
FIG. 25 is a proximal isometric view of the handle.
Figure 26:
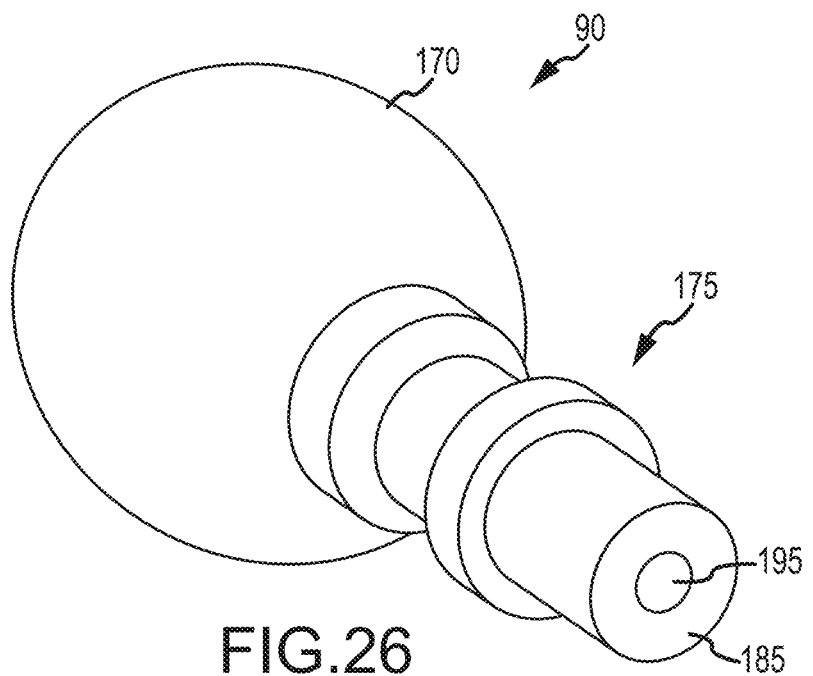
FIG. 26 is a distal isometric view of the handle.
Figure 27:
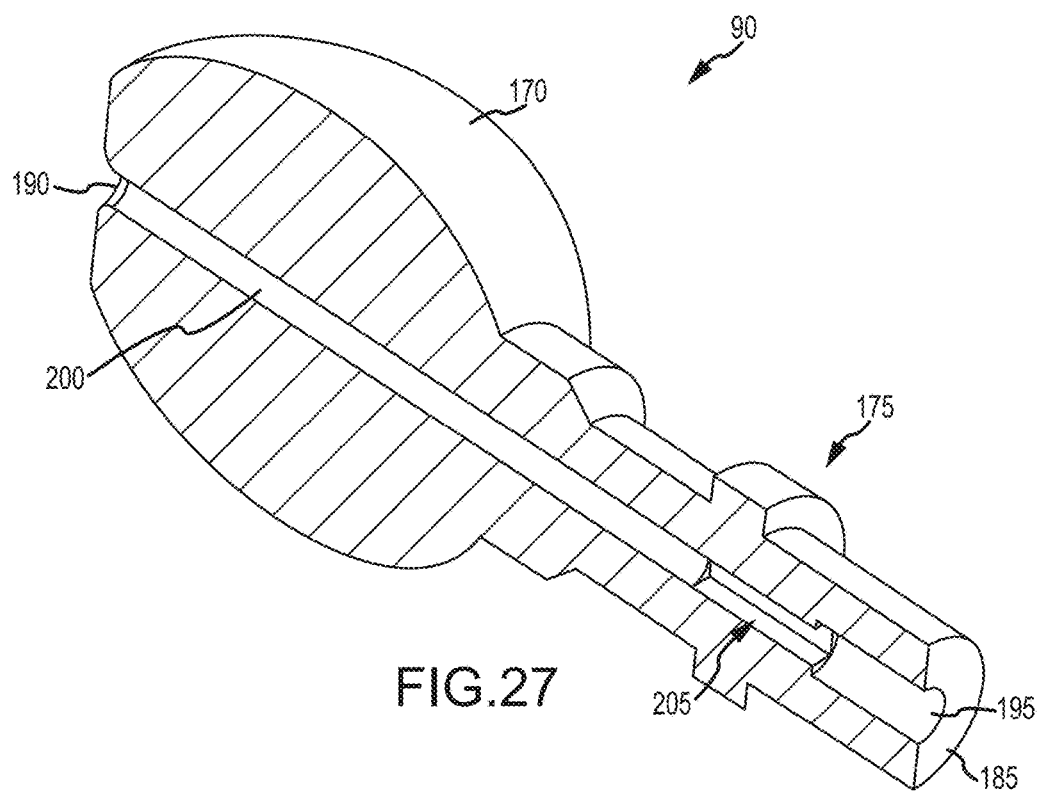
FIG. 27 is a cross sectional distal isometric view of the handle.

As shown in FIGS. 25-27, which are various isometric views of the handle 90, the handle 90 includes a gripping portion 170, a neck portion 175, a proximal end 180, a distal end 185, a proximal opening 190, a distal opening 195 and a bore 200 extending longitudinally through the handle 90 between the openings 190, 195. The proximal opening 190 is defined in the proximal end 180, which forms the extreme proximal portion of the gripping portion 170. The distal opening 195 is defined in the distal end 185, which forms the extreme distal portion of the neck portion 175. The neck portion 175 has multiple regions having different diameters, thereby forming a collared configuration. The gripping portion 170 may have a generally spherical or oval hemispheric shape.

As shown in FIG. 27, a squared inner surface configuration 205 is defined in a segment of the bore 195 located in the neck portion 175, the rest of the bore 195 having a cylindrical configuration. Thus, as can be understood from FIGS. 1, 21A and 22, when the implant arm distal end 125 is received in the handle bore 200, the squared inner surface configuration 205 facilitates a mechanical engagement arrangement with the squared outer surface configuration 135 of the implant arm distal end 125. As a result, grasping the handle so as to cause the handle to pivot about its longitudinal center axis causes the implant arm to similarly pivot about its longitudinal center axis, which is generally coaxial with the longitudinal center axis of the handle. The fit between the squared surface configurations 135, 205 may be such as to form an interference fit, thereby preventing the handle from being pulled off of the implant arm distal end without the intentional application of substantial separating force.

Figure 6:
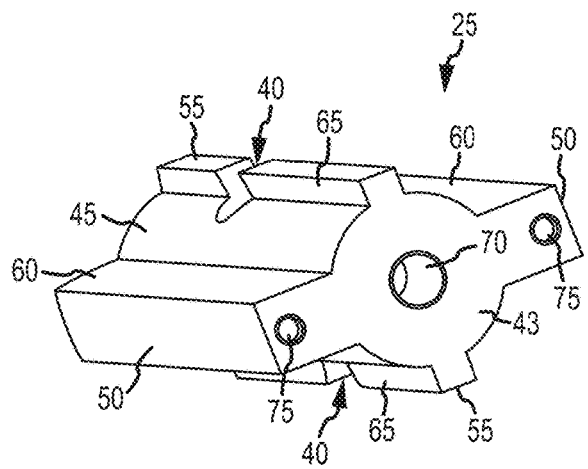
FIG. 6 is a proximal end isometric view of the implant.

As illustrated in FIGS. 28 and 29, which are full isometric and longitudinal cross sectional isometric views of the implant retainer 95, the implant retainer 95 includes a longitudinal cylindrical member 210, T-handle 215 on a proximal end of the longitudinal cylindrical member 210, and an implant engagement feature 220 on a distal end the longitudinal cylindrical member 210. As can be understood from FIGS. 2A and 21A and 22-24, when the system 10 is assembled for the delivery of the implant assembly 15 to the sacroiliac joint, the longitudinal cylindrical member 210 extending through the handle bore 200 (see FIG. 27) and implant arm bore 132 (FIG. 20) such that a distal side of the T-handle 215 abuts or nearly abuts with the handle proximal face or end 180 (FIG. 25) and the implant engagement feature 220 is received in the implant center bore 70 (FIG. 6). In one embodiment, the implant engagement feature 220 is in the form of a threaded shaft for engaging complementary threads in the center bore 70, thereby securing the implant proximal face against the implant arm distal face and the pins in the lateral bores, as depicted in FIGS. 22-24. In other embodiments, the implant engagement feature 220 and the center bore 70 are configured so as to form an interference fit between the two such that an intentional separating force is required to remove the implant engagement feature from within the center bore and allow the release of the implant from the distal end of the implant arm, as indicated in FIG. 2B.

Figure 30A:
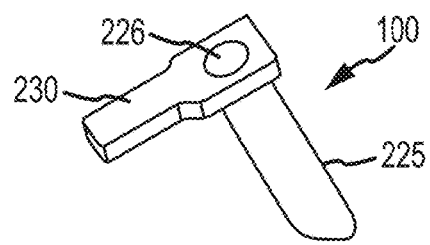
FIG. 30A is an isometric view of the sleeve.
Figure 30B:
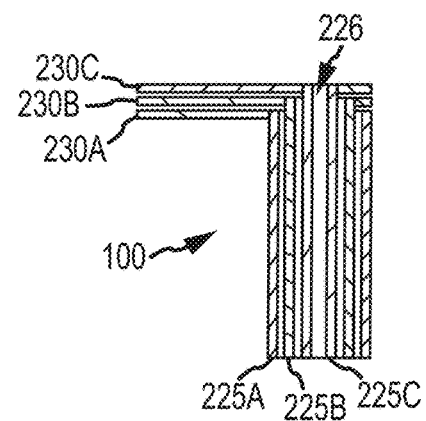
FIG. 30B is a longitudinal cross section of an embodiment of the sleeve having multiple sleeve portions.

FIG. 30A is an isometric view of a sleeve 100 that is configured to be received in the anchor arm collar 165, as can be understood from FIGS. 2A, 21A, and 22-23. The sleeve 100 may have a tubular portion 225 that extends from a plate 230 and defines a lumen 226 extending the length of the tubular portion 225. As indicated in FIG. 30B, which is a longitudinal cross section of one embodiment of the sleeve 100, the sleeve 100 is formed of multiple sleeve portions 100A-100C nested together such that the tubular portions 225A-225B are concentrically arranged and the plates 230A-230B are stacked. As each sleeve portion 100A-100C has a tubular portion 225A-225B with a different diameter, the sleeve portions 100A-100C can be employed as needed to dilate an incision opening or guide different diameter guidewires, trocars, drills, etc. in the direction of the implant bore 40.

Figure 31:
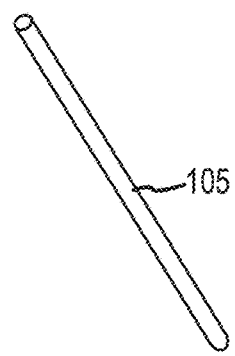
FIG. 31 is an isometric view of a trocar, guidewire, drill, screwdriver, etc. for insertion through the lumen of the sleeve.

FIG. 31 is an isometric view of a trocar, guidewire, drill, screwdriver, etc. that may be inserted through the lumen 226 of the tubular portion 225 in gaining access to, or driving the anchor member 30 into, the implant bore 40 when the implant 25 is positioned in the sacroiliac joint via the distal end of the implant arm 110.

To begin a detailed discussion of a second embodiment of the system 10, reference is made to FIGS. 32-33. FIG. 32 is an isometric view of the system 10, and FIG. 33 is the same view as FIG. 32, except the system 10 is shown exploded to better illustrate the components of the system 10.

As can be understood from FIGS. 32 and 33, the system 10 includes a delivery tool 20 and an implant assembly 15 for implanting at the sacroiliac joint via the delivery tool 20, the implant assembly 15 being for fusing the sacroiliac joint. As indicated in FIG. 33, the implant assembly 15 includes an implant 25 and an anchor element 30 (e.g., a bone screw or other elongated body). In one embodiment, the implant assembly 15 is the same as that described above with respect to FIGS. 4-17. As discussed below in greater detail, during the implantation of the implant assembly 15 at the sacroiliac joint, the implant 25 and anchor element 30 are supported by a distal end 35 of the delivery tool 20, as illustrated in FIG. 32. The delivery tool 20 is used to deliver the implant 25 into the sacroiliac joint space. The delivery tool 20 is then used to cause the anchor element 30 to extend through the ilium, sacrum and implant 25 generally transverse to the sacroiliac joint and implant 25. The delivery tool 20 is then decoupled from the implanted implant assembly 15.

As shown in FIG. 32, the delivery tool 20 includes a distal end 35 and a proximal end 80. The distal end 35 supports the implant assembly 15 components 25, 30, and the proximal end 80 is configured to be grasped and manipulated to facilitate the implantation of the implant assembly 15 in the sacroiliac joint.

As illustrated in FIG. 33, the delivery tool 20 further includes an arm assembly 85, a handle 90, an implant retainer 95, and a trocar or guidewire 105. As shown in FIG. 33 and also in FIG. 34, which is a side elevation of the system 10, the arm assembly 85 includes an implant arm 110 and an anchor arm 115.

Figure 35:
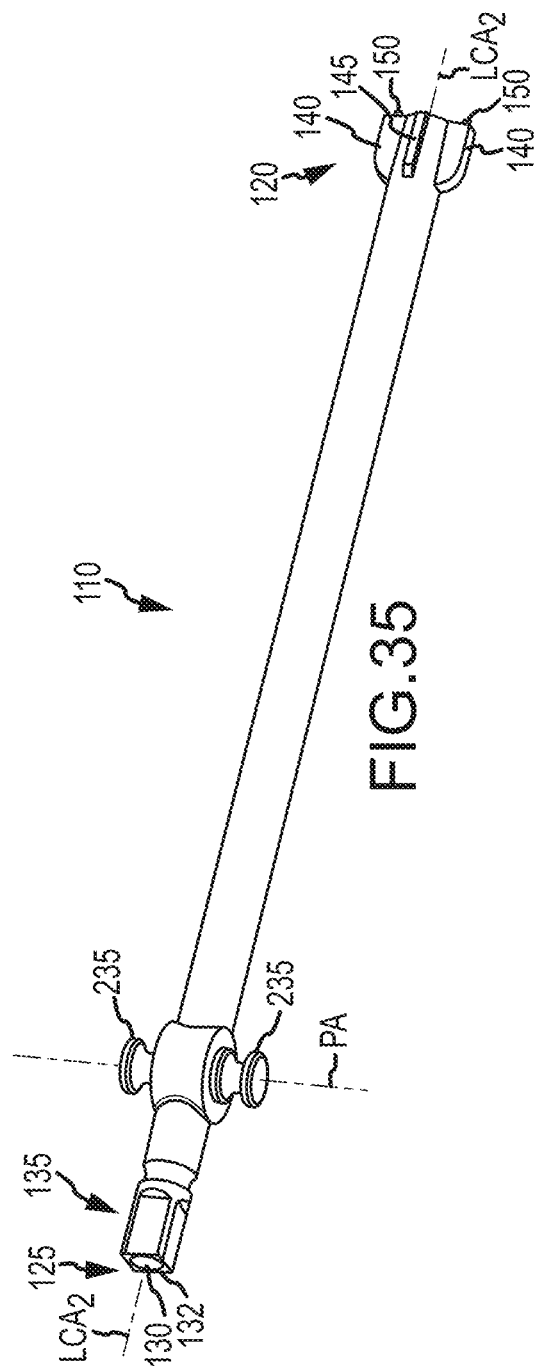
As shown in FIG. 35 is a proximal isometric view of the implant arm of the embodiment of FIG. 32.

As shown in FIG. 35, which is a proximal isometric view of the implant arm 110, the implant arm 110 includes a distal end 120, a proximal end 125 and a proximal cylindrical opening 130 of a cylindrical bore 132. The proximal end 125 includes a squared outer surface configuration 135 that facilitates a mechanical engagement arrangement with the handle 90 such as the mechanical arrangement that exists between a wrench and nut. As the handle 90 is the same as described above with respect to FIGS. 25-27, the handle 90 receives and mechanically interlocks with the distal region of the implant arm 110 as described above with respect to FIG. 22.

Figure 34:
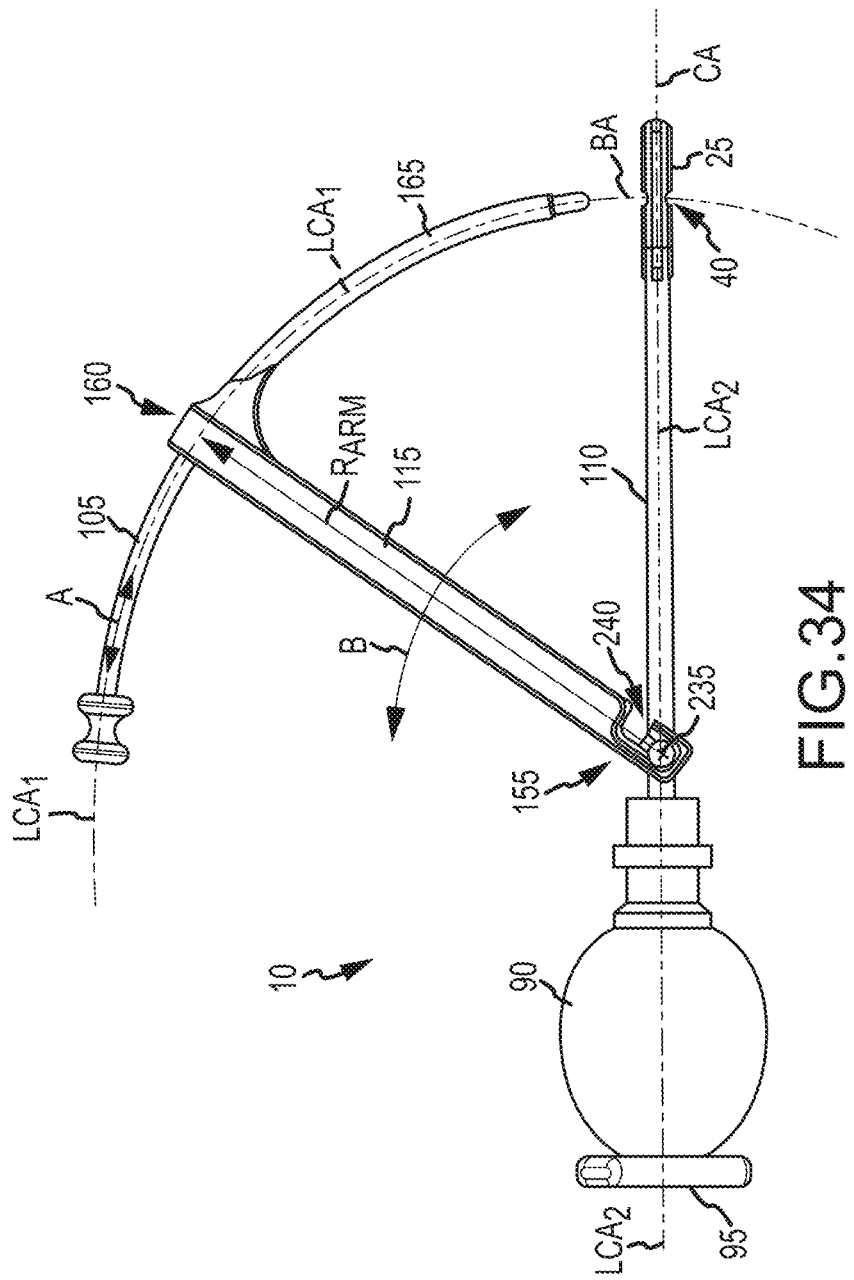
FIG. 34 is a side elevation of the system embodiment of FIG. 32.

As with the implant arm 110 discussed above with respect to FIG. 19 and as can be understood from FIG. 34, the distal end 120 of the implant arm 110 includes a cylindrical opening 137 (see FIG. 19) of a cylindrical bore 132, large planar members, keels, or fins 140 and small planar members, keels, or fins 145, pins 150, and a planar extreme distal face 152 (see FIG. 19). Just as explained with respect to FIG. 20 above, the cylindrical bore 132 of the embodiment depicted in FIG. 34 extends the full length of the implant arm 110 between the proximal opening 135 and the distal opening 137.

As the retaining member 95 of the embodiment of FIG. 33 is the same as described above with respect to FIGS. 28-29, the retainer member 95 extends through the handle 90 and implant arm 110 to mechanically interlock with the implant center bore 70 as described above with respect to FIGS. 22-24. Also, the configuration of the distal end 120 of the implant arm 110 of FIG. 35 is the same as the configuration of the distal end 120 of the implant arm 110 of FIG. 19. Accordingly, the distal end 120 of the implant arm 110 of FIG. 35 interacts with the proximal end of the implant 25 as describe above with respect to FIGS. 22-24.

As indicated in FIG. 35, the implant arm 110 includes pivot pins 235 on opposite sides of the implant arm 110, the pivot pins 235 having a pivot axis PA that is perpendicular to the plane in which the implant bore 40 passes through the implant 25. In other words, the pivot axis PA is perpendicular to the longitudinal center axis $LCA_2$ of the implant arm 110 and contained within the same plane as the longitudinal center axis $LCA_2$ of the implant arm 110. The pivot pins 235 are located on the implant arm 110 near the distal end of the handle 90.

Figure 36:
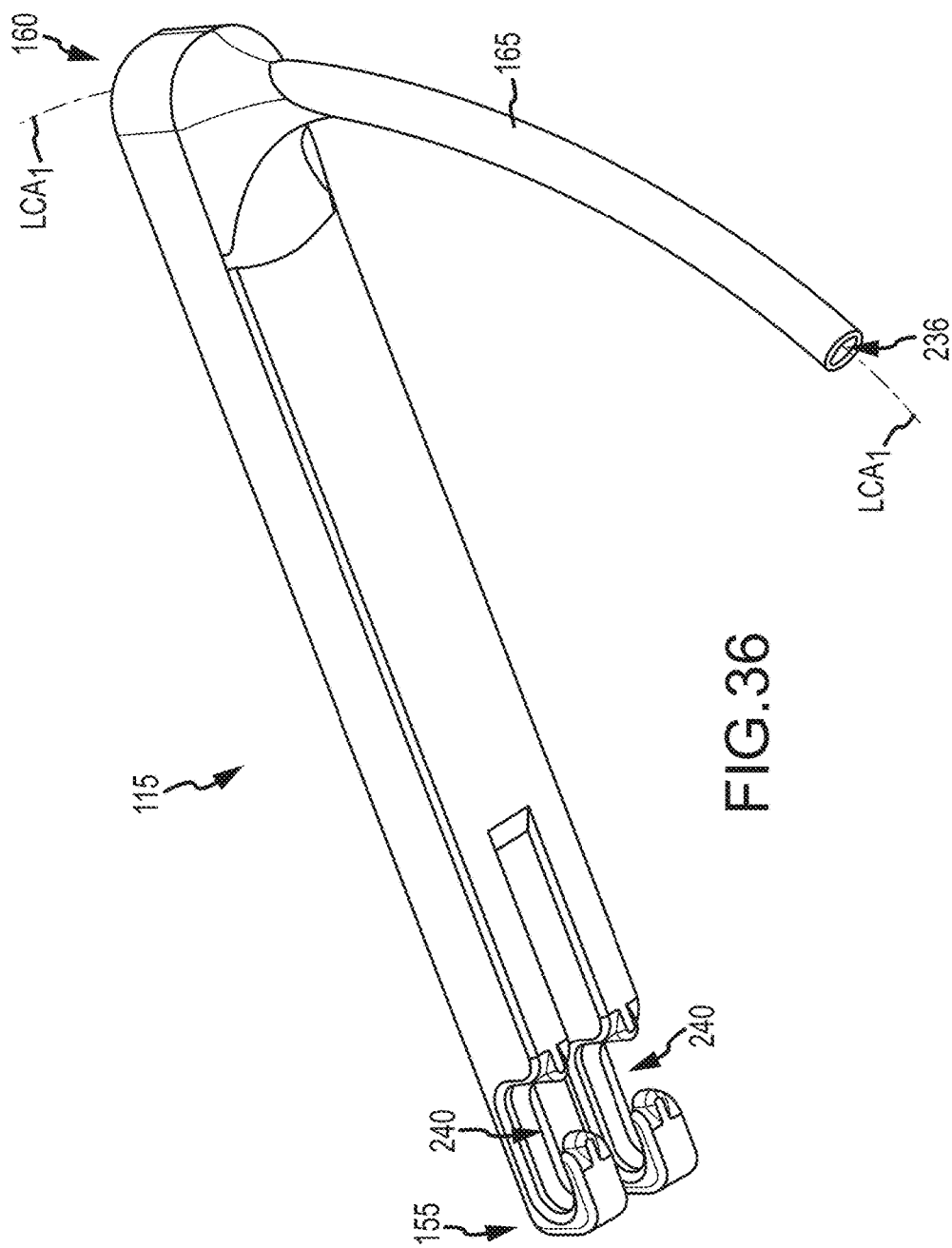
FIG. 36 is an isometric view of the anchor arm.

As illustrated in FIG. 36, which is an isometric view of the anchor arm 115, the anchor arm 115 includes a proximal end 155 and a distal end 160 distally terminating in a sleeve or collar 165 that is arcuate and substantially extended as compared to the collar 165 of the embodiment depicted in FIG. 18. The arcuate and extended collar 165 has an arcuate longitudinal center axis $LCA_T$ that is generally transverse to the longitudinal axis of the anchor arm 115. A lumen 236 extends the length of the collar 165 to daylight in openings at both ends of the collar 165.

As shown in FIG. 36, the anchor arm proximal end 155 includes notches 240, which, as can be understood from FIGS. 32 and 34, receive the respective pivot pins 235. As a result, the anchor arm 115 is pivotally supported off of the implant arm 110 via the notches 240 at the anchor arm proximal end 155 pivotally receiving the pivot pins 235 of the implant arm 110.

As can be understood from FIGS. 32-34, an arcuate member 105 can be inserted in the lumen 236 of the arcuate extended collar 165. The curvature of the arcuate member 105 matches the curvature of the lumen 236 of the arcuate collar 165. The arcuate member 105 may be a trocar, guidewire, drill, screwdriver, etc. that may be inserted through the lumen 236 of the collar 165 in gaining access to, or driving the anchor member 30 into, the implant bore 40 when the implant 25 is positioned in the sacroiliac joint via the distal end of the implant arm 110. As indicated by the arrow A in FIG. 34, the arcuate member 105 is slidably displaceable through the arcuate length of the collar 165. Also, as indicated by arrow B, the anchor arm 110 is pivotal about the pivot pins 235.

As indicated in FIG. 35, the implant arm 110 includes a longitudinal center axis $LCA_2$. As shown in FIG. 34, when the system 10 is assembled such that the implant 25 is mounted on the distal end of the implant arm 110, the longitudinal center axis CA of the implant 25 is coaxially aligned with the longitudinal center axis $LCA_2$ of the implant arm 110, and the longitudinal center axis BA of the implant bore 40 is coaxially aligned with the longitudinal center axis $LCA_1$ of the anchor arm collar 165. In other words, in the context of the embodiment of FIG. 34, the arcuate longitudinal center axis $LCA_1$ extends to be coaxially aligned with the longitudinal center axis BA of the implant bore 40. In one embodiment, as indicated in FIG. 34, the longitudinal center axis $LCA_1$ of the anchor arm collar 165 has an arm radius $R_{ARM}$ that extends into coaxial alignment with the longitudinal center axis BA of the implant bore 40. For example, the arm radius $R_{ARM}$ may be between approximately 50 mm and approximately 300 mm, with one embodiment being approximately 160 mm.

As can be understood from FIG. 34, when the system 10 is assembled such that the implant 25 is mounted on the distal end of the implant arm 110, the longitudinal center axis $LCA_2$ of the implant arm 110 is coaxial with the longitudinal center axis CA of the implant 25 and the longitudinal center axis of the handle 90. Thus, the line of action for the insertion of the implant 25 into the sacroiliac joint is coaxial with the longitudinal center axes of the implant 25, implant arm 110 and handle 90. Thus, as will be described in detail below, the anchor arm collar 165 is oriented so as to guide drills and other tools in creating a channel through tissue and bone leading to the implant bore 40 when the implant 25 is positioned in the sacroiliac joint while the implant 25 is still attached to the distal end of the implant arm 110, as shown in FIG. 34. Additionally, the anchor arm collar 165 is oriented so as to guide the anchor member 30 into the implant bore 40 when the implant 25 is positioned in the sacroiliac joint while the implant 25 is still attached to the distal end of the implant arm 110, as shown in FIG. 32.

Because the tool embodiment depicted in FIG. 32 has an anchor arm 115 that is pivotally supported off of the implant arm 110 and the anchor arm collar 165 is arcuate and slidably receives an arcuate trocar, etc. 105, the tool 20 is able to account for different patient sizes, yet still maintain the coaxial and angular relationships set out above. In other words, regardless of whether the anchor arm 115 is pivoted so as to move the anchor arm distal end 160 closer to or further away from the implant bore 40 to accommodate a smaller or larger patient, the trocar 105 can be withdrawn from or extended towards the implant bore 40 as needed to deliver the anchor 30 to the implant bore 40, the trocar 105 being maintained in the necessary coaxial alignment of the longitudinal axis $LCA_1$ of the collar 165 with the longitudinal axis BA of the implant bore 40.

Because the angular relationships are rigidly maintained between the trocar 105 and the implant bore 40 despite the anchor arm 115 being pivotal relative to the implant arm, the anchoring of the implant 25 in the sacroiliac joint via the anchor member 30 may be achieved quickly and safely. In other words, because the tool does not need to be adjusted with respect to angular relationships, the surgery is simplified, reduced in duration, and reduces the risk of the anchor member 30 being driven through a nerve, artery or vein.

Figure 37:
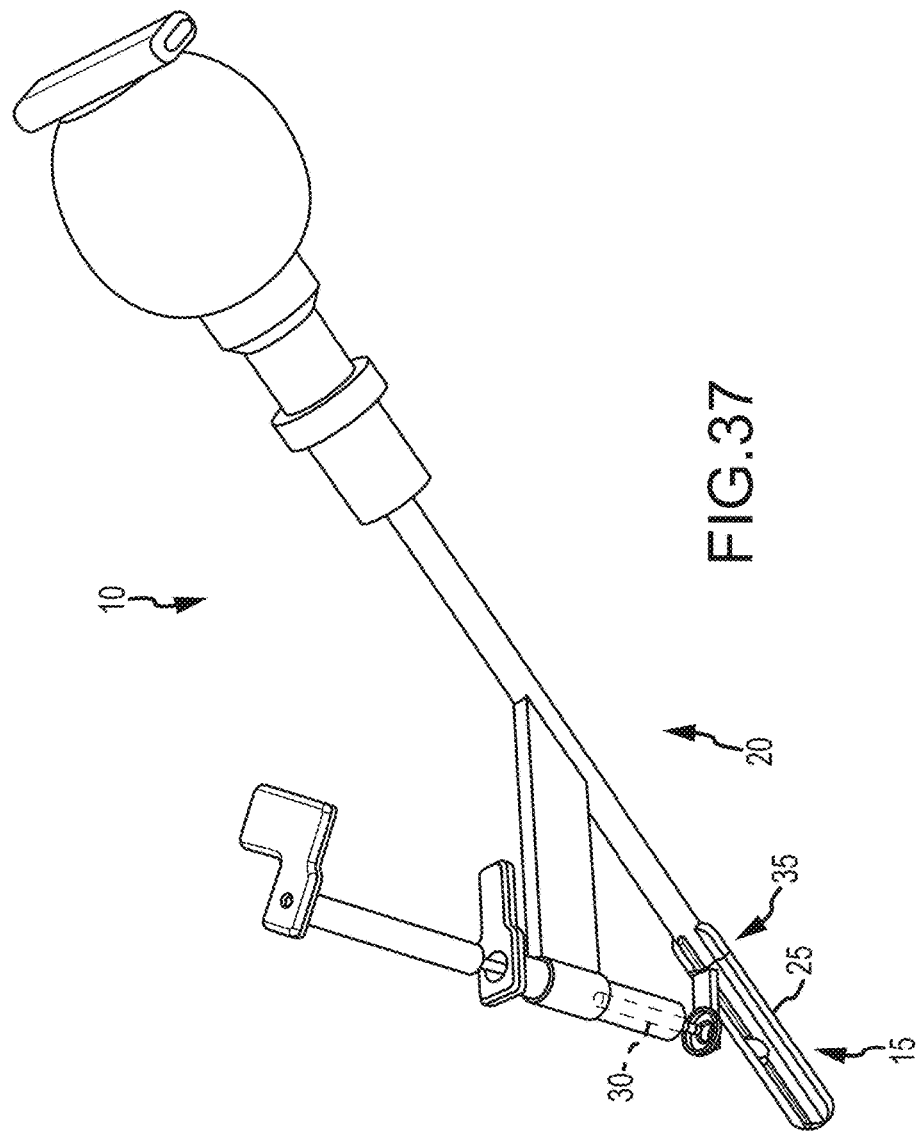
FIGS. 37 and 38 are different isometric views of a third embodiment of the system.
Figure 38:
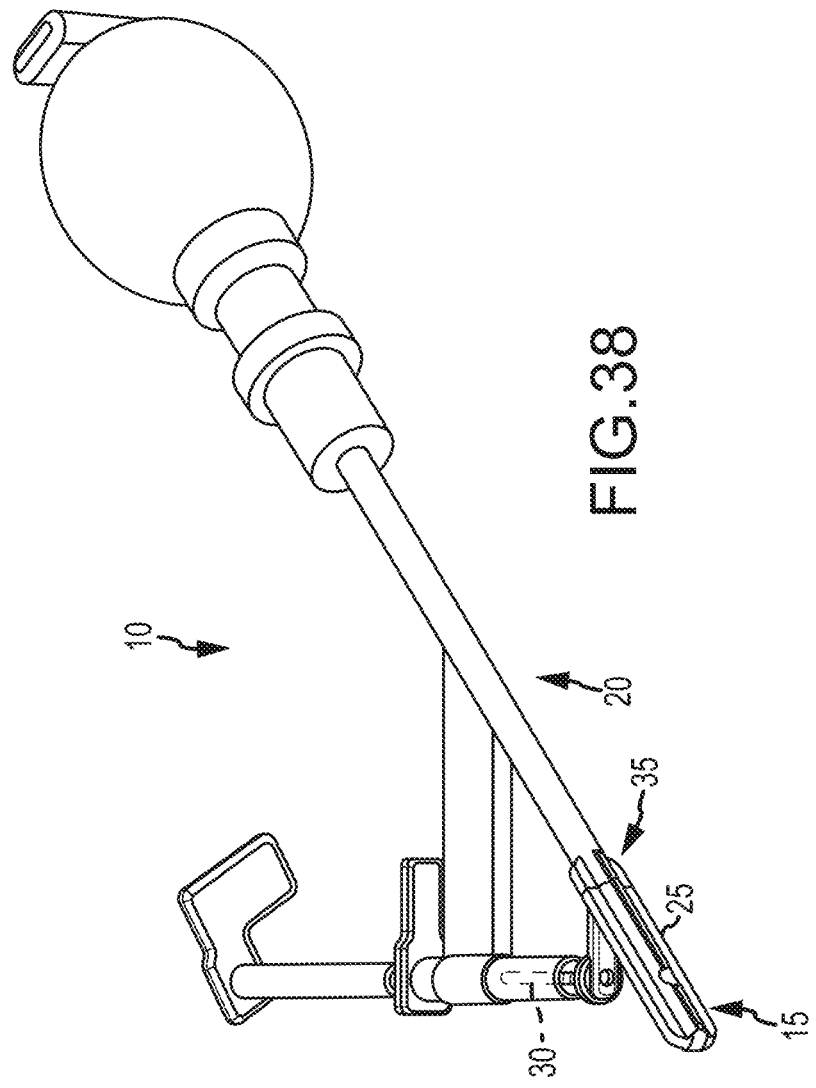
Figure 39:
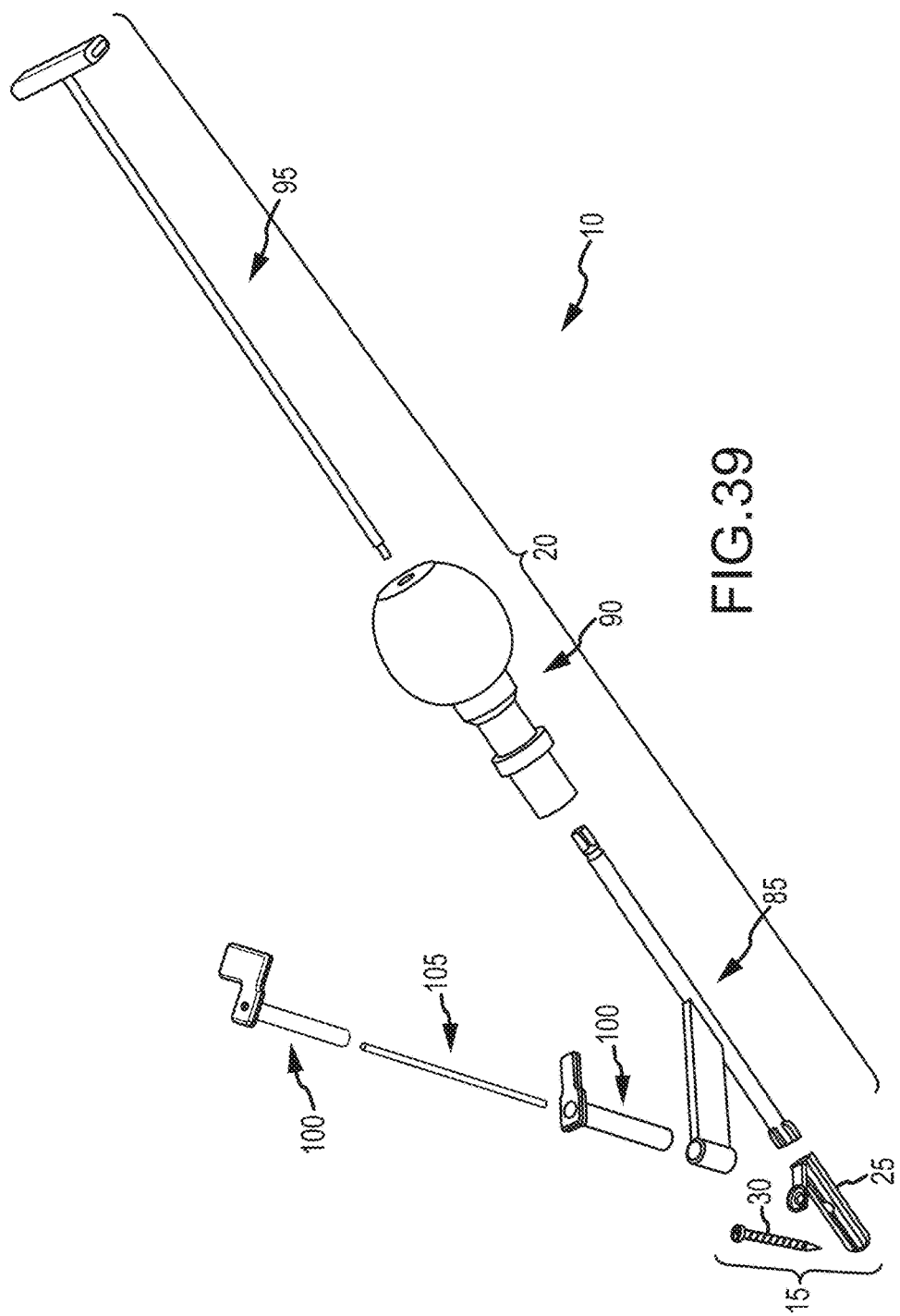
FIG. 39 is the same view as FIG. 37, except the system is shown exploded to better illustrate the components of the system.
Figure 40:
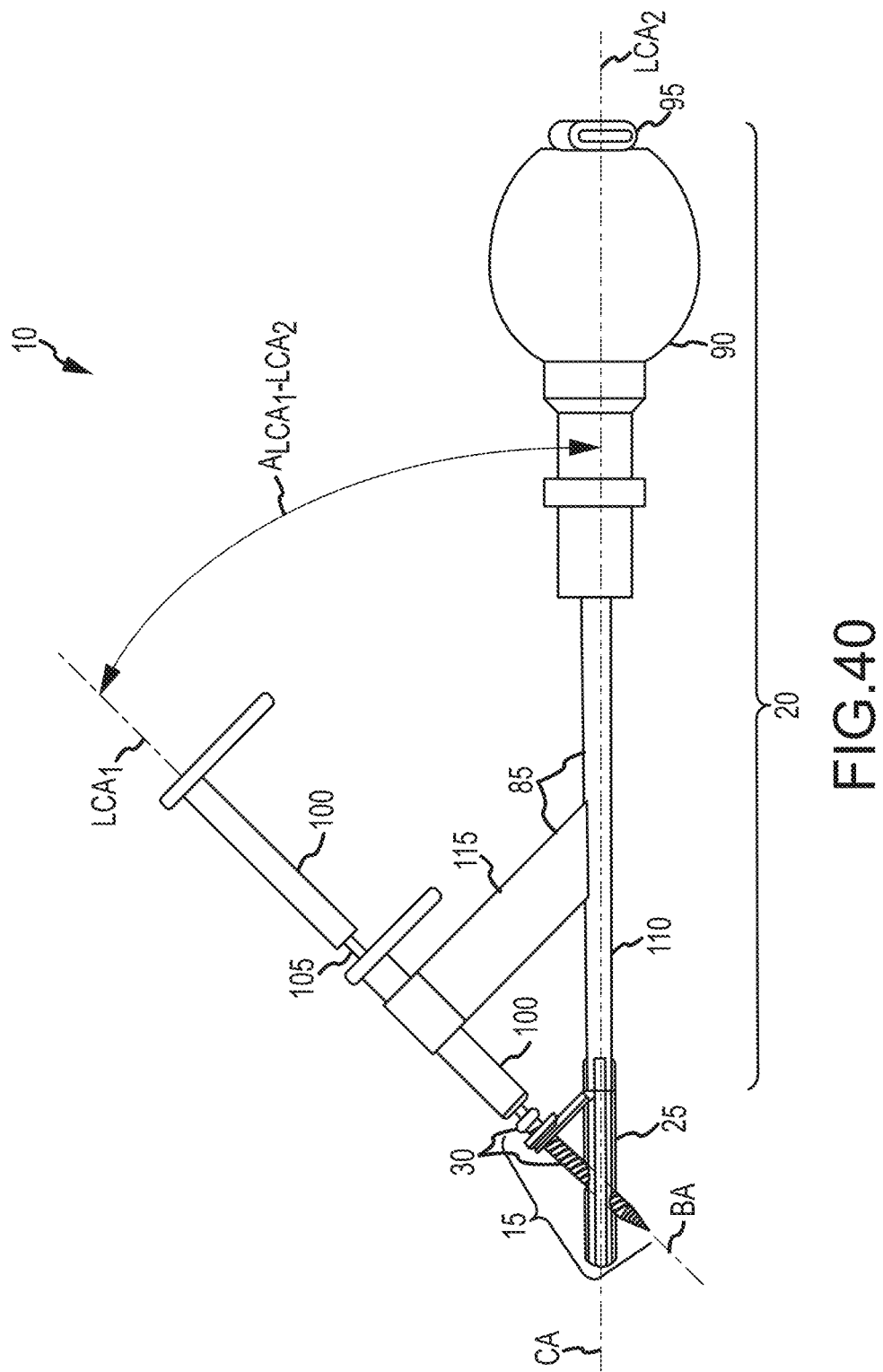
FIG. 40 is a side elevation of the system of FIG. 37, wherein the tool is attached to the implant assembly for delivery of the implant assembly to the sacroiliac joint.
Figure 41:
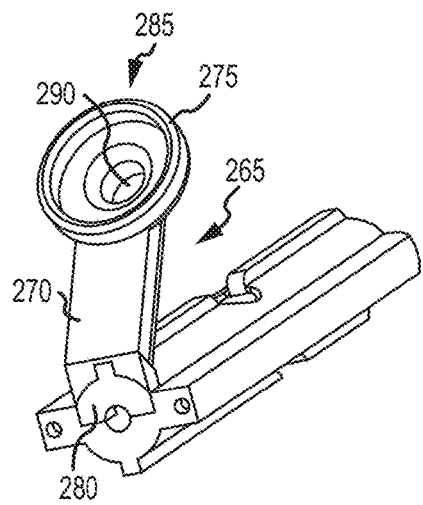
FIGS. 41-44 are various isometric views of the implant of the third embodiment of the system.
Figure 42:
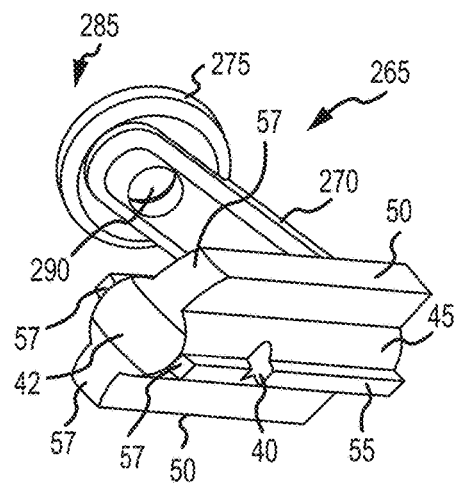
Figure 43:
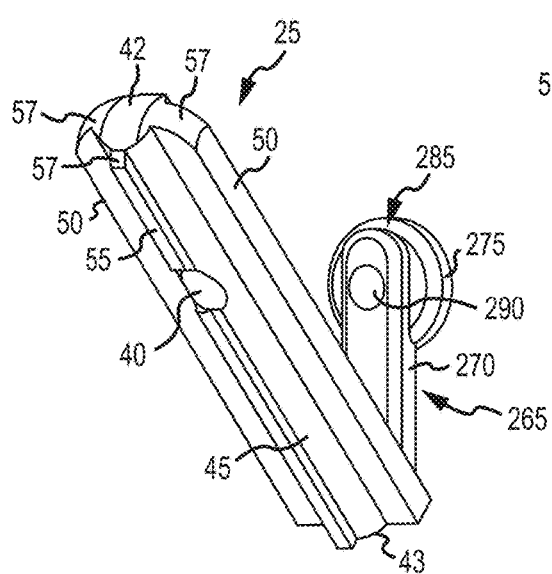
Figure 44:
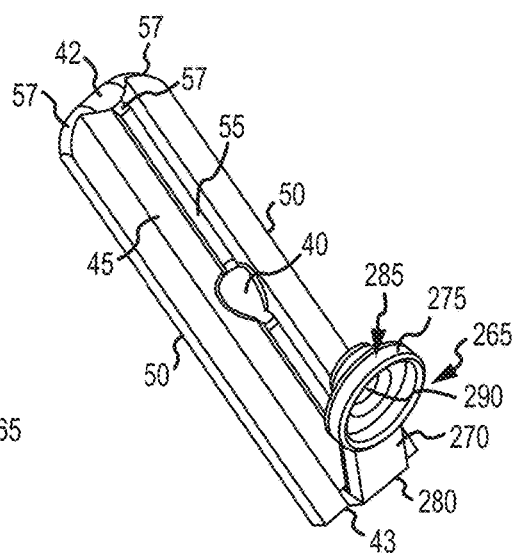

To begin a detailed discussion of a third embodiment of the system 10, reference is made to FIGS. 37-40. FIGS. 37 and 38 are different isometric views of the system 10. FIG. 39 is the same view as FIG. 37, except the system 10 is shown exploded to better illustrate the components of the system 10. FIG. 40 is a side elevation of the system wherein the tool is attached to the implant assembly for delivery of the implant assembly to the sacroiliac joint.

As can be understood from FIGS. 37-40, the system 10 includes a delivery tool 20 and an implant assembly 15 for implanting at the sacroiliac joint via the delivery tool 20, the implant assembly 15 being for fusing the sacroiliac joint. As indicated in FIG. 39, the implant assembly 15 includes an implant 25 and an anchor element 30 (e.g., a bone screw or other elongated body).

As can be understood from a comparison of FIGS. 2A-3 to FIGS. 37-40, the delivery tool 20 of FIGS. 2A-3 is the same as the delivery tool 20 of FIGS. 37-40. Thus, for a complete description of the delivery tool 20 of FIGS. 37-40 and its components, namely, the arm assembly 85, handle 90, implant retainer 95, a trocar or guidewire 105, and multiple nested sleeves 100, refer back to the corresponding discussion given above with respect to FIGS. 2A-3 and 18-31.

Figure 45:
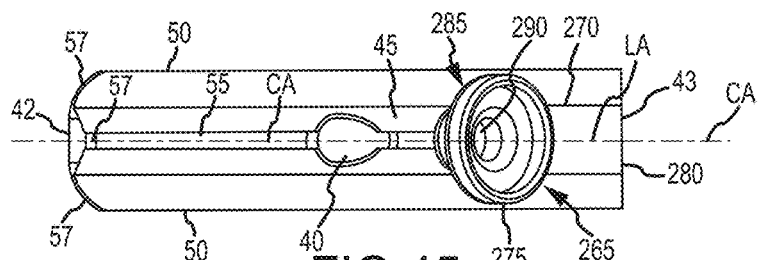
FIGS. 45-46 are opposite plan views of the implant.
Figure 46:
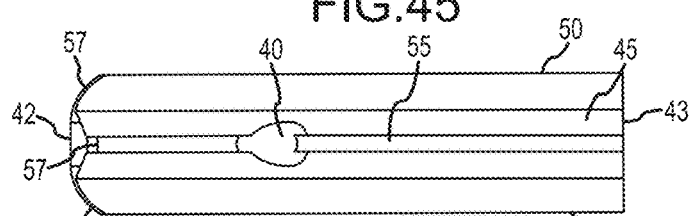
Figure 49:
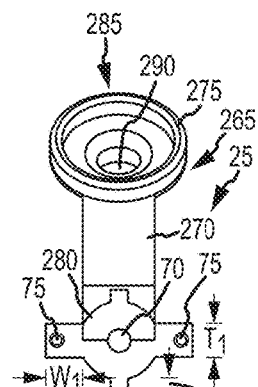
FIGS. 47-50 are various elevation views of the implant.

As indicated in FIGS. 37-40, the system 10 includes an implant assembly 15 with an implant 25 similar the implant 25 discussed above with respect to FIGS. 4-18, except the implant 25 of FIGS. 37-40 also includes a guide arm 265. To begin a detailed discussion of components of the embodiment of the implant 25 of FIGS. 37-40, reference is made to FIGS. 41-50. FIGS. 41-44 are various isometric views of the implant 25. FIGS. 45-46 are opposite plan views of the implant 25, and FIGS. 47-50 are various elevation views of the implant.

A comparison of FIGS. 41-50 to FIGS. 5-18 reveals that the two implant embodiments are the same, except the implant embodiment of FIGS. 41-50 has a guide arm 265. Thus, for a complete description of the features of the implant 25 other than the guide arm 265, which is discussed below, refer back to the corresponding discussion given above with respect to FIGS. 5-18.

As shown in FIGS. 41-45 and 46-50, the guide arm 265 includes a longitudinally extending member 270 and a guide portion 275. The guide arm 265 is cantilevered off of a side of the implant near the proximal or trailing end 43 of the implant 25. Thus, the guide arm 265 includes an attached end 280, which is attached to, or extends from, the implant proximal end 43, and a free end 285, which defines the guide portion 275.

Figure 48:
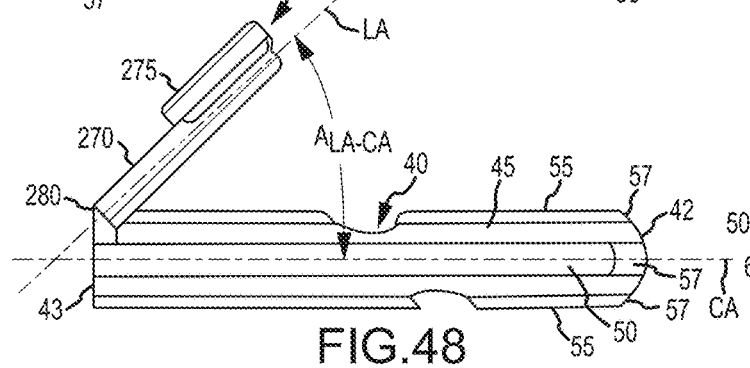
Figure 50:
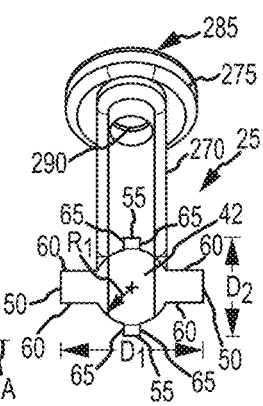
Figure 74:
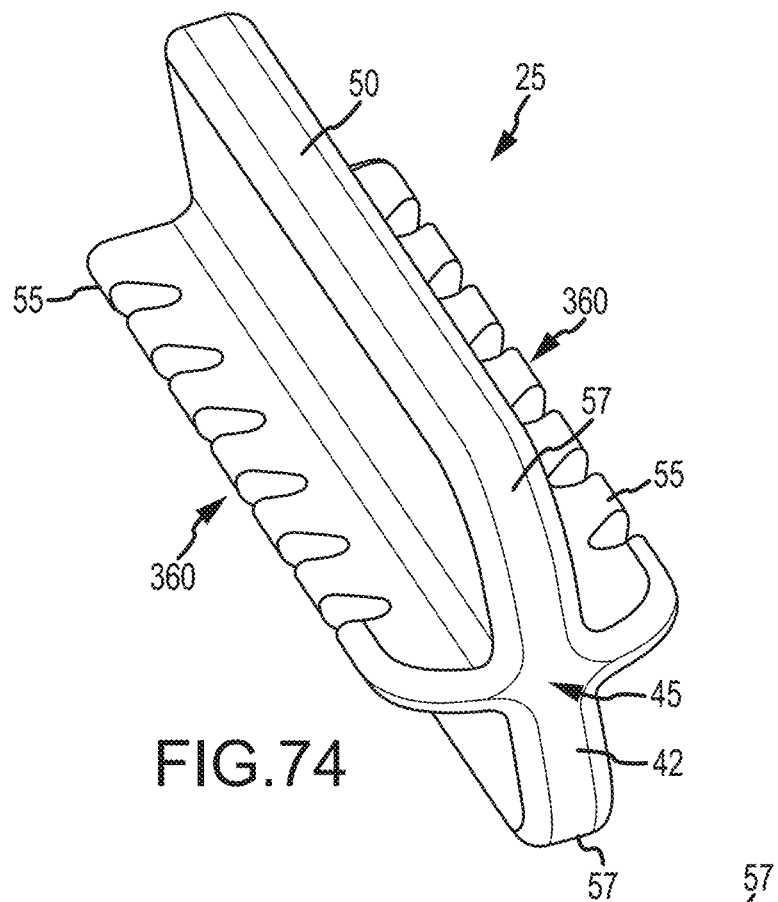
Figure 75:
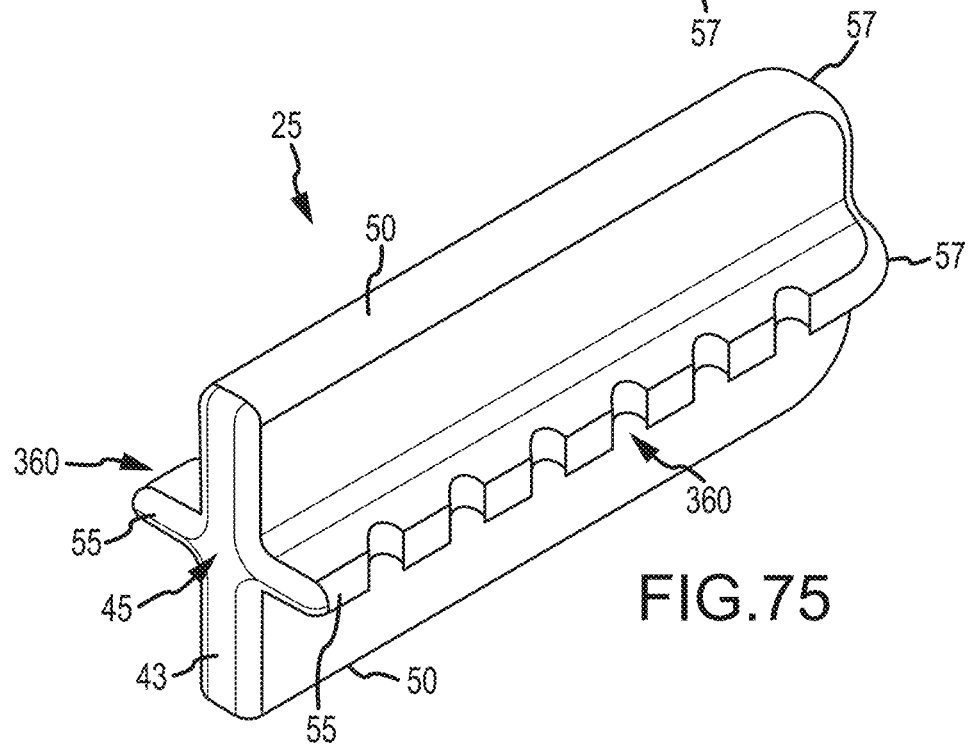
Figure 80:
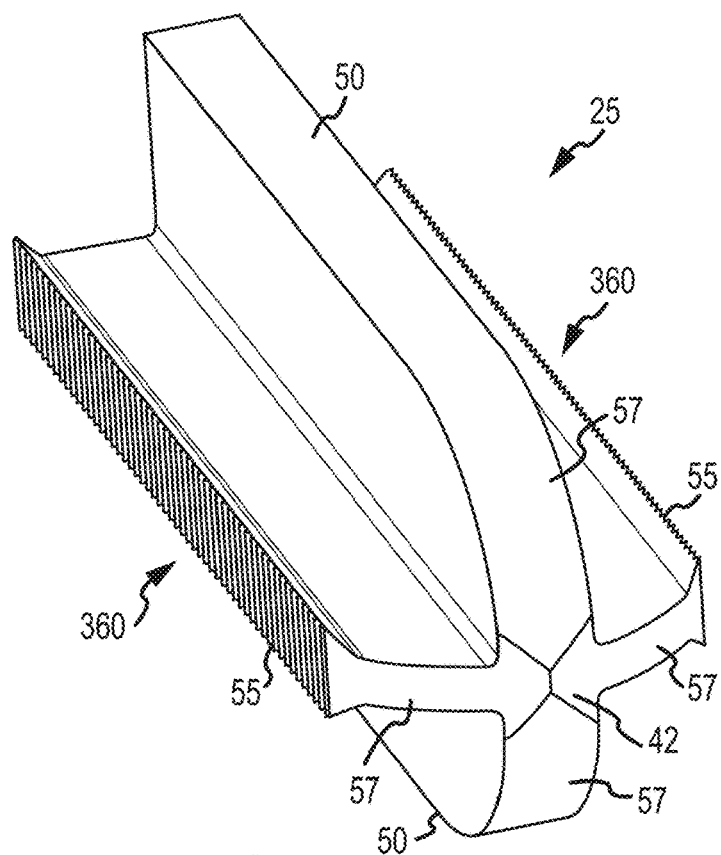
FIGS. 80-85 are, respectively, front isometric, rear isometric, side elevation, plan, front elevation, and rear elevation views of still yet another embodiment of the implant.
Figure 81:
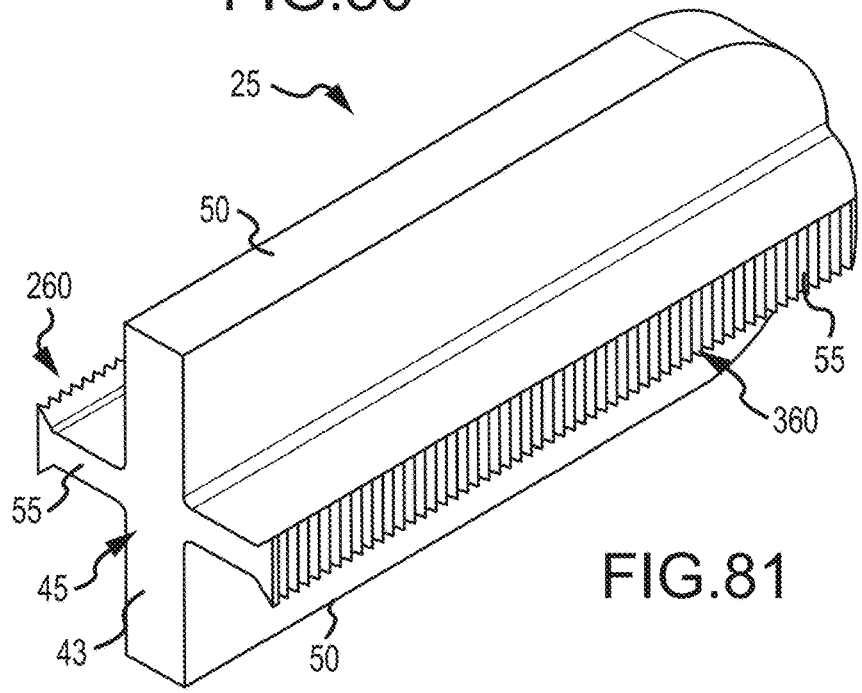
Figure 84:
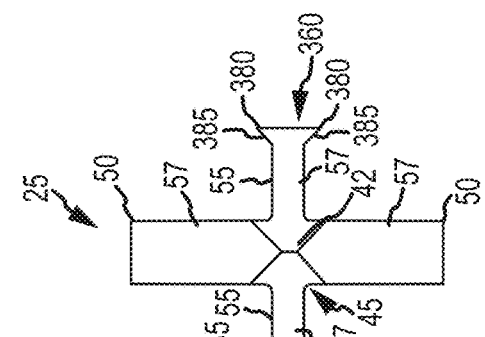
Figure 82:
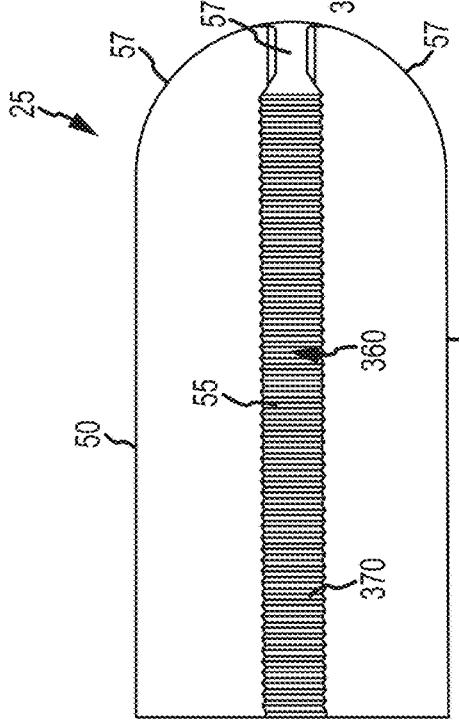

The longitudinally extending member 270 may be in the form of a planar member or other shaped member. As illustrated in FIG. 45, the longitudinal axis LA of the member 270 is generally coplanar with the longitudinal axis CA of the implant body 45. However, as indicated in FIG. 48, the longitudinal axis LA of the member 270 forms an angle $A_{LA-CA}$ with the longitudinal axis CA of the implant body 45. For example, the angle $A_{LA-CA}$ may be between approximately 5 degrees and approximately 60 degrees, with one embodiment being approximately 40 degrees.

Figure 47:
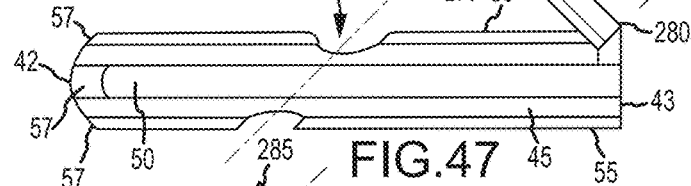

As illustrated in FIGS. 41-45 and 47-50, the guide portion 275 is in the form of a collar defining a central hole 290. As indicated in FIG. 47, the member 270 has an overall length AD from its intersection with the rest of the implant to the tip of the free end 285 of between approximately 5 mm and approximately 60 mm, with one embodiment being approximately 20 mm. Also, the center axis GA of the hole 290 is coaxially aligned with the center axis BA of the bore 40. The overall length AE from the intersection of the member 270 with the rest of the implant to the center axis GA is between approximately 2 mm and approximately 58 mm, with one embodiment being approximately 17 mm.

Since the center axis GA of the hole 290 is coaxially aligned with the center axis BA of the bore 40, when the system 10 is assembled such that the implant 25 is mounted on the distal end of the implant arm 110 with the longitudinal center axis $LCA_2$ of the implant arm 110 coaxial with the longitudinal center axis CA of the implant 25, the respective longitudinal axes $LCA_1$, BA and GA of the anchor arm collar 165, the bore 40 and the guide hole 290 are coaxially aligned, as can be understood from FIG. 40. Thus, when the implant body 45 is located in the sacroiliac joint and the guide collar 275 of the implant 25 is located near or against bone adjacent to the sacroiliac joint, the anchor member 30 may be accurately driven through the guide hole 290, through the bone and through the implant bore 40 to anchor the implant at the sacroiliac joint in such a manner to allow the implant to fuse the joint.

In one embodiment, the implant 25 may be machined, molded, formed, or otherwise manufactured from stainless steel, titanium, ceramic, polymer, composite or other biocompatible materials. The anchor member 30 may be machined, molded, formed or otherwise manufactured from similar biocompatible materials. As an example, implant 25, anchor 30 or delivery tool 20 may be manufactured by laser or electron beam additive manufacturing with, for example, EOSINT P 800 or EOSINT M 280 (available from EOS GmbH, Electro Optical Systems, Robert-Stirling-Ring 1, D-82152 Krailling/Munich), or Arcam A1 (available from Arcam AB (publ.), Krokslatts Fabriker 27A, SE-431 37 Molndal Sweden).

For the delivery tools 20 depicted in FIGS. 2A, 21A, 21C, 32, 37, and 40, the handle 90 and arm assembly 85 are coupled together so as to not allow rotational movement relative to each other, and the implant retainer 95 is rotationally displaceable within the handle 90 and arm assembly 85. In other embodiments of the tool 20, the handle 90 and implant retainer 95 are coupled together so as to rotate as a unit relative to the arm assembly 85. An example of such an embodiment is illustrated in FIG. 86, which is an isometric view of the delivery tool 20.

Figure 86:
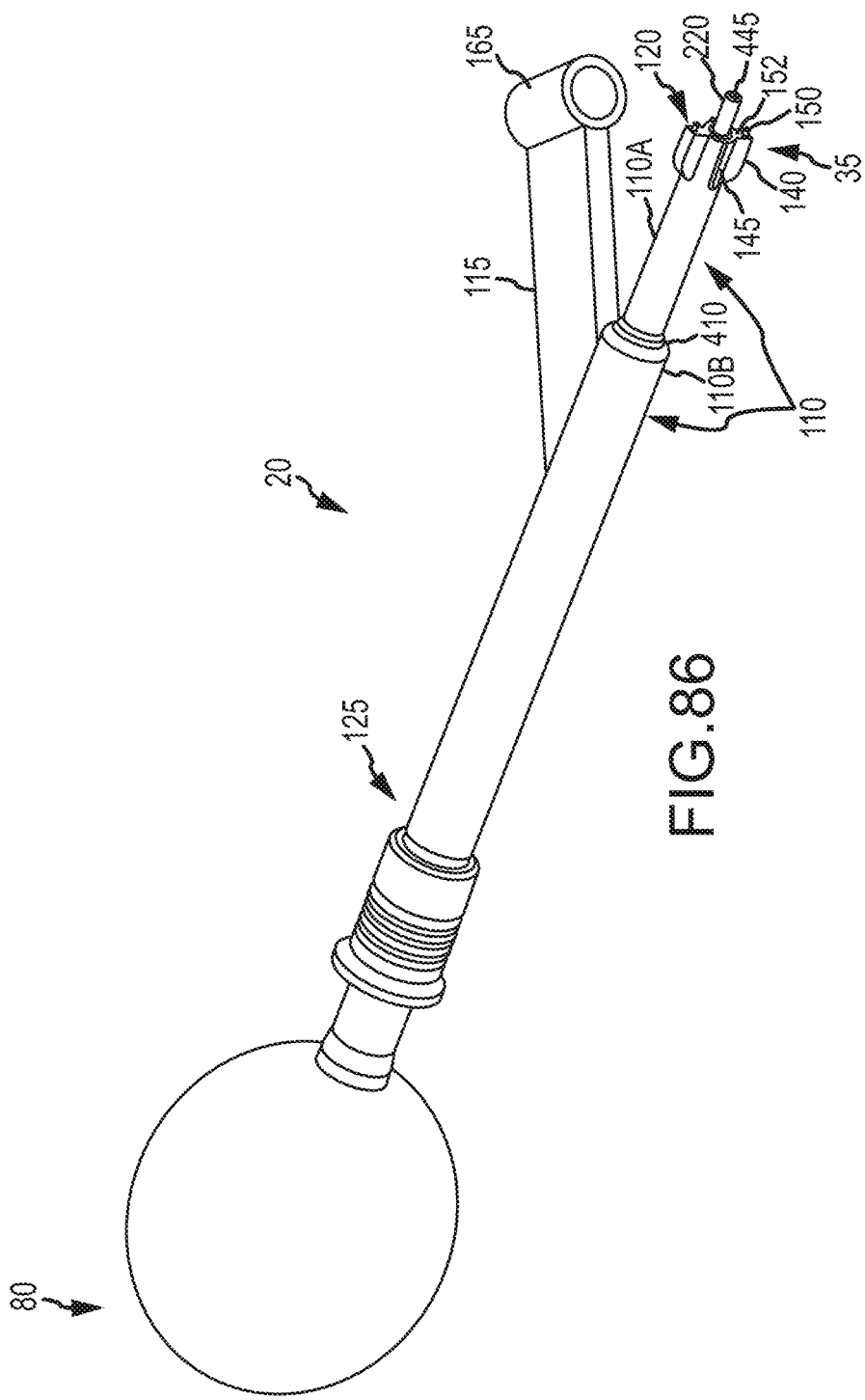
FIG. 86 is an isometric view of the delivery tool.
Figure 87:
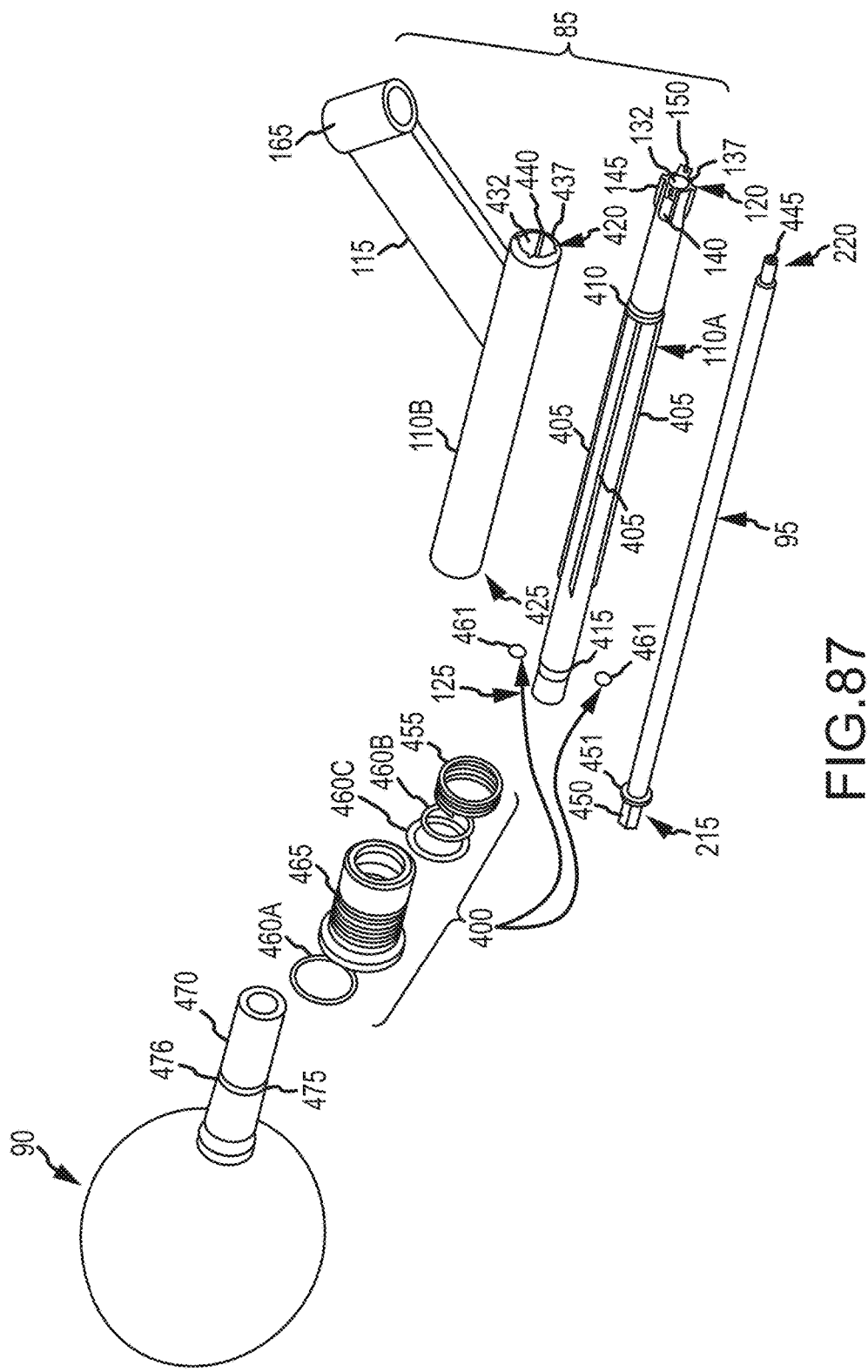
FIGS. 87-88 are generally opposite isometric views of the delivery tool in an exploded state.
Figure 88:
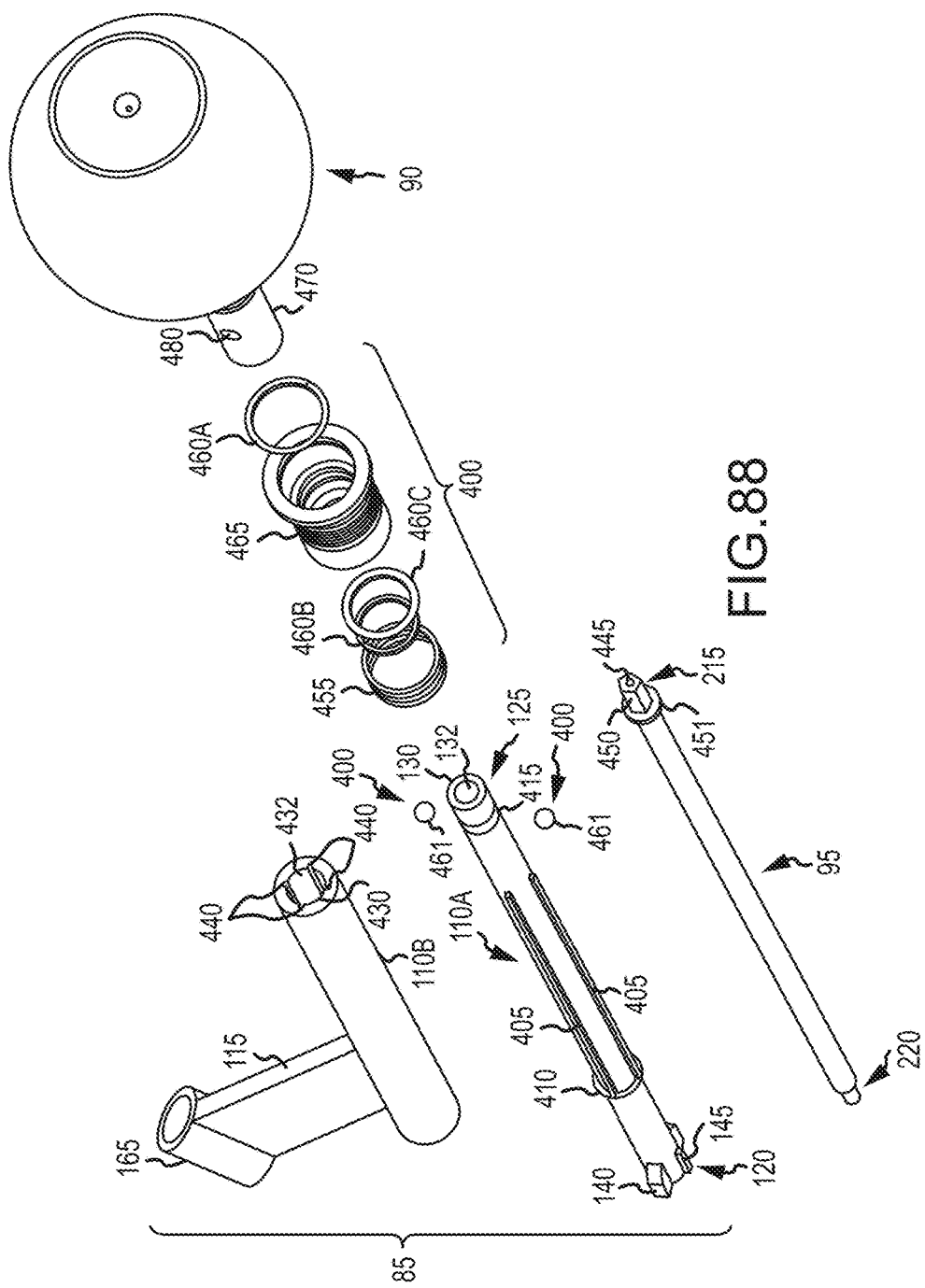

As shown in FIG. 86, the delivery tool 20 includes a distal end 35 and a proximal end 80. As shown in FIGS. 87-88, which are generally opposite isometric views of the delivery tool 20 in an exploded state, the tool 20 further includes an arm assembly 85, a handle 90, an implant retainer 95, and a collar assembly 400. The tool 20 may also include a sleeve 100 and a trocar or guidewire 105 as discussed above with respect to the embodiment of FIG. 3.

As can be understood from FIGS. 86-88, the arm assembly 85 includes an implant arm 110 and an anchor arm 115 supported off of the implant arm 110. The implant arm 110 has a two-piece construction of an inner sleeve 110A and an outer sleeve 110B. The implant arm inner sleeve 110A includes a distal end 120, a proximal end 125, a proximal cylindrical opening 130 of a cylindrical bore 132, and a distal cylindrical opening 137 of the bore 132. The cylindrical bore 132 extends the full length of the implant arm inner portion 110A between the proximal opening 135 and the distal opening 137. Longitudinally extending raised ribs 405 are radially distributed about the outer circumferential surface of the implant arm inner portion 110A. The longitudinal ribs 405 distally terminate by intersecting a raised circumferential ring 410 on the outer circumferential surface of the inner implant arm portion 110A. A groove 415 is circumferentially extends about the outer circumference of the implant arms inner portion 110A. The distal end 120 of the implant arm inner portion 110A also includes large planar members, keels, or fins 140 and small planar members, keels, or fins 145, pins 150, and a planar extreme distal face 152 similar to that discussed above with respect to the embodiment of FIG. 2A.

As illustrated in FIGS. 87-88, the implant arm outer portion 110B includes a distal end 420, a proximal end 425, a proximal cylindrical opening 430 of a cylindrical bore 432, and a distal cylindrical opening 437 of the bore 432. The cylindrical bore 432 extends the full length of the implant arm outer portion 110B between the proximal opening 435 and the distal opening 437. Longitudinally extending grooves 440 are radially distributed about the inner circumferential surface of the bore 432 in an arrangement that matches the longitudinal raised ribs 405 of the implant arm inner portion 110A such that the ribs 405 are received in the grooves 440 in a mated arrangement when the inner portion 110A is received in the bore 432 of the outer portion 110B. The anchor arm 115 extends off the implant arm outer portion 110B at an angle as described above with respect to the previously discussed embodiments. The anchor arm 115 terminates at its free end in a collar 165 similar to those already discussed above.

As shown in FIGS. 87 and 88, the implant retainer 95 includes a proximal end 215, a distal end 220, and a lumen 445 extending the full length of the implant retainer 95. The proximal end 215 includes a squared, pentagonal or hexagonal outer surface configuration 450 that facilitates a mechanical engagement arrangement with the handle 90 such as the mechanical arrangement that exists between a wrench and nut. A ring 451 radial extends from the retainer 95 at the distal edge of the squared, pentagonal or hexagonal configuration 450. The distal end 220 may be threaded or otherwise configured to engage a proximal end of anyone of the implants 25 disclosed herein.

As illustrated in FIGS. 87 and 88, the collar assembly 400 includes a helical spring 455, rings 460A and 460B, washer 460C, retainer balls 461, and a retaining collar 465. As shown in FIG. 89, which is an isometric view of the handle 90, a cylindrical neck portion 470 of the handle 90 includes a shoulder 476 which slopes down to a circumferential groove 475 and a pair of holes 480 defined in the outer circumferential surface of the neck 470.

As indicated in FIG. 90, which is an exploded isometric view of the retaining collar 465 and handle 90 shown in longitudinal cross section, the holes 480 extend through the cylindrical wall 485 that defines the neck 470 and a cylindrical void 487 within the neck. A squared, pentagonal or hexagonal inner surface configuration 490 is defined in the handle 90 distal the cylindrical void 487 to receive in a mating arrangement the complementarily shaped outer configuration 450 of the proximal end of the implant retainer 95. A lumen 495 extends from a proximal end of the handle to open into the squared, pentagonal or hexagonal inner surface configuration 490.

As shown in FIG. 90, the retaining collar 465 includes a proximal end 500, a distal end 505, an outer circumferential surface 510 and an inner circumferential surface 515 that defines the hollow interior of the collar 517. The outer circumferential surface 510 extends radially outward to form a rim 520 near the proximal end 500. The inner circumferential surface 515 has a stepped and ramped configuration. Specifically, working distal to proximal, the inner circumferential surface 515 includes a proximal inner ring 525 separated from an intermediate inner ring 530 by a proximal large diameter region 535 separated from a small diameter region 540 by a ramped surface 545. Proximal the intermediate inner ring 530 is another large diameter region 550 bordered on its proximal boundary by a groove 555.

Figure 91:
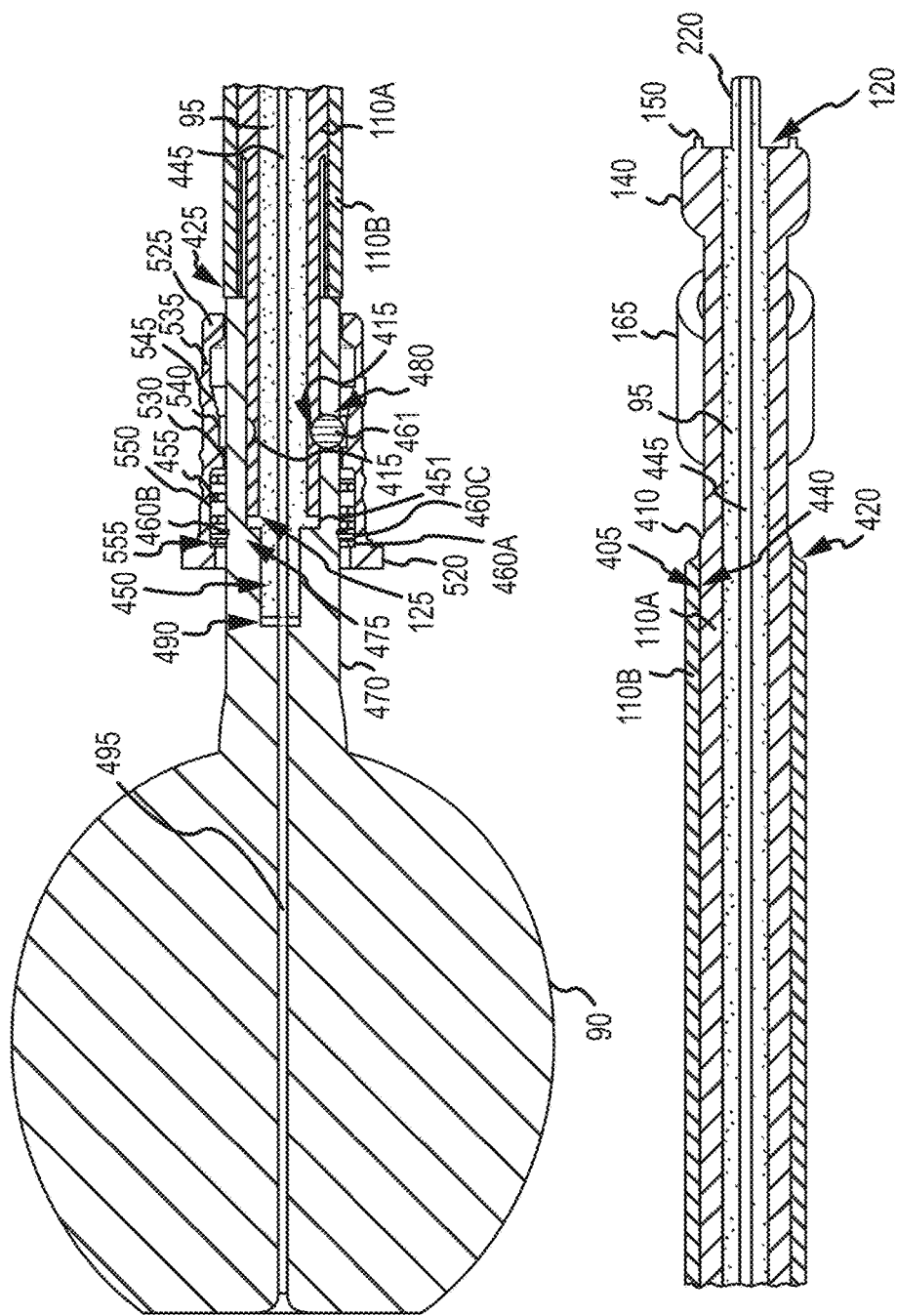
FIG. 91 is a longitudinal cross section of the delivery tool 20 when assembled as shown in FIG. 86.

As can be understood from FIG. 91, which is a longitudinal cross section of the delivery tool 20 when assembled as shown in FIG. 86, the implant arm inner portion 110A is received in the implant arm outer portion 110B such that the ribs 405 are matingly received in the corresponding slots 440 and the ring 410 abuts against the distal end 420 of the outer portion 110B. The implant retainer 95 extends through the inner portion 110A such that the distal end 220 of the implant retainer distally extends from the distal end 120 of the inner portion 110A and the ring 451 abuts against the proximal end 125 of the inner portion 110A. The proximal ends of the inner portion 110A and retainer 95 are received in the volume 487 (see FIG. 90) of the neck 470, the squared, pentagonal, or hexagonal portion 450 of the retainer 95 matingly received in the complementarily shaped volume 490 of the neck such that the ring 451 abuts against the step in the neck between the volume 490 of the neck and the rest of the volume of the neck distal thereto. The distal end of the neck 470 abuts against the proximal end 425 of the outer portion 110B.

As illustrated in FIG. 91, a first lock ring 460A is received in the groove 555 in the collar 465. A second lock ring 460B is received in the circumferential groove 475. A washer 460C is received on the neck 470 and abuts shoulder 476, which prevents washer 460C from advancing proximally beyond shoulder 476, and washer 460C is held in place distally by second lock ring 460B. Helical spring 455 circumferentially extends about the neck 470 between the washer 460C and the intermediate inner ring 530 of the collar 465. Thus, the spring biases the collar 465 distally on the neck 470. First lock ring 460A prevents collar 465 from distal disengagement from neck 470; the ring 460A, due to the forces exerted by a compressed spring 455 abuts washer 460C under normal conditions until manipulation by a medical person acting to move collar 465 proximally which in turn moves first lock ring 460A proximally thereby creating a further distance between first lock ring 460A and washer 460C.

As depicted in FIG. 91, neck holes 480 can be configured to have a sufficient diameter to allow the retaining balls 461 to enter from the opening nearest the outer circumferential surface of the neck 470 and to be seated within holes 480, the configuration further allowing a portion of the retaining balls 461 to extend into the cylindrical void 487 such to allow sufficient engagement with groove 415 as further described below. The neck holes 480 can be further configured, as depicted in FIG. 91, to have a slight reduction in their diameter, the reduction of diameter occupying a small portion of the holes 480 nearest the cylindrical void 487, thereby allowing for a configuration between neck 470, neck holes 480 and retaining balls 461 such that the retaining balls 461 are resistant to completely entering cylindrical void 487 after the removal of inner portion of the implant retainer 95 and implant arm inner portion 110A. The balls 461 are each held in their respective holes 480 in the neck 470 by the balls 461 being trapped between the neck holes 480 and inner circumferential surface of the collar 465. Therefore, when the collar 465 is biased distally on the neck, the balls 461 are inwardly forced by the reduced diameter region 540 to lock into the groove 415 of the inner portion 110A, retaining the proximal end of the anchor arm 110 in the handle/collar assembly. When the collar 465 is pulled proximally by a medical person using the tool 20, the balls 461 are exposed to the large diameter region 535, allowing the balls 461 sufficient play to radially outwardly move in the holes 480 to allow the balls to escape the groove 415, thereby allowing the proximal end of the anchor arm 110 to be removed from the handle/collar assembly.

As shown in FIG. 91, the lumens 495 and 445 are aligned to make one continuous lumen through the assembled tool 20. Thus, the tool 20 can be fed over a guidewire, stylet, needle or etc., or such implements can be fed through the lumen. Also, a bone paste, in situ curable biocompatible material, or similar material can be fed through the lumen to an implant 25 positioned in the joint via the tool.

As can be understood from FIGS. 86-91, the collar assembly 400 retains the proximal end of the implant arm 110 in the neck of the handle 90. The collar assembly 400 can be displaced proximally on the neck of the handle 90 to allow the proximal end of the implant arm 110 to be removed from the neck of the handle. When the implant arm 110 is coupled to the handle 90, the portions 110A and 110B of the implant arm 110 are locked together and prevented from displacing relative to each other, but the handle 90 and retainer 95 can be caused to rotate as a unit relative to the implant arm 110 to cause the distal end 220 of the retainer 95 engage or disengage the implant 25 as desired. Accordingly, the configuration allows for the removal of a handle 90 during the course of a procedure while allowing the retainer 95 to maintain engagement with implant 25 as desired.

Additionally, as a non-limiting example, according to particular embodiments, a reversible locking ratcheting mechanism can be employed to prevent undesired rotation of the handle and other components which could loosen the connection between implant 25 and retainer 95.

As illustrated in FIG. 92, which is a side view of an implant retainer 95 similar to that described with respect to FIGS. 86-91, except having a modified distal end 220. Specifically, the embodiment of FIG. 92 has T-shaped distal end 220. In one embodiment, the T-shaped distal end 220 includes a cylindrical center portion 220A and ears or tabs 220B oppositely positioned on the center portion 220A from each other.

Figure 94:
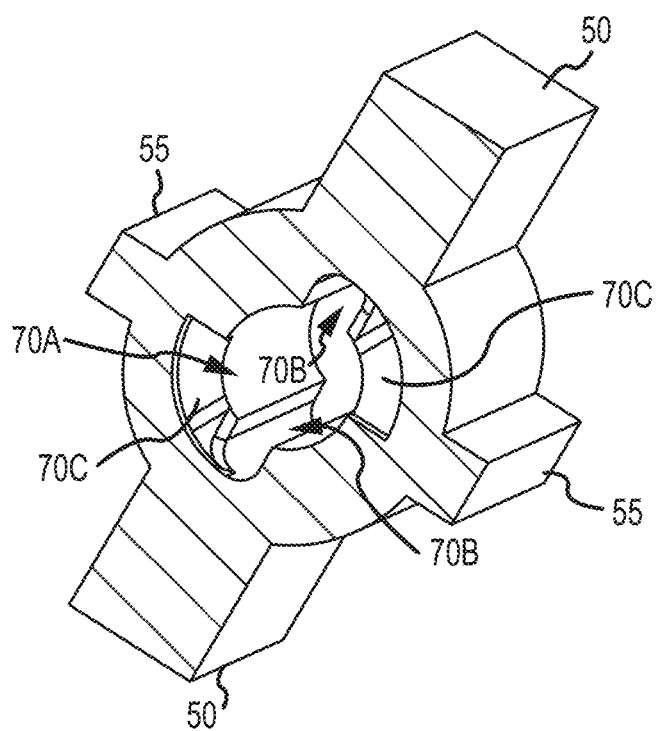

FIGS. 93-94 are, respectively, longitudinal and transverse cross sectional views of an implant 25 with an engagement hole 70 configured to complementarily engage with the T-shaped distal end 220 of the retainer 95 of FIG. 92. As illustrated in FIGS. 93-94, the hole 70 includes a cylindrical longitudinally extending center portion 70A with longitudinally extending grooves 70B located oppositely from each other. Inner radially extending grooves 70C intersect the distal ends of the grooves 70B.

As shown in FIG. 95, which is the same view as FIG. 93, except with the retainer 95 received in the hole 70, the cylindrical retainer portion 220A is received in the cylindrical hole portion 70A, and the retainer tab portions 220B are received in the hole grooves 70B. Once the distal end 220 of the retainer 95 is sufficiently received in the hole 70 such that the retainer tab portions 220B are aligned with the associated radially extending grooves 70C as illustrated in FIG. 95, the retainer 95 can be rotated within the hole 70 to cause the tab portions 220B to move into the radially extending grooves 70C, thereby locking the distal end 220 of the retainer 95 in the hole 70 of the implant 25. Grooves 70C can be configured such as to form an interference fit, thereby preventing retainer 95 from being separated from the implant 25 without the intentional application of substantial rotational separating force. Reversing the rotation of the retainer can cause the tab portions 220B to exit the radial grooves 70C, thereby unlocking the retainer distal end from the implant hole. Alternatively, according to particular embodiments, as a non-limiting example, radially extending grooves 70C can be configured to have at least one ramped surface, which upon rotation of retainer 95 into the grooves 70C, urges the distal end 220 a distance further in the direction of distal end 42 of implant 25 thereby creating increased friction between ring 45 of retainer 95 and proximal end 125 of 110A thereby preventing undesirable reverse rotation of the retainer without the intentional application of substantial rotational separating force, which otherwise could lead to an unlocking of the retainer distal end from the implant hole.

As illustrated in FIG. 93, in one embodiment, the implant 25 may include a lumen 600 extending the length of the implant through the anchor hole 40 and the retainer engagement hole 70. Such a lumen 600 may serve to receive a guidewire or stylet there through. Such a lumen 600 may serve to receive an injection of bone paste material, or other biocompatible material.

To begin a detailed discussion of a fourth embodiment of the system 10, reference is made to FIGS. 109 and 110. FIG. 109 is an isometric view of the system 10 wherein the tool 20 is attached to the implant 25 for delivery of the implant to the sacroiliac joint. FIG. 110 is a view of the system 10 wherein the implant 25 and anchor arm 115 are shown in plan view.

As can be understood from FIGS. 109-110, the system 10 includes a delivery tool 20 and an implant 25 for implanting at the sacroiliac joint via the delivery tool 20, the implant 25 being for fusing the sacroiliac joint. As can be understood from a comparison of FIGS. 109 and 86, the tool embodiment of FIG. 109 is substantially similar to the tool embodiment of FIG. 86, except the tool embodiment of FIG. 109 has an anchor arm 115 that distally ends in multiple anchor collars 165*a*-165*d*.

Figure 7:
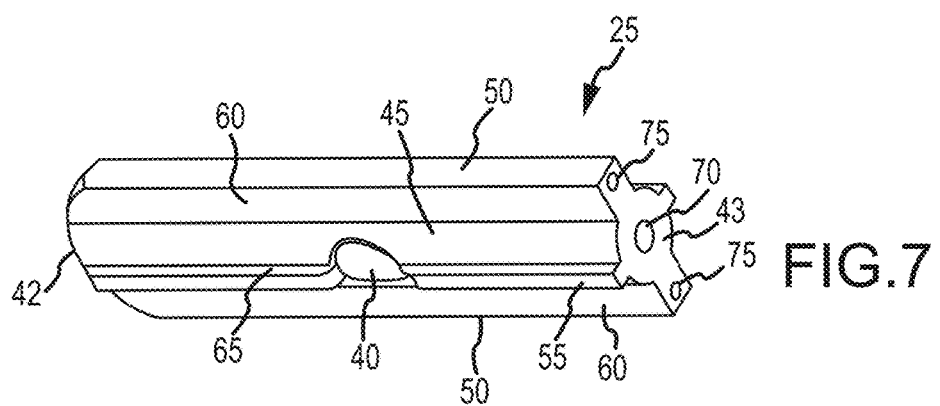
FIG. 7 is a bottom-side isometric view of the implant assembly.
Figure 8:
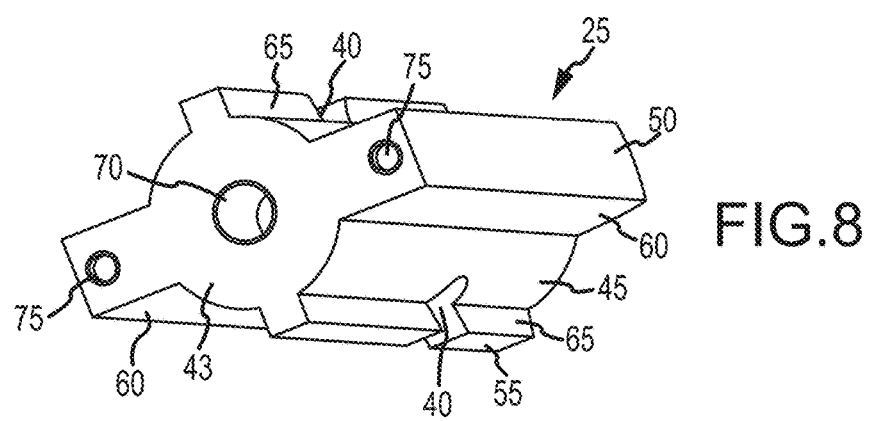
FIG. 8 is another proximal end isometric view of the implant.
Figure 9:
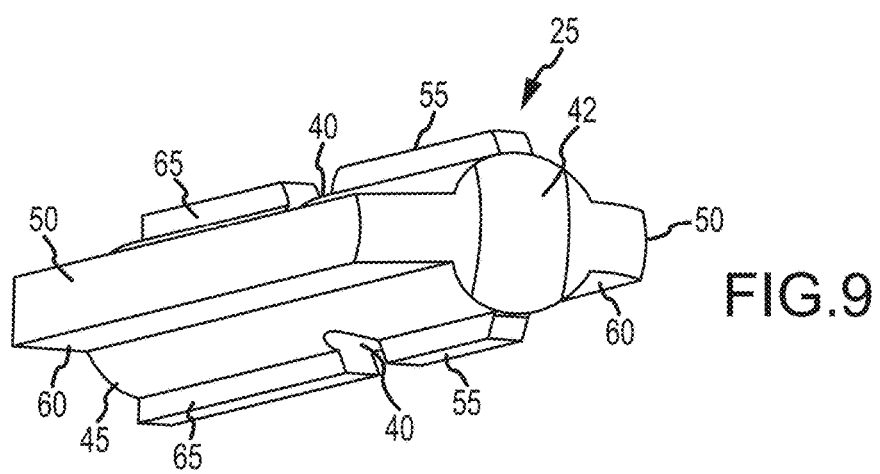
FIG. 9 is another distal end isometric view of the implant.
Figure 10:
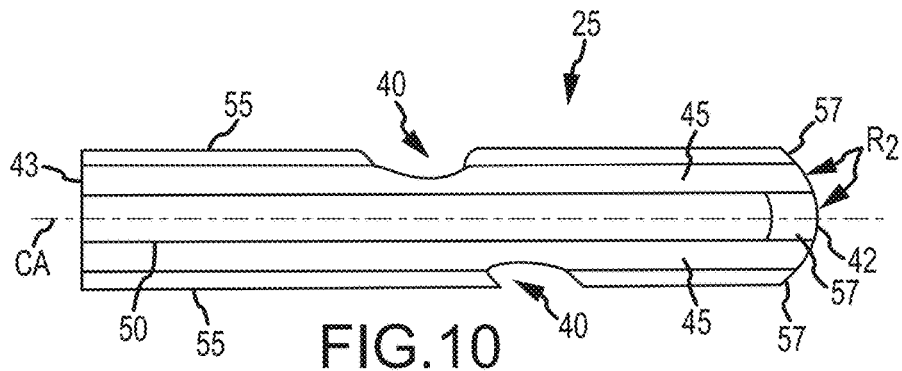
FIGS. 10 and 11 are opposite side elevation views of the implant.
Figure 11:
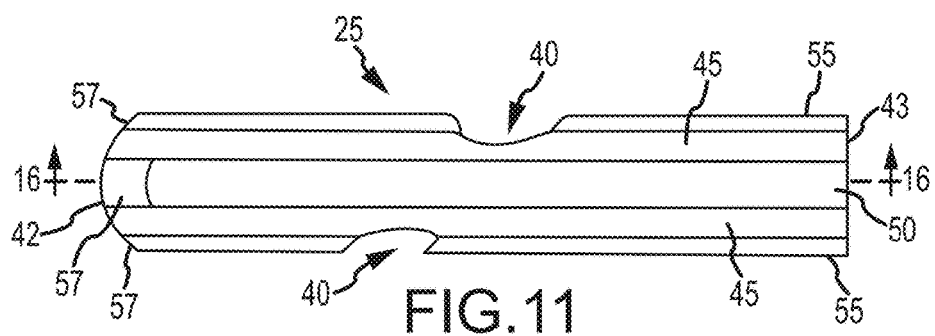

As can be understood from a comparison of FIGS. 109 and 7, the implant embodiment of FIG. 109 is substantially similar to the implant embodiment of FIG. 7, except the implant embodiment of FIG. 109 has multiple bores 40*a*-40*b*.

As illustrated in FIGS. 109-110, the anchor collars 165 may include two linearly aligned center collars 165*a* and 165*b*, and a lateral anchor collar 165*c* and 165*d* may be located on either side of the most proximal center collar 165*b*. As indicated in FIG. 110, the two center collars 165*a* and 165*b* may be axially aligned with the respective bores 40*a* and 40*b* of the implant 25 when the implant 25 is supported off of the distal end of the implant arm 110 of the tool 20. As a result, an anchor member 30 (see, for example, FIG. 4) may be delivered into each of the bores 40*a* and 40*b* via the respective anchor collars 165*a* and 165*b*. The lateral anchor collars 165*c* and 165*d* may be employed to deliver yet additional anchor members 30 to additional anchor member receiving features (e.g., bores, etc.) existing on, or extending from the sides of, the implant 25, where such additional anchor member receiving features are present on the implant 25. Alternatively, lateral collars 165*c* and 165*d* can be configured to deliver additional anchor members 30 into the bone of the ilium and sacrum while not passing through a bore 40 (i.e., preconfigured to place anchor members 30 immediately adjacent the longitudinal side edges of the implant 25.

Figure 96A:
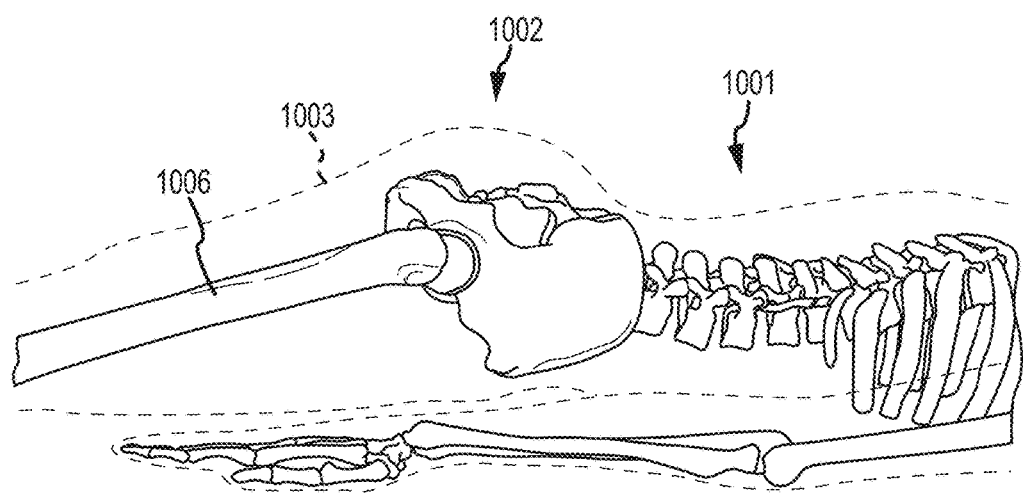
FIG. 96A is a right lateral side view of a hip region of a patient lying prone, wherein the soft tissue surrounding the skeletal structure of the patient is shown in dashed lines.
Figure 96B:
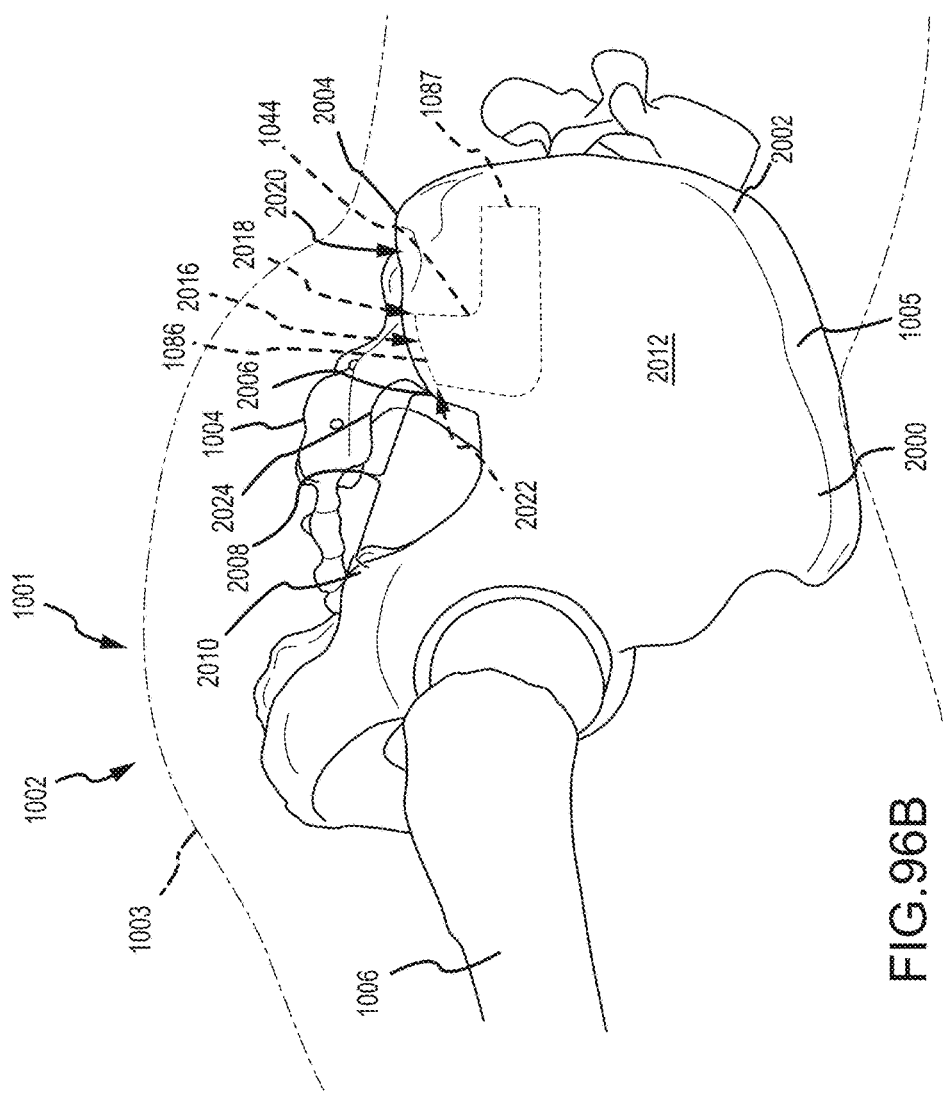
FIG. 96B is an enlarged view of the hip region of FIG. 96A.

To begin a discussion regarding the methodology associated with employing any of the above-described delivery tools 20 in implanting any of the above-described implants 25 in the sacroiliac joint 1000 of a patient 1001, reference is first made to FIGS. 96A-98B to identify the bone landmarks adjacent, and defining, the sacroiliac joint 1000. FIG. 96A is a right lateral side view of a hip region 1002 of a patient 1001 lying prone, wherein the soft tissue 1003 surrounding the skeletal structure 1006 of the patient 1001 is shown in dashed lines. FIG. 96B is an enlarged view of the hip region 1002 of FIG. 96A. As illustrated in FIGS. 96A and 96B, a lateral view of the patient's hip region 1002 reveals certain features of the ilium 1005, including the anterior superior iliac spine 2000, the iliac crest 2002, the posterior superior iliac spine 2004, the posterior inferior iliac spine 2006, the greater sciatic notch 2008 extending from the posterior inferior iliac spine 2006 to the ischial spine 2010, and the tubercle of iliac crest 2012. The sacroiliac joint articular region 1044 is shown in dashed lines. A posterior inferior access region 2016 of the sacroiliac joint articular region 1044 has a superior end 2018 on the sacroiliac joint line 2019 that is between approximately 0 mm and approximately 40 mm inferior the posterior inferior overhang 2020 of the posterior superior iliac spine 2004. The posterior inferior access region 2016 of the sacroiliac joint articular region 1044 has an inferior end 2022 on the sacroiliac joint line that is at approximately the intersection of the posterior inferior iliac spine 2006 with the lateral anterior curved boundary 2024 of the sacrum 1004. In other words, the posterior inferior access region 2016 of the sacroiliac joint articular region 1044 has an inferior end 2022 on the sacroiliac joint line that is at approximately the superior beginning of the greater sciatic notch 2008.

Figure 97A:
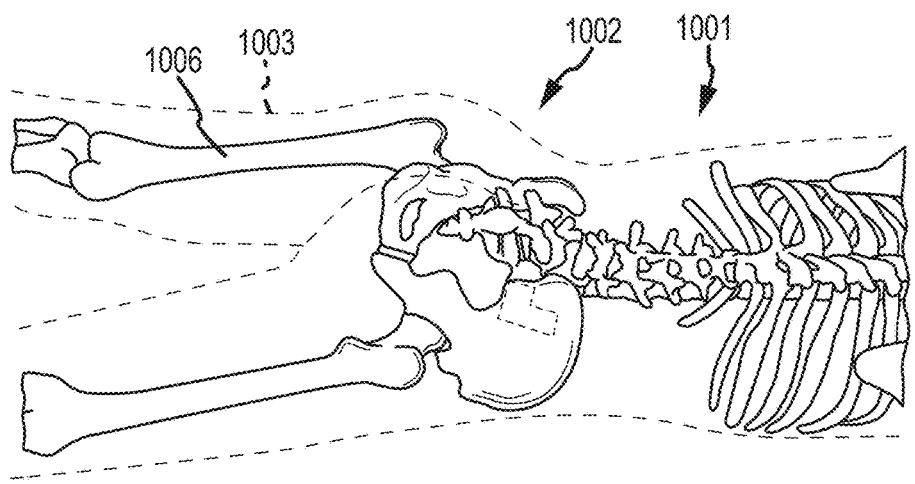
FIG. 97A is a lateral-posterior view of the hip region of the patient of FIG. 96A, wherein the patient is lying prone and the soft tissue surrounding the skeletal structure of the patient is shown in dashed lines.

FIG. 97A is a lateral-posterior view of the hip region 1002 of the patient 1001 of FIG. 96A, wherein the patient 1001 is lying prone and the soft tissue 1003 surrounding the skeletal structure 1006 of the patient 1001 is shown in dashed lines. FIG. 97B is an enlarged view of the hip region 1002 of FIG. 97A. As shown in FIGS. 97A and 97B, a lateral-posterior view of the patient's hip region 1002 reveals the same features of the sacrum 1004 and ilium 1005 as discussed above with respect to FIGS. 96A and 96B, except from another vantage point. The vantage point provided via FIGS. 97A and 97B provides further understanding regarding the posterior inferior access region 2016 of the sacroiliac joint articular region 1044 and superior end 2018 and inferior end 2022 of the posterior inferior access region 2016 relative to nearby anatomical features, such as, for example, the posterior inferior overhang 2020 of the posterior superior iliac spine 2004, the intersection of the posterior inferior iliac spine 2006 with the lateral anterior curved boundary 2024 of the sacrum 1004, and the superior beginning of the greater sciatic notch 2008.

Figure 98A:
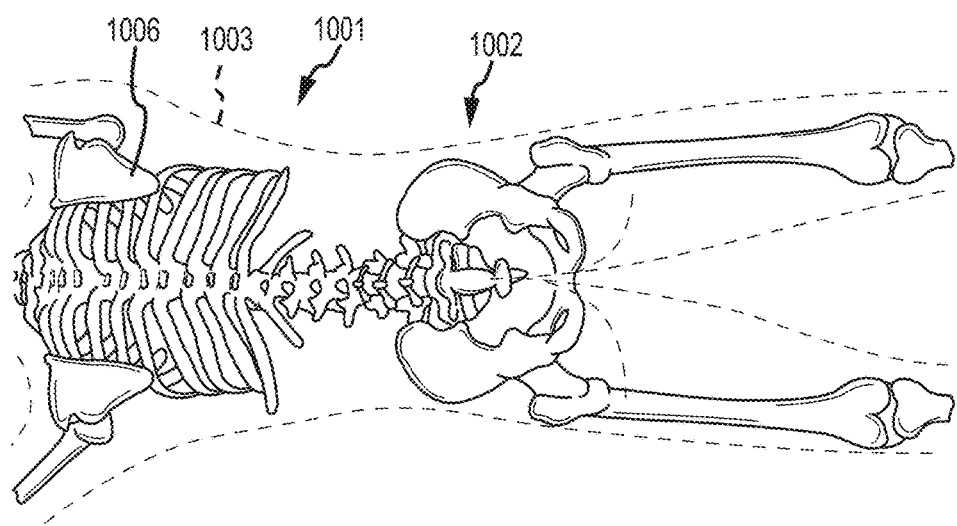
FIG. 98A is a posterior view of the hip region of the patient of FIG. 96A, wherein the patient is lying prone and the soft tissue surrounding the skeletal structure of the patient is shown in dashed lines.

FIG. 98A is a posterior view of the hip region 1002 of the patient 1001 of FIG. 96A, wherein the patient 1001 is lying prone and the soft tissue 1003 surrounding the skeletal structure 1006 of the patient 1001 is shown in dashed lines. FIG. 98B is, an enlarged view of the hip region 1002 of FIG. 98A. As shown in FIGS. 98A and 98B, a posterior view of the patient's hip region 1002 reveals the same features of the sacrum 1004 and ilium 1005 as discussed above with respect to FIGS. 96A and 96B, except from yet another vantage point. The vantage point provided via FIGS. 98A and 98B provides yet further understanding regarding the posterior inferior access region 2016 of the sacroiliac joint articular region 1044 and superior end 2018 and inferior end 2022 of the posterior inferior access region 2016 relative to nearby anatomical features, such as, for example, the posterior inferior overhang 2020 of the posterior superior iliac spine 2004, the intersection of the posterior inferior iliac spine 2006 with the lateral anterior curved boundary 2024 of the sacrum 1004, and the superior beginning of the greater sciatic notch 2008.

Now that the relevant anatomical landmarks have been identified with respect to FIGS. 96A-98B, the methodology associated with employing any of the above-described delivery tools 20 in implanting any of the above-described implants 25 in the sacroiliac joint 1000 of a patient 1001 can be discussed. In doing so, reference will be made to FIGS. 99A-99P, which are each a step in the methodology and illustrated as the same transverse cross section taken in along a plane extending medial-lateral and anterior posterior along section line 99-99 in FIG. 98B. In this cross section, articular surfaces 1016 are covered by a thick layer of articular cartilage with a joint space existing between them, the FIGS. 99A-99P are simplified for illustrative purposes and do not show these features to scale. Now referring primarily to FIG. 99A, an embodiment of the method can include the step of placing a patient under sedation prone on a translucent operating table (or other suitable surface). The sacroiliac joint 1000 can be locally anesthetized to allow for injecting a radiographic contrast 1046 (as a non-limiting example, Isoview 300 radiographic contrast) under fluoroscopic guidance into the inferior aspect of the sacroiliac joint 1000 to outline the articular surfaces 1016 of the sacroiliac joint 1000) defined between the sacrum 1004 and ilium 1005, the sacroiliac joint 1000 having an interarticular region 1044. Injection of the radiographic contrast 1046 within the sacroiliac joint 1000 can be accomplished utilizing a tubular member 1047) (such as a syringe needle) having first tubular member end 1048 which can be advanced between the articulating surfaces 1016 of the sacroiliac joint 1000 and having a second tubular member end 1049 which removably couples to a hub 1050. The hub 1050 can be configured to removably couple to a syringe barrel 1051 (or other device to contain and deliver an amount of radiographic contrast 1046). In the example of a syringe barrel 1051, the syringe barrel 1051 can have an internal volume capable of receiving an amount of the radiographic contrast 1046 sufficient for outlining the articular surfaces 1016 of the sacroiliac joint 1000, for example, under lateral fluoroscopy. A plunger 1052 can be slidingly received within the barrel 1051 to deliver the radiographic contrast 1046 through the tubular member 1047 into the sacroiliac joint 1000. The tubular member 1047 can have a gauge in the range of about 16 gauge and about 20 gauge and can further be incrementally marked on the external surface to allow determination of the depth at which the first needle end 1048 has advanced within the sacroiliac joint 1000. As the first needle end 1048 advances into the sacroiliac joint 1000 the radiographic dye 1046 can be delivered from within the syringe barrel 1051 into the sacroiliac joint 1000 to allow visualization of the sacroiliac joint 1000 and location of the tubular needle 1047 within the sacroiliac joint 1000.

Now referring primarily to FIG. 99B, once the first tubular member end 1048 has been sufficiently advanced into the sacroiliac joint 1000 and the articular surfaces 1016 of the sacroiliac joint 1000 have been sufficiently visualized, the hub 1050 can be removed from the tubular member 1047 leaving the tubular member 1047 fixed within the sacroiliac joint 1000 as an initial guide for tools subsequently used to locate or place the sacroiliac joint implant 25 non-transversely between the articulating surfaces 1016 of the sacroiliac joint 1000 (e.g., locate the implant 25 non-transversely to the joint plane 1030 generally defined by the articulating surfaces 1016 of the interarticular region 1044 of the sacroiliac joint 1000) or in removal of a portion of the sacroiliac joint 1000 within the region defined by the articular surfaces 1016 to generate an implant receiving space 1029 (see FIG. 99H). Alternately, one or more guide pins 1013 can be inserted along substantially the same path of the tubular member 1047 for fixed engagement within the sacroiliac joint 1000 and used in subsequent steps as a guide(s).

Figure 99B:
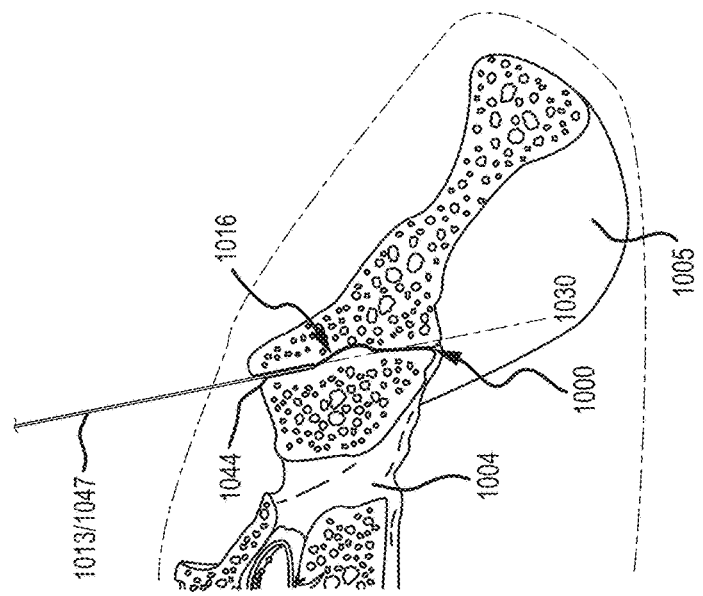
FIGS. 99A-99Q are each a step in the methodology and illustrated as the same transverse cross section taken along a plane extending medial-lateral and anterior posterior along section line 99-99 in FIG. 98B.
Figure 99A:
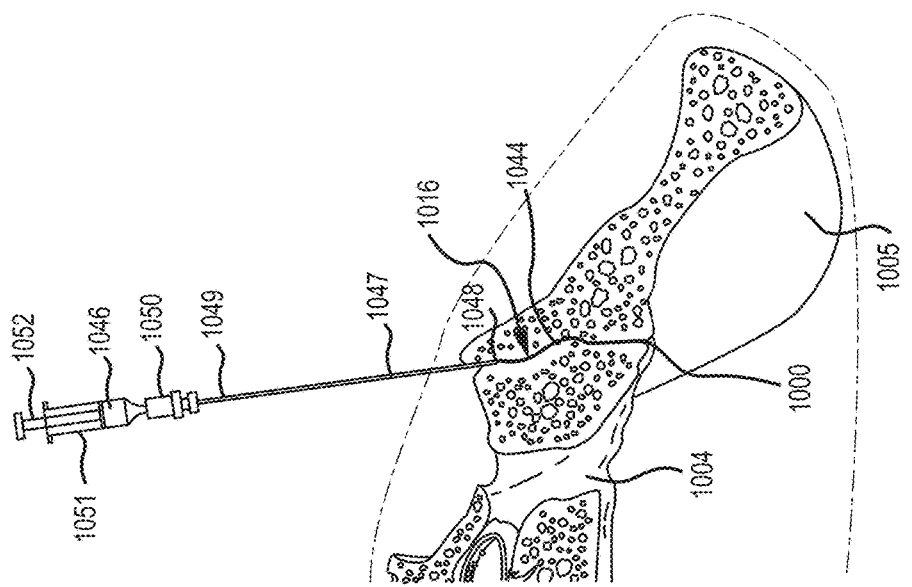
Figure 99F:
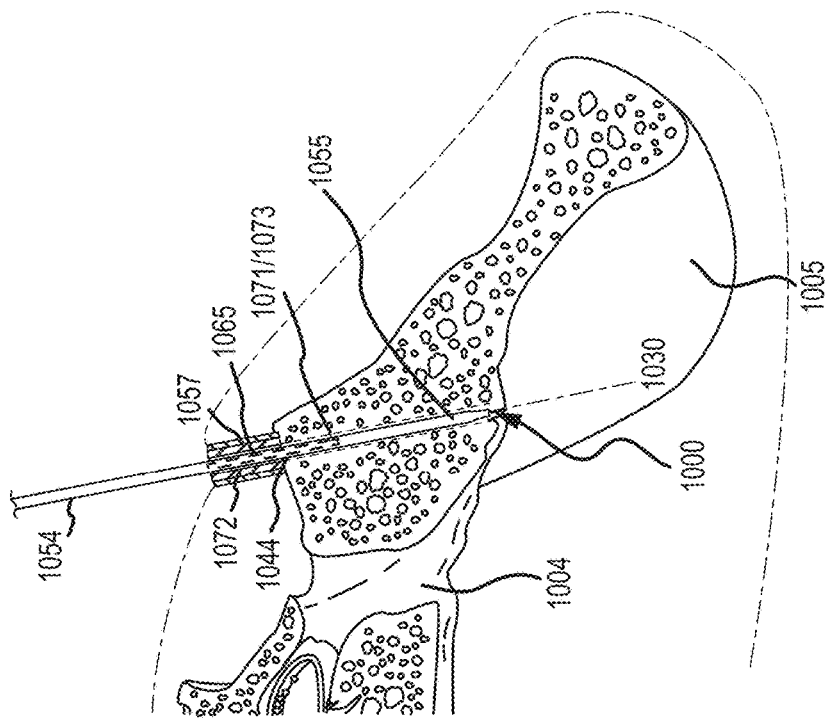

Now referring primarily to FIG. 99C, a small incision 1053 can be made in the skin at the posterior superior (or as to certain embodiments inferior) aspect of the sacroiliac joint 1000, extending proximal and distal to the tubular member 1047 along the line of the sacroiliac joint 1000 to provide a passage to access the interarticular space between the articulating surfaces 1016 (see FIG. 99B) of the sacroiliac joint 1000. More specifically, as can be understood from FIGS. 96A-98B, in one embodiment, the small incision 1053 can be made along the joint line 2019 of the sacroiliac joint 1000 in the tissue covering the posterior inferior access region 2016 of the sacroiliac joint articular region 1044. A cannulated probe 1054 can be slidingly engaged with the tubular member 1047 (or guide pin 1013) extending outwardly from the sacroiliac joint 1000 (while the sacroiliac joint may be shown in the figures as being substantially linear for illustrative purposes, it is to be understood that the normal irregular features of the sacroiliac joint have not been removed). The cannulated probe 1054 can have a probe body 1054 of generally cylindrical shape terminating in a spatulate tip 1055 at the end advanced into the sacroiliac joint 1000. A removable cannulated probe handle 1056 couples to the opposed end of the probe body 1054. The spatulate tip 1055 can be guided along the tubular needle 1047 or guide wire 1013 into the posterior portion of the sacroiliac joint 1000 and advanced to the anterior portion of the sacroiliac joint 1000 under lateral fluoroscopic visualization. The cannulated probe handle 1056 can then be removed providing the generally cylindrical probe body 1054 extending outwardly from the sacroiliac joint 1000 through the incision 1053 made in the skin.

Alternatively, probe 1054 can be used to guide, advance or place a needle, guide wire or other instrument up to, near, or into the joint.

Additionally, in particular embodiments, probe handle 1056 or the opposed end of the probe body 1054, or both, can be configured to have an interference fit or a luer lock hub to communicate with a syringe barrel 1051 in order to advance contrast, in situ curable biocompatible materials, stem cells, or etc. through the cannulated probe 1054 or cannulated probe handle 1056.

Now referring primarily to FIG. 99D, a passage from the incision 1053 (see FIG. 99C) to the sacroiliac joint 1000 can be generated by inserting a cannula 1057 into the incision. A soft tissue dilator 1058 having a blunt end 1059 can be advanced over the probe body 1054, or a plurality of soft tissue dilators of increasing size, until the blunt end 1059 of the soft tissue dilator 1058 and the corresponding cannula end contact the posterior aspect of the sacroiliac joint 1000. More specifically, as can be understood from FIGS. 96A-98B, in one embodiment, the ends of the dilator 1058 and cannula 1057 contact the joint line 2019 of the sacroiliac joint 1000 at the posterior inferior access region 2016 of the sacroiliac joint articular region 1044. The soft tissue dilator 1058 can be removed from within the cannula 1057. The external surface of the cannula 1057 can be sufficiently engaged with the surrounding tissue to avoid having the tissue locate with in the hollow inside of the cannula 1057. A non-limiting embodiment of the cannula 1057 provides a tubular body having substantially parallel opposed side walls which terminate in a radius at both ends (lozenge shape) into which a plurality of different jigs can be inserted. Alternatively, as a non-limiting example, according to particular embodiments, cannula 1057 and corresponding dilators 1058 and alignment jigs 1060 can be configured to have tubular bodies with an elliptical or circular cross section.

In some embodiments, the cannula 1057 may be additionally configured to have within or near its walls a light source such as, for example, a fiber optic or a LED light source to assist in visualization of the working area. Also, in some embodiments, irrigation and suction tubing may communicate with the inside passage of cannula 1057.

Figure 100A:
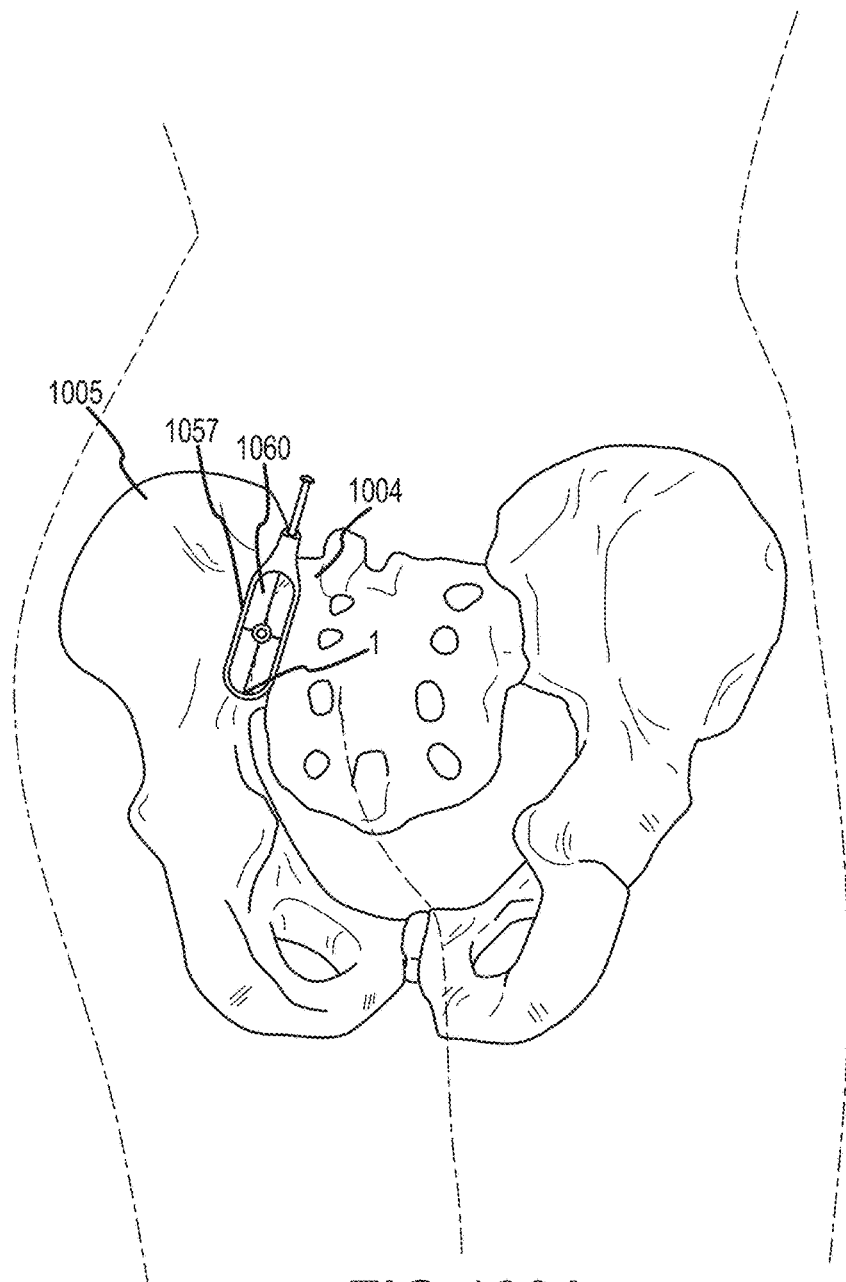
FIG. 100A is a posterior-lateral view of the hip region of the patient, illustrating the placement of a cannula alignment jig.
Figure 100B:
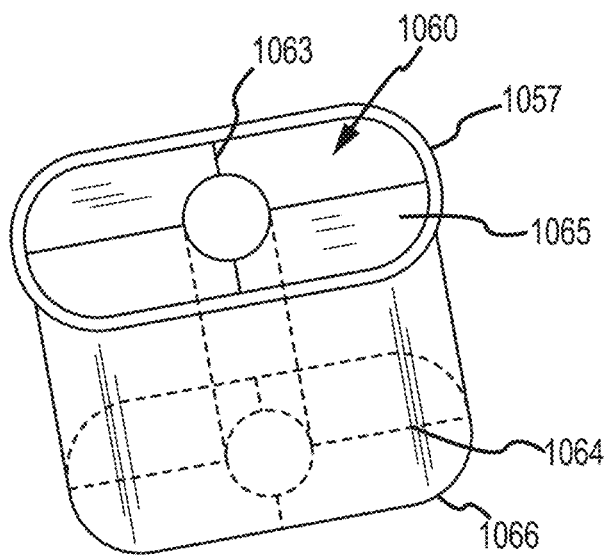
FIGS. 100B-100C are different isometric views of the cannula alignment jig.
Figure 100C:
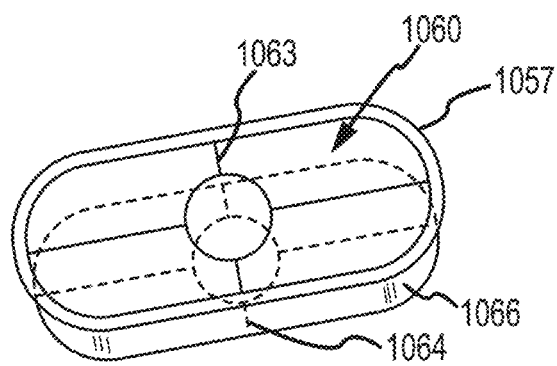

Now referring primarily to FIGS. 100A-100C, a cannula alignment jig 1060 can be advanced over the probe body 1054 (or guide pins 1013) and received within the cannula 1057. Substantially, identical cross hairs 1063, 1064 can be disposed on the upper jig surface 1065 and the lower jig surface 1066. Alignment of the cross hairs 1063, 1064 under x-ray with the sacroiliac joint 1000 can confirm that the cannula 1057 has proper orientation in relation to the paired articular surfaces 1016 of the sacroiliac joint 1000. The cannula 1057 properly oriented with the paired articular surfaces 1016 can then be disposed in fixed relation to the sacroiliac joint by placement of fasteners through the cannula 1057 into the sacrum 1004 or the ilium 1005.

Figure 101A:
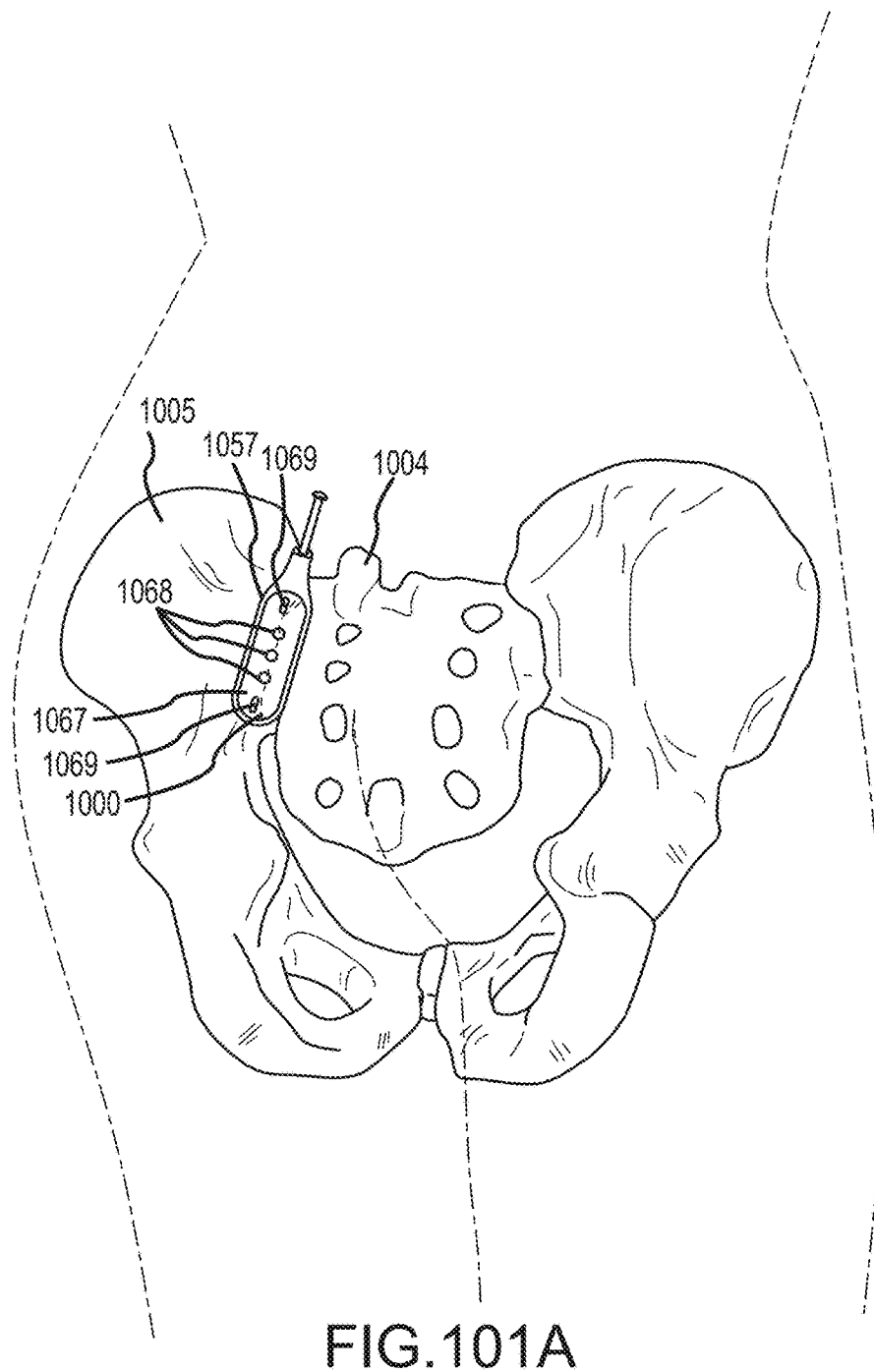
FIG. 101A is a posterior-lateral view of the hip region of the patient, illustrating the placement of a drill jig.
Figure 101B:
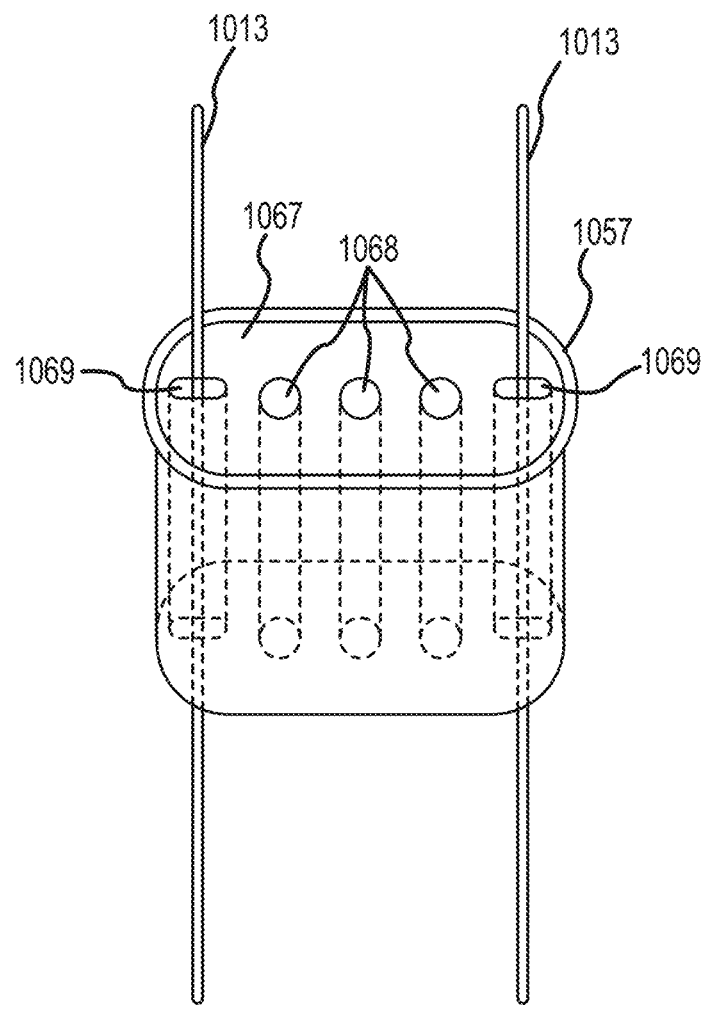
FIG. 101B is an isometric view of the drill jig.
Figure 102A:
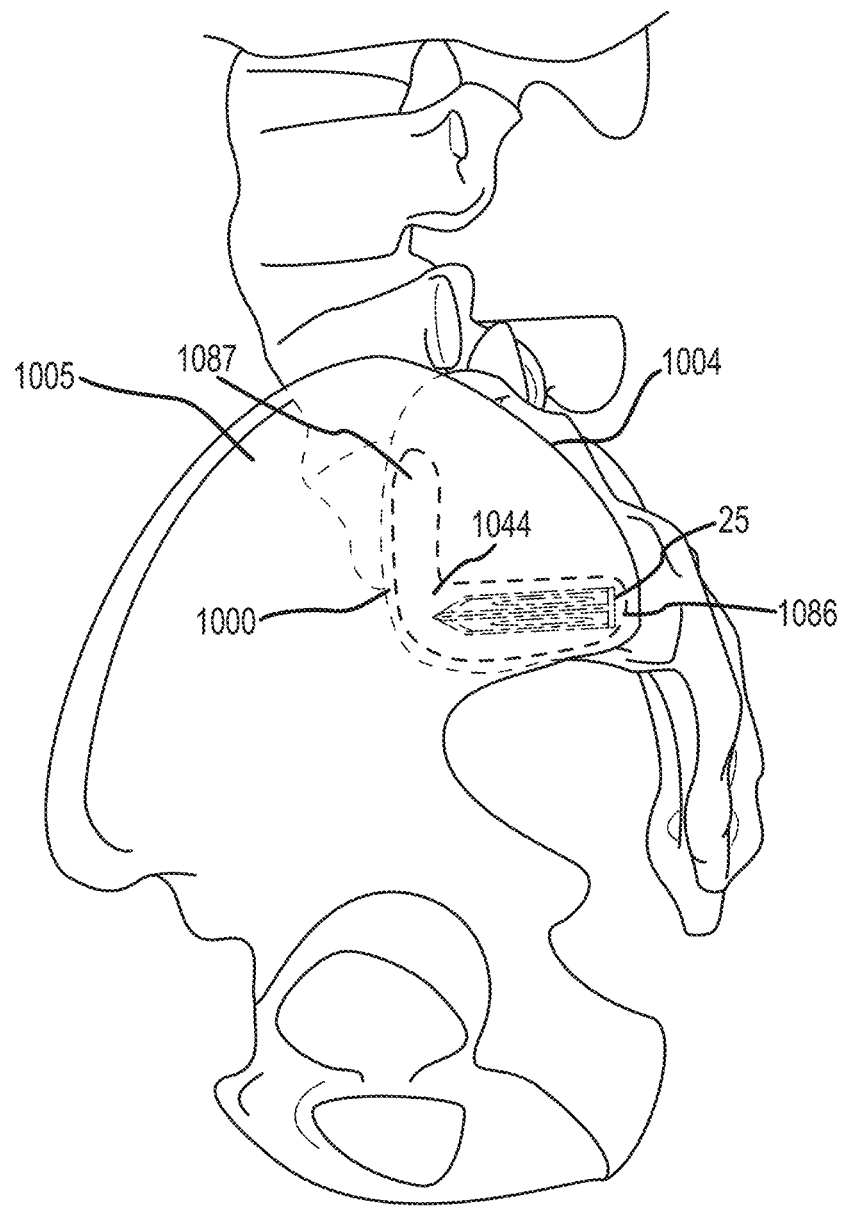
FIG. 102A is a lateral view of the hip region of the patient, illustrating the implant implanted in the caudal region of the sacroiliac joint space.
Figure 102B:
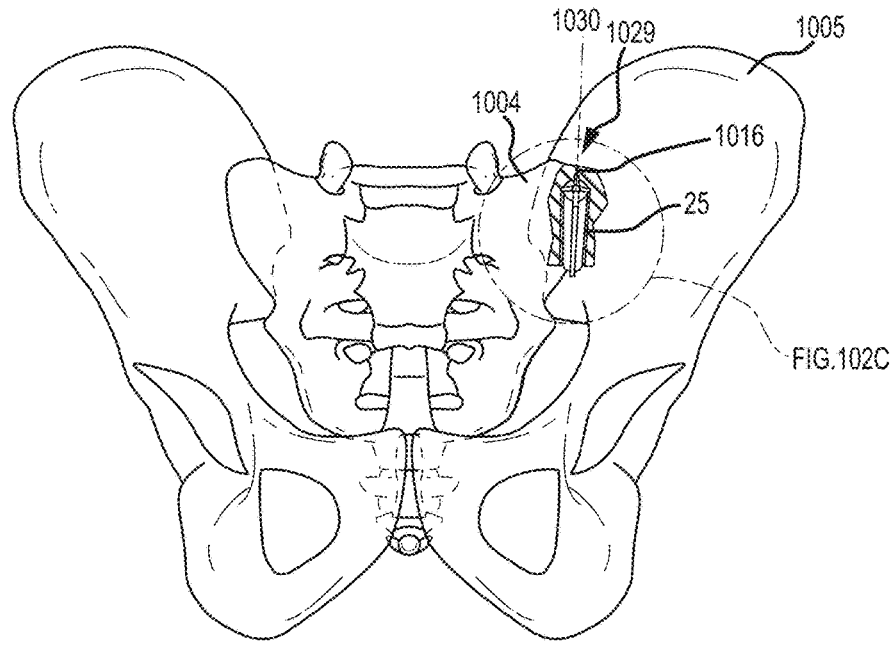
FIG. 102B is an anterior view of the hip region of the patient, illustrating the implant implanted in the caudal region of the sacroiliac joint space.
Figure 102C:
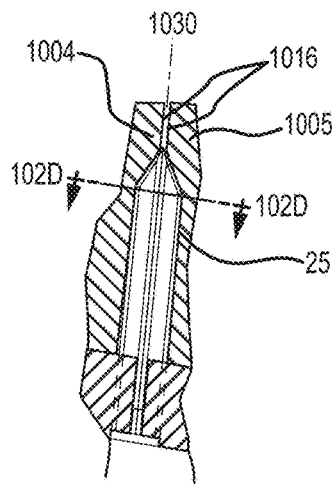
FIG. 102C is an enlarged view of the implant taken along the plane of the sacroiliac joint.
Figure 102D:
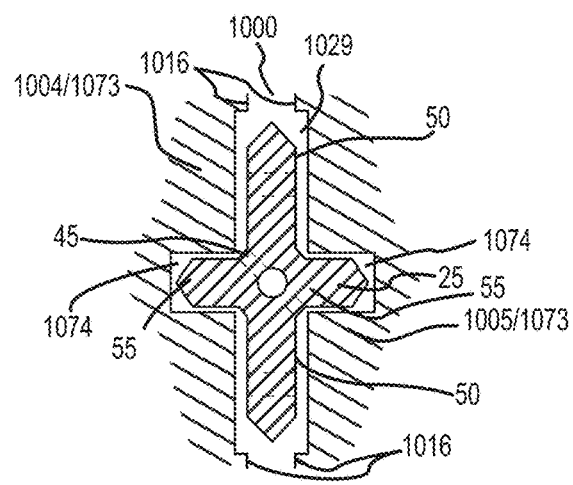
FIG. 102D is a transverse cross section of the implant and joint plane taken along section line 102D-102D of FIG. 102C.

Now referring to FIGS. 101A and 101B, a first drill jig 1067 can be advanced over the probe body 1054 (or guide pins 1013) and received within the cannula 1057. The probe body 1054 (or guide pins 1013) extending outwardly from the sacroiliac joint 1000 passes through a drill guide hole 1068 of the first drill jig 1067 (or a plurality of guide pins 1013 can extend through a corresponding plurality of guide pin holes 1069). The drill guide hole 1068 can take the form of a circular hole as shown in the Figures, a slot, or other configuration to restrict the movement of the drill bit 1062 (see FIG. 99E) within the drill jig 1060 and provide a guide for a drill bit 1062 in relation to the sacroiliac joint 1000. Guide pin holes 1069 can receive guide pins which can be positioned between the articular surfaces 1016 of the sacroiliac joint 1000 to demarcate the zone of desired treatment or safe working zones while using, for example, lateral fluoroscopy. As a non-limiting example, a first guide pin 1013 can be advanced through a first guide pin hole 1069, or alternatively a guide pin 1013 is first inserted into the sacroiliac joint 1000 and subsequently a guide jig 1067 is advanced over the guide pin 1013, the first guide pin 1013 can enter near inferior end 2022 of the posterior inferior access region 2016 of the sacroiliac joint articular region 1044 via the sacroiliac joint line 2019 to border a portion of the greater sciatic notch 2008 thereby allowing a medical person, computer guided surgical system, or other observer to more easily highlight under x-ray a border which should not be crossed during the procedure due to the presence of nerve and other structures. Additionally, as a non-limiting example, first guide pin 1013 can configured as an electrode, insulated from the operator and the patient's soft tissues, and may be connected to a monitor to signal to an operator or surgeon when implant 25, configured with a stimulating electrode (NM), as discussed below, comes into contact with first guide pin. Similarly, a second guide pin 1013 can be placed in another guide pin hole 1069 to demarcate a second limit to a desired zone of treatment, or safe working zone. For example, a second guide pin 1013 can enter near the superior end 2018 of the posterior inferior access region 2016 of the sacroiliac joint articular region 1044 via the sacroiliac joint line 2019 to be positioned to border an area of the sacroiliac joint 1000 such as a transition zone between the extra-articular 3007 (see FIG. 106B) and the interarticular region 1044 which, for example, has been highlighted by contrast material as above described.

Figure 99E:
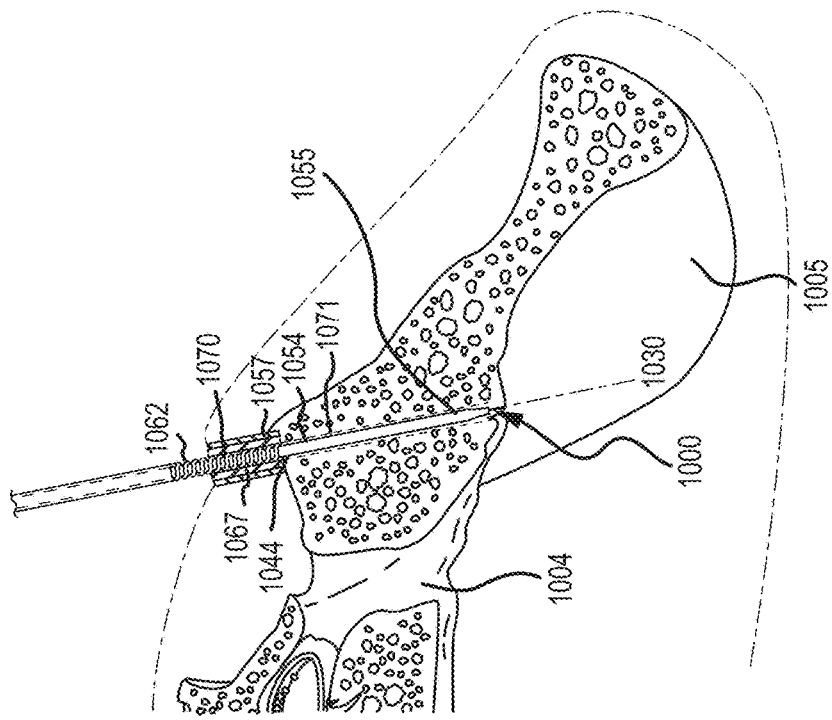
Figure 99I:
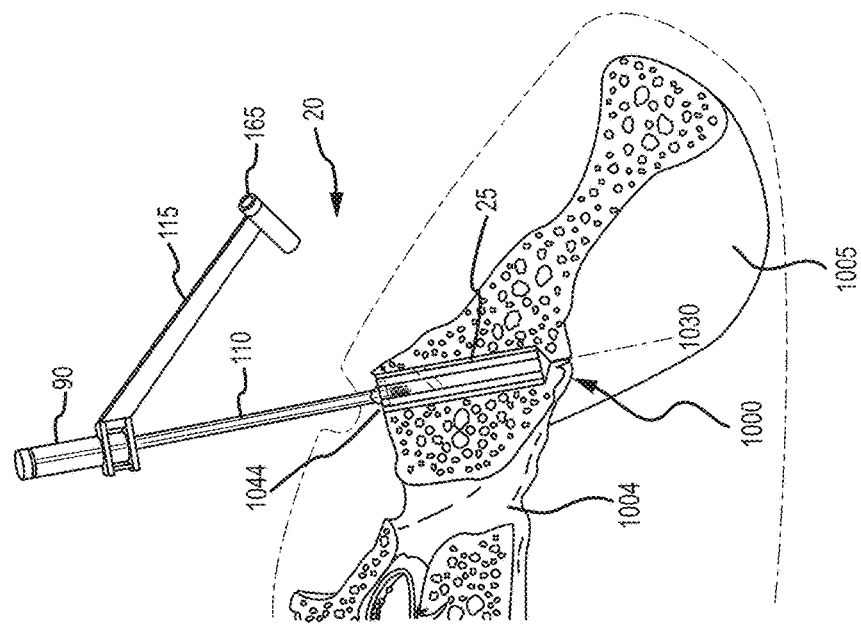

Now referring to FIG. 99E, a cannulated drill bit 1070 can be advanced over the probe body 1054 and within a drill guide hole 1068 (see FIGS. 101A and 101B) of the first drill jig 1067. The cannulated drill bit 1070 under fluoroscopic guidance can be advanced into the interarticular region 1044 between the articulating surfaces 1016 of the sacroiliac joint 1000 to produce a first bore 1071 (shown in broken line) to a determined depth. As to certain embodiments of the method, an amount of articular cartilage or other tissues from between the articular surfaces 1016 of the sacroiliac joint 1000 can be removed sufficient to allow embodiments of the sacroiliac joint implant 25 to be implanted in replacement of the removed articular cartilage or tissue. Because the method removes the degenerative articular cartilage or tissue between the articular surfaces 1016 of the sacroiliac joint 1000, the articular surfaces 1016 of the sacroiliac joint 1000 can remain intact or substantially intact allowing the sacroiliac joint implant 25 to be non-transversely located between the articular surfaces 1016 of the sacroiliac joint 1000. Understandably, other instruments can be utilized separately or in combination with a cannulated drill bit 1062 for the removal of articular cartilage or tissue between articular surfaces 1016 such as: endoscopy tools, box chisels, side cutting router bits, burs, flexible burs and bits, hole saws, curettes, lasers (such as C02, Neodymium/YAG (yttrium-aluminum-garnet), argon, and ruby), electrosurgical equipment employing electromagnetic energy (the cutting electrode can be a fine micro-needle, a lancet, a knife, a wire or band loop, a snare, an energized scalpel, or the like) where the energy transmitted can be either monopolar or bipolar and operate with high frequency currents, for example, in the range of about 300 kHz and about 1000 kHz whether as pure sinusoidal current waveform where the "crest factor" can be constant at about 1.4 for every sinus waveform, and a voltage peak of approximately 300 V to enable a "pure" cutting effect with the smallest possible coagulation effect or as amplitude modulated current waveforms where the crest factor varies between 1.5 and 8, with decreasing crest factors providing less of a coagulation effect. Electrosurgical waveforms may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces of the joint and aid in advancing a probe or guide wire into a position in between the articulating surfaces. These currents can effectively degrade the cartilage and allow advance into the joint without grossly penetrating much beyond the cartilage.

Now referring to FIG. 99F, as to certain embodiments of the invention, the first drill jig 1067 can be removed from within the cannula 1057 and a second drill jig 1072 can be advanced over the probe body 1054 and received within the cannula 1057; however, the invention is not limited to any particular number of drill jigs and as to certain embodiments of the method the first drill jig 1067 can include all the required drill guide hole(s) 1068 (or slots or other configurations of the drill guide) and as to other embodiments of the method a plurality of drill jigs can be utilized in serial order to provide all the drill guide holes 1068. As to the particular embodiment of the invention shown by the Figures, the first drill jig 1067 can provide one or more additional drill guide holes 1068 which guide in relation to the first bore 1071a second or more cannulated drills 1062 of the same or different configuration to be inserted within and advanced into the sacroiliac joint 1000 to produce a second bore 1073 (generally shown in broken line as 1071/1073) or a plurality of bores within the sacroiliac joint 1000 spaced apart in predetermined pattern to allow removal of sufficient articular cartilage 1016 or other tissue from the interarticular space of sacroiliac joint 1000 for placement of embodiments of the sacroiliac joint implant 25 within the region defined by and between the paired articular surfaces 1016 of the sacroiliac joint 1000. As to certain methods of the invention, the first drill jig 1067 or the second drill jig 1072 or a plurality of drill jigs can be utilized in serial order to remove a portion of the sacroiliac joint 1000 for generation of an implant receiving space 1029 (see, for example, FIG. 99H). As these embodiments of the method, articular cartilage or other tissues and sufficient subchondral bone can be removed from between the articular surfaces 1016 of the sacroiliac joint 1000 sufficient to allow placement of certain embodiments of the sacroiliac joint implant 25 and one or more radial member receiving channels 1074 can be cut into at least one of the articular surfaces 1016 of said sacroiliac joint 1000 sufficient to receive other embodiments of the sacroiliac implant 25. The one or more radial member receiving channels 1074 can be cut a depth into the subchondral, cortical bone or cancellous bone of the sacrum 1004 or ilium 1005.

Now referring primarily to FIG. 99G in a subsequent step, the last in the serial presentation of drill jigs 1067, 1072 can be removed from within the cannula 1057 and a broach jig 1075 can be advanced over the probe body 1054 to locate within the cannula 1057. The broach jig 1075 can include a broach guide hole 1076 which receives a first broach end 1077 of a cannulated broach 1078 advanced over the probe body 1054. The first broach end 1077 can have a configuration which can be advanced into the sacroiliac joint 1000. As to certain embodiments of the method, the first broach end 1077 can be adapted to remove an amount of articular cartilage and other tissue from between the articular surfaces 1016 within the articular region 1044 of the sacroiliac joint 1000 for non-transverse placement of a sacroiliac joint implant 25 having an elongate body 45, or having an elongate body 45 and a first radial member 50, or an elongate body 45 having a first and second radial members 50 between the articular surfaces 1016 of the sacroiliac joint 1000. As to other embodiments of the method, the cannulated broach 1078 can remove a sufficient portion of the sacroiliac joint 1000 to generate an implant receiving space 1029 to receive embodiments of the sacroiliac joint implant 25 having an elongate body 45, an elongate body 45 and at least one radial member 50 adapted for non-transverse placement between the articular surfaces 1016 or at least one radial member 55 adapted to extend into the bone of the sacrum 1004 or the ilium 1005.

As a non-limiting example, FIG. 99G shows a broach 1078 configured to remove a portion of the sacroiliac joint 1000 to produce an implant receiving space 1029 (shown in FIG. 99H) to receive embodiments of the sacroiliac joint implant 25 having an elongate body 45 to which a first radial member 50 and a second radial member 50 extend along the longitudinal axis CA of the elongate body 45 in substantially opposed relation adapted to locate between the articular surfaces 1016 of the sacroiliac joint 1000 and further having a third radial member 55 and a fourth radial member 55 which extend along the longitudinal axis CA of the elongate body 45 in substantially opposed relation adapted to correspondingly extend correspondingly into the bone of the sacrum 1004 and the ilium 1005.

Now referring primarily to FIGS. 102A-102D, the implant receiving space 1029 and the sacroiliac joint implant 25 can be configured having related dimension relations such that placement of the sacroiliac joint implant 25 within the implant receiving space 1029 disposes the sacrum 1004 and the ilium 1005 in substantially immobilized relation and substantially avoids alteration of the positional relation of the sacrum 1004 and the ilium 1005 from the normal condition, or avoids driving together or driving apart the sacrum 1004 from the ilium 1005 outside of or substantially outside of the normal positional relation. An intention in selecting configurations of the sacroiliac joint implant 25 and the implant receiving space 1029 being immobilization of the sacrum 1004 in relation to the ilium 1005 while maintaining the sacroiliac joint 1000 in substantially normal or substantially normal positional relation, or returning the sacroiliac joint 1000 to a substantially normal positional relation to correct a degenerative condition of the sacroiliac joint 1000.

As a non-limiting example, configurations of an implant receiving space 1029 allow embodiments of the sacroiliac joint implant 25 to be placed non-transversely between the caudal portion 1086 of the articular surfaces 1016 of the sacroiliac joint 1000. While certain embodiments of the sacroiliac joint implant 25 may only provide an elongate body 45 which locates within a correspondingly configured implant receiving space 1029 to engage at least a portion of the bone of the ilium 1005 or sacrum 1004, the invention is not so limited, and can further include at least a first radial member or a first and a second radial member at least a portion of the external surface of the first radial member 50 engaging a portion of the bone 1073 of the sacrum 1004 and the ilium 1005. As to those embodiments of the sacroiliac joint implant 25 which have a third radial member 55 and a fourth radial member 55, the implant receiving space 1029 can further include one or more radial member receiving channels 1074, which correspondingly allow the third and fourth radial members 55, 55 to extend into the bone 1073 of the sacrum 1004 or the ilium 1005 (whether subchondral, cortical, cancellous, or the like), or impact of the sacroiliac joint implant 25 into the implant receiving space 1029 without the radial member receiving channels 1074 can forcibly urge the radial members 55, 55 into the bone 1073 of the sacrum 1004 and the ilium 1005. An anchor member 30 (such as treaded members) can be inserted through the bore 40 in the implant 25 and into the sacrum 1004 and ilium 1005 to fix the location of the fixation fusion implant 25 within the implant receiving space 1029.

While the preceding discussion is given in the context of the implant 25 being implanted non-transversely in the caudal portion 1086 of the sacroiliac joint 1000, in other embodiments, the implant 25 may be implanted in other locations within the sacroiliac joint. For example, as disclosed in U.S. patent application Ser. No. 12/998,712, now U.S. Pat. No. 8,979,928, which is incorporated herein by reference, in some embodiments, the implant 25 may be implanted non-transversely in the cranial portion 1087 (see FIG. 102A) of the sacroiliac joint 1000 by the similar procedures or steps as above described with the incision and generation of the passage to the superior articular portion of the sacroiliac joint 1000. The implant may also be implanted in the sacroiliac joint in such a manner so as to extend between the cranial and caudal portions, as also disclosed in U.S. patent application Ser. No. 12/998,712, now U.S. Pat. No. 8,979,928.

Figure 103A:
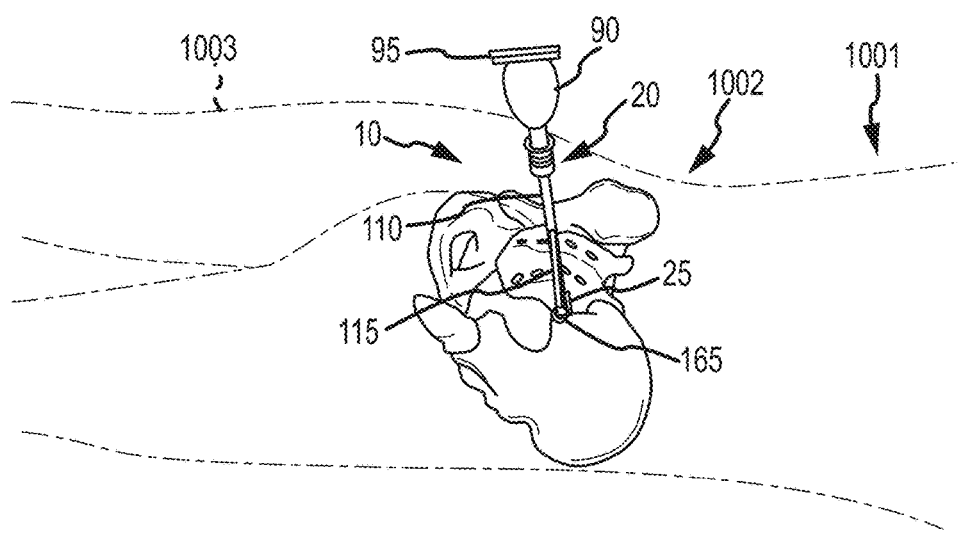
FIG. 103A is generally the same view as FIG. 97A, except illustrating the delivery tool being used to deliver the implant to the sacroiliac joint space.
Figure 103B:
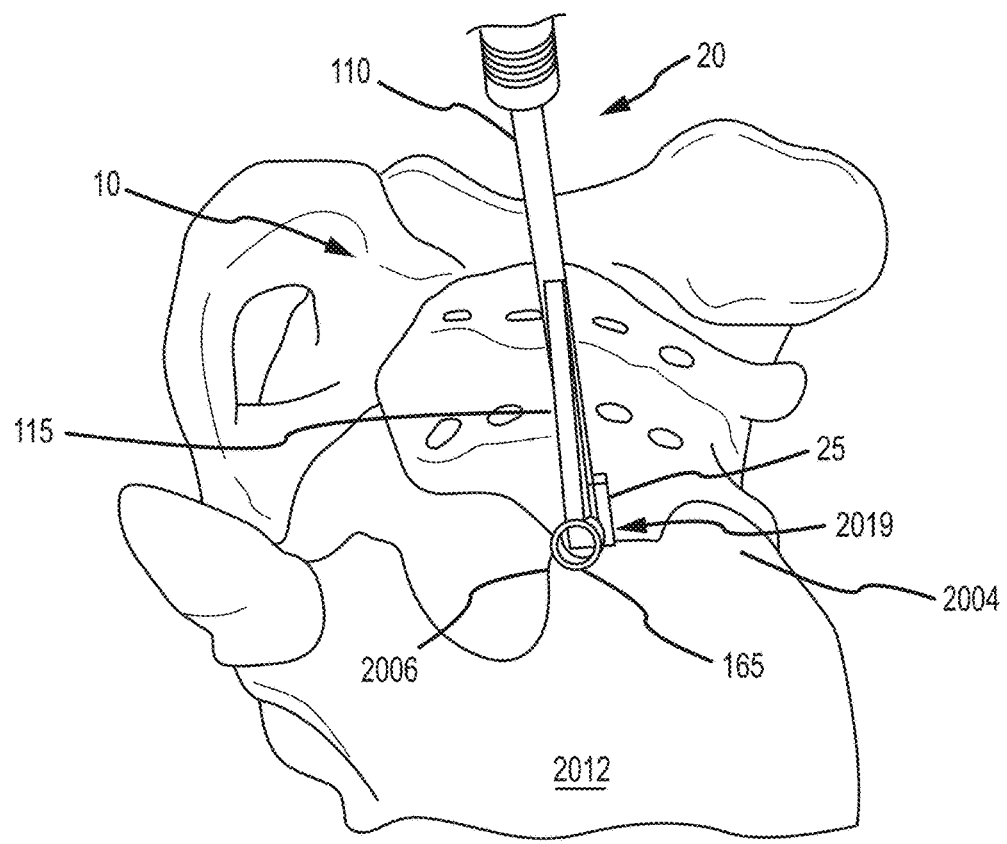
FIG. 103B is an enlarged view of the hip region of FIG. 103A.
Figure 104:
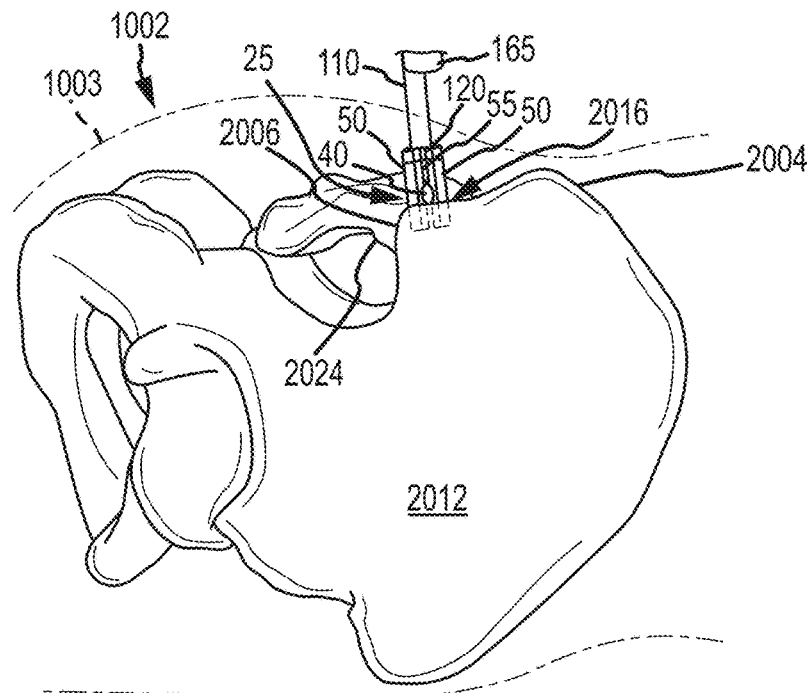
FIG. 104 is generally the same enlarged view as FIG. 96B, except illustrating the delivery tool being used to deliver the implant to the sacroiliac joint space.

To begin a discussion of employing the delivery tool 20 to implant the implant 25 in the sacroiliac joint 1000 once the implant receiving space 1029 has been created, reference is made to FIGS. 99I, 103A, 103B and 104. FIG. 103A is generally the same view as FIG. 97A, and FIG. 103B is an enlarged view of the hip region of FIG. 103A. FIG. 104 is generally the same enlarged view as FIG. 96B. As shown in FIGS. FIGS. 99I, 103A, 103B and 104, once the implant receiving space 1029 has been created as discussed above with respect to FIGS. 99A-99H, the implant 25 can be supported off of the distal end 120 of the implant arm 110 of the delivery tool 20 and positioned such that the distal end 42 of the implant 25 begins to enter the sacroiliac joint articular region 1044 via the posterior inferior access region 2016, which is described in detail above with respect to FIGS. 96A-98B. As can be understood from FIGS. 103A-104, in entering the sacroiliac joint space, the implant 25 is oriented such that its wide planar members 50 are oriented generally parallel to, and aligned with, the sacroiliac joint line 2019 (i.e., the wide planar members 50 are generally located within the joint plane 1030), and the implant's narrow planar members 55 are generally transverse to the joint plane 1030 (see, e.g., FIGS. 102C and 102D). The longitudinal axis $LCA_2$ of the implant arm 110 of the delivery tool 20 has a generally anterior trajectory that is located within the joint plane 1030. Alternatively, according to particular embodiments, as a non-limiting example, the longitudinal axis $LCA_2$ of the implant arm 110 of the delivery tool 20 can have a trajectory which can be defined as being generally lateral or, in particular embodiments, generally posterior. In some embodiments, when the implant 25 is being delivered into the joint space, the implant arm 110 can be said to be at least one of generally superior or cephalad the sciatic notch.

Figure 99J:
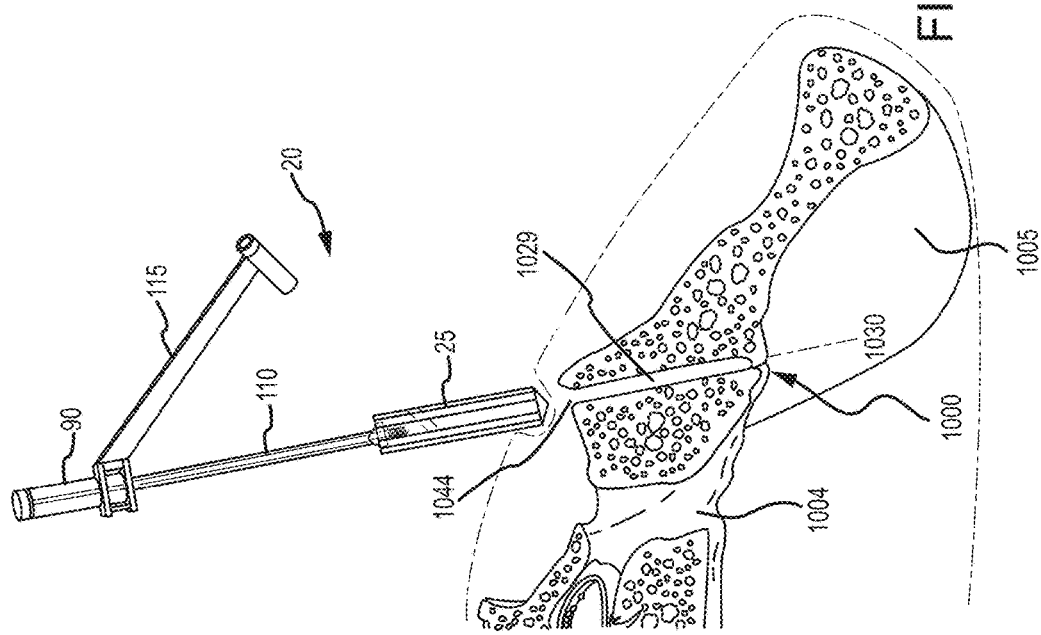
Figure 105:
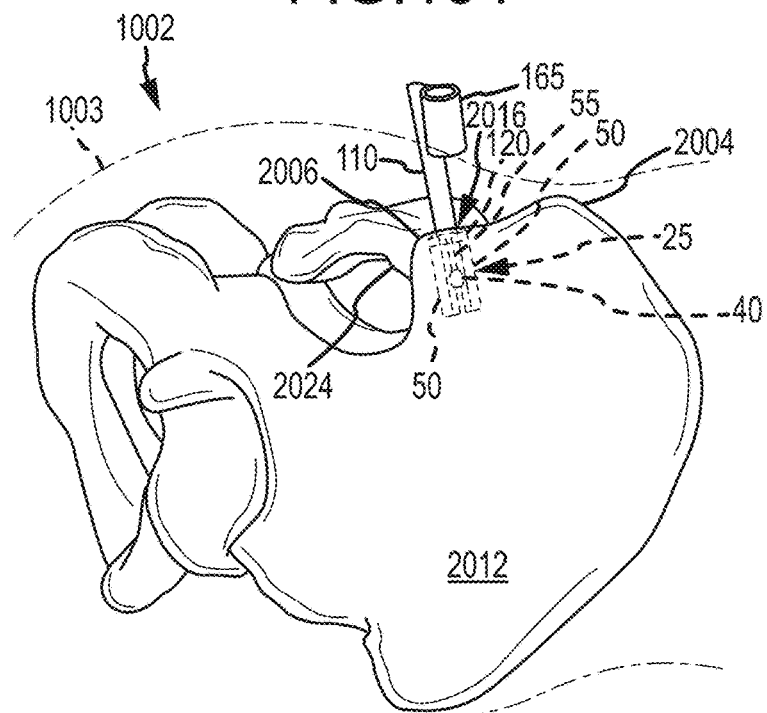
FIG. 105 is the same view as FIG. 104, except the implant has now been fully inserted into the prepared space in the sacroiliac joint.

FIG. 105 is the same view as FIG. 104, except the implant 25 has now been fully inserted into the prepared space 1029 in the sacroiliac joint 1000. As illustrated in FIGS. 99J and 105, the implant 25 is fully received in the prepared sacroiliac space 1029 such that the wide planar members 50 are oriented generally parallel to, and aligned with, the sacroiliac joint line 2019 (i.e., the wide planar members 50 are generally located within the joint plane 1030), and the implant's narrow planar members 55 are generally transverse to the joint plane 1030 and, in some embodiments, have even entered the bone material forming the sacrum and ilium articular surfaces of the sacroiliac joint (see, e.g., FIGS. 102C and 102D). As can be understood from FIG. 99J, the longitudinal axis of the implant 25 and the longitudinal axis of the implant arm 110 may be coaxially aligned with each other and generally located in the sacroiliac joint plane 1030.

Figure 106A:
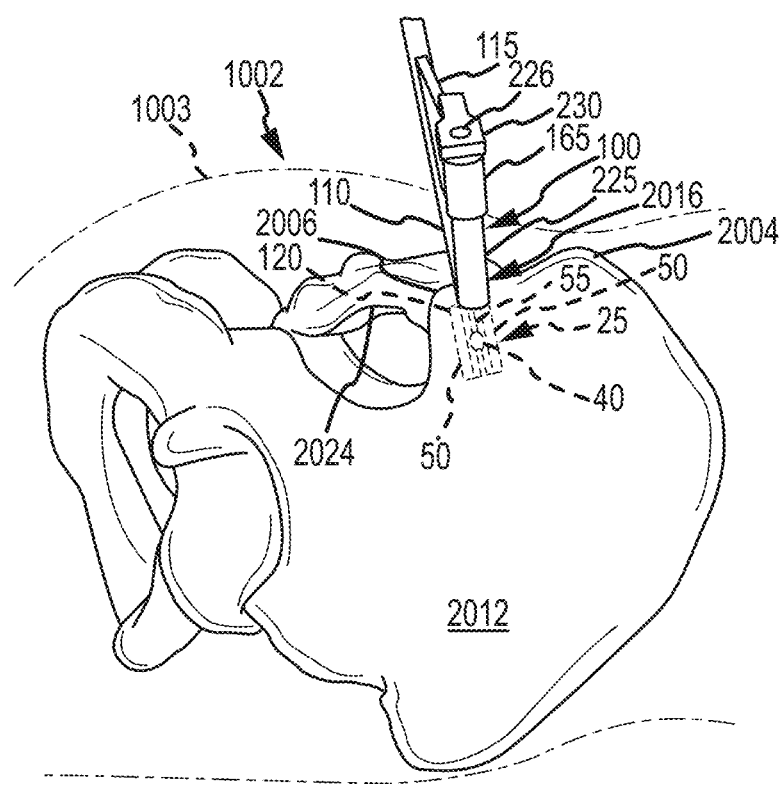
FIG. 106A is the same view as FIG. 104, except the sleeve is now received in the collar of the anchor arm.

FIG. 106A is the same view as FIG. 104, except the sleeve 100 is now received in the collar 165 of the anchor arm 115. As can be understood from FIGS. 99K and 106A, the distal end of the sleeve 100 may extend through an incision in the patient's soft tissue such that the distal end of the sleeve 100 is positioned generally against the lateral surface of the ilium 1005. The longitudinal axis of the sleeve and collar of the anchor arm can be understood to be generally coaxially aligned with the longitudinal axis of the bore 40 of the implant 25.

Figure 106B:
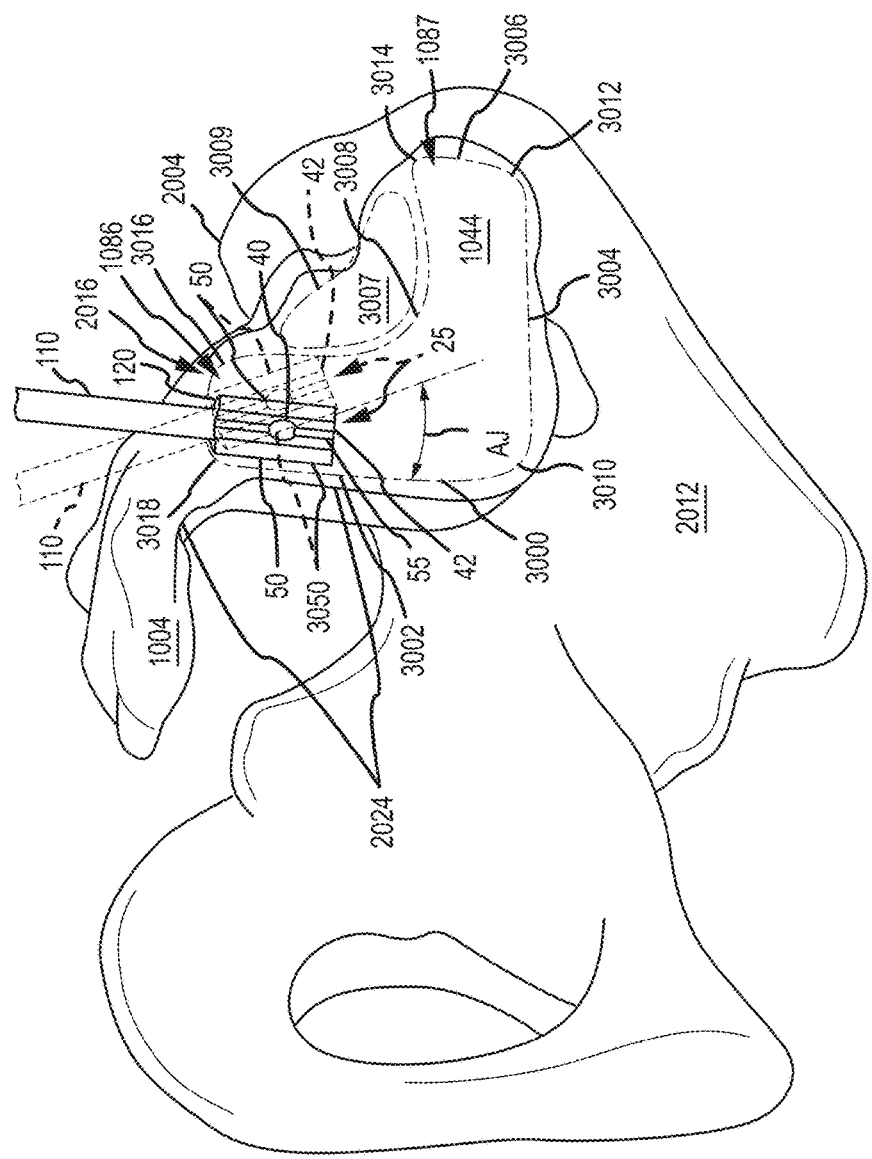
FIG. 106B is generally the same view as FIG. 106A, except the ilium is removed to show the sacroiliac joint space boundary defined along the sacrum and the implant positioned for implantation within the joint space.

FIG. 106B is generally the same view as FIG. 106A, except the ilium 1005 is removed to show the sacroiliac joint space boundary 3000 defined along the sacrum 1004 and outlining the sacroiliac joint articular region 1044, the implant 25 positioned for implantation within the sacroiliac joint articular region 1044. As shown in FIG. 106B, the sacroiliac joint space boundary includes an inferior boundary segment 3002, an anterior boundary segment 3004, a superior boundary segment 3006, and a posterior boundary segment 3008. The inferior boundary segment 3002 is immediately adjacent, and extends along, the sciatic notch 2024.

The inferior boundary segment 3002 and anterior boundary segment 3004 intersect to form an anterior-inferior corner 3010. The anterior boundary segment 3004 and superior boundary segment 3006 intersect to form an anterior-superior corner 3012. The superior boundary segment 3006 and posterior boundary segment 3008 intersect to form a superior-posterior corner 3014. The posterior boundary segment 3008 and posterior inferior access region 2016 intersect to form a superior-posterior corner 3016 of the posterior inferior access region 2016. The inferior boundary segment 3002 and posterior inferior access region 2016 intersect to form an inferior-posterior corner 3018 of the posterior inferior access region 2016.

The inferior boundary segment 3002 extends between corners 3010 and 3018. The anterior boundary segment 3004 extends between corners 3010 and 3012. The superior boundary segment 3006 extends between corners 3012 and 3014 and provides an access into the cranial portion 1087 of the sacroiliac joint. The posterior boundary segment 3008 extends between corners 3014 and 3016. The posterior inferior access region 2016 extends between corners 3016 and 3018 and provides an access into the caudal region 1086 of the sacroiliac joint. The posterior boundary segment 3008 separates articular region 1044 and extra-articular region 3007, which includes the sacral fossa on the sacrum 1004 and the corresponding iliac tuberosity on the ilium 1005 and defined by the extra-articular region boundary 3009.

As shown in FIG. 106B, the implant 25 is inserted via the implant arm 110 of the delivery tool 20 into the caudal region 1086 of the sacroiliac joint articular region 1044. As shown via the implant 25 and implant arm 110 shown in solid lines, in one embodiment, the implant 25 enters the posterior inferior access region 2016, and is further advanced into the caudal region 1086 of the sacroiliac joint articular region 1044, in an orientation such that the implant arm 110 and wide planar members 50 are in the joint plane 1030 (see, for example, FIGS. 99I-99J) and the longitudinally extending edge 3050 of the wide planar member 50 next to the inferior boundary segment 3002 is generally parallel to, and immediately adjacent to, the inferior boundary segment 3002. Thus, the distal end 42 of the implant is heading generally perpendicular to, and towards, the anterior boundary segment 3004.

As shown in FIG. 106B via the implant 25 and implant arm 110 shown in dashed lines, in one embodiment, the implant 25 enters the posterior inferior access region 2016, and is further advanced into the caudal region 1086 of the sacroiliac joint articular region 1044, in an orientation such that the implant arm 110 and wide planar members 50 are in the joint plane 1030 (see, for example, FIGS. 99I-99J) and the longitudinally extending edge 3050 of the wide planar member 50 next to the inferior boundary segment 3002 is somewhere between being generally parallel to the inferior boundary segment 3002 (as illustrated by the solid-lined implant 25 in FIG. 106B) or forming an angle AJ with the inferior boundary segment 3002 of up to approximately 50 degrees. Thus, the distal end 42 of the implant shown in dashed lines can be said to head anywhere from generally perpendicular to, and towards, the anterior boundary segment 3004 to heading generally towards the superior-anterior corner 3012, or points in between.

In one embodiment, the implant 25 may be first directed into the joint space as illustrated by the solid-lined implant 25 in FIG. 106B after which the implant 25 is rotated within the joint space to be positioned somewhere between, and including, angled position depicted by the dashed-lined implant 25. In other embodiments, the implant 25 may be first directed into the joint space as illustrated by the dashed-lined implant 25 in FIG. 106B after which the implant 25 is rotated within the joint space to be positioned somewhere between, and including, the parallel position depicted by the solid-lined implant 25.

Figure 107A:
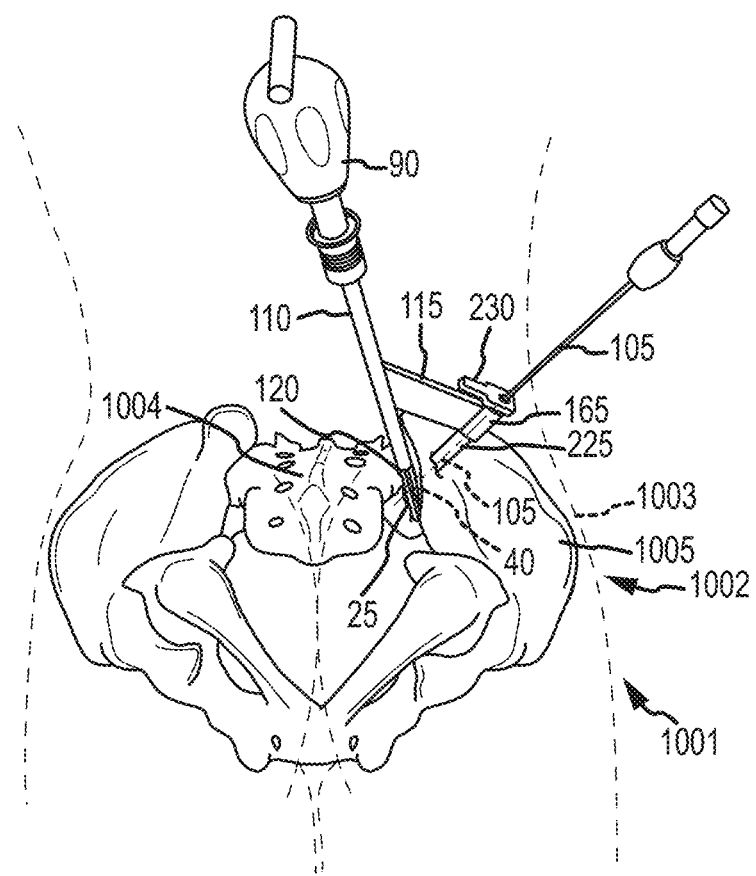
FIG. 107A is a posterior-inferior view of the hip region of the patient, wherein the soft tissue surrounding the skeletal hip bones is shown in dashed lines.
Figure 107B:
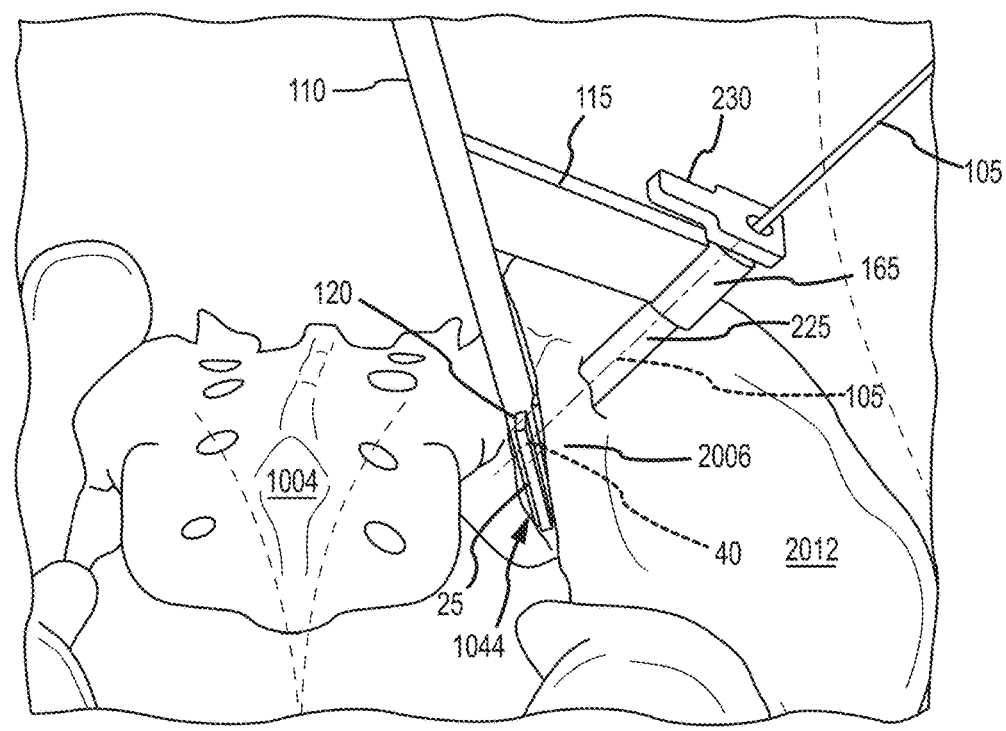
FIG. 107B is an enlarged view of the implant region of FIG. 107A.

FIG. 107A is a posterior-inferior view of the hip region 1002 of the patient 1001, wherein the soft tissue 1003 surrounding the skeletal hip bones is shown in dashed lines. FIG. 107B is an enlarged view of the implant region of FIG. 107A. As can be understood from FIGS. 99L, 107A and 107B, the anchor member 30 is positioned in the lumen of the sleeve 100. A driving tool 105 (e.g., screw driver) is extended through the lumen of the sleeve 100 so the distal end of the tool 105 is engaged with a proximal end of the anchor member 30 (e.g., screw). As shown in FIG. 99M, the tool 105 is used to drive the anchor member 30 distally through the bone of the ilium 1005 and into the bore 40 of the implant 25 generally transverse to the joint line plane 1030. As a result, as indicated in FIG. 99N, the implant assembly formed of the implant 25 and anchor member 30 is secured at the implantation site such that the implant 25 is located in the prepared space 1029 of the sacroiliac joint space, and the anchor member 30 extends through the bone of the ilium 1005 and into the implant bore 40 generally transverse to the joint space plane 1030. The tool 105 and sleeve 100 can be removed from the anchor arm collar 165, and the incision associated with the sleeve 100 can be closed. Additionally, tool 105 can be a cutting tool 105 (e.g., drill bit, hole punch, or etc.) which can used in similar steps as above describe to remove bone or other tissues in the path where anchor member 30 is to be placed.

Figure 99O:
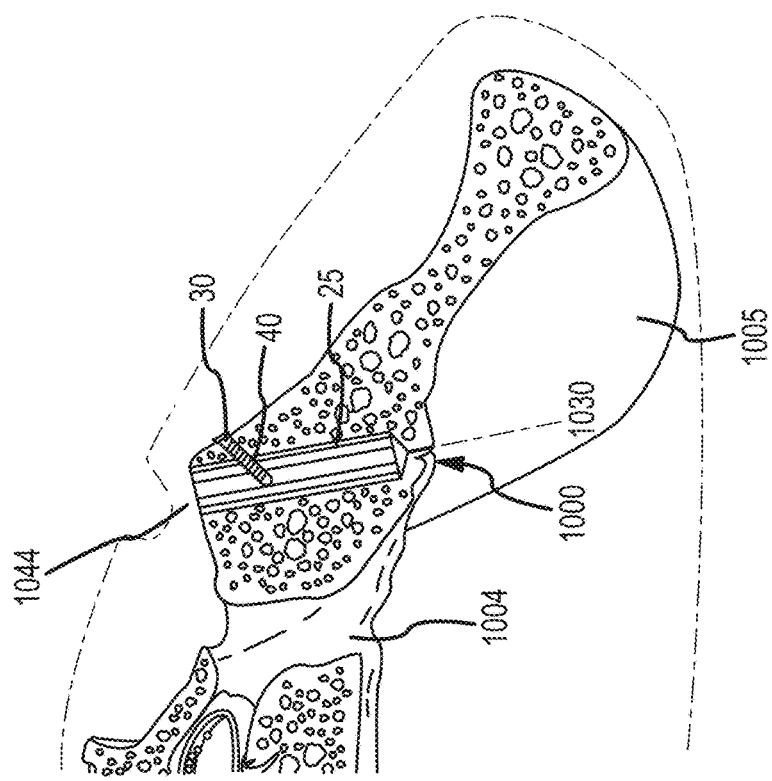
Figure 99P:
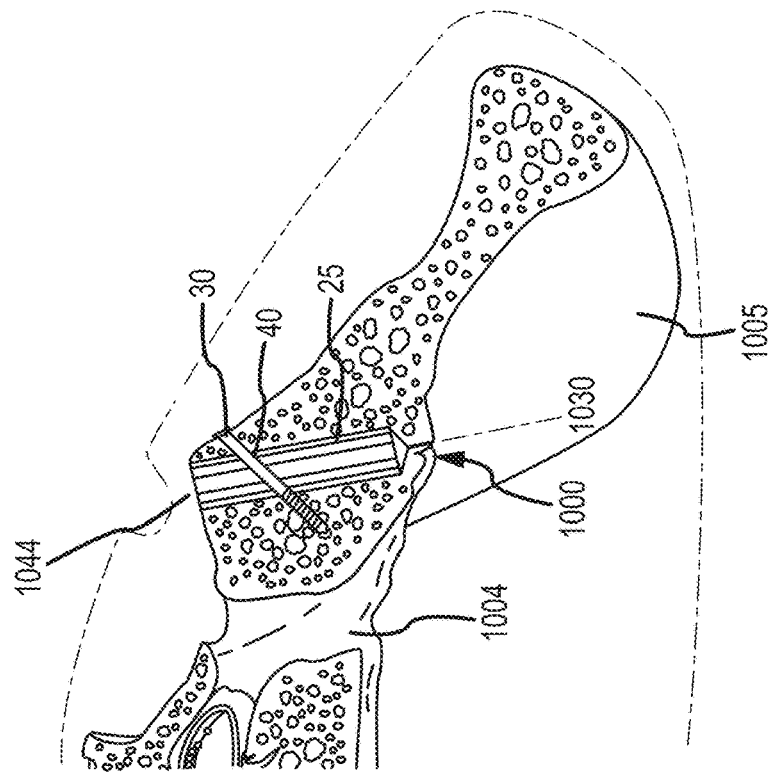
Figure 99Q:
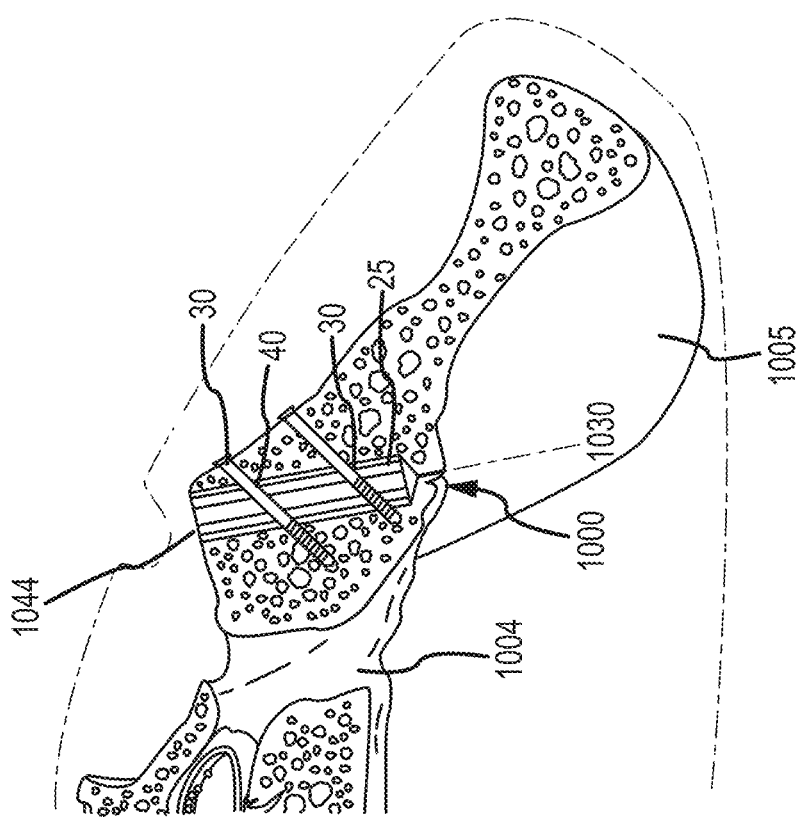

As indicated in FIG. 99O, the distal end of the implant arm is decoupled from the proximal end of the implant 25 and removed. The incision associated with the implant arm can be closed. In some embodiments, the anchor member 30 will only be long enough to span bone of the ilium 1005 and enter the implant bore 40. In other embodiments, as illustrated in FIG. 99P, the anchor member 30 will be sufficiently long to extend through the bone of the ilium, completely through the implant bore 40, and into the bone of the sacrum 1004. As illustrated in FIG. 99Q, in certain embodiments, implant 25 can be configured to have more than one implant bore 40 which can also receive an anchor member 30. The anchor member 30 prevents migration of the implant 25 within the joint space. The anchor member 30 also can draw the ilium and sacrum together about the implant 25, increasing the sturdiness of the fixation of the implant in the joint space. Where the anchor member extends through the implant bore and into the bone of both the sacrum and ilium, the anchor member 30 can be used to drawn the articular surfaces 1016 of the sacroiliac joint 1000 against the external surfaces of the sacroiliac joint implant 25. With the implant implanted in the sacroiliac joint, the body will cause the joint surfaces to fuse together about the implant 25.

Figure 108A:
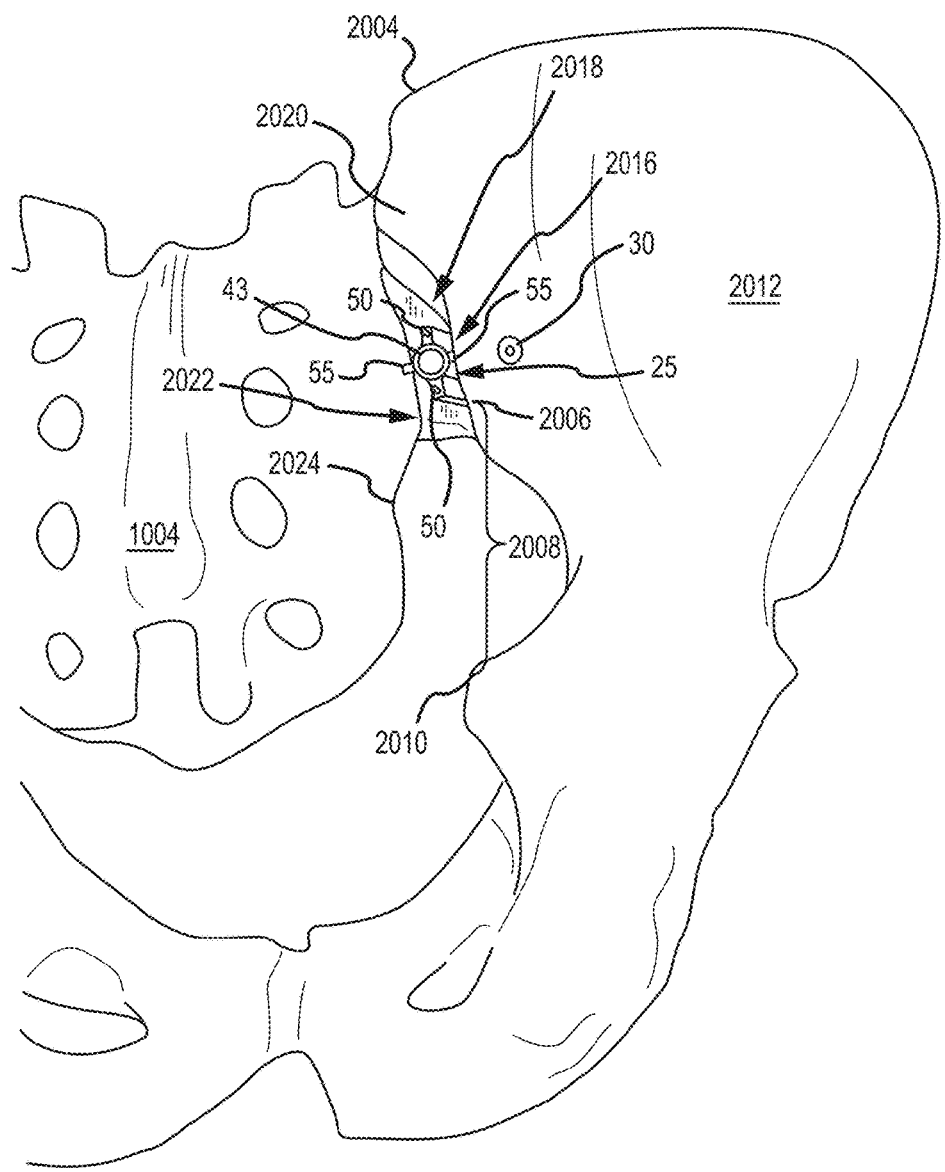
FIGS. 108A and 108B are, respectively, posterior and posterior-lateral views of the implantation area and the implant assembly implanted there.
Figure 108B:
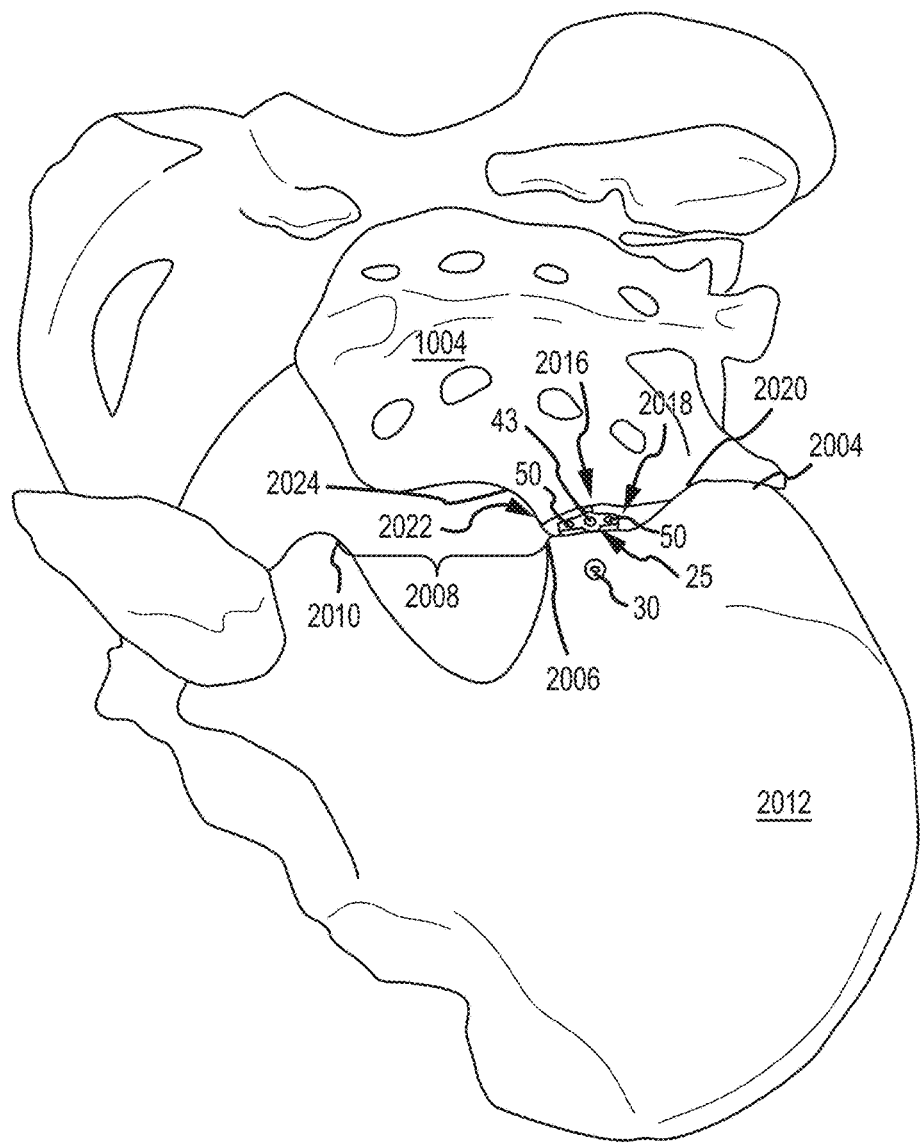

As can be understood from FIGS. 108A and 108B, which are, respectively, posterior and posterior-lateral views the implantation area and the implant assembly implanted there, proximal end 43 of the implant 25 can be seen positioned in the posterior inferior access region 2016, the implant being implanted in the caudal area of the sacroiliac joint space. The anchor member 30 can be understood to have been driven into the implant bore 40 transversely to the joint plane 1030 via a route in the ilium 1005 that avoids contact with vascular and neurological structures, thereby avoiding potentially life threatening injury to such structures. The ability to blindly, yet safely, drive the anchor member 30 into the implant bore 40 while the implant 25 is hidden in the joint space is made possible by the cooperating configurations of the implant 25 and the delivery tool 20. Specifically, the longitudinal axis $LCA_1$ of the anchor arm collar 165 being coaxially aligned with the longitudinal axis BA of the implant bore 40 when the proximal end 43 of the implant 25 is supported off of the implant arm 115 of the delivery tool 20 makes it possible to safely drive the anchor member 30 through the ilium 1005 bone and into the implant bore 40 when the implant is hidden in the joint space on account of being delivered to the joint space via the delivery tool 20.

Figure 111A:
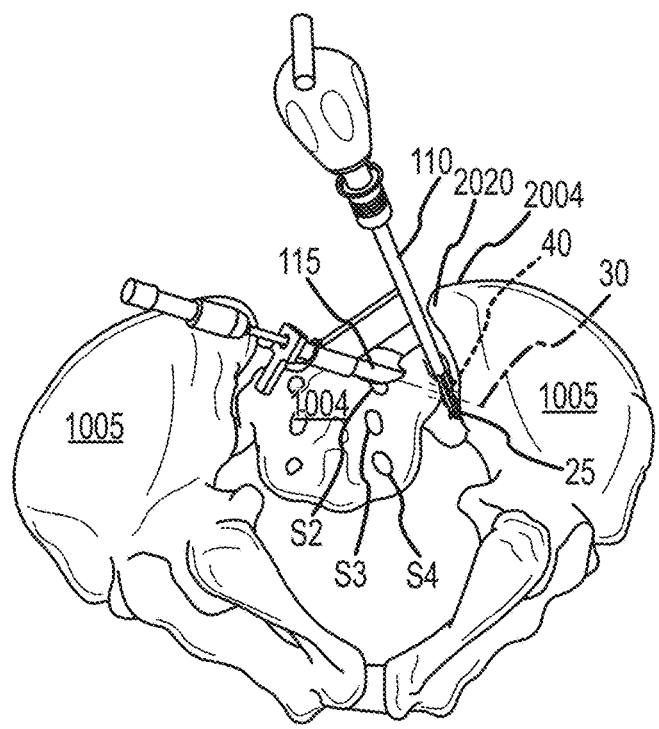
FIG. 111A is an inferior-posterior view of the patient's hip skeletal structure similar to the view depicted in FIG. 107A.
Figure 111B:
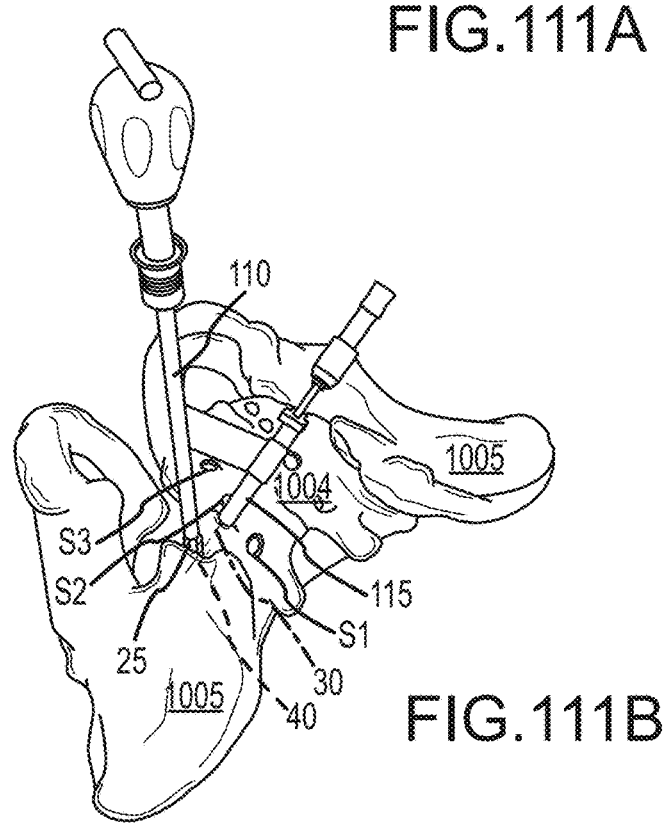
FIG. 111B is a lateral-superior-posterior view of the patient's hip skeletal structure.
Figure 111C:
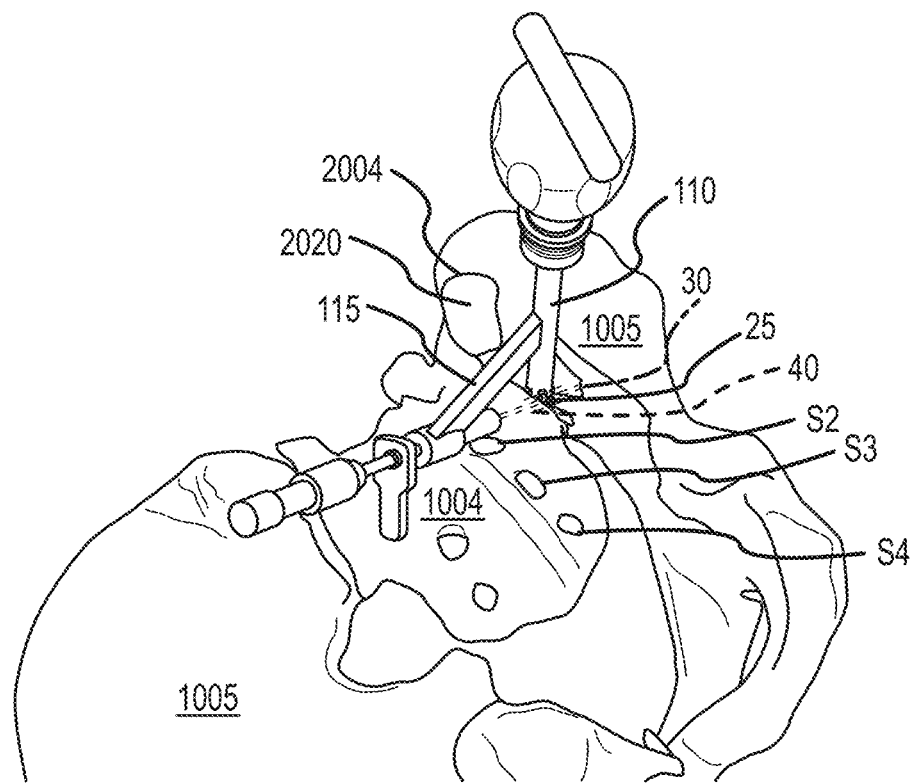
FIG. 111C is an inferior-posterior view of the patient's hip skeletal structure taken from a perspective laterally opposite the view depicted in FIG. 111B.

To begin a detailed discussion of another method of employing the system 10 to fuse the sacroiliac joint, reference is made to FIGS. 111A-111C. FIG. 111A is an inferior-posterior view of the patient's hip skeletal structure similar to the view depicted in FIG. 107A. FIG. 111B is a lateral-superior-posterior view of the patient's hip skeletal structure. FIG. 111C is an inferior-posterior view of the patient's hip skeletal structure taken from a perspective laterally opposite the view depicted in FIG. 111B. The S1 through S4 foramina can be seen at the respective indicators S1, S2, S3 and S4 in FIGS. 111A-111C.

As can be understood from a comparison of FIGS. 111A to 107A, the delivery tool 20 has been reversed such that the anchor collar 165 is oriented so as to deliver the anchor member 30 through the sacrum 1004 first and then into the bore 40 of the implant 25 and optionally further into the ilium 1005. In other words, unlike the method depicted in FIG. 107A, wherein the anchor member 30 is driven lateral to medial through the ilium 1005 first and then into the implant followed by the sacrum 1004 (optional), the method depicted in FIG. 111A shows the anchor member 30 being driven medial to lateral through the sacrum 1004 first and then into the implant followed by the ilium 1005 (optional). As can be understood from a comparison of FIGS. 111A to 107A, the implant 25 of FIG. 111A is located in the sacroiliac joint with its wide radial members 50, narrow radial members 55 and body 45 oriented as explained above with respect to FIGS. 102A-107B, the only difference being the direction the bore 40 is oriented and the way the anchor member 30 penetrates the surrounding bone structures.

In the embodiment of FIG. 111A, the anchor member 30 may be an S2 alar iliac (S2AI) screw. Such a screw may penetrate the sacrum 1004 just lateral the lateral edge of the S1 foramen and, in some instances, generally superiorly-inferiorly even with the superior edge of the S1 foramen so as to mimic an S2 alar iliac pelvic fixation. Alternatively, according to particular embodiments, for example, as shown in FIG. 111A, such a screw may penetrate the sacrum 1004 just lateral the lateral edge of the S2 foramen and, in some instances, generally superiorly-inferiorly even with the superior edge of the S2 foramen.

Figure 112A:
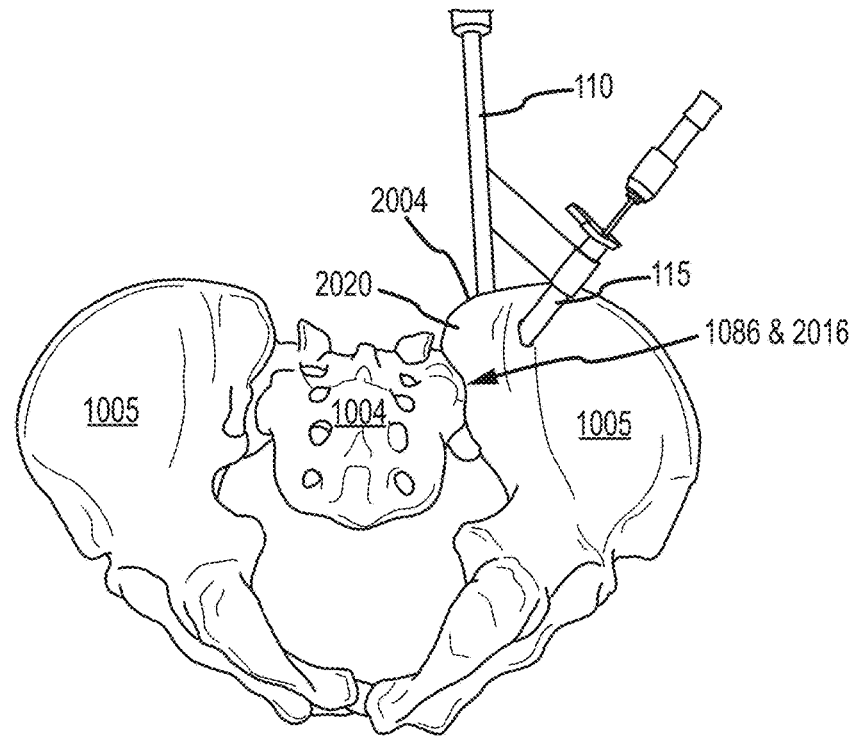
FIG. 112A is an inferior-posterior view of the patient's hip skeletal structure similar to the view depicted in FIG. 107A.
Figure 112B:
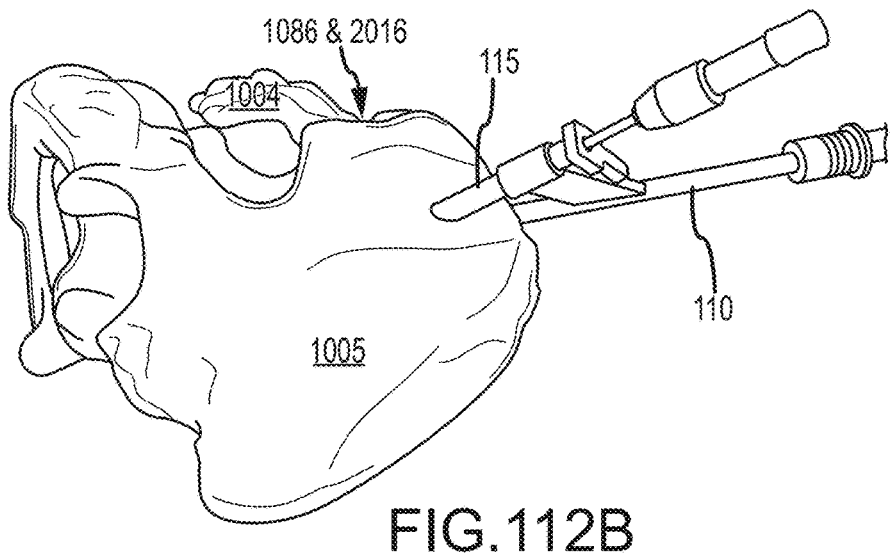
FIG. 112B is a side view of the patient's hip skeletal structure similar to the view depicted in FIG. 106A.
Figure 112C:
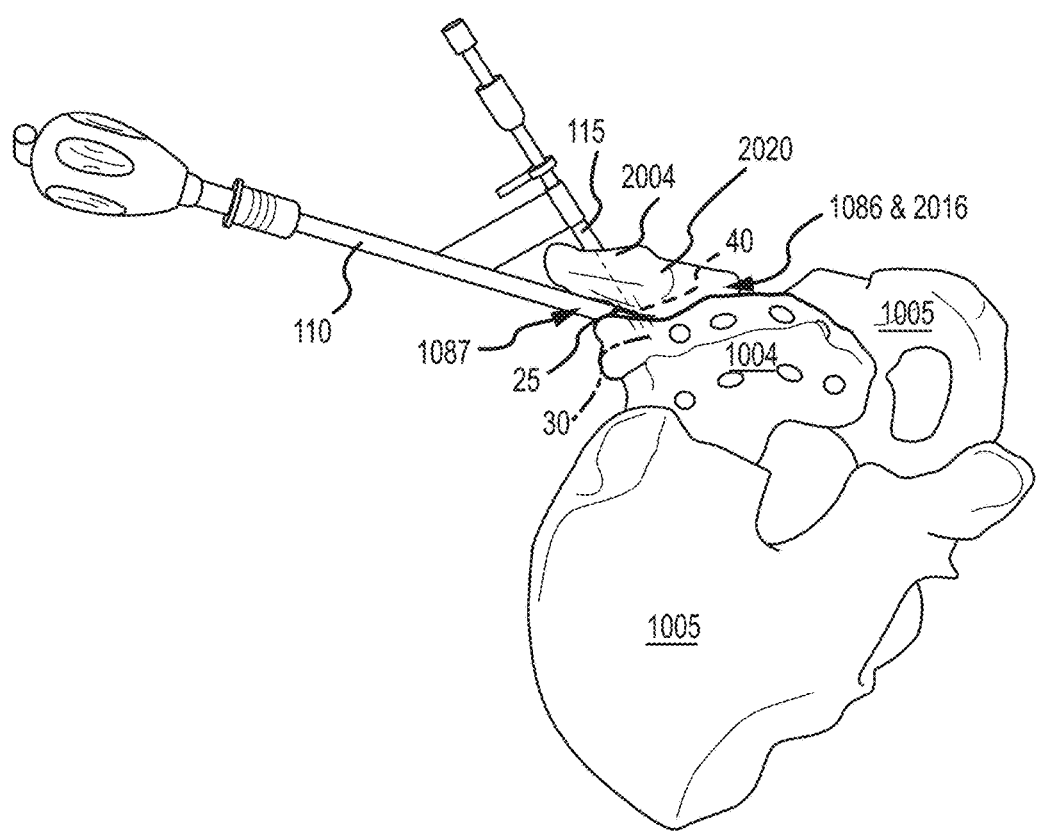
FIG. 112C is a view of the patient's hip skeletal structure similar to the view depicted in FIG. 103A, except from an opposite lateral perspective.
Figure 112D:
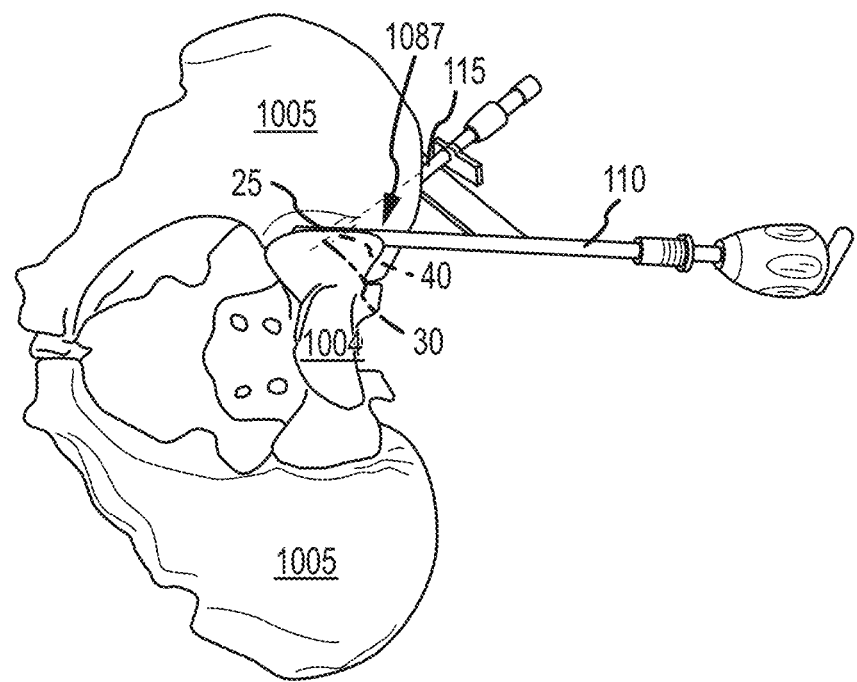
FIG. 112D is a superior view of the patient's hip skeletal structure.

To begin a detailed discussion of another method of employing the system 10 to fuse the sacroiliac joint, reference is made to FIGS. 112A-112D. FIG. 112A is an inferior-posterior view of the patient's hip skeletal structure similar to the view depicted in FIG. 107A. FIG. 112B is a side view of the patient's hip skeletal structure similar to the view depicted in FIG. 106A. FIG. 112C is a view of the patient's hip skeletal structure similar to the view depicted in FIG. 103A, except from an opposite lateral perspective. FIG. 112D is a superior view of the patient's hip skeletal structure.

As can be understood from a comparison of FIGS. 112A and 112B to FIGS. 107A and 106A, respectively, in the embodiment depicted in FIGS. 112A-112D, the delivery tool 20 has a trajectory that is generally superior-to-inferior as opposed to posterior-to-anterior. Further, unlike the embodiments described above wherein the implant 25 gains access to the sacroiliac joint space 1044 via the caudal access 2016 to be implanted in the caudal region 1086 of the sacroiliac joint space 1044 (see, for example, FIG. 106B and related figures and discussion), the embodiment of FIGS. 112A-112D gains access to gains access to the sacroiliac joint space 1044 via the cranial access 2017 (e.g., at the superior border 3006 shown in FIG. 106B) to be implanted in the cranial region 1087 of the sacroiliac joint space 1044 (see, for example, FIG. 112C-112D).

As indicated in FIGS. 112A-112D, the delivery tool 20 is oriented such that the anchor collar 165 is positioned so as to deliver the anchor member 30 through the ilium 1005 first and then into the bore 40 of the implant 25 and optionally further into the sacrum 1004. In other words, the method depicted in FIGS. 112A-112D shows the anchor member 30 being driven lateral to medial through the ilium 1005 first and then into the implant followed by the sacrum 1004 (optional). Other than being delivered via a different trajectory and access location and being implanted in a different region of the sacroiliac joint, the implant 25 of FIGS. 112C-112D is located in the sacroiliac joint with its wide radial members 50, narrow radial members 55 and body 45 oriented as explained above with respect to FIGS. 102A-102D, the only difference being the implant 25 being accessed via, and implanted in, the cranial region 1087 as opposed to the caudal region 1086.

Figure 117C:
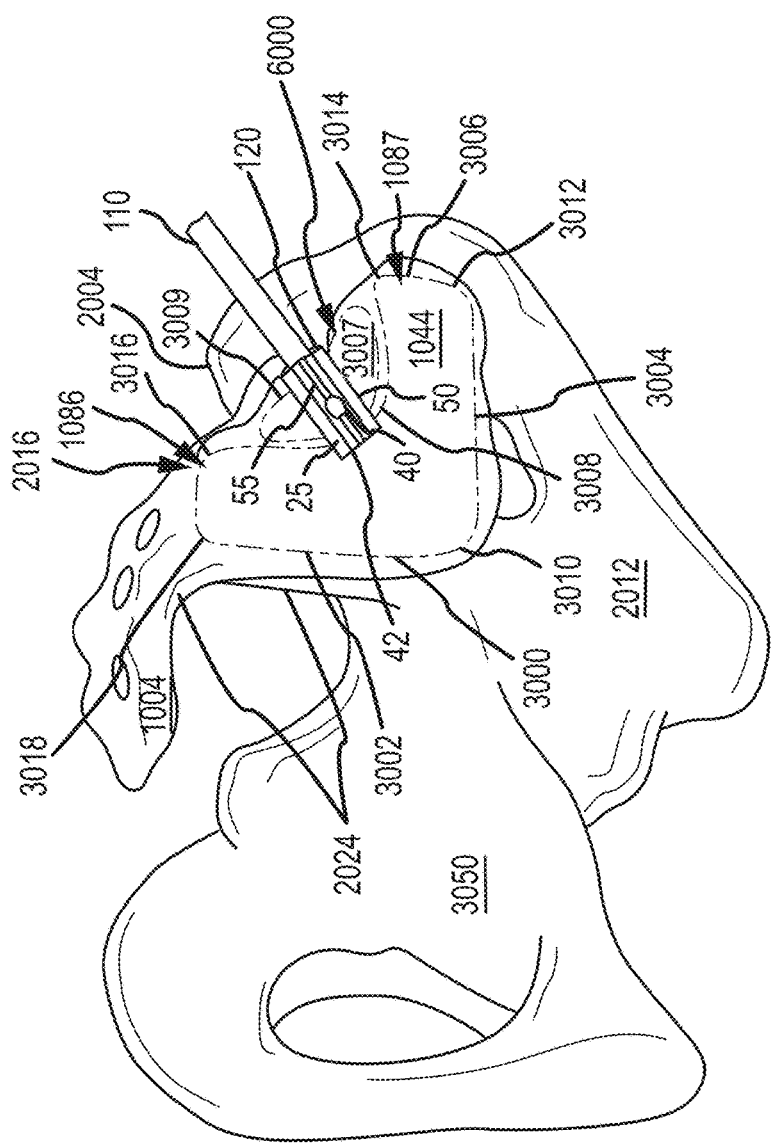
FIG. 117C is the same view as FIG. 106B, except showing the implant being implanted in the extra-articular space, as opposed to the sacroiliac joint articular region.

To begin a detailed discussion of another method of employing the system 10 to fuse the sacroiliac joint, reference is made to FIGS. 117A-117C. FIG. 117A is a lateral-inferior-posterior view of the patient's hip skeletal structure similar to the view depicted in FIG. 111C. FIG. 117B is an inferior-posterior view of the patient's hip skeletal structure similar to the view depicted in FIG. 111A. FIG. 117C is the same view as FIG. 106B, except showing the implant 25 being implanted in the extra-articular space 3007, as opposed to the sacroiliac joint articular region 1044, and accessing the extra-articular space 3007 via an extra-articular recess access region 6000. The S1 through S4 foramina can be seen at the respective indicators S1, S2, S3 and S4 in FIGS. 117A-117B.

As can be understood from a comparison of FIGS. 117A to 107A, the delivery tool 20 has been reversed such that the anchor collar 165 is oriented so as to deliver the anchor member 30 through the sacrum 1004 first and then into the bore 40 of the implant 25 and optionally further into the ilium 1005. In other words, unlike the method depicted in FIG. 107A, wherein the anchor member 30 is driven lateral to medial through the ilium 1005 first and then into the implant followed by the sacrum 1004 (optional), the method depicted in FIG. 117A shows the anchor member 30 being driven medial to lateral through the sacrum 1004 first and then into the implant followed by the ilium 1005 (optional). In the embodiment of FIG. 117A, the anchor member 30 may be a bone screw the same as or similar to an S2 alar iliac (S2AI) screw. Such a screw may penetrate the sacrum 1004 just lateral the lateral edge of the S1 foramen and just superior the superior edge of the S1 foramen. Thus, the anchor element 30 can enter the bone of sacrum near the first sacral foramen (S2AI trajectory) then into or through implant bore 40 and can further enter the bone of the ilium. The implant 25, as with any of the implantation locations and implants 25 discussed herein can optionally be employed to be configured to serve as an attachment point for structural components of a spinal support system with a spanning element as discussed below with respect to FIGS. 115 and 116 or with a coupling element as discussed below with respect to FIG. 114.

As can be understood from a comparison of FIGS. 117A to 107A, FIGS. 117B to 111C, and FIGS. 117C to 106B, the implant 25 of FIG. 117C is located in the extra-articular region 3007 as opposed to the sacroiliac joint articular region 1044. Further, the implant 25 of FIGS. 117A-C has entered the extra-articular region 3007 via an extra-articular recess access region 6000, which, is on the opposite side of the posterior inferior overhang 2020 of the posterior superior iliac spine 2004 from the caudal portion 1086 of the sacroiliac joint articular region 1014 and posterior inferior access region 2016 leading to the sacroiliac joint articular region 1044 employed to implant the implant 25 in the caudal portion 1086 of the sacroiliac joint articular region 1044, as discussed above with respect to FIGS. 103A-108B or FIGS. 111A-111C.

As can be understood from FIG. 117C, the implant 25 is oriented in the extra-articular region 3007 with its wide radial members 50 generally coplanar with the plane of the extra-articular region 3007 and the narrow radial members 55 extending into the sacrum and ilium bone defining each side of the extra-articular region 3007.

As illustrated in FIG. 117C, in some embodiments, the implant 25 is oriented within the extra-articular region 3007 such that the longitudinal axis of the body 45 is generally perpendicular to the posterior boundary segment 3008 of the boundary 3000 of the sacroiliac joint articular region 1014. Also, the distal end 42 of the implant 25, when implanted in the extra-articular region 3007, points towards the anterior-inferior corner 3010 of the boundary 3000 of the sacroiliac joint articular region 1014. The distal end 42 of the implant 25 may extend across the posterior boundary segment 3008 of the boundary 3000 of the sacroiliac joint articular region 1014 and into the sacroiliac joint articular region 1014. Thus, when implanting the implant 25 via the extra-articular recess access region 6000, the general direction of travel for the implant distal end 42 is towards the anterior-inferior corner 3010, and the implant 25 can be positioned substantially within the extra-articular region 3007 or, alternatively, the implant 25 can be further advanced to also occupy a portion of the sacroiliac joint articular region 1044.

As discussed above with respect to FIGS. 117A-117B, in implanting the implant 25 in the extra-articular region 3007, the delivery tool 20 is configured to drive the anchor element 30 medial to lateral through the sacrum 1004 into the implant bore 40 and, optionally, further into the ilium 1005. However, in some embodiments, the delivery tool 20 and implant bore 40 may have as-manufactured configurations that allow the anchor element 30 to be driven lateral to medial through the ilium 1005 into the implant bore 40 and, optionally, further into the sacrum 1004.

Figure 113:
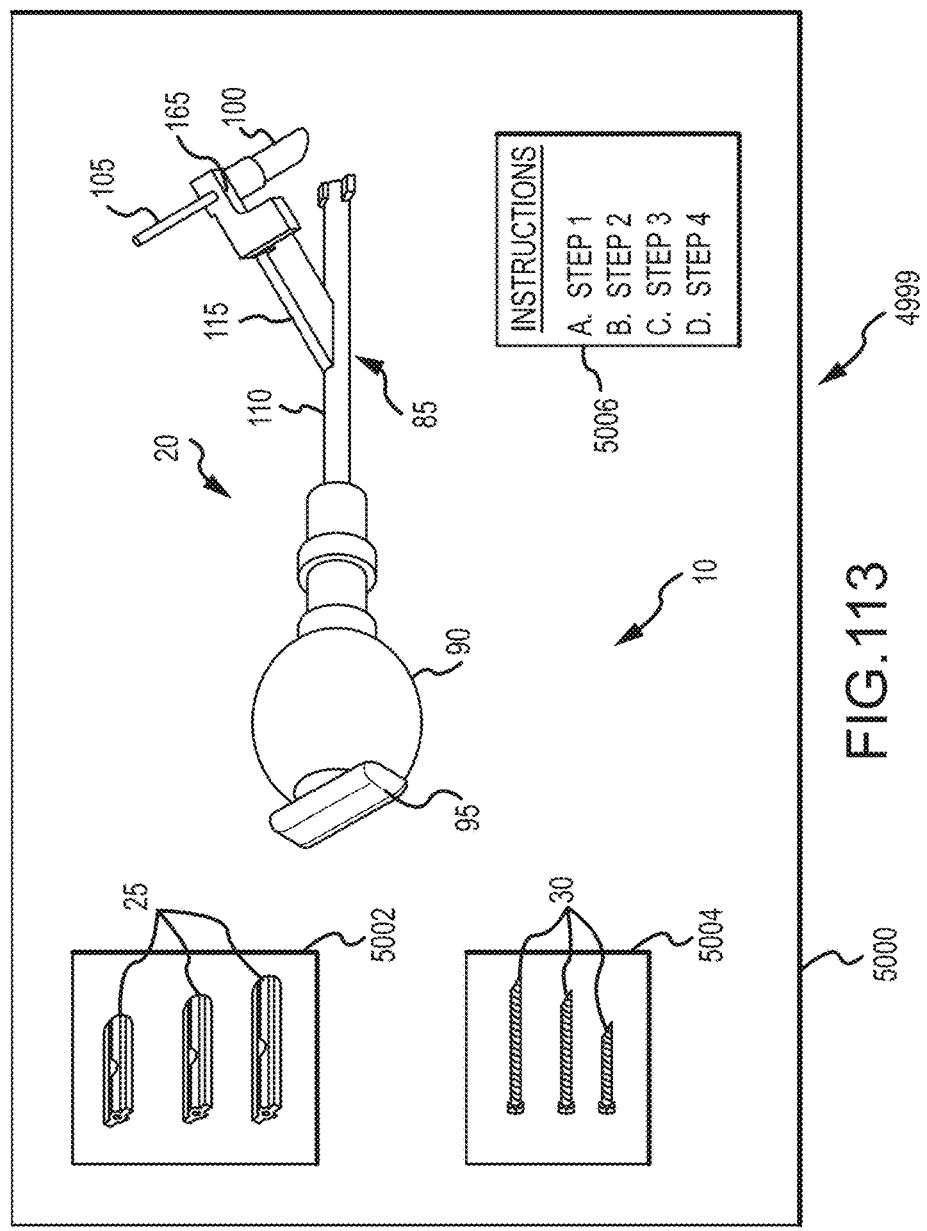
FIG. 113 is a plan view of a medical kit containing the components of the system, namely, the delivery tool, multiple implants of different sizes, and multiple anchor members of different sizes, wherein the system components are sealed within one or more sterile packages and provided with instructions for using the system.

In some embodiments, the system 10 may be provided in the form of a kit 4999. Such a kit 4999 is shown in FIG. 113. The kit 4999 may include the system 10 enclosed in a sterile main package 5000. For example, the delivery tool 20, the implant 25 and anchor member 30 may be sealed within the sterile main package 5000. The delivery tool 20 may be any of the tool embodiments disclosed herein and may include all of its components. Also, the implant 25 may be any of the implant embodiments disclosed herein.

As illustrated in FIG. 113, in some embodiments, the kit 4999 may include multiple sizes of the implant 25 and/or multiple sizes of the anchor member 30. The multiple implants 25 may be contained in a sterile individual package 5002 within the sterile main package 5000, and the multiple anchor members 30 may be contained in another sterile individual package 5004 within the sterile main package 5000. By providing the multiple sizes of implants 25 and anchor members 30, the implants and anchor members can be used as trials during certain steps of the procedure to determine appropriate implant sizes and to allow a physician, who is presented with the kit 4999 containing the delivery system 20 and multiple sizes of the implant and anchor members, to evaluate particular embodiments of an implant and anchor member as described herein that would be best suited to a particular patient, application or implant receiving space. The kit 4999 may also or alternatively contain multiple implants 25 with different angles of bore 40 to provide various desirable trajectories for an anchor member 30 and multiple delivery systems 20 with as-manufactured angular relations corresponding to the different angles of the bore. The kit 4999 may also include color coded, numeric or other indicators corresponding between delivery systems 20 and the corresponding implants 25.

In some embodiments, the kit 4999 may include instructions 5006 that lay out the steps of using the system 10. The instructions 5006 may be contained within one of the sterile packages such as, for example, the sterile main package 5000. Alternatively, the instructions 5006 may be adhered or otherwise attached to an exterior surface of one of the sterile packages such as, for example, the sterile main package 5000. Alternatively, the instructions 5006 may be simply provided separately such as, for example, via simply shipped loose with the rest of the kit 4999, emailed, available for download at a manufacturer website, or provided via a manufacture offered training seminar program.

In some embodiments, the kit 4999 may have any one or more of the tool 20, implants 25 and anchor members 30 contained in individual sterile packages that are not held within a sterile main package. Alternatively, the tool 20, implants 25 and anchor members 30 may be contained in a single common package or in any combination of packages and combination of tool, implants and anchor members.

Figure 114:
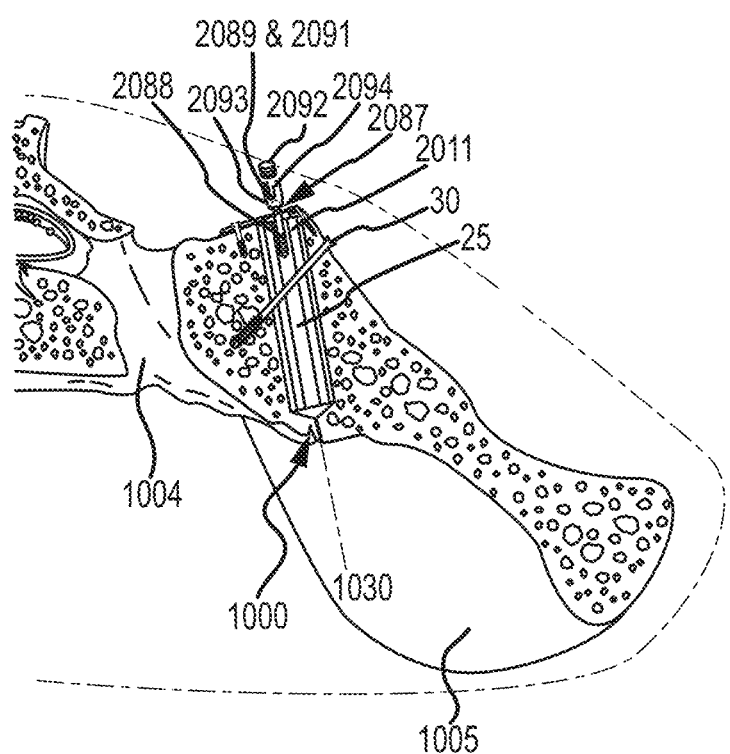
FIG. 114 is the same transverse cross sectional view of the patient's hip as shown in FIGS. 99A-99Q, except showing the implant having structure attached thereto that will allow the implant to serve as an attachment point for structural components of a spinal support system configured to support across the patient's hip structure and/or to support along the patient's spinal column.

As can be understood from FIG. 114, which is the same transverse cross sectional view of the patient's hip as shown in FIGS. 99A-99Q, once the implant 25 and anchor(s) 30 are secured at the sacroiliac joint 1000 in any of the manners depicted in FIGS. 99O-99Q, the implant 25 can be used as an attachment point for structural components of a spinal support system configured to support across the patient's hip structure and/or to support along the patient's spinal column. To serve as an attachment point for structural components of a spinal support system, a coupling element 2087 is connected to the proximal end 2011 of the sacroiliac joint implant 25. As a non-limiting example, the coupling element 2087 can be disposed in fixed relation to the proximal end 2011 of the sacroiliac joint implant 25 by threaded engagement of a fastener portion 2088; however, the invention is not so limited and the fastener portion 2088 can be connected to the first end 2011 of the sacroiliac joint implant 25 by any method such as welding, spin welding, adhesive, or the like. The coupling element 2087 can further provide a coupling portion 2089 configured to join with a numerous and wide variety of cross sectional geometries of spanning members 2090. As a non-limiting example, the coupling portion 2089 can be configured as cylindrical cup 2091 pivotally coupled to the fastener portion 2088. A spiral thread can be coupled to the internal surface of the cylindrical cup 2091 to rotationally receive a spirally threaded body 2092. The side wall 2093 of the cylindrical cup 2091 can include a pass through element 2094 in which part of a spanning member 2090 can be received. The part of the spanning member 2090 received within the pass through element 2094 can be placed in fixed relation to the cylindrical cup 2091 by rotational engagement of the spirally threaded body 2092.

Figure 115:
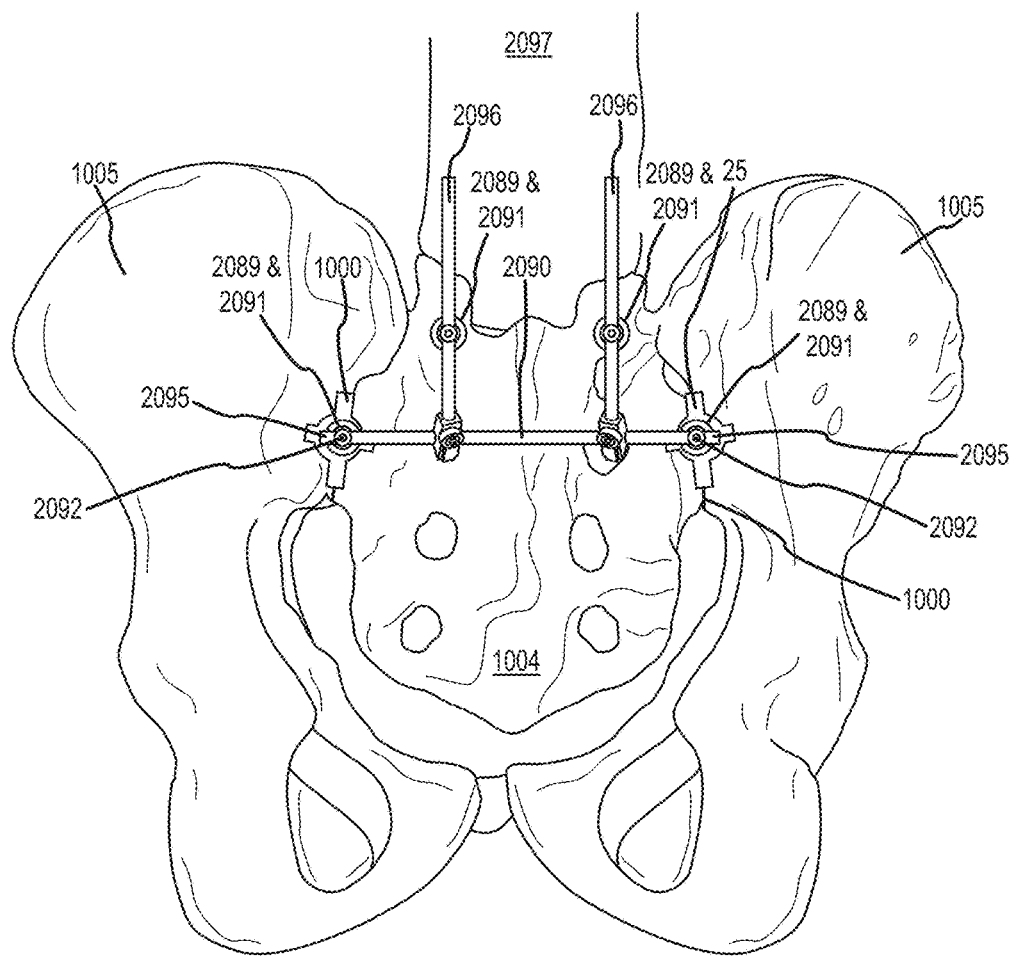
FIG. 115 is a posterior view of the patient's sacrum and ilium, wherein structural components of a spinal support system extend medial-lateral across the patient's hip structure and superiorly to support along the patient's spinal column.

FIG. 115 is a posterior view of the patient's sacrum 1004 and ilium 1005, wherein structural components of a spinal support system extend medial-lateral across the patient's hip structure and superiorly to support along the patient's spinal column. As shown in FIG. 115, in one embodiment, each of a pair of sacroiliac joints 1000 can receive an embodiment of the sacroiliac joint implants 25, above-described, each having a coupling element 2087 coupled to the first end 2011. Each of the coupling elements 2087 can receive the opposed ends 2095 of a spanning member 2090. Additionally, the spanning member 2090 in fixed relation to the sacroiliac joint implants 25 can be connected to a plurality of additional spanning members 2096 which can as a non-limiting example be placed in positional relation to the vertebral column 2097 to allow support of additional implants which can be anchored between vertebrae.

Figure 116:
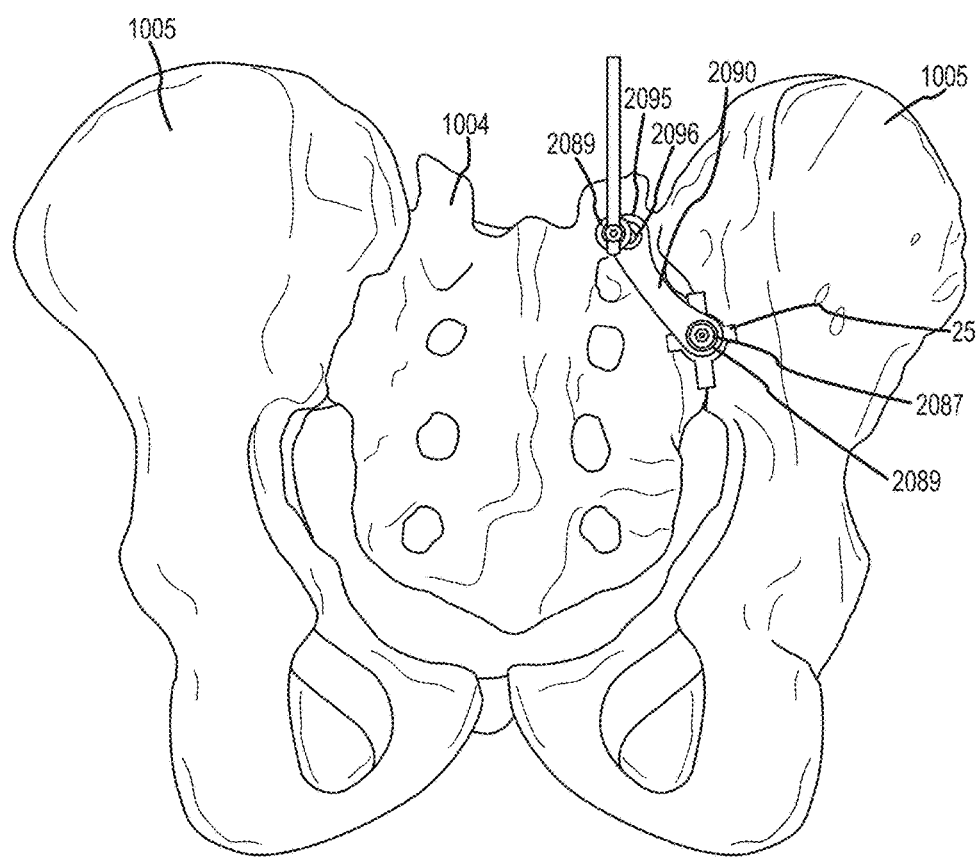
FIG. 116 is the same view as FIG. 115, except having a different spanning member structure.

FIG. 116 is the same view as FIG. 115, except having a different spanning member structure. As illustrated in FIG.

116, a first coupling element 2087 can be joined to the first end 2011 of an embodiment of a sacroiliac joint implant 25 as above described and the fastener portion 2088 of a second coupling element 2087 can be disposed directly into the bone of the sacrum 1004 or the ilium 1005, or both. The opposed ends 2095 of a spanning element 2090 in the form of a flat plate can provide apertures 2096 through which the fastener portion 2088 of the coupling element 2087 can pass. The corresponding parts of the external surface of the coupling portion 2089 and the spanning member 2090 can be engaged to fix the location of the spanning member 2090 allowing for coupling of the lumbar spine to the stabilized pelvis by a plurality of fixation elements to further increase stability. As an example, fastener 2088 can be a pedicle screw and may be implanted in the S1 pedicle and angled generally anteriorly and generally parallel to the S1 endplate. Additionally, spanning element 2090 can be coupled to an implant 25 similar to FIGS. 41-54, or configured similarly but with the spanning element coupled to one of the planar members (e.g., planar member 50 and with spanning element extending radially away from the longitudinal axis of an implant 25 and at least partially existing in the plane of a sacroiliac joint before contouring to the posterior surface of a sacrum and terminating at an opposed end 2095.)

As can be understood from FIG. 116 and with continuing reference to FIGS. 111A-C and 117A-C, according to particular embodiments, the spanning element 2090 can be configured to receive an S2AI screw positioned and directed in a trajectory as substantially shown in FIGS. 111A-C or 117A-C. As a non-limiting example, an S2AI screw or other elongate fixation body can pass through an aperture 2096, which can be located on an opposed end 2095 of the spanning element 2090 and can be disposed directly into the bone of the sacrum 1004, pass through or engage the bore 40 of an implant 25, and into the bone of the ilium 1005. According to certain embodiments, an engagement between an S2AI screw and the bore 40 can be configured, for example, as having a bore 40 which can have threads or other surface that are generally complementary to those of a fastener 2088. Said complementary surfaces can be configured to provide a virtual cold weld between components to further resist undesirable movement.

As shown in FIGS. 119A-119E, which are, respectively, distal end isometric, side elevation, plan, distal end elevation, and proximal end elevation views of another embodiment of an implant 25, the features of the implant 25 of FIGS. 119A-119E are substantially similar to the features of the implant 25 as described herein, for example with respect to FIGS. 4-17. The main differences between the implant 25 described with respect to FIGS. 119A-119E and the implant 25 described with respect to FIGS. 4-17 are the lack of the cylindrical body 45 and the edges of adjacent intersecting surfaces of the implant 25 of FIGS. 119A-119E are generally rounded or arcuate as opposed to sharp or well-defined edges, as is the case between adjacent intersecting surfaces of the implant embodiment of FIGS. 4-17. Further, the planar members 50 may taper distally and be relatively thicker as compared to the planar members 55 of the implant embodiment of FIGS. 119A-119E. For example, the taper may extend the entire length of the implant 25 with the thickness of planar member 50 near implant distal end 42 being about 3-5 mm and the thickness of the planar member 50 near the implant proximal end 43 being about 6-7 mm. Finally, the leading or distal edges 57 of the planar members 50 may be one or more tapered surfaces, as shown in FIGS. 119A-119E.

Figure 120A:
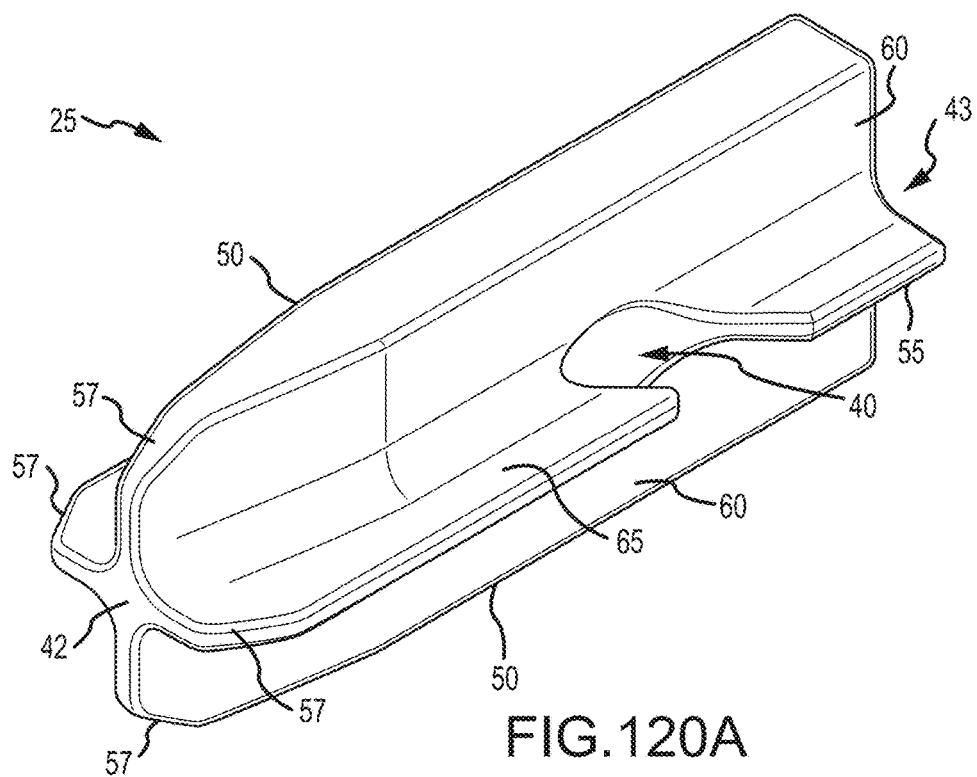
FIGS. 120A-120B are, respectively, distal end isometric and side elevation views of yet another embodiment of the implant.
Figure 120B:
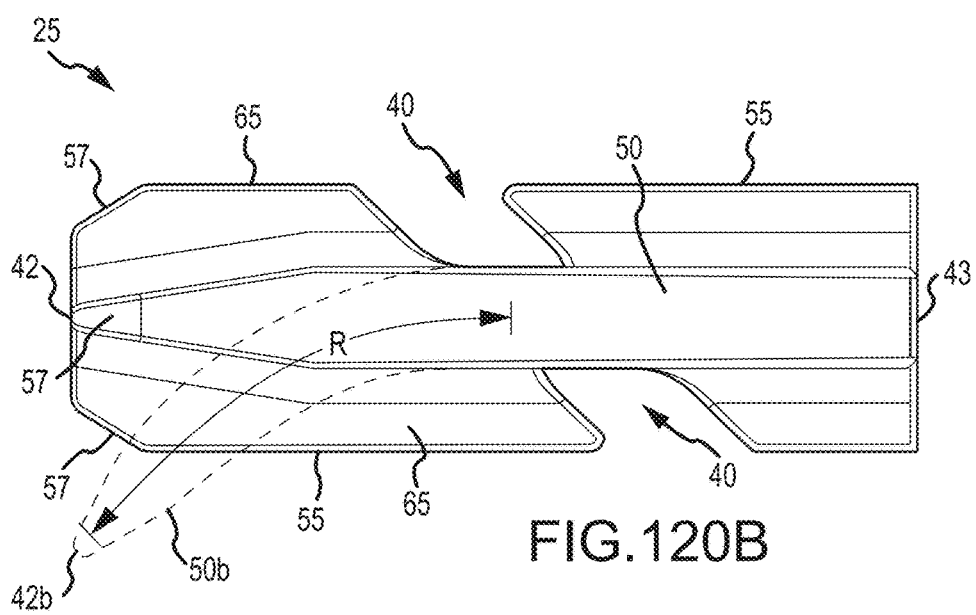

FIGS. 120A-120B are, respectively, distal end isometric and side elevation views of yet another embodiment of the implant 25. As can be understood from FIGS. 120A-120B, the features of the implant 25 are substantially similar to the features of the implant 25 described with respect to FIGS. 119A-119E, a main difference being that the leading or distal edges 57 of the planar members 55 are generally sharp, well-defined angled edges, as opposed to the generally rounded or arcuate edges of the implant embodiment of FIGS. 119A-119E.

In one embodiment, as can be understood from the dashed lines in FIG. 120B, the planar members 50 may be nonlinear between distal end 42b and proximal end 43 such that there is a radius R between implant ends (or between distal end 42b and a point, for example, midway along the longitudinal axis). The radius R may be about 100 mm to about 200 mm with one embodiment being approximately 150 mm. Accordingly, as indicated by the dashed lines in FIG. 120B, planar members 50b may terminate with a distal end 42b. Additionally, but not shown in the figures, planar members 55 may be similarly curved so as to substantially follow along or be aligned with curved planar members 50b. Such a configuration may more anatomically conform to the curvature of a sacroiliac joint while allowing planar members 50b to generally remain within a curved plane of a sacroiliac joint.

As shown in FIGS. 121A-121E, which are, respectively, distal end isometric, side elevation, plan, distal end elevation, proximal end elevation, proximal end isometric, and side elevation views of another embodiment of an implant 25, the planar members 50, 55 may have surface features or texture designed to prevent migration of the implant once implanted in the joint space. For example, the implant 25 may include anti-migration surface features 355, which are waved, undulating, or spiral ridges extending longitudinally along the planar members 50, 55. Alternatively, anti-migration surface features 355 may be configured to extend perpendicular to the longitudinal axis of planar members 50, 55.

Figure 121F:
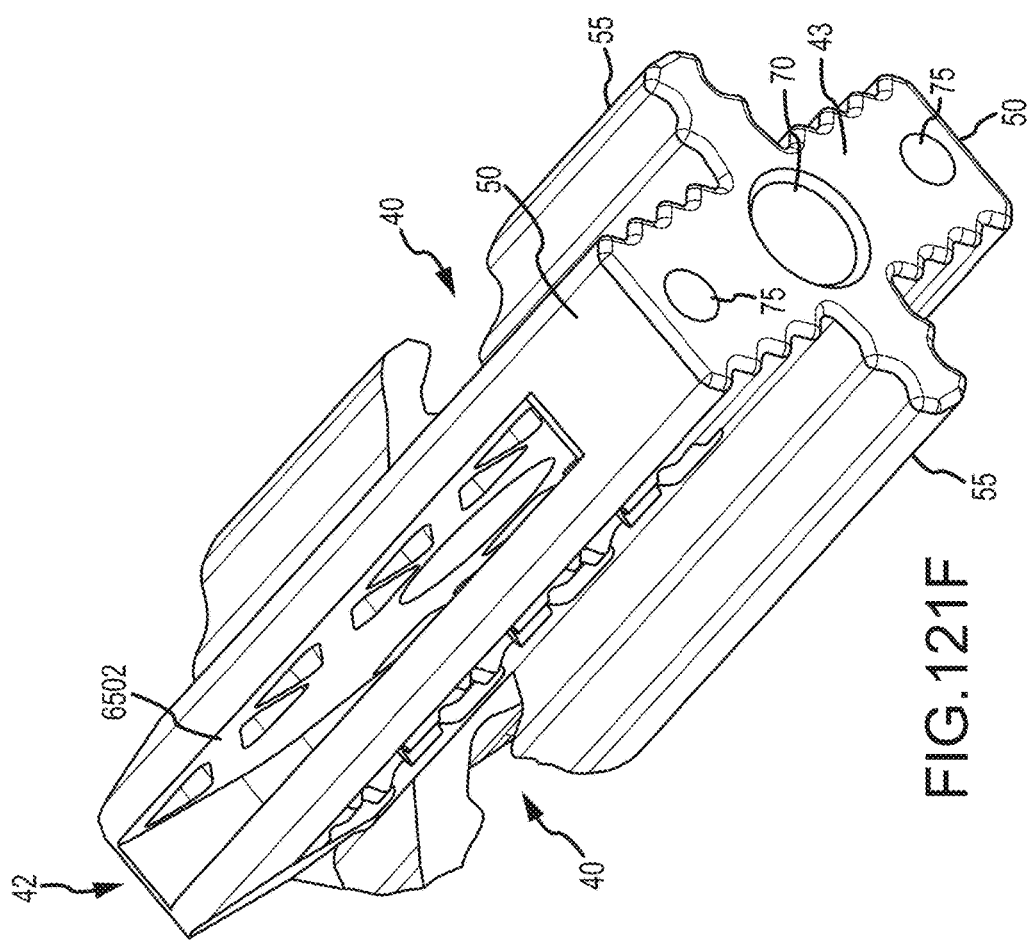
Figure 121G:
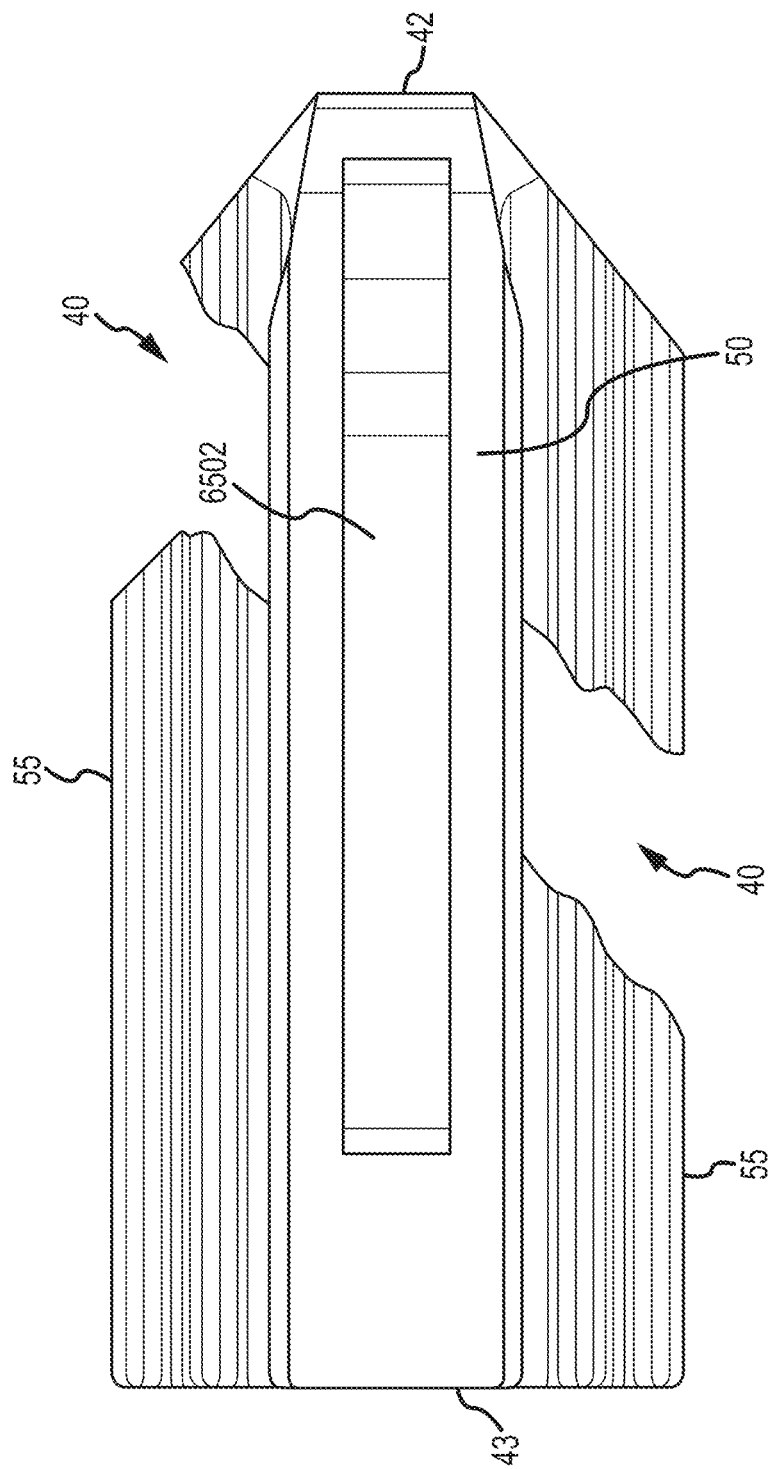

It will be appreciated that the features of the implant 25 of FIGS. 121A-121G are substantially as discussed herein, for example, with respect to the implant 25 of FIGS. 62-67, a main difference being the implant 25 is hollow and the surfaces 60 include a plurality of voids 6500, which are generally triangular in shape. The voids 6500 of the implant 25 may be filled with a biological material (e.g., a protein, demineralized bone matrix, or lattice structure containing or substantially comprised of stem cells) via an access opening 6502 leading to the hollow interior of the implant. The biological material is designed to improve growth of bone around the implant 25 and to strength the integration of the implant 25 to the bone. The voids 6500 improve integration of the implant 25 to the bone. Further, the leading or distal edges 57 of the planar members 50 and the implant distal end 42 of FIGS. 121A-121G may be relatively thicker as compared to the implant embodiment of FIGS. 62-67. Additionally, as can be best understood from FIG. 121C, the leading or distal edges 57 of the planar members 50 may differ in length and general shape. For example, as can be understood from FIGS. 121B-121C, a first leading or distal edge 57 may be generally round and arcuate and relatively longer as compared to a second leading or distal edge 57 that is generally flat and relatively shorter. Further, as shown in FIGS. 121D, 121F and 121G, the planar member 50 may include an access opening 6502 leading to the hollow interior of the implant.

With an opening 6502 on one side of the implant and not on the opposite side of the implant, the implant is configured to allow and promote boney growth, or expansion of biological material inserted within, toward, for example, certain areas within the sacroiliac joint and away or not toward certain other areas of the sacroiliac joint when the implant is implanted in the sacroiliac joint. For example, when the implant 25 of FIGS. 121A-121G is inserted into the sacroiliac joint similar to the manner indicated in FIG. 106B, wherein the opening 6502 of the implant 25 is oriented towards the posterior boundary segment 3008, boney growth or the expansion of biological material contained in the implant will extend through the implant opening 6502 in the direction of the posterior boundary segment 3008 and be specifically directed away from inferior boundary 3002, anterior-inferior boundary 3010 and anterior boundary segment 3004 to limit potential bone growth, or seepage of biologically active agents near the neurovascular structures which are present beyond said boundaries.

Additionally, as can be best understood from FIGS. 121A and 121C, and with continuing reference to FIGS. 106B and 117C, as indicated by arrow F in FIGS. 121A and 121C, one of the leading distal edges 57 (e.g., the edge located opposite the side with opening 6502) of the planar member 50 of the implant may be curved and of a substantially greater radius as compared to the distal edge 57 of the opposite planar member 50. Such a curved section (indicated by arrow F) on the distal edge 57 of planar member 50 may be configured to anatomically generally mimic and even substantially conform to an anterior-inferior corner 3010 (see, e.g., FIGS. 117C and 106B) in order to more fully occupy this region of the joint nearest neurological and vascular structures which are present anterior to and inferior to corner 3010.

The curved section (indicated by arrow F) (or according to particular embodiments located anywhere in implant 25) can additionally be configured to include an inlayed radiopaque marker, for example tantalum, to assist the surgeon with navigation while using fluoroscopy. Further, according to particular embodiments, the curved section (arrow F) can be configured to include a stimulating electrode (NM) connected to an internal controllable power source or external controllable power source. For example, the external controllable power sources may be either in the delivery system instrumentation 20 itself or a separate controller unit located in the operating suite and electrically coupled to the implant supported electrode NM via electrical conductors extending through the implant body and the implant arm 110 of the delivery system 20 to electrically couple to the separate controller unit via a cable extending proximally from the delivery system 20 to the separate controller. With the exception of the electrode (NM) itself, the entirety of the rest of the implant surfaces may be electrically insulated so as to prevent current shunting into surrounding tissues or the operator.

In one embodiment, the stimulating electrode (NM) during navigation can have an amperage of about 8 milliamperes (mA) or, nearing final placement, an amperage of about 1-4 mA and, in certain cases, up to 5 mA. The electrode (NM) may be attached to or at least partially imbedded in implant 25 (either permanently or retrievable/removable after implantation) (or according to particular embodiments, located within, near or on the anchor 30, probe 1054, on or within a trial, broach, drill or other tools of system 10) to reduce the risk to the patient of iatrogenic damage to the nervous system by using intraoperative neurophysiological monitoring, for example electromyography (EMG), which is able to alert the surgeon or technician reliably and in real-time of implant 25 advancing beyond, for example, inferior boundary segment 3002 or beyond anterior-inferior corner 3010.

Figure 121H:
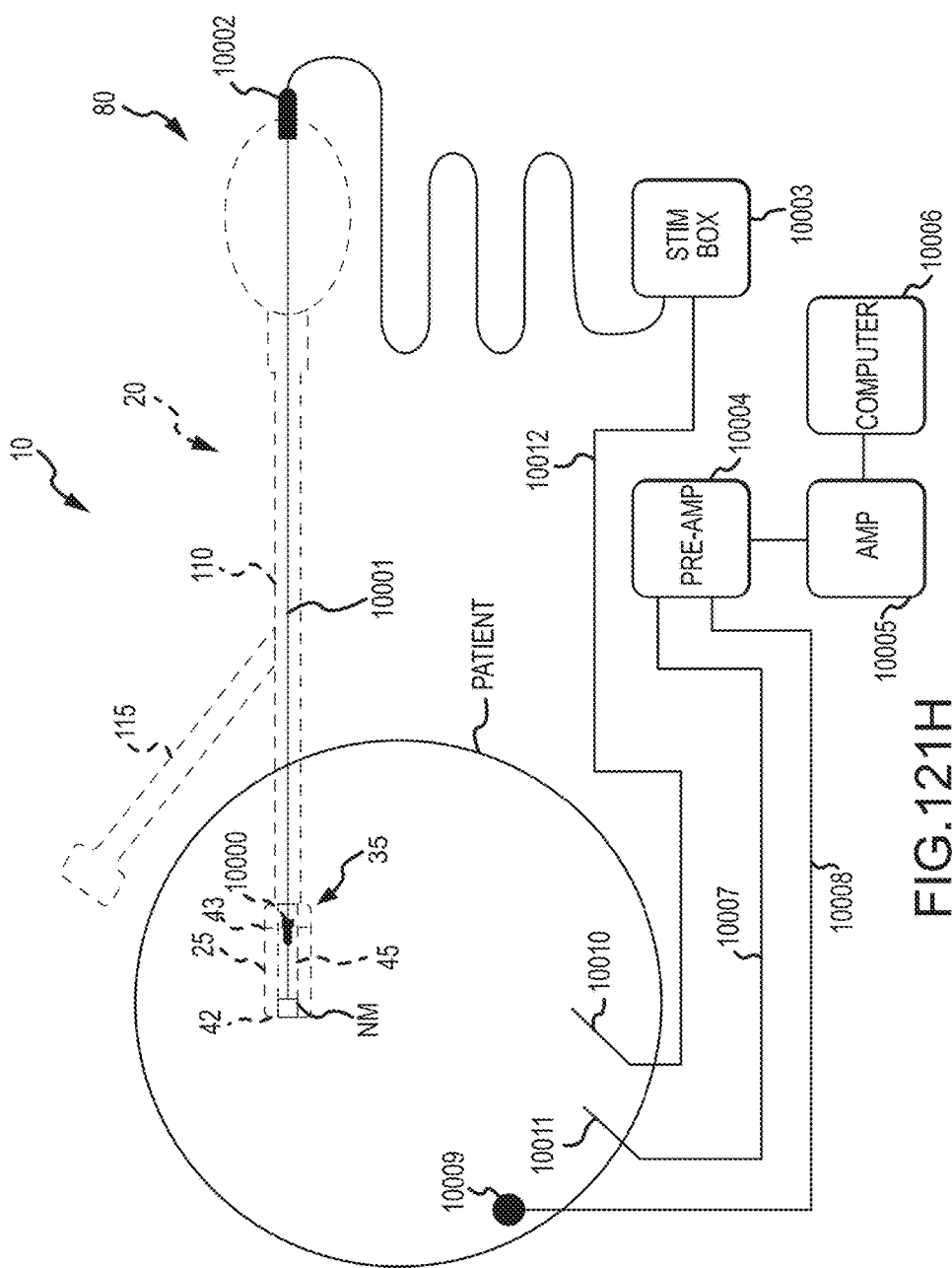
FIG. 121H is a schematic depiction of a system for fusing a joint, wherein the joint implant includes an electrode in electrical communication with a nerve sensing system.

As illustrated in FIG. 121H, which is a schematic depiction of a joint implantation system 10 configured for nerve stimulating and sensing, in one embodiment, the system 10 includes a joint implant 25, a delivery tool 20, a nerve stimulating system 10003, a pre-amplifier unit 10004, an amplifier unit 10005, a computer 10006, and an electrical conductor pathway 10001. The joint implant 25 includes an electrode NM and a body 45 including a distal end 42 and a proximal end 43 opposite the distal end. The electrode NM is supported on the implant 25. The delivery tool 20 includes an implant arm 110 with a distal end 35 configured to releasably couple to the proximal end 43 of the body 45 of the joint implant 25. The nerve stimulating system 10003 is configured to stimulate electrode NM in order to sense nerve contact made with the electrode NM or when NM is approaching and near a nerve. The electrical conductor pathway 10001 extends from the electrode NM along the implant 25 and implant arm 110 to the nerve stimulating system 10003. The electrical conductor pathway 10001 places the electrode NM and nerve stimulating system 10003 in electrical communication.

A sensing (or recording) electrode 10011 can be placed in, for example, a quadriceps femoris, tibialis anterior, gastrocnemius, or abductor hallucis muscle and may be coupled to an electrical conductor pathway 10007 that extends to the pre-amplifier 10004. A reference electrode 10010 can also be placed in, for example, a quadriceps femoris, tibialis anterior, gastrocnemius, or abductor hallucis muscle, but in a location between the area subject to stimulation from the stimulating electrode (NM) and the sensing (or recording) electrode 10011; and may be coupled to an electrical conductor pathway 10012 that extends to the nerve stimulating system 10003. An additional needle 10009 can be placed in proximity to the aforementioned needles (i.e., electrodes 10010, 10011) within a muscle (or when the electrode is in the form of a patch it may be applied to the skin of the patient) and may be coupled to an electrical conductor pathway 10008 that extends to the pre-amplifier 10004 and a ground.

The pre-amplifier 10004 may be connected to the amplifier 10005 that itself may be connected to the computer unit 10006. The computer unit 10006 may process or interpret the signal from the amplifier 10005 and display or otherwise alert (e.g., auditory signals with varying amplitude or frequency) or convey to an observer or operator in an operating suite or to a monitoring physician in a remote location (e.g., by employing computer software and processing and networking hardware) the state of the various electrical connections and pathways (e.g., connected versus disconnected) and electrical activity caused by the stimulating electrode NM.

In one embodiment, the proximal end 43 of the implant 25 and the distal end 35 of the implant arm include a cooperatively mating electrical connection 10000 that form a segment of the electrical conductor pathway 10001. An example of such a cooperatively mating electrical connection includes a male-female pin contact assembly 10000. The proximal end 80 of the delivery tool 20 and a distal end of an electrical conductor segment of the pathway 10001 between the sensing system 10003 and the proximal end 80 include a cooperatively mating electrical connection 10002 that form a segment of the electrical conductor pathway 10001. The electrical conductor pathway 10001 may be in the form of one or more multi-filar cables, one or more solid core wires, etc. The electrode NM is at or near the distal end 42 of the implant 25 and the rest of the implant (or only an area directly surrounding the electrode NM) has an electrically insulative coating or is formed of an electrically nonconductive material.

As can be understood from FIGS. 121A-121G, in one embodiment, the joint implant 25 includes a longitudinal axis and a bore 40 extending non-parallel to the longitudinal axis. The joint implant 25 also includes a hollow interior and an exterior surface having a plurality of openings 6500 defined therein that extend into the hollow interior. Prior to implantation of the implant into the joint space, the hollow interior can be filled with a biological material via the access opening 6502 that leads into the hollow interior of the implant.

The implant of FIGS. 121A-121G also includes a distal end 42, a proximal end 43, and a body extending between the proximal and distal ends. The bore 40 extends non-parallel to the hollow interior. A first pair of planar members 50 radially extend from the body of the joint implant 25. Depending on the embodiment, the body may be similar to the body 45 depicted in FIGS. 5-15 or the body may simply be an intersecting or intermediate region of the first pair of planar members 50, as can be understood from FIGS. 121A-121G.

As shown in FIGS. 121A-121G, the hollow interior extends within the confines of the first pair of planar members 50. Also, the exterior surface in which the plurality of openings 6500 is defined includes exterior planar surfaces 60 of the first pair of planar members 50. A second pair of planar members 55 radially extend from the body of the joint implant 25 generally perpendicular to the first pair of planar members 50. As can be understood from FIG. 121F, in some embodiments, the hollow interior is limited to within the confines of the first pair of planar members 50 while the second pair of planar members 55 are solid such that the hollow interior does not enter the confines of the second pair of planar members. In other embodiments, the hollow interior is limited to the confines of the second pair of planar members or the hollow interior may extend into the confines of both pairs of planar members. As indicated in FIG. 121E, in one embodiment, the first pair of planar members 50 extend over a wider radial extent than the second pair of planar members 55.

Figure 122:
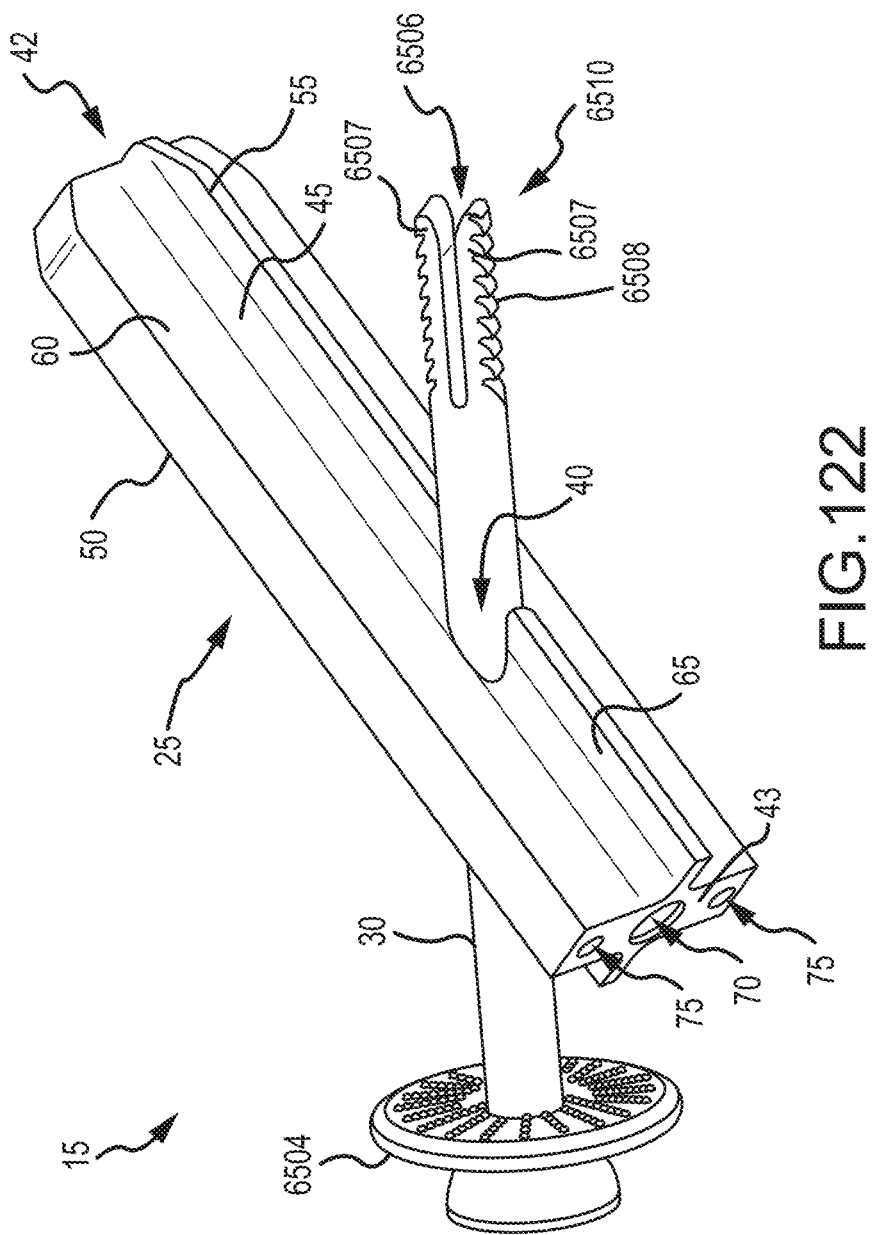
FIG. 122 is a proximal end isometric view of another embodiment of the implant assembly.
Figure 123A:
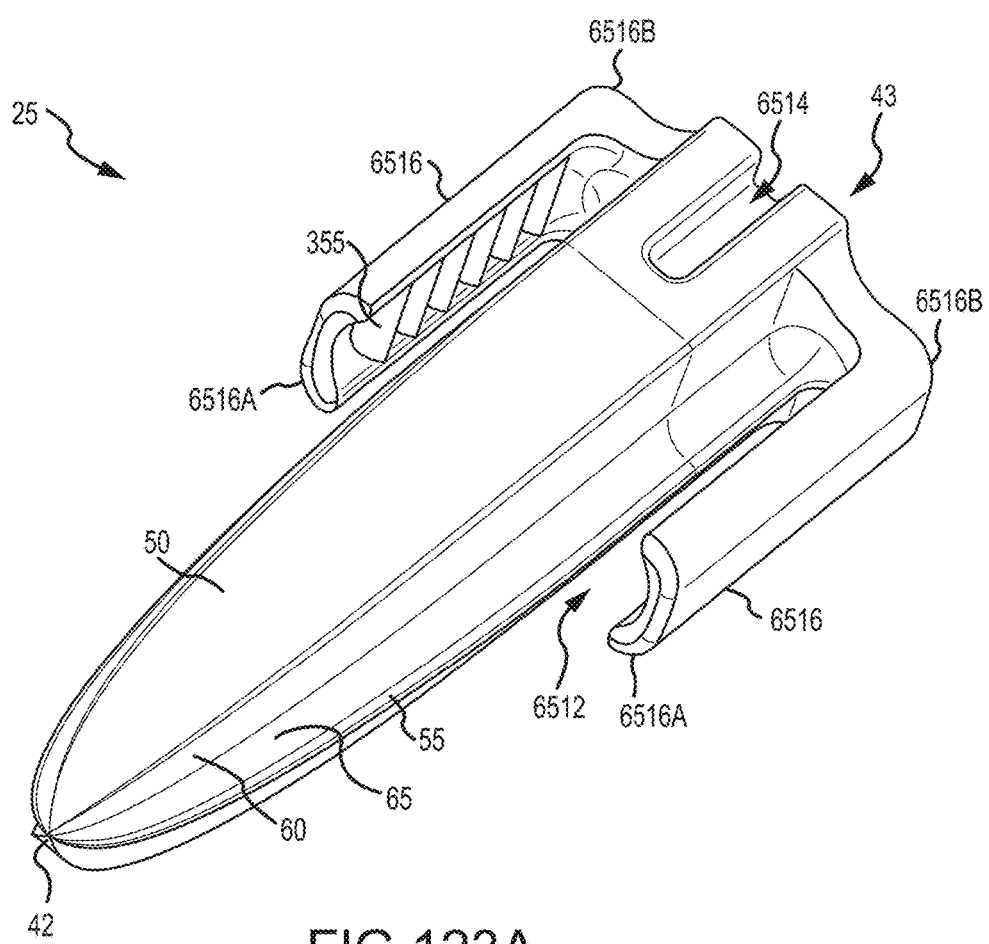
FIGS. 123A-123E are, respectively, distal end isometric, side elevation, plan, distal end elevation, and proximal end elevation views of yet another embodiment of the implant.
Figure 123B:
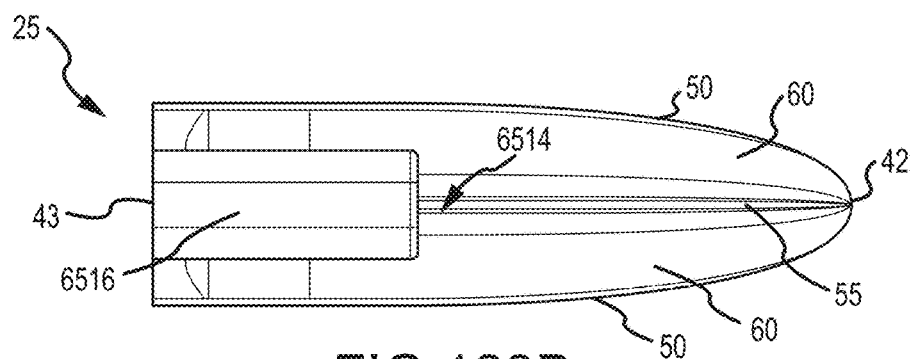
Figure 123C:
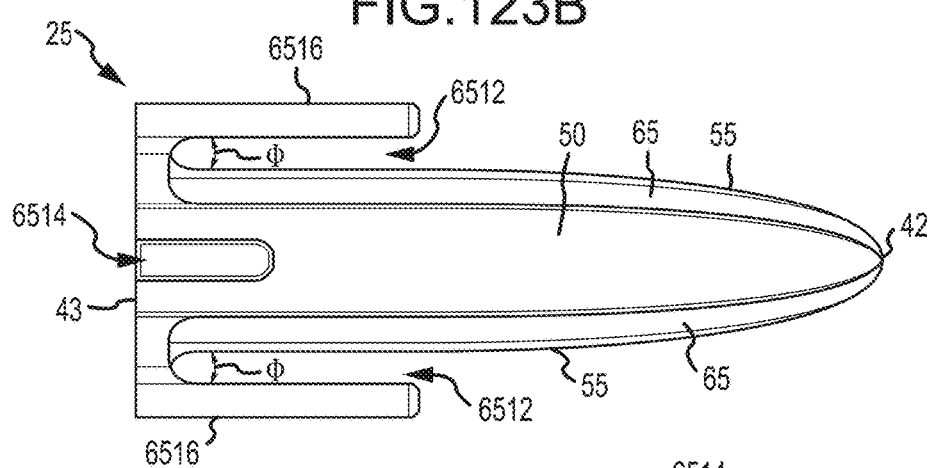
Figures 123D, 123E:
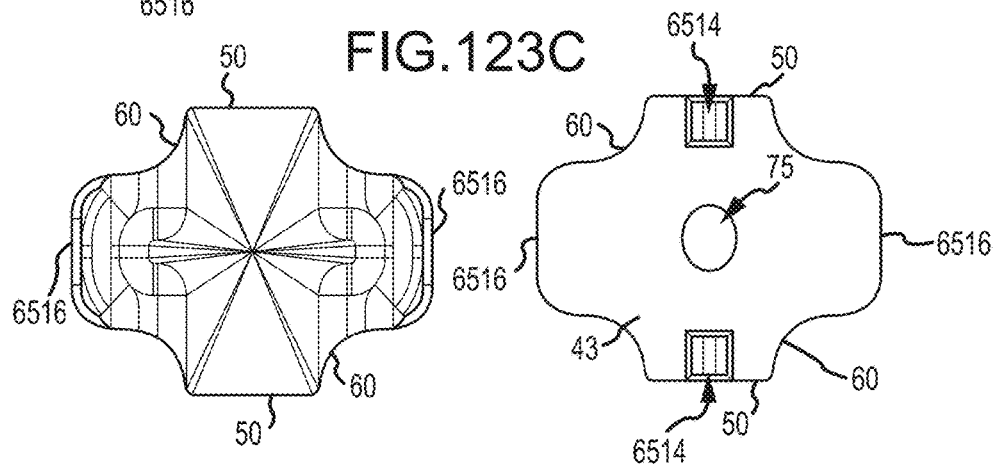

FIG. 122 is a proximal end isometric view of another embodiment of the implant assembly 15. As can be understood from FIG. 122, the features of the implant assembly 15 are substantially the features described herein, for example, with respect to FIG. 3, a main difference being that a distal end 6510 of the anchor element 30 includes an opening 6506 and edges 6508 in the form of serrated teeth or notches with parallel sides inwardly terminating as an arcuate end. The opening 6508 creates a generally "clothes-pin" like shape of the anchor element distal end 6510. In one embodiment, the edges 6508 may be triangular, trapezoidal, rectangular, or another angular cross-sectional elevation and generally evenly distributed along the surface of the anchor element distal end 6510. The edges 6508 help drive the implant assembly 15 into the joint and prevent migration of the implant assembly 15 once in place.

In one embodiment, opening 6506 is defined by arms 6507. The opening 6506 and arms 6507 are configured such that, after passing through a channel created in a first bone and after passing through bore 40 and then subjected to impaction into a second bone, for example that of the ilium, bone of the second bone can be received into opening 6506 to urge the "clothes pin" arms 6507 apart from one another thereby further embedding the edges 6508 into bone for enhanced fixation. Alternatively, in other embodiments, anchor 30 may be configured in part or completely of shape memory biomaterials (e.g., Nitinol or PEEK ALTERA, available from MedShape, Inc. located at 1575 Northside Drive, NW, Suite 440, Atlanta, Ga. 30318 USA), which are capable of changing shape in response to temperature, light and/or mechanical forces. An anchor 30 configured with a shape memory biomaterial can be configured, for example, immediately prior to insertion as substantially shown in FIG. 122 with "clothes-pins" arms 6507 in general parallel relation. Upon final placement in the ilium or other second bone, the "clothes-pins" arms 6507 (in response to temperature, light and/or mechanical force) can separate away from one another and in certain embodiments "curl" outwardly and back toward the proximal end of anchor 30 in order to further resist undesirable movement of implant assembly 15. Another main difference between the implant assembly embodiment of FIG. 122 and of FIG. 3 is that a washer 6504 is coupled to the anchor element 30. The washer 6504 and the shape and texture of the anchor member distal end 6510 secure the implant assembly 15 in the sacroiliac joint. The washer can be (pivotably) coupled to the anchor such that when inserted or explanted the washer remains coupled to the anchor and need not be removed separately.

FIGS. 123A-123E are, respectively, distal end isometric, side elevation, plan, distal end elevation, and proximal end elevation views of yet another embodiment of the implant 25. As can be understood from FIGS. 123A-123E, many of the features of the implant 25 are substantially the features of the implant 25 described herein, for example, with respect to FIGS. 119A-119E, a main difference being that the planar members 50, 55 are generally round or arcuate and the implant distal end 42 is generally rounded. Specifically, the leading or distal edges 57 of the implant embodiment of FIGS. 119A-119E are not separate features in the embodiment of FIGS. 123A-123E and instead are generally incorporated in the rounded or arcuate surfaces of the planar members 50, 55, which intersect at the implant distal tip 42. Additionally, the implant proximal end 43 is generally flat with round edges, and relatively wider than the implant embodiment of FIGS. 119A-119E. The planar members 50 may each include a channel 6514 extending longitudinally and opening into the implant proximal end 43 adapted for receiving a distal end of the delivery device as described herein.

Further, another main difference is that the implant 25 shown in FIGS. 123A-123E includes wings 6516, which are separated from the planar members 50, 55 by a gap 6512. In other words, the gap 6512 extends longitudinally between the planar members 55 and the wings 6516 until the implant proximal end 43. The wings 6516 allow the implant 25 to be driven into the joint region with the wings existing in a plane transverse to the joint plane such that one of the wings 6516 is delivered into the sacrum and the other wing 6516 into the ilium. The wings 6516 may include anti-migration surface features 355 in the form of notches or ribs extending inwardly in the gaps 6512 that are generally evenly distributed longitudinally along the wings 6516 parallel to the planar members 55 and oriented transversely to the longitudinal axis of the respective wing. The anti-migration surface features 355 and the wings 6516 prevent migration of the implant 25 once placed, as described herein. As can be understood from FIGS. 124E-124H, the implant of FIGS. 123A-123E may additionally include a bore 40 extending through the implant 25 to receive an anchor 30 delivered via an anchor arm 115 of the system 10 as described herein.

Such a bore 40 may extend through the implant so as to extend in generally the same plane in which the wings 6516 exist.

In some embodiments, for example, the relative location and angles between wings 6516 and planar members 50, 55 can remain substantially the same before and after implantation.

Alternatively, in some embodiments, the wings 6516 can be configured to deflect a distance away from planar members 50, 55 upon insertion and contact with bone. In other words, the gaps 6512 may enlarge upon placement and, to facilitate such enlargement of the gaps 6512, anti-migration features 355, or distal ends 6516A of wings 6516, may be configured with a sloping surface to urge wings 6516 a distance away from planar members 50, 55. Upon final placement, the deflected wings 6516 urge bone or joint surfaces against the implant 25 in order to enhance bone contact with the implant 25 by compression to enhance bone fusion and to enhance fixation of the bones or bone fragments by potential energy stored in the deflected wings 6516. Alternatively, according to particular embodiments, the implant 25, or only the wings 6516, may be manufactured from a shape memory biomaterial. In such embodiments, the position of the wings 6516 before implantation may be such that their distal ends 6516A are a further distance from planar members 50, 55 than shown in FIG. 123A-E. After final placement of the implant in the sacroiliac joint, an angle Φ of the gap 6512 can decrease and the distance between distal ends 6516A of wings 6516 and planar members 50, 55 can decrease by the shape memory biomaterial biasing or shaping to appear substantially as shown in FIGS. 123A-E. As a result, the wings 6516 provide compression of the bone in gap 6512 against the surfaces of the implant 25.

Alternatively, proximal ends 6516B of wings 6516 can be configured with a hinge between the proximal ends 6516B and the proximal end 43 of implant 25 to allow wings 6516 to deflect away from planar members 50, 55 upon implantation. Additionally, the proximal ends 6516B can extend a distance proximally further than the proximal end 43 of implant 25. Also, an end cap can be secured to the proximal end 43 of implant 25. Advancing the end cap distally can bias the extended proximal ends 6516B away from the longitudinal axis of implant 25 by causing rotation of the wings about the hinges. Such rotation causes the portion of the wings 6516 distal said hinges to rotate an opposite complementary angular distance toward the longitudinal axis of the implant 25, resulting in compression of bone against implant 25 for enhanced fusion and fixation.

Alternatively, proximal ends 6516B of wings 6516 may be attached to proximal end 43 of implant 25 by slidable interlocking elements. Upon implantation the wings 6516 may be located a maximum distance away from implant 25 as allowed by the slidable interlocking elements and, after final placement of implant 25, the wings may be drawn toward the implant 25 by various methods. For example, the slidable interlocking elements may be configured with sloped elements which prevent movement in the direction away from the longitudinal axis of implant 25 yet allow a compressive force, for example from a surgeon employing hemostats on the surfaces of wings 6516 facing opposite implant 25, to irreversibly draw the wings 6516 toward implant 25. As a second example, a gear can be located on the proximal end 43 of implant 25, which when driven by rotational forces, by, for example, a screw driver or hex wrench, can force wings 6516 to draw toward implant 25 while sliding along the slidable interlocking elements.

Figure 1:
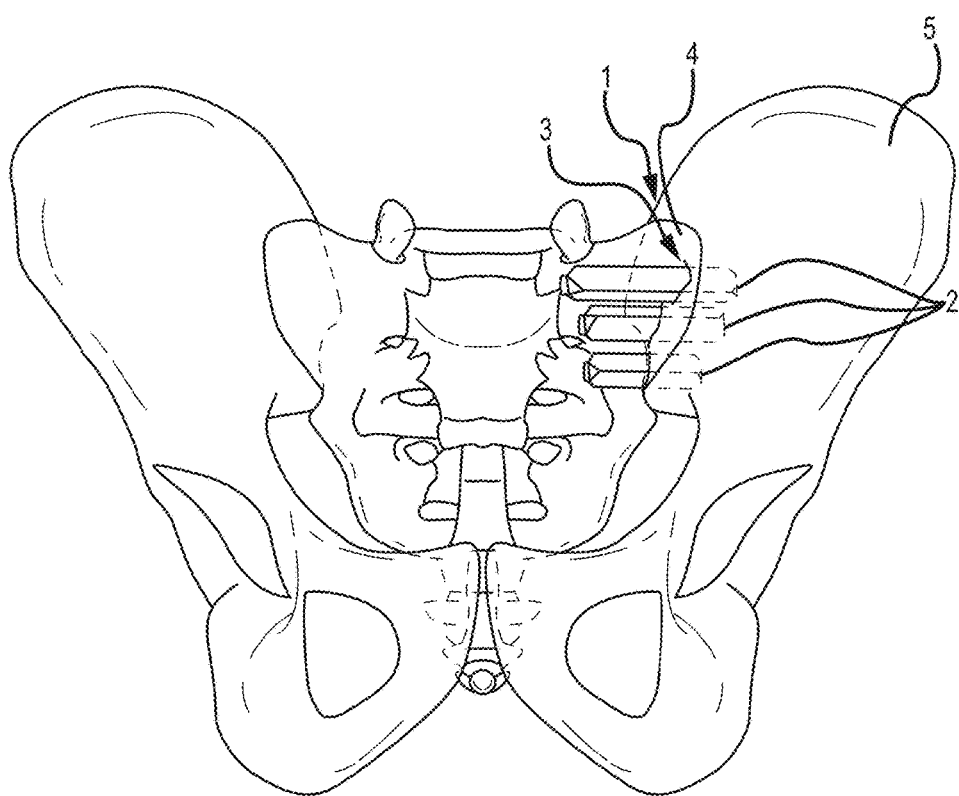
FIG. 1 is an anterior view of the pelvic region and a conventional method and device for stabilizing the sacroiliac joint.
Figure 124A:
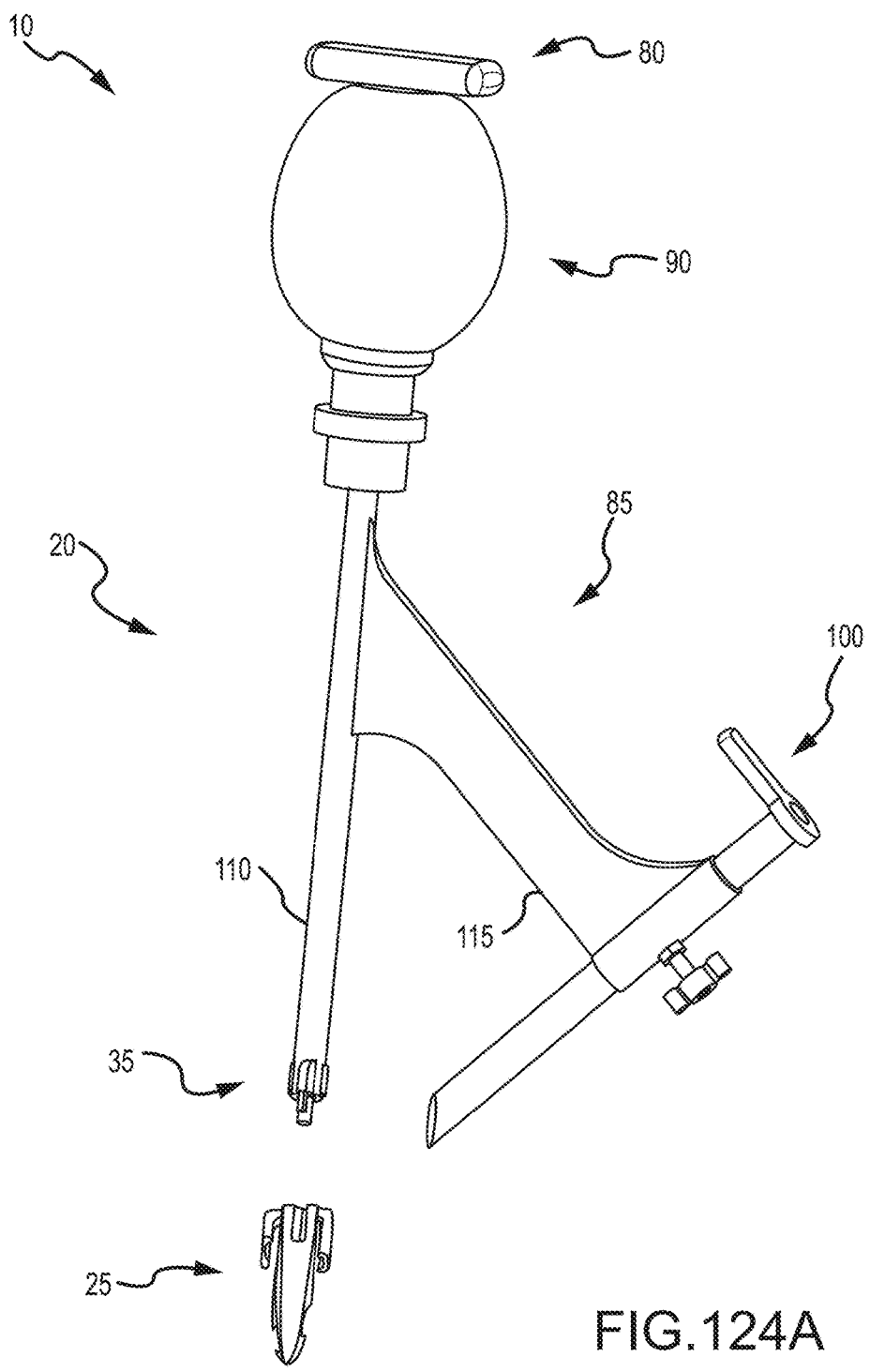

FIGS. 124A and 124B1 are isometric views of another embodiment of the delivery tool 20 coupled and decoupled with the implant 25, respectively. FIG. 124C is an isometric view of the delivery tool 20 in an exploded state. FIG. 124D is an enlarged view of the distal end 120 of the implant arm 110 of the delivery tool 20. As can be understood from a comparison of FIGS. 124A-124D and FIGS. 86-88, the delivery tool embodiment of FIGS. 124A-124D is substantially similar to the delivery tool embodiment of FIGS. 86-88, a main difference being the distal end 120 of the implant arm 110, as shown in FIG. 124D is adapted to engage the channels 6514 of the implant 25 described with respect to FIGS. 123A-123E. For example. The large planar members, keels, or fins 140 and the small planar members, keels, or fins 145, as described herein, for example, with respect to FIG. 19, may match the relative shape and size of the channels 6514 of the implant 25. Accordingly, the delivery tool embodiment of FIGS. 124A-124D is adapted to deliver the implant 25 into the joint region with the wings extending in a plane that is generally transverse to the joint plane such that each wing is received into a respective bone (e.g., sacrum or iliac) bordering the joint, as described with respect to FIGS. 123A-123E.

Figure 124E:
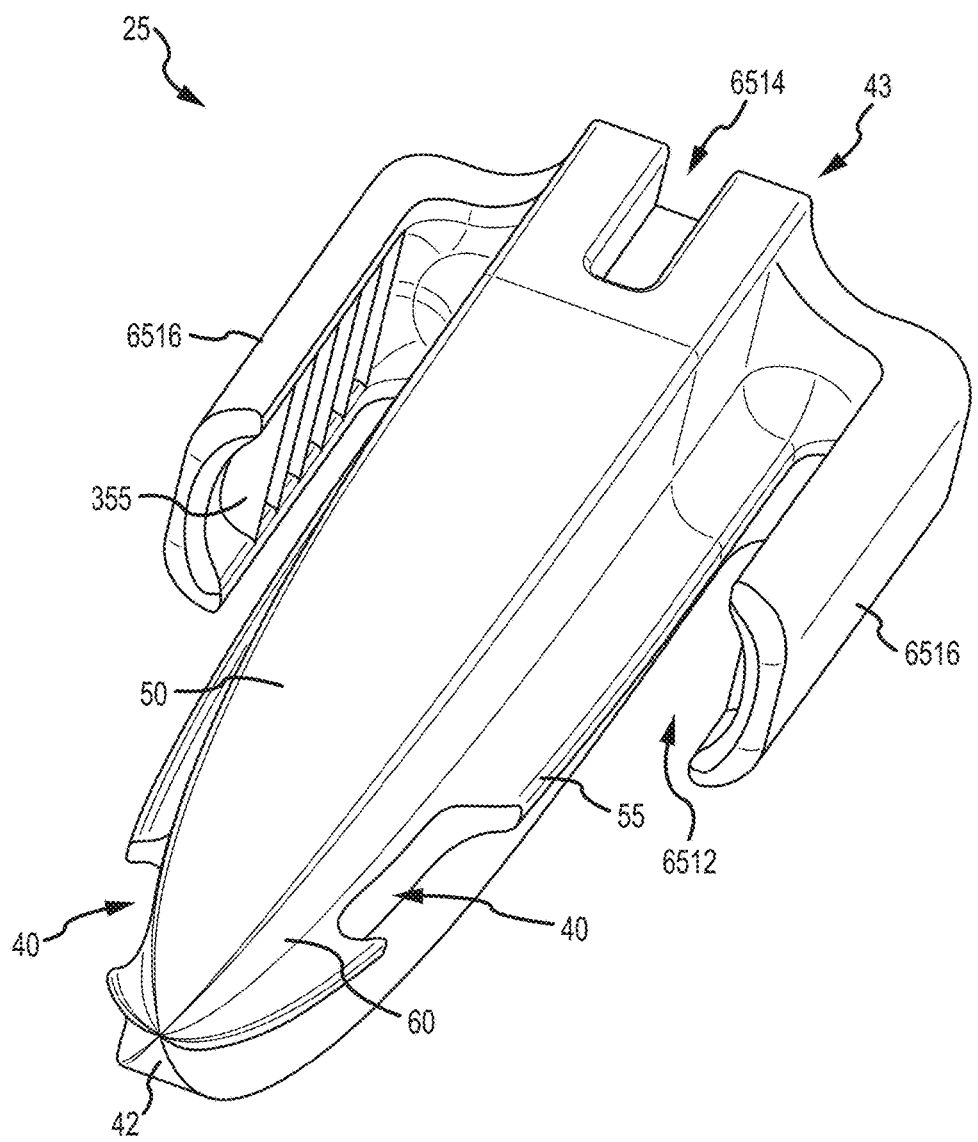
Figure 124G:
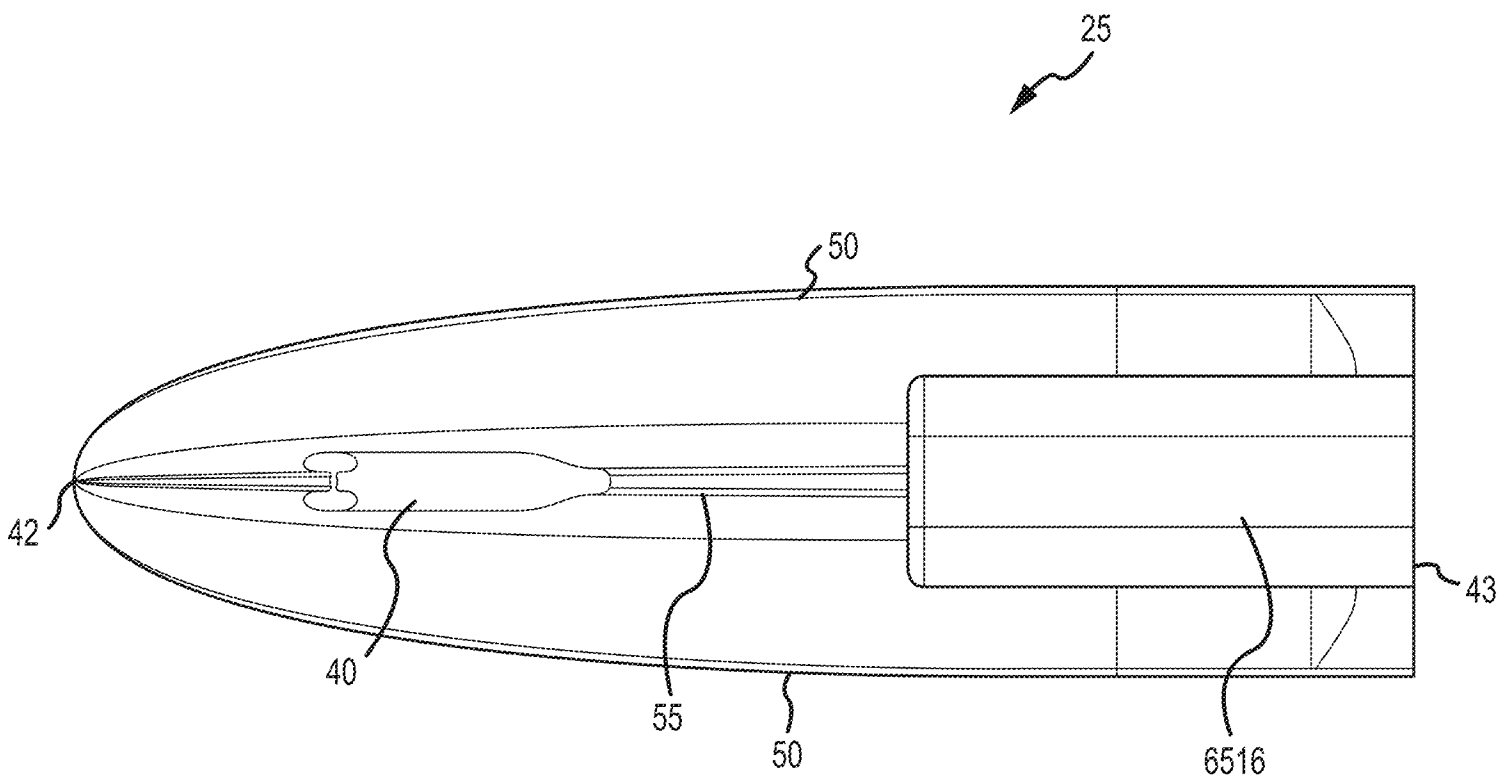
Figure 124H:
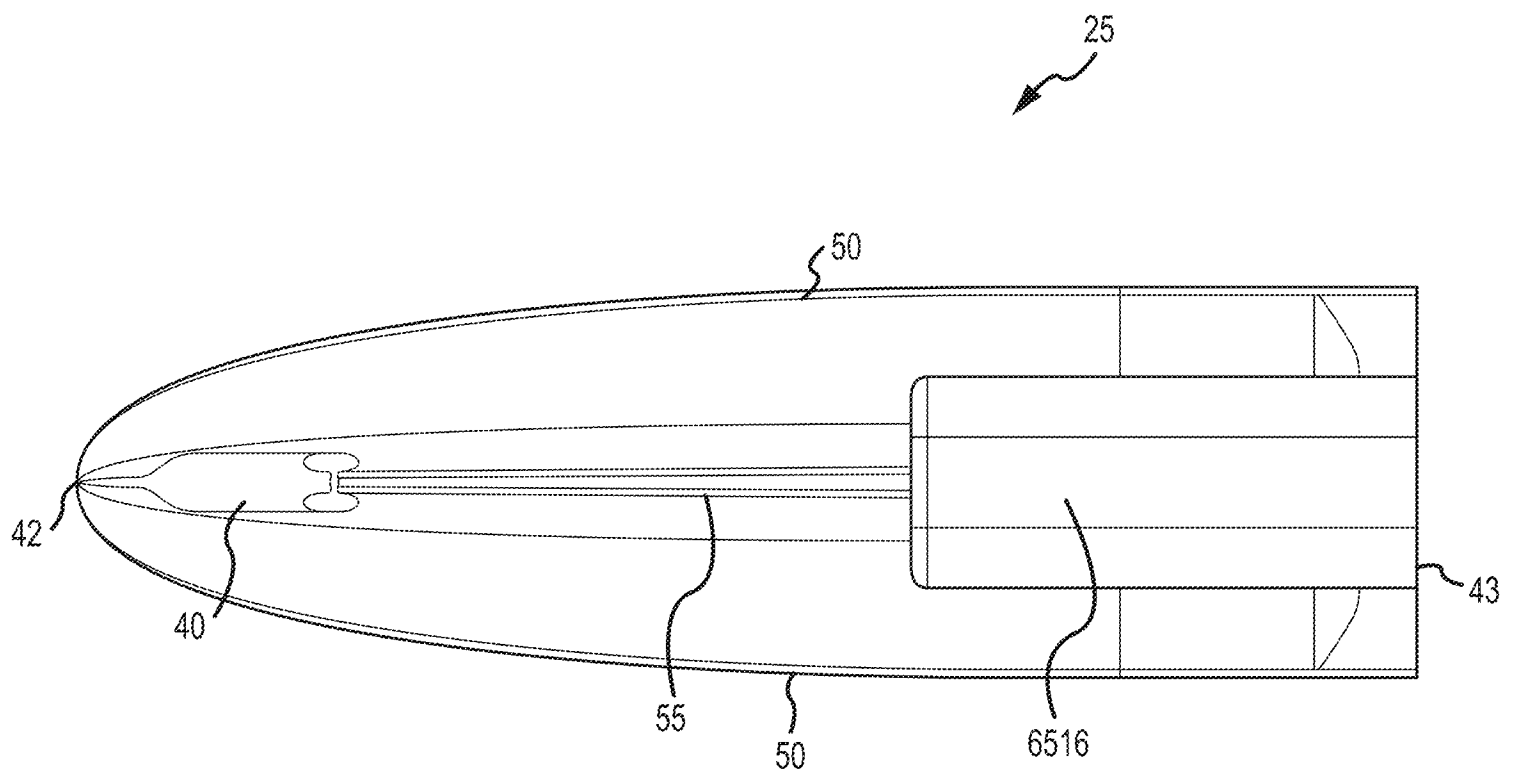

As can be understood from FIGS. 124E and 124G, in some embodiments, the implant has a bore 40 that has a non-circular (e.g., oblong) cross section as taken along a cross section plane that is generally perpendicular to the length of the bore 40 extending through the implant. The delivery tool 20 of FIGS. 124A-D can be configured to align a non-circular anchor 30 through the non-circular bore 40 of implant 25. For example, as shown in FIG. 124B2, a guide sleeve 100 is concentrically contained in a collar 165 of the anchor arm 115. The sleeve 100 has a guide hole 2444 that has a non-circular (e.g., oblong) transverse cross section that prevents rotational movement of the oblong anchor when distally displaced through the guide hole 2444. The sleeve 100 may have a groove 2333 extending along a portion of its exterior surface length that mechanically interfaces with a complementary feature defined in the collar, thereby preventing rotation of the sleeve within the collar. Since the non-circular (e.g., oblong) cross sectioned anchor 30 is prevented from rotation within the complementarily shaped guide hole 2444 and the sleeve 100 is prevented from rotation within the collar 165 due to the structural impediment presented by the groove 2333, the non-circular anchor 30 can be accurately and reliably delivered into the non-circular bore 40 of the implant 25 of FIGS. 124E and 124G The delivery tool 20 can also be configured to be able to deliver a non-circular anchor 30 adjacent implant 25. Further, another difference between the embodiment of FIGS. 124A-124D and FIGS. 86-88 is that the anchor arm 115 as shown in FIGS. 124A-124C is contoured to permit the transverse delivery of the transfixing anchor screw 30 (e.g., see FIG. 3) through and/or adjacent the implant 25 and across the sacroiliac joint space.

As can be understood from FIGS. 124E-124H, in one embodiment, a joint implant 25 includes a longitudinal axis, a body 25, a distal end 42, a proximal end 43, a first wing 6516, a second wing 6516 and a bore 40 extending non-parallel to the longitudinal axis. The proximal end is opposite the distal end. The first wing is connected to the body near the proximal end and extends distally in an offset manner from a first lateral side of the body. The second wing is connected to the body near the proximal end and extends distally in an offset manner from a second lateral side of the body opposite the first lateral side of the body. The body of the implant tapers extending proximal to distal.

As shown in FIGS. 124E-124H, the joint implant also includes a first pair of planar members 55 radially extending from the body of the joint implant. The first pair of planar members 55 forms at least a portion of the first and second lateral sides of the body from which the first and second wings 6514 are offset. The implant may also include a second pair of planar members 50 radially extending from the body of the joint implant generally perpendicular to the first pair of planar members 55. The second pair of planar members may have a thickness greater than a thickness of the first pair of planar members. As already stated, the first and second wings extend distally in an offset manner from the respective first and second lateral sides, thereby defining first and second respective gaps or slots 6512 between the wings and the respective lateral sides. The bore and the first and second wings reside in generally the same plane.

Figure 125A:

FIG. 125A is an isometric view of another embodiment of the implant.

As can be understood from FIG. 125A, which is an isometric view of another embodiment of the implant 25, the longitudinally extending body 45 may include helical spiral threads 6524 rather than keels, fins or planar members 50, 55 that radially extend outwardly away from the body 45, as described herein. The helical spiral threads 6524 engage with the bone in the joint region to prevent migration of the implant 25. Additionally, in the embodiment shown in FIG. 125A, the body 45 is generally cylindrical with anti-migration surface features 355 in the form of ridges or ribs extending longitudinally along the body 45. Further, in addition to the bore 40, the body 45 may include anchor member receiving features 6520 and 6522, which are substantially similar to the bore 40, to provide a choice of a plurality of locations to transfix the anchor member 30, as described herein. Additionally, bores 40 can allow bone to grow into the hollow interior of the implant as discussed below. For example, as shown in FIG. 125A, the body 45 may include three bores, 40, 6520, and 6522 positioned relative to one another along the same longitudinal surface of the body 45. The implant 25 may be delivered into the joint region with an embodiment of the delivery tool 20 that includes three collars supported off of the anchor arm 115 similar to the embodiment of FIG. 110, except having at least three longitudinally oriented holes similar to holes 165a and 165b, which are at pre-set locations corresponding to the bores 40, 6520, and 6522. The rest of the features shown in the implant embodiment of FIG. 125A may be substantially similar to the features of implant embodiments described herein.

Figure 125B:
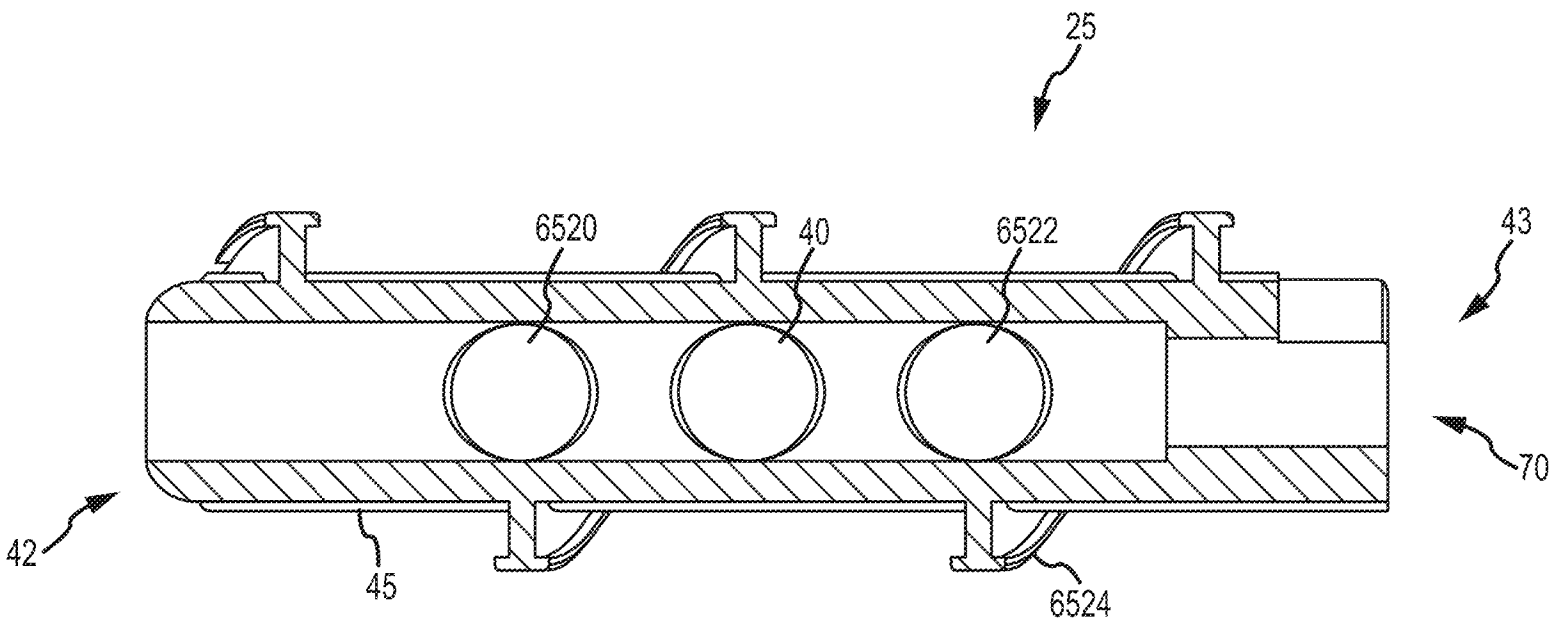
FIG. 125B is a longitudinal cross section view of the implant of FIG. 125A.

As shown in FIG. 125B, which is a longitudinal cross section view of the implant 25 of FIG. 125A, the longitudinal body of implant 25 may be substantially hollow with a distal end 42 configured with an aperture opening to the hollow interior. The hollow interior may be filled with a biological material for promoting bone growth into the hollow interior, as discussed above. Additionally, helical threads 6524 may be "T-shaped" in cross section in order to hold bone to resist a first bone from moving relative to a second bone.

Figure 126A:
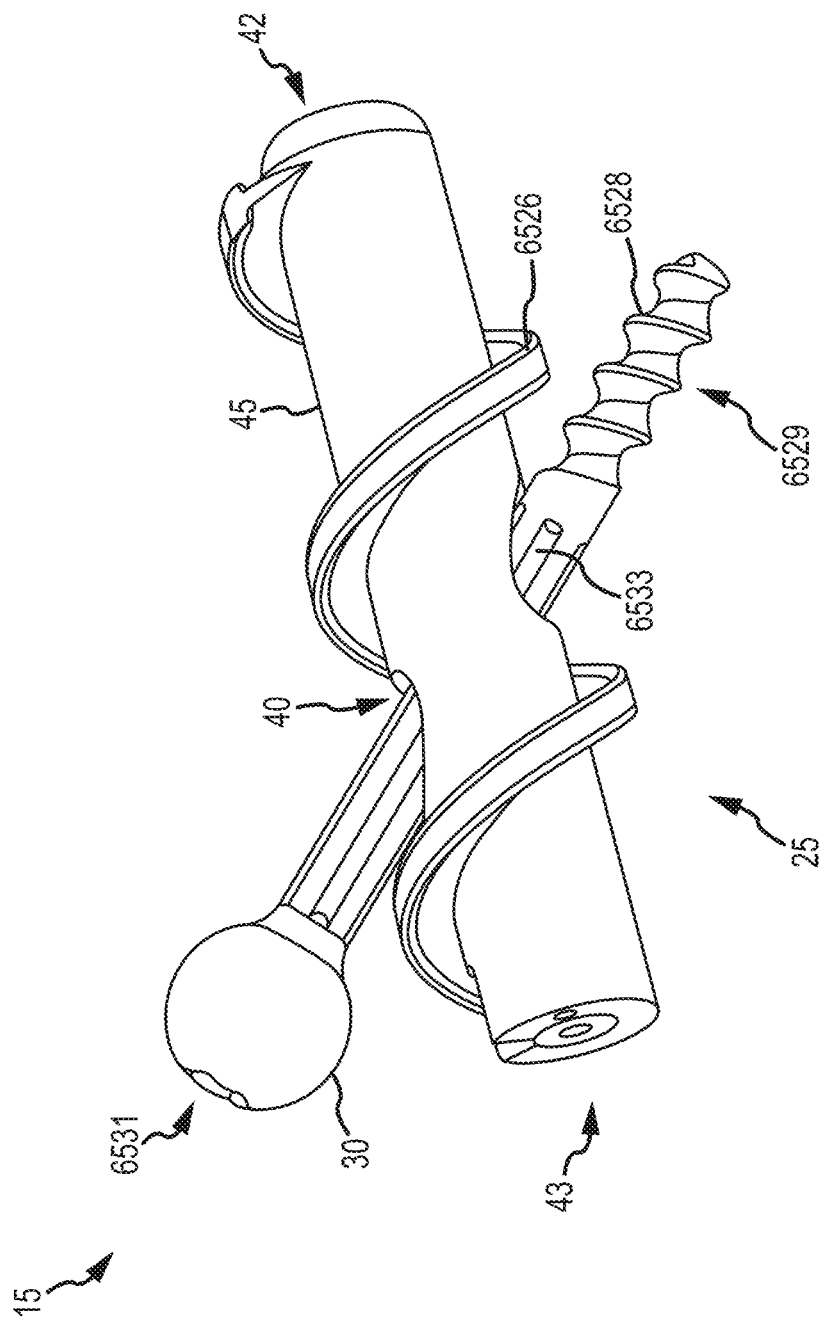
FIG. 126A is an isometric view of another embodiment of the implant assembly.

As shown in FIG. 126A, which is an isometric view of another embodiment of the implant assembly 15, the implant 25 of FIG. 126A is substantially the implant 25 of FIG. 125A, a main difference being that the additional bores 6520 and 6522 are not included on the body 45. Further, features of the anchor element 30 are substantially similar to the features of the anchor element 30 described herein, for example, with respect to FIG. 3. However, the anchor element 30 as shown in FIG. 126A includes helical spiral threads 6528 at the anchor element distal end 6529. The helical spiral threads 6528 of the anchor element 30 are rotationally driven and secured into the bone. For example, the anchor element proximal end 6531 may be adapted to engage an Allen wrench, hex key, or other tool with a hexagonal cross section to deliver the anchor element 30 through the bore 40 and into the bone. Additionally, anchor 30, when configured as a screw can be self-tapping.

As illustrated in FIG. 126C, which is a longitudinal cross section of the proximal head of the anchor 30 of FIG. 126A, in one embodiment, the hex key can be cannulated and configured to receive an anchor retainer rod with a threaded end that engages complementary threads 6537 located on the anchor element proximal end 6531 set below the hex key engagement cutout.

As illustrated in FIGS. 126A and 126B, the anchor 30 may have flutes 6533 extending longitudinally down a portion of the shaft configured to engage a setscrew 6534, as discussed below, in order to prevent rotation of anchor 30 within the bore 40. Alternatively, anchor 30 can be configured with spiral flutes. Alternatively, anchor 30, whether configured as a screw with threads or as a nail, may be further configured with flutes which extend circumferentially in order for a setscrew 6534, as discussed below, to engage said flutes and thereby prevent axial movement of anchor 30 within the bore 40.

As shown in FIG. 126B, which is a longitudinal cross section view of the implant assembly 15 of FIG. 126A, the proximal end 43 of the longitudinal body of implant 25 may be configured to receive a setscrew 6534, or pair of setscrews positioned in longitudinal series in the setscrew hole to lock the setscrews in place against each other in the set screw hole. The setscrew 6534 (or the most distal setscrew of a pair of setscrews in longitudinal series) can threadably advance distally in the setscrew hole such that a distal end of the setscrew enters the bore 40 to be received in a groove 6533 and abut against the anchor 30 to resist movement between the anchor 30 and implant 25.

As can be understood from FIGS. 125A-126B, in one embodiment, a joint implant 25 includes a longitudinal axis, a proximal end 43, a distal end 42, a body 45, a bore 40 extending non-parallel to the longitudinal axis, and a helical thread 6524 extending around the body between the proximal and distal ends. The implant body may be substantially cylindrical, and the bore may be a single bore 40 (see FIG. 126A) or multiple bores 40.

Figure 127:
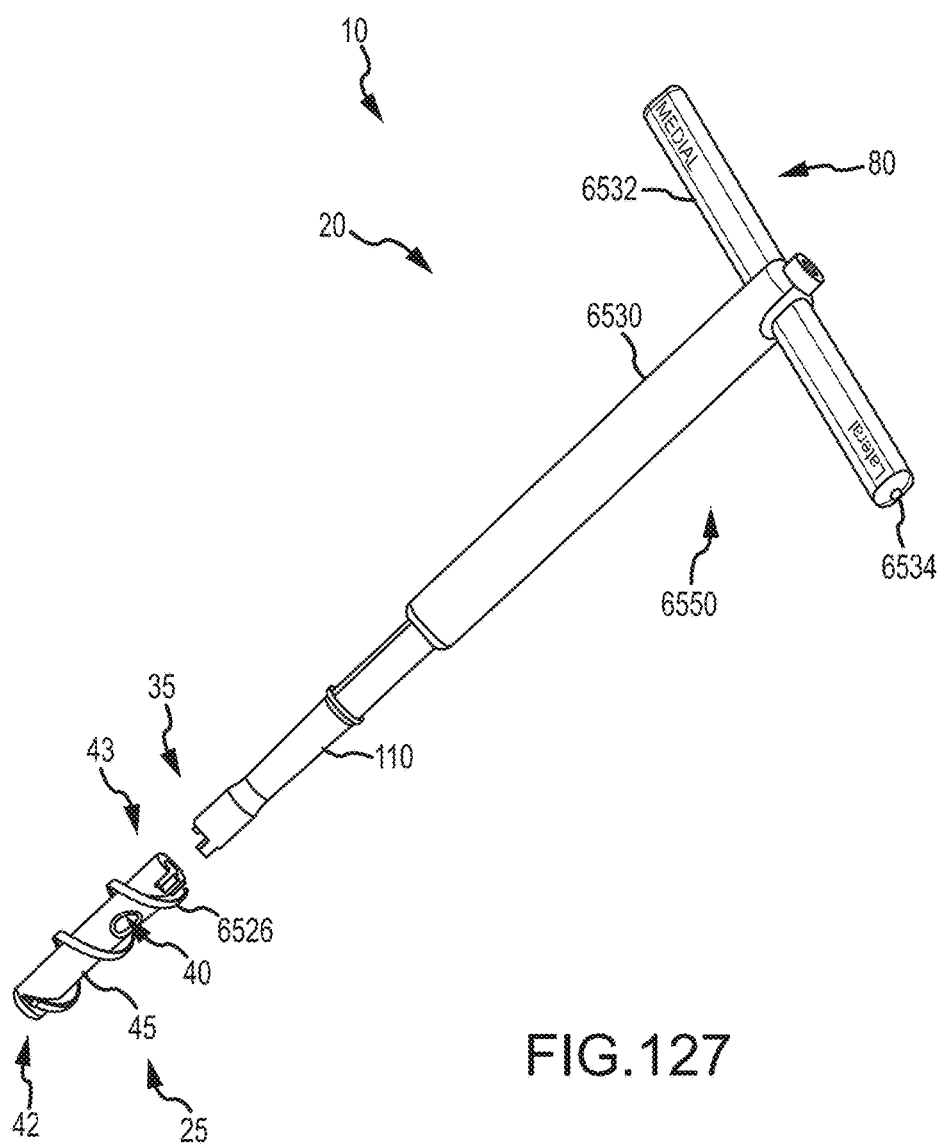
FIG. 127 is an isometric view of an embodiment of a sleeve mounted on an implant arm of a delivery system similar to the delivery system of FIG. 88, wherein the sleeve facilitates visualization of the trans screw and trajectory.
Figure 128A:
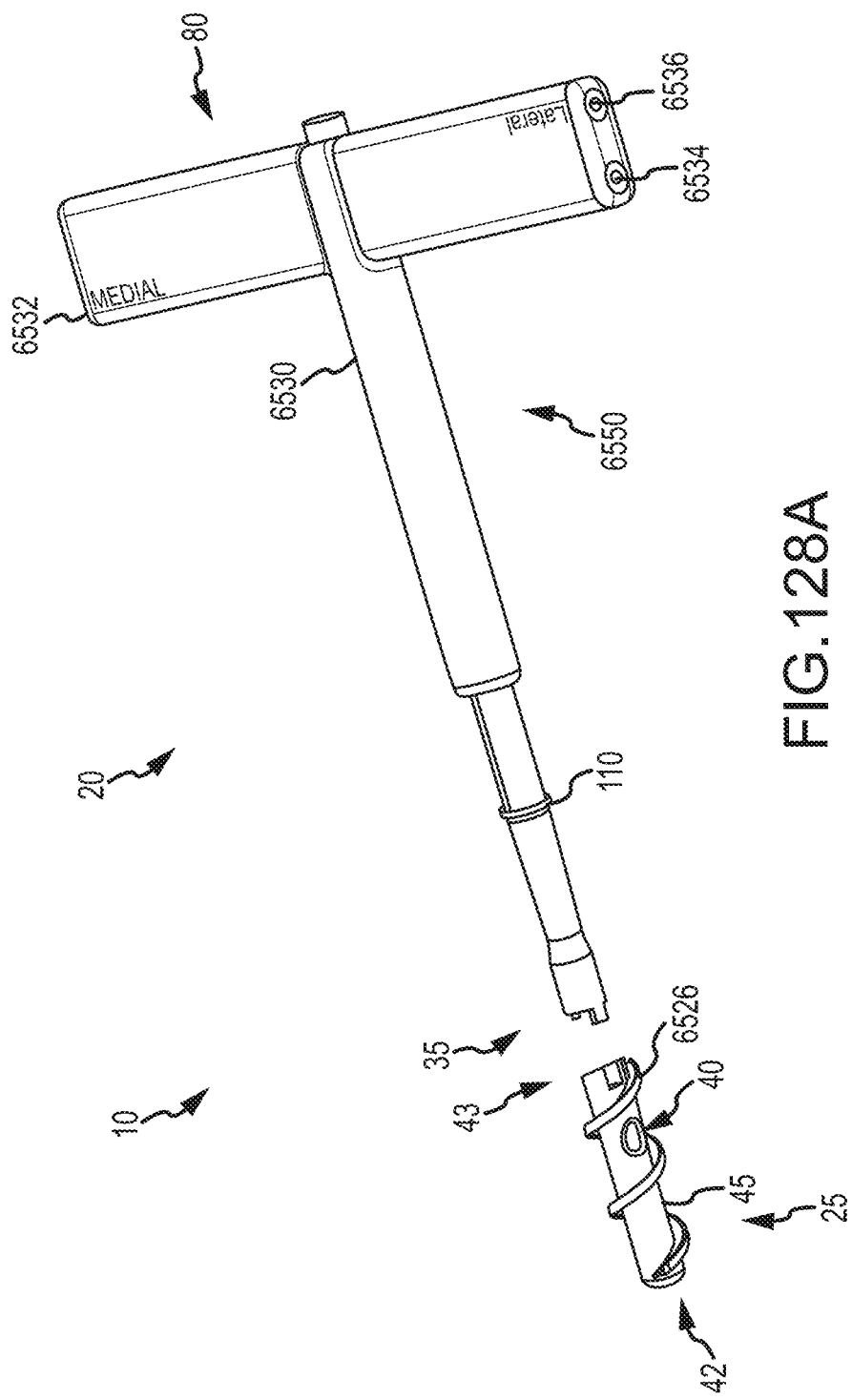

As can be understood from FIGS. 127-128A, the implant arm 110 may include a handle at a proximal end of the implant arm, wherein the handle includes an elongated handle member 6532 that has a length perpendicular to a longitudinal axis of the implant arm. A radiopaque elongated member 6534 extends through the elongated handle member parallel to the length of the elongated handle member. The radiopaque elongated member is contained in a non-radiopaque portion of the elongated handle member. As indicated in FIG. 128A, the radiopaque elongated member may be two such members 6534, 6536 spaced apart from each other in the elongated handle member 6532 and residing in a plane at least parallel with, if not including, a longitudinal axis of the implant arm 110.

As can be understood from FIGS. 126A-126B, the joint implant may also include a setscrew 6534 with a distal end that is configured to enter the first bore 40 to abut against the anchor element 30 so as to limit movement of the anchor element in the first bore. For example, in abutting against the anchor element, the distal end of the setscrew engages a flute 6533 defined in the anchor element.

FIG. 127 is an isometric view of an embodiment of a sleeve 6550 mounted on an implant arm 110 of a delivery device 20 similar to that of FIG. 88, wherein the sleeve facilitates visualization of trans screw trajectory. When delivering the implant 25, the arm assembly 85 is decoupled from the implant 25 and the sleeve 6550 is coupled to the implant arm 110. The handle members 6532 may be rotated to cause implant arm 110 to rotate, thereby causing the helical spiral threads 6526 to threadably engage the bone and advancing the implant 25 into the joint region. In one embodiment, the sleeve 6550, which may be formed of a radiotranslucent material such as PEEK or carbon fiber, includes a tantalum inlay 6534 for transcrew trajectory visualization. In other words, the handles 6532 may include a cylindrical member 6534, which is a radiopaque marker to aid in alignment, for example, using fluoroscopy with the x-ray beam aligned generally in parallel relation to the joint. The marker 6534 runs within the handle 6532 parallel to a longitudinal center axis of the handle. Once the implant 25 is implanted in the joint space as desired, the sleeve 6550 can be removed from the implant arm 110 and the arm assembly 85 with its anchor arm 115 can be coupled to the implant arm 110 in order to allow for the guided delivery of the anchor 30 into the bore 40 of the implant 25 as described herein. As can be understood from FIG. 128A, which is an isometric view of another embodiment of the sleeve 6550 of FIG. 127, the features of the sleeve of FIG. 127 are substantially the features of the sleeve embodiment of FIG. 128A, a main difference being that the handle members 6532 of the embodiment of FIG. 128 include another cylindrical member 6536, which may be another radiopaque marker for alignment visualization. Both markers 6534 and 6536 run within the handle 6532 parallel to a longitudinal center axis of the handle.

Figure 128B:
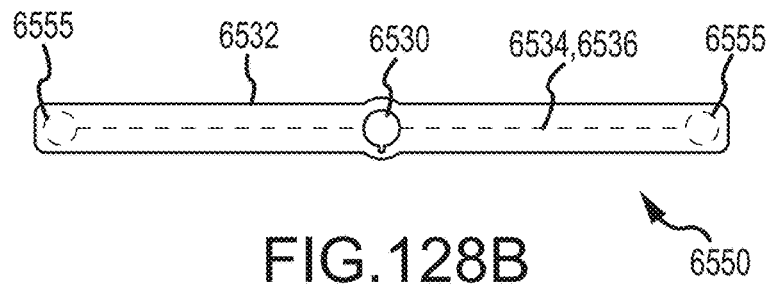
Figure 128C:
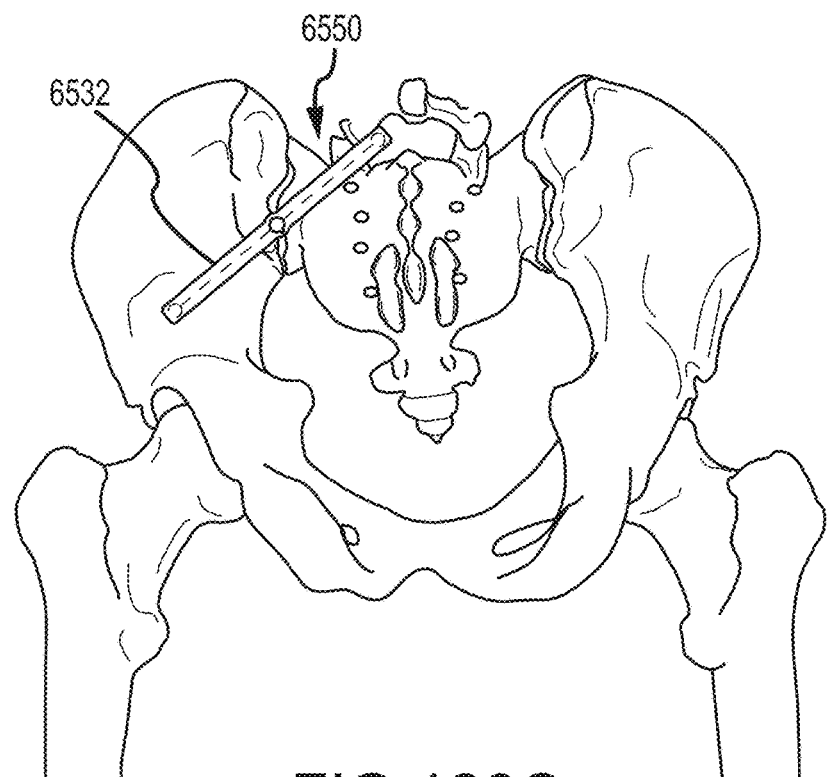

FIG. 128B is an end view of sleeve 6550 of FIG. 128A showing overlapping radiopaque markers 6534 and 6536, which are configured with terminal circle shaped markers 6555. FIG. 128C is a posterior view of the hip region, wherein the sleeve 6550 is being employed. As can be understood from FIGS. 128A-128C, the configuration of the sleeve 6550 permits the operator (e.g. surgeon, computer controlled navigation system, or surgical robot) to visualize and adjust with rotational force the trajectory, relative to anatomic structures, of an anchor 30 which can pass through a bore 40 or pass adjacent to implant 25 in order to avoid violating neurovascular structures or other implants which may already be present or are anticipated to be implanted in proximity to implant assembly 15.

As can be understood from FIGS. 128A-128C, when the implant 25 is coupled to the implant arm 110, a longitudinal axis of the implant 25, a longitudinal axis of the bore 40, and the longitudinal axes of the radiopaque elongated members 6534, 6536 exist in a common plane. In other words, when the implant 25 is coupled to the implant arm 110, the two radiopaque elongated members 6534, 6536, which are spaced apart from each other in the elongated handle member 6532, reside in a plane at least parallel with, if not including, a longitudinal axis of the implant arm 110 and/or a longitudinal axis of the bore 40. As a result, as can be understood from FIGS. 128A-128C, the radiopaque members can be used to ascertain the location and orientation of the bore when the implant is located within the joint space, thereby helping the physician to understand if the anchor to be delivered to or near the implant will adversely impact neurovascular structures.

Referring to FIG. 128B, it can be seen that the two radiopaque markers 6534, 6536 form a single line when viewed along the plane in which both radiopaque markers reside. This single line indicates to the physician the orientation of the bore 40 and a trajectory of an anchor that would be received in the bore 40. Other radiopaque markers may be located on the handle 6550 to convey other information to the physician. For example, additional radiopaque markers similar to markers 6534, 6536 may be located parallel to, and offset from, markers 6534, 6536 so as to convey to the physician a trajectory of an anchor intended to not pass through the bore, but to instead pass adjacent to a side of the implant.

FIGS. 129A-129B show isometric views of another embodiment of the system 10, wherein the delivery tool 20 has a header 6539 with a series of collars 165 and associated sleeves 100 having a variety of pre-defined angular alignments to guide one or more transfixing anchor members 30 into place, thereby providing a choice of delivery angles that are complementary to the implant 25. According to particular embodiments, a sleeve or collar 165 of the header 6539 depicted in FIGS. 129A-129B may have a longitudinal center axis $LCA_1$ similar to the longitudinal center axis $LCA_1$ depicted in FIG. 18, the a longitudinal center axis $LCA_1$ being aligned with a trajectory which either passes into or through a bore 40 of the implant 25 or passes near an implant 25 to further locate an anchor 30 into the bone of a sacrum within certain desirable areas to avoid neurovascular elements and to place the anchor within sacral bone with a higher bone density. For example, depending on the trajectory of the implant 25 and the location of the bore 40 when $LCA_1$ is aligned with said bore versus placing an anchor near an implant and not through a bore, an anchor can terminate generally within the sacral ala, or terminate in the body of the first sacral vertebra while avoiding the first sacral foramina, or terminate in a S2 vertebral body between the first and second sacral foramina, or terminate into the apex of the sacral promontory, or terminate through or within an anterior sacral cortex, or terminate through or near an S1 endplate.

The system 10 includes a delivery tool 20 and an implant 25 for implanting at the sacroiliac joint via the delivery tool 20, the implant 25 being for fusing the sacroiliac joint. As shown in FIGS. 129A and 129B, the delivery tool 20 includes an implant arm 110 and an anchor arm 115. As described herein, the implant arm 110 is configured to releasably couple to the implant 25, and the anchor arm 115 is coupled to the implant arm 110 and configured to deliver the anchor element 30 to the bore 40 of the implant 25. An impactor arm 6546 of the impactor assembly 6550 is removably coupled to handle members 6538 of the arm assembly 85. Additionally, the impactor arm 6546 is removably coupled to the implant arm 110. When the impactor assembly 6550 is coupled to the handle members 6538 as shown in FIG. 129B, impacting an impactor handle 6547 of the impactor assembly 6550 distally causes the implant arm 110, and the rest of the assembly 10 as whole, to displace distally and deliver the implant 25 into the sacroiliac joint space. The delivery tool 20 further includes a retaining member 6548 configured to couple the arm assembly 85 to the implant arm 110 and to engage the implant 25. The other features of the retaining member 6548 may be substantially similar to the retaining member 95 as described above with respect to FIGS. 28-29. Specifically, the retainer member 6548 extends through the implant arm 110 to mechanically interlock with a bore (e.g., center bore 70) of the implant 25 as described herein. During delivery of the implant 25, the arm assembly 85 may be decoupled from the delivery tool 20 for easier delivery of the implant 25 into the joint region. Additionally, the markers 6534 and 6536 can be removable.

As discussed below in greater detail, during the implantation of the implant assembly 15 at the sacroiliac joint, the implant 25 is supported by the implant arm 110 and the arm assembly 85 with its collar header 6539 may be coupled to the implant arm 110 to guide and support one or more anchor elements 30 (not shown). The handle members 6538 may be used to position or guide the implant as it is being distally driven into the sacroiliac joint via impacts delivered to the impactor handle 6547. In some embodiments, the handle 6538 may be constructed of a radiolucent material and may include radiopaque markers 6534 and 6536 similar to those shown in FIGS. 127 and 128 for positioning the implant in the plane of the joint under fluoroscopy.

As described below, the delivery tool 20 is then used to cause the one or more anchor elements 30 to extend through the ilium, the sacrum and the implant 25 generally transverse to the sacroiliac joint and implant 25. The delivery tool 20 is then decoupled from the implanted implant assembly 15, as described herein.

The arm assembly 85 includes the anchor arm 115 with a collar header 6539 extending from the anchor arm. The collar header includes a series of arm members 6540, 6542, and 6544 in which a series of collars 165 are defined at different horizontal and vertical angles. The anchor arm 115 is coupled to the implant arm 110 via the handle members 6538. Depending on the embodiment, the horizontal linear arm member 6540 may include five collars 165e, 165f, 165g, 165h, and 165i, each providing different alignment angles, the horizontal linear arm member 6542 may include two collars 165k and 165j, each providing different alignment angles. The vertical arcuate arm member 6544 may include one additional collar 165l plus already mentioned collar 165f, each providing different alignment angles. It will be appreciated that the collar positions and alignments shown in the embodiment of FIGS. 129A-C are for illustrative purposes only and that other positions and alignments are contemplated.

In one embodiment, as shown in FIGS. 124A-124C, the anchor arm 115 is contoured having an arcuate shape. The anchor arm 115 is received in a vertically extending arm member 6544 of the header 6539. The vertically extending arm member 6544 has an arcuate configuration over its vertical extension that is generally the same as the arcuate configuration of the anchor arm 115 with respect to degree of curvature. Thus, the vertical arcuate arm member 6544 extends from the anchor arm 115 following the same general arcuate path. The arcuate arm member 6544 may be thicker relative to the anchor arm 115 to provide stability during the delivery of the one or more anchor members 30 and sufficient width to accommodate the collars 165f and 165l defined therein as shown in FIG. 129C. The collars 165f and 165l are defined in the generally planar surface of the vertical arcuate arm member 6544.

The collar header 6539 may further include horizontal linear arm members 6540 and 6542, which extend perpendicularly from the vertical arcuate arm member 6544. Members 6540 and 6542 may be manufactured in a fixed configuration or removable configuration with fixed attachment points located along collar header 6539. The horizontal linear arm members 6540 and 6542 have a relative thickness similar to the vertical arcuate arm member 6544 and are generally linear. The horizontal linear arm members 6540 and 6542 include one or more collars 165e-165i and 165k-165j defined on a generally planar surface of each of the horizontal linear arm members 6540 and 6542. The generally planar surfaces of the horizontal linear arm members 6540 and 6542 intersect with the general planar surface of the vertical arcuate arm member 6544 to form a substantially single generally planar surface, as shown best in FIG. 129C. Accordingly, one or more of the collars 165f may be positioned on an intersecting surface of the arcuate arm member 6544 and one of the linear arm members 6540 or 6542.

Each of the collars 165 are configured to receive a sleeve 100 to cause the one or more anchor elements 30 to extend through the ilium, the sacrum and the implant 25 (and/or immediately adjacent to the implant) generally transverse to the sacroiliac joint and implant 25, as described herein. Some collars 165, such as collars 165f, 165i and 165l, may be axially aligned with respective bores of the implant 25 when the implant 25 is supported off of the distal end of the implant arm 110 of the tool 20. As a result, an anchor member 30 may be delivered into each of the bores via the respective anchor collars 165. Collars 165f, 165i and 165l are each indicated to be directed to the bore 40 by a marker 6543 showing two concentric circles. As discussed below and can be understood from FIG. 129C, collar 165l has a zero degree horizontal offset by virtue of being on the vertical arm 6544, which is in parallel alignment to the plane occupied by the implant arm 110 and anchor arm 115. However, collar 165l has a 90 degree vertical offset to the longitudinal axis of the implant arm 110 and the implant 25 mounted thereon such that a sleeve 100 extending through the collar 165l extends in the plane occupied by the implant arm and anchor arm and further extends perpendicular to the longitudinal axis of the implant arm and implant. Because collar 165l is aligned with the bore 40, the anchor delivered to the bore by the sleeve extending through collar 165l will orient the anchor in the bore in a plane occupied by the implant arm and anchor arm, but perpendicular to the longitudinal axis of the implant. Collar 165l may include three overlapping bores that provide a 90 degree alignment angle (or slight angular variations greater than or less than 90 degrees), thereby allowing placement of an anchor 30 (or multiple anchors in general parallel relation), for example through a slot or multiple bores 40 in implant 25, at varied distances between implant ends.

As can be understood from FIG. 129C, collar 165f has a zero degree horizontal offset by virtue of being on the vertical arm 6544, which is in parallel alignment to the plane occupied by the implant arm 110 and anchor arm 115. However, collar 165f has a 45 degree vertical offset to the longitudinal axis of the implant arm 110 and the implant 25 mounted thereon such that a sleeve 100 extending through the collar 165l extends in the plane occupied by the implant arm and anchor arm and further extends at a 45 degree angle to the longitudinal axis of the implant arm and implant. Because collar 165f is aligned with the bore 40, the anchor delivered to the bore by the sleeve extending through collar 165f will orient the anchor in the bore in a plane occupied by the implant arm and anchor arm, but at 45 degrees to the longitudinal axis of the implant.

As can be understood from FIG. 129C, collar 165i has a 30 degree horizontal offset by virtue of being on horizontal arm 6540 at a 30 degree location. In other words, a sleeve 100 extending through collar 165i will approach the implant at an angle that is 30 degrees right of the plane occupied by the implant arm 110 and anchor arm 115. Further, because horizontal arm 6540 is centered horizontally on collar 165f, which has a 45 degree vertical offset to the longitudinal axis of the implant arm 110 and the implant 25 mounted thereon, collar 165i will have a 45 degree vertical offset as described with respect to collar 165f. Thus, a sleeve 100 extending through collar 165i extends at a 30 degree horizontal offset angle to the plane occupied by the implant arm and anchor arm and further extends at a 45 degree offset angle to the longitudinal axis of the implant arm and implant. Because collar 165i is aligned with the bore 40, the anchor delivered to the bore by the sleeve extending through collar 165i will orient the anchor in the bore 30 degrees offset from the plane occupied by the implant arm and anchor arm and at 45 degrees to the longitudinal axis of the implant.

The collars 165e, 165g, 165h, 165j and 165k may be employed to deliver anchor members 30 into the bone of the ilium and sacrum while not passing through a bore 40 of the implant 25 (i.e., according to particular embodiments, preconfigured to place anchor members 30 immediately adjacent the longitudinal side edges of the implant 25). Such offset placement collars 165e, 165g, 165h, 165j and 165k are each indicated as such by a marker 6547 showing a circle tangent to a rectangle, as illustrated in FIG. 129C.

As can be understood from FIG. 129C, collar 165h has a 30 degree horizontal offset by virtue of being on horizontal arm 6540 at a 30 degree location. In other words, a sleeve 100 extending through collar 165i will approach the implant at an angle that is 30 degrees right of the plane occupied by the implant arm 110 and anchor arm 115 and, because the adjacent marker 6547 indicates that the anchor 30 will be delivered adjacent to the implant 25 and not through its bore 40, the anchor will be delivered at the 30 degree angle to the left of the implant. Further, because horizontal arm 6540 is centered horizontally on collar 165f, which has a 45 degree vertical offset to the longitudinal axis of the implant arm 110 and the implant 25 mounted thereon, collar 165h will have a 45 degree vertical offset as described with respect to collar 165f. Thus, a sleeve 100 extending through collar 165h extends at a 30 degree horizontal offset angle to the plane occupied by the implant arm and anchor arm and further extends at a 45 degree offset angle to the longitudinal axis of the implant arm and implant. Because collar 165h is not aligned with the bore 40, the anchor will be adjacent the implant (i.e., not in the bore 40). Also, the anchor 30 delivered by the sleeve extending through collar 165h will orient the anchor adjacent the implant 30 degrees offset from the plane occupied by the implant arm and anchor arm and at 45 degrees to the longitudinal axis of the implant.

As can be understood from FIG. 129C, collar 165j has a 20 degree horizontal offset by virtue of being on horizontal arm 6542 at a 20 degree location. In other words, a sleeve 100 extending through collar 165j will approach the implant at an angle that is 20 degrees right of the plane occupied by the implant arm 110 and anchor arm 115 and, because the adjacent marker 6547 indicates that the anchor 30 will be delivered adjacent to the implant 25 and not through its bore 40, the anchor will be delivered at the 20 degree angle to the left of the implant. Further, because horizontal arm 6542 is centered horizontally at a 70 degree vertical offset to the longitudinal axis of the implant arm 110 and the implant 25 mounted thereon, collar 165j will have a 70 degree vertical offset. Thus, a sleeve 100 extending through collar 165j extends at a 20 degree horizontal offset angle to the plane occupied by the implant arm and anchor arm and further extends at a 70 degree offset angle to the longitudinal axis of the implant arm and implant. Because collar 165j is not aligned with the bore 40, the anchor will be adjacent the implant (i.e., not in the bore 40). Also, the anchor 30 delivered by the sleeve extending through collar 165j will orient the anchor adjacent the implant 20 degrees offset from the plane occupied by the implant arm and anchor arm and at 70 degrees to the longitudinal axis of the implant.

As can be understood from FIG. 129C, collar 165e has a leftward parallel offset by virtue of being on horizontal arm 6540 at a leftward parallel offset location. In other words, a sleeve 100 extending through collar 165e will approach the implant leftward offset from, and parallel to, the plane occupied by the implant arm 110 and anchor arm 115 and, because the adjacent marker 6547 indicates that the anchor 30 will be delivered adjacent to the implant 25 and not through its bore 40, the anchor will be delivered at such a parallel arrangement and to the left of the implant. Further, because horizontal arm 6540 is centered horizontally on collar 165f, which has a 45 degree vertical offset to the longitudinal axis of the implant arm 110 and the implant 25 mounted thereon, collar 165e will have a 45 degree vertical offset as described with respect to collar 165f. Thus, a sleeve 100 extending through collar 165e extends at a leftward parallel offset to the plane occupied by the implant arm and anchor arm and further extends at a 45 degree offset angle to the longitudinal axis of the implant arm and implant. Because collar 165e is not aligned with the bore 40, the anchor will be adjacent the implant (i.e., not in the bore 40). Also, the anchor 30 delivered by the sleeve extending through collar 165h will orient the anchor adjacent the implant at the leftward parallel offset from the plane occupied by the implant arm and anchor arm and at 45 degrees to the longitudinal axis of the implant.

As can be understood from FIG. 129C, collar 165k has a leftward parallel offset by virtue of being on horizontal arm 6542 at a leftward parallel offset location. In other words, a sleeve 100 extending through collar 165k will approach the implant leftward offset from, and parallel to, the plane occupied by the implant arm 110 and anchor arm 115 and, because the adjacent marker 6547 indicates that the anchor 30 will be delivered adjacent to the implant 25 and not through its bore 40, the anchor will be delivered at such a parallel arrangement and to the left of the implant. Further, because horizontal arm 6542 is centered horizontally at a 70 degree vertical offset to the longitudinal axis of the implant arm 110 and the implant 25 mounted thereon, collar 165k will have a 70 degree vertical offset. Thus, a sleeve 100 extending through collar 165k extends at a leftward parallel offset to the plane occupied by the implant arm and anchor arm and further extends at a 70 degree offset angle to the longitudinal axis of the implant arm and implant. Because collar 165k is not aligned with the bore 40, the anchor will be adjacent the implant (i.e., not in the bore 40). Also, the anchor 30 delivered by the sleeve extending through collar 165j will orient the anchor adjacent the implant at the leftward parallel offset from the plane occupied by the implant arm and anchor arm and at 70 degrees to the longitudinal axis of the implant.

Because of the multiple collars 165, the delivery tool 20 may be adjusted to accommodate patients of different sizes and still maintain the angular relationships between the components of system 10 that allows one or more anchor members 30 to be delivered into a bore of the implant 25 and/or into the bone of the ilium and sacrum immediately adjacent the implant, or around the implant with anchor 30 passing through regions 3007 or 1044, without any further adjustment to the delivery tool 20. Because the angular relationships are rigidly maintained between the arms 110, 115, the arm members 6540, 6542, and 6544, the collars 165 of the header 6539, and the implant 25, the anchoring of the implant 25 in the sacroiliac joint via one or more anchor members 30 may be achieved quickly and safely. In other words, because the delivery tool 20, via the multi-angle collar options of the header 6539, provides multiple angular alignments for deploying one or more anchor members 30 and does not need to be adjusted with respect to angular relationships, the surgery is simplified, reduced in duration, and reduces the risk of an anchor member 30 being driven through a nerve, artery or vein. Additionally, collars may be color coded to correspond with particular implants of the same color, which indicates a complementary configuration. Furthermore, sleeves 100 may encounter interference elements within the collars to restrict or reduce axial movement of the sleeve during the course of the procedure (e.g., see discussion above with respect to FIG. 124B2).

While any one or more of the implant embodiments disclosed herein could be employed with the delivery device discussed with respect to FIGS. 129A-129C, one version of the implant as now discussed with respect to FIGS. 129D-129L may be especially advantageous. FIGS. 129D-129K are various views of the implant 25, and FIG. 129L is an enlarged isometric view of the implant 25 of FIGS. 129D-129K mounted on the extreme distal end of the implant arm 110 of the delivery tool 20 of FIGS. 129A-129C.

As shown in FIGS. 129D-129K, the implant 25 includes a distal end 42 and a proximal end 43. The implant also includes a middle planar member 6579 in which a central bore slot 40 is defined so as to extend through the middle planar member 6579. The bore slot 40 may be an elongated oval shape that has a longitudinal axis that is parallel with the longitudinal axis of the implant 25. The elongated shape allows for an anchor 30 to be delivered through the bore slot 40 at a variety of angles via the collars 165f, 165i, and 165l discussed above with respect to FIG. 129C.

The distal end 42 of the middle planar member 6579 has a truncated shape with chamfered edges transition between the planar sides of the planar member and the blunt planar distal face of the distal end of the middle planar member. A small planar wing 6580 forms a T-shaped perpendicular intersection with a first lateral edge of the middle planar member 6579, and a large planar wing 6581 forms a T-shaped perpendicular intersection with a second lateral edge of the middle planar member 6579 opposite the first lateral edge of the middle planar member. Accordingly, as can be understood from FIGS. 129J and 129K, the implant has an I-shaped cross section as viewed from either the distal or proximal ends, the large wing 6581 having a substantially larger (e.g., nearly double) width than the small wing 6580. Additionally, as illustrated in FIGS. 129J and 129K, the implant 25 may include one or more bore shafts 10020 extending between, and daylighting at, the implant distal end 42 and implant proximal end 43. Such shafts 10020 are configured to receive or pass over, for example, guide pins placed in the plane of a sacroiliac joint.

As illustrated in FIG. 129D, like the distal end 42 of the middle planar member 6579, the distal ends of the wings 6580 and 6581 also have truncated shapes with chamfered edges transitioning between the planar sides of the wings and the blunt planar distal faces of the distal ends of the wings. While the planar surfaces of the small wing 6580 may be generally smooth, the planar surfaces of the large wing 6581 may have longitudinally extending evenly spaced apart grooves 6582 defined therein. Alternatively, grooves 6582 may extend perpendicular to length of the implant.

As shown in FIG. 129E, the proximal end 43 of the implant 25 has a groove 6514 that extends from wing to wing across the blunt proximal end 43 of the implant, the groove even extending into the outermost planar surfaces of the wings 6580 and 6581. As can be understood from FIG. 129L, when the implant 25 is mounted on the extreme distal end of the implant arm 110, members 140 similar to those already described herein with respect to FIG. 124D are received in the groove 6514, and the central cylindrical member 220 of the retaining member 95 is received in the proximal opening 70 to retain the implant securely on the distal end of the implant arm 110.

As indicated in FIGS. 129E and 129L, the implant 25 may have similar alignment marks 6583 that help a user to properly mount the implant on the implant arm distal end in a correct orientation relative to each other.

While all the various embodiments of the implant arm 110 discussed above are illustrated in their associated figures as having an arrangement that results in the implant 25 being supported off of the distal end 120 of the implant arm 110 such that the longitudinal axis of the implant arm is essentially axially aligned with the longitudinal axis of the implant arm, in other embodiments, as mentioned above, the implant can be supported off of the distal end of the implant arm in other manners. For example, as can be understood from FIG. 129M, the distal end 120 of the implant arm 110, which forms a distal end 35 of the overall delivery device 20, may be oriented so as to support the implant 25 such that the longitudinal axis of the implant is offset from, but substantially parallel to the longitudinal axis of the implant arm 110. Alternatively, as can be understood from FIG. 129N, the distal end 120 of the implant arm 110 may be oriented so as to support the implant 25 such that the longitudinal axis of the implant is substantially non-parallel to the longitudinal axis of the implant arm 110. For example, the longitudinal axis of the implant may form an acute angle (e.g., 45 degree) angle with the longitudinal axis of the implant arm. Alternatively, the implant arm and sleeve can be arcuate. Regardless of whether the longitudinal axis of the implant is axially aligned with, parallel with, or at an acute angle with the longitudinal axis of the implant arm, the overall delivery device with be so configured such that an anchor 30 can be delivered via the implant arm 115 to a bore 40 in the implant 25 and/or a predetermined location immediately adjacent the implant without having to adjust an angular relationship between the implant arm and the anchor arm.

As shown in FIG. 129O, the implant arm 110 of FIGS. 129M and 129N may be formed mainly of a sleeve 110Z and a retainer rod 110X. The retainer rod 110X may be received coaxially within the sleeve 110Z, as illustrated in FIGS. 129M and 129N.

The retainer rod 110X includes a shaft 10030 that distally terminates in opposed arms 10032, which in turn terminate in retainer arms or prong arms 140. As shown in FIG. 129O, when the rod 110X is free of the sleeve 110Z, the opposed arms 10032 are biased apart, resulting in a space-apart distance indicated by arrow D that is sufficiently wide to allow the implant 25 to be received between the prong arms 140 at the rod distal end 120.

As indicated in FIG. 129O, the sleeve 1102 includes a distal end 10040, a proximal end 10042, slots 10044 that extend into the hollow interior of the shaft of the sleeve 110Z. The slots 10044 provide opening into the hollow interior to facilitate sterilization of the sleeve 110Z via an autoclave. A knurled gripping surface 10046 is defined near the sleeve proximal end 10042 so as to facilitate rotation of the sleeve relative to the rod when the threads 110Y are being threadably engaged.

As can be understood from a comparison of FIGS. 129M, 129N and 129O, when the sleeve 110Z is advanced distally over the retainer rod 110X, complementary threads 110Y on both the sleeve 110Z and retainer rod 110X can be engaged and the sleeve can be rotatably driven distally by said thread engagement. The sleeve 110Z advancing distally causes prong arms 140 of the retainer rod 110X to draw toward one another and in turn cause the portion of the retainer rod which couples to the implant 25 to grasp said implant as can be understood from FIGS. 129L, 131G and 131H. The complementary threads when engaged may prevent proximal movement of the sleeve 110Z relative to the rod 110X and allow the coupling of implant and retainer rod to continue throughout the course of the procedure. After implantation the sleeve 1102 may be caused to move proximally along the retainer rod 110X in order to decouple the aforementioned tool and implant arrangement.

To illustrate the methodology associated with employing the delivery tool 20 of FIGS. 129A-129C in implanting any of the above-described implants 25 in the sacroiliac joint 1000 of a patient 1001, reference is made to FIGS. 130A-130I. Specifically, FIGS. 130A-130B show anterior views of the hip region with the system of FIGS. 129A-129C, wherein the ilium is shown and hidden, respectively. FIGS. 130C-130G show anterior-superior-lateral, posterior, superior, lateral, and inferior views of the hip region with the system of FIGS. 129A-129C. FIGS. 130H and 130I show inferior and posterior-lateral views of a patient, wherein the system of FIGS. 129A-129C is inserted through the soft tissue of the hip region. As can be understood from FIGS. 130A-130I, the curvature of the anchor arm 115 and the arm members 6540, 6542, and 6544 mirror the shape of the hip region 1002 to simplify surgery and increase reliability of alignment. Also, the implant 25 may be inserted into the sacroiliac joint via the implant arm 110 via the approach discussed in detail with respect to FIGS. 103A-108A, the main difference being that the multi-collar header 6539 facilitating the delivery of the one or more anchors 30 into or around implant at a variety of locations and angled approaches.

A tool similar to that of FIGS. 129A-129C can be configured to be employed for the approaches illustrated in FIGS. 111-112. For example, for an approach similar to FIG. 111, a tool similar to FIGS. 129A-129C may be configured without collars 165*e*, 165*g*-165*h*, 165*j* and 165*k*, because these omitted collars if used for a procedure as shown in FIG. 111 could undesirably direct an anchor anterior of the sacrum or ilium and outside a safe and desirable anchor trajectory. Additionally, collar 165*i* may be employed to direct an anchor 30 which passes through an ilium and into and terminating in a bore 40 of an implant 25 as to not pass into the bone of the sacrum.

As another example, a tool similar to FIGS. 129A-129C may be configured, with 6540 and 6542 being mirrored over 6544 as to generally direct an anchor through a bore 40 of an implant 25 with a trajectory that is more anterior to posterior or which directs an anchor generally posterior to an implant 25 when the anchor is being positioned adjacent to an implant 25.

According to particular embodiments, for example, for an approach similar to FIG. 112, a tool similar to FIGS. 129A-129C may be configured without collars 165*e*, 165*g*-*h*, 165*j* and 165*k*, because these omitted collars if used for a procedure as shown in FIG. 112 could undesirably direct an anchor inferior to the sciatic notch and outside a safe and desirable anchor trajectory. As an example, a collar or series of collars could be configured to align with a bore 40 or aligned to pass an anchor 30 above or superior to an adjacent implant 25 with, for example, collars with a 45-70 degree vertical offset to the longitudinal axis of the implant arm 110 (and the implant 25 mounted thereon), and 0-45 degree horizontal offset (with 0 degrees being parallel alignment to the plane occupied by the implant arm 110 and anchor arm 115).

As can be understood from FIGS. 131A-131B, which show isometric views of another embodiment of the system 10, the delivery tool 20 of FIGS. 131A-131B is substantially the delivery tool of FIGS. 129A-129C, a main difference being that the collar header 6539 does not include the second horizontal linear arm member 6542 extending from the vertical arcuate arm member 6544 and that the arm members 6540 and 6544 include fewer collars 165, as described below with respect to FIG. 131C. Specifically, the first horizontal linear arm member 6540 and the vertical arm 6544 of the embodiment of FIGS. 131A-131C include the same collar locations, angular arrangements and markers as is the case of the arms 6540 and 6544 of the embodiment of FIGS. 129A-129C. FIGS. 131A-131C show the impactor assembly 6550 decoupled from the implant arm 110 and the handle members 6538. However it will be understood that the impactor assembly 6550 may be coupled to the implant arm 110 and the handle members 6538, as described with respect to FIGS. 129A-129C.

For a detailed discussion of the angular alignments of the collars 165, reference is made to FIG. 131C, which shows an enlarged view of the arm assembly 85 with the collar header 6539. As discussed with respect to FIG. 129C, the horizontal linear arm member 6540 intersects with the vertical arcuate arm member 6544 such that one or more of the collars 165 may be positioned on both the arcuate arm member 6544 and the linear arm member 6540. As shown in FIG. 131C, the arcuate arm member 6544 may include two linearly aligned collars 165*p* and 165*q* providing different alignment angles that are respectively the same as collars 165*f* and 165*l* of the embodiment discussed with respect to FIG. 129C. For example, the collar 165*p* may provide a 45 degree alignment angle and the collar 165*q* may include three overlapping bores that provide a 90 degree alignment angle. The linear arm member 6540 may include four collars 165*p*, 165*o*, 165*n*, and 165*m* that are respectively the same as collars 165*f*, 165*g*, 165*h* and 165*i* of the embodiment discussed with respect to FIG. 129C. For example, the collar 165*o* may provide a 15 degree alignment angle and the collars 165*n* and 165*m* may each provide a 30 degree alignment angle from different locations on the linear arm member 6540. It will be appreciated that the collar positions and alignments shown in the embodiment of FIGS. 131A-C are for illustrative purposes only and that other positions and alignments are contemplated.

FIGS. 131D-131E are isometric view of a version of the implant of FIGS. 129D-121K adapted for use with the delivery system of FIGS. 131A-131C. As can be understood from a comparison of implant embodiment shown in FIGS. 131D-131E to the implant embodiment illustrated in FIGS. 129D-129E, the main difference between the two versions of the implant is that the elongated single bore slot 40 has changed to two circular bores 40. Polyethylene bushings may define a portion of the bore holes 40 of FIGS. 131D-131E.

In one embodiment, the implant 25 and a distal extension 5777 of the distal end of the implant arm 110 can be configured to receive and remove cartilage from the sacroiliac joint. For example, as shown in FIG. 131F, which is an isometric view of a version of the implant of FIGS. 129D-129K, the body 45 of the implant 25 is hollow along its longitudinal length and daylights at its proximal end 43 and distal end 42 in the form of proximal opening 5778 and distal opening 5779. The side walls of the body 45 extending between the large wing 6581 and small wing 6580 may include openings 5780 that extend into the hollow interior of the body 45. The openings may have a triangular or other shape.

As illustrated in FIG. 131G which is an isometric view of the distal extension 5777 of the distal end of the implant arm 110, the distal extension 5777 is a hollow rectangular box having generally smooth outer wall surfaces. As can be understood from FIG. 131H, which is an isometric view of the implant arm distal extension 5777 received in the hollow body of the implant 25, the distal extension 5777 is configured to be received in a mating fashion that substantially matches and fills the hollow body of the implant 25 when the implant is supported off of the distal end of the implant arm 110. The matching arrangement between the distal extension 5777 and the hollow interior of the body 45 of the implant 25 is readily understandable from FIG. 131I, which is an isometric longitudinal cross section of the implant arm distal extension and implant supported thereon as taken along section line 131I-131I of FIG. 131H. As indicated in FIG. 131I, the interior wall surfaces of the implant arm distal extension 5777 includes raised teeth-like ridges 5781 that are oriented proximally to prevent cartilage contained in the hollow interior of the extension 5777 from distally exiting the extension 5777.

In use, the implant 25 is supported on the extension 5777 as depicted in FIGS. 131H and 131I and driven into the sacroiliac joint, thereby causing cartilage to be sliced by the leading distal rectangular edges 5782 of the extension 5777 and received in the confines of the hollow interior of the extension 5777. Once the implant 25 is positioned as desired in the sacroiliac joint and then decoupled from the distal end of the implant arm 110, the implant arm 110 can be proximally withdrawn, thereby causing the extension 5777 to proximally exit the confines of the hollow interior of the implant body 45. As the extension 5777 proximally withdraws, the teeth 5781 engage the cartilage located in the confines of the hollow extension 5777, causing the cartilage to be maintained in the confines of the hollow extension as it is proximally withdrawn from the sacroiliac joint, thereby extracting the cartilage from the sacroiliac joint. The void resulting from the withdrawal of the cartilage, which happens to be the hollow interior of the implant body 45, can then be filled with a metal or polymer structure to support the walls of the implant body 45 or, alternatively, the void can be filled with a bone growth promoting material to cause bone to infill the body of the implanted implant.

In one embodiment, the hollow extension 5777 is not part of the distal end of the implant arm 110, but is instead simply an insert 5777 portion of the implant 25. Thus, the insert 5777 is placed in the implant 25 and both are then supported off of the distal end of the implant arm 110. The implant and insert 5777 are then driven into the sacroiliac joint. The implant and insert 5777 are then decoupled from the distal end of the implant arm 110 and left in the sacroiliac joint as the implant arm 110 is proximally withdrawn from the patient. The extractor 6583 described below with respect to FIGS. 134A-134E can then be employed to extract the cartilage filled insert 5777 from the confines of the implant 25, which remains behind in the sacroiliac joint.

FIG. 132A is an isometric view of yet another embodiment of the system 10 for fusing a sacroiliac joint. The system 10 includes an impactor assembly 6550, an impactor arm 110, and a retainer 6548, which is substantially the impactor assembly, impactor arm, and retainer described with respect to FIGS. 129A-129C. The system 10 further includes an arm assembly 85 having handle members 6528, which have substantially the same features as the handle members 6538 described with respect to FIGS. 129A-129C, a main difference being that the handle members 6538 of FIGS. 132A-132B are generally cylindrical, as opposed to the generally rectangular shape of the handle members 6538 of FIGS. 129A-129C.

As shown in FIG. 132B, which is the same view as FIG. 132A, except the system is exploded to better illustrate its components, the anchor arm 115 is contoured and curves along an arcuate path to provide axial alignment between a collar 165 and a bore or other anchor member receiving features on the implant 25. The collar 165 is configured to receive a sleeve 100 to cause the one or more anchor elements 30 to extend through the ilium, the sacrum and the implant 25 generally transverse to the sacroiliac joint and implant 25, as described herein.

The anchor arm 115 is coupled to the implant arm 110 with a locking member 6556. Specifically, as can be best understood from FIG. 132B, the anchor arm 115 includes an engaging member 6568 configured to slidably couple with a channel 6566 of the implant arm 110. The coupling arrangement may be achieved via a dovetail arrangement of the channel and pins received in holes of the coupling arrangement. Once the anchor arm 115 is coupled to the implant arm 110, a distal end 6572 of the locking member 6556 is introduced through an opening 6570 to secure the anchor arm 115 to the implant arm 110. To engage the implant 25, the retaining member 6548 is introduced through an opening 6564 in the implant arm 110 such that a distal end 6562 of the retaining member 6548 may engage the implant 25, as described herein. Finally, a distal end 6558 of the impactor assembly 6550 may be introduced into an opening 6560 on the implant arm 110 to couple the impactor assembly 6550 to the implant arm 110 such that displacing the impactor assembly 6550 causes the implant arm 110 to deliver the implant 25 to the joint region, as described herein. The handles 6538 are removable from the rest of the assembly.

For a detailed discussion of yet another of the system 10 for fusing a sacroiliac joint, reference is made to FIGS. 133A-133G As can be understood from FIGS. 133A, 133B, and 133E, an implant assembly includes the implant arm 110, an elbow 6581, and a linear implant member 6580. The implant arm 110 has generally the same features as the implant arm 110 described above and have an implant removably coupled to a distal end of the implant arm via any of the above described configurations, including a retainer member 6548 (see FIG. 132B) extending through the implant arm. As shown in FIGS. 133A, 133B, and 133E, the implant arm 110 is coupled to the linear implant member 6580 via the elbow 6581. Specifically, the linear implant member 6580 and the implant arm 110 intersect at the elbow 6581 such that the implant arm 110 and the linear implant member 6580 are positioned at an angle relative to each other. The elbow 6581 may serve as an impactor area for being impacted by an impactor in driving the implant supported on the end of the implant arm into the joint. The linear implant member 6580 is removably coupled to the arm assembly 85 at the anchor arm 115. In other words, the linear implant member 6580 is inserted into or otherwise couple to the anchor arm 115 and secured with the locking member 6556.

The anchor arm 115 is coupled to a linear arm member 6578, which is coupled to an arcuate arm member 6576. In one embodiment, the linear arm member 6578 is generally parallel with the linear implant member 6580 and the arcuate arm member is generally parallel with the anchor arm 115. The arcuate arm member 6576 is contoured and curves along an arcuate path to provide axial alignment between collars 165 and a bore or other anchor member receiving features on the implant 25. The collars 165 are each configured to receive a sleeve 100 to cause the one or more anchor elements 30 to extend through the ilium, the sacrum and the implant 25 generally transverse to the sacroiliac joint and implant 25, as described herein.

As indicated in FIG. 133A by dimension line R, the arcuate arm member 6576 may have a curvature with a radius of between approximately 120 mm and approximately 180 mm with an arcuate length between the arrow ends of dimension line R of between approximately 200 mm and approximately 400 mm. As shown in FIG. 133B, the U-shaped linear arm member 6578 of the anchor arm 115 extending from the proximal end of the arcuate arm member 6576 and leading to the proximal end of the implant arm 110 has a distal linear segment with a length L1 of approximately 145 mm, a middle linear segment with a with a length L2 of between approximately 50 mm and approximately 80 mm, and a proximal linear segment with a length L3 of between approximately 95 mm and approximately 145 mm.

To illustrate the methodology associated with employing the delivery tool 20 of FIGS. 133A, 133B, and 133E in implanting any of the above-described implants 25 in the sacroiliac joint 1000 of a patient 1001, reference is made to FIGS. 133C, 133D, 133F and 133G Specifically, FIGS. 133C and 133F show the same tool orientations as FIGS. 133B and 133E, respectively, except the system 10 is inserted through the soft tissue 1003 of the hip region 1002 of the patient 1001. FIG. 133D is the same view as FIG. 133C, except the soft tissue is hidden to show the patient bone structure. FIG. 133G is the same view as FIG. 133F, except the soft tissue is hidden to show the patient bone structure.

As can be understood from FIGS. 133C and 133F, the curvature and relative positions of the features of the implant assembly and the arm assembly mirror the shape of the hip region 1002 to simplify surgery and increase reliability of alignment. Further, the system 10 is relatively compact such that it does not hinder movement during an operation. Also, the implant 25 may be inserted into the sacroiliac joint via the implant arm 110 via the approach discussed in detail with respect to FIGS. 103A-108A, the main difference being that the arcuate arm member 6576 is contoured and curves along an arcuate path to provide axial alignment between multiple collars 165 and a bore or other anchor member receiving features on the implant 25.

The embodiment of FIGS. 133A-133G can be used for other surgical approaches such as, for example, the approaches illustrated in FIGS. 111A-112C. For example, for the approach shown in FIGS. 111A-111C, it may be preferred to employ the 45 degree collar of the anchor arm 115, while for the approach depicted FIGS. 112A-112D, it may be preferred to employ the 90 degree collar of the anchor arm 115 (i.e., the sleeve 100 that is generally perpendicular to the longitudinal axis of the implant arm 110 and the implant 25 supported off of the implant arm.

The embodiment depicted in FIGS. 133A-133G offers a number of advantages. First, this embodiment provides more grasping area for the medical professional employing the device and allows for the hand and other body parts of the medical professional to be further from the x-ray beam of the fluoroscope. Also, the embodiment provides for increased visualization of the surgical site by the medical professional. Portions of the device, for example, 6578 are out of the area being x-rayed for fluoro visualization, increasing the visualization possible via fluoroscopy. Finally, clamps can be employed on the device that can be used to secure the device to a surgical table out of the way of the x-ray beam or the imaging equipment.

For a detailed discussion of an embodiment of a system 6583 for extracting an implant, reference is made to FIGS. 134A-134E. As can be understood from FIG. 134A, the system 6583 includes a handle 90 and an implant retainer 95, which have features substantially similar to the handle 90 and implant retainer 95 described herein, for example, with respect to FIG. 3. Further, the system 6583 includes a distal end 6584 having a hook 6586, which is adapted to engage with an engaging portion 6588 of the implant 25.

In one embodiment, as can be understood from FIGS. 129A-129C (and in a similar fashion from FIGS. 131A-131C, and 133A, 133B and 133E for other embodiments), a sacroiliac joint fusion system 10 includes a joint implant 25, an anchor element 30 and a delivery tool 20. The joint implant includes a distal end 42 and a proximal end 43 opposite the distal end. The anchor element comprising a distal end and a proximal end. The delivery tool includes an implant arm 110 and an anchor arm 115. The implant arm includes a proximal end and a distal end. The implant arm distal end is configured to releasably couple to the proximal end of the joint implant. The anchor arm includes a proximal end, a distal end, a header 6539 and a member 100. The proximal end of the anchor arm is coupled to the implant arm, and the header is supported on the anchor arm near the distal end of the anchor arm. The header includes at least first and second guide holes (e.g., any two or more of guide holes 165e-165l). The first guide hole (e.g., anyone of guide holes 165e-165l) is configured to orient the member 100 when received in the first guide hole in a first approach aimed at least in the vicinity of the joint implant 25 when the proximal end 43 of the joint implant is releasably coupled to the distal end of the implant arm 110. Similarly, the second guide hole (e.g., any one of guide holes 165e-165l other than the first guide hole) is configured to orient the member when received in the second guide hole in a second approach aimed at least in the vicinity of the joint implant 25 when the proximal end 43 of the joint implant is releasably coupled to the distal end of the implant arm 110. The first and second approaches are different. The member 100 is configured to guide the delivery of the anchor element 30 to at least in the vicinity of the joint implant 25 when the proximal end 43 of the joint implant is releasably coupled to the distal end of the implant arm 110.

Depending on the embodiment, the joint implant 25 includes a body 45 extending between the distal and proximal ends 42, 43 of the joint implant 25 and an anchor hole 40 extends through the body non-parallel to a longitudinal axis of the joint implant. The first approach is aimed so as to cause the member 100 when received in the first guide hole to guide the anchor element 30 into the anchor hole. A longitudinal axis of the implant arm 110 may be substantially at least one of coaxial or parallel with the longitudinal axis of the joint implant 25.

The header 6539 may include a first arm 6544 that generally exists in a plane defined by at least portions of the implant arm 110 and the anchor arm 115. The first and second guide holes 165f, 165l are spaced apart from each other along the first arm and the respective first and second approaches are non-parallel to each other.

The header 6539 may include a first arm 6540 or 6542 that generally exists in a plane generally perpendicular to a plane defined by at least portions of the implant arm 110 and the anchor arm 115. The first and second guide holes (e.g., any two of 165e-165i or 165j-165k, depending on which arm

6540, 6542) are spaced apart from each other along the first arm and the respective first and second approaches are non-parallel to each other.

The header 6539 may include a first arm 6544 and a second arm 6540 or 6542. The first arm generally exists in a first plane defined by at least portions of the implant arm 110 and the anchor arm 115. The second arm generally exists in a second plane generally perpendicular to the first plane. The first guide hole (e.g., any one of 165f or 165l) is located on the first arm and the second guide hole (e.g., any one of 165e-165i or 165j-165k, depending on which arm 6540, 6542) is located on the second arm. In such an embodiment, the first and second approaches are substantially parallel to each other (e.g., where the first and second guide holes are 165f and 165e) or the first and second approaches are non-parallel to each other (e.g., where the first and second guide holes are 165l and 165h).

In one embodiment, as can be understood from FIGS. 129D-129K, the joint implant 25 includes a distal end 42, a proximal end 43, and a body 6579 extending between the distal and proximal ends. An anchor hole 40 extends through the body non-parallel to a longitudinal axis of the joint implant. A first planar member 6581 extends generally perpendicular to a first lateral edge of the body 6579 of the joint implant 25, and a second planar member 6580 extends generally perpendicular to a second lateral edge of the body of the joint implant opposite the first lateral edge. The body 6579 is substantially a planar member. The first planar member 6581 is larger in at least one of length or width than the second planar member 6580.

As can be understood from FIGS. 131F-131I, in one embodiment, the body 45 may be generally hollow and include a hollow open-ended insert 5777 that substantially occupies in a generally mating manner the hollow body. The insert is removable from the body. The insert may include textured interior wall surfaces. The interior wall surfaces define a hollow interior of the insert. The insert may be separate from the distal end of the implant arm 110 or may be an extension of the implant arm.

As will be appreciated from FIGS. 134B-134C, which show enlarged views of the distal end 6584 of the system of FIG. 134A, wherein the distal end 6584 is decoupled and coupled to the implant, respectively, the handle 90 may displace longitudinally to advance the distal end 6584 towards the implant 25. As best shown in FIGS. 132B, 134C and 134D, the hook 6586 may have angular features to form a general "L-shape." As can be understood from FIG. 134D and FIG. 134F, which is an isometric view of the proximal end of the implant of FIGS. 134B-134C, the proximal end 43 of the implant has a central opening 70 which has an elongated section 70A extending radially outward from a centerline of the central opening 70. The elongated section 70A transitions to a side opening 70B that is a transverse radial extension of the central opening that daylights at the surface of a wing portion 50 of the implant 25.

The hook 6586 may engage the implant 25 by entering the opening 70 in the proximal end of the implant 25 such that the hook 6586 passes through the elongated section 70A and enters the side opening 70B to engage with an inner surface of the implant 25 in the engaging portion 6588. After the hook 6586 is coupled to the engaging portion 6588, the implant 25 may be extracted via repeatedly sliding the handle along the retainer 95 to cause the handle to repeatedly impact the cap 6599 of the retainer 95.

As can be understood from FIG. 134E, which is the same view as FIG. 134A, except the system is exploded to better illustrate its components, the implant retainer 95 and the handle 90 have substantially similar features to the handle 90 and the implant retainer 95 described herein, for example, with respect to FIG. 3, a main difference being that the shape of the handle 90 is contoured to fit into the palm of a user's hand and the handle is configured to slide along the retainer so as to allow impacting against the cap 6599 to create a proximally directed impacting force that can be used to extract the implant from a sacroiliac joint. The implant retainer 95 is introduced through the handle 90, as described herein, such that a distal end 6582 of the implant retainer 95 may be coupled with a proximal end 6590 of the distal end 6584.

In one embodiment, as can be understood from FIGS. 134A-134E, the extractor 6583 is configured to remove a joint implant 25 including a distal end 42, a proximal end 43 opposite the distal end, a body extending between the distal and proximal ends, and an opening 70 defined in the proximal end so as to define an inward edge 6591. The extractor 6583 includes a distal end 6584, a proximal end 6599, a shaft 95 extending between the distal and proximal ends of the extractor, and a handle 90 displaceable along the length of the shaft back and forth proximal-distal. The shaft 95 includes a distal abutment 6593 and a proximal abutment 6599 respectively near distal and proximal ends of the shaft. The handle 90 is supported on the shaft 95 between the distal and proximal abutments. The distal end 6584 of the extractor 6583 includes a feature 6586 configured to engage the inward edge 6591 when the feature is received in the opening 70. The feature may be a hook or L-shaped.

As can be understood from FIGS. 134A-134E, and with continuing reference to FIG. 126B, in one embodiment, an anchor 40 can be configured as a cable with an end that is able to be received in side opening 70B and further configured to allow a setscrew that may be advanced down central opening 70 (and with abutting elements received in 70A) to abut the cable end so as to anchor the cable end within implant 25. The other end of the cable can pass through the plane of the sacroiliac joint and communicate with components of a pelvic or spinal fixation system.

For a discussion of an embodiment of the implant 25 that is configured to have a shape that generally mimics and even substantially fills a sacroiliac joint space, reference is made to FIGS. 135A-135C. As can be understood from a comparison of the side view of the implant 25 as illustrated in FIG. 135C to the shape of the sacroiliac joint articular region 1044 depicted in FIG. 106B, the implant has an overall exterior shape that generally mimics the sacroiliac joint articular region 1044. The anatomic implant 25 can be provided from the manufacturer in the configuration generally as shown in the FIGS. 135A-135C or assembled or deployed in situ from multiple pieces, as discussed in further detail below. As illustrated in FIGS. 135A-135C, the implant 25 includes a proximal end 43 for being removably coupled to the extreme distal end of an implant arm of any of the above described delivery devices 20. The implant proximal end 43 includes grooves 6514 and holes 75 that interface and couple with members 140 and 150 on the implant arm 110 similar to those described above with respect to FIG. 124D and FIG. 19, respectively.

The implant 25 includes a long portion 7100 and a short portion 7101 perpendicularly oriented to the long portion. The long portion transitions smoothly into the short portion via a small radius 7102 and a large radius 7103 opposite the small radius. The large radius and small radius form an elbow region 7104 of the implant. The large radius forms a heal region 7105 of the implant, and opposite the heal region is a blunt toe region 7106 forming a right angle with a base region 7107 that is generally parallel to the proximal end 43. These regions 7105-7107 form the distal end 42 of the implant 25.

The implant 25 can be configured similar to previously described implant embodiments wherein the body of the implant is a generally continuous solid surface with one or more bores 40 defined therein. However, as indicated in FIGS. 135A-135C, the implant 25 may have a skeletonized configuration, wherein the is an outside frame boundary 7110 that extends unbroken and unitary through all of the above-mentioned regions of the implant, thereby forming it outer boundary while the interior of the implant is generally open space across which support members 7112 extend to join the outside frame boundary 7110 at different locations. As a result of its open configuration, one or more anchors 30 may be extended through the implant when implanted in the sacroiliac joint. When implanted via the approach depicted in FIGS. 103A-108B, it can be understood that the shape of the implant 25 of FIGS. 135A-135C may at least somewhat resemble the sacroiliac joint space and more fully occupy the joint space than some of the more linearly shaped rectangle and cylindrical implant embodiments described above.

As can be understood from FIGS. 135A-135C, in one embodiment, a sacroiliac joint fusion implant 25 includes a proximal end 43, a distal end 42 generally opposite the proximal end, and first and second lateral sides 7117, 7118 extending between the proximal and distal ends and defining a long portion of the implant 7100 and a short portion 7107 of the implant. The long portion is longer than the short portion and the two portions extend in directions generally perpendicular to each other. The proximal end terminates proximally in a generally blunt end 7119 and the distal end terminates distally in a generally blunt end 7106 facing in a direction generally perpendicular of the direction faced by the generally blunt end of the proximal end.

The generally blunt end of the proximal end is configured to releasably couple to an implant delivery system. The region of the implant between the lateral sides is open except for at least one cross member 7112 extending between the lateral sides 7117, 7118. An offset distance between the lateral sides is substantially greater than a thickness of the implant. The first lateral side 7118 transitions between the long and short portions 7100, 7101 via a first curved portion 7103 and the second lateral side 7117 transitions between the long and short portions via a second curved portion 7102 having a radius smaller than the first curved portion. The first and second lateral sides define a shape resembling a shape of an adult human sacroiliac joint as viewed in a direction perpendicular a plane of the sacroiliac joint. For example, the first and second lateral sides define a shape resembling a boot for a human foot.

For a discussion of an embodiment of the implant 25 that is configured to have a shape that generally mimics and even substantially fills a sacroiliac joint space after in situ deployment of certain components of the implant 25, reference is made to FIGS. 136A-136J. As shown in FIGS. 136A-136B and 136F-136I, in one embodiment, the implant 25 includes a distal or leading end 42, a proximal or trailing end 43, a longitudinally extending body 45, a rectangular void 7540 extending through the body, and keels, fins or planar members 50, 55 that radially extend outwardly away from the body 45. In one embodiment, the radially extending planar members 50, 55 may be grouped into pairs of planar members 50, 55 that are generally coplanar with each other. For example, planar members 50 that are opposite the body 45 from each other generally exist in the same plane. More specifically, as best understood from FIGS. 136F and 136G, the planar faces 60 of a first planar member 50 are generally coplanar with the planar faces 60 of a second planar member 50 opposite the body 45 from the first planar member 50. Likewise, the planar faces 65 of a third planar member 55 are generally coplanar with the planar faces 65 of a fourth planar member 55 opposite the body 45 from the third planar member 55. The body 45 may be a distinct central portion of the implant or may simply be an intersection of the four planar members 50, 55.

As best understood from FIGS. 136F and 136G, one set of planar members 50 (i.e., the large planar members 50) may extend radially a greater distance than the distance extended radially by the other set of planar members 55 (i.e., the small planar members 55). Also, the width of a large planar member 50 from its outer edge to its intersection with the body 45 may be greater than the width of a small planar member 55 from its outer edge to its intersection with the body 45. Also, the thickness of the large planar members 50 may be greater than the thickness of the small planar members 55. Thus, one set of planar members 50 may be both wider and thicker than the other set of planar members 55. In other words, one set of planar members 50 may be larger than the other set of planar members 55.

As can be understood from FIGS. 136A-136D, a toe member 7541 having a square or rectangular boxed shape is supported in the implant body 45 near the distal end 42. The toe member 7541 is moveably supported on rails 7542 relative to the rest of the implant and can be caused to move perpendicularly to the longitudinal axis of the implant 25 from a recessed location in the implant to a position that causes the toe member 7541 to project past the extreme edge face of one of the large planar members 50 such that the implant changes from having a rectangular box-like configuration to a boot or L-shaped configuration.

As can be understood from FIGS. 136E and 136J, the toe member 7541 includes slots 7543 that matingly engage with the rails 7542 such that the slots can slide along the rails. A fluid conduit 7545 extends from the proximal end 43 to a cylinder housing 7546 in which a piston 7547 of the toe member is displaceably received. An O-ring 7548 seals the interface between the cylinder inner wall and the outer circumferential piston surface. A pressurized fluid applied to the piston 7547 via the fluid conduit 7545 causes the toe member 7541 to move out of the rest of the implant so as to project laterally from the rest of the implant as indicated in FIGS. 136C-136D.

As illustrated in FIG. 136J and more clearly in FIGS. 136K and 136L, which are respective enlarged views of the upper and lower cylinder regions of FIG. 136J, a lip 10050 defined in the upper end of the cylinder housing 7546 and a lip 10051 defined in the lower end of the piston 7547 interact to provide an extreme limit to outer movement of the toe member 7541. Thus, the lips act as stops to prevent the toe member from extending off of the rest of the implant due to over extension of the piston in the cylinder.

While the deployment mechanism depicted in FIGS. 136E and 136J accomplishes the deployment of the toe member 7541 hydraulic or pneumatic lifting mechanism, in other embodiments the deployment mechanism may be via a screw or gear arrangement (e.g., spur, helical, rack, bevel, miter, worm, ratchet or pawl gears). Additionally, locking mechanisms may be employed to prevent backward movement of the toe member after deployment.

As can be understood from FIGS. 136A-136J, in one embodiment, the sacroiliac joint fusion implant 25 includes a proximal end 43, a distal end 42 generally opposite the proximal end, first and second lateral sides 50, 50 extending between the proximal and distal ends, and a member 7541 near the distal end configured to displace from a first position to a second position. As indicated in FIGS. 136A-136B, the first position may be such that the member 7541 is generally recessed within the implant 25 such that a lateral side surface of the member is generally flush with the first lateral side 50. As shown in FIGS. 136C-136D, the second position may be such that the member 7541 extends from the first lateral side 50, the lateral side surface of the member being offset from and generally parallel to the first lateral side. The member 7541 may be displaceably supported on the implant via a rail arrangement 7542, 7543. As indicated in FIGS. 136E and 136J, the implant 25 may be in the form of an actuation mechanism that drives the member from the first position to the second position and is actuatable via an access at the proximal end. For example, the actuation mechanism may include a hydraulic, pneumatic, geared or screwed mechanical arrangement.

Figure 137C:
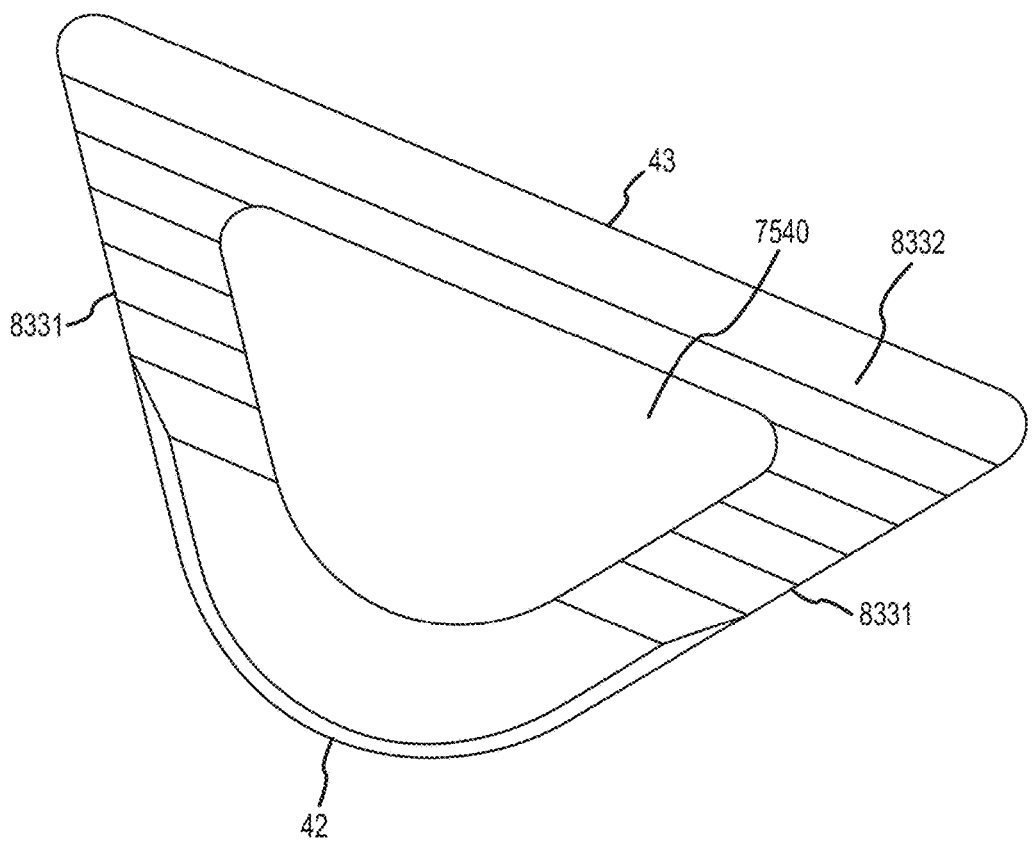
Figure 137D:
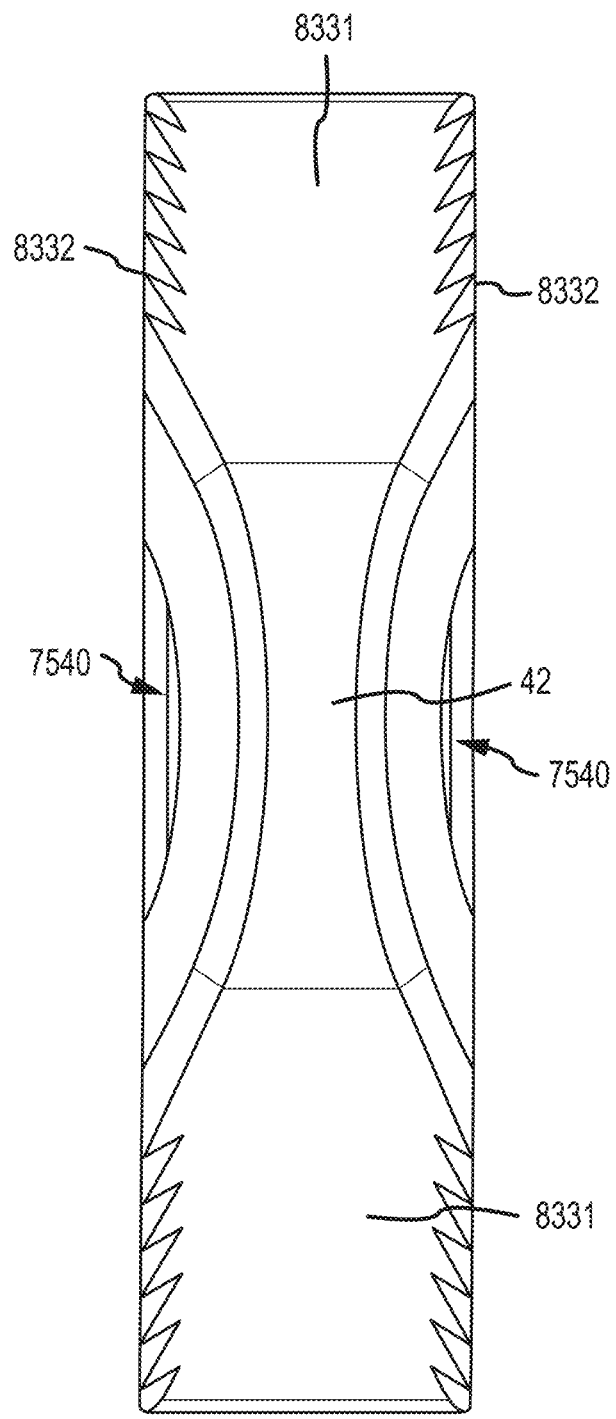
Figure 137E:
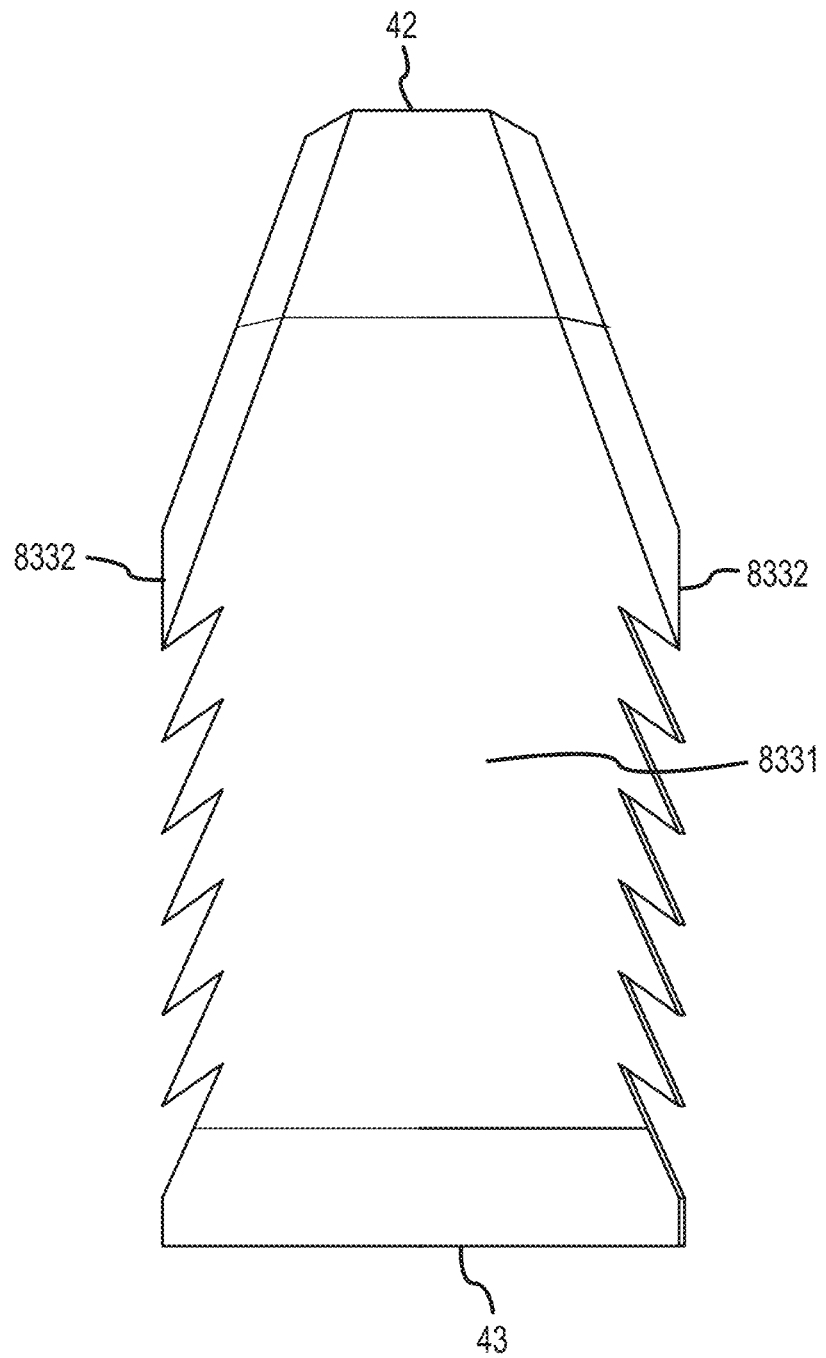
Figure 137F:
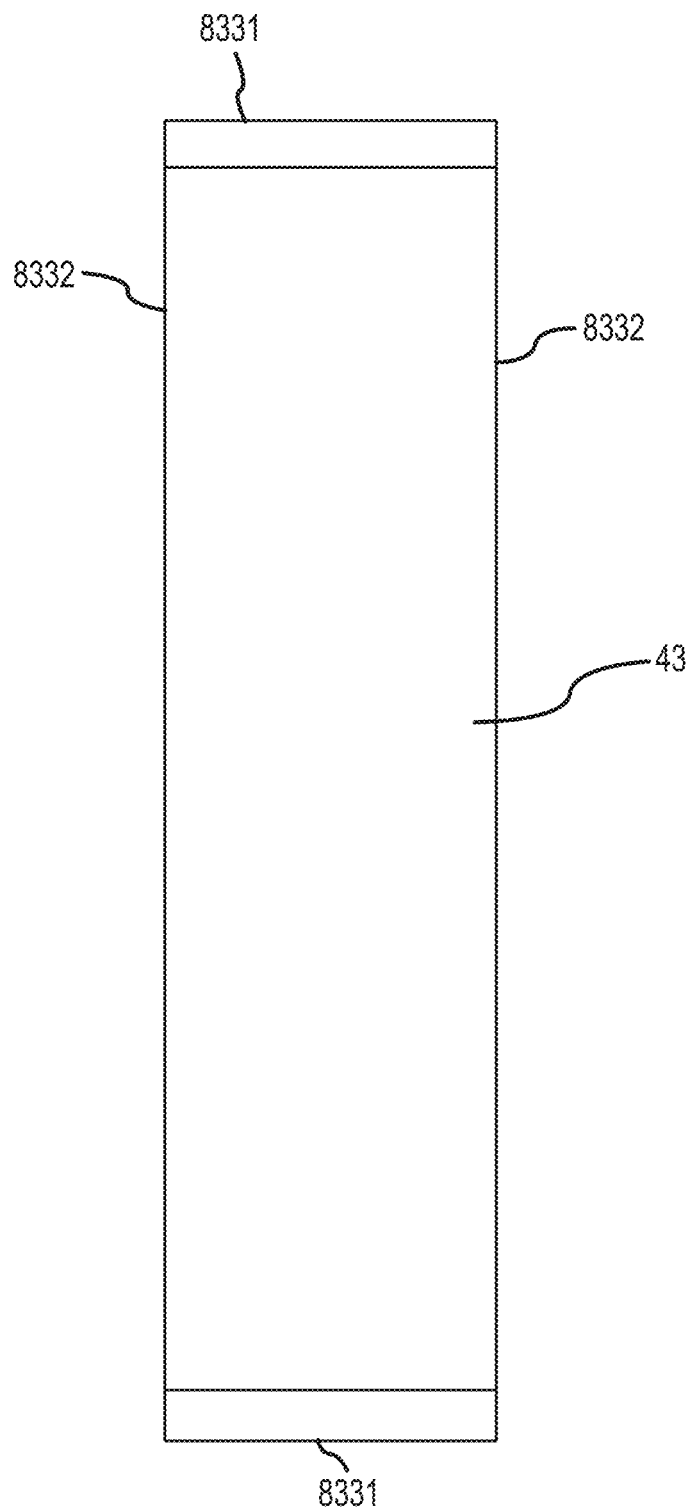

For a discussion of an embodiment of the implant 25 that is configured to have a shape that generally mimics and even substantially fills a portion of a sacroiliac joint space, reference is made to FIGS. 137A-137F. As can be understood from a comparison of the top plan view of the implant 25 as illustrated in FIG. 137C to the shape of the sacroiliac joint extra-articular region 3007 depicted in FIG. 106B, the implant has an overall exterior shape that generally mimics the sacroiliac joint extra-articular region 3007. The implant has a generally isosceles triangle shape in the top plan view. The implant 25 includes a generally truncated, flat proximal end 43 from which two tapering lateral sides 8331 extend and converge at the distal end 42, which forms a rounded or arcuate distal point. A void 7540 of a shape generally the same as the outer shape of the implant itself is defined in the body of the implant generally centered in the implant. The top and bottom surfaces 8332 of the implant have a serrated surface with edges oriented proximally so as to prevent proximal self-migration of the implant once implanted in the joint. The serrated edges extend parallel to the truncated, flat proximal end 43. One or more anchors can be extended through the void 7540 or a bone growth material can be located in the void 7540.

FIGS. 138A-138F illustrate another embodiment the implant 25 that is configured to have a shape that generally mimics and even substantially fills a portion of a sacroiliac joint space. A comparison of the embodiment of FIGS. 138A-138F to the embodiment of FIGS. 137A-137F reveals that the embodiments are substantially similar except the embodiment of FIGS. 138A-138F has a flat, truncated distal end 42 as opposed to an arcuate end, and the void 7540 is generally a circular bore as opposed to a shape that is generally triangular like the exterior boundaries of the implant. As can be understood from FIGS. 138C and 138D, the bore 7540 does not extend completely perpendicular between the opposed top and bottom faces 7540, but instead has a slight cant or tilt.

As an example, due to idiopathic anatomic (e.g., skeletal or neurovascular) variations of certain patients it may be advantageous to have a custom implant, anchor, alignment tool or targeting arm manufactured for a particular individual. Pre-surgical imaging studies (e.g., CT or MRI) may be performed and post-processing, including 3D rendering, may assist in planning desired anchor trajectories, anchor dimensions or implant dimensions. The result of these studies and their interpretation may provide details specific to the manufacture of particular tools or implants and their implantation.

As can be understood from the foregoing, various embodiments of the delivery tools or system configurations as described herein can be similarly configured to operate with various embodiments of the sacroiliac joint implants disclosed in U.S. Provisional 61/520,956.

In summary and as can be understood from the preceding discussion, the sacroiliac joint fusion systems 10 disclosed herein include a joint implant 25, an anchor element 30 and a delivery tool 20. The joint implant 25 includes a longitudinal axis CA (e.g., see FIG. 10) and a bore 40 extending non-parallel to the longitudinal axis CA. The anchor element 30 is configured to be received in the bore 40.

The delivery tool 20 includes an implant arm 110 and an anchor arm 115. The implant arm 110 is configured to releasably couple to the joint implant 25. The anchor arm 115 is coupled to the implant arm and configured to deliver the anchor element 30 to the bore 40.

The final manufactured configuration of the tool 20 and final manufactured configuration of the joint implant 25 are such that, when the system 10 is assembled such that the implant arm 110 is releasably coupled to the joint implant 25 (e.g., as shown in FIGS. 2A, 21A, 21C, 32, 37 and 109), a delivery arrangement automatically exists such that the anchor arm 115 is correctly oriented to deliver the anchor element 30 to the bore 40. Thus, when the system 10 is shipped from the manufacturer to the medical facility where the sacroiliac joint fusion will take place, the components 20, 25, 30, 40, 110, 115 are each configured such that simply plugging them together such that the tool 20 is fully assembled and the implant 25 is supported off of the distal end of the tool 20 is all that is required to employ the tool 20 to both deliver the implant 25 into the sacroiliac joint 1000 and deliver the anchor element 30 into the bore 40 so as to anchor the implant 25 in the sacroiliac joint. In other words, once the components of the system 10 are coupled together, the cumulative result of the as-manufactured three dimensional configurations of each component of the system 10 is that the system 10 has a delivery arrangement such that the anchor arm 115 is correctly oriented to deliver the anchor element 30 to the bore 40 without having to adjust the as-manufactured three dimensional configurations of any of the components of the system 10. This automatically arrived-at delivery arrangement is even the case wherein the anchor arm 115 being employed is part of a plurality of anchor arms (as discussed with respect to FIG. 21B) or where the anchor arm 115 is pivotally coupled to the implant arm 110 and further equipped with an arcuate slider 105 at a free distal end of the anchor arm, the arcuate radius of the anchor arm 115 at the arcuate slider 105 being such that the radius extends through the bore 40 (as discussed with respect to FIG. 34).

While the implant embodiment of FIGS. 5-17 and many of the other implant embodiments described herein depict the bore 40 as being defined in the implant body 45 such that the longitudinal axis of the bore 40 and the longitudinal axis of the implant body 45 are coincident, in other embodiments, the bore 40 may be defined elsewhere in the implant 25. For example the bore 40 may be defined in the implant body 45 such that the longitudinal axes of the bore and implant body are offset from each other. As another such example, the bore 40 may even be defined to extend across a wing 50, 55 so as to daylight at opposed planar surfaces 60 of a large wing 50 or the opposed planar surfaces 65 of a small wing 55.

Implementations of the present disclosure involve a system 10 for fusing a sacroiliac joint. The system 10 includes a delivery tool 20 and an implant assembly 15 for delivery to a sacroiliac joint via the delivery tool 20. The implant assembly 15, which includes an implant 25 and one or more side pieces 12/14, is configured to fuse a sacroiliac joint once implanted at the joint. The side pieces 12/14 are integrally supported on the implant 25 and configured to laterally project from sides of the implant. By acting on the side pieces 12/14 or a portion of the implant at a proximal end 43 of the implant 25 (e.g., by rotational or longitudinally displacing forces actuated by a component of the delivery tool 20 or by a separate tool 10088), the side pieces 12/14 may be caused to deploy from the sides of the implant so as to penetrate into bone material defining the joint space in which the implant 25 is implanted. The tool 20 is configured to support the implant 25 from a distal end 35 of the delivery tool 20 for delivery of the implant into the joint space and further configured to facilitate the deployment of the side pieces 12/14 from the sides of the implant. Thus, the system 10 is configured such that the implant 25 can be quickly, accurately and reliably delivered to, and anchored in, a sacroiliac joint.

Figure 139:
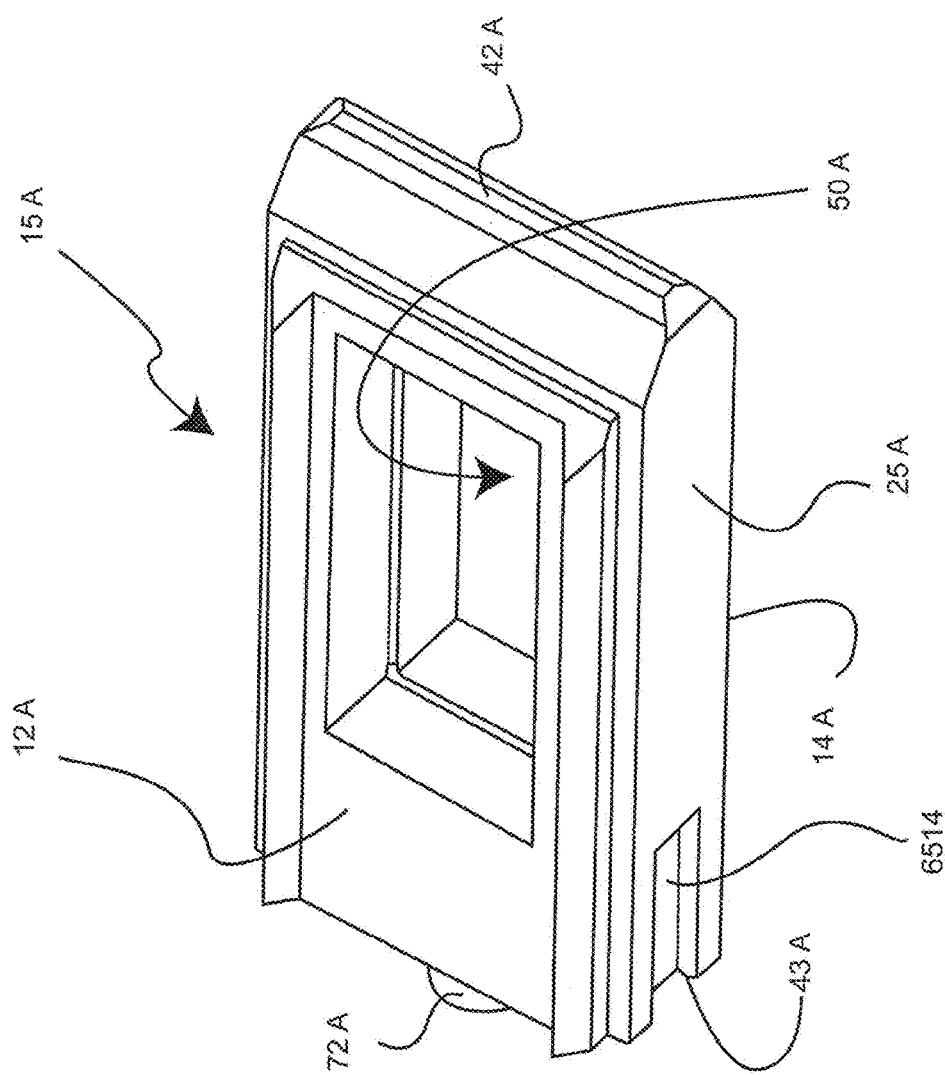
Figure 140:
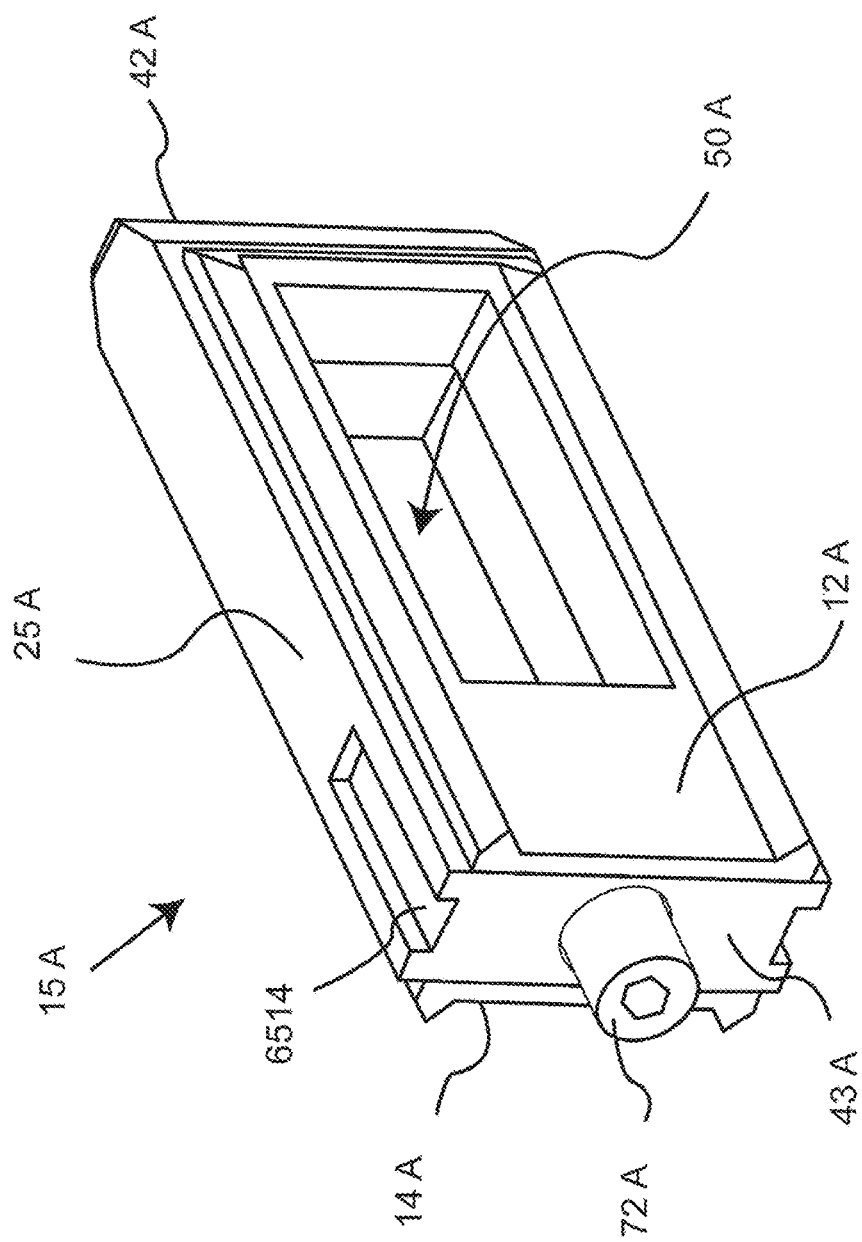
Figure 141:
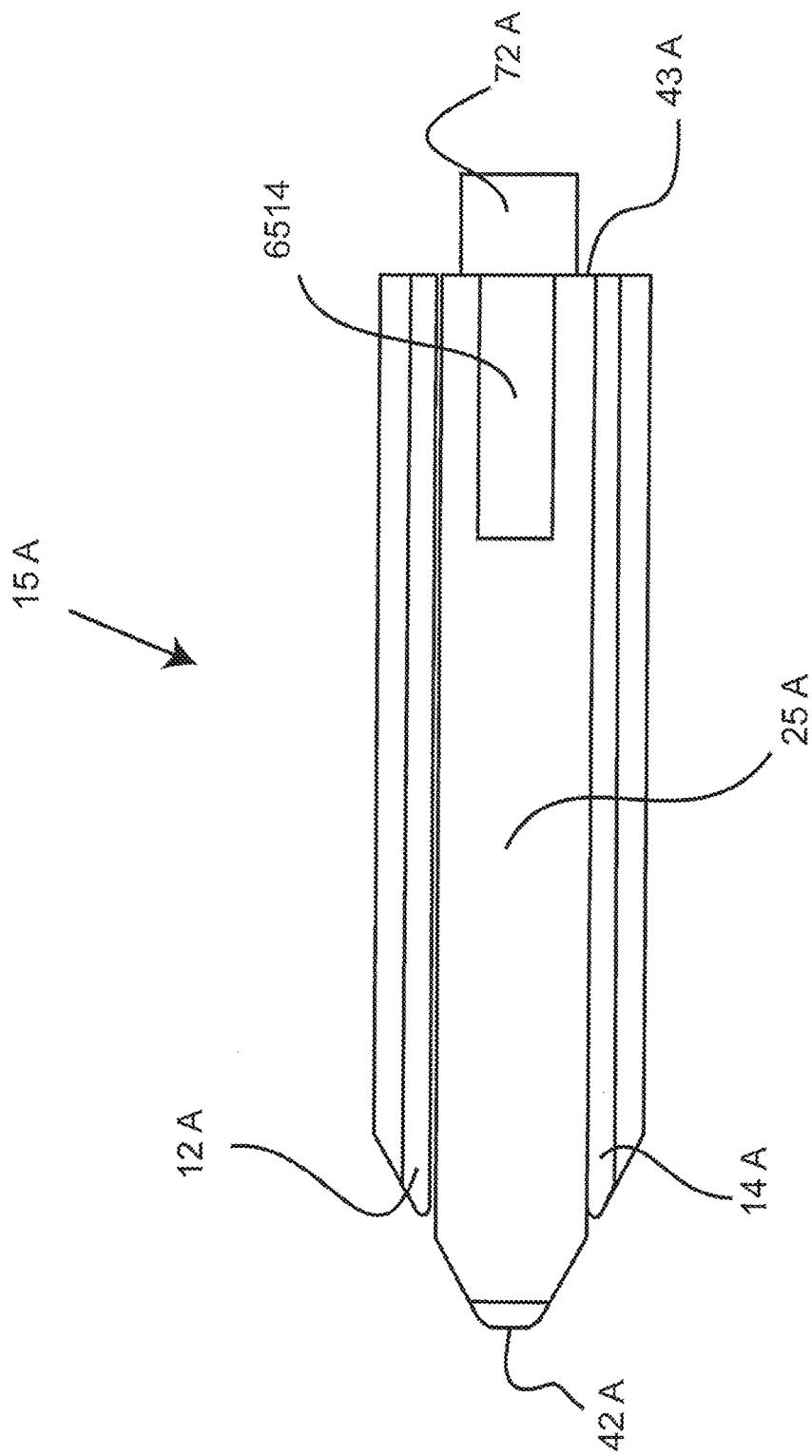
Figure 142:
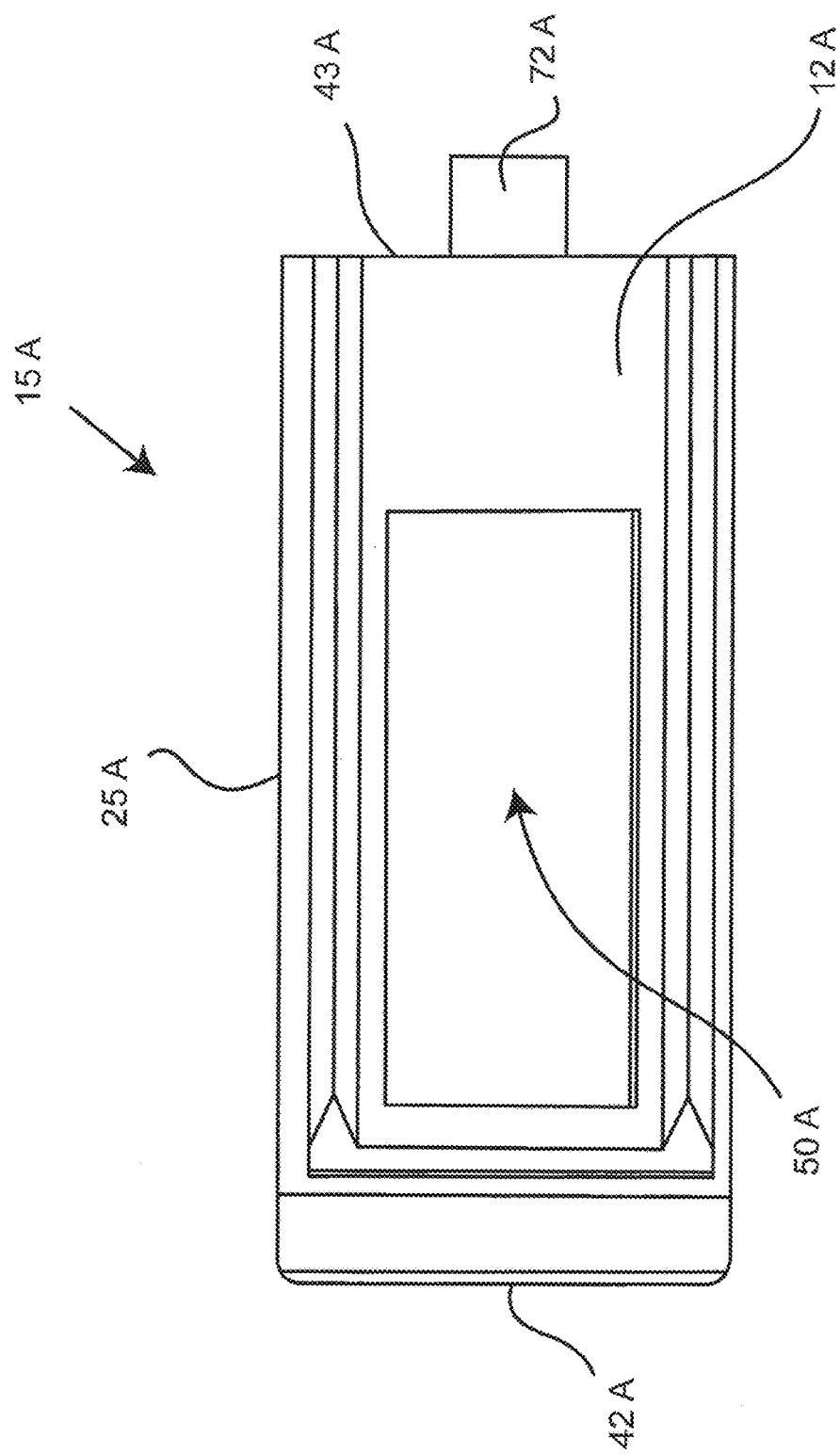
Figure 143:
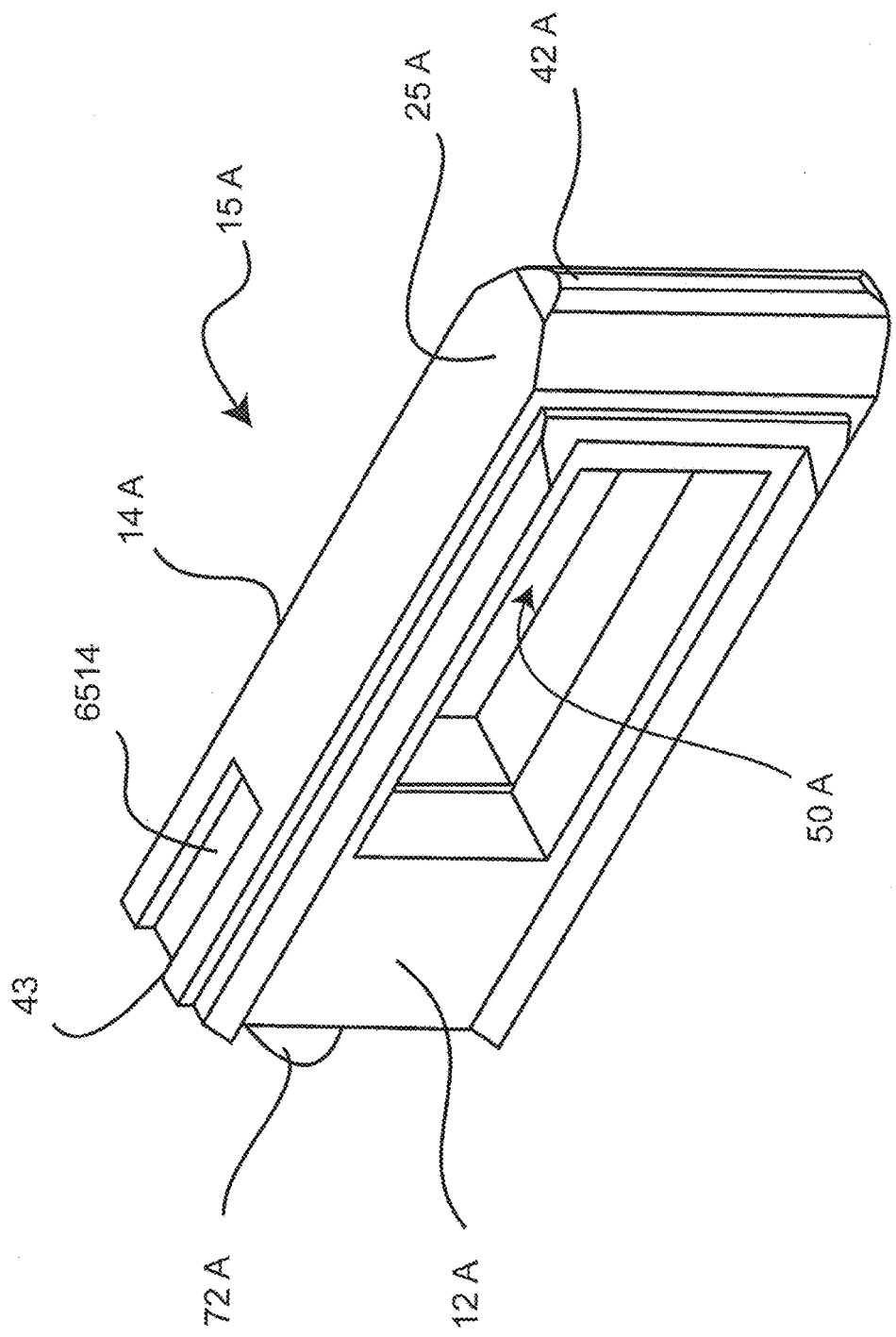
Figure 144:
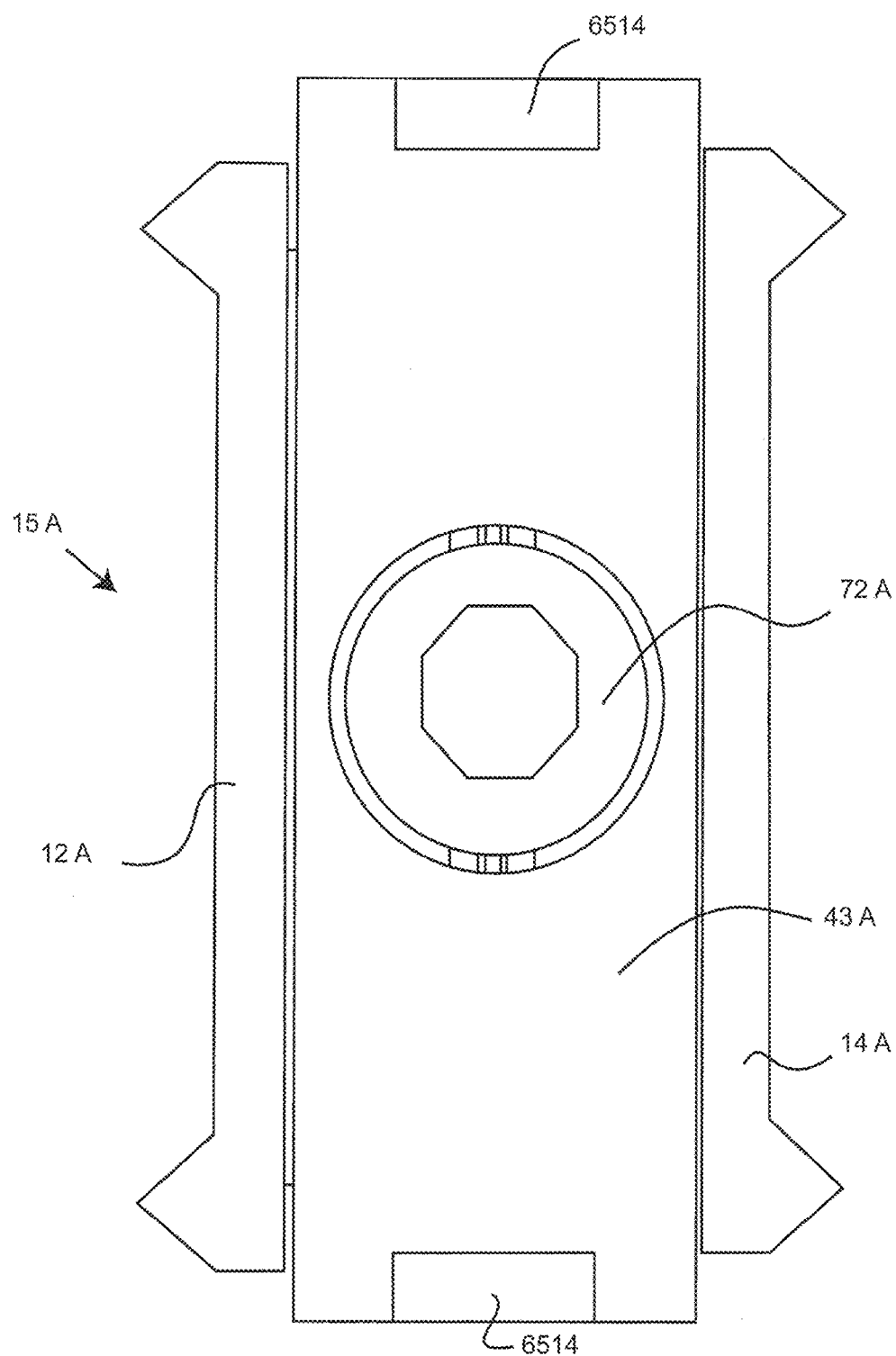
Figure 145:
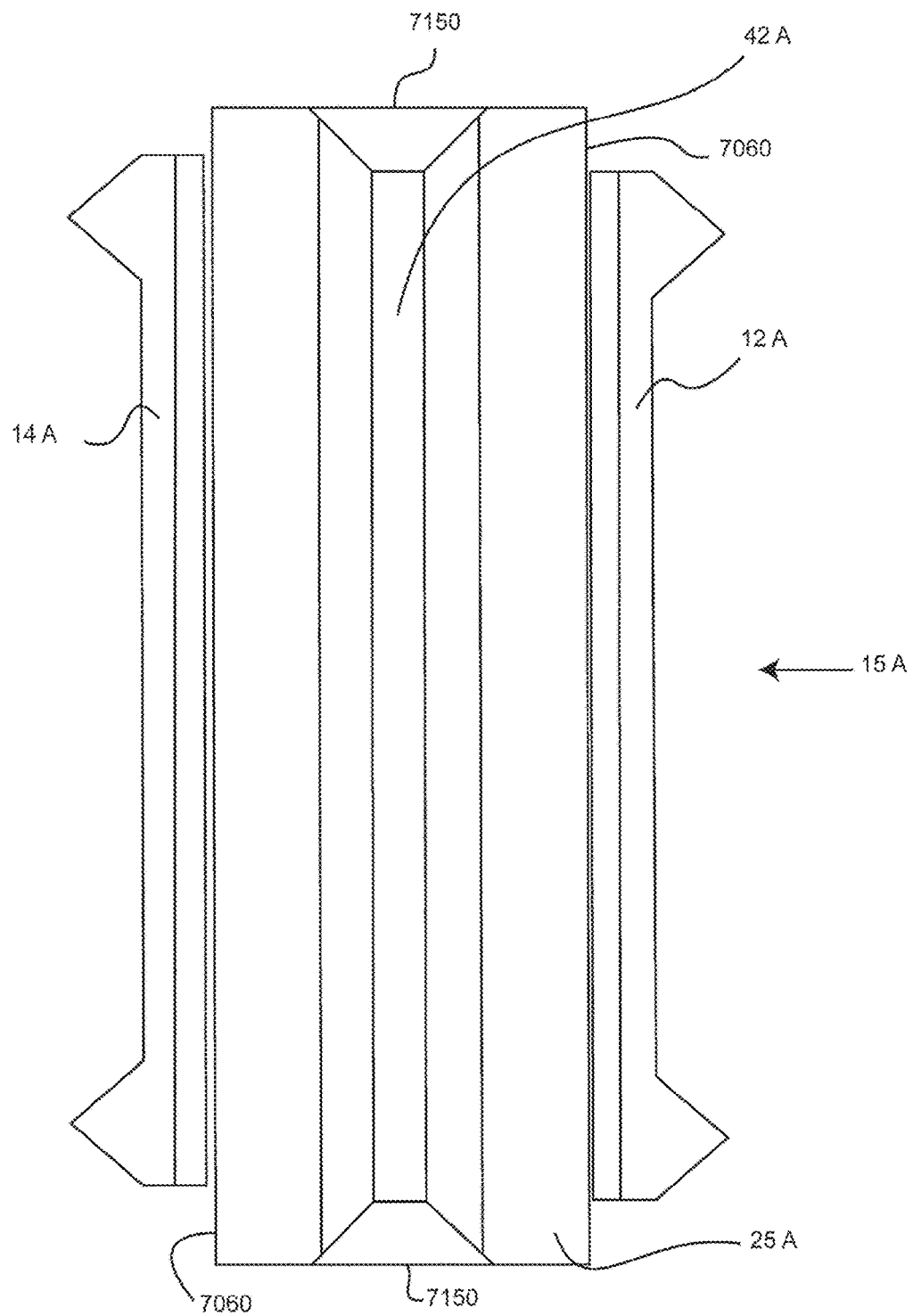
Figure 146:
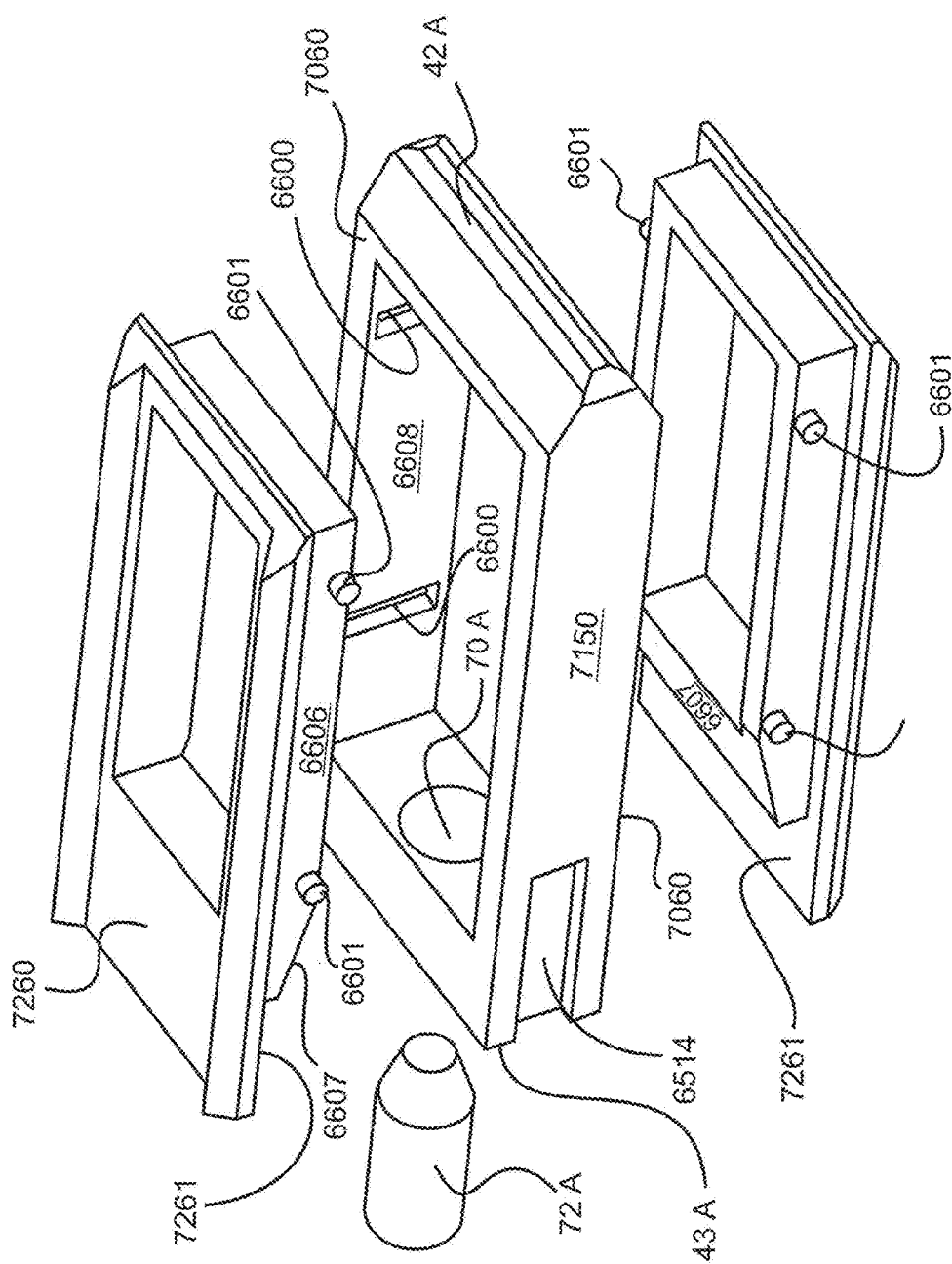
Figure 147:
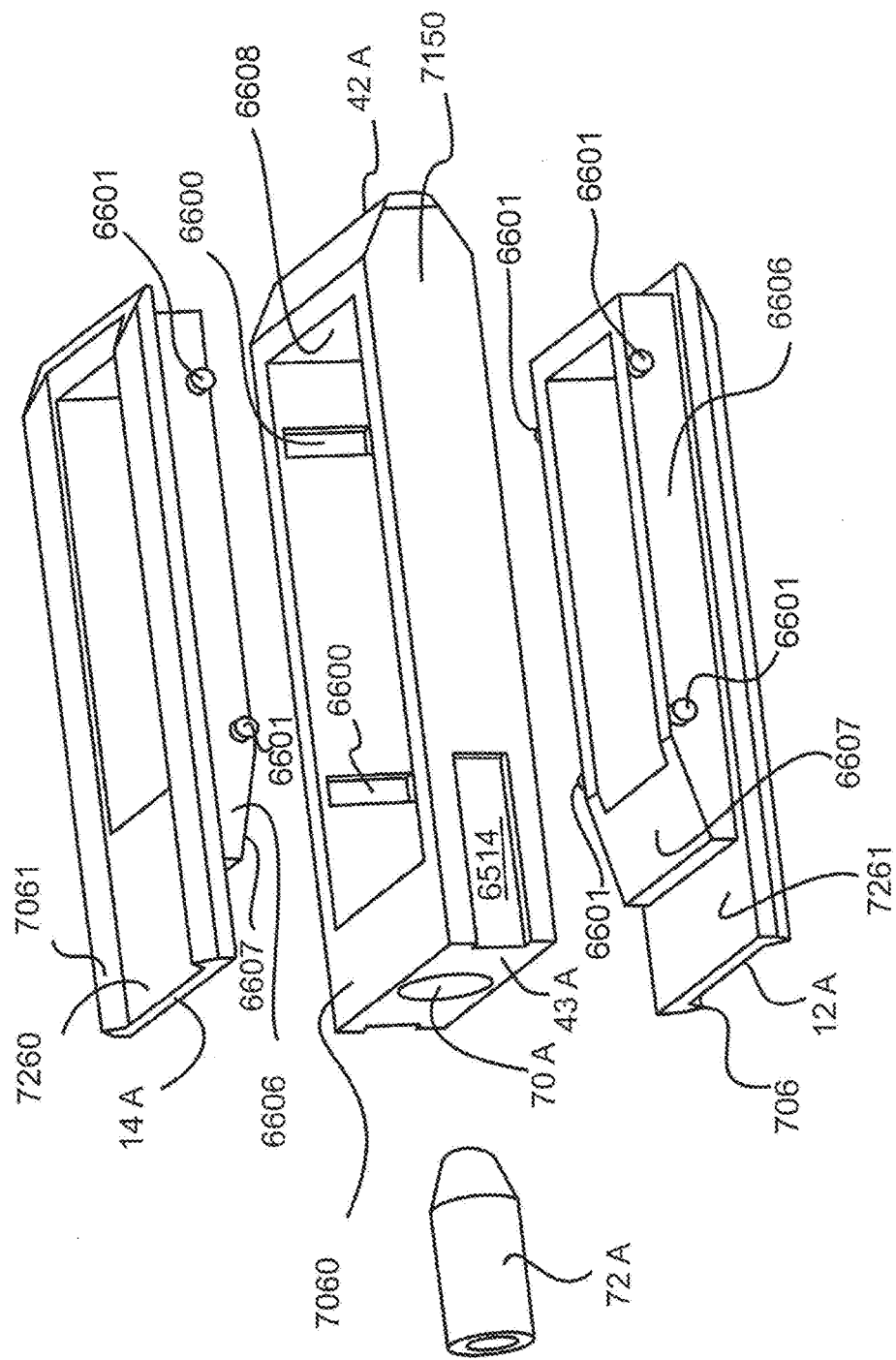

To begin a detailed discussion of yet other aspects and embodiments of the present invention, reference is made to FIGS. 139-144. FIGS. 139-140 and FIG. 143 are isometric views of the implant assembly 15A. FIG. 141 is an edge side elevation view of the implant assembly 15A. FIG. 142 is a lateral side plan view of the implant assembly 15A. FIG. 144 is a proximal end view of the implant assembly 15A. FIG. 145 is a distal end view of the implant assembly 15A. FIGS. 146-147 are exploded views of the implant assembly 15A to better illustrate its components.

As can be understood from FIGS. 139-155, the system 10A includes a delivery tool 20A and an implant assembly 15A for implanting at the sacroiliac joint via the delivery tool 20A, the implant assembly 15A being for fusing the sacroiliac joint. The implant assembly 15A includes a distal or leading end portion 42A, a proximal or trailing end portion 43A with a longitudinal body 25A extending between the distal and proximal ends. The implant body 25A further includes first and second side pieces or members 12A/14A, each including an opening 50A disposed therein. The parts 6515 of distal end 35A of the delivery tool 20A may interface with longitudinally extending rectangular notches 6514 formed in the body 25A as discussed in the aforementioned related patent applications and in greater detail below. In one embodiment as shown in FIGS. 144 and 145, a sacroiliac joint fusion implant 25A includes a proximal end 43A, a distal end 42A generally opposite the proximal end, and side edge surfaces 7150 extending between the proximal and distal ends. An offset distance between the side edge surfaces 7150 is substantially greater than a thickness of the implant as defined by an offset distance between the planar lateral side surfaces 7060.

As can be understood from FIGS. 146-147, and with continuing reference to FIGS. 139-155, the implant body 25A, includes oppositely disposed first and second side members 12A/14A structured and arranged to expand into and engage the sacroiliac joint following insertion therein and an actuating body 72A. The side pieces 12A/14A are integrally supported on the implant 25A and configured to laterally project from sides of the implant. Side pieces 12A/14A each include a bone facing surface 7260, an implant facing surface 7261, ridges 7061, a guide mechanism for guiding the expandable movement of the side pieces and including guide piece 6606 disposed in the body portion and having, a slope 6607, and pins 6601 (or as indicated in particular in FIG. 151, 6601A-D). Implant 25A may further include slots 6600. The guide piece 6606 may be sized to allow side piece 12A/14A to be housed in implant housing 6608. Slots 6600 may be configured to house pins 6601 to limit the amount of laterally projecting movement of side pieces 12A/14A. The ridges 7061 are structured and arranged to securely engage the sides of the sacroiliac joint when urged into operative engagement therewith by the actuating body 72.

Figure 148:
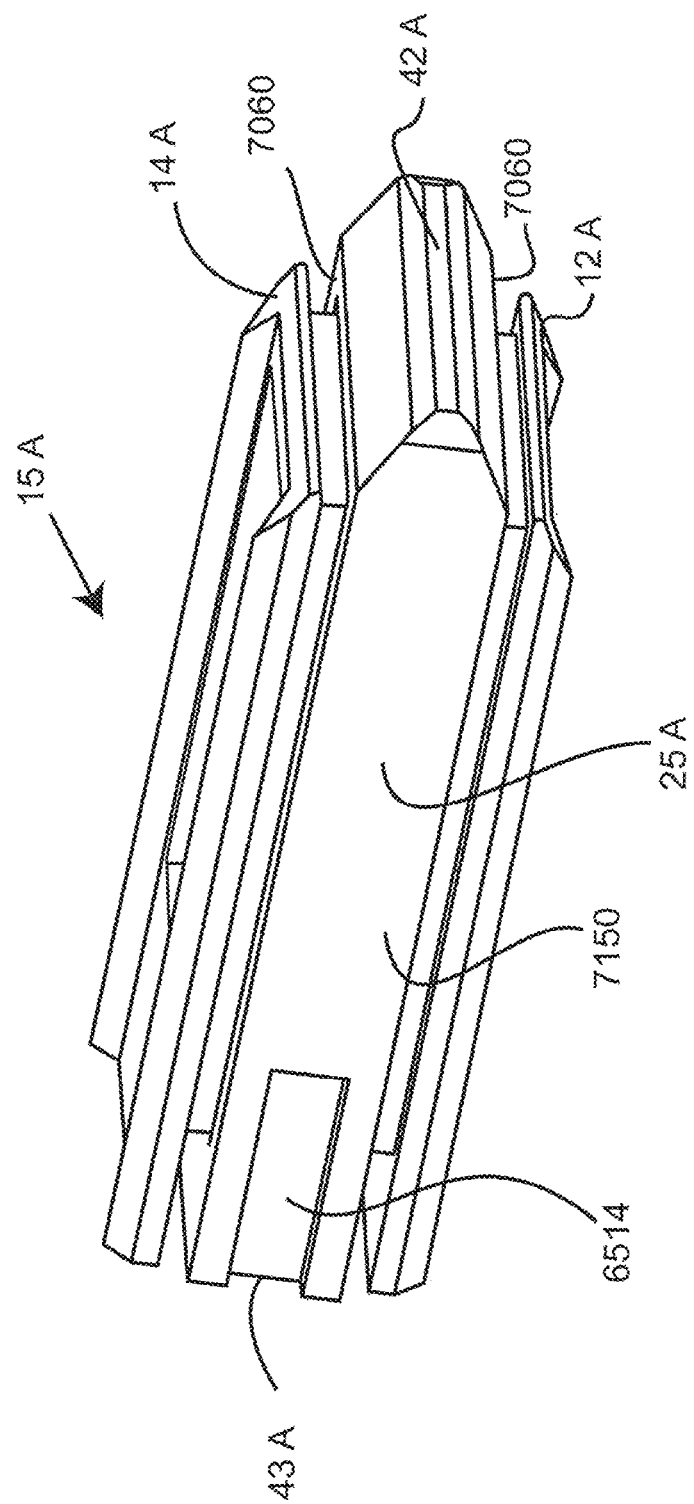
Figure 149:
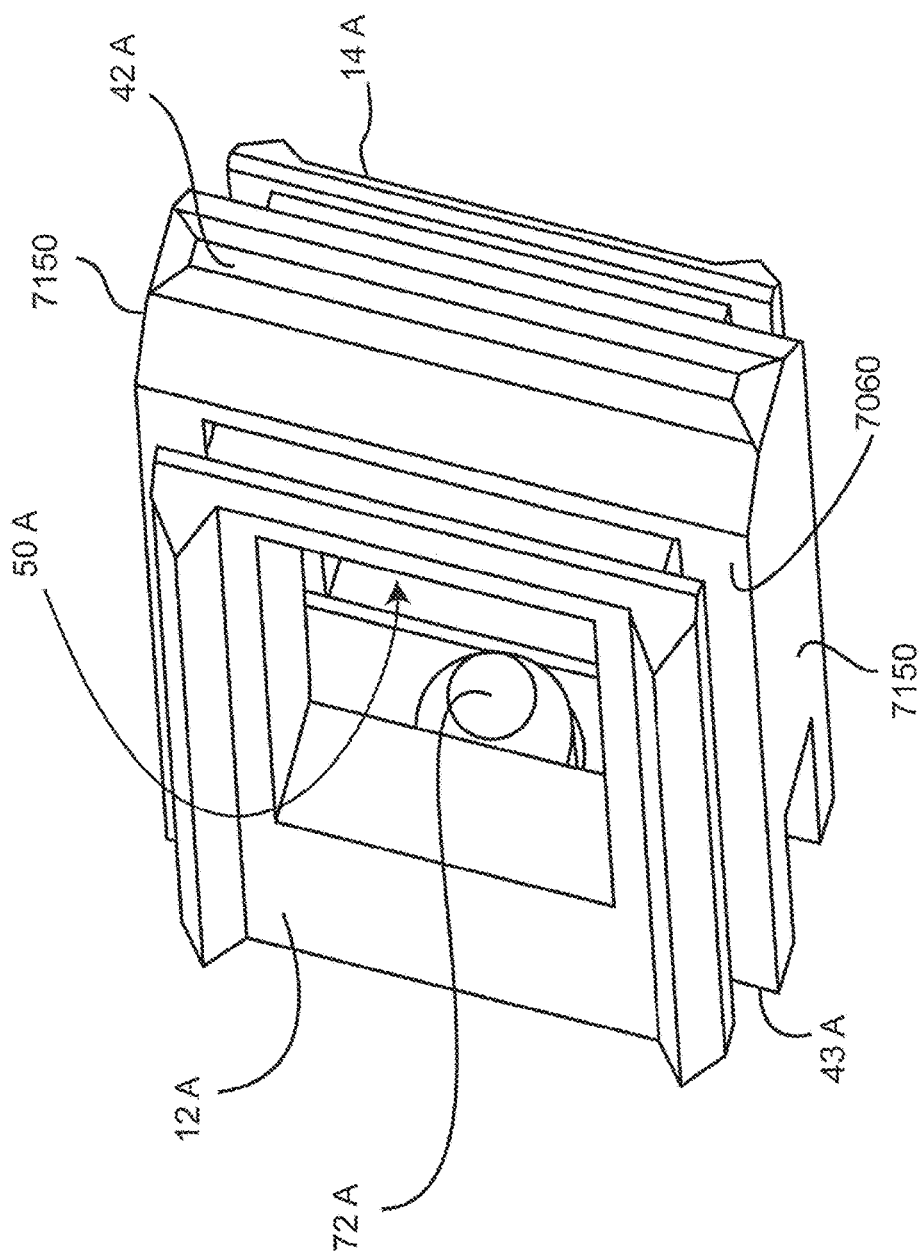
Figure 150:
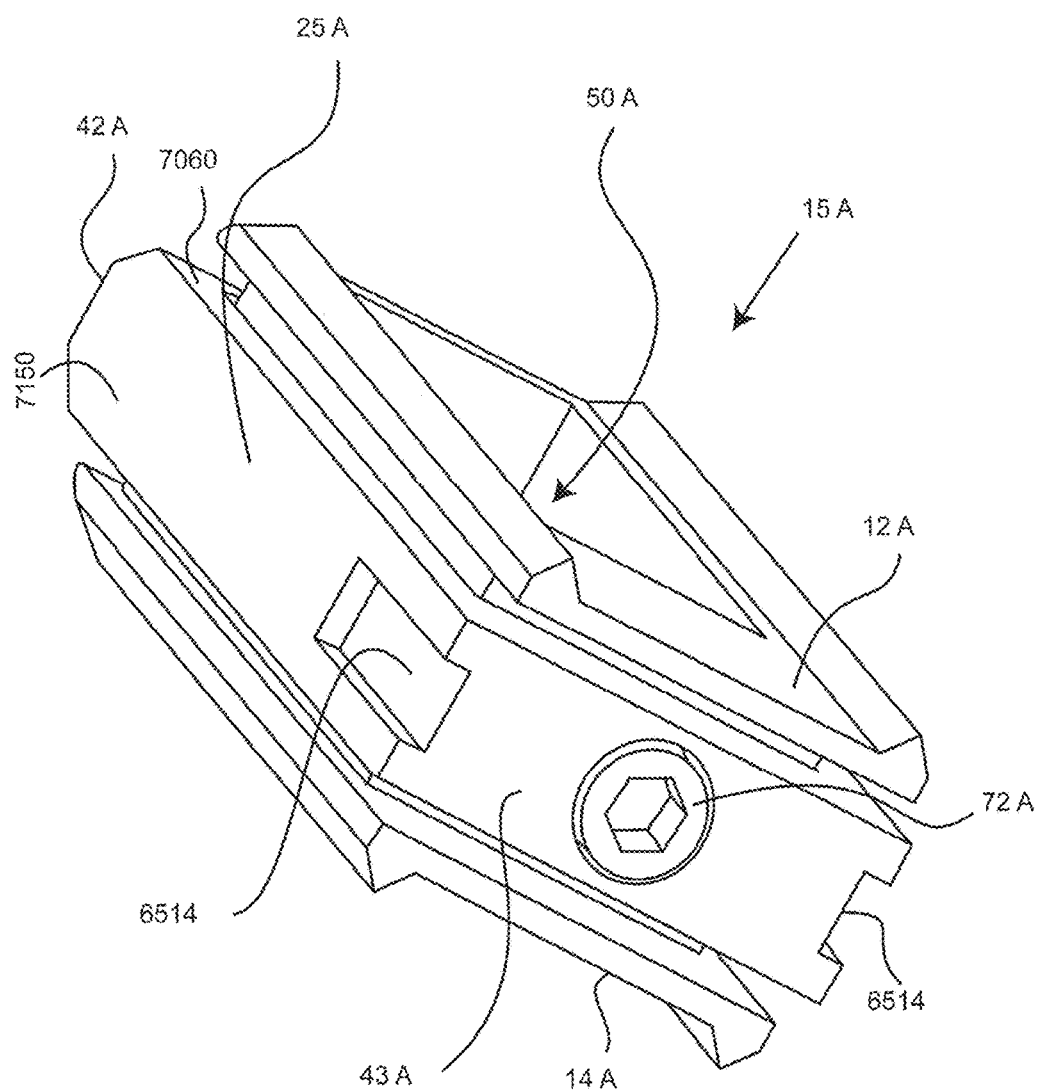
Figure 151:
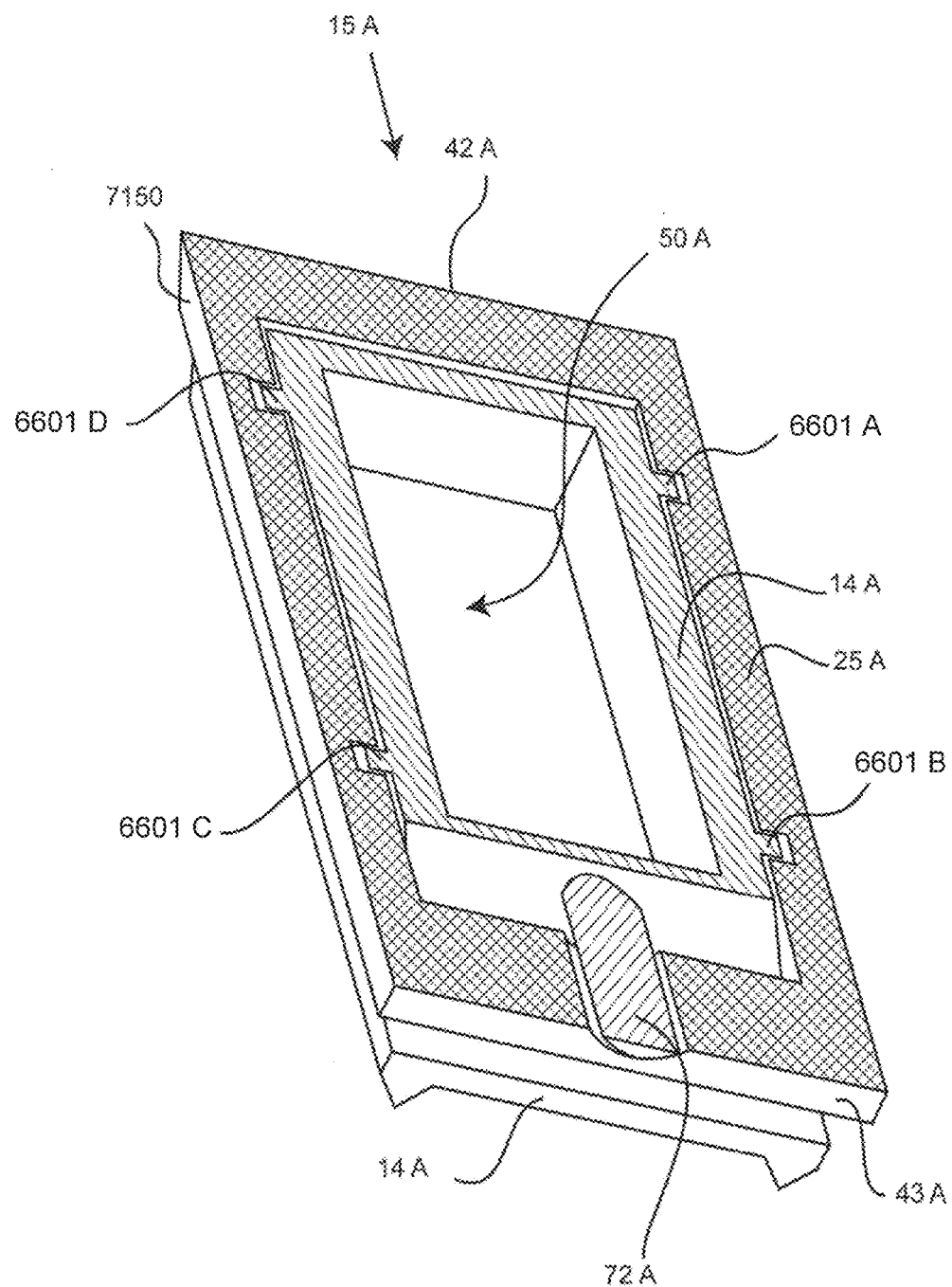
Figure 152:
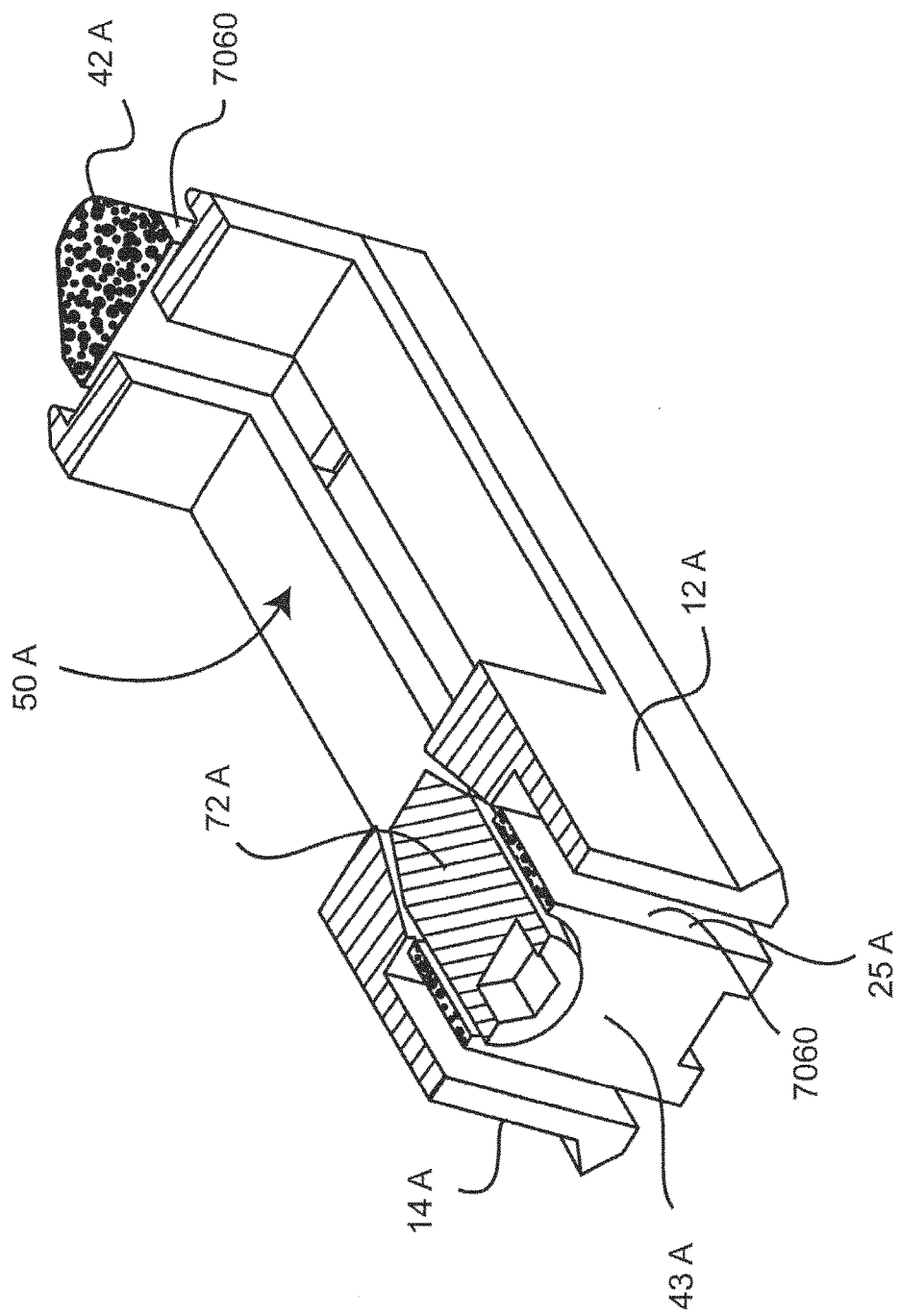
Figure 153:
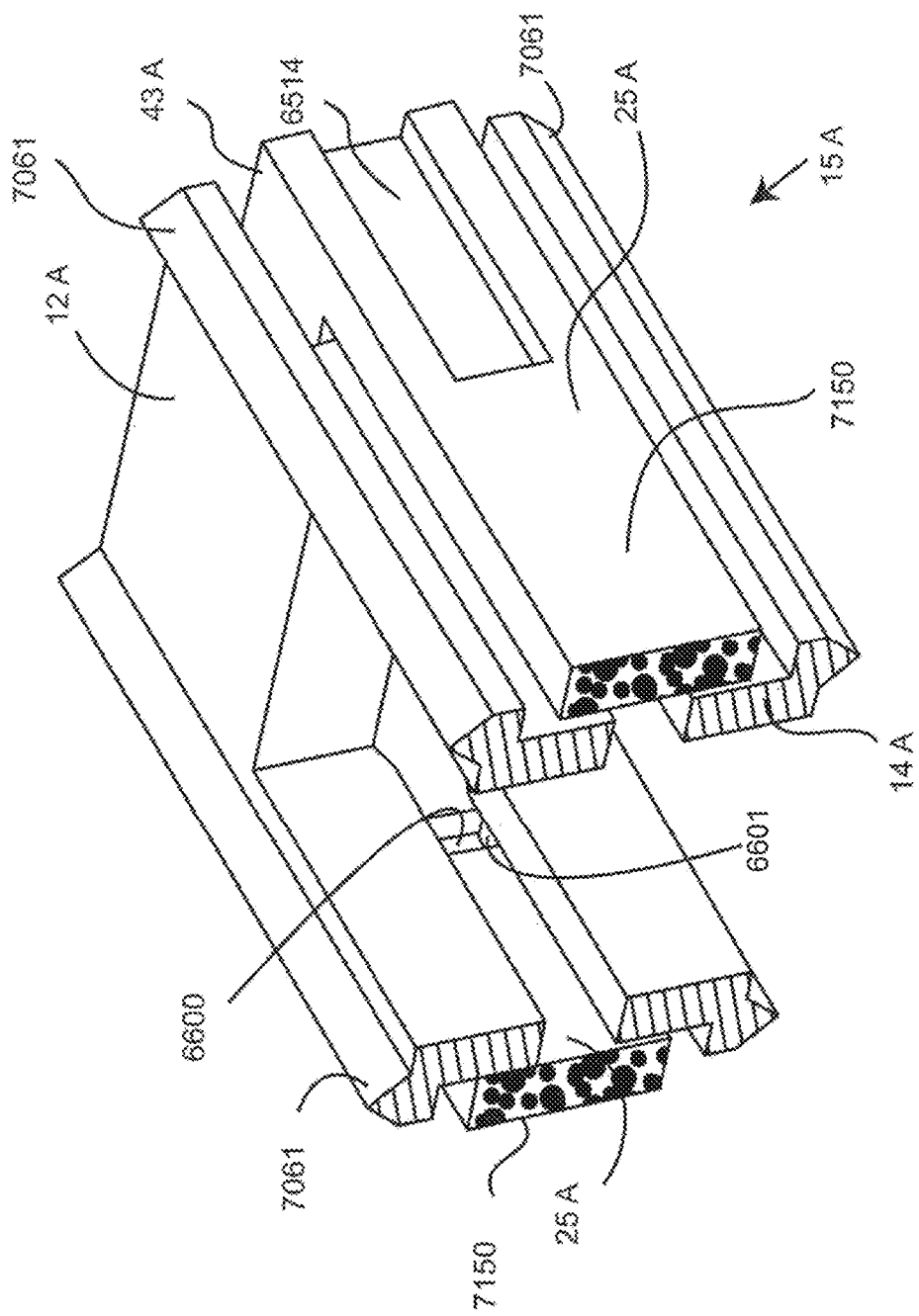
Figure 154:
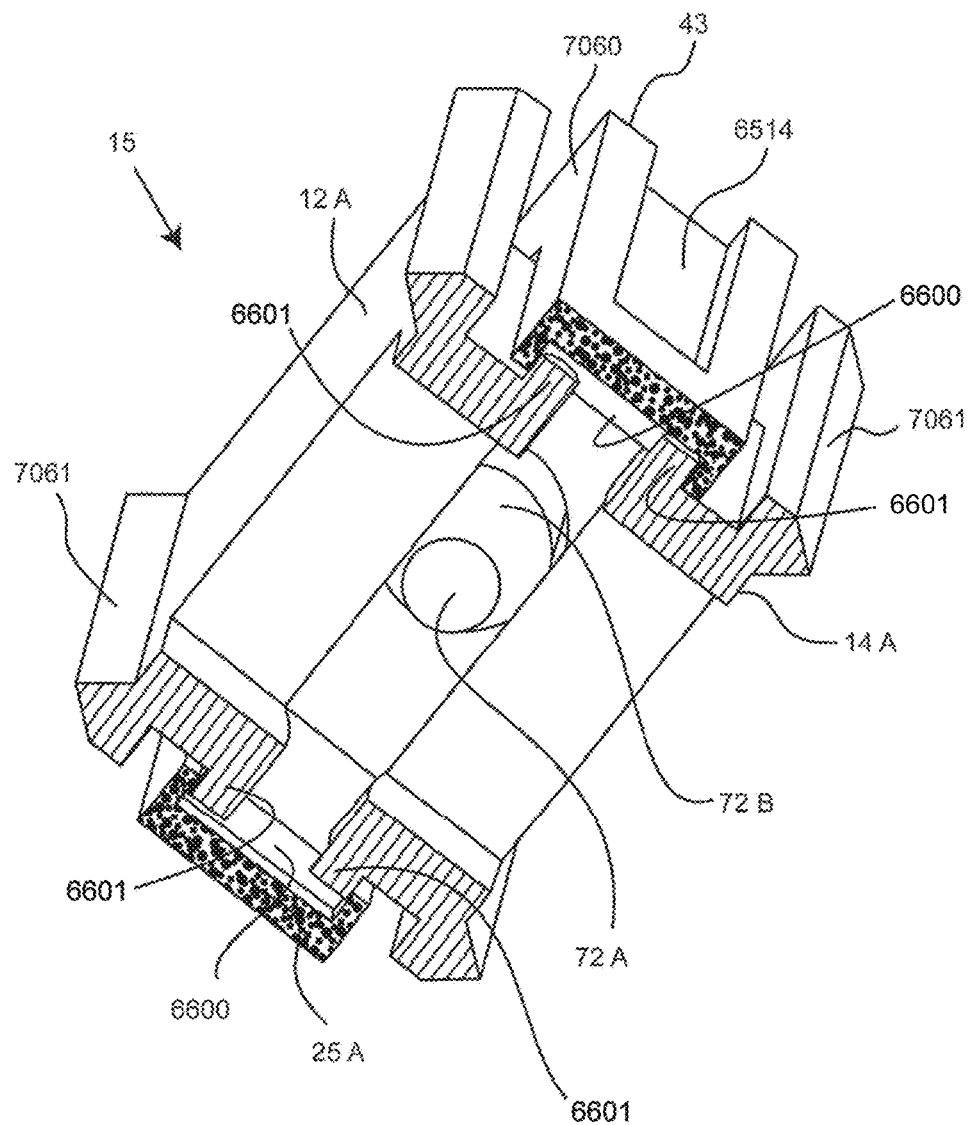

To begin a detailed discussion of an implant assembly 15A in a deployed or expanded state, reference is made to FIGS. 148-154. FIGS. 148-150 are isometric views of the implant assembly 15A in a deployed or expanded state. FIGS. 151-154 are cross section views of the implant assembly 15A in a deployed or expanded state. As can be understood from the figures, body 72A when inserted into implant 25A via bore 70A can cause the side pieces 12A/14A to laterally project from sides of the implant. Body 72A may be fully or partially threaded and may have a leading end which is tapered. Body 72A may be driven by longitudinally acting forces or by rotational forces by a tool 10088 through bore 70A and further driven to hit the slopes or slope surfaces 6607, thereby causing the side pieces 12A/14A to laterally project from sides of the implant.

To begin a detailed discussion of a delivery tool 20A of the system 10A, reference is made to FIG. 155. In one embodiment, a delivery tool 20A for use with the implant embodiments of the FIGS. 139-154 may be configured as illustrated in FIG. 155. Such a tool 20A may have an implant arm 110A formed mainly of a sleeve 110Z and a retainer rod 110X. The retainer rod 110X may be received coaxially within the sleeve 1102.

The retainer rod 110X includes a shaft 10030 that distally terminates in opposed arms 10032, which in turn terminate in retainer arms or prong arms 6515. As shown in FIG. 155, when the rod 110X is free of the sleeve 110Z, the opposed arms 1032 are biased apart, resulting in a space-apart distance indicated by arrow D that is sufficiently wide to allow the implant 25A to be received between the prong arms 6515 at the rod distal end 120A.

As indicated in FIG. 155, the sleeve 110Z includes a distal end 10040, a proximal end 10042, slots 10044 that extend into the hollow interior of the shaft of the sleeve 110Z. The slots 10044 provide opening into the hollow interior to facilitate sterilization of the sleeve 110Z via an autoclave. A knurled gripping surface 10046 is defined near the sleeve proximal end 10042 so as to facilitate rotation of the sleeve relative to the rod when the threads 110Y are being threadably engaged.

As can be understood from a comparison of FIG. 155, when the sleeve 110Z is advanced coaxially distally over the retainer rod 110X, complementary threads 110Y on both the sleeve 110Z and retainer rod 110X can be engaged and the sleeve can be rotatably driven distally by said thread engagement. The sleeve 110Z advancing coaxially distally causes prong arms 6515 of the retainer rod 110X to draw toward one another and in turn cause the portion of the retainer rod which couples to the implant 25A to grasp the implant. The complementary threads when engaged may prevent proximal movement of the sleeve 110Z relative to the rod 110X and allow the coupling of implant and retainer rod to continue throughout the course of the procedure. While the tool 20A is coupled to the implant 15A, a hex-head 10083 wrench or screwdriver 10088 with a handle 10082 may be extended down a central lumen of the shaft 10030 to engage the hex-head end of the body 72A to drive body 72A a distance towards implant proximal end 42A thereby causing the side pieces 12A/14A to laterally project from sides of the implant. After implantation the sleeve 110Z may be caused to move proximally along the retainer rod 110X in order to decouple the aforementioned tool and implant arrangement.

Referring now to FIGS. 158-164, another embodiment of an implant insertion tool 1000A is shown. Tool 1000A is in the form of a tong apparatus and includes a handle 10004A pivotally connected at a first end 1006A thereof to a multi-segmented elongated arm 1008A/1013A, the segments being pivotally joined at pin 1015A. The elongated arm 1008A/1013A includes a proximal end 1020A and distal end 1021A. A second multi-segmented elongated arm 1010A/1011A is pivotally connected at a midpoint 1012 thereof at approximately the midpoint of arm 1008A/1013A and is operatively engaged at a proximal end 1014A thereof to a ratchet 1016A positioned on handle 1004A. The segments 1010A and 1011A are pivotally connected at pin 1019A. Arm 1010A further includes a distal end 1017A oppositely disposed from distal end 1021 of arm 1008A, as is more clearly illustrated in FIGS. 161 and 162. The arms 1018A and 1010A are structured and arranged to form a tong-type tool adapted for insertion of an implant into a sacroiliac joint as hereinabove described with respect to an alternate embodiment of this invention.

FIGS. 164-170 illustrate yet another embodiment of a sacroiliac implant device 3000A and insertion tool 1000B. With the exception of distal ends 1017B and 1021B, insertion tool 1000B is structured in the same manner as tool 1000A described above. According, similar numerals followed by the letter "B" are shown in the drawings to differentiate between the two embodiments.

As best shown in FIGS. 169 and 170, insert 3000A comprises a body portion 3002A having an elastic generally U-shaped middle portion 3004A and a pair of opposite disposed legs 3006A/3008A having a proximal end 3007A/3009A respectively operatively connected to the U-shaped middle portion and extending therefrom creating a spring-like force extending transversely therefrom. Each leg includes a generally U-shaped opening or channel 3012A/3014A formed in a distal end 3016A/3018A thereof respectively, each channel adapted to receive a respective end 1017B/1021B of tool 1000B for insertion into a joint. Each end 3016A/3018A includes a plurality of outwardly extending wedge or V-shaped projections 3020A structured and arranged to be urged by the spring force of the implant into engagement with the joint interfaces into which it is implanted.

Referring to FIGS. 171-173, yet another embodiment of a sacroiliac joint implant is shown at 4000A. Similar in configuration and operation to the embodiment of FIGS. 169 and 170, the implant device of the instant embodiment has legs 4006A/4008A extending substantially parallel from an elastic U-shaped middle portion 4004A. Outwardly extending wedge or V-shaped projections are structured and arranged to be forcibly driven into a joint interface upon insertion by a tool such as tool 1000A hereinabove described.

Yet another embodiment of an implant device 5000A is depicted in FIG. 174. Implant 5000A includes an expandable body portion 5002A having a first end configured in the shape of a chisel 5004A and a second end 5006A having an aperture 5008A formed therein and adapted to receive a wedge element 5012A. After insertion into a sacroiliac or other applicable joint, wedge 5012A is forced into aperture 5008A, thereby expanding the body portion of the implant into contact with the joint interfaces. Four orthogonally positioned projections 5012A are structured and arranged to be forced into engagement with the joint interfaces, thereby securely retaining the implant in its desired location.

Insertion tool 1000A further includes a pair of oppositely disposed spring elements positioned intermediate a proximate end 1020A of the first arm 1008A and a proximate end 1022A of the second arm 1010A to urge the proximate ends away from one another, thereby urging the distal ends 1017A and 1021A into engagement with an implant 1025A. The tool further includes a guide member 1026A adapted to receive expanding member 72A and tool 10088 for engagement with the expandable implant device for insertion and fixation in a sacroiliac joint. An x-shaped pivotal cross-brace 1028A pivotally connects at a pair of oppositely disposed ends 1030A thereof to each of the arms 1008A and 1010A and slidably connected at a pair of second ends 1032A to the arms to reinforce and stabilize the distal end of tool 1000A during the insertion process.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

To begin a detailed discussion of another method of accessing a sacroiliac joint space to treat a musculoskeletal condition, reference is made to FIGS. 175-177. To begin and as can be understood from FIGS. 175 and 176, a stab incision is made in the patient's skin to create an entry point near the coccyx 1007 and the sacrotuberous ligament 1008. A cannulated blunt dissecting tool for deflecting soft tissue away from the sacrum 1004 may be advanced through the entry point 1009 and advanced while following the sacrum up to a sacroiliac joint inferior boundary 3002 which is immediately adjacent, and extends along, the sciatic notch 2024. A guide wire may then be placed through the cannulation in the dissecting tool and advanced into the sacroiliac joint. Optionally, after the dissecting tool has been removed an inflatable bowel retractor may be advanced over the guide wire and, once in place, inflated to provide a protected passageway 1111 for access to a sacroiliac joint. A working cannula may then be advanced over the guide wire to further protect the soft tissues from subsequent use of tools during the remainder of the procedure. The guide wire may then be removed or alternatively left in place to be used to guide an implant delivery tool up to the sacroiliac joint. Regardless, as can be understood from FIG. 177, any of the tools 20 disclosed herein can be used along the surgical pathway depicted in FIGS. 175 and 176 to deliver corresponding implant assemblies 15 into the sacroiliac joint space.

The invention claimed is:

1. A method of fusing a sacroiliac joint defined between a sacrum and an ilium, the method comprising:
  implanting a joint implant at the sacroiliac joint, the joint implant comprising:
    a length extending between a proximal end and a distal end;
    an exterior surface extending the length;
    an interior surface opposite the exterior surface and extending the length, the interior surface defining an internal volume therein;

a wall thickness defined between the external surface and the interior surface;

a proximal opening extending into the internal volume;

a first wall section comprising a first plurality of struts arranged along the length and defining a first plurality of openings extending through the wall thickness; and a second wall section comprising a second plurality of struts arranged along the length and defining a second plurality of opening extending through the wall thickness, wherein the first and second plurality of struts are each arranged along lengths of the first and second wall sections, respectively, such that each opening of the first and second plurality of openings are generally polygonal in shape.

2. The method of claim 1, wherein the first and second wall sections are generally planar.

3. The method of claim 1, wherein the exterior surface of the implant body defines a non-circular cross-section transverse to the length.

4. The method of claim 1, wherein at least a portion of each of the first and second plurality of struts are arranged in a repeating strut pattern.

5. The method of claim 4, wherein the repeating strut pattern of the first and second plurality of struts are identical to each other.

6. The method of claim 1, wherein the first and second wall sections are generally parallel to each other.

7. The method of claim 1, wherein each of the first and second wall sections comprises anti-migration surface features on the exterior surface.

8. The method of claim 1, wherein the each opening of the first and second plurality of openings is generally triangular in shape.

9. The method of claim 1, wherein the joint implant further comprises an access opening extending through the wall thickness and configured for the passage of biological material therethrough, a portion of the access opening is defined at a tapered distal portion of the exterior surface at the distal end.

10. The method of claim 1, wherein the joint implant is implanted non-transversely into the sacroiliac joint.

11. The method of claim 1, wherein the joint implant is implanted into the sacroiliac joint such that portions of the joint implant extend into the ilium and the sacrum.

12. The method of claim 1, further comprising packing the internal volume at least partially with bone growth material prior to implanting the joint implant into the sacroiliac joint.

13. The method of claim 1, further comprising forming an implant receiving space in at least one of the sacrum, the ilium, or the sacroiliac joint for receiving the joint implant prior to implanting the joint implant into the sacroiliac joint.

14. The method of claim 1, wherein each of the first and second plurality of openings includes at least two openings that are arranged in a mirror image fashion relative to each other.

15. The method of claim 1, wherein the joint implant further comprises a third wall section comprising a third plurality of struts arranged along the length and defining a third plurality of openings extending through the wall thickness.

16. A method of fusing a sacroiliac joint defined between a sacrum and an ilium, the method comprising:

implanting a joint implant at the sacroiliac joint, the joint implant comprising a length extending between a proximal end and a distal end, a non-circular cross-section transverse to the length, an exterior surface, an interior surface defining an internal volume therein, a wall thickness defined between the external surface and the interior surface, a proximal opening extending into the internal volume, a first wall section, and a second wall section, each of the first and second wall sections comprising a plurality of struts defining a pattern of polygonal-shaped openings extending between groups of multiple struts of the plurality of struts, the polygonal-shaped openings extending from the exterior surface to the interior surface.

17. The method of claim 16, wherein the first and second wall sections are generally planar.

18. The method of claim 16, wherein the non-circular cross-section is generally polygonal in shape.

19. The method of claim 16, wherein the pattern of the plurality of struts on the first and second wall sections are identical to each other.

20. The method of claim 16, wherein the first and second wall sections are generally parallel to each other.

21. The method of claim 16, wherein each of the first and second wall sections comprise anti-migration surface features on the exterior surface.

22. The method of claim 16, wherein the joint implant further comprises an access opening extending from the exterior surface to the interior surface, and is configured for the passage of biological material therethrough, a portion of the access opening is defined at a tapered distal portion of the exterior surface at the distal end.

23. The method of claim 16, wherein the joint implant is implanted non-transversely into the sacroiliac joint.

24. The method of claim 16, wherein the joint implant is implanted into the sacroiliac joint such that portions of the joint implant extend into the ilium and the sacrum.

25. The method of claim 16, further comprising packing the internal volume at least partially with bone growth material prior to implanting the joint implant into the sacroiliac joint.

26. The method of claim 16, further comprising forming an implant receiving space in at least one of the sacrum, the ilium, or the sacroiliac joint for receiving the joint implant prior to implanting the joint implant into the sacroiliac joint.

27. The method of claim 16, wherein the polygonal-shaped openings defined by the plurality of struts on the first and second wall sections include at least two openings that are arranged in a mirror image fashion relative to each other.

28. The method of claim 16, wherein the joint implant further comprises a third wall section comprising the plurality of struts defining the pattern of polygonal-shaped openings extending between groups of multiple struts of the plurality of struts.

29. A method of fusing a sacroiliac joint defined between a sacrum and an ilium, the method comprising:

implanting a joint implant at the sacroiliac joint, the joint implant comprising:

a length extending between a proximal end and a distal end;

an exterior surface extending the length and having a non-circular cross-section transverse to the length;

an interior surface opposite the exterior surface and extending the length, the interior surface defining an internal volume therein;

a wall thickness defined between the external surface and the interior surface;

a proximal opening extending into the internal volume;

a first wall section comprising a first plurality of struts arranged along the length and defining a first plurality of openings extending through the wall thickness; and a second wall section comprising a second plurality of struts arranged along the length and defining a second plurality of opening extending through the wall thickness, wherein the first and second plurality of struts are each arranged along lengths of the first and second wall sections, respectively, in a repeating strut pattern.

30. The method of claim 29, wherein the first and second wall sections are generally planar.

31. The method of claim 29, wherein the exterior surface includes a polygonal cross-section transverse to the length.

32. The method of claim 29, wherein the repeating strut pattern defines at least two openings that are arranged in a mirror image fashion relative to each other.

33. The method of claim 29, wherein the repeating strut pattern of the first and second plurality of struts, respectively, are identical to each other.

34. The method of claim 29, wherein the first and second wall sections are generally parallel to each other.

35. The method of claim 29, wherein each of the first and second wall sections comprises anti-migration surface features on the exterior surface.

36. The method of claim 29, wherein each opening of the first and second plurality of openings is generally polygonal in shape.

37. The method of claim 29, wherein the joint implant further comprises an access opening extending through the wall thickness and configured for the passage of biological material therethrough, a portion of the access opening is defined at a tapered distal portion of the exterior surface at the distal end.

38. The method of claim 29, wherein the joint implant is implanted non-transversely into the sacroiliac joint.

39. The method of claim 29, wherein the joint implant is implanted into the sacroiliac joint such that portions of the joint implant extend into the ilium and the sacrum.

40. The method of claim 29, further comprising packing the internal volume at least partially with bone growth material prior to implanting the joint implant into the sacroiliac joint.

41. The method of claim 29, further comprising forming an implant receiving space in at least one of the sacrum, the ilium, or the sacroiliac joint for receiving the joint implant prior to implanting the joint implant into the sacroiliac joint.

42. The method of claim 29, wherein the joint implant further comprises a third wall section comprising a third plurality of struts arranged along the length and defining a third plurality of openings extending through the wall thickness.

43. The method of claim 1, wherein the interior surface of the joint implant defines a non-circular cross-section transverse to the length.

44. The method of claim 43, wherein the proximal opening defines a circular bore extending into a non-cylindrical internal volume, the non-circular cross-section having an area which is substantially greater than an area of a cross-section of the circular bore.

45. The method of claim 3, wherein the interior surface of the joint implant defines a non-circular interior cross-sectional shape transverse to the length which generally matches a shape of the non-circular cross-section defined by the external surface.

46. The method of claim 16, wherein the interior surface of the joint implant defines a non-circular interior cross-section transverse to the length.

47. The method of claim 46, wherein the proximal opening defines a circular bore extending into the internal volume defining a non-cylindrical shape, the non-circular interior cross-section having an area which is substantially greater than an area of a cross-section of the circular bore.

48. The method of claim 16, wherein the exterior surface defines the non-circular cross-section transverse to the length, and wherein the interior surface of the joint implant defines a non-circular interior cross-sectional shape transverse to the length which generally matches a shape of the non-circular cross-section defined by the external surface.

49. The method of claim 29, wherein the interior surface of the joint implant defines a non-circular interior cross-section transverse to the length.

50. The method of claim 49, wherein the proximal opening defines a circular bore extending into the internal volume defining a non-cylindrical shape, the non-circular interior cross-section having an area which is substantially greater than an area of a cross-section of the circular bore.

51. The method of claim 29, wherein the interior surface of the joint implant defines a non-circular interior cross-sectional shape transverse to the length which generally matches a shape of the non-circular cross-section defined by the external surface.

\* \* \* \* \*